(12) United States Patent
Combs et al.

(10) Patent No.: US 7,141,596 B2
(45) Date of Patent: Nov. 28, 2006

(54) INHIBITORS OF PROTEINS THAT BIND PHOSPHORYLATED MOLECULES

(75) Inventors: Andrew P. Combs, Kennett Square, PA (US); Eddy Wai Tsun Yue, Landenberg, PA (US); Michael J. Bower, Newark, DE (US); Wenyu Zhu, Media, PA (US); Matthew L. Crawley, Swarthmore, PA (US); Richard B. Sparks, Boothwyn, PA (US); James R. Pruitt, Landenberg, PA (US); Amy Takvorian, Swedesboro, NJ (US)

(73) Assignee: Incyte Corporation, Wilmington, DE (US)

( * ) Notice: Subject to any disclaimer, the term of this patent is extended or adjusted under 35 U.S.C. 154(b) by 156 days.

(21) Appl. No.: 10/960,344

(22) Filed: Oct. 7, 2004

(65) Prior Publication Data

US 2005/0272778 A1    Dec. 8, 2005

Related U.S. Application Data

(60) Provisional application No. 60/600,506, filed on Aug. 11, 2004, provisional application No. 60/529,372, filed on Dec. 11, 2003, provisional application No. 60/510,002, filed on Oct. 8, 2003.

(51) Int. Cl.
*A61K 41/425* (2006.01)
*A61K 31/4439* (2006.01)
*C07D 275/02* (2006.01)
*C07D 239/24* (2006.01)
*C07D 417/04* (2006.01)

(52) U.S. Cl. .................. 514/372; 514/236.8; 514/256; 514/342; 544/134; 544/335; 546/271.1

(58) Field of Classification Search ................ 514/372; 546/271.1
See application file for complete search history.

(56) References Cited

U.S. PATENT DOCUMENTS

| | | | |
|---|---|---|---|
| 4,428,956 A | 1/1984 | Cragoe, Jr. et al. | |
| 5,276,049 A | 1/1994 | Himmelsbach et al. | |
| 5,478,942 A | 12/1995 | Himmelsbach et al. | |
| 5,650,424 A | 7/1997 | Himmelsbach et al. | |
| 5,789,374 A | 8/1998 | Sprecker et al. | |
| 5,798,374 A | 8/1998 | Tang et al. | |
| 5,852,192 A | 12/1998 | Himmelsbach et al. | |
| 6,001,867 A | 12/1999 | Wrobel et al. | |
| 6,057,316 A | 5/2000 | Wrobel et al. | |
| 6,110,963 A | 8/2000 | Malamas | |
| 6,166,069 A | 12/2000 | Malamas et al. | |
| 6,310,081 B1 | 10/2001 | Malamas et al. | |
| 6,479,493 B1 * | 11/2002 | Whitehead et al. | 514/241 |
| 2002/0086853 A1 | 7/2002 | Cherney et al. | |
| 2003/0060419 A1 | 3/2003 | Hu et al. | |
| 2004/0167188 A1 | 8/2004 | Xin et al. | |

FOREIGN PATENT DOCUMENTS

| | | |
|---|---|---|
| WO | WO 97/40017 | 10/1997 |
| WO | WO 98/27065 | 6/1998 |
| WO | WO 98/27092 | 6/1998 |
| WO | WO 98/53814 | 12/1998 |
| WO | WO 98/56376 | 12/1998 |
| WO | WO 99/11606 | 3/1999 |
| WO | WO 99/58514 | 11/1999 |
| WO | WO 99/58518 | 11/1999 |
| WO | WO 99/58519 | 11/1999 |
| WO | WO 99/58521 | 11/1999 |
| WO | WO 99/58522 | 11/1999 |
| WO | WO 99/61410 | 12/1999 |
| WO | WO 00/17211 | 3/2000 |
| WO | WO 00/53583 | 9/2000 |
| WO | WO 00/69899 | 11/2000 |
| WO | WO 01/16097 | 3/2001 |
| WO | WO 01/16122 | 3/2001 |
| WO | WO 01/16123 | 3/2001 |
| WO | WO 01/17516 | 3/2001 |
| WO | WO 01/19830 | 3/2001 |
| WO | WO 01/19831 | 3/2001 |
| WO | WO 01/46203 | 6/2001 |
| WO | WO 01/46204 | 6/2001 |
| WO | WO 01/46205 | 6/2001 |
| WO | WO 01/46206 | 6/2001 |
| WO | WO 01/70753 | 9/2001 |
| WO | WO 01/70754 | 9/2001 |
| WO | WO 02/04412 | 1/2002 |
| WO | WO 02/11722 | 2/2002 |
| WO | WO 02/012359 | 2/2002 |
| WO | WO 02/18321 | 3/2002 |
| WO | WO 02/18323 | 3/2002 |
| WO | WO 02/18363 | 3/2002 |
| WO | WO 02/26707 | 4/2002 |

(Continued)

OTHER PUBLICATIONS

Unterhalt et al., "Investigations of the cross reactivity of isothiazol-3(2 H)-one 1,1-dioxides," Pharmazie, vol. 52, Iss. 11, pp. 764-766 (1998).*

(Continued)

*Primary Examiner*—Joseph K. McKane
*Assistant Examiner*—Andrew B. Freistein
(74) *Attorney, Agent, or Firm*—Fish & Richardson P.C.

(57) ABSTRACT

The present invention provides compounds that can modulate the activity of a target protein, such as a phosphatase, that selectively binds phosphorylated peptides or proteins. The present compounds can be useful in treating diseases or disorders, including, for example, diabetes and obesity, that are connected directly or indirectly to the activity of the target protein.

61 Claims, No Drawings

FOREIGN PATENT DOCUMENTS

| WO | WO 02/26743 | 4/2002 |
|---|---|---|
| WO | WO 02/28846 | 4/2002 |
| WO | WO 03/32916 | 4/2003 |
| WO | WO 03/033496 | 4/2003 |
| WO | WO 03/037328 | 5/2003 |
| WO | WO 03/82841 | 10/2003 |
| WO | WO 03/092679 | 11/2003 |
| WO | WO 04/041799 | 5/2004 |
| WO | WO 04/050646 | 6/2004 |
| WO | WO 04/062664 | 7/2004 |
| WO | WO 04/106305 | 12/2004 |

OTHER PUBLICATIONS

Arbuzov et al., "Reaction of azomethines with acylisocyanates in the presence of sulfur dioxide," *Izvestiya Akademii Nauk SSSR, Seriya Khimicheskaya* (1980) 5:1164. (Abstract only).

Arbuzov et al., "Synthesis of substituted 4-oxo-1,2,3,5-oxathiadiazine 2-oxides," *Izvestiya Akademii Nauk SSSR, Seriya Khimicheskaya* (1975) 6:1438. (Abstract only).

Beebe et al., "Substrate recognition through a PDZ domain in tail-specific protease," *Biochemistry* (2000) 39:3149-3155.

Breslav et al., "Dithioketal formation during synthesis of Bpa containing peptides," *Tetrahedron Letters* (1997) 38:2219.

Bright et al., "Competitive particle concentration fluorescene immunoassays for measuring anti-diabetic drug levels in mouse plasma," *J. of Immunological Methods* (1997) 207:23.

Chou et al., "The syntheses of triazole, sulfur-containing diazole and N-phenylthiatriazole biphenyltetrazoles as potential angiotensin II receptor antagonists," *J. of the Chinese Chemical Society* (1996) 43:83-93.

Davlatyan et al., "Reaction of thionylanilines with cyanohydrins and a-aminoisobutyronitrile," *Armyanskii Khimicheskii Zhurnal* (1976) 29:764. (Abstract only).

Durcy et al., "Synthesis of 1,2,5-thiadiazolidin-3-one, 1,1-dioxide derivatives and evaluation of their affinity for MHC class-II proteins," *Helvetica Chemica Acta* (1999) 82:2432.

Gao et al., "Macrocyclization in the design of a conformationally contrained Grb2 SH2 domain inhibitors," *Bioorganic & Medicinal Chemistry Letters* (2001) 11:1889-1892.

Liu et al., "Small peptides containing phosphotyrosine and adjacent αMe-phosphotyrosine or its mimetics as highly potent inhibitors of Grb2 SH2," *J. Med. Chem.* (1999) 42:3737-3741.

Schoepfer et al. "Convergent synthesis of potent peptide inhibitors of the Grb-2-SH2 domain by palladium catalyzed coupling of a terminal alkyne," *Bioorganic & Medicinal Chemistry Letters* (2001) 11:1201-1203.

* cited by examiner

INHIBITORS OF PROTEINS THAT BIND PHOSPHORYLATED MOLECULES

CROSS REFERENCE TO RELATED APPLICATIONS

This application claims the priority benefit of U.S. Provisional App. Ser. Nos. 60/510,002, filed Oct. 8, 2003; 60/529,372, filed Dec. 11, 2003; and 60/600,506, filed Aug. 11, 2004, the disclosures of each of which are incorporated herein by reference in their entireties.

FIELD OF THE INVENTION

The present invention relates to compounds that can modulate the activity of proteins, such as phosphatases, that selectively bind phosphorylated proteins. The present compounds can be useful in treating diseases or disorders, including for example diabetes and obesity, that are connected directly or indirectly to the activity of phosphatases and related proteins.

BACKGROUND OF THE INVENTION

Coordinated, reversible protein phosphorylation is a mechanism by which the activity of enzymes in cellular metabolic pathways is often regulated. Kinases and phosphatases catalyze the phosphorylation and dephosphorylation of substrates, respectively. A dynamic balance between the activities of kinases and phosphatases modulates a plethora of intracellular signaling pathways, including pathways responsive to hormones such as insulin and leptin. In the classic model, kinases act as positive regulators, whereas phosphatases serve to negatively regulate these signaling pathways; however, phosphatases have also been shown to positively regulate some pathways. Phosphatases are generally classified into three groups: the serine-threonine phosphatases, tyrosine phosphatases, and the dual-specificity phosphatases, the latter of which dephosphorylate serine, threonine and tyrosine phosphoamino acids (see, e.g., van Huijsduijnen et al., *Drug Discov. Today,* 2002, 7, 1013–1019).

Several proteins that bind to phosphorylated tyrosines, threonines, or serines have been identified; some are known as adaptor molecules for their presumptive role in mediating the physical interaction of signaling pathway components. Protein domains known as src-homology 2 (SH2) domains and phosphotyrosine binding (PTB) domains have been found to mediate the interaction between phosphorylated amino acid residues of activated plasma membrane-spanning receptor molecules and intracellular adaptor proteins. As one example, the classic adaptor molecule, growth factor receptor-bound protein 2 (GRB2), features a hallmark SH2 domain through which GRB2 interacts with phosphotyrosine-containing activated receptors. The potential antiproliferative effects of inhibiting signal transduction with the use of agents (small peptides and macrocycles) which specifically block the interaction between adaptor proteins and phosphorylated residues of activated receptors represents an active area of anticancer therapeutic research (see, e.g., Gao et al., *Bioorg Med Chem Lett,* 2001, 11, 1889–1892; Groves et al., *Biochemistry,* 1998, 37, 17773–17783; Liu et al., *J Med Chem,* 1999, 42, 3737–3741; Schoepfer et al., *Bioorg Med Chem Lett,* 2001, 11, 1201–1203; Yan et al., *FEBS Lett,* 2002, 513, 67–70).

Protein tyrosine phosphatases (PTPases) which reverse the phosphorylation of activated growth factor receptors are another means of attenuating signal transduction cascades. For example, autophosphorylation of the insulin receptor is essential for mediating the effects of insulin in a variety of cell types. Insulin signaling is initiated when insulin binds to extracellular subunits of the heterotetrameric insulin receptor tyrosine kinase (IRTK) and induces rapid autophosphorylation of several tyrosine residues in the intracellular part of the receptor, thus activating it. A fully phosphorylated IRTK transmits a signal to downstream cellular substrates, and activity of the phosphorylated IRTK can be reversed by dephosphorylation. The phosphotyrosine residues functioning as a control switch of IRTK activity appear to be tightly regulated by PTP-mediated dephosphorylation. The phosphatase PTP1B, first cloned from human placenta (Tonks et al., *J Biol Chem,* 1988, 263, 6722–6730), is believed to downregulate the insulin receptor (Faure et al., *J Biol Chem,* 1992, 267, 11215–11221; Zinker et al., *Proc Natl Acad Sci U S A,* 2002, 99, 11357–11362).

Insulin regulates important metabolic processes and plays a key role in control of blood glucose levels. The role of the adipocyte-derived hormone, leptin, appears to be the regulation of body mass, via suppression of food intake and increased energy expenditure. Type 2 diabetes mellitus and obesity are characterised by resistance to hormones insulin and leptin, attributed to attenuated or diminished receptor signaling. A large body of data from cellular, biochemical, mouse and human genetic and chemical inhibitor studies have identified PTP1B as a major negative regulator of both insulin and leptin signaling, implicating PTP1B in both insulin resistance and leptin resistance (Cheng et al., *Dev Cell,* 2002, 2, 497–503; Cook and Unger, *Dev Cell,* 2002, 2, 385–387; Ukkola and Santaniemi, *J Intern Med,* 2002, 251, 467–475; Zabolotny et al., *Dev Cell,* 2002, 2, 489–495).

Additionally, evidence suggests that insulin and leptin action can be enhanced by the inhibition of PTP1B. Because PTP1B dephosphorylates and thereby downregulates signaling by IRTK and the leptin receptor, specific inhibition, deletion or disruption of PTP1B function would be expected to lead to undiminished insulin receptor and leptin receptor signaling, and, therefore, insulin sensitivity and resistance to obesity. This hypothesis is strongly supported by the observation that mice lacking the PTP1B gene are generally healthy but exhibit increased insulin sensitivity and are able to maintain glucose homeostasis with about half the level of circulating insulin, making them resistant to diet-induced obesity. In response to insulin administration, PTP1B deficient mice exhibit a significant increase in insulin receptor phosphorylation in liver and muscle compared to wild type controls. The insulin-sensitive phenotype of the PTP1B knockout mouse is reproduced when the phosphatase is knocked down with an antisense oligonucleotide in obese mice (Zinker et al., *Proc Natl Acad Sci U S A,* 2002, 99, 11357–11362).

Inhibitors of PTPases, in general, are currently under intense study as potential therapeutic agents for treatment of obesity, diabetes, autoimmune diseases, infectious disease, inflammation, osteoporosis, cancer and neurodegenerative diseases. Because blocking PTPases with non-specific inhibitors results in massive and rapid stimulation of kinase-catalyzed phosphorylation cascades, the presiding assumption is that blocking individual PTPases could result in stimulation of specific pathways (van Huijsduijnen et al., *Drug Discov Today,* 2002, 7, 1013–1019). PTP1B appears to be a very attractive candidate for the design of pharmacological agents capable of inhibiting these negative regulator(s) of the insulin and leptin signaling pathways and therefore beneficial for the treatment of Type 2 diabetes and obesity. Furthermore, PTP1B has also been reported to regulate neurite extension mediated by cell-cell and cell-matrix adhesion molecules (Pathre et al., *J Neurosci Res*, 2001, 63, 143–150) and to be a major player in catalyzing the dephosphorylation and activation of c-Src in human breast cancer cell lines (Bjorge et al., *J Biol Chem*, 2000, 275, 41439–41446). Thus, PTP1B has emerged as an ideal target for these inhibitors, not only for the management or treatment of diabetes and obesity, but also cancer and neurodegeneration, (Asante-Appiah and Kennedy, *Am J Physiol Endocrinol Metab*, 2003, 284, E663–670; Ukkola and Santaniemi, *J Intern Med*, 2002, 251, 467–475; van Huijsduijnen et al., *Drug Discov Today*, 2002, 7, 1013–1019).

Some small molecules such as insulinomimetics, phosphotyrosine mimetics, substituted carboxylic acids, non-carboxylic acid-containing ligands, difluromethylphosphophonates, and hydroxamido vanadates have been studied as inhibitors of PTPases (Burke et al., *Biochemistry*, 1996, 35, 15989–15996; Faure et al., *J Biol Chem*, 1992, 267, 11215–11221; Jia et al., *J Med Chem*, 2001, 44, 4584–4594; Larsen et al., *J Med Chem*, 2002, 45, 598–622; Liu et al., *J Med Chem*, 2003, 46, 3437–3440). Many reported inhibitors of PTPases have been phosphorus-containing compounds, tight-binding inhibitors, and/or inhibitors that covalently modify the enzymes (Iversen et al., *J Biol Chem*, 2002, 277, 19982–19990; Leung et al., *Bioorg Med Chem*, 2002, 10, 2309–2323; Shen et al., *J Biol Chem*, 2001, 276, 47311–47319; Zhang et al., *J Biol Chem*, 2000, 275, 34205–34212). In a search for a general, reversible, competitive PTP inhibitor that could be used as a common scaffold for lead optimization for specific PTPs, 2-(oxalylamino)-benzoic acid (OBA) was identified and reported to be a competitive inhibitor of several PTPs (Andersen et al., *J Biol Chem*, 2000, 275, 7101–7108). However, as with many PTPase inhibitors, OBA exhibits a lack of specificity for inhibition of PTP1B. Thus, OBA has been used as a starting point in a screen for selective PTP1B inhibitors (Iversen et al., *J Biol Chem*, 2000, 275, 10300–10307).

Reports of various phosphatase inhibitors have been published in WO 04/062664; WO 04/041799; WO 03/82841; WO 03/092679; WO 02/18321; WO 02/18323; WO 02/18363; WO 03/37328; WO 02/102359; WO 02/04412; WO 02/11722; WO 02/26707; WO 02/26743; WO 01/16122; WO 01/16123; WO 00/17211; WO 00/69889; WO 01/46203; WO 01/46204; WO 01/46205; WO 01/46206; WO 01/70753; WO 01/70754; WO 01/17516; WO 01/19830; WO 01/19831; WO 98/27065; WO 00/53583; WO 99/11606; WO 03/32916; WO 01/16097; WO 98/27092; WO 98/56376; WO 03/33496; WO 99/58514; WO 99/58518; WO 99/58519; WO 99/58521; WO 99/58522; WO 99/61410; WO 97/40017; and U.S. Pat. Nos. 6,166,069; 6,310,081; 6,110,963; 6,057,316; 6,001,867; and 5,7983,74. Other compounds have been reported in U.S. 2003/0060419 U.S. 2004/0167188 and WO 98/53814.

Thus, PTP1B is an ideal therapeutic target for intervention in type 2 diabetes and obesity, as well as, neurodegenerative and anarchic cell proliferative diseases such as cancer, and there remains a long felt need for inhibitors of proteins that bind to tyrosine phosphonates, threonine phosphonates or serine phosphonates, and in particular, inhibitors of PTP1B with modified or improved profiles of activity.

SUMMARY OF THE INVENTION

The present invention provides compounds and compositions containing the same that can modulate the activity of proteins which are capable of selectively binding to phosphorylated peptides or proteins.

The present invention provides, in part, a compound of Formula Ia or Ib:

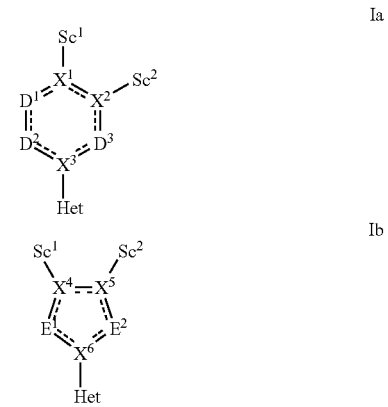

or pharmaceutically acceptable salt or prodrug thereof, wherein constituent members are defined below.

The present invention further provides compositions containing at least one compound of the present invention and a pharmaceutically acceptable carrier.

The present invention further provides a method of modulating the activity of a target protein that selectively binds to a phosphorylated peptide or protein comprising contacting the target protein with a compound of the invention.

The present invention further provides a method of treating diseases or disorders, such as diabetes and obesity, which are associated with activity of a target protein that selectively binds to a phosphorylated peptide or protein, comprising administering to a patient a therapeutically effective amount of a compound of the invention.

DETAILED DESCRIPTION OF EMBODIMENTS OF THE INVENTION

The present invention is directed, in part, to compounds that can modulate the activity of target proteins that selectively bind phosphorylated peptides or phosphorylated proteins. While not wishing to be bound by theory, the compounds contain a moiety that is believed to structurally and/or functionally mimic a phosphorylated amino acid residue. This moiety, containing a 5- or 6-membered heterocycle (Het) linked to an aromatic ring, is believed to bind at or in the vicinity of the binding pocket, thus blocking normal target-ligand interaction and disrupting biochemical pathways involving dephosphorylation of proteins.

The present invention provides a compound of Formula Ia or Ib:

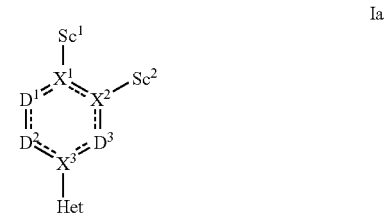

-continued

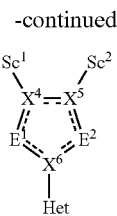

or pharmaceutically acceptable salt or prodrug thereof, wherein:
a dashed line indicates an optional bond;
$Sc^1$ is a first molecular scaffold or absent;
$Sc^2$ is a second molecular scaffold or absent, wherein at least one of $Sc^1$ and $Sc^2$ is present; or
$Sc^1$ and $Sc^2$ together with $X^1$ and $X^2$ or $X^4$ and $X^5$ form a 5-, 6-, or 7-membered fused carbocyclic ring or a 5-, 6-, or 7-membered fused heterocarbocyclic ring, each optionally substituted by one or more —$(CH_2)_{p1}$-$J^2$-$K^2$;
$X^1$ is C or N when $Sc^1$ is present;
$X^1$ is $CR^1$, N, $NR^2$, CO, CS, SO, or $SO_2$ when $Sc^1$ is absent;
$X^2$ is C or N when $Sc^2$ is present;
$X^2$ is $CR^1$, N, $NR^2$, CO, CS, SO, or $SO_2$ when $Sc^2$ is absent;
$X^3$ is C or N;
each $D^1$, $D^2$, and $D^3$ is, independently, $CR^1$, N, $NR^2$, CO, CS, SO, or $SO_2$, wherein the ring formed by $X^1$, $X^2$, $X^3$, $D^1$, $D^2$, and $D^3$ is an aromatic ring;
$X^4$ is C or N when $Sc^1$ is present;
$X^4$ is O, S, $CR^3$, N, $NR^4$, CO, CS, SO, or $SO_2$ when $Sc^1$ is absent;
$X^5$ is C or N when $Sc^2$ is present;
$X^5$ is O, S, $CR^3$, N, $NR^4$, CO, CS, SO, or $SO_2$ when $Sc^2$ is absent;
$X^6$ is C or N;
each $E^1$ and $E^2$ is, independently, O, S, $CR^3$, N, $NR^4$, CO, CS, SO, or $SO_2$, wherein the ring formed by $X^4$, $X^5$, $X^6$, $E^1$, and $E^2$ is an aromatic ring;
each $R^1$ and $R^3$ is, independently, H, halo, $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $OR^5$, $SR^5$, $NO_2$, CN, $SOR^6$, $SO_2R^6$, $COR^7$, $COOR^8$, $NR^9R^{10}$, aryl, a 5- or 6-membered heterocarbocyclyl group, or tetrazolyl;
each $R^2$ and $R^4$ is, independently, H, $C_1$–$C_4$ alkyl, $C_1$–$C_4$ haloalkyl, $C_3$–$C_6$ cycloalkyl, $SOR^6$, $SO_2R^6$, $COR^7$, or $COOR^8$;
or i) $R^1$ and a second $R^1$, ii) $R^2$ and a second $R^2$, or iii) $R^1$ and $R^2$, together with the atoms to which they are attached, form a fused 5- or 6-membered carbocycyl or heterocarbocyclyl group, provided said i) $R^1$ and second $R^1$, ii) $R^2$ and second $R^2$, or iii) $R^1$ and $R^2$ are attached to adjacent atoms;
each $R^5$ is, independently, H, $C_1$–$C_4$ alkyl, $C_2$–$C_4$ alkenyl, $C_2$–$C_4$ alkynyl, $C_3$–$C_6$ cycloalkyl, or $C_1$–$C_4$ haloalkyl;
each $R^6$ is, independently, H, $C_1$–$C_4$ alkyl, $C_3$–$C_6$ cycloalkyl, $C_1$–$C_4$ haloalkyl, $N(R^{6a})_2$, or 5- or 6-membered heterocycloalkyl;
each $R^{6a}$ is, independently, H, $C_1$–$C_4$ alkyl, $C_3$–$C_6$ cycloalkyl, $C_4$–$C_{10}$ cycloalkylalkyl, aryl, or aralkyl;
each $R^7$ is, independently, H, $C_3$–$C_6$ cycloalkyl, $C_1$–$C_4$ alkyl, $N(R^{7a})_2$, or 5- or 6-membered heterocycloalkyl;
each $R^{7a}$ is, independently, H, $C_1$–$C_4$ alkyl, $C_3$–$C_6$ cycloalkyl, $C_4$–$C_{10}$ cycloalkylalkyl, aryl, or aralkyl;
each $R^8$ is, independently, H, $C_1$–$C_4$ alkyl, $C_3$–$C_6$ cycloalkyl, or $C_1$–$C_4$ haloalkyl;

each $R^9$ and $R^{10}$ is, independently, H, $C_1$–$C_4$ alkyl, $C_3$–$C_6$ cycloalkyl, $C_1$–$C_4$ haloalkyl, $SO_2R^{11}$, $COR^{12}$, $COOR^{13}$, or $R^9$ and $R^{10}$ together with the N atom to which they are attached form a 5- or 6-membered heterocycloalkyl group;
$R^{11}$ is H, $C_1$–$C_4$ alkyl, $C_3$–$C_6$ cycloalkyl, $C_1$–$C_4$ haloalkyl, $N(C_1$–$C_4$ alkyl$)_2$, $NH(C_1$–$C_4$ alkyl), $NH_2$, or 5- or 6-membered heterocycloalkyl;
$R^{12}$ is H, $C_3$–$C_6$ cycloalkyl, $C_1$–$C_4$ alkyl, $N(C_1$–$C_4$ alkyl$)_2$, $NH(C_1$–$C_4$ alkyl), $NH_2$, or 5- or 6-membered heterocycloalkyl;
$R^{13}$ is H, $C_1$–$C_4$ alkyl, $C_3$–$C_6$ cycloalkyl, or $C_1$–$C_4$ haloalkyl;
Het is a heterocarbocyclic ring of Formula:

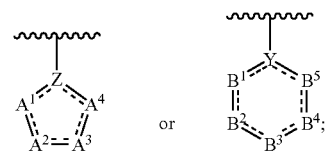

Y is C, $CR^Y$, or N;
Z is C, $CR^Z$, or N;
each $A^1$, $A^2$, $A^3$, and $A^4$ is, independently, O, N, $NR^{14}$, $CR^{15}$, $CR^{16}R^{17}$, CO, CS, S, SO, $SO_2$, $PR^{18}$, $PO(OR^{19})$, or —C=$NR^{20}$;
each $B^1$, $B^2$, $B^3$, $B^4$, and $B^5$ is, independently, O, N, $NR^{21}$, $CR^{22}$, $CR^{23}R^{24}$, CO, CS, S, SO, $SO_2PR^{25}$, $PO(OR^{26})$, —C=$NR^{27}$;
each $R^Y$ and $R^Z$ is, independently, H, halo, $C_1$–$C_4$ alkyl, $C_3$–$C_6$ cycloalkyl, haloalkyl, $OR^{28}$, $SR^{28}$, $NO_2$, CN, $SOR^{29}$, $SO_2R^{29}$, $COR^{30}$, $COOR^{31}$, $NR^{32}R^{33}$, a 5- or 6-membered heterocarbocyclyl group, or tetrazolyl;
each $R^{28}$ is, independently, H, $C_1$–$C_4$alkyl, $C_2$–$C_4$ alkenyl, $C_2$–$C_4$ alkynyl, $C_3$–$C_6$ cycloalkyl, or haloalkyl;
each $R^{29}$ is, independently, H, $C_1$–$C_4$ alkyl, $C_3$–$C_6$ cycloalkyl, haloalkyl, $N(C_1$–$C_4$ alkyl$)_2$, $NH(C_1$–$C_4$ alkyl), or $NH_2$;
each $R^{30}$ is, independently, H, $C_3$–$C_6$ cycloalkyl, $C_1$–$C_4$ alkyl, $N(C_1$–$C_4$ alkyl$)_2$, $NH(C_1$–$C_4$ alkyl), $NH_2$, or 5- or 6-membered heterocarbocyclyl;
each $R^{31}$ is, independently, H, $C_1$–$C_4$ alkyl, $C_3$–$C_6$ cycloalkyl, or haloalkyl;
each $R^{32}$ and $R^{33}$ is, independently, H, $C_1$–$C_4$ alkyl, $C_3$–$C_6$ cycloalkyl, haloalkyl, $SO_3H$, $SO_2(C_1$–$C_4$ alkyl), $SO_2(C_1$–$C_4$ haloalkyl), $SO_2(C_3$–$C_6$ cycloalkyl), CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), or $R^{32}$ and $R^{33}$ together with the N atom to which they are attached form a 5- or 6-membered heterocycloalkyl group;
$J^2$ is $(CR^{a1}R^{a2})_{p2}$, $(CR^{a1}R^{a2})_{p2}O(CR^{a1}R^{a2})_{p3}$, $(CR^{a1}R^{a2})_{p4}S(CR^{a1}R^{a2})_{p3}$, $(CR^{a1}R^{a2})_{p2}NR^{a3}(CR^{1a}R^{a2})_{p2}$, $(CR^{a1}R^{a2})_{p2}CONR^{a3}(CR^{a1}R^{a2})_{p3}$, $(CR^{a1}R^{a2})_{p2}SONR^{a3}(CR^{a1}R^{a2})_{p3}$, $(CR^{a1}R^{a2})_{p2}SO_2NR^{a3}(CR^{a1}R^{a2})_{p3}$, $(CR^{a1}R^{a2})_{p2}CO(CR^{a1}R^{a2})_{p3}$, $(CR^{a1}R^{a2})_{p2}COO(CR^{a1}R^{a2})_{p3}$, $(CR^{a1}R^{a2})_{p2}NR^{a3}CONR^{a3}(CR^{a1}R^{a2})_{p3}$, $(CR^{a1}R^{a2})_{p2}NR^{a3}C(=NR^{a3})NR^{a3}(CR^{a1}R^{a2})_{p3}$, $(CR^{a1}R^{a2})_{p2}OCO(CR^{a1}R^{a2})_{p3}$, or absent;
$K^2$ is H, halo, $C_1$–$C_8$ alkyl, aryl, heteroaryl, $C_3$–$C_7$ cycloalkyl, heterocycloalkyl, wherein said $C_1$–$C_8$ alkyl, aryl, heteroaryl, $C_3$–$C_7$ cycloalkyl or heterocycloalkyl is optionally substituted by one or more halo, $C_2$–$C_6$ alkenyl, $C_2$–$C_6$ alkynyl, $C_1$–$C_6$ haloalkyl, $C_3$–$C_7$ cycloalkyl, aryl, heterocycloalkyl, heteroaryl, cyano, nitro, $OR^{a4}$, $SR^{a4}$, $NR^{a5}R^{a6}$, $SONR^{a5}R^{a6}$, $SO_2NR^{a5}R^{a6}$, $CONR^{a5}R^{a6}$, $COOR^{a4}$ $COR^{a7}$;

$R^{a1}$ and $R^{a2}$ are each, independently, H, halo, $C_1$–$C_4$ alkyl, $C_2$–$C_4$ alkenyl, $C_2$–$C_4$ alkynyl or $C_1$–$C_4$ haloalkyl;

$R^{a3}$ is H, $C_1$–$C_4$ alkyl, $C_1$–$C_4$ haloalkyl, aryl, or $C_3$–$C_7$ cycloalkyl;

$R^{a4}$ is H, $C_1$–$C_6$ alkyl, $C_1$–$C_6$ haloalkyl, aryl or $C_3$–$C_7$ cycloalkyl;

$R^{a5}$ and $R^{a6}$ are each, independently, H, $C_1$–$C_6$ alkyl, $C_1$–$C_6$ haloalkyl or $C_3$–$C_7$ cycloalkyl, or $R^{a5}$ and $R^{a6}$ together with the N atom to which they are attached form a 5- or 6-membered heterocycloalkyl ring;

$R^{a7}$ is H, $C_1$–$C_6$ alkyl, aryl, heteroaryl, $C_3$–$C_7$ cycloalkyl or heterocycloalkyl;

p1 is 0, 1, or 2;

p2 is 0, 1, or 2; and p3 is 0, 1, or 2.

each $R^{14}$ and $R^{21}$ is, independently, H, $C_1$–$C_4$ alkyl, $C_1$–$C_4$ haloalkyl, $C_3$–$C_6$ cycloalkyl, CHO, COOH, CO($C_1$–$C_4$ alkyl), CO($C_3$–$C_6$ cycloalkyl), CO($C_1$–$C_4$ haloalkyl), CO-(heterocarbocyclyl), COO($C_1$–$C_4$ alkyl), COO($C_3$–$C_6$ cycloalkyl), COO($C_1$–$C_4$ haloalkyl), CONH$_2$, CONH($C_1$–$C_4$ alkyl), CON($C_1$–$C_4$ alkyl)$_2$, CONH($C_3$–$C_6$ cycloalkyl), CON($C_3$–$C_6$ cycloalkyl)$_2$, SO($C_1$–$C_4$ alkyl), SO($C_1$–$C_4$ haloalkyl), SO($C_3$–$C_6$ cycloalkyl), SONH$_2$, SO$_3$H, SO$_2$($C_1$–$C_4$ alkyl), SO$_2$($C_1$–$C_4$ haloalkyl), SO$_2$($C_3$–$C_6$ cycloalkyl), SO$_2$NH$_2$, NH$_2$, NH($C_1$–$C_4$ alkyl), N($C_1$–$C_4$ alkyl)$_2$, NH($C_3$–$C_6$ cycloalkyl), or N($C_3$–$C_6$ cycloalkyl)$_2$;

each $R^{15}$ and $R^{22}$ is, independently, H, halo, $C_1$–$C_4$ alkyl, $C_3$–$C_6$ cycloalkyl, haloalkyl, OH, $C_1$–$C_4$ alkoxy, $C_1$–$C_4$ haloalkoxy, SH, $C_1$–$C_4$ thioalkoxy, CN, NO$_2$, SO($C_1$–$C_4$ alkyl), SO($C_1$–$C_4$ haloalkyl), SO($C_3$–$C_6$ cycloalkyl), SONH$_2$, SO$_3$H, SO$_2$($C_1$–$C_4$ alkyl), SO$_2$($C_1$–$C_4$ haloalkyl), SO$_2$($C_3$–$C_6$ cycloalkyl), SO$_2$NH$_2$, CHO, COOH, CO($C_1$–$C_4$ alkyl), CO($C_3$–$C_6$ cycloalkyl), CO($C_1$–$C_4$ haloalkyl), CO-(heterocarbocyclyl), COO($C_1$–$C_4$ alkyl), COO($C_3$–$C_6$ cycloalkyl), COO($C_1$–$C_4$ haloalkyl), CONH$_2$, CONH($C_1$–$C_4$ alkyl), CON($C_1$–$C_4$ alkyl)$_2$, CONH($C_3$–$C_6$ cycloalkyl), CON($C_3$–$C_6$ cycloalkyl)$_2$, NH$_2$, NH($C_1$–$C_4$ alkyl), N($C_1$–$C_4$ alkyl)$_2$, NH($C_3$–$C_6$ cycloalkyl), or N($C_3$–$C_6$ cycloalkyl)$_2$;

each $R^{16}$, $R^{17}$, $R^{23}$, and $R^{24}$ is, independently, H, halo, $C_1$–$C_4$ alkyl, $C_3$–$C_6$ cycloalkyl, haloalkyl, OH, $C_1$–$C_4$ alkoxy, $C_1$–$C_4$ haloalkoxy, SH, $C_1$–$C_4$ thioalkoxy, CN, NO$_2$, SO($C_1$–$C_4$ alkyl), SO($C_1$–$C_4$ haloalkyl), SO($C_3$–$C_6$ cycloalkyl), SONH$_2$, SO$_3$H, SO$_2$($C_1$–$C_4$ alkyl), SO$_2$($C_1$–$C_4$ haloalkyl), SO$_2$($C_3$–$C_6$ cycloalkyl), SO$_2$NH$_2$, CHO, COOH, CO($C_1$–$C_4$ alkyl), CO($C_3$–$C_6$ cycloalkyl), CO($C_1$–$C_4$ haloalkyl), CO-(heterocarbocyclyl), COO($C_1$–$C_4$ alkyl), COO($C_3$–$C_6$ cycloalkyl), COO($C_1$–$C_4$ haloalkyl), CONH$_2$, CONH($C_1$–$C_4$ alkyl), CON($C_1$–$C_4$ alkyl)$_2$, CONH($C_3$–$C_6$ cycloalkyl), CON($C_3$–$C_6$ cycloalkyl)$_2$, NH$_2$, NH($C_1$–$C_4$ alkyl), N($C_1$–$C_4$ alkyl)$_2$, NH($C_3$–$C_6$ cycloalkyl), or N($C_3$–$C_6$ cycloalkyl)$_2$;

or $R^{16}$ and $R^{17}$ together with the carbon atom to which they are attached form a $C_3$–$C_6$ cycloalkyl group or a 3–7 membered heterocycloalkyl group;

or $R^{23}$ and $R^{24}$ together with the carbon atom to which they are attached form a $C_3$–$C_6$ cycloalkyl group;

each $R^{18}$ and $R^{25}$ is, independently, $C_1$–$C_4$ alkyl;

each $R^{19}$ and $R^{26}$ is, independently, H or $C_1$–$C_4$ alkyl; and each $R^{20}$ and $R^{27}$ is, independently, H, OH, CN, $C_1$–$C_4$ alkyl, $C_1$–$C_4$ alkoxy, aryloxy, or $C_3$–$C_6$ cycloalkyloxy.

In some embodiments, when Het is thiadiazolyl, the compound has Formula Ib.

In further embodiments, when Het is a 2,4-thiazolidinedione, 2-thioxo-4-thiazolidinedione, isoxazolidinedione, 2,4-imidazolidinedione, or 2-thioxo-4-imidazolidinedione group, $Sc^2$ is absent or $Sc^1$ and $Sc^2$ form a fused-ring molecular scaffold.

In yet further embodiments, when Het is furyl, thienyl, tetrazolyl, pyrryl, triazolyl, triazol-3-one, imidazolyl, pyrazolyl, isothiazolyl, furazanyl, isoxazolyl, or furan-2-one, the compound has Formula Ib.

In some embodiments, each $R^1$ and $R^3$ is, independently, C—F, C—Cl, C—Br, C—Me, C—Et, C—CH=CH$_2$, C—C≡CH, C—Ph, C—OMe or C—CN.

In yet further embodiments, when Z is C; $A^4$ is N; $A^3$ is NR$^{14}$ or N; $A^2$ is CS, CO, or CR$^{15}$; and $A^1$ is O, S, or CR$^{15}$; then $Sc^1$ and $Sc^2$, together, do not form a fused-ring scaffold; and In yet further embodiments, Het is other than a heterocyclic ring wherein Z is N; $A^4$ is SO$_2$; $A^3$ is NR$^{14}$; $A^2$ is CO or CS; and $A^1$ is CR$^{16}$R$^{17}$.

According to some embodiments, Het has the Formula:

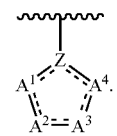

In some embodiments, Z is C.

In some embodiments, Z is N.

In some embodiments, $A^4$ is SO or SO$_2$.

In some embodiments, $A^4$ is PO(OR$^{19}$).

In some embodiments, $A^4$ is S, SO, SO$_2$ and $A^3$ is N or NR$^{14}$.

In some embodiments, $A^3$ is S, SO, SO$_2$ and $A^2$ is N or NR$^{14}$.

In some embodiments, $A^4$ is N or NR$^{14}$ and $A^3$ is S, SO, or SO$_2$.

In some embodiments, $A^3$ is N or NR$^{14}$ and $A^2$ is CO or CS.

In some embodiments, $A^4$ is S, SO, or SO$_2$ and $A^2$ is N or NR$^{14}$.

In some embodiments, at least one of $A^1$, $A^2$, $A^3$, and $A^4$ is SO or SO$_2$.

In some embodiments, $A^4$ is CO, CS, SO, SO$_2$, or PO(OR$^{19}$); $A^2$ is CO, CS, SO, SO$_2$, PO(OR$^{19}$); and $A^3$ is NH.

In some embodiments, $A^4$ is CO or SO$_2$; $A^2$ is CO or SO$_2$; and $A^3$ is NH.

In some embodiments, $R^{14}$ is H.

In some embodiments, $R^{14}$ is H, Na or K.

In some embodiments, each $A^1$, $A^2$, and $A^3$, is, independently, O, N, NR$^{14}$, CR, CR$^{16}$R$^{17}$, CO, CS, S, SO, SO$_2$, PR$^{18}$, PO(OR$^{19}$), or —C=NR$^{20}$ and $A^4$ is S, SO, SO$^2$, or PO(OR$^{19}$).

In some embodiments, each $A^1$ and $A^2$ is, independently, O, N, NR$^{14}$, CR$^{15}$, CR$^{16}$R$^{17}$, CO, CS, S, SO, SO$_2$, PR$^{18}$, PO(OR$^{19}$), or —C=NR$^{20}$; $A^3$ is S, SO, or SO$_2$; and $A^4$ is N or NR$^{14}$.

In some embodiments, each $A^1$ and $A^4$ is, independently, O, N, NR$^{14}$, CR$^{15}$, CR$^{16}$R$^{17}$, CO, CS, S, SO, SO$_2$, PR$^{18}$, PO(OR$^{19}$), or —C=NR$^{20}$; $A^2$ is N or NR$^{14}$; and $A^3$ is S, SO, or SO$_2$.

In some embodiments, $A^1$ and $A^4$ is, independently, O, N, NR$^{14}$, CR$^{15}$, CR$^{16}$R$^{17}$, CO, CS, S, SO, SO$_2$, PR$^{18}$, PO(OR$^{19}$), or —C=NR$^{20}$; $A^2$ is CO or CS; and $A^3$ is N or NR$^{14}$.

In some embodiments, each $R^{15}$ and $R^{22}$ is, independently, H, halo, $C_1$–$C_4$ alkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO((C_1$–$C_4$ haloalkyl), $SONH_2$, $SO_3H$, $SO_2(C_1$–$C_4$ alkyl), $SO_2(C_1$–$C_4$ haloalkyl), $SO_2NH_2$, CHO, COOH, $CO(C_1$–$C_4$ alkyl), $CO(C_1$–$C_4$ haloalkyl), COO $(C_1$–$C_4$ alkyl), $COO(C_1$–$C_4$ haloalkyl), $CONH_2$, $CONH$ $(C_1$–$C_4$ alkyl), $CON(C_1$–$C_4$ alkyl)$_2$, $NH_2$, $NH(C_1$–$C_4$ alkyl), or $N(C_1$–$C_4$ alkyl)$_2$.

In some embodiments, each $R^{15}$ and $R^{22}$ is, independently, H, halo, $C_1$–$C_4$ alkyl, haloalkyl, OH, $C_1C_4$ alkoxy, $C_1$–$C_4$ haloalkoxy, CN, $NO_2$, $NH_2$, $NH(C_1$–$C_4$ alkyl), or $N(C_1$–$C_4$ alkyl)$_2$.

In some embodiments, each $R^{15}$ and $R^{22}$ is, independently, H, halo, $C_1$–$C_4$ alkyl, haloalkyl, OH, $C_1$–$C_4$ alkoxy, or $C_1$–$C_4$ haloalkoxy.

In some embodiments, each $R^{16}$, $R^{17}$, $R^{23}$, and $R^{24}$ is, independently, H, halo, $C_1$–$C_4$ alkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SONH_2$, $SO_3H$, $SO_2(C_1$–$C_4$ alkyl), $SO_2(C_1$–$C_4$ haloalkyl), $SO_2NH_2$, CHO, COOH, $CO(C_1$–$C_4$ alkyl), $CO(C_1$–$C_4$ haloalkyl), COO $(C_1$–$C_4$ alkyl), $COO(C_1$–$C_4$ haloalkyl), $CONH_2$, CONH $(C_1$–$C_4$ alkyl), $CON(C_1$–$C_4$ alkyl)$_2$, $NH_2$, $NH(C_1$–$C_4$ alkyl) or $N(C_1$–$C_4$ alkyl)$_2$.

In some embodiments, each $R^{16}$, $R^{17}$, $R^{23}$, and $R^{24}$ is, independently, H, halo, $C_1$–$C_4$ alkyl, haloalkyl, OH, $C_1$–$C_4$ alkoxy, $C_1$–$C_4$ haloalkoxy, CN, $NO_2$, $NH_2$, $NH(C_1$–$C_4$ alkyl) or $N(C_C$–$C_4$ alkyl)$_2$.

In some embodiments, $R^{16}$ and $R^{17}$ together with the carbon atom to which they are attached form a $C_3$–$C_6$ cycloalkyl group.

In some embodiments, $R^{23}$ and $R^{24}$ together with the carbon atom to which they are attached form a $C_3$–$C_6$ cycloalkyl group.

In some embodiments, Het is selected from a heterocycle of Chart I or II. In further embodiments, at least one CO of the Het moiety in Chart I or II is replaced with CS or at least one CS of the Het moiety in Chart I or II is replaced with CO.

In some embodiments, Het is

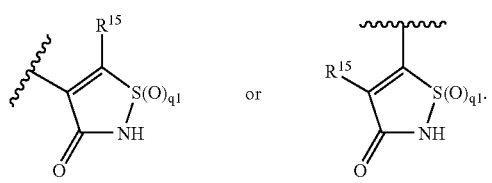

In some embodiments, Het is

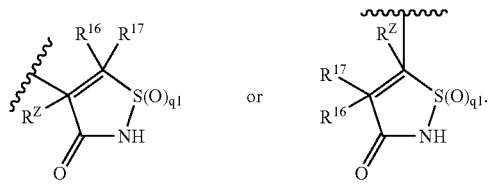

In some embodiments, Het is

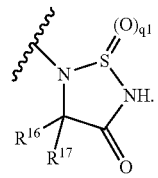

According to any of the embodiments of the present invention, q1 can be 1 or 2. In some embodiments, q1 is 2. In other embodiments, q1 is 1.

According to further embodiments, Het has the Formula:

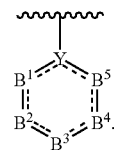

In some embodiments, Y is C.
In some embodiments, Y is N.
In some embodiments, $B^5$ is N or $NR^{21}$ and $B^3$ is N or $NR^{21}$.
In some embodiments, $B^5$ is N or $NR^{21}$, $B^4$ is N or $NR^{21}$, and $B^2$ is N or $NR^{21}$.
In some embodiments, $B^5$ is N or $NR^{21}$ and $B^4$ is N or $NR^{21}$.
In some embodiments, $B^4$ is N or $NR^{21}$, $B^3$ is S, SO, or $SO^2$, and $B^2$ is N or $NR^{21}$.
In some embodiments, $B^4$ is S, SO, or $SO_2$ and $B^3$ is N or $NR^{21}$.
In some embodiments, $B^5$ is CO or CS, $B^4$ is N or $NR^{22}$, $B_2$ is N or $NR^{21}$, and $B^1$ is O, N, $NR^{21}$, $CR^{23}R^{24}$, CO, CS, S, SO, $SO_2$, $PR^{25}$, $PO(OR^{26})$.
In some embodiments, $B^5$ is CO or $SO_2$; $B^3$ is CO or $SO_2$; and $B^4$ is NH.
In some embodiments, $B^1$, $B^2$, and $B^4$ is, independently, O, N, $NR^{21}$, $CR^{22}$, $CR^{23}R^{24}$, CO, CS, S, SO, $SO_2$, $PR^{25}$, $PO(OR^{26})$, —C=$NR^{27}$; and each $B^3$ and $B^5$ is, independently, N or $NR^{21}$.
In some embodiments, each $B^1$ and $B^5$ is, independently, O, N, $NR^{21}$, $CR^{22}$, $CR^{23}R^{24}$, CO, CS, S, SO, $SO_2$, $PR^{25}$, $PO(OR^{26})$, —C=$NR^{27}$; each $B^2$ and $B^4$ is, independently, N or $NR^{21}$; and $B^3$ is S, SO, or $SO_2$.
In some embodiments, each $B^1$, $B^2$, and $B^3$ is, independently, O, N, $NR^{21}$, $CR^{22}$, $CR^{23}R^{24}$, CO, CS, S, SO, $SO_2$, $PR^{25}$, $PO(OR^{26})$, —C=$NR^{27}$; $B^4$ is N or $NR^{21}$; and $B^5$ is S, SO, or $SO_2$.
In some embodiments, $R^{21}$ is H, Na or K.
In some embodiments, $R^{21}$ is H.
In some embodiments, Het is a heterocycle shown in Chart III. The Het moiety can be optionally substituted by one or more halo, $C_1$–$C_4$ alkyl, $C_3$–$C_6$ cycloalkyl, haloalkyl, OH, $C_1$–$C_4$ alkoxy, $C_1$–$C_4$ haloalkoxy, $NH_2$, $NH(C_1$–$C_4$ alkyl), or $N(C_1$–$C_4$ alkyl)$_2$. Further, at least one CO of the Het moiety of Chart III can be replaced with CS.

According to some embodiments, the compounds of the invention have Formula Ia.

In some embodiments, the ring formed by $X^1$, $X^2$, $X^3$, $D^1$, $D^2$, and $D^3$ is substituted or unsubstituted pyridyl, pyrimidinyl, pyridonyl, or triazinyl.

In some embodiments, the ring formed by $X^1$, $X^2$, $X^3$, $D^1$, $D^2$, and $D^3$ is substituted or unsubstituted phenyl.

In some embodiments, $X^1$ is C.
In some embodiments, $X^2$ is C.
In some embodiments, $X^3$ is C.
In some embodiments, $CR^1$ or N.
In some embodiments, $X^1$ and $X^3$ are both C.
In some embodiments, $X^1$, $X^2$, and $X^3$ are each C.
In some embodiments, $X^1$ and $X^3$ are C and $X^2$ is $CR^1$ or N.
In some embodiments, $D^1$, $D^2$, and $D^3$ are each $CR^1$.
In some embodiments, $X^1$, $X^2$, and $X^3$ are each C and $D^1$, $D^2$, and $D^3$ are each $CR^1$.
In some embodiments, one of $D^1$, $D^2$, and $D^3$ is N.
In some embodiments, two of $D^1$, $D^2$, and $D^3$ is N.
In some embodiments, $D^2$ and $D^3$ are both N.
In some embodiments, $X^3$ is N and $D^2$ or $D^3$ is CO.
In some embodiments, $X^1$ is N and $D^1$ or $X^2$ is CO.
In some embodiments, $X^2$ is N and $D^3$ is CO.
In some embodiments, at least one of $D^2$ or $D^3$ is $CR^1$ wherein $R^1$ is other than H.
In some embodiments, at least one of $D^2$ or $D^3$ is $CR^1$ wherein $R^1$ is halo, $C_1$–$C_4$ alkyl, $C_2$–$C_4$ alkenyl, $C_2$–$C_4$ alkynyl, $C_1$–$C_4$ haloalkyl, CN, $OR^5$, $SR^5$, $COOR^8$, aryl, heteroaryl or tetrazolyl.
In some embodiments, at least one of $D^2$ or $D^3$ is C—F, C—Cl, C—Br, C—Me, C—Et, C—CH=$CH_2$, C—C≡CH, C—Ph, C—OMe or C—CN.
In some embodiments, $D^2$ and $D^3$ are both CH.

According to some embodiments, the compounds of the invention have Formula Ib.

In some embodiments, $X^4$ is C.
In some embodiments, $X^5$ is C.
In some embodiments, $X^6$ is C.
In some embodiments, $X^4$, $X^5$, and $X^6$ are C.
In some embodiments, $X^5$ is $CR^3$ or N.
In some embodiments, $X^4$ and $X^6$ are C and $X^5$ is $CR^3$ or N.
In some embodiments, one of $E^1$ and $E^2$ is O or S and the other is $CR^3$, N, or $NR^4$.
In some embodiments, $X^4$ is C, $X^5$ is C, $X^6$, is C, $E^2$ is S, and $E^1$ is $CR^3$, N, or $NR^4$.
In some embodiments, $E^2$ is $NR^4$ or SO and $E^1$ is $CR^3$ or $NR^4$.
In some embodiments, the ring formed by $X^4$, $X^5$, $X^6$, $E^1$, and $E^2$ is substituted or unsubstituted thienyl, furyl, imidazolyl, thiazolyl, pyrryl, oxazolyl, isoxazolyl, pyrazolyl, triazolyl, or tetrazolyl.
In some embodiments, the ring formed by $X^4$, $X^1$, $X^6$, $E^1$, and $E^2$ is substituted or unsubstituted thienyl, furyl, or imidazolyl.
In some embodiments, at least one of $E^1$ or $E^2$ is $CR^3$ wherein $R^3$ is other than H.
In some embodiments, at least one of $E^1$ or $E^2$ is $CR^3$ wherein $R^3$ is halo, $C_1$–$C_4$ alkyl, $C_2$–$C_4$ alkenyl, $C_2$–$C_4$ alkynyl, $C_1$–$C_4$ haloalkyl, aryl, heteroaryl CN, $OR^5$, $SR^5$, $COOR^8$, or tetrazolyl.
In some embodiments, at least one of $E^1$ or $E^2$ is C—F, C—Cl, C—Br, C—Me, C—Et, C—CH=$CH_2$, C—C≡CH, C—Ph, C—OMe or C—CN.

According to further embodiments of the invention, the molecular scaffolds can include any molecular entity.

In some embodiments, $Sc^1$ and $Sc^2$ together with $X^1$ and $X^2$ or $X^4$ and $X^5$ form a fused-ring molecular scaffold.
In some embodiments, $Sc^2$ is absent.
In some embodiments, $Sc^1$ is absent.

In some embodiments, $Sc^1$ comprises at least 4 carbon atoms.
In some embodiments, $Sc^1$ comprises at least 6 carbon atoms.
In some embodiments, $Sc^2$ comprises at least 4 carbon atoms.
In some embodiments, $Sc^2$ comprises at least 6 carbon atoms.
In some embodiments, at least one of $Sc^1$ and $Sc^2$ has a molecular weight of greater than about 200.
In some embodiments, $Sc^1$ is carbocyclyl, carbocyclylalkyl, heterocarbocyclyl, or heterocarbocyclylalkyl.
In some embodiments, $Sc^2$ is carbocyclyl, carbocyclylalkyl, heterocarbocyclyl, or heterocarbocyclylalkyl.
In some embodiments, $Sc^1$ and $Sc^2$ are each, independently, $C_1$–$C_{10}$ alkyl, $C_2$–$C_{10}$ alkenyl, $C_2$–$C_{10}$ alkynyl, $C_3$–$C_7$ cycloalkyl, aryl, heterocycloalkyl, heteroaryl, aralkyl, heteroarylalkyl, cycloalkylalkyl, heterocycloalkyl, OH, alkoxy, aryloxy, heteroaryloxy, cycloalkyloxy, heterocyclalkyloxy, CO-alkyl, CO-aryl, CO-heteroaryl, CO-cycloalkyl, CO-heterocycloalkyl, CO-amino, CO-alkylamino, CO-dialkylamino, NHCO-alkyl, NHCO-aryl, NHCO-heteroaryl, NHCO-cycloalkyl, NHCO-heterocycloalkyl, NHCO-amino, NHCO-alkylamino, NHCO-dialkylamino, amino, alkylamino, or dialkylamino, wherein $Sc^1$ and $Sc^2$ are each optionally substituted by one or more Het, halo, $C_1$–$C_6$ alkyl, $C_2$–$C_6$ alkenyl, $C_2$–$C_6$ alkynyl, $C_3$–$C_7$ cycloalkyl, heterocycloalkyl, aryl, heteroaryl, $C_1$–$C_6$ haloalkyl, cyano, nitro, amino, alkylamino, dialkylamino, hydroxy, alkoxy, aryloxy, heteroaryloxy, or cycloalkyloxy.

In some embodiments, at least one of the first and second molecular scaffolds has the Formula S:

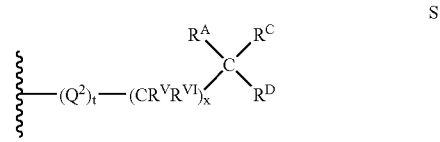

S wherein:
$R^A$ has the Formula:

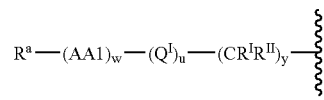

$R^C$ has the Formula:

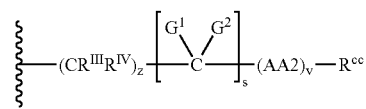

$R^D$ is H, halo, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, $COR^e$, $OCOR^e$, $COOR^f$, $SOR^g$, $SO_2R^g$, $OR^h$, $SR^h$, or $NR^iR^j$, wherein $R^d$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

or $R^A$ and $R^D$ together with the carbon atom to which the are attached form a cycloalkyl or heterocycloalkyl group optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

or $R^A$ and $R^D$ together form the divalent moiety —$NR^y$—CO—$(CR^{z1}R^{z2})_{xx}$—;

or $R^C$ and $R^D$ together with the carbon atom to which they are attached form a cycloalkyl or heterocycloalkyl group optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

$Q^1$ is O, S, CO, COO, $CONR^b$, $NR^bCONR^b$, $NR^bSO_2NR^b$, SO, $SO_2$, $SONR^b$, $SO_2NR^b$, or $NR^b$;

$Q^2$ is O, S, CO, COO, $CONR^d$, $NR^dCONR^d$, $NR^bSO_2NR^b$, SO, $SO_2$, $SONR^d$, $SO_2NR^d$, or $NR^d$;

$R^a$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, $COR^k$, $OCOR^k$, $CONR^{k1}R^{k2}$, $COOR^L$, $C(S)R^k$, $OC(S)R^k$, $C(S)NR^{k1}R^{k2}$, $SOR^k$, or $SO_2R^k$, wherein $R^a$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, haloalkoxy, aryloxy, cycloalkyloxy, mercapto, thioalkoxy, thioaryloxy, cyano, nitro, $NR^rR^s$, carboxy, carboxy alkyl ester, carboxy aryl ester, —$(CH_2)_k$—$R^q$, —$(CF_2)_k$—$R^q$, $SOR^m$, or $SO_2R^m$;

or $R^a$ is —$(CR^{VII}R^{VIII})_p$-$Cy^1$-$(L^1)_q$—$Cy^2$;

$R^b$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, $COR^k$, $OCOR^k$, $CONR^{k1}R^{k2}$, $COOR^L$, $C(S)R^k$, $OC(S)R^k$, $C(S)NR^{k1}R^{k2}$, $SOR^k$, or $SO_2R^k$, wherein $R^b$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, haloalkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

or $R^a$ and $R^b$ together with the N atom to which they are attached form a 5- or 6-membered heterocycloalkyl ring when w is 0, wherein said 5- or 6-membered heterocycloalkyl ring is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, aralkyl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

$R^{cc}$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, -aryl-Het, -heteroaryl-Het, $OR^n$, $SR^n$, or $NR^oR^p$, wherein $R^{cc}$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, aralkyl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, or carboxy;

or $R^{cc}$ is a moiety of Formula:

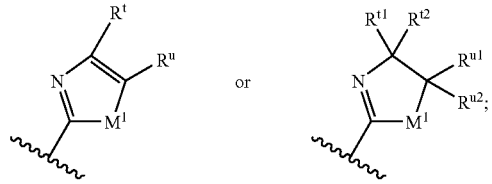

$R^d$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, wherein $R^d$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, aralkyloxy, cycloalkyloxy, mercapto, thioalkoxy, thioaryloxy, cyano, nitro, amino, alkylamino, dialkylamino, carboxy, carboxy alkyl ester, or carboxy aryl ester;

each $R^e$ and $R^k$ is, independently, H, $C_1$–$C_6$ alkyl, $C_1$–$C_6$ haloalkyl, $C_3$–$C_{14}$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein $R^e$ and $R^k$ is optionally substituted by one or more halo, $C_1$–$C_4$ alkyl, $C_1$–$C_4$ haloalkyl, cyano, nitro, COOH, carboxy alkyl ester, carboxy aryl ester, OH, SH, alkoxy, thioalkoxy, haloalkoxy, amino, alkylamino, dialkylamino, $Cy^3$, —$OCy^3$, —$SCy^3$, or heterocycloalkyl;

$R^{k1}$ and $R^{k2}$ are each, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein $R^{k1}$ and $R^{k2}$ are optionally substituted by one or more halo, $C_1$–$C_4$ alkyl, $C_1$–$C_4$ haloalkyl, $C_3$–$C_6$ cycloalkyl, cyano, nitro, COOH, carboxy alkyl ester, carboxy aryl ester, OH, SH, alkoxy, thioalkoxy, aryloxy, thioaryloxy, aryl, heteroaryl, heterocycloalkyl, amino, alkylamino, dialkylamino, or heterocycloalkyl;

or $R^{k1}$ and $R^{k2}$ together with the N atom to which they are attached form a 5- or 6-membered heterocarbocyclyl group;

each $R^f$ and $R^L$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, or heterocycloalkylalkyl;

each $R^g$ and $R^m$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino;

each $R^h$ and $R^n$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, or heterocycloalkylalkyl, wherein said $R^h$ or $R^n$ is optionally substituted by one or more halo, hydroxy, carboxy, carboxy alkyl ester, carboxy aryl ester, amino, alkylamino, dialkylamino, or heterocycloalkyl;

each $R^i$ and $R^j$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, CO-alkyl, CO-aryl, CO-cycloalkyl, CO-heterocycloalkyl, CO-aryl, CO-heteroaryl, CO-amino, CO-alkylamino, CO-dialkylamino, COO-alkyl, COO-aryl, COO-cycloalkyl, COO-heterocycloalkyl, COO-aryl, or COO-heteroaryl, or $R^i$ and $R^j$ together with the N atom to which they are attached form a heterocycloalkyl group;

each $R^o$ and $R^p$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, CO-alkyl, CO-aryl, CO-cycloalkyl, CO-heterocycloalkyl, CO-aryl, CO-heteroaryl, CO-amino, CO-alkylamino, CO-dialkylamino, COO-alkyl, COO-aryl, COO-cycloalkyl, COO-heterocycloalkyl, COO-aryl, COO-heteroaryl, or —$(CH_2)_n$—$(J^1)_m$—$K^1$, or $R^o$ and $R^p$ together with the N atom to which they are attached form a heterocycloalkyl group;

$Cy^1$, $Cy^2$, $Cy^3$ and $Cy^4$ are each, independently, carbocyclyl, heterocarbocyclyl, carbocyclylalkyl or heterocarbocyclylalkyl, each optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $SOR^{b6}$, $SO_2R^{b6}$, $NR^{b4}COR^{b6}$, $NR^{b4}SO_2R^{b6}$, $COOR^{b3}$ or $COR^{b6}$;

$R^q$ is OH, alkoxy, carboxy, alkoxycarbonyl, aryloxycarbonyl, carbocyclyl, heterocarbocyclyl, amino, alkylamino, dialkylamino, or $PO(OR^{Ph})_2$, wherein $R^{Ph}$ is H or $C_1$–$C_4$ alkyl;

$R^r$ and $R^s$ are each, independently, H, $C_1$–$C_4$ alkyl, carbocyclyl, alkylcarbonyl, arylcarbonyl or aralkyl carbonyl, or $R^r$ and $R^s$ together with the N atom to which they are attached form a 5- or 6-membered heterocycloalkyl group;

$L^1$ is O, S, $NR^{b1}$, SO, $SO_2$, $NR^{b1}CO$, $N(R^{b1})CON(R^{b1})$, $N(R^{b1})SO$, $N(R^{b1})SO_2$, CO or COO;

$J^1$ is O, S, $NR^{b2}$, SO, $SO_2$, $NR^{b2}CO$, $N(R^{b2})CON(R^{b2})$, $N(R^{b2})SO$, $N(R^{b2})SO_2$, CO or COO;

$K^1$ is $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylakyl, wherein said $K^1$ is optionally substituted by one or more halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, $COO(C_1$–$C_4$ alkyl), $NH_2$, $NH(C_1$–$C_4$ alkyl), or $N(C_1$–$C_4$ alkyl)$_2$, $CONH_2$, $CONH(C_1$–$C_4$ alkyl), or $CON(C_1$–$C_4$ alkyl)$_2$;

$M^1$ is $NR^{v1}$, O, S, or $CR^{v2}R^{v3}$;

$R^{b1}$ and $R^{b2}$ are each, independently, H, $C_1$–$C_6$ alkyl, $C_1$–$C_6$ haloalkyl or $C_3$–$C_7$ cycloalkyl;

$R^{b3}$ is H, $C_1$–$C_6$ alkyl, $C_1$–$C_6$ haloalkyl, aryl or $C_3$–$C_7$ cycloalkyl;

$R^{b4}$ and $R^{b5}$ are each, independently, H, $C_1$–$C_6$ alkyl, $C_1$–$C_6$ haloalkyl or $C_3$–$C_7$ cycloalkyl, or $R^{b4}$ and $R^{b5}$ together with the N atom to which they are attached form a 5- or 6-membered heterocycloalkyl ring;

$R^{b6}$ is H, $C_1$–$C_6$ alkyl, aryl, heteroaryl, $C_3$–$C_7$ cycloalkyl or heterocycloalkyl;

each $R^I$, $R^{II}$, $R^{III}$, $R^{IV}$, $R^V$, $R^{VI}$, $R^{VII}$, and $R^{VIII}$ is, independently, H, $C_1$–$C_6$ alkyl, $C_1$–$C_6$ haloalkyl, aryl or $C_3$–$C_7$ cycloalkyl;

$R^t$ and $R^u$ are each, independently, H, $C_1$–$C_{10}$ alkyl, $C_2$–$C_{10}$ alkenyl, $C_2$–$C_{10}$ alkynyl, carbocyclyl, heterocarbocyclyl, carbocyclylalkyl, heterocarbocyclylalkyl, carbocyclylalkenyl, or heterocarbocyclylalkenyl, each optionally substituted by one or more halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, $COO(C_1$–$C_4$ alkyl), COH, $CO(C_1$–$C_4$ alkyl), $NH_2$, $NH(C_1$–$C_4$ alkyl), $N(C_1$–$C_4$ alkyl)$_2$, $NHCONH_2$, $CONH_2$, $CONH(C_1$–$C_4$ alkyl), $CON(C_1$–$C_4$ alkyl)$_2$, —$L^3$—$W^4$ or —$L^3$—$Cy^4$;

or $R^t$ and $R^u$ together with the carbon atoms to which they are attached form a 4–14 membered carbocyclyl group or a 4–14 membered heterocarbocyclyl group, each optionally substituted by 1, 2, 3 or 4 substituents selected from halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, $COO(C_1$–$C_4$ alkyl), COH, $CO(C_1$–$C_4$ alkyl), $NH_2$, $NH(C_1$–$C_4$ alkyl), $N(C_1$–$C_4$ alkyl)$_2$, $NHCONH_2$, $CONH_2$, $CONH(C_1$–$C_4$ alkyl), $CON(C_1$–$C_4$ alkyl)$_2$, —$L^3$—$W^4$ or —$L^3$—$Cy^4$;

or $R^t$ and $R^u$ together with the carbon atoms to which they are attached form the divalent group —$P^1$=$P^2$—$P^3$=$P^4$—;

$R^{t1}$, $R^{t2}$, $R^{u1}$, and $R^{u2}$ are each, independently, H, $C_1$–$C_{10}$ alkyl, $C_2$–$C_{10}$ alkenyl, $C_2$–$C^{10}$ alkynyl, carbocyclyl, heterocarbocyclyl, carbocyclylalkyl, or heterocarbocyclylalkyl, each optionally substituted by one or more halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, $COO(C_1$–$C_4$ alkyl), COH, $CO(C_1$–$C_4$ alkyl), $NH_2$, $NH(C_1$–$C_4$ alkyl), $N(C_1$–$C_4$ alkyl)$_2$, $NHCONH_2$, $CONH_2$, $CONH(C_1$–$C_4$ alkyl), $CON(C_1$–$C_4$ alkyl)$_2$, —$L^3$—$W^4$ or —$L^3$—$Cy^4$;

or $R^{t1}$ and $R^{u1}$ together with the carbon atoms to which they are attached form a 4–14 membered cycloalkyl group or a 4–14 membered heterocycloalkyl group, each optionally substituted by 1, 2, 3 or 4 substituents selected from halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, $COO(C_1$–$C_4$ alkyl), COH, $CO(C_1$–$C_4$ alkyl), $NH_2$, $NH(C_1$–$C_4$ alkyl), $N(C_1$–$C_4$ alkyl)$_2$, $NHCONH_2$, $CONH_2$, $CONH(C_1$–$C_4$ alkyl), CON$(C_1$–$C_4$ alkyl)$_2$, —$L^3$—$W^4$ or —$L^3$—$Cy^4$;

or $R^{t1}$ and $R^{t2}$ together with the carbon atom to which they are attached form a 4–14 membered cycloalkyl group or a 4–14 membered heterocycloalkyl group, each optionally substituted by 1, 2, 3 or 4 substituents selected from halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, $COO(C_1$–$C_4$ alkyl), COH, $CO(C_1$–$C_4$ alkyl), $NH_2$, $NH(C_1$–$C_4$ alkyl), $N(C_1$–$C_4$ alkyl)$_2$, $NHCONH_2$, $CONH_2$, $CONH(C_1$–$C_4$ alkyl), $CON(C_1$–$C_4$ alkyl)$_2$, —$L^3$—$W^4$ or —$L^3$—$Cy^4$;

or $R^{u1}$ and $R^{u2}$ together with the carbon atom to which they are attached form a 4–14 membered cycloalkyl group or a 4–14 membered heterocycloalkyl group, each optionally substituted by 1, 2, 3 or 4 substituents selected from halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, $COO(C_1$–$C_4$ alkyl), COH, $CO(C_1$–$C_4$ alkyl), $NH_2$, $NH(C_1$–$C_4$ alkyl), $N(C_1$–$C_4$ alkyl)$_2$, $NHCONH_2$, $CONH_2$, $CONH(C_1$–$C_4$ alkyl), CON$(C_1$–$C_4$ alkyl)$_2$, —$L^3$—$W^4$ or —$L^3$—$Cy^4$;

$L^3$ is $(CR^{a8}R^{a9})_{p4}$, $(CR^{a8}R^{a9})_{p4}O(CR^{a8}R^{a9})_{p5}$, $(CR^{a8}R^{a9})_{p4}S(CR^{a8}R^{a9})_{p5}$, $(CR^{a8}R^{a9})_{p4}NR^{a10}(CR^{a8}R^{a9})_{p5}$, $(CR^{a8}R^{a9})_{p4}CONR^{a10}(CR^{a8}R^{a9})_{p5}$, $(CR^{a8}R^{a9})_{p4}SONR^{a10}(CR^{a8}R^{a9})_{p5}$, $(CR^{a8}R^{a9})_{p4}SO_2NR^{a10}(CR^{a8}R^{a9})_{p5}$, $(CR^{a8}R^{a9})_4CO(CR^{a8}R^{a9})_{p5}$, $(CR^{a8}R^{a9})_{p4}COO(CR^{a8}R^{a9})_{p5}$, $(CR^{a8}R^{a9})_{p4}NR^{a10}CONR^{a10}(CR^{a8}R^{a9})_{p5}$, $(CR^{a8}R^{a9})_{p4}NR^{a10}C(=NR^{a10})NR^{a10}(CR^{a8}R^{a9})_{p5}$, or $(CR^{a8}R^{a9})_{p4}OCO(CR^{a8}R^{a9})_{p5}$;

$R^{a8}$ and $R^{a9}$ are each, independently, H, halo, $C_1$–$C_4$ alkyl, $C_2$–$C_4$ alkenyl, $C_2$–$C_4$ alkynyl or $C_1$–$C_4$ haloalkyl;

$R^{a10}$ is H, $C_1$–$C_4$ alkyl, $C_1$–$C_4$ haloalkyl, aryl, or $C_3$–$C_7$ cycloalkyl;

$W^4$ is $C_1$–$C_8$ alkyl, $C_2$–$C_8$ alkenyl, $C_2$–$C_8$ alkynyl carbocyclyl or heterocarbocyclyl, each optionally substituted by 1, 2 or 3 halo, $C_1$–$C_6$ haloalkyl, $C_3$–$C_7$ cycloalkyl, aryl, heterocycloalkyl, heteroaryl, CN, $SOR^{b6}$, $SO_2R^{b6}$, $ORb3$, $SR^{b3}$, $NR^{b4}R^{b5}$, $SONR^{b4}R^{b5}$, $SO_2NR^{b4}R^{b5}$, $CONR_{b4}R^{b5}$, $COOR^{b3}$ or $COR^{b6}$;

$P^1$, $P^2$, $P^3$, and $P^4$ are each, independently, N or $CR^{v4}$;

$R^{v1}$ is H or $C_1$–$C_4$ alkyl;

$R^{v2}$ and $R^{13}$ are each, independently, H, $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylakyl, each optionally substituted by one or more halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, COO($C_1$–$C_4$ alkyl), $NH_2$, NH($C_1$–$C_4$ alkyl), or N($C_1$–$C_4$ alkyl)$_2$;

$R^{v4}$ is H, halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, COO($C_1$–$C_4$ alkyl), $NH_2$, NH($C_1$–$C_4$ alkyl), or N($C_1$–$C_4$ alkyl)$_2$;

or two $R^{v4}$, each on adjacent carbon atoms, together with the carbon atoms to which they are attached form a fused 3–14 membered carbocyclyl group or fused 3–14 membered heterocarbocyclyl group, each optionally substituted by 1, 2, or 3 halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, COO($C_1$–$C_4$ alkyl), $NH_2$, NH($C_1$–$C_4$ alkyl), or N($C_1$–$C_4$ alkyl)$_2$;

$R^y$ is H or $C_1$–$C_4$ alkyl;

$R^{z1}$ and $R^{z2}$ are each, independently, H, $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylakyl, each optionally substituted by one or more halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, COO($C_1$–$C_4$ alkyl), $NH_2$, NH($C_1$–$C_4$ alkyl), or N($C_1$–$C_4$ alkyl)$_2$;

$G^1$ is H, $C_1$–$C_6$ alkyl, $C_1$–$C_6$ haloalkyl, or $C_3$–$C_7$ cycloalkyl;

$G^2$ is H, $C_1$–$C_6$ alkyl, $C_1$–$C_6$ haloalkyl, or $C_3$–$C_7$ cycloalkyl;

or $G^6$ and $G^2$ together form O or S;

each AA1 and AA2 is, independently, an amino acid residue;

a dashed line indicates an optional bond;

k is 1, 2, 3, 4, 5 or 6;

n is 1 to 12;

m is 0 or 1;

each s, t, and u is, independently, 0 or 1;

p is 0, 1, 2, 3, 4, 5 or 6;

q is 0 or 1;

each v and w is, independently, 0, 1, 2, 3, 4, or 5;

x is 0, 1, 2, 3, or 4;

xx is 1, 2 or 3;

y is 0, 1, 2, 3, 4, or 5; and z is 0, 1, 2, 3, 4, or 5.

In some embodiments, at least one of said first and second molecular scaffolds has the Formula S1:

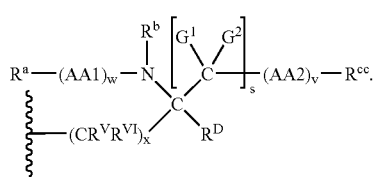

S1

In some embodiments, at least one of said first and second molecular scaffolds has the Formula S2:

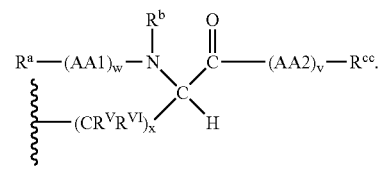

S2

In some embodiments, at least one of said first and second molecular scaffolds has the Formula S3:

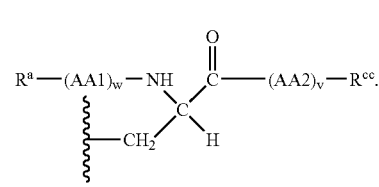

S3

In some embodiments, at least one of said first and second molecular scaffolds has the Formula S4:

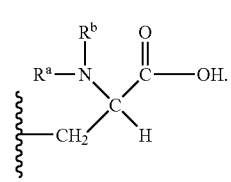

S4

In some embodiments, at least one of said first and second molecular scaffolds has the Formula S5:

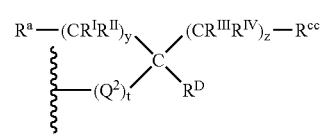

S5

In some embodiments, at least one of said first and second molecular scaffolds has the Formula S6a or S6b:

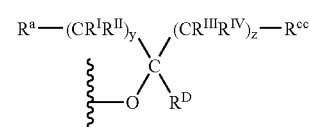

S6a

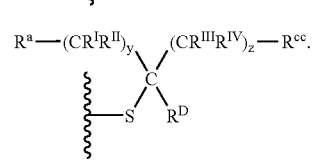

S6b

In some embodiments, at least one of said first and second molecular scaffolds has the Formula S7:

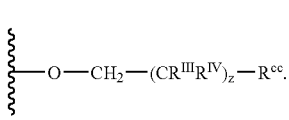

S7

In some embodiments, at least one of said first and second molecular scaffolds has the Formula S8:

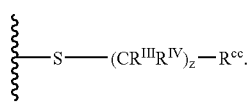

S8

In some embodiments, at least one of said first and second molecular scaffolds has the Formula S9:

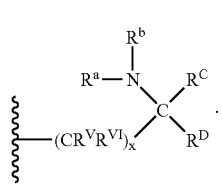

S9

In some embodiments, $R^b$ is substituted or unsubstituted heteroaryl in the scaffold of Formula S9.

In some embodiments, $R^b$ is substituted or unsubstituted benzothiazoloyl in the scaffold of Formula S9.

In some embodiments, at least one of said first and second molecular scaffolds has the Formula S10a or S10b:

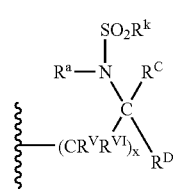

S10a

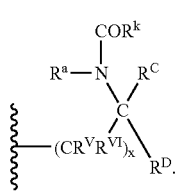

S10b

In some embodiments, at least one of said first and second molecular scaffolds has the Formulas S11a and S11b:

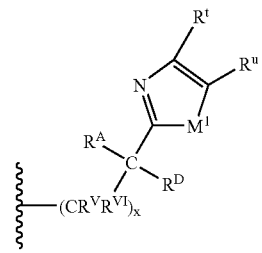

S11a

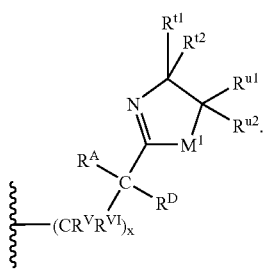

S11b

In some embodiments, at least one of said first and second molecular scaffolds has the Formulas S12a and S12b:

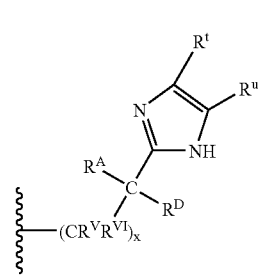

S12a

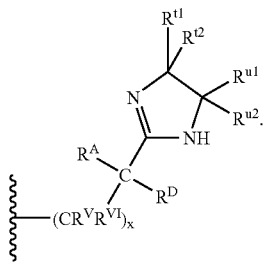

S12b

In some embodiments, at least one of said first and second molecular scaffolds has the Formula S13:

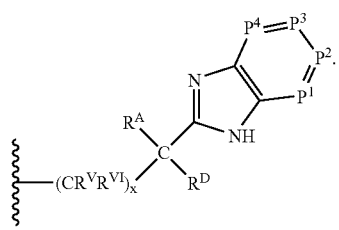

S13

In some embodiments, at least one of said first and second molecular scaffolds has the Formula S14a or S14b:

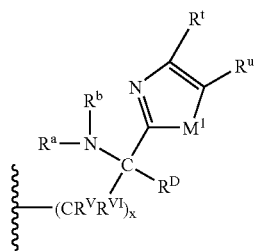
S14a

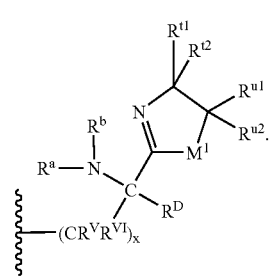
S14b

In some embodiments, $R^b$ is substituted or unsubstituted heteroaryl in the scaffold of Formula S14a or S14b.

In some embodiments, $R^b$ is substituted or unsubstituted benzothiazolyl in the scaffold of Formula S14a or S14b.

In some embodiments, at least one of said first and second molecular scaffolds has the Formulas S15a and S15b:

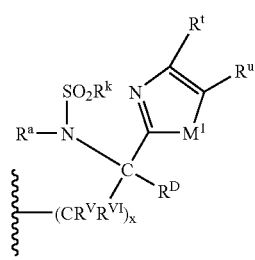
S15a

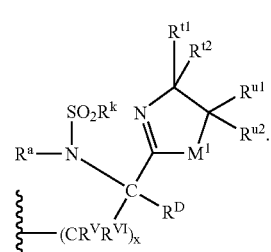
S15b

In some embodiments, at least one of said first and second molecular scaffolds has the Formulas S15c and S15d:

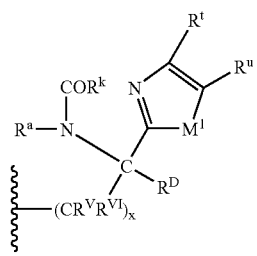
S15c

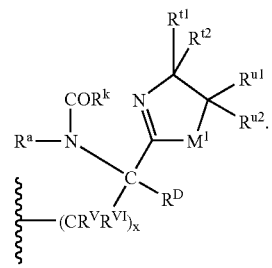
S15d

In some embodiments, at least one of said first and second molecular scaffolds has the Formulas S16a and S16b:

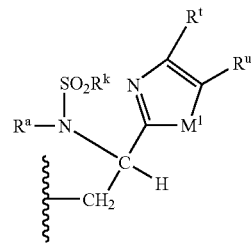
S16a

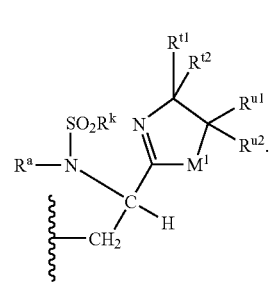
S16b

In some embodiments, at least one of said first and second molecular scaffolds has the Formula S17:

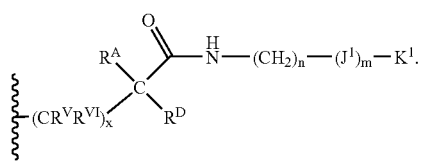
S17

In some embodiments, at least one of said first and second molecular scaffolds has the Formula S18:

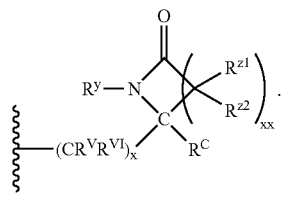

S18

In some embodiments, at least one of said first and second molecular scaffolds has the Formula S19:

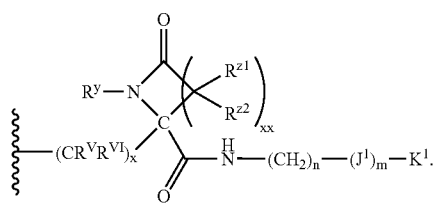

S19

In some embodiments, at least one of said first and second molecular scaffolds has the Formula S20:

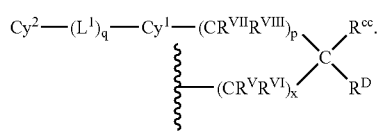

S20

In some embodiments, at least one of said first and second molecular scaffolds has the Formula S21:

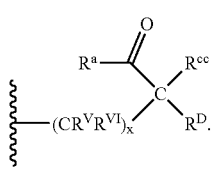

S21

In some embodiments, at least one of said first and second molecular scaffolds has the Formula S22:

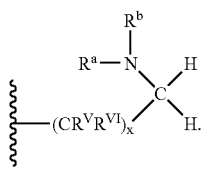

S22

In some embodiments, at least one of said first and second molecular scaffolds has the Formula S23:

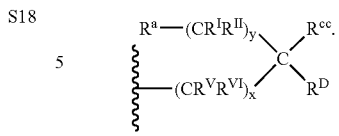

S23

In some embodiments, $R_{cc}$ is optionally substituted aryl or biaryl, $R^a$ is optionally substituted aryl, heteroaryl, cycloalkyl, or heterocycloalkyl, and y is 1 or 2, in the scaffold of Formula S23. In further embodiments, $R^D$ is H in the scaffold of Formula S23.

In some embodiments, at least one of said first and second molecular scaffolds has the Formula S24a: $—(CR^VR^{VI})_x—CH_2—Q^1—R^a$.

In some embodiments, at least one of said first and second molecular scaffolds has the Formula S24b: $—(CR^VR^{VI})_x—CH_2—Q^1—(CR^{VII}R^{VIII})_p—Cy^1—(L^1)_q—Cy^2$.

In some embodiments, at least one of said first and second molecular scaffolds has the Formula S24c: $—(CR^VR^{VI})_x—CH_2—O—(CR^{VII}R^{VIII})_p—Cy^1—(L^1)_q—Cy^2$.

In some embodiments, at least one of said first and second molecular scaffolds has the Formula S24d: $—(CR^VR^{VI})_x—CH_2—S—(CR^{VII}R^{VIII})_p—Cy^1—(L^1)_q—Cy^2$.

In some embodiments, at least one of said first and second molecular scaffolds has the Formula S25: $—CH_2—Q^1—CH_2—Cy^1—(L^1)_q—Cy^2$.

In some embodiments, at least one of said first and second molecular scaffolds has the Formula S26: $—CH_2—Q^1—CH_2Cy^1—Cy^2$.

In some embodiments, at least one of said first and second molecular scaffolds has the Formula S27: $—CH_2—Q^1—(CH_2)_p—Cy^1—Cy^2$.

In some embodiments, $Sc^1$ has formula S, S1, S2, S3, S4, S5, S6a, S6b, S7, S8, S9, S10, S11a, S11b, S12a, S12b, S13, S14a, S14b, S15a, S15b, S16a, S16b, S17, S18, S19, S20, S21, S22, S23, S24a, S24b, S24c, S24d, S25, S26, or S27 and $Sc^2$ is absent.

In some embodiments, $Sc^2$ has formula S, S1, S2, S3, S4, S5, S6a, S6b, S7, S8, S9, S10, S11a, S11b, S12a, S12b, S13, S14a, S14b, S15a, S15b, S16a, S16b, S17, S18, S19, S20, S21, S22, S23, S24a, S24b, S24c, S24d, S25, S26, or S27 and $Sc^1$ is absent.

In some embodiments, x is 1.
In some embodiments, xx is 1 or 2.
In some embodiments, xx is 2.
In some embodiments, each v and w is, independently, 0, 1, 2, 3, 4, or 5.
In some embodiments, v is 0.
In some embodiments, w is 0.
In some embodiments, $R^V$ and $R^{VI}$ are both H.
In some embodiments, $R^{cc}$ is H, $C_1$–$C_{10}$ alkyl, $OR^n$, or $NR^oR^p$, wherein $R^{cc}$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$, cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, or carboxy.

In some embodiments, $R^{cc}$ is aryl, heteroaryl, heterocycloalkyl, aralkyl, heteroarylalkyl, cycloalkylalkyl, heterocycloalkylalkyl, biaryl, biheteroaryl, arylheteroaryl, or heteroarylaryl, wherein $R^{cc}$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, or carboxy.

In some embodiments, $R^{cc}$ is aryl or heteroaryl, each optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, or carboxy.

In some embodiments, $R^{cc}$ is aryl or heteroaryl.

In some embodiments, $R^{cc}$ is $NR^oR^p$.

In some embodiments, $R^{cc}$ is a moiety of Formula:

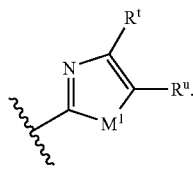

In some embodiments, $R^{cc}$ is a moiety of Formula:

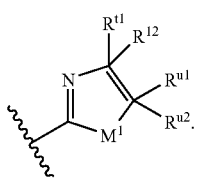

In some embodiments, $R^a$ is aryl or heteroaryl, each optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, $NR^rR^s$, carboxy, carboxy alkyl ester, carboxy aryl ester, —$(CH_2)_k$—$R^q$, $SOR^m$, or $SO_2R^m$.

In some embodiments, $R^1$ is aryl or heteroaryl.

In some embodiments, $R^a$ is $SO_2R^k$.

In some embodiments, $R^a$ is —$(CR^{VII}R^{VIII})_p$—$Cy^1$—$(L^1)_q$—$Cy^2$.

In some embodiments, $R^k$ is $C_1$–$C_6$ alkyl, $C_3$–$C_{14}$ cycloalkyl, aryl, heteroaryl, heterocycloalkyl, aralkyl, heteroarylalkyl, cycloalkylalkyl, heterocycloalkylalkyl, each optionally substituted by one or more halo, $C_1$–$C_4$ alkyl, $C_1$–$C_4$ haloalkyl, cyano, nitro, COOH, carboxy alkyl ester, carboxy aryl ester, OH, SH, alkoxy, thioalkoxy, haloalkoxy, amino, alkylamino, dialkylamino, $Cy^3$, —$OCy^3$, or —$SCy^3$.

In some embodiments, $R^k$ is aryl, heteroaryl, aralkyl, or heteroarylalkyl, each optionally substituted by one or more halo, $C_1$–$C_4$ alkyl, $C_1$–$C_4$ haloalkyl, cyano, nitro, COOH, carboxy alkyl ester, carboxy aryl ester, OH, SH, alkoxy, thioalkoxy, haloalkoxy, amino, alkylamino, dialkylamino, $Cy^3$, —$OCy^3$, or —$SCy^3$.

In some embodiments, $R^m$ is $C_1$–$C_6$ alkyl, aryl, heteroaryl, heterocycloalkyl, aralkyl, heteroarylalkyl, cycloalkylalkyl, or heterocycloalkylalkyl.

In some embodiments, $R^m$ is aryl.

In some embodiments, $R^a$ and $R^b$ are each H.

In some embodiments, $Q^1$ is $NR^b$.

In some embodiments, $R^D$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, or heterocycloalkylalkyl.

In some embodiments, $R^D$ is H.

In some embodiments, $R^A$ and $R^D$ together form the divalent moiety —$NR^y$—CO—$(CR^{z1}R^{z2})_{xx}$—.

In some embodiments, y is 0.

In some embodiments, $R^a$ is H.

In some embodiments, $R^D$ is H, $R^a$ is H, and y is 0.

In some embodiments, $Q^2$ is O.

In some embodiments, $M^1$ is $NR^{v1}$.

In some embodiments, $M^1$ is NH.

In some embodiments, $R^t$ and $R^u$ together with the carbon atoms to which they are attached form the divalent group —$P^1$=$P^2$—$P^3$=$P^4$—.

In some embodiments, $P^1$, $P^2$, $P^3$, and $P^4$ are each, $CR^{V4}$.

In some embodiments, —$P^1$=$P^2$—$P^3$=$P^4$— is selected from —$CR^{V4}$=$CR^{V4}$—$CR^{V4}$=N—, —$CR^{V4}$=$CR^{V4}$—N=$CR^{V4}$—, —N=$CR^{V4}$—N=$CR^{V4}$— or —N=$CR^{V4}$—$CR^{V4}$=N—.

In some embodiments, $R^t$ and $R^u$ are each, independently, H, $C_1$–$C_{10}$ alkyl, aryl arylalkyl, heteroaryl, heteroarylalkyl, each optionally substituted by one or more halo, $C_1$–$C_4$ alkyl, $C_1$–$C_4$ haloalkyl, $Cy^4$, —$OCy^4$, —$SCy^4$, CN, $NO_2$, OH, $C_1$–$C_4$ alkoxy, $C_1$–$C_4$ haloalkoxy, COOH, COO($C_1$–$C_4$ alkyl), COH, CO($C_1$–$C_4$ alkyl), $NH_2$, NH($C_1$–$C_4$ alkyl), N($C_1$–$C_4$ alkyl)$_2$, $NHCONH_2$, $CONH_2$, CONH($C_1$–$C_4$ alkyl), or CON($C_1$–$C_4$ alkyl)$_2$.

In some embodiments, $R^{t1}$, $R^{t2}$, $R^{u1}$, and $R^{u2}$ are each, independently, H, $C_1$–$C_{10}$ alkyl, aryl, arylalkyl, heteroaryl, or heteroarylalkyl, each optionally substituted by one or more halo, $C_1$–$C_4$ alkyl, $C_1$–$C_4$ haloalkyl, $Cy^4$, —$OCy^4$, —$SCy^4$, CN, $NO_2$, OH, $C_1$–$C_4$ alkoxy, $C_1$–$C_4$ haloalkoxy, COOH, COO($C_1$–$C_4$ alkyl), COH, CO($C_1$–$C_4$ alkyl), $NH_2$, NH($C_1$–$C_4$ alkyl), N($C_1$–$C_4$ alkyl)$_2$, $NHCONH_2$, $CONH_2$, CONH($C_1$–$C_4$ alkyl), or CON($C_1$–$C_4$ alkyl)$_2$.

In some embodiments, $R^y$ is H.

In some embodiments, $R^{z1}$ is H.

In some embodiments, $R^{z2}$ is H.

In some embodiments, $Cy^1$ is aryl or heteroaryl each optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

In further embodiments, $Cy^1$ is phenyl optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

In further embodiments, $Cy^2$ is aryl or heteroaryl each optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

In further embodiments, $Cy^2$ is phenyl optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

The present invention further provides compounds wherein $Sc^1$ and $Sc^2$ together form a 5-, 6-, or 7-membered fused carbocyclic ring or a 5-, 6-, or 7-membered fused heterocarbocyclic ring, each optionally substituted by one or more —$(CH_2)_{p1}$—$J^2$—$K^2$; wherein:

$J^2$ is $(CR^{a1}R^{a2})_{p2}$, $(CR^{a1}R^{a2})_{p2}O(CR^{a1}R^{a2})_{p3}$, $(CR^{a1}R^{a2})_{p2}S(CR^{a1}R^{a2})_{p3}$, $(CR^{a1}R^{a2})_{p2}NR^{a3}(CR^{a1}R^{a2})_{p3}$, $(CR^{a1}R^{a2})_{p2}CONR^{a3}(CR^{a1}R^{a2})_{p3}$, $(CR^{a1}R^{a2})_{p2}SONR^{a3}(CR^{a1}R^{a2})_{p3}$, $(CR^{a1}R^{a2})_{p2}SO_2NR^{a3}(CR^{a1}R^{a2})_{p3}$, $(CR^{a1}R^{a2})_{p2}CO(CR^{a1}R^{a2})_{p3}$, $(CR^{a1}R^{a2})_{p2}COO(CR^{a1}R^{a2})_{p3}$, $(CR^{a1}R^{a2})_{p2}NR^{a3}CONR^{a3}CONR^{a3}(CR^{a1}R^{a2})_{p3}$, $(CR^{a1}R^{a2})_{p2}NR^{a3}C(=NR^{a3})NR^{a3}(CR^{a1}R^{a2})_{p3}$, $(CR^{a1}R^{a2})_{p2}OCO(CR^{a1}R^{a2})_{p3}$, or absent;

$K^2$ is H, halo, $C_1-C_8$ alkyl, aryl, heteroaryl, $C_3-C_7$ cycloalkyl, heterocycloalkyl, wherein said $C_1-C_8$ alkyl, aryl, heteroaryl, $C_3-C_7$ cycloalkyl or heterocycloalkyl is optionally substituted by one or more halo, $C_2-C_6$ alkenyl, $C_2-C_6$ alkynyl, $C_1-C_6$ haloalkyl, $C_3-C_7$ cycloalkyl, aryl, heterocycloalkyl, heteroaryl, cyano, nitro, $OR^{a4}$, $SR^{a4}$, $NR^{a5}SR^{a6}$, $SONR^{a5}R^{a6}$, $SO_2NR^{a5}R^{a6}$, $CONR^{a5}R^{a6}$, $COOR^{a4}$ or $COR^{a7}$;

$R^{a1}$ and $R^{a2}$ are each, independently, H, halo, $C_1-C_4$ alkyl, $C_2-C_4$ alkenyl, $C_2-C_4$ alkynyl or $C_1-C_4$ haloalkyl;

$R^{a3}$ is H, $C_1-C_4$ alkyl, $C_1-C_4$ haloalkyl, aryl, or $C_3-C_7$ cycloalkyl;

$R^{a4}$ is H, $C_1-C_6$ alkyl, $C_1-C_6$ haloalkyl, aryl or $C_3-C_7$ cycloalkyl;

$R^{a5}$ and $R^{a6}$ are each, independently, H, $C_1-C_6$ alkyl, $C_1-C_6$ haloalkyl or $C_3-C_7$ cycloalkyl, or $R^{a5}$ and $R^{a6}$ together with the N atom to which they are attached form a 5- or 6-membered heterocycloalkyl ring;

$R^{a7}$ is H, $C_1-C_6$ alkyl, aryl, heteroaryl, $C_3-C_7$ cycloalkyl or heterocycloalkyl;

p1 is 0, 1, or 2;
p2 is 0, 1, or 2; and
p3 is 0, 1, or 2.

In some embodiments, $Sc^1$ and $Sc^2$ together form a 6-membered fused heterocarbocyclic ring optionally substituted by one or more $-(CH_2)_{p1}-J^2-K^2$.

In some embodiments, $Sc^1$ and $Sc^2$ together form a 6-membered fused heterocycloalkyl ring optionally substituted by one or more $-(CH_2)_{p1}-J^2-K^2$.

In some embodiments, $Sc^1$ and $Sc^2$ together form a 6-membered fused heterocycloalkyl ring containing at least one nitrogen atom ring member, said heterocycloalkyl ring optionally substituted by one or more $-(CH_2)_{p1}-J^2-K^2$.

In some embodiments, $Sc^1$ and $Sc^2$ together form $-CH_2-CH_2-NH-CH_2-$ optionally substituted by one or more $-(CH_2)_{p1}-J^2-K^2$.

In some embodiments, $Sc^1$ and $Sc^2$ together form $-CH_2-CH_2-NH-CH_2-$ substituted by at least $-(CH_2)_{p1}-J^2-K^2$.

In some embodiments, $Sc^1$ and $Sc^2$ together form $-CH_2-CH_2-N\{(CH_2)_{p1}-J^2-K^2\}-CH\{(CH_2)_{p1}-J^2-K^2\}$.

In some embodiments, p1 is 0.

In some embodiments, at least one $J^2$ is $(CR^{a1}R^{a2})_{p2}CONR^{a3}(CR^{a1}R^{a2})_{p3}$.

In some embodiments, at least one $J^2$ is $(CH)_2CONR^{a3}$.

In some embodiments, wherein at least one $K^2$ is phenyl optionally substituted by one or more halo, $C_2-C_6$ alkenyl, $C_2-C_6$ alkynyl, $C_1-C_6$ haloalkyl, $C_3-C_7$ cycloalkyl, aryl, heterocycloalkyl, heteroaryl, cyano, nitro, $OR^{a4}$, $SR^{a4}$, $NR^{a5}R^{a6}$, $SONR^{a5}R^{a6}$, $SO_2NR^{a5}R^{a6}$, $CONR^{a5}R^{a6}$, $COOR^{a4}$ or $COR^{a7}$.

In some embodiments, wherein at least one $K^2$ is heteroaryl optionally substituted by one or more halo, $C_2-C_6$ alkenyl, $C_2-C_6$ alkynyl, $C_1-C_6$ haloalkyl, $C_3-C_7$ cycloalkyl, aryl, heterocycloalkyl, heteroaryl, cyano, nitro, $OR^{a4}$, $SR^{a4}$, $NR^{a5}R^{a6}$, $SONR^{a5}R^{a6}$, $SO_2NR^{a5}R^{a6}$, $CONR^{a5}R^{a6}$, $COOR^{a4}$ or $COR^{a7}$.

The present invention further provides compounds wherein one of said first and second molecular scaffolds is absent and the other is a 3- to 7-membered carbocyclic or 3- to 7-membered heterocarbocyclic group optionally substituted by one or more halo, $C_1-C_{10}$ alkyl, $C_2-C_{10}$ alkenyl, $C_2-C_{10}$ alkenyl, $C_1-C_{10}$ haloalkyl, cyano, nitro, carbocyclyl, heterocarbocyclyl, carbocyclylalkyl, heterocarbocyclylalkyl, hydroxy, alkoxy, haloalkoxy, aryloxy, amino, alkylamino, dialkylamino, carboxy, carboxy alkylester, or carboxy aryl ester.

The present invention further provides a compound of Formula IIa or IIb:

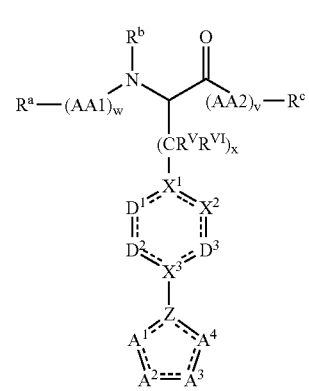

IIa

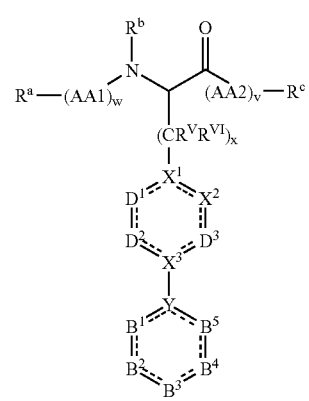

IIb or pharmaceutically acceptable salt or prodrug thereof, or pharmaceutically acceptable salt or prodrug thereof, wherein:

a dashed line indicates an optional bond;

$R^a$ is H, $C_1-C_{10}$ alkyl, $C_1-C_{10}$ haloalkyl, $C_3-C_7$ cycloalkyl, $C_2-C_{10}$ alkenyl, $C_2-C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, $COR^k$, $OCOR^k$, $CONR^{k1}R^{k2}$, $COOR^L$, $SOR^m$, or $SO_2R^m$, wherein $R^a$ is optionally substituted by one or more halo, $C_1-C_6$ alkyl, $C_1-C_6$ haloalkyl, $C_2-C_6$ alkenyl, $C_2-C_6$ alkynyl, $C_3-C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, $NR^rR^s$, carboxy, carboxy alkyl ester, carboxy aryl ester, $-(CH_2)_k-R^q$, $SOR^m$, or $SO_2R^m$;

$R^b$ is H, $C_1-C_{10}$ alkyl, $C_1-C_{10}$ haloalkyl, $C_3-C_7$ cycloalkyl, $C_2-C_{10}$ alkenyl, $C_2-C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, $COR^k$, $OCOR^k$, $COOR^L$, SOR$^m$, or SO$_2$R$^m$, wherein R$^b$ is optionally substituted by one or more halo, C$_1$–C$_6$ alkyl, C$_1$–C$_6$ haloalkyl, C$_2$–C$_6$ alkenyl, C$_2$–C$_6$ alkynyl, C$_3$–C$_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

or R$^a$ and R$^b$ together with the N atom to which they are attached form a 5- or 6-membered heterocycloalkyl ring when w is 0, wherein said 5- or 6-membered heterocycloalkyl ring is optionally substituted by one or more halo, C$_1$–C$_6$ alkyl, C$_1$–C$_6$ haloalkyl, C$_2$–C$_6$ alkenyl, C$_2$–C$_6$ alkynyl, C$_3$–C$_7$ cycloalkyl, aryl, heterocycloalkyl, heteroaryl, aralkyl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

R$^{cc}$ is H, C$_1$–C$_{10}$ alkyl, C$_1$–C$_{10}$ haloalkyl, C$_3$–C$_7$ cycloalkyl, C$_2$–C$_{10}$ alkenyl, C$_2$–C$_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, OR$^n$, SR$^n$, or NR$^o$R$^p$, wherein R$^{cc}$ is optionally substituted by one or more halo, C$_1$–C$_6$ alkyl, C$_1$–C$_6$ haloalkyl, C$_2$–C$_6$ alkenyl, C$_2$–C$_6$ alkynyl, C$_3$–C$_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, or carboxy;

each R$^k$ is, independently, H, C$_1$–C$_6$ alkyl, C$_1$–C$_6$ haloalkyl, C$_3$–C$_7$ cycloalkyl, C$_2$–C$_6$ alkenyl, C$_2$–C$_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein R$^k$ is optionally substituted by one or more halo, C$_1$–C$_4$ alkyl, C$_1$–C$_4$ haloalkyl, C$_3$–C$_6$ cycloalkyl, cyano, nitro, COOH, carboxy alkyl ester, carboxy aryl ester, OH, SH, alkoxy, thioalkoxy, aryloxy, thioaryloxy, aryl, heteroaryl, heterocycloalkyl, amino, alkylamino or dialkylamino;

R$^{k1}$ and R$^{k2}$ are each, independently, H, C$_1$–C$_6$ alkyl, C$_1$–C$_6$ haloalkyl, C$_3$–C$_7$ cycloalkyl, C$_2$–C$_6$ alkenyl, C$_2$–C$_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein R$^{k1}$ and R$^{k2}$ are optionally substituted by one or more halo, C$_1$–C$_4$ alkyl, C$_1$–C$_4$ haloalkyl, C$_3$–C$_6$ cycloalkyl, cyano, nitro, COOH, carboxy alkyl ester, carboxy aryl ester, OH, SH, alkoxy, thioalkoxy, aryloxy, thioaryloxy, aryl, heteroaryl, heterocycloalkyl, amino, alkylamino or dialkylamino;

or R$^{k1}$ and R$^{k2}$ together with the N atom to which they are attached form a 5- or 6-membered heterocarbocyclyl group;

each R$^L$ is, independently, H, C$_1$–C$_6$ alkyl, C$_1$–C$_6$ haloalkyl, C$_3$–C$_7$ cycloalkyl, C$_2$–C$_6$ alkenyl, C$_2$–C$_6$ alkynyl, aryl, heteroaryl, heterocycloalkyl, aralkyl, heteroarylalkyl, cycloalkylalkyl, or heterocycloalkylalkyl;

each R$^m$ is, independently, H, C$_1$–C$_6$ alkyl, C$_1$–C$_6$ haloalkyl, C$_3$–C$_7$ cycloalkyl, C$_2$–C$_6$ alkenyl, C$_2$–C$_6$ alkynyl, aryl, heteroaryl, heterocycloalkyl, aralkyl, heteroarylalkyl, cycloalkylalkyl, heterocycloalkylalkyl, amino, alkylamino, or dialkylamino;

each R$^n$ is, independently, H, C$_1$–C$_6$ alkyl, C$_1$–C$_6$ haloalkyl, C$_3$–C$_7$ cycloalkyl, C$_2$–C$_6$ alkenyl, C$_2$–C$_6$ alkynyl, aryl, heteroaryl, heterocycloalkyl, aralkyl, heteroarylalkyl, cycloalkylalkyl, or heterocycloalkylalkyl, wherein said R$^n$ is optionally substituted by one or more halo, hydroxy, carboxy, carboxy alkyl ester, carboxy aryl ester, amino, alkylamino, or dialkylamino;

each R$^o$ and R$^p$ is, independently, H, C$_1$–C$_6$ alkyl, C$_1$–C$_6$ haloalkyl, C$_3$–C$_7$ cycloalkyl, C$_2$–C$_6$ alkenyl, C$_2$–C$_6$ alkynyl, aryl, heteroaryl, heterocycloalkyl, aralkyl, heteroarylalkyl, cycloalkylalkyl, heterocycloalkylalkyl, CO-alkyl, CO-aryl, CO-cycloalkyl, CO-heterocycloalkyl, CO-aryl, CO-heteroaryl, CO-amino, CO-alkylamino, CO-dialkylamino, COO-alkyl, COO-aryl, COO-cycloalkyl, COO-heterocycloalkyl, COO-aryl, COO-heteroaryl or —(CH$_2$)$_n$—(J$^j$)$_m$—K$^l$, or R$^o$ and R$^p$ together with the N atom to which they are attached form a heterocycloalkyl group;

R$^q$ is OH, alkoxy, carboxy, alkoxycarbonyl, aryloxycarbonyl, amino, alkylamino or dialkylamino;

R$^r$ and R$^s$ are each, independently, H, C$_1$–C$_4$ alkyl, carbocyclyl, alkylcarbonyl, arylcarbonyl or aralkyl carbonyl, or R$^r$ and R$^s$ together with the N atom to which they are attached form a 5- or 6-membered heterocycloalkyl group;

J$^j$ is O, S, NH, N(C$_1$–C$_4$ alkyl), SO, SO$_2$, NHCO, N(C$_1$–C$_4$ alkyl)CO, N(C$_1$–C$_4$ alkyl)CONH, N(C$_1$–C$_4$ alkyl)CON(C$_1$–C$_4$ alkyl), NHCONH, NHSO, N(C$_1$–C$_4$ alkyl)SO, NHSO$_2$, N(C$_1$–C$_4$ alkyl)SO$_2$, CO, or COO;

K$^1$ is C$_1$–C$_{10}$ alkyl, C$_2$–C$_{10}$ alkenyl, C$_2$–C$_{10}$ alkynyl, carbocyclyl, heterocarbocyclyl, carbocyclylalkyl, or heterocarbocyclylalkyl, wherein said K$^1$ is optionally substituted by one or more halo, C$_1$–C$_4$ alkyl, C$_1$–C$_4$ haloalkyl, CN, NO$_2$, OH, C$_1$–C$_4$ alkoxy, C$_1$–C$_4$ haloalkoxy, COOH, COO(C$_1$–C$_4$ alkyl), NH$_2$, NH(C$_1$–C$_4$ alkyl), or N(C$_1$–C$_4$ alkyl)$_2$;

each R$^V$ and R$^{VI}$ is, independently, H, C$_1$–C$_6$ alkyl, C$_1$–C$_6$ haloalkyl, or C$_3$–C$_7$ cycloalkyl;

each AA1 and AA2 is, independently, an amino acid residue;

k is 1, 2, 3, 4, 5 or 6;

m is 0 or 1;

n is 1 to 12;

v and w are each, independently, 0, 1, 2, 3, 4, or 5;

x is 0, 1, 2, 3, or 4;

X$^1$ is C or N;

X$^2$ is CR$^1$, N, NR$^2$, CO, CS, SO, or SO$_2$;

X$^3$ is C or N;

each D$^1$, D$^2$, and D$^3$ is, independently, CR$^1$, N, NR$^2$, CO, CS, SO, or SO$_2$, wherein the ring formed by X$^1$, X$^2$, X$^3$, D$^1$, D$^2$, and D$^3$ is an aromatic ring;

each R$^1$ is, independently, H, halo, C$_1$–C$_4$ alkyl, C$_3$–C$_6$ cycloalkyl, haloalkyl, OR$^5$, SR$^5$, NO$_5$, NO$_2$, CN, SOR$^6$, SO$_2$R$^6$, COR$^7$, COOR$^8$, NR$^9$R$^{10}$, a 5- or 6-membered heterocarbocyclyl group, or tetrazolyl;

each R$^2$ is, independently, H, C$_1$–C$_4$ alkyl, C$_1$–C$_4$ haloalkyl, C$_3$–C$_6$ cycloalkyl, SOR$^6$, SO$_2$R$^6$, COR$^7$, or COOR$^8$;

or i) R$^1$ and R$^1$, ii) R$^2$ and R$^2$, or iii) R$^1$ and R$^2$, together with the atoms to which they are attached, form a fused 5- or 6-membered carbocycyl or heterocarbocyclyl group, provided said i) R$^1$ and R$^1$, ii) R$^2$ and R$^2$, or iii) R$^1$ and R$^2$ are attached to adjacent atoms;

each R$^5$ is, independently, H, C$_1$–C$_4$ alkyl, C$_2$–C$_4$ alkenyl, C$_2$–C$_4$ alkynyl, C$_3$–C$_6$ cycloalkyl, or C$_1$–C$_4$ haloalkyl;

each R$^6$ is, independently, H, C$_1$–C$_4$ alkyl, C$_3$–C$_6$ cycloalkyl, C$_1$–C$_4$ haloalkyl, N(R$^{6a}$)$_2$, or 5- or 6-membered heterocycloalkyl;

each R$^{6a}$ is, independently, H, C$_1$–C$_4$ alkyl, C$_3$–C$_6$ cycloalkyl, C$_4$–C$_{10}$ cycloalkylalkyl, aryl each R$^7$ is, independently, H, C$_3$C$_6$ cycloalkyl, C$_1$–C$_4$ alkyl, N(R$^{7a}$)$_2$, or 5- or 6-membered heterocycloalkyl;

each R$^{7a}$ is, independently, H, C$_1$–C$_4$ alkyl, C$_3$–C$_6$ cycloalkyl, C$_4$–C$_{10}$ cycloalkylalkyl, aryl, or aralkyl;

each R$^8$ is, independently, H, C$_1$–C$_4$ alkyl, C$_3$–C$_6$ cycloalkyl, or C$_1$–C$_4$ haloalkyl;

each $R^9$ and $R^{10}$ is, independently, H, $C_1$–$C_4$ alkyl, $C_3$–$C_6$ cycloalkyl, $C_1$–$C_4$ haloalkyl, $SO_2R^{11}$, $COR^{12}$, $COOR^{13}$, or $R^9$ and $R^{10}$ together with the N atom to which they are attached form a 5- or 6-membered heterocycloalkyl group;

$R^{11}$ is H, $C_1$–$C_4$ alkyl, $C_3$–$C_6$ cycloalkyl, $C_1$–$C_4$ haloalkyl, $N(C_1$–$C_4$ alkyl$)_2$, $NH(C_1$–$C_4$ alkyl), $NH_2$, or 5- or 6-membered heterocycloalkyl;

$R^{12}$ is H, $C_3$–$C_6$ cycloalkyl, $C_1$–$C_4$ alkyl, $N(C_1$–$C_4$ alkyl$)_2$, $NH(C_1$–$C_4$ alkyl), $NH_2$, or 5- 6-membered heterocycloalkyl;

$R^{13}$ is H, $C_1$–$C_4$ alkyl, $C_3$–$C_6$ cycloalkyl, or $C_1$–$C_4$ haloalkyl;

Y is C, $CR^Y$, or N;

Z is C, $CR^Z$, or N;

each $R^Y$ and $R^Z$ is, independently, H, halo, $C_1$–$C_4$ alkyl, $C_3$–$C_6$ cycloalkyl, haloalkyl, $OR^{28}$, $SR^{28}$, $NO_2$, CN, $SOR^{29}$, $SO_2R^{29}$, $COR^{30}$, $COOR^{31}$, $NR^{32}R^{33}$, a 5- or 6-membered heterocarbocyclyl group, or tetrazolyl;

each $R^{28}$ is, independently, H, $C_1$–$C_4$ alkyl, $C_2$–$C_4$ alkenyl, $C_2$–$C_4$ alkynyl, $C_3$–$C_6$ cycloalkyl, or haloalkyl;

each $R^{29}$ is, independently, H, $C_1$–$C_4$ alkyl, $C_3$–$C_6$ cycloalkyl, haloalkyl, $N(C_1$–$C_4$ alkyl$)_2$, $NH(C_1$–$C_4$ alkyl), or $NH_2$;

each $R^{30}$ is, independently, H, $C_3$–$C_6$ cycloalkyl, $C_1$–$C_4$ alkyl, $N(C_1$–$C_4$ alkyl$)_2$, $NH(C_1$–$C_4$ alkyl), $NH_2$, or 5- or 6-membered heterocarbocyclyl;

each $R^{31}$ is, independently, H, $C_1$–$C_4$ alkyl, $C_3$–$C_6$ cycloalkyl, or haloalkyl;

each $R^{32}$ and $R^{33}$ is, independently, H, $C_1$–$C_4$ alkyl, $C_3$–$C_6$ cycloalkyl, haloalkyl, $SO_3H$, $SO_2(C_1$–$C_4$ alkyl), $SO_2(C_1$–$C_4$ haloalkyl), $SO_2(C_3$–$C_6$ cycloalkyl), CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), or $R^{32}$ and $R^{33}$ together with the N atom to which they are attached form a 5- or 6-membered heterocycloalkyl group;

each $A^1$, $A^2$, $A 3$, and $A^4$ is selected according to one of the following four options:

1) each $A^1$, $A^2$, and $A^3$, is, independently, O, N, $NR^{14}$, $CR^{15}$, $CR^{16}R^{17}$, CO, CS, S, SO, $SO_2$, $PR^{18}$, $PO(OR^{19})$, or $—C=NR^{20}$; and $A^4$ is S, SO, $SO_2$, or $PO(OR^{19})$; or 2) each $A^1$ and $A^2$ is, independently, O, N, $NR^{14}$, $CR^{15}$, $CR^{16}R^{17}$, CO, CS, S, SO, $SO_2$, $PR^{18}$, $PO(OR^{19})$, or $—C=NR^{20}$; $A^3$ is S, SO, or $SO_2$; and $A^4$ is N or $NR^{14}$; or 3) each $A^1$ and $A^4$ is, independently, O, N, $NR^{14}$, $CR^{15}$, $CR^{16}R^{17}$, CO, CS, S, SO, $SO_2$, $PR^{18}$, $PO(OR^{19})$, or $—C=NR^{20}$; $A^2$ is N or $NR^{14}$; and $A^3$ is S, SO, or $SO_2$; or 4) each $A^1$ and $A^4$ is, independently, O, N, $NR^{14}$, $CR^{15}$, $CR^{16}R^{17}$, CO, CS, S, SO, $SO_2$, $PR^{18}$, $PO(OR^{19})$, or $—C=NR^{20}$; $A^2$ is CO or CS; and $A^3$ is N or $NR^{14}$;

each $B^1$, $B^2$, $B^3$, $B^4$, and $B^5$ is selected according to one of the following three options:

1) each $B^1$, $B^2$, and $B^4$ is, independently, O, N, $NR^{21}$, $CR^{22}$, $CR^{23}R^{24}$, CO, CS, S, SO, $SO_2$, $PR^{25}$, $PO(OR^{26})$, $—C=NR^{27}$; and each $B^3$ and $B^5$ is, independently, N or $NR^{21}$;

2) each $B^1$ and $B^5$ is, independently, O, N, $NR^{21}$, $CR^{22}$, $CR^{23}R^{24}$ CO, CS, S, SO, $SO_2$, $PR^{25}$, $PO(OR^{26})$, $—C=NR^{27}$; each $B^2$ and $B^4$ is, independently, N or $NR^{21}$; and $B^3$ is S, SO, or $SO_2$; or 3) each $B^1$, $B^2$, and $B^3$ is, independently, O, N, $NR^{21}$, $CR^{22}$, $CR^{23}R^{24}$, CO, CS, S, SO, $SO_2$, $PR^{25}$, $PO(OR^{26})$, $—C=NR^{27}$; $B^4$ is N or $NR^{21}$; and $B^5$ is S, SO, or $SO_2$;

each $R^{14}$ and $R^{21}$ is, independently, H, Na, K, $C_1$–$C_4$ alkyl, $C_1$–$C_4$ haloalkyl, $C_3$–$C_6$ cycloalkyl, CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl$)_2$, $CONH(C_3$–$C_6$ cycloalkyl), $CON(C_3$–$C_6$ cycloalkyl$)_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl), $SO_2(C_3$–$C_6$ cycloalkyl), $SO_2NH_2$, $NH_2$, $NH(C_1$–$C_4$ alkyl), $N(C_1$–$C_4$ alkyl$)_2$, $NH(C_3$–$C_6$ cycloalkyl), or $N(C_3$–$C_6$ cycloalkyl$)_2$;

each $R^{15}$ and $R^{22}$ is, independently, H, halo, $C_1$–$C_4$ alkyl, $C_3$–$C_c$ cycloalkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl), $SO(C_3$–$C_6$ cycloalkyl), $SO_2NH_2$, CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl$)_2$, $CONH(C_3$–$C_6$ cycloalkyl), $CON(C_3$–$C_6$ cycloalkyl$)_2$, $NH_2$, $NH(C_1$–$C_4$ alkyl$)_2$, $NH(C_3$–$C_6$ cycloalkyl), or $N(C_3$–$C_6$ cycloalkyl$)_2$;

each $R^{16}$, $R^{17}$, $R^{23}$, and $R^{24}$ is, independently, H, halo, $C_1$–$C_4$ alkyl, $C_3$–$C_6$ cycloalkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl), $SO_2(C_3$–$C^6$ cycloalkyl), $SO_2NH_2$, CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl$)_2$, $CONH(C_3$–$C_6$ cycloalkyl), $CON(C_3$–$C_6$ cycloalkyl$)_2$, $NH_2$, $NH(C_1$–$C_4$ alkyl), $N(C_1$–$C_4$ alkyl$)_2$, $NH(C_3$–$C_6$ cycloalkyl), or $N(C_3$–$C_6$ cycloalkyl$)_2$;

or $R^{16}$ and $R^{17}$ together with the carbon atom to which they are attached form a $C_3$–$C_6$ cycloalkyl group;

or $R^{23}$ and $R^{24}$ together with the carbon atom to which they are attached form a $C_3$–$C_6$ cycloalkyl group;

each $R^{18}$ and $R^{25}$ is, independently, $C_1$–$C_4$ alkyl;

each $R^{19}$ and $R^{26}$ is, independently, H or $C_1$–$C_4$ alkyl; and each $R^{20}$ and $R^{27}$ is, independently, H, OH, CN, $C_1$–$C_4$ alkyl, $C_1$–$C_4$ alkoxy, aryloxy, or $C_3$–$C_6$ cycloalkyloxy.

In some embodiments for compounds of IIa and IIb, when Z is N, at least one of $A^1$, $A^2$, $A^3$, and $A^4$ is N or $NR^{14}$.

In some embodiments for compounds of IIa and IIb, the ring formed by Z, $A^4$, $A^3$, $A^2$, and $A^1$ is other than a heterocyclic ring wherein Z is N, $A^4$ is $SO_2$, $A^3$ is $NR^{14}$, $A^2$ is CO or CS, and $A^1$ is $CR^{16}R^{17}$.

The present invention further provides a compound of Formula III:

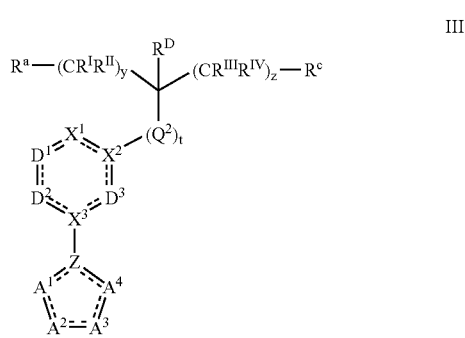

or pharmaceutically acceptable salt or prodrug thereof, wherein:

a dashed line indicates an optional bond;

$R^D$ is H, halo, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, $COR^e$, $OCOR^e$, $COOR^f$, $SOR^g$, $SO_2R^g$, $OR^h$, $SR^h$, or $NR^iR^j$, wherein $R^D$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

$Q^2$ is O, S, CO, COO, $CONR^d$, $NR^dCONR^d$, SO, $SO_2$, $SONR^d$, $SO_2NR^d$, or $NR^d$;

$R^a$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, $COR^k$, $OCOR^k$, $CONR^{k1}R^{k2}$, $COOR^L$, $SOR^m$, or $SO_2R^m$, wherein $R^a$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, $NR^rR^s$, carboxy, carboxy alkyl ester, carboxy aryl ester, —$(CH_2)_k$—$R^q$, $SOR^m$, or $SO_2R^m$;

$R^{cc}$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, $OR^n$, $SR^n$, or $NR^oR^p$, wherein $R^{cc}$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, or carboxy;

$R^d$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, wherein $R^d$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, aralkyloxy, cycloalkyloxy, mercapto, thioalkoxy, thioaryloxy, cyano, nitro, amino, alkylamino, dialkylamino, carboxy, carboxy alkyl ester, or carboxy aryl ester;

each $R^e$ and $R^k$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein $R^e$ and $R^k$ is optionally substituted by one or more halo, $C_1$–$C_4$ alkyl, $C_1$–$C_4$ haloalkyl, $C_3$–$C_6$ cycloalkyl, cyano, nitro, COOH, carboxy alkyl ester, carboxy aryl ester, OH, SH, alkoxy, thioalkoxy, aryloxy, thioaryloxy, aryl, heteroaryl, heterocycloalkyl, amino, alkylamino or dialkylamino;

$R^{k1}$ and $R^{k2}$ are each, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein $R^{k1}$ and $R^{k2}$ are optionally substituted by one or more halo, $C_1$–$C_4$ alkyl, $C_1$–$C_4$ haloalkyl, $C_3$–$C_6$ cycloalkyl, cyano, nitro, COOH, carboxy alkyl ester, carboxy aryl ester, OH, SH, alkoxy, thioalkoxy, aryloxy, thioaryloxy, aryl, heteroaryl, heterocycloalkyl, amino, alkylamino or dialkylamino;

or $R^{k1}$ and $R^{k2}$ together with the N atom to which they are attached form a 5- or 6-membered heterocarbocyclyl group;

each $R^f$ and $R^L$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, or heterocycloalkylalkyl;

each $R^g$ and $R^m$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino;

each $R^h$ and $R^n$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, or heterocycloalkylalkyl, wherein said $R^h$ or $R^n$ is optionally substituted by one or more halo, hydroxy, carboxy, carboxy alkyl ester, carboxy aryl ester, amino, alkylamino or dialkylamino;

each $R^i$ and $R^j$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, CO-alkyl, CO-aryl, CO-cycloalkyl, CO-heterocycloalkyl, CO-aryl, CO-heteroaryl, CO-amino, CO-alkylamino, CO-dialkylamino, COO-alkyl, COO-aryl, COO-cycloalkyl, COO-heterocycloalkyl, COO-aryl, or COO-heteroaryl, or $R^i$ and $R^j$ together with the N atom to which they are attached form a heterocycloalkyl group;

each $R^o$ and $R^p$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, CO-alkyl, CO-aryl, CO-cycloalkyl, CO-heterocycloalkyl, CO-aryl, CO-heteroaryl, CO-amino, CO-alkylamino, CO-dialkylamino, COO-alkyl, COO-aryl, COO-cycloalkyl, COO-heterocycloalkyl, COO-aryl, COO-heteroaryl or —$(CH_2)_n$—$(J^1)_m$—$K^1$, or $R^o$ and $R^p$ together with the N atom to which they are attached form a heterocycloalkyl group;

$R^q$ is OH, alkoxy, carboxy, alkoxycarbonyl, aryloxycarbonyl, amino, alkylamino or dialkylamino;

$R^r$ and $R^s$ are each, independently, H, $C_1$–$C_4$ alkyl, carbocyclyl, alkylcarbonyl, arylcarbonyl or aralkyl carbonyl, or $R^r$ and $R^s$ together with the N atom to which they are attached form a 5- or 6-membered heterocycloalkyl group;

$J^1$ is O, S, NH, N($C_1$–$C_4$ alkyl), SO, $SO_2$, NHCO, N($C_1$–$C_4$ alkyl)CO, N($C_1$–$C_4$ alkyl)CONH N($C_1$–$C_4$ alkyl)CON ($C_1$–$C_4$ alkyl), NHCONH, NHSO, N($C_1$–$C_4$ alkyl)SO, $NHSO_2$, N($C_1$–$C_4$ alkyl)$SO_2$, CO, or COO;

$K^1$ is $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylakyl, wherein said $K^1$ is optionally substituted by one or more halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, COO($C^1$–$C_4$ alkyl), $NH_2$, NH($C_1$–$C_4$ alkyl), or N($C_1$–$C_4$ alkyl)$_2$;

each $R^I$, $R^{II}$, $R^{III}$, and $R^{IV}$ is, independently, H, $C_1$–$C_6$ alkyl, $C_1$–$C_6$ haloalkyl, or $C_3$–$C_7$ cycloalkyl;

k is 1, 2, 3, 4, 5 or 6;

m is 0 or 1;

n is 1 to 12;

t is 0 or 1;

y is 0, 1, 2, 3, 4, or 5;

z is 0, 1, 2, 3, 4, or 5;

$X^1$ is $CR^1$, N, $NR^2$, CO, CS, SO, or $SO_2$;

$X^2$ is C or N;

$X^3$ is C or N;

each $D^1$, $D^2$, and $D^3$ is, independently, $CR^1$, N, $NR^2$, CO, CS, SO, or $SO_2$, wherein the ring formed by $X^1$, $X^2$, $X^3$, $D^1$, $D^2$, and $D^3$ is an aromatic ring;

each $R^1$ is, independently, H, halo, $C_1$–$C_4$ alkyl, $C_3$–$C_6$ cycloalkyl, haloalkyl, $OR^5$, $SR^5$, $NO_2$, CN, $SOR^6$, $SO_2R^6$, $COR^7$, $COOR^8$, $NR^9R^{10}$, a 5- or 6-membered heterocarbocyclyl group, or tetrazolyl;

each $R^2$ is, independently, H, $C_1$–$C_4$ alkyl, $C_1$–$C_4$ haloalkyl, $C_3$–$C_6$ cycloalkyl, $SOR^6$, $SO_2R^6$, $COR^7$, or $COOR^8$;

or i) $R^1$ and $R^1$, ii) $R^2$ and $R^2$, or iii) $R^1$ and $R^2$, together with the atoms to which they are attached, form a fused 5- or 6-membered carbocycyl or heterocarbocyclyl group, provided said i) $R^1$ and $R^1$, ii) $R^2$ and $R^2$, or iii) $R^1$ and $R^2$ are attached to adjacent atoms;

each $R^5$ is, independently, H, $C_1$–$C_4$ alkyl, $C_2$–$C_4$ alkenyl, $C_2$–$C_4$ alkynyl, $C_3$–$C_6$ cycloalkyl, or $C_1$–$C_4$ haloalkyl;

each $R^6$ is, independently, H, $C_1$–$C_4$ alkyl, $C_3$–$C_6$ cycloalkyl, $C_1$–$C_4$ haloalkyl, $N(R^{6a})_2$, or 5- or 6-membered heterocycloalkyl;

each $R^{6a}$ is, independently, H, $C_1$–$C_4$ alkyl, $C_3$–$C_6$ cycloalkyl, $C_4$–$C_{10}$ cycloalkylalkyl, aryl, or aralkyl;

each $R^7$ is, independently, H, $C_3$–$C_6$ cycloalkyl, $C_1$–$C_4$ alkyl, $N(R^{7a})_2$, or 5- or 6-membered heterocycloalkyl;

each $R^{7a}$ is, independently, H, $C_1$–$C_4$ alkyl, $C_3$–$C_6$ cycloalkyl, $C_4$–$C_{10}$ cycloalkylalkyl, aryl, or aralkyl;

each $R^8$ is, independently, H, $C_1$–$C_4$ alkyl, $C_3$–$C_6$ cycloalkyl, or $C_1$–$C_4$ haloalkyl;

each $R^9$ and $R^{10}$ is, independently, H, $C_1$–$C_4$ alkyl, $C_3$–$C_6$ cycloalkyl, $C_1$–$C_4$ haloalkyl, $SO_2R^{11}$, $COR^{12}$, $COOR^{13}$, or $R^9$ and $R^{10}$ together with the N atom to which they are attached form a 5- or 6-membered heterocycloalkyl group;

$R^{11}$ is H, $C_1$–$C_4$ alkyl, $C_3$–$C_6$ cycloalkyl, $C_1$–$C_4$ haloalkyl, $N(C_1$–$C_4$ alkyl$)_2$, $NH(C_1$–$C_4$ alkyl), $NH_2$, or 5- or 6-membered heterocycloalkyl;

$R^{12}$ is H, $C_3$–$C_6$ cycloalkyl, $C_1$–$C_4$ alkyl, $N(C_1$–$C_4$ alkyl$)_2$, $NH(C_1$–$C_4$ alkyl), $NH_2$, or 5- or 6-membered heterocycloalkyl;

$R^{13}$ is H, $C_1$–$C_4$ alkyl, $C_3$–$C_6$ cycloalkyl, or $C_1$–$C_4$ haloalkyl;

Z is C, $CR^Z$, or N;

$R^Z$ is, independently, H, halo, $C_1$–$C_4$ alkyl, $C_3$–$C_6$ cycloalkyl, haloalkyl, $OR^{28}$, $SR^{28}$, $NO_2$, CN, $SOR^{29}$, $SO_2R^{29}$, $COR^{30}$, $COOR^{31}$, $NR^{32}R^{33}$, a 5- or 6-membered heterocarbocyclyl group, or tetrazolyl;

each $R^{28}$ is, independently, H, $C_1$–$C_4$ alkyl, $C_2$–$C_4$ alkenyl, $C_2$–$C_4$ alkynyl, $C_3$–$C_6$ cycloalkyl, or haloalkyl;

each $R^{29}$ is, independently, H, $C_1$–$C_4$ alkyl, $C_3$–$C_6$ cycloalkyl, haloalkyl, $N(C_1$–$C_4$ alkyl$)_2$, $NH(C_1$–$C_4$ alkyl), or $NH_2$;

each $R^{30}$ is, independently, H, $C_3$–$C_6$ cycloalkyl, $C_1$–$C_4$ alkyl, $N(C_1$–$C_4$ alkyl$)_2$, $NH(C_1$–$C_4$ alkyl), $NH_2$, or 5- or 6-membered heterocarbocyclyl;

each $R^{31}$ is, independently, H, $C_1$–$C_4$ alkyl, $C_3$–$C_6$ cycloalkyl, or haloalkyl;

each $R^{32}$ and $R^{33}$ is, independently, H, $C_1$–$C_4$ alkyl, $C_3$–$C_6$ cycloalkyl, haloalkyl, $SO_3H$, $SO_2(C_1$–$C_4$ alkyl), $SO_2(C_1$–$C_4$ haloalkyl), $SO_2(C_3$–$C_6$ cycloalkyl), CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), or $R^{32}$ and $R^{33}$ together with the N atom to which they are attached form a 5- or 6-membered heterocycloalkyl group;

each $A^1$, $A^2$, $A^3$, and $A^4$ is, independently, O, N, $NR^{14}$, $CR^{15}$, $CR^{16}R^{17}$, CO, CS, S, SO, $SO_2$, $PR^{18}$, $PO(OR^{19})$, or —C=$NR^{20}$;

each $R^{14}$ is, independently, H, Na, K, $C_1$–$C_4$ alkyl, $C_1$–$C_4$ haloalkyl, $C_3$–$C_6$ cycloalkyl, CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl$)_2$, $CONH(C_3$–$C_6$ cycloalkyl), $CON(C_3$–$C_6$ cycloalkyl$)_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl), $SO_2(C_3$–$C_6$ cycloalkyl), $SO_2NH_2$, $NH_2$, $NH(C_1$–$C_4$ alkyl), $N(C_1$–$C_4$ alkyl$)_2$, $NH(C_3$–$C_6$ cycloalkyl), or $N(C_3$–$C_6$ cycloalkyl$)_2$;

each $R^{15}$ is, independently, H, halo, $C_1$–$C_4$ alkyl, $C_3$–$C_c$ cycloalkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl), $SO_2(C_3$–$C_6$ cycloalkyl), $SO_2NH_2$, CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl$)_2$, $CONH(C_3$–$C_6$ cycloalkyl), $CON(C_3$–$C_6$ cycloalkyl$)_2$, $NH_2$, $NH(C_1$–$C_4$ alkyl), $N(C_1$–$C_4$ alkyl$)_2$, $NH(C_3$–$C_6$ cycloalkyl), or $N(C_3$–$C_6$ cycloalkyl$)_2$;

each $R^{16}$ and $R^{17}$ is, independently, H, halo, $C_1$–$C_4$ alkyl, $C_3$–$C_6$ cycloalkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl) $SO_2(C_3$–$C_6$ cycloalkyl), $SO_2NH_2$, CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl$)_2$, $CONH(C_3$–$C_6$ cycloalkyl), $CON(C_3$–$C_6$ cycloalkyl$)_2$, $NH_2$, $NH(C_1$–$C_4$ alkyl), $N(C_1$–$C_4$ alkyl$)_2$, $NH(C_3$–$C_6$ cycloalkyl), or $N(C_3$–$C_6$ cycloalkyl$)_2$;

or $R^{16}$ and $R^{17}$ together with the carbon atom to which they are attached form a $C_3$–$C_6$ cycloalkyl group;

each $R^{18}$ is, independently, $C_1$–$C_4$ alkyl;

each $R^{19}$ is, independently, H or $C_1$–$C_4$ alkyl; and each $R^{20}$ is, independently, H, OH, CN, $C_1$–$C_4$ alkyl, $C_1$–$C_4$ alkoxy, aryloxy, or $C_3$–$C_6$ cycloalkyloxy.

In some embodiments for compounds of III, when Z is N, at least one of $A^1$, $A^2$, $A^3$, and $A^4$ is N or $NR^{14}$.

In some embodiments for compounds of III, the ring formed by Z, $A^4$, $A^3$, $A^2$, and $A^1$ is other than a heterocyclic ring wherein Z is N, $A^4$ is $SO^2$, $A^3$ is $NR^{14}$, $A^2$ is CO or CS, and $A^1$ is $CR^{16}R^{17}$.

In some embodiments for compounds of III, wherein $Q^2$ is O.

In some embodiments for compounds of III, $R^D$ is H, $C_1$–$C_{10}$ alkyl, $C_1C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, or heterocyloalkylalkyl.

The invention further provides a compound of Formula IIIa or IIIb:

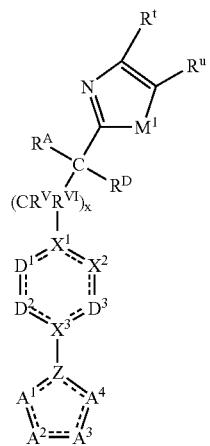

IIIa

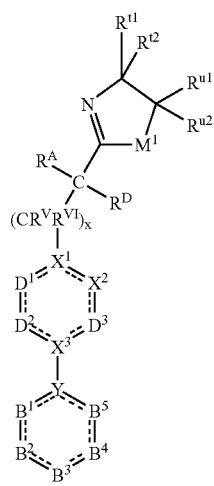

IIIb or pharmaceutically acceptable salt or prodrug thereof wherein constituent members are defined hereinabove.

The present invention further provides a compound of Formula IVa, IVb, IVc, or IVd:

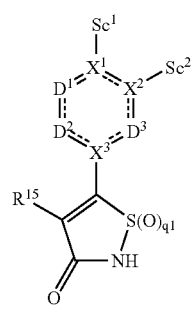

IVa

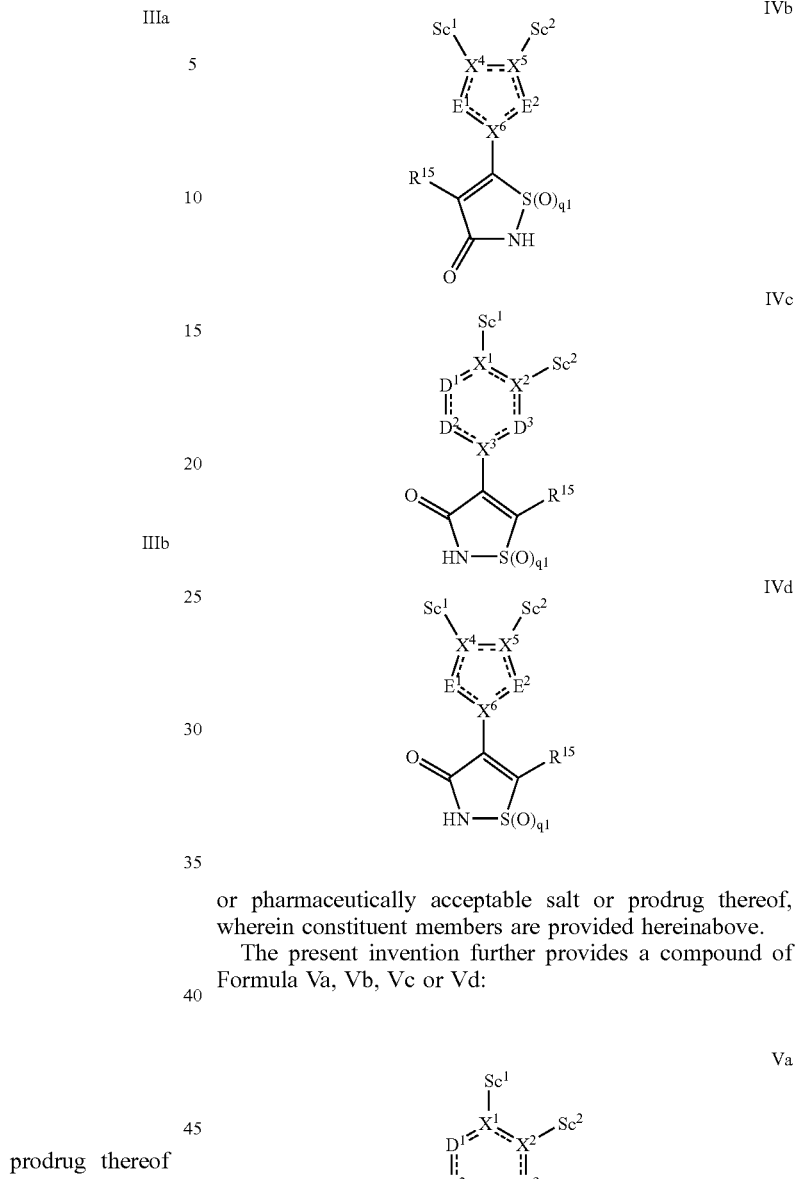

or pharmaceutically acceptable salt or prodrug thereof, wherein constituent members are provided hereinabove.

The present invention further provides a compound of Formula Va, Vb, Vc or Vd:

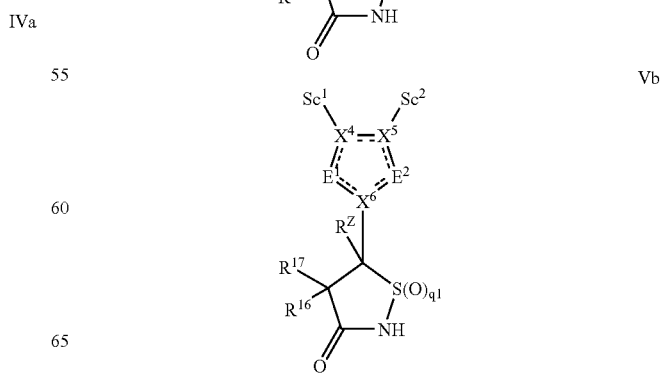

-continued

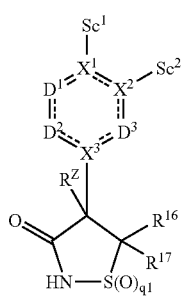
Vc

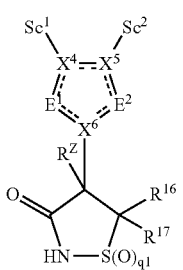
Vd or pharmaceutically acceptable salt or prodrug thereof, wherein constituent members are defined hereinabove.

The present invention further provides a compound of Formula VIa or VIb:

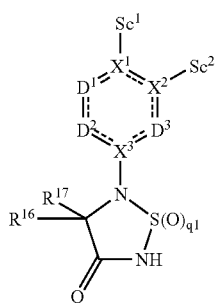
VIa

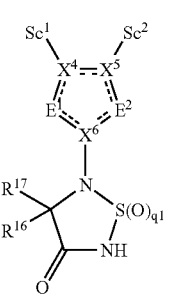
VIb or pharmaceutically acceptable salt or prodrug thereof, wherein constituent members are defined hereinabove.

The present invention further provides a compound of Formula VIIa, VIIb, VIIc, VIId or VIIe:

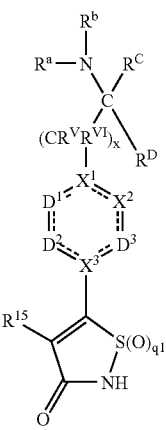
VIIa

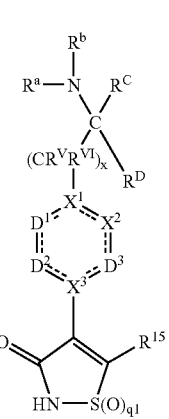
VIIb

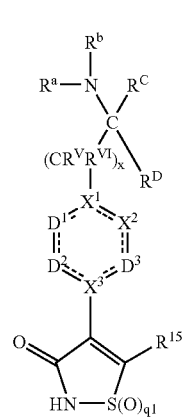
VIIc

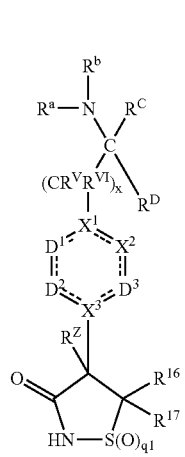

VIId

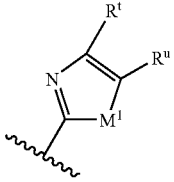 or 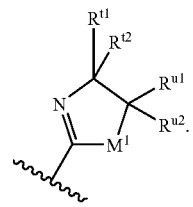

In some embodiments of Formulas VIIa, VIIb, VIIc, VIId and VIIe, $R^b$ is $SO_2R^k$ and $R^C$ is:

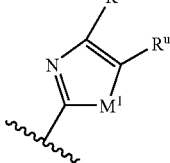 or 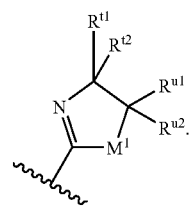

In some embodiments of Formulas VIIa, VIIb, VIIc, VIId and VIIe, $R^b$ is $COR^k$ and $R^C$ is:

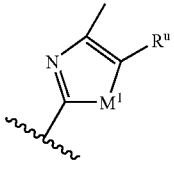 or 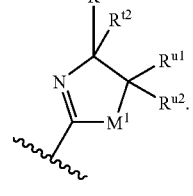

The present invention further provides a compound of Formula VIIIa, VIIIb, VIIIc, VIIId or VIIIe:

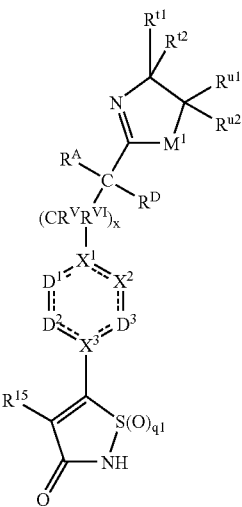

VIIIa

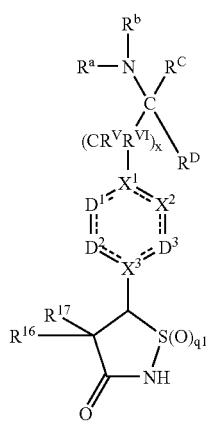

VIIe or pharmaceutically acceptable salt or prodrug thereof, wherein constituent members are defined hereinabove.

In some embodiments of Formulas VIIa, VIIb, VIIc, VIId and VIIe, $R^a$ is H.

In some embodiments of Formulas VIIa, VIIb, VIIc, VIId and VIIe, $R^b$ is $SO_2R^k$.

In some embodiments of Formulas VIIa, VIIb, VIIc, VIId and VIIe, $R^b$ is $COR^k$.

In some embodiments of Formulas VIIa, VIIb, VIIc, VIId and VIIe, $R^D$ is H.

In some embodiments of Formulas VIIa, VIIb, VIIc, VIId and VIIe, $R^C$ is $R^{cc}$.

In some embodiments of Formulas VIIa, VIIb, VIIc, VIId and VIIe, $R^C$ is or pharmaceutically acceptable salt or prodrug thereof, wherein constituent members are defined hereinabove.

In some embodiments of Formulas VIIIa, VIIIb, VIIIc, VIIId and VIIIe, $R^A$ is H.

In some embodiments of Formulas VIIIa, VIIIb, VIIIc, VIIId and VIIIe, $R^A$ is $NR^aR^b$.

In some embodiments of Formulas VIIIa, VIIIb, VIIIc, VIIId and VIIIe, $R^D$ is H.

In some embodiments of Formulas VIIIa, VIIIb, VIIIc, VIIId and VIIIe, $R^A$ is $NR^aR^b$ and $R^b$ is $SO_2R^k$.

In some embodiments of Formulas VIIIa, VIIIb, VIIIc, VIIId and VIIIe, $R^A$ is $NR^aR^b$ and $R^b$ is $COR^k$.

The present invention further provides a compound of Formula IXa, IXb, IXc, IXd or IXe:

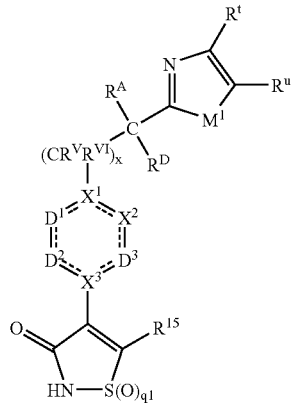

IXb

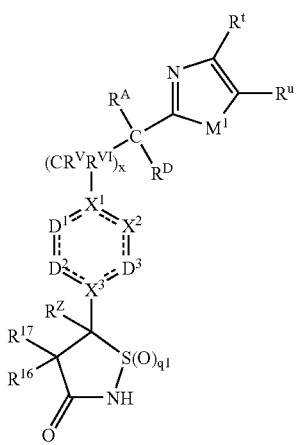

IXc

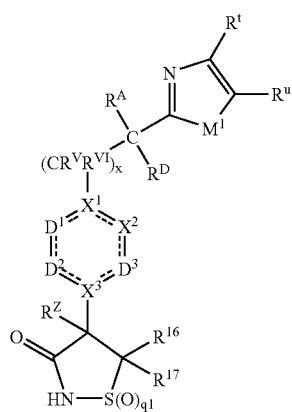

IXd

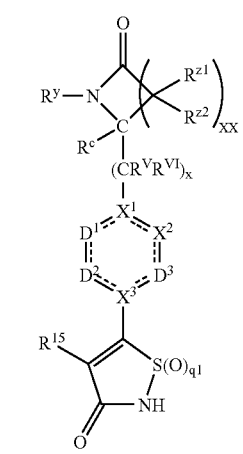

IXe or pharmaceutically acceptable salt or prodrug thereof, wherein constituent members are defined hereinabove.

In some embodiments of Formulas IXa, IXb, IXc, IXd and IXe, $R^A$ is H.

In some embodiments of Formulas IXa, IXb, IXc, IXd and IXe, $R^A$ is $NR^aR^b$.

In some embodiments of Formulas IXa, IXb, IXc, IXd and IXe, $R^A$ is $NR^aR^b$ and $R^b$ is $SO_2R^k$.

In some embodiments of Formulas IXa, IXb, IXc, IXd and IXe, $R^A$ is $NR^aR^b$ and $R^b$ is $COR^k$.

The present invention further provides a compound of Formula XIIa, XIIb, XIIc, XIId or XIIe:

XIIa

-continued
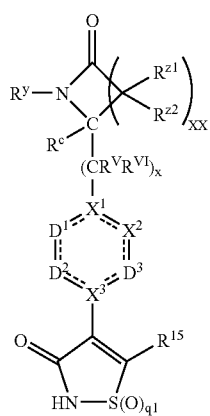
XIIb
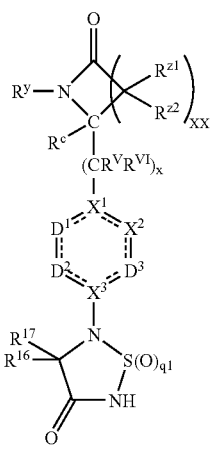
XIIe
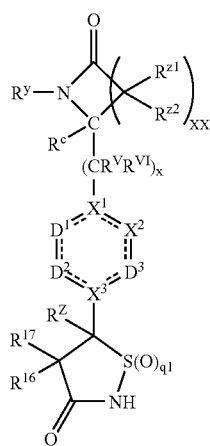
XIIc
or pharmaceutically acceptable salt or prodrug thereof, wherein constituent members are defined hereinabove.
The present invention further provides a compound of Formula XIIIa, XIIIb, XIIIc, XIIId or XIIIe:
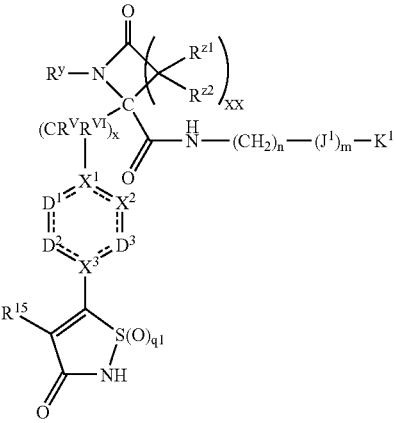
XIIIa
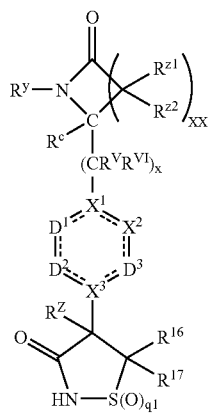
XIId
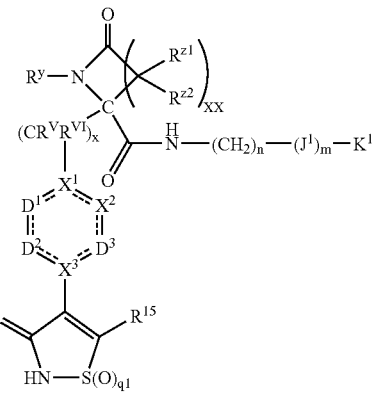
XIIIb -continued
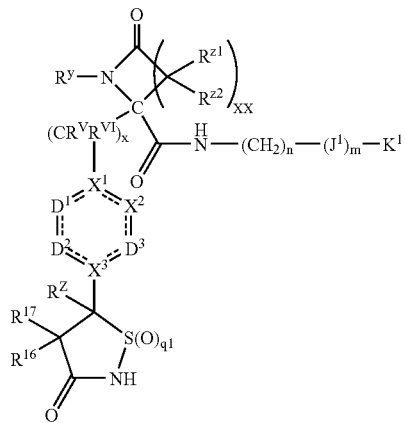
XIIIc
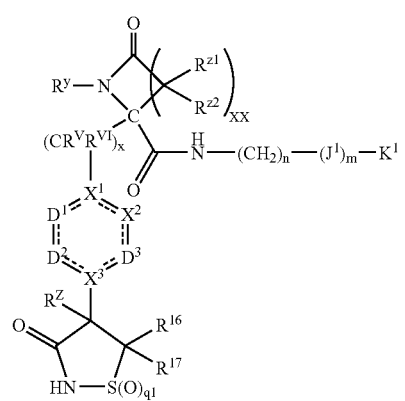
XIIId
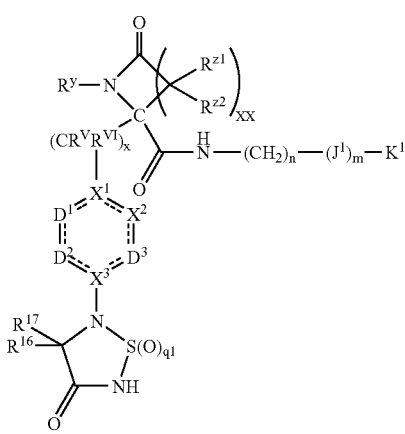
XIIIe
or pharmaceutically acceptable salt or prodrug thereof, wherein constituent members are defined hereinabove.
The present invention further provides a compound of Formula XIVa, XIVb, XIVc, XIVd or XIVe:
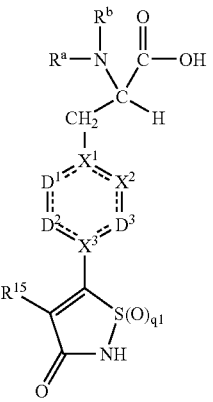
XIVa
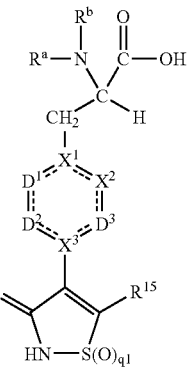
XIVb
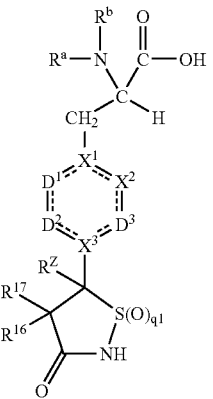
XIVc
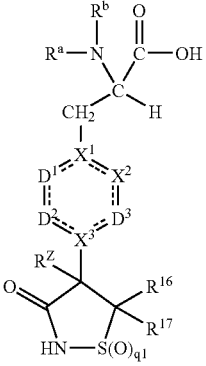
XIVd or pharmaceutically acceptable salt or prodrug thereof, wherein constituent members are defined hereinabove.

The present invention further provides a compound of Formula IVa–IVd, Va–Vd, VIa–VIb, VIIa–VIIe, VIIIa–VIIIe, IXa–IXe, XIIa–XIIe, XIIIa–XIIIe, or XIVa–XIVd wherein one or more —NH— moieties are replaced by —NPg— wherein Pg is an amino protecting group.

The present invention further provides methods for preparing the compounds of the invention and intermediates thereof. In some embodiment, the present invention provides processes for preparing a compound of Formula XVa:

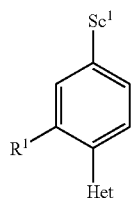

XVa wherein:
Sc¹ is a molecular scaffold;
R¹ is H, halo, $C_1$–$C_4$ alkyl, $C_2$–$C_4$ alkenyl, $C_2$–$C_4$ alkynyl, $C_1$–$C_4$ haloalkyl, aryl, heteroaryl, CN, $C_1$–$C_4$ alkoxy, $C_1$–$C_4$ thioalkoxy, COOR⁸, or tetrazolyl;
R⁸ is, independently, H, $C_1$–$C_4$ alkyl, $C_3$–$C_6$ cycloalkyl, or $C_1$–$C_4$ haloalkyl; and
Het is selected from:

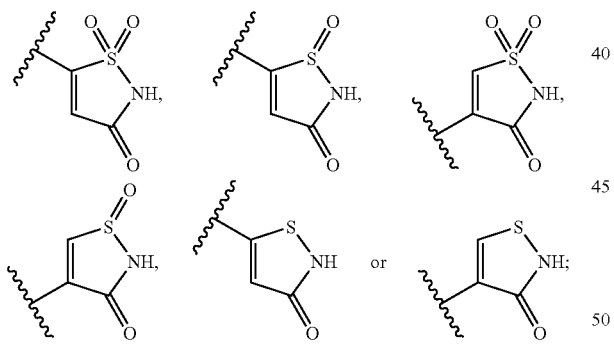

comprising:
a) coupling a compound of Formula XVb:

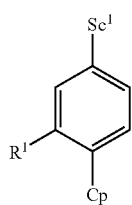

XVb wherein Cp is a coupling group;

with a heterocycle of Formula XXa, XXb, XXc, XXd, XXe or XXf:

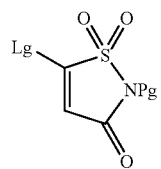

XXa

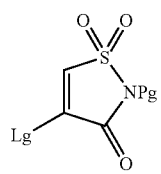

XXb

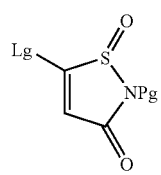

XXc

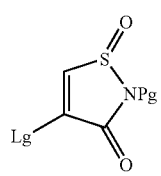

XXd

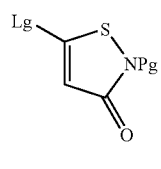

XXe

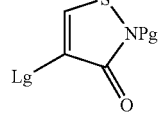

XXf wherein Lg is F, Cl, Br, I or H and Pg is an amino protecting group, for a time and under conditions suitable for forming a compound of Formula XVc:

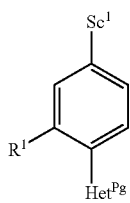

XVc wherein Het$^{Pg}$ is a moiety of Formula:

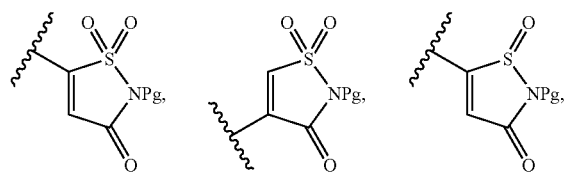

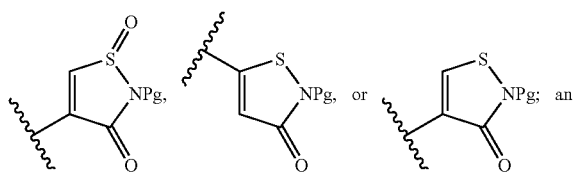

b) deprotecting the compound of Formula XVc for a time and under conditions suitable for forming said compound of Formula XVa.

The present invention further provides processes for preparing a compound of Formula XVa:

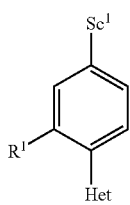
XVa wherein:
Sc$^1$ is a molecular scaffold;
R$^1$ is H, halo, C$_1$–C$_4$ alkyl, C$_2$–C$_4$ alkenyl, C$_2$–C$_4$ alkynyl, C$_1$–C$_4$ haloalkyl, aryl, CN, C$_1$–C$_4$ alkoxy, C$_1$–C$_4$ thioalkoxy, COOR$^8$, heteroaryl or tetrazolyl;
R$^8$ is, independently, H, C$_1$–C$_4$ alkyl, C$_3$–C$_6$ cycloalkyl, or C$_1$–C$_4$ haloalkyl;
Het is selected from:

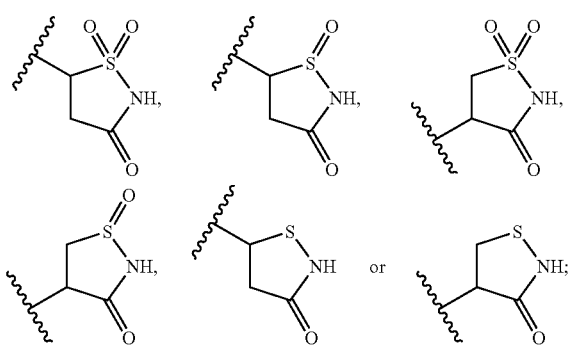

comprising:

a) coupling a compound of Formula XVb:

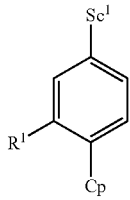
XVb wherein Cp is a coupling group;

with a heterocycle of Formula XXa, XXb, XXc, XXd, XXe or XXf:

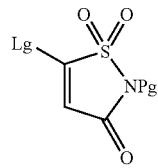
XXa

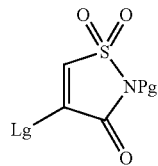
XXb

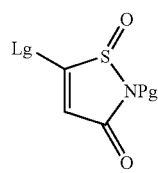
XXc

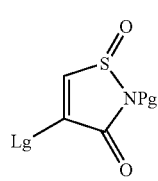
XXd

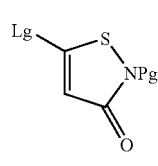
XXe

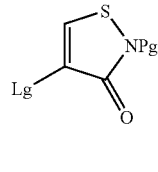
XXf wherein Lg is F, Cl, Br, I or H and Pg is an amino protecting group, for a time and under conditions suitable for forming a compound of Formula XVc:

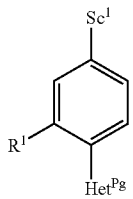

wherein Het$^{Pg}$ is a moiety of Formula:

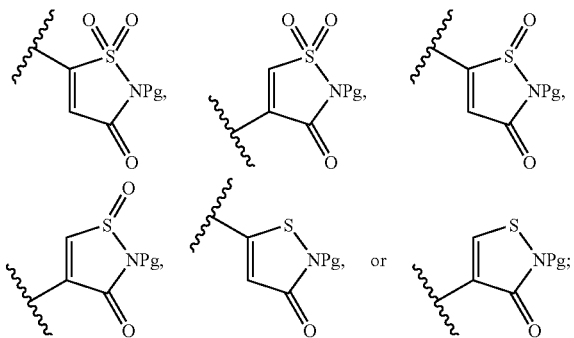

b) reducing said compound of Formula XVc with a reducing agent for a time and under conditions suitable for forming a compound of Formula XVd:

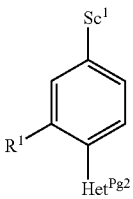

wherein Het$^{Pg2}$ has the Formula:

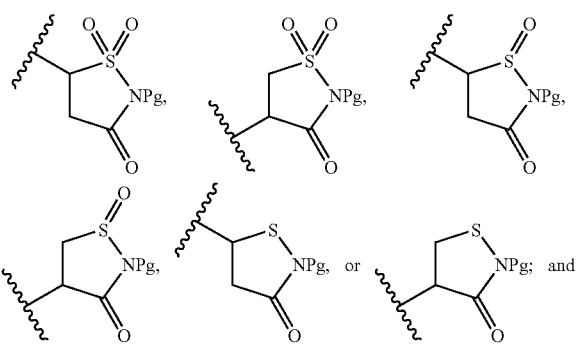

c) deprotecting the compound of Formula XVd for a time an under conditions suitable for forming said compound of Fromula XVa.

In some embodiments according to the above processes, Cp is halo, Sn(R$^{Sn}$)$_3$, or B(OR$^{Bo}$)$_2$, each R$^{Sn}$ is C$_1$–C$_6$ alkyl, and each R$^{Bo}$ is, independently, H, C$_1$–C$_6$ alkyl, aryl, C$_3$–C$_7$ cycloalkyl, (C$_3$–C$_7$ cycloalkyl)alkyl, or two R$^{Bo}$ together form an C$_1$–C$_3$ alkylene bridge optionally substituted by 1, 2 or 3 C$_1$–C$_6$ alkyl, aryl, C$_3$–C$_7$ cycloalkyl, or (C$_3$–C$_7$ cycloalkyl)alkyl. In some embodiments, Cp is iodo. In some embodiments, Cp is Sn(Bu)$_3$. In some embodiments, Cp is B(OH)$_2$.

In some embodiments, Pg is C$_1$–C$_6$ alkyl or arylalkyl, each optionally substituted by halo, C$_1$–C$_4$ alkyl, C$_1$–C$_4$ haloalkyl, C$_1$–C$_4$ alkoxy, C$_1$–C$_4$ haloalkoxy, nitro, cyano, amino, alkylamino, or dialkylamino. In some embodiments, Pg is t-butyl or benzyl.

In some embodiments, R$^1$ is halo or C$_1$–C$_4$ alkyl.

In some embodiments, Sc$^1$ has the Formula S9.

Reaction conditions for carrying out the above coupling reaction can be determined by the skilled artisan according to routine methods. Cp is a coupling group which is any moiety that facilitates the coupling reaction and is not present in the coupled product (i.e.). For example, when Cp is halo, such as iodo, the coupling can be carried out under conditions suitable for a Heck reaction. Additionally, when Cp is Sn(R$^{sn}$)$_3$, the coupling can be carried out under conditions favorable for a Stille reaction. Also, when Cp is —B(OR$^{bo}$)$_2$, the coupling can be carried out under conditions suitable for a Suzuki coupling reaction. The heterocycle of Formula XXa, XXb, XXc, XXd, XXe or XXf can be provided in molar excess relative to the compound of Formula XVb. In some embodiments, the molar ratio of compound of Formula XXa, XXb, XXc, or XXd to compound of Formula XVb is about 5:1 to about 1:5, about 2:1 to about 1:2, about 2:1 to about 1:1, about 2:1 or about 1:1.

In the reducing step, the unsaturated heterocycle moiety of the compound of Formula XVc is reduced with a suitable reducing agent to form the corresponding saturated heterocycle moiety of the compound of Formula XVd. Suitable reducing agents include, for example, borohydride salts (e.g., NaBH$_4$, LiBH$_4$), aluminum hydride salts (NaAlH$_4$, LiAlH$_4$), or H$_2$ in the presence of a metal catalyst (e.g., Pd or Pt). In some embodiments, the reducing step can be carried out in the presence of a chiral catalyst. In further embodiments, the reducing agent can be chiral. In some embodiments, the reducing agent can be provided in molar excess relative to the compound of Formula XVc or at a molar ratio of about 1:1 reducing equivalents.

In the deprotecting step, the amino protecting group, Pg, can be replaced with H under any suitable conditions effective to accomplish the conversion. In some embodiments, the compound of Formula XVd or XVc is reacted with a strong acid optionally at elevated temperatures (e.g., above about 30, about about 50, about 70° C. or higher) to carry out the deprotection step. Example strong acids include, for example trifluoroacetic acid (TFA) or methanesulfonic acid (MSA). In some embodiments, deprotection can be carried out under hydrogenation conditions such as in the presences of H$_2$ and optionally a suitable catalyst. Deprotection can be carried out in the absence of presence of solvent. In some embodiments, the strong acid can be used as solvent. In some embodiments, suitable solvents include alkanes or halogenated alkanes (e.g., methylene chloride).

The present invention further provides compounds of Formula XVc or XVd. In some embodiments, Sc$^1$ is a scaffold of Formula S9 in the compounds of Formula XVc or XVd. in further embodiments, Sc$^1$ is a scaffold of Formula S9 wherein x is 1, $R^V$ is H, $R^{VI}$ is H, $R^D$ is H, and $R^C$ is CO—$OR''$ in the compound of Formula XVc or XVd.

The present invention further provides processes for preparing a compound of Formula XVa:

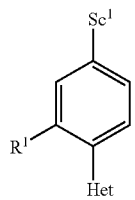

XVa wherein:

$Sc^1$ is a molecular scaffold;

$R^1$ is H, halo, $C_1$–$C_4$ alkyl, $C_2$–$C_4$ alkenyl, $C_2$–$C_4$ alkynyl, $C_1$–$C_4$ haloalkyl, aryl, CN, $C_1$–$C_4$ alkoxy, $C_1$–$C_4$ thioalkoxy, $COOR^8$, heteroaryl, or tetrazolyl;

$R^8$ is, independently, H, $C_1$–$C_4$ alkyl, $C_3$–$C_6$ cycloalkyl, or $C_1$–$C_4$ haloalkyl;

Het is selected from:

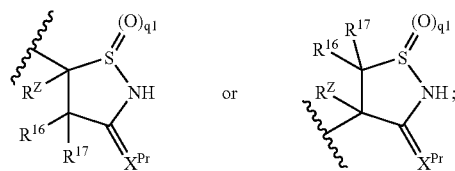

wherein:

$X^{Pr}$ is O or S;

$R^Z$ is H, halo, $C_1$–$C_4$ alkyl, $C_3$–$C_6$ cycloalkyl, haloalkyl, a 5- or 6-membered heterocarbocyclyl group, or tetrazolyl;

$R^{16}$ and $R^{17}$ are each, independently, H, halo, $C_1$–$C_4$ alkyl, $C_3$–$C_6$ cycloalkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl), $SO_2(C_3$–$C_6$ cycloalkyl), $SO_2NH_2$, CHO, COOH, $CO(C_1$–$C_4$ alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl)$_2$, $CONH(C_3$–$C_6$ cycloalkyl), $CON(C_3$–$C_6$ cycloalkyl)$_2NH_2$, $NH(C_1$–$C_4$ alkyl), $N(C_1$–$C_4$ alkyl)$_2$, $NH(C_3$–$C_6$ cycloalkyl), or $N(C_3$–$C_6$ cycloalkyl)$_2$;

or $R^{16}$ and $R^{17}$ together with the carbon atom to which they are attached form a $C_3$–$C_6$ cycloalkyl group or a 3–7 membered heterocycloalkyl group;

q1 is 1 or 2;

comprising cyclizing a compound of Formula XXXa or XXXb:

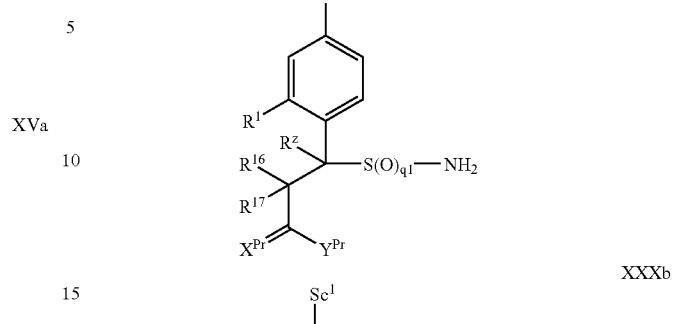

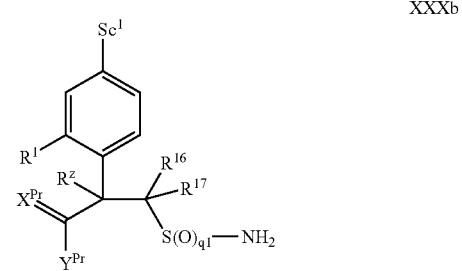

wherein:

$Y^{Pr}$ is $OR^{L1}$ or $NR^{L1}R^{L2}$; and $R^{L1}$ and $R^{L1}$ are each, independently, H, $C_1$–$C_{10}$ alkyl or carbocyclyl; optionally in the presence of a cyclizing reagent for a time and under conditions suitable for forming said compound of Formula XVa.

The "cyclizing reagent" can be any reagent, combination of reagents, or reaction conditions that affects cyclization of the appropriate intermediates to form compounds of Formula XVa. Example cyclization reagents include acids such as HCl and other strong acids. Example cyclization reagents also include bases such as hydroxides, alkoxides (e.g., methoxide, ethoxide, t-butoxide, etc.), aryloxides (e.g., phenoxide) as well as carbonates (e.g., sodium carbonate or potassium carbonate). The cyclizing reagent can also include the application of heat without the addition of any catalyst or compound.

Cyclization can be carried out in any suitable solvent and any suitable dilution. In some embodiments, solvent contains a protic solvent such as water or an alcohol (e.g., methanol, ethanol, etc.). Solvent can be selected based on choice of cyclizing reagent. For example, a suitable solvent/cyclizing reagent system is $RO^-$/ROH where R is $C_1$–$C_{10}$ alkyl. In some embodiments, cyclization is carried out in the presence of sodium methoxide in methanol. In further embodiments, cyclization is carried out in the presence of potassium carbonate in methanol. Any suitable amount of cyclizing reagent can be provided, such as about 0.1 to about 10 eq, about 0.5 to about 5 eq, or about 1 to about 2 eq relative to the amount of compound of Formula XXXa or XXXb.

Cyclization can further be carried out under any suitable temperature such as from about 0 to about 100° C. In some embodiments, such as when the cyclizing agent is an acid, cyclization can be carried out at solvent reflux temperature, such as about 80 to about 120° C., or about 100° C. In some embodiments, such as when the cyclizing agent is a base, cyclization can be carried out at ambient temperature, or at a temperature of about 0 to about 25° C. In the absence of a cyclizing reagent, the cyclization temperature can be any elevated temperature, such as from about 30 to about 120° C.

In some embodiments, the compound of Formula XXXa or XXXb can be prepared by reacting a compound of Formula XXXIa or XXXIb:

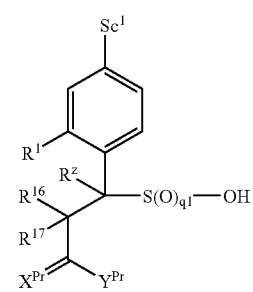

XXXIa

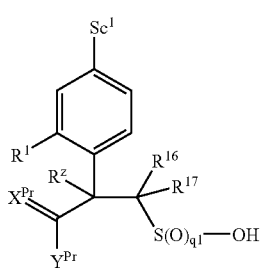

XXXIb with an aminating reagent for a time and under conditions suitable for forming said compound of Formula XXXa or XXXb.

Suitable "aminating reagents" include reagents or combinations of reagents that are capable of converting a sulfonic acid group (—SO$_2$OH) or sulfonyl halide (—SO$_2$—X', where X' is F, Cl, Br, or I) to a sulfonamide (—SO$_2$NH$_2$). An example animating reagent comprises ammonium, such as ammonium hydroxide or other ammonium salt (e.g., ammonium carbonate, ammonium bicarbonate, ammonium phosphate, etc). Treatment with an amination reagent can be carried out at any suitable temperature such as at a temperature below about 50° C. A suitable solvent can be selected by one skilled in the art, or amination can be conducted in the absence of a solvent. Aminating reagent can be added in excess relative to the amount of compound of Formula XXXIa or XXXIb.

In some embodiments, the compounds of Formula XXXIa and XXXIb can be treated with a "halogenating reagent" that is capable of converting the sulfonic acid moiety to a sulfonyl halide moiety, which can then be treated with the aminating reagent to ultimately produce the sulfonamide derivative. Numerous suitable halogenating reagents and their reactions are known in the art and are described, for example, *Org. Syn. Coll*. Vol. 4, 1966, pg. 571; *Synthesis*, 1974, pg. 877; and *Synthesis*, 1982, pg. 423, each of which is incorporated herein by reference in its entirety. Some example halogenating reagents include SOCl$_2$, POCl$_3$, PCl$_5$, and the like. In some embodiments, the compounds of Formula XXXIa and XXXIb can be treated with a base to form a sulfonic acid salt (e.g., treatment with sodium methoxide or sodium hydroxide can produce the sulfonic acid sodium salt) prior to treatment with a halogenating reagent. Halogenating reagent can be added in excess relative to the amount of compound of Formula XXXIa or XXXIb.

In some embodiments, the compound of Formula XXXIa or XXXIb can be prepared by reacting a compound of Formula XXXIIa or XXXIIb:

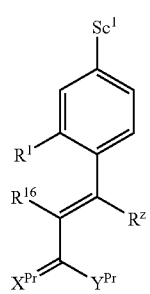

XXXIIa

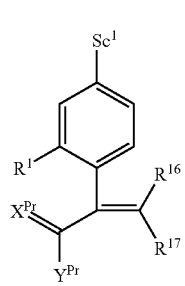

XXXIIb with a sulfonating reagent for a time and under conditions suitable for forming said compound of Formula XXXIa or XXXIb.

The "sulfonating reagent" can be any suitable reagent or combination of reagents that can add a sulfonic acid moeity to an olefin. Suitable sulfonating reagents and their reactions are provided, for example, in U.S. Pat. No. 2,402,512, which is incorporated herein by reference in its entirety. An example sulfonating reagent comprises a bisulfite moiety. In some embodiments, the sulfonating reagent is and alkali bisulfite such as sodium bisulfite. For example, about 0.5 to about 5 eq or about 1 to about 2 eq of bisulfate can be provided relative to the amount of compound of Formula IVa or IVb.

Sulfonation of an olefin with a sulfonating reagent can be carried out in any suitable solvent such as a protic solvent comprising, for example, water and/or an alcohol (e.g., ethanol). The sulfonation reaction can also be carried out at elevated temperature, elevated pressure, optionally in the presence of microwaves. For example, a sulfonation reaction can be carried out in a microwave generator (e.g., an oven) to heat the reaction mixture to a temperature greater than about 100° C., such as about 100 to about 180° C. (e.g. about 165° C.). In some embodiments, pressure can also be elevated to about 5 to about 20 bar (e.g., about 14 bar).

The present invention further provides compounds of Formula XXXa, XXXb, XXXIa or XXXIb:

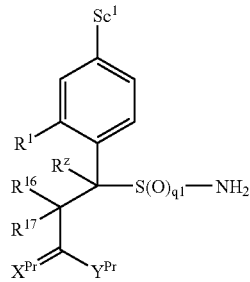

XXXa

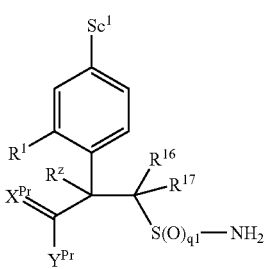

XXXb

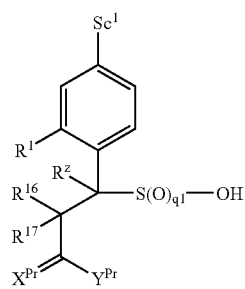

XXXIa

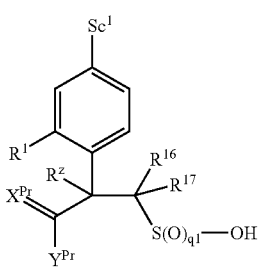

XXXIb wherein constituent members are defined hereinthroughout.

In some embodiments, $Sc^1$ has the Formula S9 in the compounds of Formula XXXa, XXXb, XXXIa and XXXIb. In some embodiments, $X^{Pr}$ is O. In some embodiments, $Y^{Pr}$ is $OR^{L1}$. In some embodiments, $Y^{Pr}$ is $NR^{L1}R^{L2}$. In some embodiments, $R^{L1}$ and $R^{L1}$ are each, independently, H, $C_1$–$C_{10}$ alkyl. In some embodiments, $R^{L1}$ and $R^{L1}$ are each, independently, H, Me or Et. In some embodiments, $R^{16}$ and $R^{17}$ are each H. In some embodiments, $R^Z$ is H.

As used herein, the term "reacting" is used as known in the art and generally refers to the bringing together of chemical reagents in such a manner so as to allow their interaction at the molecular level to achieve a chemical or physical transformation. Reacting can be carried out in the presence of absence of a solvent.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 20° C.) and "reduced temperature" refers to temperatures below room temperature.

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

The processes described herein can be stereoselective such that any given reaction starting with one or more chiral reagents enriched in one stereoisomer forms a product that is also enriched in one stereoisomer. The reaction can be conducted such that the product of the reaction substantially retains one or more chiral centers present in the starting materials. The reaction can also be conducted such that the product of the reaction contains a chiral center that is substantially inverted relative to a corresponding chiral center present in the starting materials.

According to the present invention, the Het moiety can be any 5-membered heterocycle that can be stably formed by the combination of moieties listed for Z, $A^1$, $A^2$, $A^3$, and $A^4$ or any 6-membered heterocycle that can be stably formed by the combination of moieties listed for Y, $B^1$, $B^2$, $B^3$, $B^4$ and $B^5$. Thus, at least one of Z, $A^1$, $A^2$, $A^3$, and $A^4$ and at least one of Y, $B^1$, $B^2$, $B^3$, $B^4$ and $B^5$ contains a ring-forming heteroatom. In some embodiments, the Het moiety contains at least one ring-forming NH. In other embodiments, the Het moiety contains at least one ring-forming atom bearing an oxo or sulfido (e.g., CO, CS, SO, $SO_2$, PO(OH), etc).

The $X^1$, $X^2$, $X^3$, $D^1$, $D^2$, $D^3$ and $X^4$, $X^5$, $X^6$, $E^1$, $E^2$ ring moieties of the invention form aromatic carbocycles or heterocycles that link the Het moiety with a first and/or second molecular scaffold. Thus, variables $X^1$, $X^2$, $X^3$, $D^1$, $D^2$, $D^3$ and $X^4$, $X^5$, $X^6$, $E^1$, $E^2$ are selected such that an aromatic ring is formed. For example, each $X^1$, $X^2$, $X^3$, $D^1$, $D^2$, and $D^3$ can be selected so that an optionally substituted phenyl, pyridinyl, pyrimidinyl, triazinyl, pyridonyl, or other 6-membered aromatic ring is formed. In another example, $X^4$, $X^5$, $X^6$, $E^1$, and $E^2$ can be selected so that an optionally substituted thienyl, furyl, imidazolyl, thiazolyl, pyrryl, oxazolyl, isoxazolyl, pyrazolyl, triazolyl, tetrazolyl, or other 5-membered heteroaryl ring is formed.

As used herein, "stably formed," "stable compound" or "stable structure" refers to a compound that is sufficiently robust to survive isolation to a useful degree of purity from a reaction mixture, and preferably capable of formulation into an efficacious therapeutic agent. Based on fundamental chemical principals, one skilled in the art would be able to recognize stable and unstable moieties. For example, one skilled in the art would be able to recognize combinations of ring-forming atoms (e.g., $X^4$, $X^5$, $X^6$, $E^1$, and $E^2$) that would result in stable or unstable carbocyclic or heterocarbocyclic moieties.

As used herein, the term "molecular scaffold" refers to a molecular fragment of 2 or more atoms substituted by and serving primarily, but not exclusively, as structural support for the (aromatic ring)-Het moiety of compounds of the invention (wherein "aromatic ring" refers to the ring defined by $X^1$, $X^2$, $X^3$, $D^1$, $D^2$, and $D^3$ or $X^4$, $X^5$, $X^6$, $E^1$, and $E^2$). While not wishing to be bound by theory, it is believed that the (aromatic ring)-Het portion of compounds of the present invention serve as, for example, phosphorylated amino acid mimics (e.g., phosphorylated tyrosine) that can occupy and/or block the binding pockets of phosphatases, SH2 domain-containing proteins, and related proteins. Accordingly, the molecular scaffold portions of compounds of the invention can be formed from any molecular fragment that would not substantially interfere with the occupying or blocking of binding pockets by the attached (aromatic ring)-Het moiety. Such molecular scaffolds can be readily determined by the art-skilled using, inter alia, theoretical predictions based on molecular modeling. Numerous X-ray crystal structures of phosphatases and related enzymes are readily available to the public and provide ample data for carrying out such modeling. For example, more than 25 crystal structures of the phosphatase PTPB1 are publicly accessible from the PDB (Protein Data Bank).

Molecular scaffolds can further be selected so as to impart stability, as well as, desirable pharmacodynamic, pharmacokinetic, protein binding, cell membrane permeability, oral bioavailability, target selectivity, and other properties to compounds of the invention. For example, molecular scaffolds can be selected to provide suitable solubility, crystallinity, hydrophilicity, hydrophobicity, and other properties desirable for the preparation and administration of pharmaceutical compositions.

In some embodiments, molecular scaffolds are composed of 3 to about 500, 4 to about 500, or 5 to about 500 atoms. In further embodiments, the molecular scaffold contains at least one carbon atom. In yet further embodiments, the molecular scaffold contains at least 2, at least 3, at least 4, at least 5, or at least 6 carbon atoms. In other embodiments, the molecular scaffold contains no carbon atoms. In some embodiments, the molecular scaffold has a molecular weight greater than about 100, about 200, about 300, about 400, about 500, about 600, about 700, about 800, or about 900 Da. In some embodiments, the molecular scaffold has a molecular weight of about 10 to about 900, about 50 to about 800, about 100 to about 700, or about 200 to about 600 Da.

In further embodiments, $Sc^1$ and $Sc^2$ combine to form a fused-ring molecular scaffold. As used herein, the term "fused" describes chemical moieties, such as ring moieties that share at least one bond. Thus, a fused-ring molecular scaffold can be a carbocyclyl or heterocarbocyclyl scaffold moiety fused to the aromatic ring defined by either $X^1$, $X^2$, $X^3$, $D^1$, $D^2$, and $D^3$ or $X^4$, $X^5$, $X^6$, $E^1$, and $E^2$, where the bond between $X^1$ and $X^2$ or $X^4$ and $X^5$ is shared with the fused-ring molecular scaffold. The fused-ring molecular scaffold can be substituted or unsubstituted. Some example substituents include $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclyl alkyl, each of which can be substituted by one or more carbocyclyl, heterocyclyl, halo, haloalkyl, $C_1$–$C_4$ alkyl, $C_1$–$C_4$ alkoxy, carbocyclyloxy, heterocarbocyclyloxy, acyl, or acyloxy.

As used herein, the term "alkyl" or "alkylene" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, butenyl, pentenyl, hexenyl, butadienyl, pentadienyl, hexadienyl, and the like.

As used herein, "alkynyl" refers to an alkyl group having one or more triple carbon-carbon bonds. Example alkynyl groups include ethynyl, propynyl, butynyl, pentynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl." Examples perhaloalkyl groups include $CF_3$ and $C_2F_5$.

As used herein, "carbocyclyl" groups are saturated (i.e., containing no double or triple bonds) or unsaturated (i.e., containing one or more double or triple bonds) cyclic hydrocarbon moieties. Carbocyclyl groups can be aromatic (e.g., "aryl") or non-aromatic (e.g., "cycloalkyl"). Carbocyclyl groups can be mono- or polycyclic. Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, napthyl, and the like. In some embodiments, carbocyclyl groups can have from 3 to about 20, 3 to about 10, or 3 to about 7 carbon atoms.

As used herein, "aryl" refers to aromatic carbocyclyl groups including monocyclic or polycyclic aromatic hydrocarbons such as, for example, phenyl, naphthyl, anthracenyl, phenanthrenyl, indanyl, indenyl, and the like. In some embodiments, aryl groups have from 6 to about 18 carbon atoms.

As used herein, "cycloalkyl" refers to non-aromatic carbocyclyl groups including cyclized alkyl, alkenyl, and alkynyl groups. Cycloalkyl group can include mono- or polycyclic (e.g. 2, 3, or 4 fused rings) ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of cyclopentane (indanyl), cyclohexane (tetrahydronaphthyl), and the like. Additionally, one or more ring-forming carbon atoms of the cycloalkyl group can be oxidized (e.g., bear an oxo or sulfido group). Cycloalkyl groups can have 0, 1, 2 or more double or triple bonds.

As used herein, the term "heterocarbocyclyl" or "heterocyclyl" refers to saturated or unsaturated carbocyclyl groups wherein one or more of the ring-forming atoms of the heterocarbocyclyl group is a heteroatom such as O, S, N, or P (or oxo, sulfido, dioxo or disulfido derivative thereof). Heterocyclyl groups can be aromatic (e.g., "heteroaryl") or non-aromatic (e.g., "heterocycloalkyl"). Heterocyclyl groups can correspond to fully hydrogenated and partially hydrogenated heteroaryl groups. Heterocarbocyclyl groups can contain, in addition to at least one heteroatom, from about 1 to about 20, about 2 to about 10, or about 2 to about 7 carbon atoms and can be attached through a carbon atom or heteroatom. Additionally, one or more ring-forming members of the heterocarbocyclyl group can be oxidized (e.g., bear an oxo, dioxo, sulfido, or disulfido group) such as in the case of a heterocycloalkyl group. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like.

As used herein, "heteroaryl" groups are aromatic heterocarbocyclyl groups and include monocyclic and polycyclic (e.g., 2, 3, 4 or more fused rings) aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, pyridonyl, furyl (furanyl), quinolyl, isoquinolyl, thienyl, imidazolyl, thiazolyl, indolyl, pyrrolyl (pyrryl), oxazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, and the like. In some embodiments, heteroaryl groups can have from 1 to about 20 carbon atoms, and in further embodiments from about 3 to about 20 carbon atoms. In some embodiments, heteroaryl groups have 1 to about 4, 1 to about 3, or 1 to 2 heteroatoms.

As used herein, "heterocycloalkyl" refers to a non-aromatic heterocyclyl group including cyclized alkyl, alkenyl, and alkynyl groups where one or more of the ring-forming atoms is a heteroatom such as an O, N, S, or P atom (or oxo or dioxo derivative thereof). Additionally, one or more ring-forming members of the heterocycloalkyl group can be oxidized (e.g., bear an oxo, dioxo, sulfido, or disulfido group). Heterocycloalkyl groups include monocyclic and polycyclic (e.g., 2, 3, 4 or more fused rings) systems. Also included in the definition of heterocycloalkyl are moieties that have one or more aromatic rings fused (i.e., having a bond in common with) to the nonaromatic heterocyclic ring, for example phthalimidyl, naphthalimidyl pyromellitic diimidyl, phthalanyl, and benzo derivatives such as indolene and isoindolene groups. Heterocycloalkyl groups can have 0, 1, 2, 3 or more double or triple bonds.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like. Alkoxy groups can have, for example, from 1 to about 10 carbon atoms, about 1 to about 8 carbon atoms, about 1 to about 6 carbon atoms, or about 1 to about 4 carbon atoms.

As used herein, "haloalkoxy" refers to alkoxy substituted by one or more halo.

As used herein, "thioalkoxy" refers to an alkoxy group in which the O atom is replaced by an S atom.

As used herein, "aryloxy" refers to an —O-aryl group. An example aryloxy group is phenoxy.

As used herein, "thioaryloxy" refers to an aryloxy group in which the O atom is replaced by an S atom.

As used herein, "cycloalkyloxy" refers to an —O-cycloalkyl group.

As used herein, "heterocyloalkyloxy" refers to an —O-heterocycloalkyl group.

As used herein, "biaryl" refers to an aryl group substituted by a further aryl group. An example biaryl group is biphenyl.

As used herein, "biheteroaryl" refers to a heteroaryl group substituted by a further heteroaryl group. An example of a biheteroaryl group is bipyridyl.

As used herein, "amino" refers to an —NH$_2$ group. "Alkylamino" refers to an amino group substituted by an alkyl group and "dialkylamino" refers to an amino group substituted by two alkyl groups. The term "aminoalkyl" refers to an alkyl group substituted by an amino group.

As used herein, "acyl" refers to alkanoyl or aroyl groups, which may be substituted, for example, by one or more halo. Specific examples of acyl groups include formyl, acetyl, pivaloyl, trifluoroacetyl, trichloroacetyl, and the like.

As used herein, "acyloxy" refers to —O-acyl.

As used herein, "carbonyl" refers to C=O.

As used herein, "carboxy" or "carboxyl" refers to COOH.

As used herein, "carboxy alkyl ester" or "alkoxycarbonyl" refers to an alkyl ester of COOH.

As used herein, "carboxy aryl ester" or "aryloxycarbonyl" refers to an aryl ester of COOH.

As used herein, "hydroxy" refers to OH.

As used herein, "mercapto" refers to SH.

As used herein, "ureido" refers to NHCONH$_2$.

As used herein, "guanidino" refers to NHC(=NH)NH$_2$.

As used herein, "sulfinyl" refers to SO.

As used herein, "sulfonyl" refers to SO$_2$.

As used herein, "oxy" refers to —O—.

As used herein, "oxo" refers to =O.

As used herein, "sulfido" refers to =S.

As used herein, "cyano" refers to CN.

As used herein, "nitro" refers to NO$_2$.

The above chemical terms can be combined to refer to moieties containing a combination of chemical groups. This combination term is generally read such that a term is understood to be a substituent of a following term going from left to right. For example, "alkylcarbonylalkenyl" refers to an alkenyl group substituted by a carbonyl group which in turn is substituted by an alkyl group. The following terms can also exemplify such combinations.

As used herein, "arylheteroaryl" refers to heteroaryl substituted by aryl.

As used herein "heteroarylaryl" refers to aryl substituted by heteroaryl.

As used herein, "arylalkyl" or "aralkyl" refers to an alkyl moiety substituted by an aryl group. Example aralkyl groups include benzyl and naphthylmethyl groups. In some embodiments, aralkyl groups have from 7 to about 20, 7 to about 15, or 7 to about 12 carbon atoms.

As used herein, "arylalkyloxy" or "aralkyloxy" refers to oxy substituted by arylalkyl.

As used herein, "heteroarylalkyl" refers to alkyl substituted by heteroaryl.

As used herein "cyloalkylalkyl" refers to alkyl substituted by cycloalkyl.

As used herein, "heterocycloalkylalkyl" refers to alkyl substituted by heterocycloalkyl.

As used herein, "carbocyclylalkyl" refers to alkyl substituted by carbocyclyl.

As used herein, "heterocarbocyclylalkyl" refers to alkyl substituted by hetercarbocyclyl.

As used herein, "biaryl" refers to aryl substituted by aryl.

As used herein, "biheteroaryl" refers to heteroaryl substituted by heteroaryl.

The term "amino acid" as used herein refers to an organic compound containing both a basic amino group and an acidic carboxyl group. Included within this term are natural amino acids or protected forms thereof, modified and unusual amino acids, as well as amino acids which are known to occur biologically in free or combined form but typically do not occur in proteins. Included within this term are modified and unusual amino acids, such as those disclosed in, for example, Roberts and Vellaccio (1983) *The Peptides*, 5: 342–429, the disclosure of which is hereby incorporated by reference. Modified or unusual amino acids which can be used to practice the invention include, but are not limited to, D-amino acids, beta-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid. Examples of some protected amino acids include alkyl or aryl esters of tyrosine, aspartate, glutamate, serine or theonine.

The term "amino acid residue" as used herein refers to the portion of an amino acid molecule that is present in a compound containing the amino acid. For example, the amino acid residue of a phenylalanine in a peptide or peptide analog would typically have the formula —NH—CH($CH_2Ph$)—C(O)—.

The term "peptide" as used herein refers to a compound that consists of two to about 100 amino acids that are linked by means of a peptide bond. The term "peptide" also includes compounds containing both peptide and non-peptide components, such as pseudopeptide or peptide mimetic residues or other non-amino acid components. Such a compound containing both peptide and non-peptide components can also be referred to as a "peptide analog". In some embodiments, peptides contain from 2 to about 100, 2 to about 50, 2 to about 10, or 2, 3, 4, 5, 6, 7, 8, 9, or 10 amino acids.

The term "peptide bond" is used as known in the art and refers generally to a covalent amide linkage formed by loss of a molecule of water between the carboxyl group of one amino acid and the amino group of a second amino acid.

As used herein, the phrase "protecting group" refers to a chemical functional group that can be selectively appended to and removed from functionalities, such as hydroxyl groups, amino groups, and carboxyl groups. Protecting groups are usually introduced into a chemical compound to render such functionality inert to chemical reaction conditions to which the compound is exposed. Any of a variety of protecting groups can be employed with the present invention. A protecting group of an amino moiety can be referred to as an "amino protecting group" and a protecting group of a guanidino moiety can be referred to as a "guanidino protecting group." Amino and guanidino protecting groups can have the formulas aryl-$SO_2$—, alkyl-$SO_2$—, aryl-C(=O)—, aralkyl-C(=O)—, alkyl-C(=O)—, aryl-OC(=O)—, aralkyl-OC(=O)—, alkyl-OC(=O)—, aryl-NHC(=O)—, alkyl-NHC(=O)—, and the like, wherein said alkyl, aryl and aralkyl groups may be substituted or unsubstituted. Example specific amino and guanidino protecting groups can also include $C_1$–$C_6$ alkyl (e.g., t-butyl), arylalkyl (e.g., benzyl), t-butyloxycarbonyl (BOC), fluorenylmethoxycarbonyl (Fmoc), benzyloxycarbonyl (Cbz), and a phthalimido group. Examples of a "carboxyl protecting group" include alkyl (e.g., Me, Et, t-Bu), aryl, arylalkyl (e.g., benzyl), and the like. Further representative protecting groups can be found in T. W. Green and P. G. M. Wuts, *Protective Groups in Organic Synthesis,* 3rd. Ed., Wiley & Sons, Inc., New York (1999), which is incorporated herein by reference in its entirety.

As used herein, "substituted" indicates that at least one hydrogen atom of a chemical group is replaced by a non-hydrogen moiety. Example substituents include F, Cl, Br, I, $C_1$–$C_6$ alkyl, $C_1$–$C_6$ alkenyl, $C_1$–$C_6$, alkynyl, haloalkyl, NR'R", $N_3$, $NO_2$, CN, CNO, CNS, C(=O)OR', R'CO, R'C(=O)O, R'CONR', R'R"NCO, ureido, OR', SR', $SO_2$-alkyl, $SO_2$-aryl, and $SO_2$-NR'R", wherein R' and R" are each, independently, H or $C_1$–$C_6$ alkyl. Alternatively, R' and R" may be combined, with the nitrogen to which they are attached, to form a 5 to 7 membered heterocyclic ring, for example pyrrolidinyl, piperidinyl, morpholinyl, piperazinyl, and N-methylpiperazinyl. When a chemical group herein is "substituted" it may have up to the full valance of substitution, provided the resulting compound is a stable compound or stable structure; for example, a methyl group may be substituted by 1, 2, or 3 substituents, a methylene group may be substituted by 1 or 2 substituents, a phenyl group may be substituted by 1, 2, 3, 4, or 5 substituents, and the like.

As used herein, "leaving group" refers to any group that can be replaced by a nucleophile upon nucleophilic substitution. Example leaving groups include, halo (F, Cl, Br, I), hydroxyl, alkoxy, mercapto, thioalkoxy, triflate, alkylsulfonyl, substituted alkylsulfonyl, arylsulfonyl, substituted arylsulfonyl, heterocyclosulfonyl or trichloroacetimidate. Representative examples include p-(2,4-dinitroanilino) benzenesulfonyl, benzenesulfonyl, methylsulfonyl, p-methylbenzenesulfonyl, p-bromobenzenesulfonyl, trichloroacetimidate, acyloxy, 2,2,2-trifluoroethanesulfonyl, imidazolesulfonyl and 2,4,6-trichlorophenyl.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Compounds of the invention can also include tautomeric forms, such as keto-enol tautomers. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

The present invention also includes prodrugs of the compounds described herein. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, $C_6$ alkyl.

For compounds of the invention in which a variable appears more than once, each variable can be a different moiety selected from the Markush group defining the variable. For example, where a structure is described having two $R^1$ groups that are simultaneously present on the same compound; the two $R^1$ groups can represent different moieties selected from the Markush group defined for $R^1$.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Synthesis

Compounds of the invention, including salts and solvates thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Green and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The compounds of the invention can be readily synthesized by those skilled in the art such as according to the methods described below. Some example Het moieties are provided in Charts 1, 2, and 3 and referred to in the below preparations. Substituents R, R', R'', R''', and R'''' represent H or any reasonable substituent of the moieties on which they appear in the preparations provided below.

Chart I

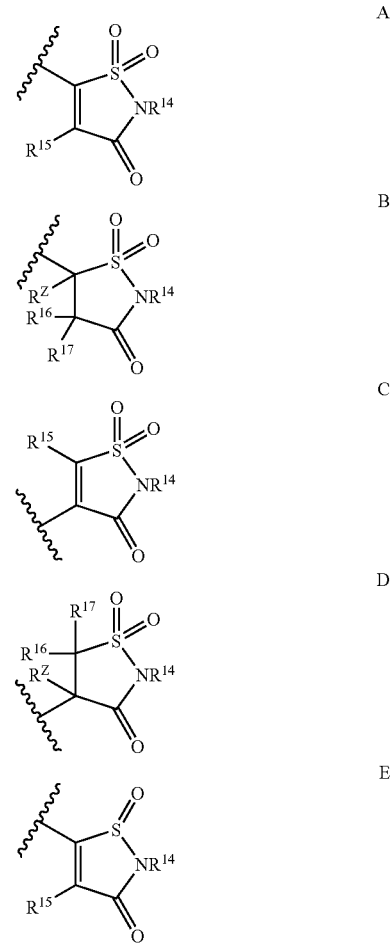

-continued
F
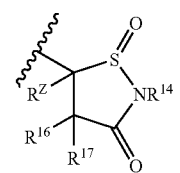
G
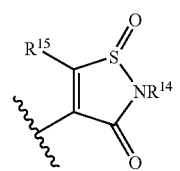
H
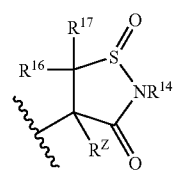
I
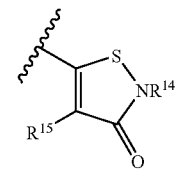
J
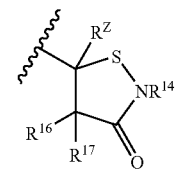
K
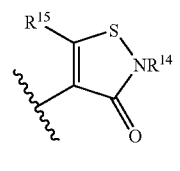
L
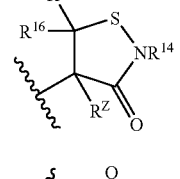
M
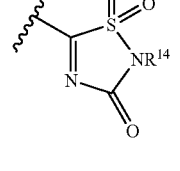
N
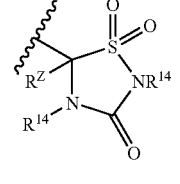
-continued
O
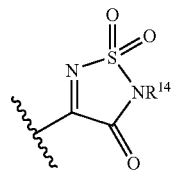
P
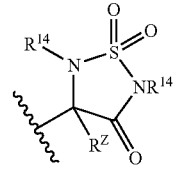
Q
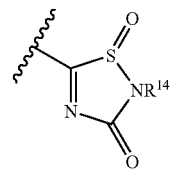
R
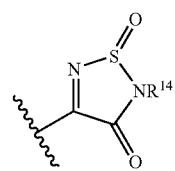
S
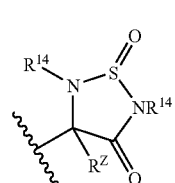
T
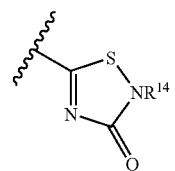
U
V
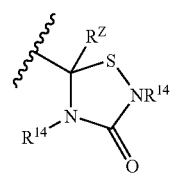
W

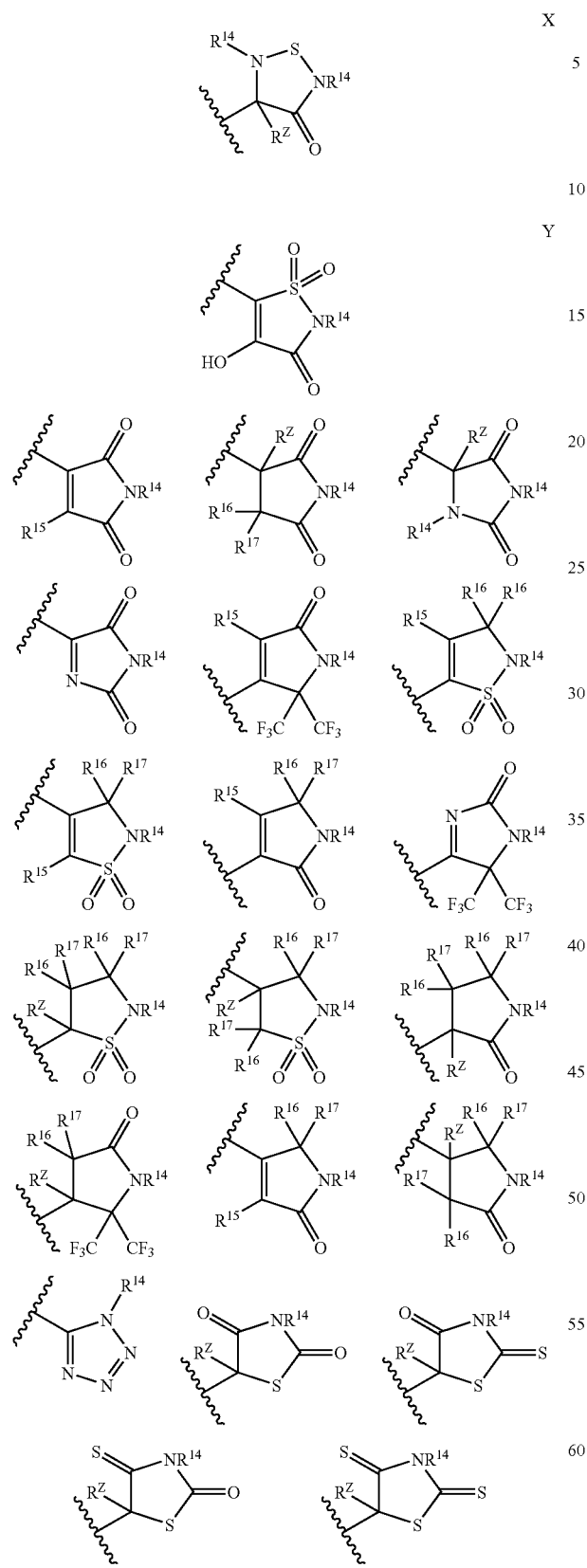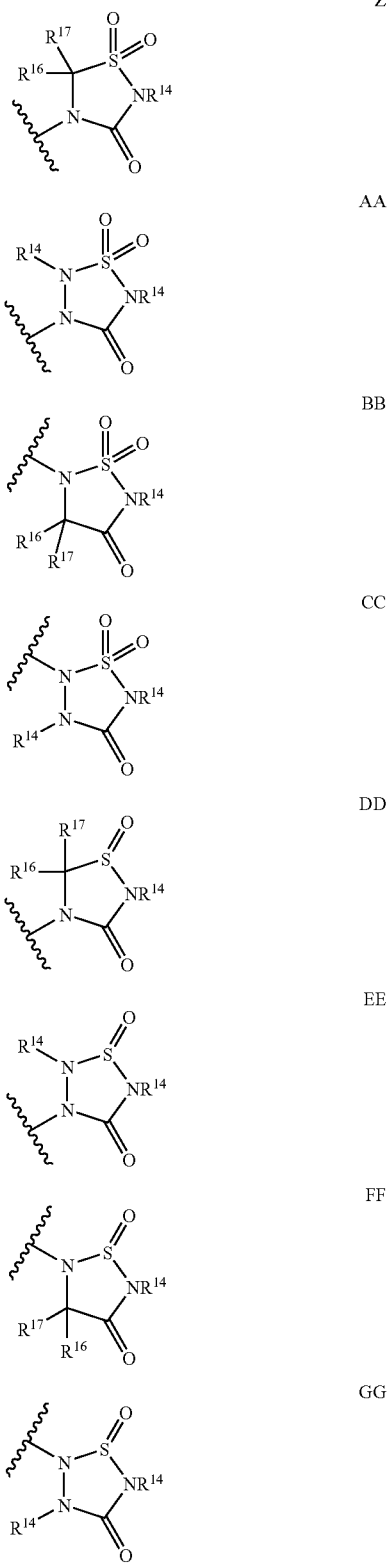

-continued
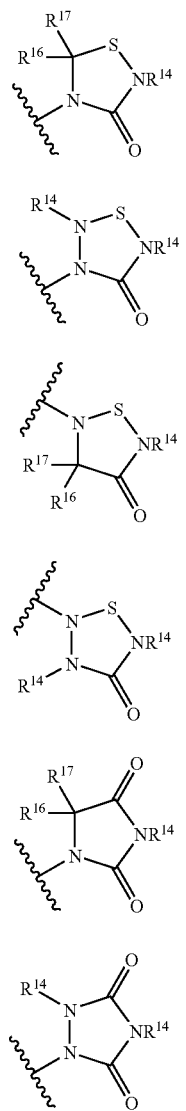
HH
II
JJ
KK
LL
MM
Chart 3
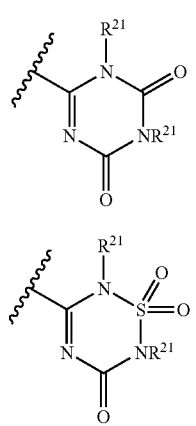
NN
OO
-continued
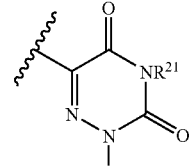
PP
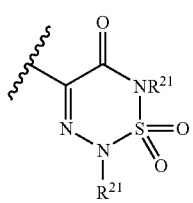
QQ
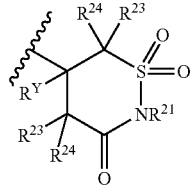
AAA
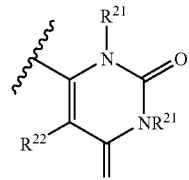
RR
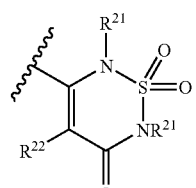
SS
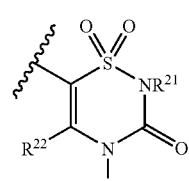
TT
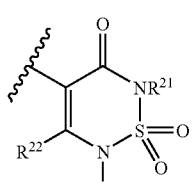
UU
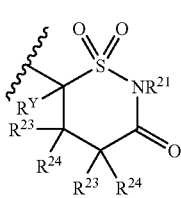
BBB -continued VV
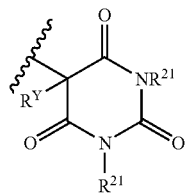

WW
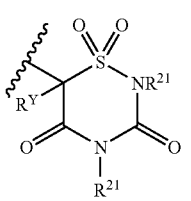

XX
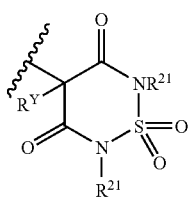

YY
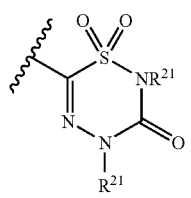

ZZ
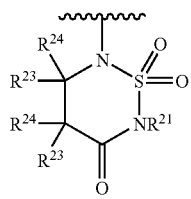

The below Schemes provide example routes to compounds of the invention or to intermediates useful in preparing compounds of the invention. The compounds and reactions depicted therein are meant to be representative and the skilled artisan will recognize numerous variations that are accessible through routine methods. For example, while many of the compounds depicted in the Schemes show unsubstituted carbocycles or heterocycles, the skilled artisan will recognize that analogous procedures can be carried out for numerous substituted carbocycles as well as substituted and unsubstituted heterocycles. Additionally, variables used in the Schemes have the definitions already defined above if not defined in the descriptive paragraphs related to each of the Schemes.

The isothiazolones A, C, E, G, I, and K (Chart 1) can be synthesized as shown in Scheme 1 (R is, e.g., $R^{14}$ or an amino protecting group; see, e.g., Journal of Heterocyclic Chemistry (1971), 8(4), 571–80). A variety of bis-amides (1-2) can be prepared from 3,3'-dithiopropionic acid 1-1 via the bis-acid chloride using conditions known to those skilled in the art. Treatment of the bis-amides 1-2 with a chlorinating agent, such as sulfuryl chloride, can provide the chloro isothiazolone 1-3 and the des-chloro isothiazolone 1-4 which can be brominated using typical halogenating reagents such as bromine or N-bromosuccinimide to give 1-5. Compounds 1-3, 1-4 and 1-5 can be oxidized with typical oxidizing reagents, such as m-CPBA, to give the corresponding sulfoxides 1-6, 1-7 and 1-8 and the corresponding sulfones 1-9, 1-10, and 1-11.

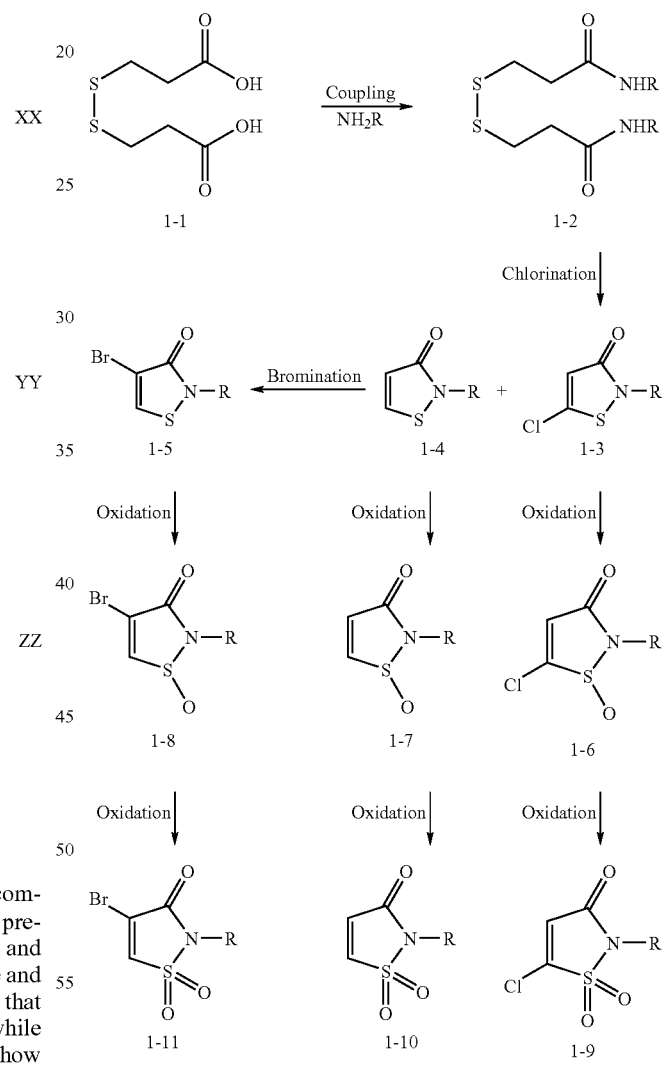

Scheme 1

1,2,4-Thiadiazol-3-ones (e.g., M, Q, and U, Chart 1) are also known in the art and can be synthesized as illustrated in Scheme 2 (R is, e.g., $R^{14}$ or an amino protecting group; see, e.g., Acta Chem. Scand. Ser. B (1988), 42, 362–366). Isocyanates 2-1 can be treated with methoxymethyl isothiocyanate 2-2 in sulfuryl chloride to give the cyclized 1,2,4-thiadiazol-3-ones 2-3. The 1,2,4-thiadiazol-3-ones 2-3 can be oxidized, with reagents such as m-CPBA, to the corresponding sulfoxides 2-4 and sulfones 2-5.

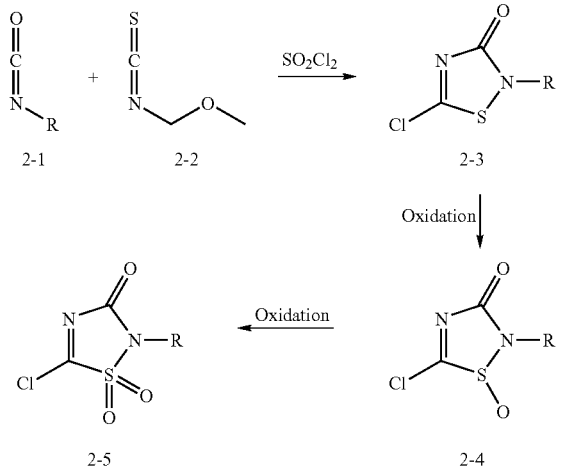

1,2,5-Thiadiazol-3-ones (e.g., O, S, W, Chart 1) are also known in the art and can be synthesized as illustrated in Scheme 3 (R is, e.g., $R^{14}$ or an amino protecting group; see, e.g., *J. Org. Chem.* (1979), 44, 1118–1124). The glycinamides 3-1, which can be readily synthesized by those skilled in the art, can be treated with sulfur monochloride to give the 4-chloro-1,2,5-thiadiazol-3-one 3-2 and the des-chloro 1,2,5-thiadiazol-3-ones 3-3. Chlorination of 3-3 with sulfuryl chloride can also give 3-2. The 1,2,5-thiadiazol-3-ones 3-2 can be oxidized, using reagents such as m-CPBA, to the corresponding sulfoxides 3-4 and sulfones 3-5.

Additionally, compounds of the invention containing saturated heterocycles B, D, F, H, J, L, N, P, R, T, V, X, and the like (see Chart 1) can be prepared by reaction of their unsaturated counterparts (e.g., A, C, E, G, I, K, M, O, G, S, U, and W) with suitable reducing agents such as hydrogen optionally in the presence of catalyst (e.g., Pd/C or Pd/BaSO$_4$). Acidic moieties such as NH present in the heterocycles can be optionally protected during the reduction.

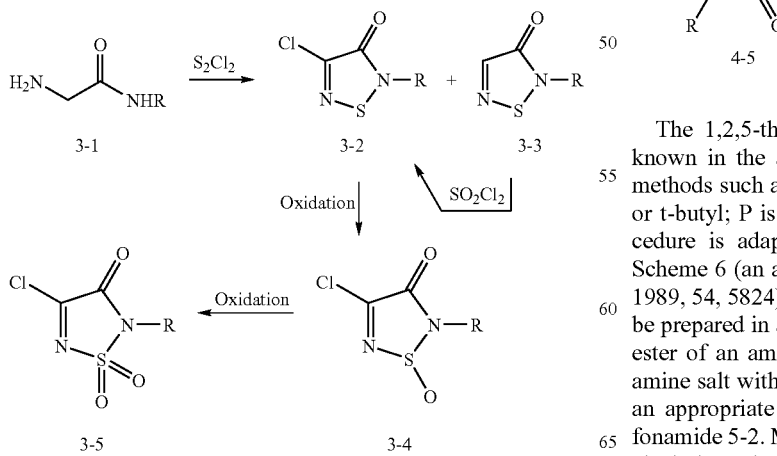

The 1,2,4-thidiazolidin-3-ones (e.g., Z and DD, Chart 2) are known in the art. Derivatives containing these heterocycles (4-6) can be prepared according to literature procedures shown in Scheme 4 (R is e.g., $R^{14}$ or an amino protecting group) (*Angew. Chem.* 1976, 120). Commercial aniline 4-1 or related aromatic-amine (substituted or unsubstituted) is reacted with thioisocyanate 4-2 to give thiourea 4-3. Thiourea 4-3 when treated with diiodomethane affords heterocycle 4-4. Heterocycle 4-4 undergoes an oxidative rearrangement to heterocycle 4-5 in the presence of hydrogen peroxide in acetic acid. Heterocycle 4-5 can be further oxidized to heterocycle 4-6 by addition of hydrogen peroxide in acetic acid.

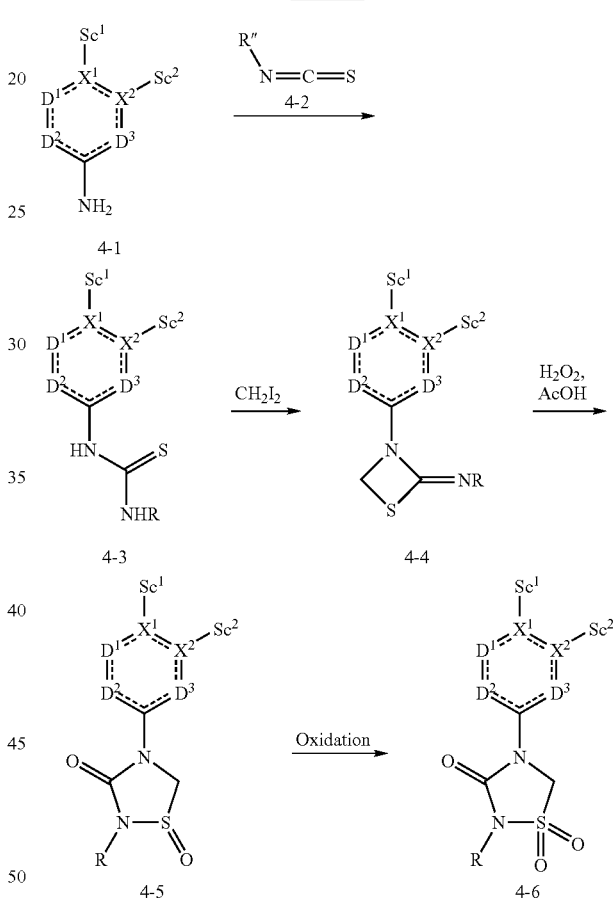

The 1,2,5-thiadiazolidin-3-ones (BB, Chart 2) are also known in the art and can be synthesized by at least two methods such as shown in Scheme 5 (R is, for example, Bn or t-butyl; P is an amino protecting group). Synthesis procedure is adapted from *Tetrahedron* 1996, 52, 993 and Scheme 6 (an adaptation of procedures from *J. Org. Chem.* 1989, 54, 5824). In Scheme 5, protected heterocycle 5-5 can be prepared in a four-step sequence beginning with an alkyl ester of an aminoacid hydrochloride 5-1 Treatment of the amine salt with the adduct of chlorosulfonyl isocyanate and an appropriate alcohol, such as t-butanol, can afford sulfonamide 5-2. Mitsunobu reaction of 5-2 with an appropriate alcohol, such as benzyl alcohol, can give sulfamide 5-3 which can in turn be readily deprotected, TFA for the Boc example. Acyclic sulfamide 5-4 can be cyclized to heterocycle 5-5 with a suitable catalyst, such as sodium methoxide or AlMe₃.

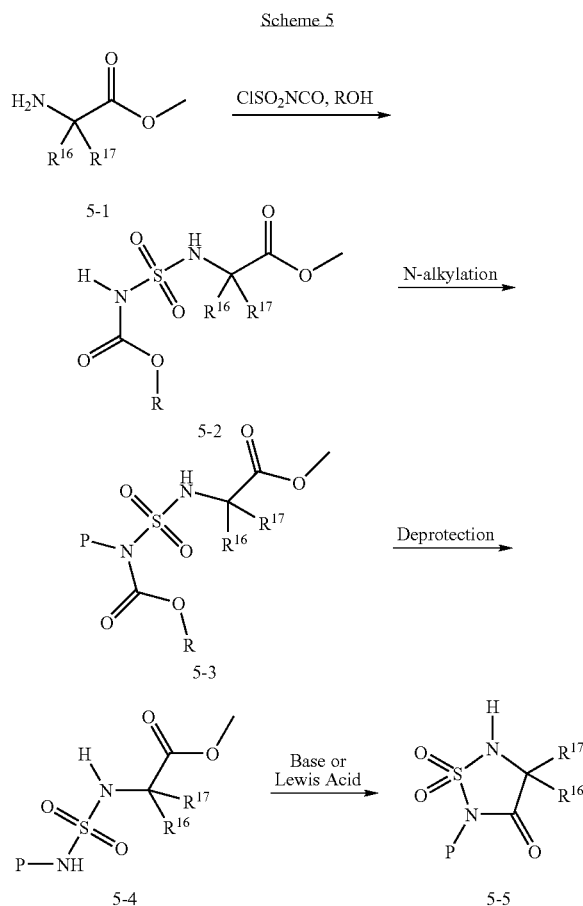

A second method to access 1,2,5-thiadiazolidin-3-ones BB is as shown in Scheme 6 (X is a leaving group; R" is, e.g., Me, Et, Bn). Substituted aniline 6-1 or related aromatic-amine can be alkylated with an alkylating reagent, such as bromoalkylacetate 6-2, to give compound 6-3. Treatment of 6-3 with sulfamoyl chloride affords sulfamide 6-4. Sulfamide 6-4 is readily cyclized to 1,2,5-thiadiazolidin-3-ones 6-5 using an appropriate base or Lewis acid, such as sodium methoxide or AlMe₃.

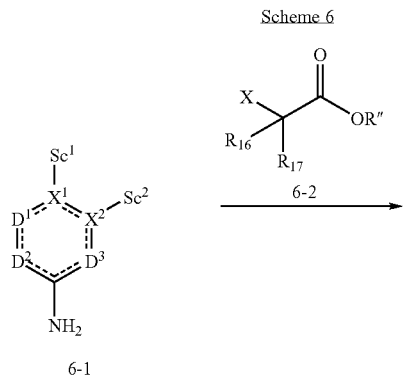

The 1-aryl-imidazolidine-2,4-diones (e.g., LL, Chart 2) can be prepared in two steps according to literature procedures as illustrated in Scheme 7 (X is a leaving group; R is an amino protecting group; R" is, e.g., Me, Et, Bn). Ureas of type 7-3 can be synthesized by those skilled in the art using procedures such as the reaction of an aniline 7-1 or related an aromatic-amine with isocyanate 7-2. Urea 7-3 when treated with an alkylating reagent, such as alkylchloroacetate 7-4, gives heterocycle 7-5 (see, e.g., *Biorg. Med. Chem. Lett.* 1999, 9, 749).

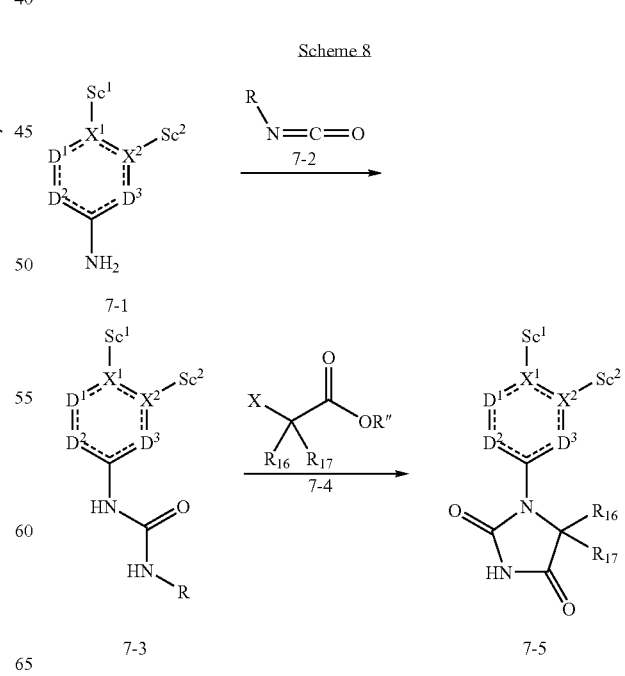

Compounds of type 8-1 can also be synthesized by N-arylation (*Tet. Lett.* (1998), 39, 2941) of a scaffold 8-2 bearing a boronic acid/ester with a heterocycle 8-3 and cleavage of the protecting group R (R is e.g., $R^{14}$ or an amino protecting group) as illustrated in Scheme 8.

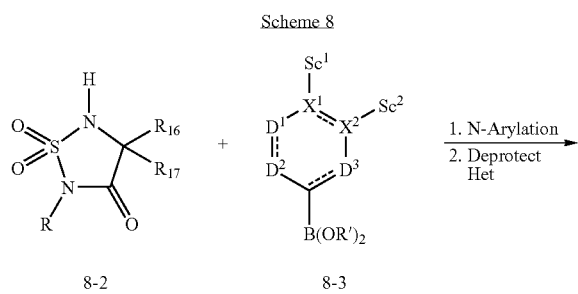

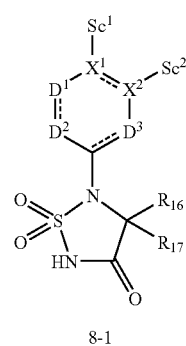

Halogenated heterocycles, such as the products of Schemes 1, 2, and 3, can be coupled to aromatic moieties by any of numerous methods known in the art. For example, Suzuki couplings (*Acc. Chem. Res.* (1982), 15, 178; *Pure & Appl. Chem.* (1985), 57, 1749; *Tet. Lett.* (1999), 40, 213) can be used to couple heterocycles (e.g., 9-1 or 9-5) with either an arylboronic acid or ester derivatives (9-2) to give coupled product 9-3 or 9-7 (Scheme 9; where X is halo; Y is N or $CR^{15}$; and R is $R^{14}$ or an amino protecting group; R'' and R''' are each, independently, e.g., H, alkyl, cycloalkyl, aryl, arylalkyl etc.). Stille couplings can also be used to couple heterocycles (9-1 or 9-5) with arylstannanes (9-6) (see, e.g., *Pure & Appl. Chem.* (1985), 57, 1771; *Angew. Chem. Int. Ed.* 9-1. (1986), 25, 508) to give 9-3 or 9-7. Reduction of the olefin in 9-3 or 9-7 to 9-4 or 9-8, respectively, can be accomplished using methods known to those skilled in the art, such as catalytic hydrogenation with a metal, such as palladium on carbon with hydrogen or hydride-type reductions, to give the saturated heterocycles B, D, F, H, J, L, N, P, R, T, V, and X (Chart 1).

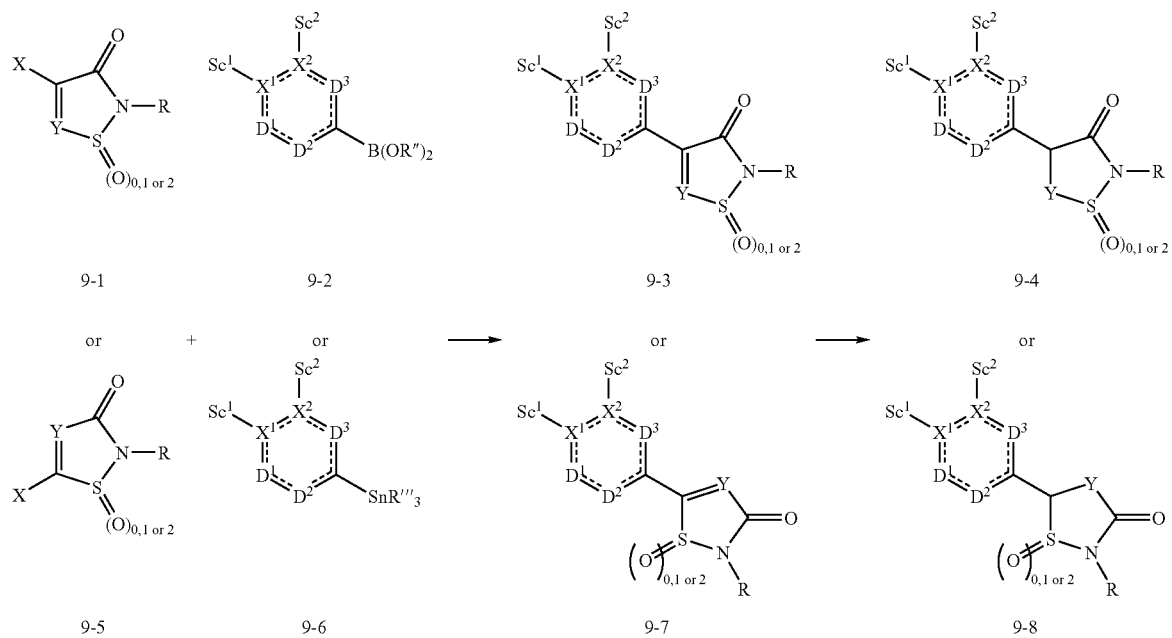

The compounds of the invention having peptide-like scaffolds can be synthesized, for example, as shown in Scheme 10 (P is an amino protecting group; R is, e.g., alkyl, acyl, amino acid, etc.; R' is e.g., Me, Et, Bn) using conditions known to those skilled in the art. Compound 10-4 can be synthesized by a series of sequential peptide couplings and deprotections starting from 10-1. Further elaboration of the N-terminus of 10-4 can be carried out by coupling of $R^a$ groups to give 10-5. For example, a variety of alkyl halides, carboxylic acids, acyl halides, alkyl or aryl sulfonyl chlorides, and the like can be coupled to the N-terminus of AA1 by standard procedures.

The 1H-[1,3,5]triazine-2,4-diones (e.g., NN, Chart 3) can be prepared as outlined in Scheme 12 (R' is, e.g., H, alkyl, etc.). An appropriately substituted boronic acid/ester 12-1 or related aromatic-boronic acid/ester can be coupled with cyanuric chloride 12-2 to provide, after acidic hydrolysis, the triazine 12-3 (see, e.g., *Heterocycles* (1987), 26(10), 2711–2716).

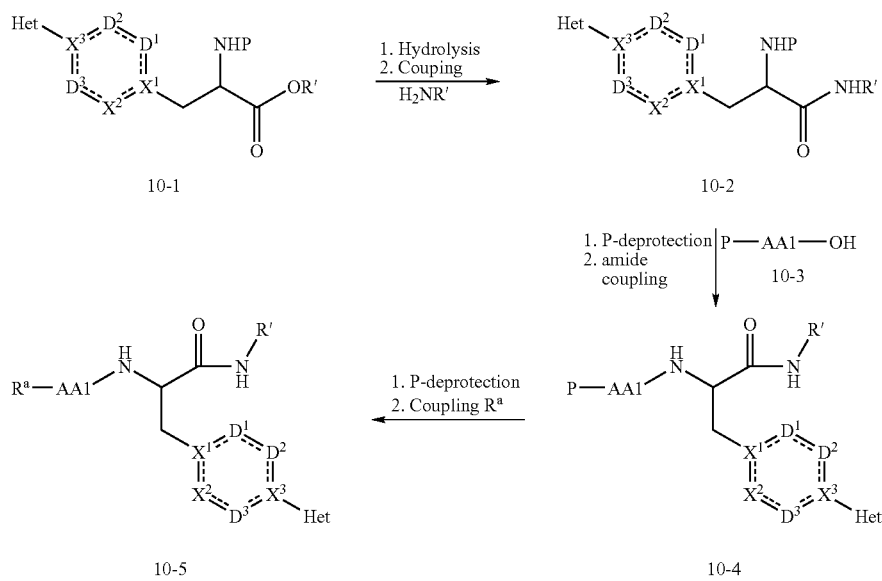

The synthesis of further compounds of the invention (e.g., with ether-linked scaffold) is illustrated in Scheme 11 (X is a leaving group). Condensation of 11-1 with a $X—(CR^VR^{VI})_x—CR^DR^A—(CR^{III}R^{IV})_z—X$, such as 1,4-dibromobutane or other dihaloalkane, and subsequent further elaboration via deprotection and etherification gives 11-2.

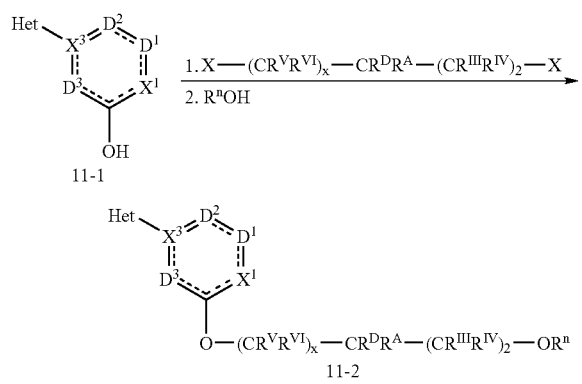

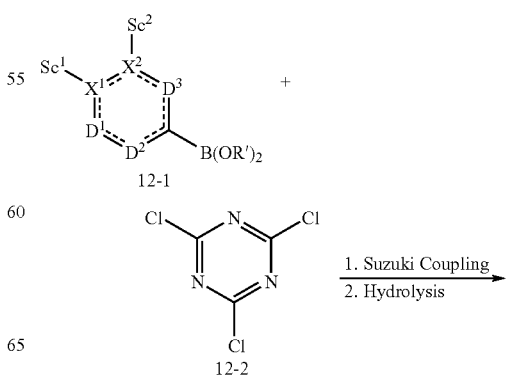

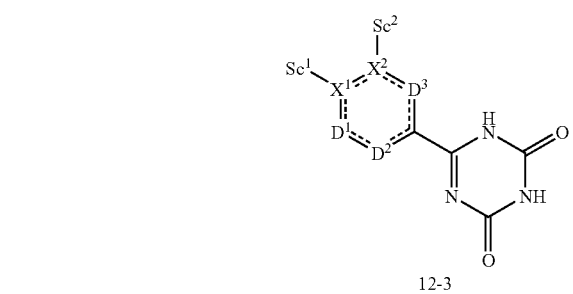

12-3

To prepare the 2H-1,2,4,6-thiatriazin-3(6H)-one 1,1-dioxides (e.g., OO, Chart 3) an appropriate nitrile 13-1 or related aromatic-nitrile can be transformed into the amidine 13-2 as shown in Scheme 13 (*J. Org. Chem.* (2000), 65(23), 8100–8104). The amidine can then be reacted with chlorosulfonylisocyanate to give the thiatriazinone 13-3 (see, e,g., *Heterocycles* (1979), 12, 815–818).

Scheme 13

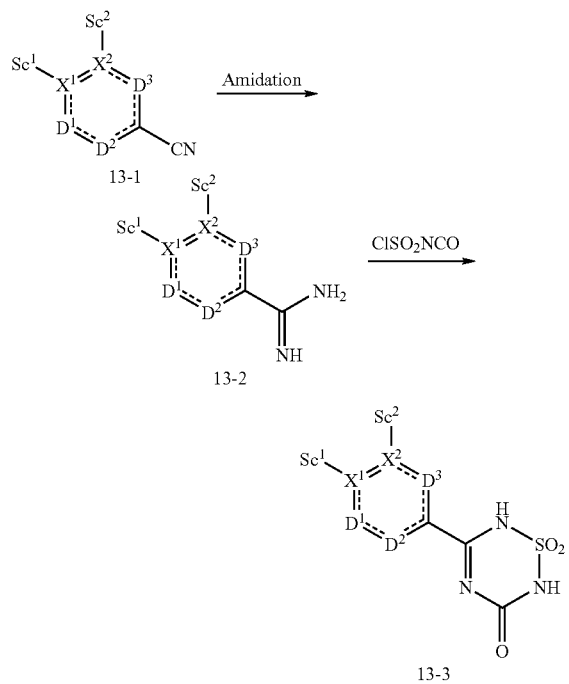

6-Azauracils (e.g., PP, Chart 3) can be prepared by reacting substituted alpha-ketoacids with semicarbazides (*J. Org. Chem.* (1958), 23, 1951–3). Similarly the 2H-1,2,3,6-thiatriazin-5(6H)-one 1,1-dioxides (QQ) can be prepared by the reaction of alpha-ketoacids with sulfamic acid hydrazides. Scheme 14 (R is, e.g., H, alkyl, etc.) outlines an example preparation of uracil 14-3 (e.g., RR, Chart 3). An appropriately substituted boronic acid 14-1 or related aromatic boronic acid/ester can be coupled with 5-bromouracil 14-2 to provide the uracil 14-3 (see, e.g., *Heterocycles* (1987), 26(10), 2711–2716. The preparation of the related 2H-1,2,6-thiadiazin-3(6H)-one 1,1-dioxides SS and TT are described in the literature (*J. Heterocycl. Chem.* (1978), 15, 477).

Scheme 14

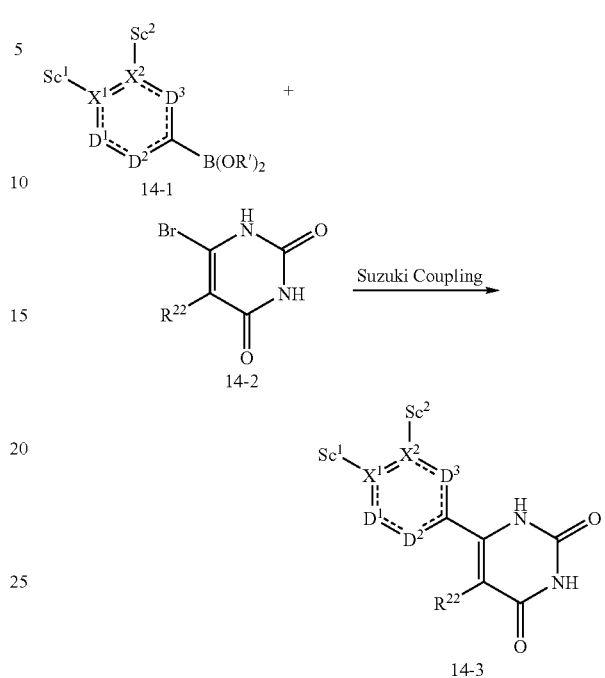

The barbituric acids (UU, Chart 3) can be prepared from the corresponding malonate esters and urea (*Justus Liebigs Ann. Chem.* (1904), 335, 364). The related 1,2,6-thiadiazinane-3,5-dione 1,1-dioxides (WW) can be prepared similarly with thiourea (*Can. J. Chem.* (1987), 65, 298–302). The 1,2,4-thiadiazinane-3,5-dione 1,1-dioxides (VV), the 2H-1,2,4,5-thiatriazin-3(4H)-one 1,1-dioxides (XX) and the 2H-1,2,4-thiadiazin-3(4H)-one 1,1-dioxides (YY) are described in the literature (see, e.g., *J. Org. Chem.* (1961), 26, 3461–3467; *J. Org. Chem.* (1958), 23, 1951–3; and *Synthesis* (1988), 9, 733–735, respectively.) The 1,2,6-thiadiazin-3-ones (ZZ) are also described in the literature (see, e.g., *J. Comb. Chem.* (2001), 3, 290–300).

The synthesis of further compounds of the invention (e.g., with representative thioether scaffolds) is illustrated in Scheme 15 (Ar is aryl or heteroaryl). Thioetherification of aldehyde 15-1 with thiol 15-2 can provide 15-3.

Scheme 15

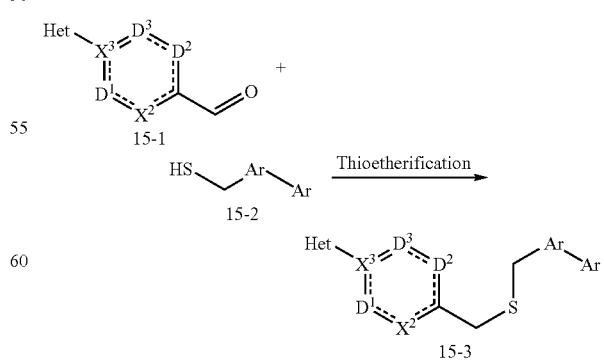

The synthesis of further compounds of the invention (e.g., with representative amine scaffolds) is illustrated in Scheme 16. Amine derivatives 16-3 can be synthesized via reductive amination of aldehyde 16-1 with amines of formula HNR°R$^p$. When, for example, reductive amination results in a secondary amine, acylation of 16-2 with acylation reagents such as R'Y—X; where X is a leaving group and Y is, e.g., SO$_2$, SO, CO, NR'CO, CO$_2$ or bond and R' is, e.g., H, alkyl, cycloalkyl, aryl, heteroaryl, etc., can afford compounds 16-3.

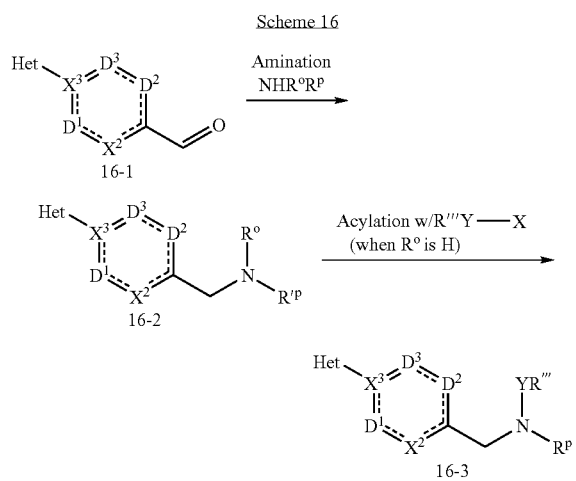

The synthesis of further compounds of the invention with representative molecular scaffolds where Sc1 is joined with Sc2 to form a fused ring system (e.g., piperidinylthiophene scaffolds) is illustrated in Scheme 17 (R is an amino protecting group, R' is, e.g., H, alkyl, etc.). Boronation of 17-1, for example by lithiation of 17-1 followed by treatment with trimethylborate can give the boronic acid 17-2. Suzuki coupling of 17-2 with an appropriate heterocycle can give 17-3.

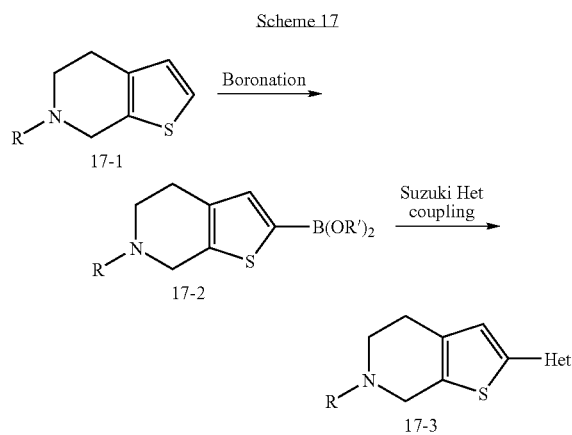

The synthesis of further compounds of the invention (e.g., with representataive 2-deoxybenzoin scaffolds) is illustrated in Scheme 18 (X is a leaving group; Ar is an aromatic moiety). The alkylation of 2-deoxybenzoin 18-2 (optionally substituted) with alkylating reagents 18-1 can give product 18-3.

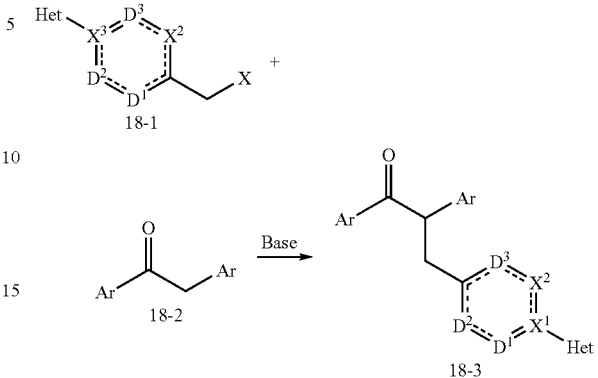

The synthesis of further compounds of the invention (e.g., with representative imidazole or imidazoline scaffolds) is illustrated in Scheme 19 (R is, e.g., H, alkyl, etc.). The primary amide 19-1 can be dehydrated to the nitrile 19-2. The nitrile 19-2 in turn can be treated with hydrogen chloride gas to give the imidate 19-3. Treatment of the imidate 19-3 with amino ketones 19-4 can provide imidazoles 19-6. Imidazolines 19-6 can be prepared by reacting the imidate 19-3 with diamines 19-5.

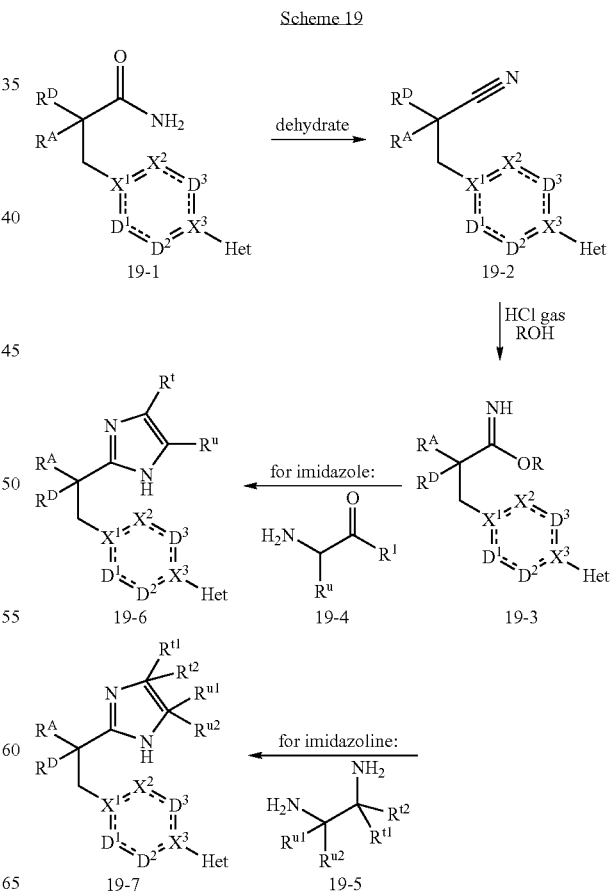

The synthesis of further compounds of the invention with representative tetrahedal scaffolds (C. K. Lau, et al., *Bio. Med. Chem. Lett.*, 2004, 1043–1048) is illustrated in Scheme 20 (Ar is an aromatic moiety; X is a leaving group). Alkylation of the benzotriazole 20-1 (optionally substituted) with an appropriate electrophile can give 20-2 which in turn can be alkylated with a further electrophile substituted with a heterocycle 20-3 to give 20-4.

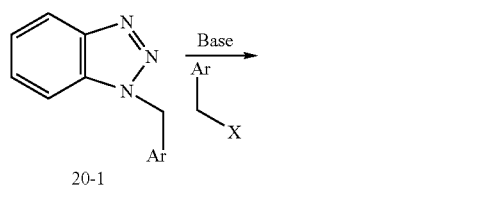

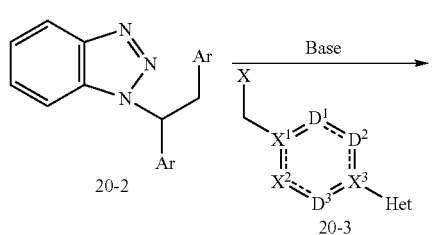

An example synthetic route to compounds of the invention with ortho-aryl substitutents (e.g., ortho to the Het moiety) is provided in Scheme 21 via an alternative method (e.g., via Heck reaction) for coupling heterocycles to the aromatic moieties in compounds of the invention. Compound 21-1 can be coupled to compound 21-2 (R is $R^{14}$ or an amino protecting group) in a modified Heck reaction to afford adduct 21-3. Adduct 21-3 can be reduced and deprotected to afford compound 21-4.

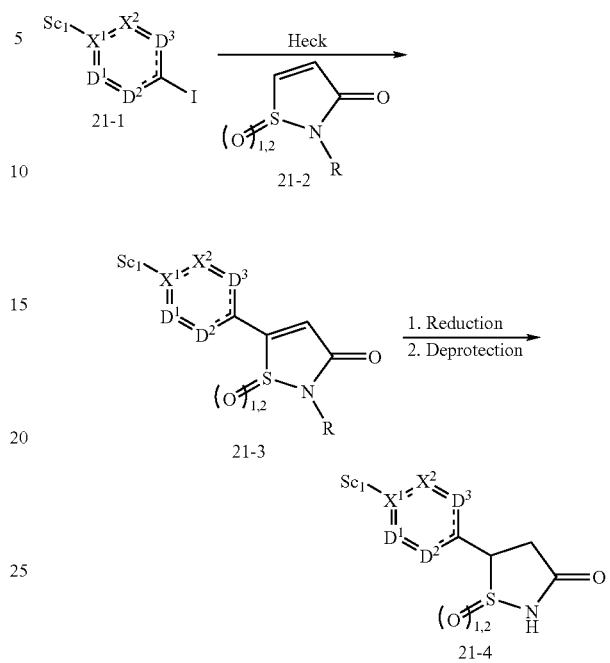

Compounds of the invention containing benzimidazole-type scaffolds, can be obtained as illustrated in Scheme 22 (P is an amino protecting group). Coupling of an ortho $M^1$H-substituted aniline 22-2 (optionally further substituted) to compound 22-1 (optionally further substituted) can afford an amide that can be cyclized by a variety of conditions by one skilled in the art to afford benziazole-like compounds 22-3. Example cyclizing conditions include stirring in acetic acid. Deprotection of the primary amine and reacting with an appropriate acylation/arylation agent such as R'Y—X (where X is a leaving group or boronic acid/ester and Y is, e.g., $SO_2$, SO, CO, NR'CO, $CO_2$ or bond, and R' is, e.g., H, alkyl, cycloalkyl, aryl, heteroaryl, etc.) can afford 22-4.

-continued

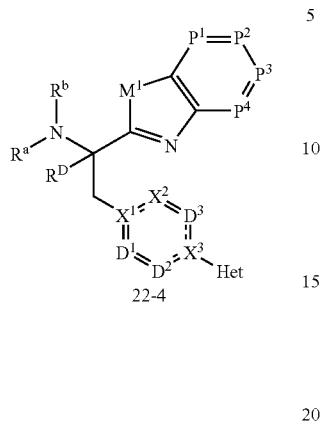
22-4

An alternative synthesis of further compounds of the invention with heterocycle XX is illustrated in Scheme 23. Heck reaction and sulfonylation of Iodo-scaffold 23-1 can yield compound 23-2. Sulfonyl chloride formation via treatment with a chlorinating reagent, such as PCl$_5$, followed by sulfonylamide formation with for example ammonia, and ring closure with, e.g., AlMe$_3$ or NaOMe can yield 23-3.

Scheme 23

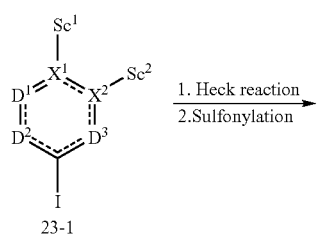
23-1

1. Heck reaction
2. Sulfonylation

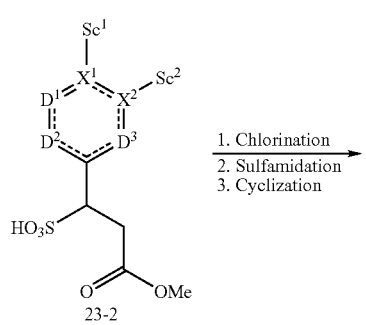
23-2

1. Chlorination
2. Sulfamidation
3. Cyclization

-continued

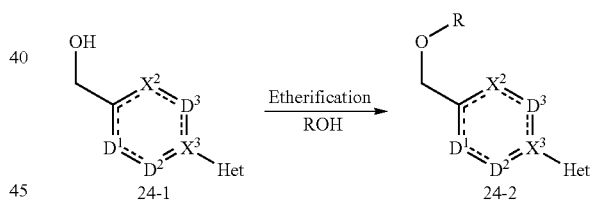
23-3

The synthesis of representative ether-type scaffolds is illustrated in Scheme 24. Alcohol 24-1 can undergo reductive etherification with aldehydes (e.g., RCHO where R is, e.g., alkyl, cycloalkyl, aryl, heteroaryl and the like) using for example trifluoroacetic acid and triethylsilane to give ethers 24-2.

Scheme 24

OH → Etherification ROH → O-R 24-1    24-2

The synthesis of further compounds of the invention with representative lactam-type scaffolds is illustrated in Scheme 25. Lactam 25-1 (R is a carboxylic acid protecting group, e.g., alkyl, arylalkyl, etc.) can be alkylated with a benzyl-halide 25-2 under basic conditions to afford quaternary lactam 25-3 as reported in the literature Tetrahedron (1998), 54, 9447. Coupling of an appropriate heterocycle, for example Suzuki coupling of heterocycle 1-9 to a boronic acid/ester substituted 25-3, can afford 25-4. Further elaboration of 25-4, for instance saponification of the ester and coupling to appropriate amine, can afford further substituted derivatives 25-5.

Scheme 25

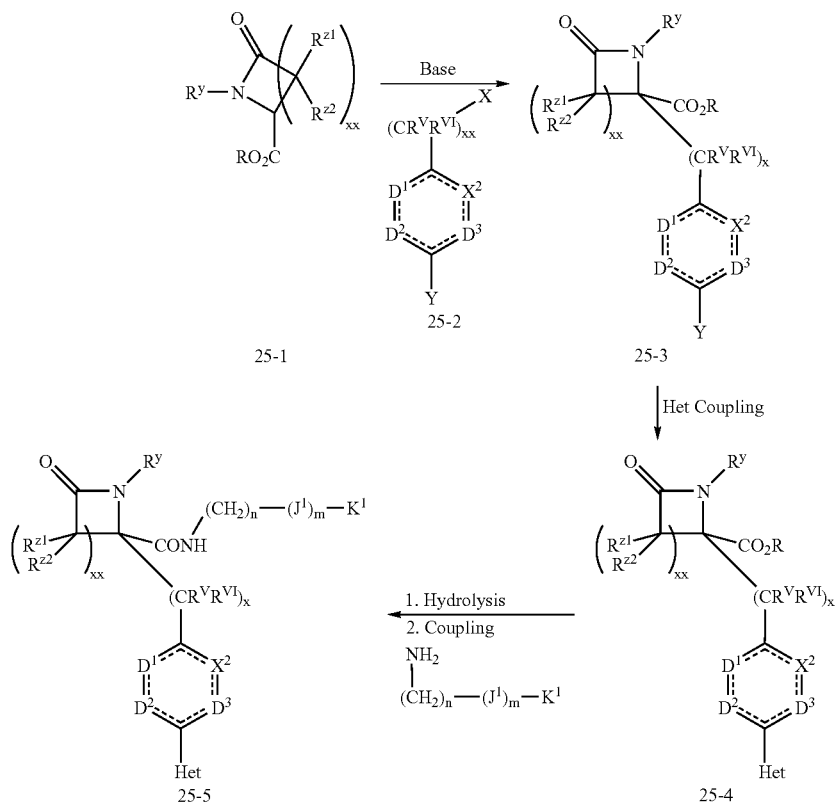

Methods

The present compounds can modulate the activity of a target protein. The "target protein" can be any protein that selectively binds a phosphorylated protein or peptide. Phosphorylated proteins or peptides have at least one amino acid residue that bears a phosphorous-containing moiety such as a phosphate or related moiety (e.g., phosphite, phosphonate, etc.) which is typically present on the amino acid side chain. Example amino acids that can be phosphorylated include tyrosine, serine, and threonine.

The target proteins, according to the invention, can be selective binders, indicating for example that binding affinity for a phosphorylated protein or peptide is greater than for the corresponding non-phosphorylated version. Binding of the present compounds to a target protein can reduce or block the target protein's ability to selectively bind to and/or catalyze dephosphorylation of a phosphorylated protein or peptide. Accordingly, the present compounds are useful in the treatment of various diseases and disorders related to the dephosphorylating activity of some target proteins.

In some embodiments, target proteins include phosphatases such as tyrosine phosphatases, serine-theonine phosphatases, or dually active phosphatases (enzymes which dephosphorylate any of tyrosine, serine, or threonine residues). A tyrosine phosphatase can be any of the non-receptor type (intracellular type) PTPases such as, for example, PTPN1 (PTP1B), PTPN2 (T-cell protein tyrosine phosphatase), PTPN3 (PTPH1), PTPN4 (MEG1), PTPN5 (PTP-STEP), PTPN6 (SHP1), PTPN7 (LC-PTP), PTPN9 (MEG2), PTPN11 (SHP2), PTPN12 (PTPG1, PTP-BEST), PTPN13 (PTPL1, PTP-BAS), PTPN14 (PEZ), PTPN18 (BDP1), PTPN21 (PTPD1), PTPN22 (LYP), and PTPN23 (HD-PTP). In other embodiments, the tyrosine phosphatases can be any of the receptor-type (transmembrane type) PTPases such as, for example, PTPRA (PTPalpha), PTPRB (PTPbeta), PTPRC (CD45), PTPRD (PTPdelta), PTPRE (PTPepsilon), PTPRF (LAR), PTPRG (PTPgamma), PTPRH (SAP1), PTPRJ (PTPeta, DEP1), PTPRK (PTP-kappa), PTPRM (PTPmu), PTPRN (IA2), PTPRN2 (1A2beta), PTPRO (GLEPP1), PTPRR, PTPRS (PTPsigma), PTPRU, PTPRZ1, and PTPRZ2. Other suitable PTPases include, for example, PTP4A1 (PRL1), PTP4A2 (PRL2), PTP4A3 (PRL3), and PTP9q22.

In further embodiments, the target protein can be a PTPase-related protein such as a phosphatidylinositol phosphatase PTEN (phosphatase tensin homolog).

In further embodiments, target proteins of the invention include proteins containing an SH2 domain. Example proteins containing an SH2 domain are provided below in Table A.

TABLE A

| SH2 Domain-Containing Protein: Swissprot Name | Description |
| --- | --- |
| 3BP2_HUMAN | SH3 domain-binding protein 2 (3BP-2). |
| ABL1_HUMAN | Proto-oncogene tyrosine-protein kinase ABL1 (EC 2.7.1.112) (p150) |
| ABL2_HUMAN | Tyrosine-protein kinase ABL2 (EC 2.7.1.112) (Tyrosine kinase ARG) |

TABLE A-continued

SH2 Domain-Containing Protein:

| Swissprot Name | Description |
|---|---|
| BLK_HUMAN | Tyrosine-protein kinase BLK (EC 2.7.1.112) (B lymphocyte kinase) |
| BMX_HUMAN | Cytoplasmic tyrosine-protein kinase BMX (EC 2.7.1.112) (Bone marrow |
| BTK_HUMAN | Tyrosine-protein kinase BTK (EC 2.7.1.112) (Bruton's tyrosine kinase) |
| CHIN_HUMAN | N-chimaerin (NC) (N-chimerin) (Alpha chimerin) (A-chimaerin). |
| CHIO_HUMAN | Beta-chimaerin (Beta-chimerin). |
| CISH_HUMAN | Cytokine-inducible SH2-containing protein (CIS) (CIS-1) (Suppressor |
| CRKL_HUMAN | Crk-like protein. |
| CRK_HUMAN | Proto-oncogene C-crk (P38) (Adapter molecule crk). |
| CSK_HUMAN | Tyrosine-protein kinase CSK (EC 2.7.1.112) (C-SRC kinase) |
| EAT2_HUMAN | EWS/FLI1 activated transcript 2 (EAT-2). |
| FER_HUMAN | Proto-oncogene tyrosine-protein kinase FER (EC 2.7.1.112) (p94-FER) |
| FES_HUMAN | Proto-oncogene tyrosine-protein kinase FES/FPS (EC 2.7.1.112) (C-FES). |
| FGR_HUMAN | Proto-oncogene tyrosine-protein kinase FGR (EC 2.7.1.112) (P55-FGR) |
| FRK_HUMAN | Tyrosine-protein kinase FRK (EC 2.7.1.112) (Nuclear tyrosine protein |
| FYN_HUMAN | Proto-oncogene tyrosine-protein kinase FYN (EC 2.7.1.112) (P59-FYN) |
| GRAP_HUMAN | GRB2-related adaptor protein. |
| GRB2_HUMAN | Growth factor receptor-bound protein 2 (GRB2 adapter protein) |
| GRB7_HUMAN | Growth factor receptor-bound protein 7 (GRB7 adapter protein) |
| GRBA_HUMAN | Growth factor receptor-bound protein 10 (GRB10 adaptor protein) |
| GRBE_HUMAN | Growth factor receptor-bound protein 14 (GRB14 adapter protein). |
| GRP2_HUMAN | GRB2-related adaptor protein 2 (GADS protein) (Growth factor receptor |
| HCK_HUMAN | Tyrosine-protein kinase HCK (EC 2.7.1.112) (p59-HCK/p60-HCK) |
| ITK_HUMAN | Tyrosine-protein kinase ITK/TSK (EC 2.7.1.112) (T-cell-specific |
| JAK1_HUMAN | Tyrosine-protein kinase JAK1 (EC 2.7.1.112) (Janus kinase 1) (JAK-1). |
| JAK2_HUMAN | Tyrosine-protein kinase JAK2 (EC 2.7.1.112) (Janus kinase 2) (JAK-2). |
| JAK3_HUMAN | Tyrosine-protein kinase JAK3 (EC 2.7.1.112) (Janus kinase 3) (JAK-3) |
| KSYK_HUMAN | Tyrosine-protein kinase SYK (BC 2.7.1.112) (Spleen tyrosine kinase). |
| LCK_HUMAN | Proto-oncogene tyrosine-protein kinase LCK (EC 2.7.1.112) (P56-LCK) |
| LCP2_HUMAN | Lymphocyte cytosolic protein 2 (SH2 domain-containing leucocyte |
| LNK_HUMAN | Lymphocyte specific adapter protein Lnk (Signal transduction protein |
| LYN_HUMAN | Tyrosine-protein kinase LYN (EC 2.7.1.112). |
| MATK_HUMAN | Megakaryocyte-associated tyrosine-protein kinase (BC 2.7.1.112) |
| NCK1_HUMAN | Cytoplasmic protein NCK1 (NCK adaptor protein 1) (SH2/SH3 adaptor |
| NCK2_HUMAN | Cytoplasmic protein NCK2 (NCK adaptor protein 2) (SH2/SH3 adaptor |
| P55G_HUMAN | Phosphatidylinositol 3-kinase regulatory gamma subunit (PI3-kinase |
| P85A_HUMAN | Phosphatidylinositol 3-kinase regulatory alpha subunit (PI3-kinase |
| P85B_HUMAN | Phosphatidylinositol 3-kinase regulatory beta subunit (PI3-kinase |
| PIG1_HUMAN | 1-phosphatidylinositol-4,5-bisphosphate phosphodiesterase gamma1 |
| PIG2_HUMAN | 1-phosphatidylinositol-4,5-bisphosphate phosphodiesterase gamma2 |
| PTK6_HUMAN | Tyrosine-protein kinase 6 (EC 2.7.1.112) (Breast tumor kinase) |
| PTN6_HUMAN | Protein-tyrosine phosphatase, non-receptor type 6 (EC 3.1.3.48) |
| PTNB_HUMAN | Protein-tyrosine phosphatase, non-receptor type 11 (EC 3.1.3.48) |
| RIN1_HUMAN | Ras and Rab interactor 1 (Ras interaction/interference protein 1) (Ras |
| RSG1_HUMAN | Ras GTPase-activating protein 1 (GTPase-activating protein) (GAP) (Ras |
| SCK_HUMAN | Protein Sck (Fragment). |
| SH1A_HUMAN | SH2 domain protein 1A (SLAM-associated protein) (T cell signal |
| SH2A_HUMAN | SH2 domain protein 2A (T cell-specific adapter protein) (TSAd) |
| SHC_HUMAN | SHC transforming protein. |
| SOC1_HUMAN | Suppressor of cytokine signaling 1 (SOCS-1) (JAK-binding protein) |
| SOC2_HUMAN | Suppressor of cytokine signaling 2 (SOCS-2) (Cytokine-inducible SH2 |
| SOC3_HUMAN | Suppressor of cytokine signaling 3 (SOCS-3) (Cytokine-inducible SH2 |
| SOC4_HUMAN | Suppressor of cytokine signaling 4 (SOCS-4) (Cytokine-inducible SH2 |
| SOC5_HUMAN | Cytokine inducible SH2-containing protein 5 (Suppressor of cytokine |
| SOC6_HUMAN | Suppressor of cytokine signaling 6 (SOCS-6) (Nck, Ash and |
| SOC7_HUMAN | Suppressor of cytokine signaling 7 (SOCS-7). |
| SRC_HUMAN | Proto-oncogene tyrosine-protein kinase SRC (EC 2.7.1.112) (p60-SRC) |
| SRMS_HUMAN | Tyrosine-protein kinase Srms (EC 2.7.1.112). |
| ST5A_HUMAN | Signal transducer and activator of transcription 5A. |
| ST5B_HUMAN | Signal transducer and activator of transcription 5B. |
| STA1_HUMAN | Signal transducer and activator of transcription 1-alpha/beta |
| STA2_HUMAN | Signal transducer and activator of transcription 2 (p113). |
| STA3_HUMAN | Signal transducer and activator of transcription 3 (Acute-phase |
| STA4_HUMAN | Signal transducer and activator of transcription 4. |
| STA6_HUMAN | Signal transducer and activator of transcription 6 (IL-4 Stat). |
| TEC_HUMAN | Tyrosine-protein kinase Tec (EC 2.7.1.112). |
| TXK_HUMAN | Tyrosine-protein kinase TXK (EC 2.7.1.112). |
| VAV2_HUMAN | Vav-2 protein. |
| VAV3_HUMAN | Vav-3 protein. |
| VAV_HUMAN | Vav proto-oncogene. |
| YES_HUMAN | Proto-oncogene tyrosine-protein kinase YES (EC 2.7.1.112) (p61-YES) |
| ZA70_HUMAN | Tyrosine-protein kinase ZAP-70 (EC 2.7.1.112) (70 kDa zeta-associated |
| O00145 | SHIP.SH2 containing inositol-5-phosphatase. |
| O00428 | Adapter protein (Fragment). |
| O14492 | APS.SH2 and PH domain-containing adapter protein APS. |
| O14916 | STAT3.Transcription factor (Signal transducer and activator of transcrip tion3) (Hypothetical protein). |
| O15357 | SHIP2.Inositol polyphosphate 5-phosphatase. |
| O75498 | B cell linker protein BLNK. |
| O75499 | B cell linker protein BLNK-S. |
| O75815 | BCAR3.Breast cancer ANTIESTROGEN resistance 3 protein (DJ1033H22.2). |
| P78453 | C-FGR.Tyrosine kinase (FGR proto-oncogene encoded P55-C-FGR protein)(Fragment). |
| Q12897 | Phospholipase C-like (Fragment). |
| Q13196 | P72SYK.P72syk. |
| Q13545 | Signaling inositol polyphosphate 5 phosphatase SIP-145(Fragment). |
| Q13848 | Bcr/c-abl oncogene protein (Fragment). |
| Q13915 | ABL1.C-abl (Fragment). |
| Q14020 | Bcr/c-abl oncogene protein (Fragment). |
| Q15464 | Shb. |

TABLE A-continued

| SH2 Domain-Containing Protein: Swissprot Name | Description |
|---|---|
| Q15737 | SUPT6H OR SPTH6.SUPT6H (EMB-5) (Chromatin structural protein). |
| Q16176 | LSK.Lsk protein. |
| Q16248 | Tyrosine kinase p59fyn(T). |
| Q8IXA2 | Phosphoinositide 3-kinase p85 subunit splicing variant p46. |
| Q8IXP2 | Janus kinase 2 (a protein tyrosine kinase). |
| Q8IYW3 | Similar to SHC. |
| Q8IYZ4 | SOCS5 OR CISH5 OR CIS6 OR CISH6 OR KIAA0671.Cytokine inducible SH2-containing protein 5 |
| Q8IZW7 | Tensin 3. |
| Q8IZW8 | C-terminal tensin-like protein. |
| Q8NIC5 | Similar to phosphoinositide 3-kinase p85. |
| Q8NIE8 | Similar to janus kinase 3 (a protein tyrosine kinase, leukocyte). |
| Q8N381 | Hypothetical protein. |
| Q8N4K5 | Hypothetical protein. |
| Q8N5D7 | Hypothetical protein. |
| Q8N5H7 | SH2 domain-containing 3C. |
| Q8N6X3 | SH2 domain-containing 3C. |
| Q8NDL6 | DKFZP43412435.Hypothetical protein (Fragment). |
| Q8NFF9 | KIAA1075.KIAA1075 protein splice variant 1. |
| Q8NFG0 | Hypothetical protein. |
| Q8NI18 | EWS/FLI1 activated transcript 2-like protein. |
| Q8TAP2 | Neuronal Shc. |
| Q8TC17 | Hypothetical protein (Fragment). |
| Q8TEQ5 | FLJ00138.FLJ00138 protein (Fragment). |
| Q8WB28 | ND3.NADH dehydrogenase subunit 3. |
| Q8WUM3 | Hypothetical protein. |
| Q8WV28 | B-cell linker. |
| Q8WV64 | Hypothetical protein. |
| Q8WWS8 | Partial STAT5B signal transducer and activator of transcription 5B, exon2 and joined CDS. |
| Q8WWS9 | STAT5A.Signal transducer and activator of transcription 5A. |
| Q92529 | P64 isoform of N-SHC (P52 isoform of N-SHC). |
| Q92656 | HP51CN.Inositol polyphosphate 5-phosphatase. |
| Q92835 | HSHIP.SH2-containing inositol 5-phosphatase. |
| Q969V8 | PTPN6 OR PTP1C OR HCP.Protein-tyrosine phosphatase, non-receptor type 6(EC 3.1.3.48) |
| Q96AH3 | Hypothetical protein (Fragment). |
| Q96C88 | Similar to hypothetical protein FLJ20967. |
| Q96CK7 | Hypothetical protein. |
| Q96CL1 | Hypothetical protein. |
| Q96D37 | Hypothetical protein. |
| Q96EV4 | Hypothetical protein (Fragment). |
| Q96FK3 | Hypothetical protein. |
| Q96GA9 | Similar to v-crk avian sarcoma virus CT10 oncogene homolog. |
| Q96HD7 | Protein tyrosine phosphatase, non-receptor type 11 (Noonan syndrome1). |
| Q96HJ0 | V-crk avian sarcoma virus CT10 oncogene homolog (V-crk sarcoma virus CT10 oncogene homolog) (Avian). |
| Q96IE8 | Hypothetical protein (Fragment). |
| Q96IN1 | Hypothetical protein (B lymphoid tyrosine kinase). |
| Q96IW2 | Similar to src homology 2 domain-containing transforming proteinD. |
| Q96JV4 | Hypothetical protein FLJ14950. |
| Q96JZ2 | Hypothetical protein FLJ14886 (Hematopoietic SH2 protein). |
| Q96NC2 | Hypothetical protein FLJ31111. |
| Q96PE0 | TEM6.Tumor endothelial marker 6. |
| Q96S48 | Thyroid specific PTB domain protein. |
| Q96SX3 | Hypothetical protein FLJ14582. |
| Q99699 | JAK3.JAK3. |
| Q9BQD2 | Signal transducer and activator of transcription 6, interleukin-4induced |
| Q9BRG2 | Hypothetical protein. |
| Q9BTH9 | Hypothetical protein (Fragment). |
| Q9BTI2 | Similar to suppressor of Ty (S. cerevisiae) 6 homolog (Fragment). |
| Q9BW54 | Signal transducer and activator of transcription 3. |
| Q9BZ10 | FRK.BA702N8.1 (Fyn-related kinase) (Fragment). |
| Q9H788 | Hypothetical protein FLJ21146. |
| Q9H7F7 | Hypothetical protein FLJ20967. |
| Q9H8D5 | Hypothetical protein FLJ13732. |
| Q9HAG1 | RIN3.Ras and Rab interactor 3 (Ras interaction/interference protein 3). |
| Q9HBL0 | Tensin. |
| Q9NPN8 | Similar to (NP_033194.1) src homology 2 domain-containing transforming protein D (Fragment). |
| Q9NRB7 | GRID.Adapter protein GRID. |
| Q9NRF1 | SH2B.SH2-B gamma signaling protein. |
| Q9NRF2 | SH2B OR DKFZP7271201.SH2-B beta signaling protein (Hypothetical protein) |
| Q9NRF3 | SH2B.SH2-B alpha signaling protein. |
| Q9NST8 | DKFZP434N1212.Hypothetical protein (Fragment). |
| Q9NT29 | DKFZP434D098.Hypothetical protein (Fragment). |
| Q9NXI2 | Hypothetical protein FLJ20234. |
| Q9P2P7 | KIAA1299.Hypothetical protein KIAA1299 (Fragment). |
| Q9P2U9 | MIST.MIST (Fragment). |
| Q9UCX4 | SLI, SHCB = 53.6 kDa SHC-related protein/SCK homolog. |
| Q9UCX5 | RAI, SHCC = 51.9 kDa SHC-related protein. |
| Q9UE80 | Signaling inositol polyphosphate phosphatase SHIP II. |
| Q9UFN8 | DKFZP434G162.Hypothetical protein (Fragment). |
| Q9UGK3 | BKS.BRK kinase substrate (Hypothetical protein). |
| Q9UHF2 | BAM32.B lymphocyte adapter protein BAM32. |
| Q9UK67 | 70 kDa SHP-1L protein. |
| Q9ULZ2 | BRDG1.Docking protein BRDG1 (BCR downstream signaling 1). |
| Q9UN19 | DAPP1.Adaptor protein DAPP1 (Protein-tyrosine phosphatase D) (HSPC066). |
| Q9UPH9 | PIK3R2.P85B_HUMAN. |
| Q9UPS7 | Tensin2. |
| Q9Y2X4 | SH2-containing protein Nsp1. |
| Q9Y2X5 | SH2-containing protein Nsp3. |
| Q9Y3Y3 | DKFZP564G1182.Hypothetical protein (Fragment). |
| Q9Y6S2 | JAK3.JAK3_HUMAN (Janus kinase 3) (a protein tyrosine kinase, leukocyte). |

In yet further embodiments, target proteins of the invention can contain a PTB domain (or PID for phosphotyrosine interacting domains). Example proteins containing a PTB domain include SHC (accession number P29353), SHK (accession number P98077), ANSI (accession number Q92625).

Futher target proteins can contain FHA domains that can bind, for example, phosphothreonine or phosphotyrosine. Example proteins containing an FHA domain include CHK2 (accession number 096017) and protein phosphatase-1.

Yet further target proteins include 14-3-3 proteins that bind phosphoserine and phosphothreonine. Some example 14-3-3 protein are KCIP-1 (accession number P29312) and stratifin (accession number P31947).

Activity of phosphatases such as PTP1B is known to be associated with a variety of diseases, including for example, diabetes and obesity. Thus, the compounds of the invention can be useful in the treatment of phosphatase-related diseases such as diabetes (e.g., Type 2 diabetes) and obesity. Other phosphatase-related diseases and disorders include autoimmune diseases, infectious diseases, inflammation, osteoporosis, cancer, neurodegenerative diseases, and the like.

Activity of proteins containing an SH2 domain is also known to be associated with a variety of diseases. Thus, the compounds of the invention can be useful in the treatment of cancers (e.g., Grb2), osteoporosis (e.g., Src), and autoimmune diseases (e.g., ZAP-70). Other SH2 domain-related diseases and disorders include infectious diseases, inflammation, neurodegenerative diseases, and the like.

Pharmaceutical Formulations and Dosage Forms

When employed as pharmaceuticals, the compounds of the invention can be administered in the form of pharmaceutical compositions. These compositions can be administered by a variety of routes including oral, rectal, transdermal, subcutaneous, intravenous, intramuscular, and intranasal, and can be prepared in a manner well known in the pharmaceutical art.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. In some embodiments, the active compound can be prepared in the form of nanoparticles having an average particle size of less than, for example, about 400 nm as described in U.S. Pat. No. 5,145,684, which is incorporated herein by reference in its entirety.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. An amount adequate to accomplish this is referred to as "therapeutically effective amount." Effective doses will depend on the disease condition being treated as well as by the judgement of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral adminstration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present invention also includes pharmaceutical kits useful, for example, in the treatment or prevention of diseases involving insulin resistance, which comprise one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention is described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example compounds according to the present invention and example assays for determining activity of the compounds are provided below. Examples where Het is:

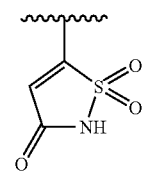

are numbered 1.n; examples where Het is:

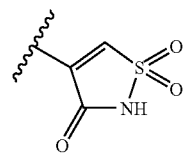

are numbered 2.n; examples where Het is:

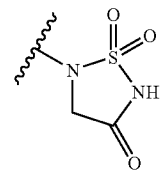

are numbered 3.n; and examples where Het is:

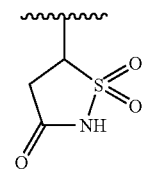

are numbered 4.n, and examples where Het is:

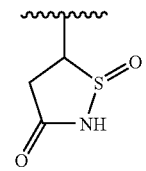

are numbered 5.n, and examples where Het is:

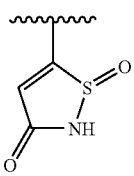

are numbered 6.n, where n is an integer. The compounds of the Examples have been tested for activity according to the PTPB1 assay of Example A provided below and have been found active with $IC_{50}$ values less than 30 μM.

Example 1.1

(S)-2-((S)-3-Phenyl-2-{2-[4-(1,1,3-trioxo-2,3-dihydro-1H-1λ⁶-isothiazol -5-yl)-phenyl]-acetylamino}-propionylamino)-3-[4-(1,1,3-trioxo-2,3-dihydro-1H-1λ⁶-isothiazol-5-yl)-phenyl]-propionamide

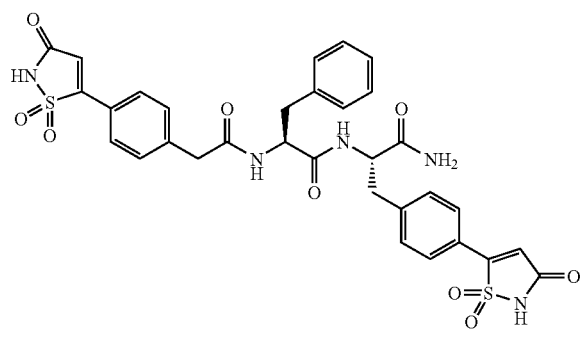

Step 1. 2-tert-butyl-5-chloro-isothiazol-3-one (1-A) and 2-tert-butyl-isothiazol-3-one (1-B)

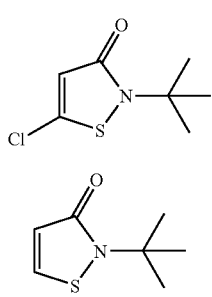

A stirred solution of N-tert-butyl-3-(2-tert-butylcarbamoyl-ethyldisulfanyl)-propionamide (*Journal of Heterocyclic Chemistry* (1971), 8(4), 571–80) (11.3 g, 35 mmol) in dichloroethane (177 mL) was treated with sulfuryl chloride (8.5 mL, 106 mmol). The reaction mixture was stirred at 25° C. for 3 h, diluted with $CH_2Cl_2$ (150 mL) and $H_2O$ (250 mL). The organic layer was separated, dried with $Na_2SO_4$, filtered, and concentrated in vacuo to a crude yellow oil which was purified using flash column chromatography (100% hexane→40% EtOAc/hexane) to yield 1-A as a white glassy solid (4.3 g, 63%) and 1-B as a yellow-white solid (2.8 g, 50%). 1-A: $^1H$ NMR (400 MHz, $CDCl_3$): δ 6.19 (s, 1H), 1.62 (s, 9H); LCMS found for $C_7H_{11}ClNOS$ $(M+H)^+$: m/z=192. 1-B: $^1H$ NMR (400 MHz, $CDCl_3$): δ 7.91 (d, J=6.2 Hz, 1H), 6.16 (d, J=6.1 Hz, 1H), 1.62 (s, 9H); LCMS found for $C_7H_{12}NOS$ $(M+H)^+$: m/z=158.

Step 2. [4-(2-tert-Butyl-3-oxo-2,3-dihydro-isothiazol-5-yl)-phenyl]-acetic acid methyl ester (1-C)

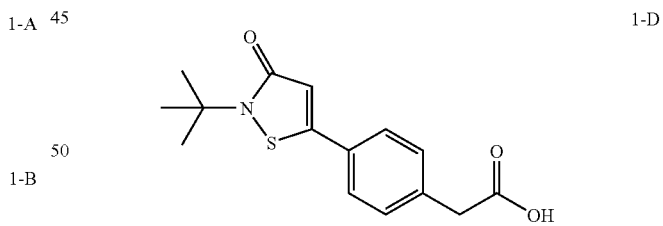

A solution of 4-borono-benzeneacetic acid α-methyl ester (*Organic Letters* (2002), 4(16), 2675–2678) (0.3 g, 1.6 mmol), 1-A (0.1 g, 0.52 mmol), and 2 N $Na_2CO_3$ (1 mL) in toluene (2.5 mL) was degassed with nitrogen for 5 min. The reaction mixture was treated with $Pd(PPh_3)_4$ (18 mg, 16 μmol), degassed with nitrogen for 5 min, and heated at 150° C. for 5 min in a microwave. The reaction mixture was diluted with EtOAc (10 mL) and washed with $H_2O$ (2×10 mL), brine (10 mL), dried with $Na_2SO_4$, filtered, and concentrated in vacuo to a crude yellow oil which was purified using flash column chromatography (10%→40% EtOAc/hexane) to yield 1-C as a white solid (98 mg, 62%). $^1H$ NMR (400 MHz, $CDCl_3$): δ 7.44 (d, J=8.4 Hz, 2H), 7.36 (d, J=8.4 Hz, 2H), 6.40 (s, 1H), 3.72 (s, 3H), 3.67 (s, 2H), 1.68 (s, 9H); LCMS found for $C_{16}H_{20}NO_3S$ $(M+H)^+$: m/z=306.

Step 3. [4-(2-tert-Butyl-3-oxo-2,3-dihydro-isothiazol-5-yl)-phenyl]-acetic acid (1-D)

A solution of 1-C (0.35 g, 1.2 mmol) and 10% LiOH (0.8 mL, 3.5 mmol) in THF (4 mL) and methanol (1 mL) was stirred at 25° C. for 2 h. The reaction mixture was diluted with 1 N NaOH (75 mL) and extracted with $CH_2Cl_2$ (3×25 mL). The aqueous layer was adjusted to pH~2 with 10% HCl and extracted with EtOAc (3×50 mL). The combined organic layers were dried with $Na_2SO_4$, filtered, and concentrated in vacuo to yield 1-D as a brown solid (quantitative) which was used in the next step without further purification. $^1H$ NMR (400 MHz, $CD_3OD$): δ 7.57 (d, J=8.2 Hz, 2H), 7.42 (d, J=8.0 Hz, 2H), 6.51 (s, 1H), 3.67 (s, 2H), 1.68 (s, 9H); LCMS found for $C_{15}H_{16}NO_3S$ $(M-H)^-$: m/z=290.

Step 4. Synthesis of {(S)-1-Carbamoyl-2-[4-(1,1,3-trioxo-2,3-dihydro-1H-1λ⁶-isothiazol-5-yl)-phenyl]-ethyl}-carbamic acid tert-butyl ester (1-E)

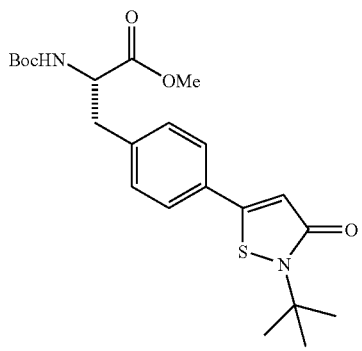

1-E

A stirred solution of 1-A (1.0 g, 3.1 mmol), 4-borono-N-[(1,1-dimethylethoxy)carbonyl]-L-Phenylalanine α-methyl ester (*J. Org. Chem.* (1999), 64, 2976–2977) (0.65 g, 3.4 mmol), PdCl$_2$(dppf) CH$_2$Cl$_2$ (0.16 g, 0.22 mmol), and K$_2$CO$_3$ (2.1 g, 15.5 mmol) in dimethoxyethane (11 mL) was degassed with nitrogen for 10 min and heated to 80° C. in a sealed tube for 24 h. The reaction mixture was filtered over a short pad of silica gel, washed with EtOAc, concentrated in vacuo, and purified using flash column chromatography (100% hexane→50% EtOAc/hexane) to yield 1-E as a white-yellow solid (0.79 g, 59%). $^1$H NMR (400 MHz, CDCl$_3$): δ 7.40 (d, J=8.2 Hz, 2H), 7.20 (d, J=8.0 Hz, 2H), 6.39 (s, 1H), 5.02 (d, J=8.2 Hz, 1H), 4.62 (dd, J=12.5, 5.7 Hz, 1H), 3.73 (s, 3H), 3.18 (dd, J=13.9, 6.1 Hz, 1H) 3.07 (dd, J=14.1, 6.5 Hz, 1H), 1.68 (s, 9H), 1.42 (s, 9H); LCMS found for C$_{22}$H$_{31}$N$_2$O$_5$S (M+H)$^+$: m/z=435.

Step 5. (S)-2-tert-Butoxycarbonylamino-3-[4-(2-tert-butyl-3-oxo-2,3-dihydro-isothiazol-5-yl)-phenyl]-propionic acid (1-F)

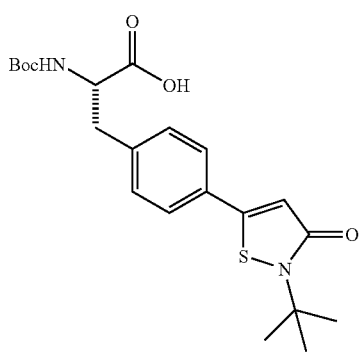

1-F

Compound 1-F was prepared according to the procedure of Example 1.1, Step 3, using 1-E as the starting material, and used in the next step without further purification. $^1$H NMR (400 MHz, CD$_3$OD): δ 7.53 (d, J=8.0 Hz, 2H), 7.37 (d, J=8.0 Hz, 2H), 6.48 (s, 1H), 4.37 (dd, J=9.4, 5.1 Hz, 1H), 3.23 (dd, J=14.3, 5.3 Hz, 1H), 2.95 (dd, J=13.7, 9.4 Hz, 1H), 1.68 (s, 9H), 1.37 (s, 9H); LCMS found for C$_{21}$H$_{29}$N$_2$O$_5$S (M+H)$^+$: m/z=420.

Step 6. {(S)-2-[4-(2-tert-Butyl-3-oxo-2,3-dihydro-isothiazol-5-yl)-phenyl]-1-carbamoyl-ethyl}-carbamic acid tert-butyl ester (1-G)

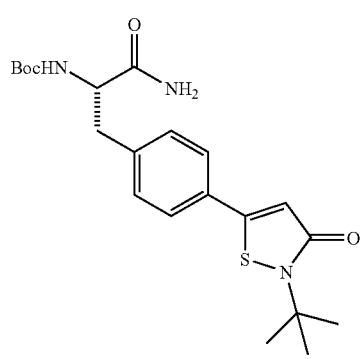

1-G

A solution of 1-F (0.76 g, 1.8 mmol), Boc$_2$O (0.52 g, 2.4 mmol), pyridine (99 μL, 1.3 mmol), and NH$_4$CO$_3$H (0.22 g, 2.8 mmol) in dioxane (4 mL) and DMF (1 mL) was stirred at 25° C. for 12 h. The reaction mixture was diluted with EtOAc (100 mL) and washed with 0.1 N HCl (2×20 mL), saturated NaHCO$_3$ (2×20 mL), and brine (20 mL), dried with Na$_2$SO$_4$, filtered, and concentrated to give a crude residue which was purified using flash column chromatography (100% CH$_2$Cl$_2$→10% MeOH/CH$_2$Cl$_2$) to yield 1-G as a brown-red solid (0.76 g, 100%). $^1$H NMR (400 MHz, CDCl$_3$): δ 7.41 (d, J=8.2 Hz, 2H), 7.30 (d, J=8.2 Hz, 2H), 6.38 (s, 1H), 6.01 (br s, 1H), 5.45 (br s, 1H), 5.15–5.10 (m, 1H), 4.50–4.38 (m, 1H), 3.15 (dd, J=13.9, 6.8 Hz, 1H), 3.08 (dd, J=13.5, 6.5 Hz, 1H), 1.68 (s, 9H), 1.41 (s, 9H); LCMS found for C$_{21}$H$_{30}$N$_3$O$_4$S (M+H)$^+$: m/z=420.

Step 7. (S)-2-Amino-3-[4-(2-tert-butyl-3-oxo-2,3-dihydro-isothiazol-5-yl)-phenyl]-propionamide trifluoroacetate (1-H)

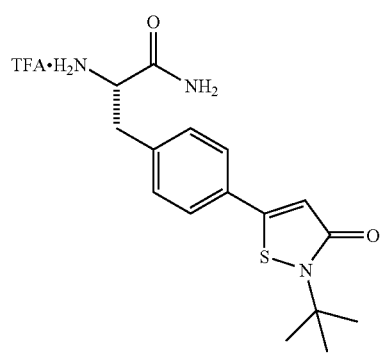

1-H

A solution of 1-G (0.76 g, 1.8 mmol) in 30% TFA in CH$_2$Cl$_2$ (15 mL) was stirred at 25° C. for 2 h. The reaction mixture was concentrated in vacuo to give a solid. The salt was co-evaporated with toluene (2×20 mL) to yield 1-H as a tan solid (quantitative) which was used in the next step without further purification.

Step 8. ((S)-1-{(S)-2-[4-(2-tert-Butyl-3-oxo-2,3-dihydro-isothiazol-5-yl)-phenyl]-1-carbamoyl-ethylcarbamoyl}-2-phenyl-ethyl)-carbamic acid tert-butyl ester (1-I)

Step 9. (S)-2-Amino-N-{(S)-2-[4-(2-tert-butyl-3-oxo-2,3-dihydro-isothiazol-5-yl)-phenyl]-1-carbamoyl-ethyl}-3-phenyl-propionamide trifluoroacetate (1-J)

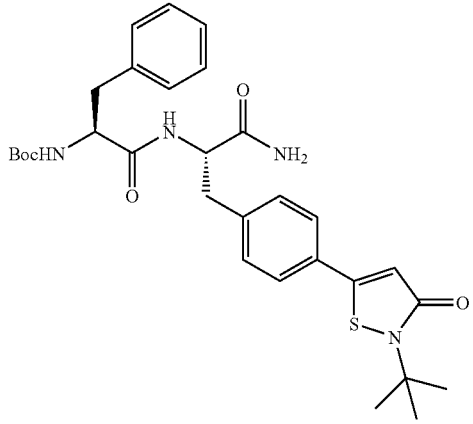

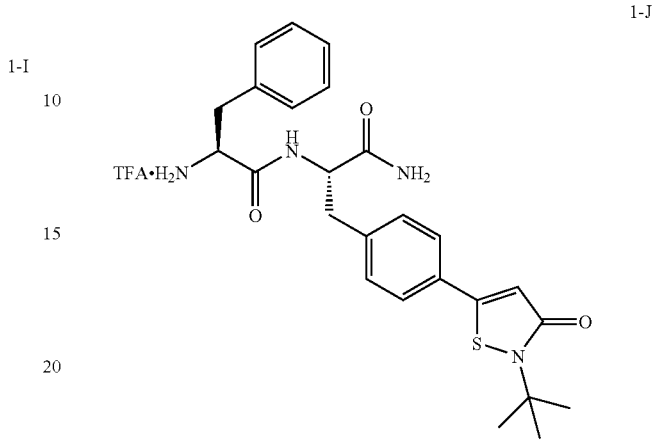

A solution of 1-H (0.37 g, 0.86 mmol), PheBocOH (0.27 g, 1.0 mmol), HOAt (0.35 μL, 0.2 mmol), and DIEA (0.38 mL, 1.9 mmol) in $CH_2Cl_2$ (3 mL) and DMF (1 mL) was treated with EDC (0.25 g, 1.3 mmol) and stirred at 25° C. for 4 h. The reaction mixture was diluted with EtOAc (50 mL) and washed with 0.1 N HCl (2×20 mL), saturated $NaHCO_3$ (2×20 mL), and brine (20 mL), dried with $Na_2SO_4$, filtered, and concentrated to give a crude residue which was purified using flash column chromatography (5% MeOH/$CH_2Cl_2$) to yield 1-I as a tan solid (0.48 g, 99%). $^1$H NMR (400 MHz, $CDCl_3$): δ 7.36–7.20 (m, 5H), 7.17 (d, J=7.0 Hz, 2H), 7.12 (d, J=7.4 Hz, 2H), 6.50–6.45 (m, 1H), 6.36 (s, 1H), 6.16 (br s, 1H), 5.27 (br s, 1H), 4.89 (d, J=5.9 Hz, 1H), 4.74 (d, J=7.0 Hz, 1H), 4.28 (dd, J=12.5, 6.1, 1H), 3.30–3.18 (m, 1H), 3.10–2.95 (m, 3H), 1.67 (s, 9H), 1.31 (s, 9H); LCMS found for $C_{30}H_{39}N_4O_5S$ (M+H)$^+$: m/z=567.

Compound 1-J was prepared according to the procedure of Example 1.1, Step 7, using 1-I as the starting material. $^1$H NMR (400 MHz, $CD_3OD$): δ 7.54 (d, J=8.4 Hz, 2H), 7.41 (d, J=8.2 Hz, 2H), 7.37–7.26 (m, 5H), 6.48 (s, 1H), 4.84 (s, 1H), 4.70 (dd, J=8.4, 6.1 Hz, 1H), 4.07 (dd, J=8.6, 5.3 Hz, 1H), 3.80 (s, 1H), 3.28–3.17 (m, 2H), 3.04–2.95 (m, 2H), 1.68 (s, 9H); LCMS found for $C_{25}H_{31}N_4O_3S$ (M+H)$^+$: m/z=467.

Step 10. (S)-3-[4-(2-tert-Butyl-3-oxo-2,3-dihydro-isothiazol-5-yl)-phenyl]-2-((S)-2-{2-[4-(2-tert-butyl-3-oxo-2,3-dihydro-isothiazol-5-yl)-phenyl]-acetylamino}-3-phenyl-propionylamino)-propionamide (1-K)

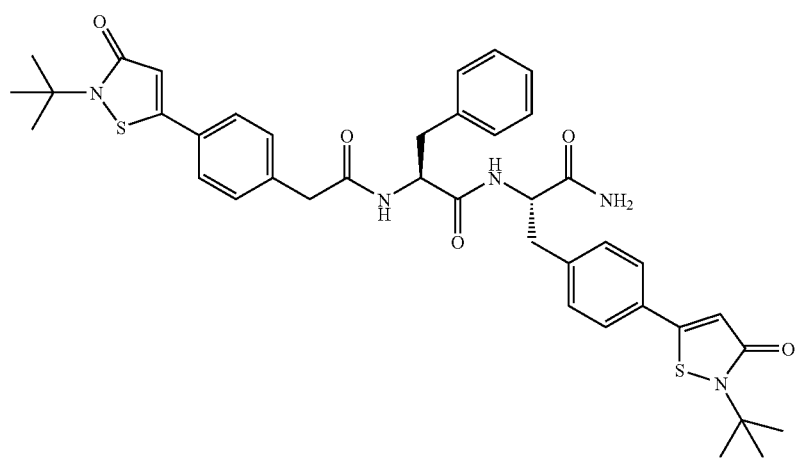

Compound 1-K was prepared according to the procedure of Example 1.1, Step 8, using 1-J and 1-D as starting materials. $^1$H NMR (400 MHz, $CDCl_3$): δ 7.68 (d, J=8.2 Hz, 1H), 7.40–7.37 (m, 4H), 7.28–7.16 (m, 7H), 7.11–7.05 (m, 2H), 7.00 (d, J=7.8 Hz, 1H), 6.42 (s, 1H), 6.39 (s, 1H), 4.59 (dd, J=13.3, 5.5 Hz, 2H), 3.47 (s, 2H), 3.14 (dd, J=13.9, 6.3

Hz, 1H), 3.01–2.83 (m, 3H), 1.69 (s, 9H), 1.66 (s, 9H); LCMS found for $C_{40}H_{46}N_5O_5S_2$ (M+H)$^+$: m/z=740.

Step 11. (S)-3-[4-(2-tert-Butyl-1,1,3-trioxo-2,3-dihydro-1H-1λ$^6$-isothiazol-5-yl)-phenyl]-2-((S)-2-{2-[4-(2-tert-butyl-1,1,3-trioxo-2,3-dihydro-1H-1λ$^6$-isothiazol-5-yl)-phenyl]-acetylamino}-3-phenyl-propionylamino)-propionamide (1-L)

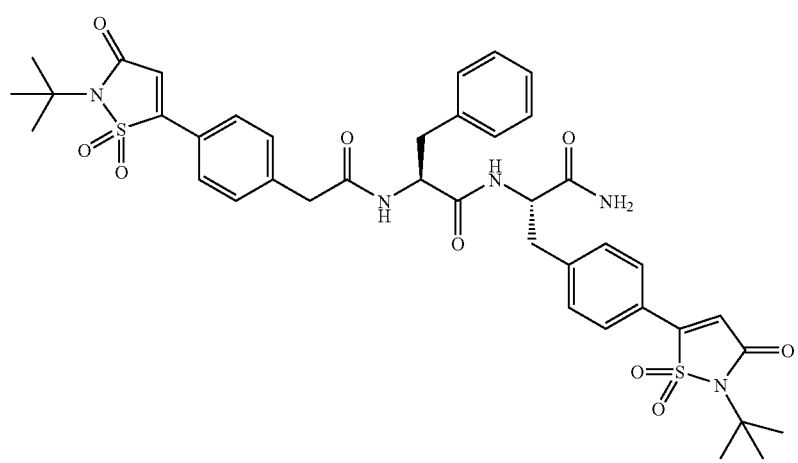

1-L

A solution of 1-K (0.18 g, 0.24 mmol) in CH$_2$Cl$_2$ (5 mL) and MeOH (0.5 mL) at 0° C. was treated with m-CPBA (0.28 g, 1.2 mmol) portionwise. The reaction mixture was stirred at 25° C. for 48 h, diluted with CH$_2$Cl$_2$ (20 mL) and H$_2$O (20 mL). The organic layer was separated and washed with 10% sodium bisulfite (2×20 mL) and NaHCO$_3$ (2×20 mL), dried with Na$_2$SO$_4$, filtered, and concentrated to give a crude residue which was purified using preparative HPLC (20% CH$_3$CN/H$_2$O→100% CH$_3$CN) to yield 1-L as a white solid (83 mg, 43%). $^1$H NMR (400 MHz, CD$_3$OD): δ 8.23 (d, J=8.4 Hz, 1H), 7.76 (d, J=8.4 Hz, 2H), 7.70 (d, J=8.4 Hz, 2H), 7.42 (d, J=8.6 Hz, 2H), 7.23–7.16 (m, 6H), 7.04 (s, 1H), 7.01 (s, 1H), 4.69–4.63 (m, 2H), 3.51 (2, 2H), 3.23 (dd, J=14.3, 5.1 Hz, 1H), 3.09 (dd, J=13.7, 5.1 Hz, 1H), 2.97 (dd, J=13.9, 9.0 Hz, 1H), 2.83 (dd, J=13.5, 9.6 Hz, 1H), 1.71 (s, 9H), 1.69 (s, 9H); LCMS found for $C_{40}H_{46}N_5O_9S_2$ (M+H)$^+$: m/z=804.

Step 12. (S)-2-((S)-3-Phenyl-2-{2-[4-(1,1,3-trioxo-2,3-dihydro-1H-1λ$^6$-isothiazol-5-yl)-phenyl]-acetylamino}-propionylamino)-3-[4-(1,1,3-trioxo-2,3-dihydro-1H-1λ$^6$-isothiazol-5-yl) -phenyl]-propionamide A stirred solution of 1-L (83 mg, 0.1 mmol) in TFA was heated at 80° C. for 16 h. The reaction mixture was concentrated and purified using preparative HPLC (100% H$_2$O→50% CH$_3$CN/H$_2$O) to yield Example 1.1 as a white solid (18 mg, 25%). $^1$H NMR (400 MHz, CD$_3$OD): δ 8.34 (d, J=8.4 Hz, 1H), 8.16 (d, J=8.4 Hz, 1H), 7.77 (d, J=8.2 Hz, 2H), 7.68 (d, J=8.2 Hz, 2H), 7.40 (d, J=8.2 Hz, 2H), 7.37–7.11 (m, 10H), 4.52–4.46 (m, 2H), 3.48 (d, J=14.1 Hz, 1H), 3.37 (d, J=14.1 Hz, 1H), 3.07 (dd, J=13.7, 4.9 Hz, 1H), 2.98–2.87 (m, 2H), 2.68 (dd, J=14.1, 10.6 Hz, 1H); LCMS found for $C_{32}H_{30}N_5O_9S_2$ (M+H)$^+$: m/z=692.

Example 1.2

N-{1-Carbamoyl-2-[4-(1,1,3-trioxo-2,3-dihydro-1H-1λ$^6$-isothiazol-5-yl)-phenyl]-ethyl}-3-{2-[4-(1,1,3-trioxo-2,3-dihydro-1H-1λ$^6$-isothiazol-5-yl)-phenyl]-acetylamino}-succinamic acid

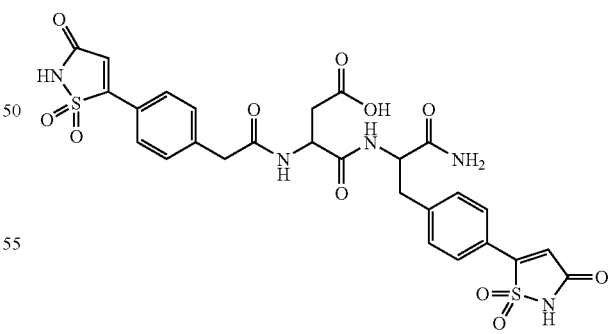

This compound was prepared according to the procedure of Example 1.1 using appropriate reagents and starting materials. $^1$H NMR (400 MHz, CD$_3$OD): δ 7.86–7.78 (m, 4H), 7.50–7.39 (m, 4H), 7.05–6.98 (m, 2H), 4.70–4.60 (m, 2H), 3.71 (s, 2H), 3.66–3.63 (m, 2H), 3.00–2.80 (m, 2H), 2.65–2.60 (m, 1H); LCMS found for $C_{27}H_{24}N_5O_{11}S_2$ (M−H)$^-$: m/z=658.

Example 1.3

5-(3-Benzyloxy-phenyl)-1,1-dioxo-1,2-dihydro-1λ⁶-isothiazol-3-one

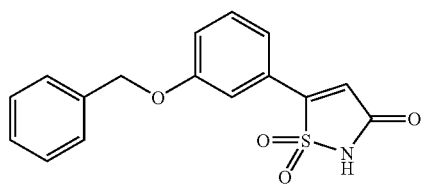

Step 1. 5-(3-Benzyloxy-phenyl)-2-tert-butyl-isothiazol-3-one (3-A)

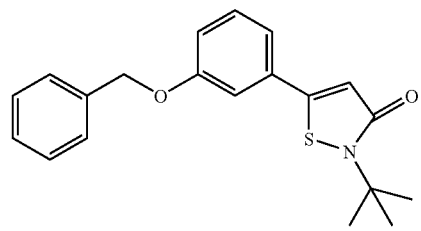

3-A

Compound 3-A was prepared, using 1-A and 3-benzyloxyphenylboronic acid as the starting materials, according to the procedure of Example 1.1, Step 2, as a colorless solid (122 mg, 69%). $^1$H NMR (400 MHz, CDCl$_3$): δ 7.45–7.33 (m, 7H), 7.28–7.26 (m, 1H), 7.13–7.10 (m, 1H), 6.63 (s, 1H), 5.11 (s, 2H), 1.69 (s, 9H); LCMS found for C$_{20}$H$_{22}$NO$_2$S (M+H)⁺: m/z=340.

Step 2. 5-(3-Benzyloxy-phenyl)-2-tert-butyl-1,1-dioxo-1,2-dihydro-1λ⁶-isothiazol-3-one (3-B)

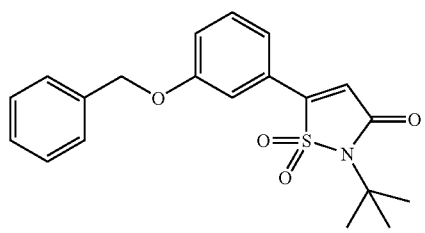

3-B

Compound 3-B was prepared, using 3-A as the starting material, according to the procedure of Example 1.1, Step 11, as a colorless solid (122 mg, 69%). $^1$H NMR (400 MHz, CDCl$_3$): δ 7.45 –7.33 (m, 8H), 7.17–7.14 (m, 1H), 6.61 (s, 1H), 5.11 (s, 2H), 1.73 (s, 9H); LCMS found for C$_{20}$H$_{22}$NO$_4$S (M+H)⁺: m/z=372.

Step 3. 5-(3-Benzyloxy-phenyl)-1,1-dioxo-1,2-dihydro-1λ⁶-isothiazol-3-one

A stirred solution of 3-B (100 mg, 0.3 mmol) in TFA was heated at reflux for 2 h. The reaction mixture was concentrated and purified using preparative HPLC (100% H$_2$O→50% CH$_3$CN/H$_2$O) to yield Example 1.3 (4 mg, 5%) as a yellow solid. $^1$H NMR (400 MHz, CD$_3$OD): δ 7.30–7.15 (m, 9H), 6.89 (br s, 1H), 3.99 (br s, 2H); LCMS found for C$_{16}$H$_{12}$NO$_4$S (M–H)⁻: m/z=314.

Example 1.4

5-(3-Hydroxy-phenyl)-1,1-dioxo-1,2-dihydro-1λ⁶-isothiazol-3-one

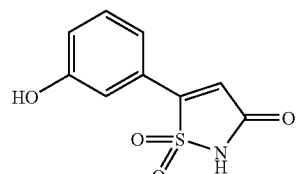

During the HPLC purification of Example 1.3, a small amount of Example 1.4 was isolated. $^1$H NMR (400 MHz, DMSO-d$_6$): δ 10.0 (br s, 1H), 7.38–7.26 (m, 4H), 6.98 (d, J=7.2 Hz, 1H); LCMS found for C$_9$H$_6$NO$_4$S (M–H)⁻: m/z=224.

Example 1.5

2-tert-Butyl-1,1-dioxo-5-(3-{4-[3-(1,1,3-trioxo-2,3-dihydro-1H-1λ⁶-isothiazol-5-yl)phenoxy]-butoxy}-phenyl)-1,2-dihydro-1λ⁶-isothiazol-3-one

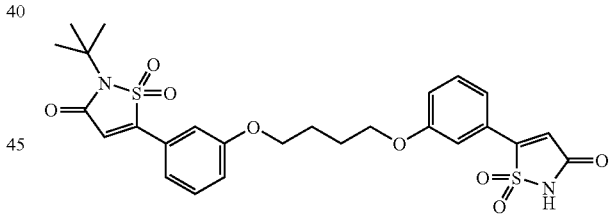

Step 1. 2-tert-Butyl-5-(3-hydroxy-phenyl)-isothiazol 3-one (5-A)

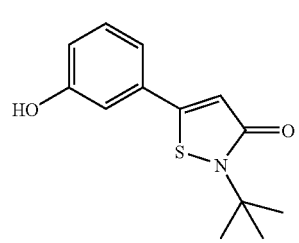

5-A

A stirred solution of 3-A (2.0 g, 6.0 mmol) in TFA was heated at 75° C. for 1 h. The reaction mixture was concentrated and purified using flash column chromatography (100% hexane →35% EtOAc/hexane) to yield 5-A as an off-white solid (0.81 g, 54%). $^1$H NMR (400 MHz, DMSO-$d_6$): δ 9.82 (s, 1H), 7.27 (dd, J=7.8, 7.8 Hz, 1H), 7.03 (ddd, J=7.6, 1.8, 1.0 Hz, 1H), 6.95 (dd, J=2.0, 2.0 Hz, 1H), 6.88 (ddd, J=8.2, 2.3, 0.8 Hz, 1H), 6.57 (s, 1H), 1.57 (s, 9H); LCMS found for $C_{13}H_{14}NO_2S$ (M−H)$^-$: m/z=248.

Step 2, 5'-[butane-1,4-diylbis(oxy-3,1-phenylene)]bis(2-tert-butylisothiazol-3(2H)-one) 5-B

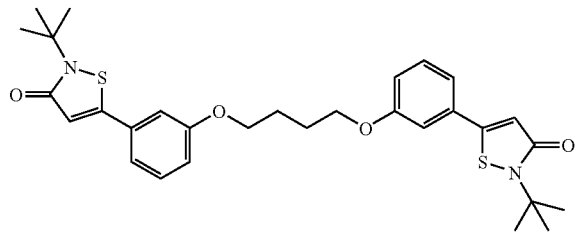

5-B

A stirred solution of 5-A (0.3 g, 1.2 mmol), 1,4-dibromobutane (70 ml, 0.6 mmol), and cesium carbonate (0.59 g, 1.8 mmol) in acetonitrile was heated at reflux for 24 h. The reaction mixture was cooled, filtered over a short pad of silica gel, and concentrated to give a crude solid which was purified using flash column chromatography (5% MeOH/CH$_2$Cl$_2$) to yield 5-B as a white solid (0.19 g, 60%). $^1$H NMR (400 MHz, CDCl$_3$): δ 7.36–7.32 (m, 2H), 7.06 (ddd, J=7.6, 1.6, 1.0 Hz, 2H), 6.98–6.96 (m, 4H), 6.40 (s, 2H), 4.15–4.02 (m, 4H), 2.05–2.01 (m, 4H), 1.68 (s, 18H); LCMS found for $C_{30}H_{37}N_2O_4S_2$ (M+H)$^+$: m/z=553.

Step 3. 5,5'-[butane-1,4-diylbis(oxy-3,1-phenylene)]bis(2-tert-butylisothiazol-3(2H)-one) 1,1,1',1'-tetraoxide. 5-C

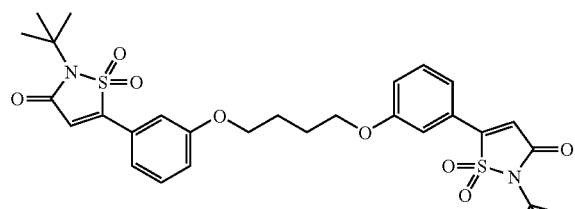

5-C

Compound 5-C was prepared, using 5-B as the starting material, according to the procedure of Example 1.1, Step 11, as a white solid (0.15 g, 95%). $^1$H NMR (400 MHz, CDCl$_3$): δ 7.41 (dd, J=8.0, 7.8 Hz, 2H), 7.34 (ddd, J=7.6, 2.5, 1.0 Hz, 2H), 7.28–7.26 (m, 2H), 7.08 (ddd, J=8.4, 2.5, 1.0 Hz, 2H), 6.63 (s, 2H), 4.13–4.07 (m, 4H), 2.03–2.00 (m, 4H), 1.73 (s, 18H); LCMS found for $C_{30}H_{37}N_2O_8S_2$ (M+H)$^+$: m/z=617.

Step 4. 2-tert-Butyl-1,1-dioxo-5-(3-{4-[3-(1,1,3-trioxo-2,3-dihydro-1H-1λ$^6$-isothiazol-5-yl)phenoxy]-butoxy}-phenyl)-1,2-dihydro-1λ$^6$-isothiazol-3-one The final compound was prepared, using 5-C as the starting material, according to the procedure of Example 1.1, Step 12, as a beige solid (21 mg, 28%). $^1$H NMR (400 MHz, CD$_3$OD): δ 7.46–7.41 (m, 4H), 7.40–7.35 (m, 2H), 7.17–7.13 (m, 2H), 7.02 (s, 2H), 4.15–4.10 (m, 4H), 2.05–2.00 (m, 4H), 1.69 (s, 9H); LCMS found for $C_{26}H_{27}N_2O_8S_2$ (M−H)$^-$: m/z 559.

Example 1.6

5,5'-[Butane-1,4-diylbis(oxy-3,1-phenylene)]bis(isothiazol-3(2H)-one) 1,1,1',1'-tetraoxide

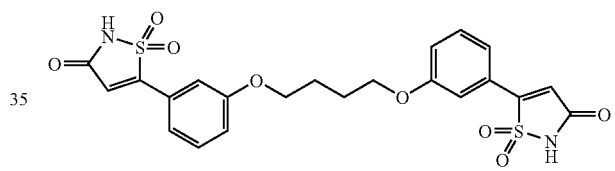

This compound was prepared, using Example 1.5 as the starting material, according to the procedure of Example 1.1, Step 12, as a white solid (9 mg, 62%). $^1$H NMR (400 MHz, CD$_3$OD): δ 7.46–7.44 (m, 4H), 7.40 (s, 1H), 7.19–7.16 (m, 2H), 7.10 (s, 2H), 4.20–4.10 (m, 2.05–1.95 (m, 4H); LCMS found for $C_{22}H_{21}N_2O_8S_2$ (M+H)$^+$: m/z=505.

Example 1.7

2-tert-Butyl-1,1-dioxo-5-(3-{6-[3-(1,1,3-trioxo-2,3-dihydro-1H-1λ$^6$-isothiazol-5-yl)-phenoxy]-hexyloxy}-phenyl)-1,2-dihydro-1λ$^6$-isothiazol-3-one

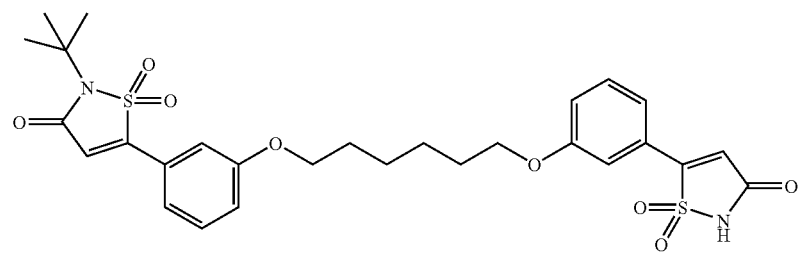

This compound was prepared, using 5-A and 1,6-dibromohexane as the starting materials, according to the procedure of Example 1.5. $^1$H NMR (400 MHz, DMSO-d$_6$): δ 7.53–7.45 (m, 3H), 7.42–7.38 (m, 5H), 7.21–7.15 (m, 2H), 4.05–3.98 (m, 4H), 1.80–1.70 (m, 4H), 1.62 (s, 9H), 1.55–1.45 (m, 4H); LCMS found for C$_{24}$H$_{25}$N$_2$O$_8$S$_2$ (M+H-isobutylene)$^+$: m/z=533.

Example 1.8

5,5'-[Hexane-1,6-diylbis(oxy-3,1-phenylene)]bis(isothiazol-3(2H)-one) 1,1,1',1'-tetraoxide

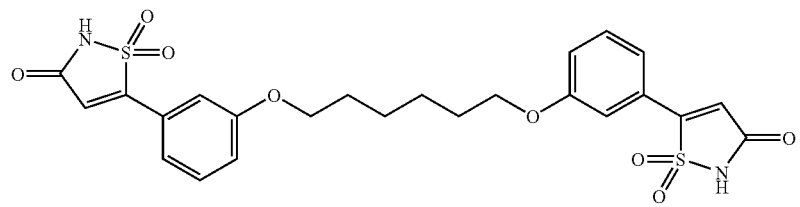

This compound was prepared, using the compound of Example 1.7 as the starting material, according to the procedure of Example 1.1, Step 12, as a pale yellow solid (89 mg, 39%). $^1$H NMR (400 MHz, DMSO-d$_6$): δ 7.48 (dd, J=8.2, 8.0 Hz, 2H), 7.42–7.40 (m, 6H), 7.19–7.16 (m, 2H), 4.03 (t, J=6.5 Hz, 4H), 1.80–1.70 (m, 4H), 1.50–1.43 (m, 4H); LCMS found for C$_{24}$H$_{25}$N$_2$O$_8$S$_2$ (M+H)$^+$: m/z =533.

Example 1.9

(S)-2-{(S)-2-[2-(4-Methoxy-phenyl)-acetylamino]-3-phenyl-propionylamino}-N-pentyl-3-[4-(1,1,3-trioxo-2,3-dihydro-1H-1λ$^6$-isothiazol-5-yl)-phenyl]-propionamide

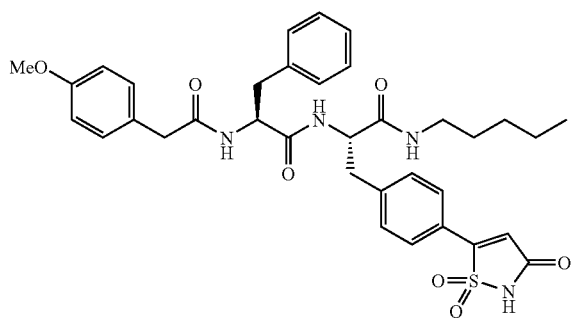

Step 1. 2-tert-Butyl-5-chloro-1,1-dioxo-1,2-dihydro-1λ$^6$-isothiazol-3-one (9-A)

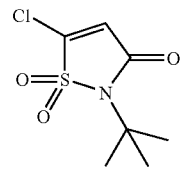

A stirred solution of 1-A (23.2 g, 0.12 mol) in dichloromethane (700 mL) was cooled to 0° C. m-CPBA (109 g, 0.48 mol) was added portionwise and the reaction mixture was stirred at 25° C. for 4 days. The reaction mixture was cooled to 0° C. and 10% aqueous sodium bisulfite (400 mL) was added dropwise from an addition funnel. The reaction mixture was concentrated to a volume of ~600 mL and diluted with ethyl acetate (1.2 L). The organic layer was separated and washed with 10% sodium bisulfite (2×200 mL), saturated sodium bicarbonate (5×200 mL), and brine (2×200 mL). The organic layer was dried with Na$_2$SO$_4$, filtered and concentrated in vacuo to a crude white solid which was purified using flash column chromatography (10% EtOAc/hexane→25% EtOAc/hexane) to yield 9-A as a white solid (18.5 g, 69%). $^1$H NMR (500 MHz, CDCl$_3$): δ 6.56 (s, 1H), 1.69 (s, 9H); LCMS found for C$_3$H$_3$ClNO$_3$S (M-isobutylene)$^+$: m/z=168.

Step 2. N-(tert-butoxycarbonyl)-4-(dihydroxyboryl)-L-phenylalanine 9-B

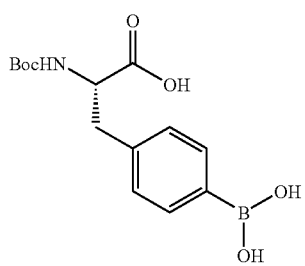

An aqueous solution of sodium hydroxide (1 N, 220 mL) was added to solid 4-borono-N-[(1,1-dimethylethoxy)carbonyl]-L-phenylalanine α-methyl ester (14.1 g, 43.6 mmol) at ambient temperature. The solution was stirred for 1 h and then acidified with aqueous hydrochloric acid (1 N, ca. 200 mL) to pH 1. The product 9-B precipitated as a white solid and was collected by vacuum filtration (13.4 g, 99%). $^1$H NMR (500 MHz, DMSO-$d_6$): δ 12.6 (br s, 1H), 7.98 (s, 2H), 7.70 (d, J=7.3 Hz, 2H), 7.21 (d, J=7.2 Hz, 2H), 7.12 (d, J=8.3 Hz, 1H), 4.10–4.07 (m, 1H), 3.01 (dd, J=13.6, 4.2 Hz, 1H), 2.82 (dd, J=13.4, 10.0 Hz, 1H), 1.38 (s, 9H); LCMS found for $C_{14}H_{19}BNO_6$ (M−H)$^-$: m/z=308.

Step 3. N-α-(tert-butoxycarbonyl)-4-(dihydroxyboryl)-N-pentyl-L-phenylalaninamide 9-C

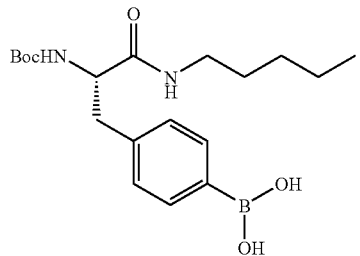

9-C

Acid 9-B (92.7 mg, 0.3 mmol) in methylene chloride/DMF=5/1 (1.5 mL) was treated with EDC (86.3 mg, 0.45 mmol), triethylamine (125 μL, 0.9 mmol), and HOAt (15 μL). Amylamine (52.3 mg, 0.6 mmol) in methylene chloride/DMF=5/1 (1.5 mL) was added. The solution was stirred under nitrogen for 2 h and then diluted with methylene chloride (10 mL) washed with aqueous hydrochloric acid solution (0.1 N, 30 mL) and saturated aqueous sodium bicarbonate solution (30 mL). The organic phase was separated, dried over sodium sulfate, and concentrated in vacuo. The residue was purified by LCMS reverse phase preparative chromatography to afford product 9-C as a white solid (52 mg, 41%). $^1$H NMR (500 MHz, $CD_3OD$): δ 7.90 (t, J=5.6 Hz, 1H), 7.70 (d, J=7.9 Hz, 2H), 7.57 (d, J=7.6 Hz, 2H), 7.26 (d, J=8.14 Hz, 1H), 7.22 (d, J=8.3 Hz, 2H), 6.70 (d, J=8.3 Hz, 1H), 6.24 (br s, 1H), 4.28–4.26 (m, 1H), 3.20–3.06 (m, 3H), 2.86 (dd, J=13.6, 8.1 Hz, 1H), 1.40 (s, 9H), 1.38–1.24 (m, 6H), 0.92 (t, J=6.7 Hz, 3H). LCMS found for $C_{19}H_{32}BN_2O_5$ (M+H)$^+$: m/z=379.

Step 4. {(S)-2-[4-(2-tert-Butyl-1,1,3-trioxo-2,3-dihydro-1H-1λ$^6$-isothiazol-5-yl)-phenyl]-1-pentylcarbamoyl-ethyl}-carbamic acid tert-butyl ester (9-D)

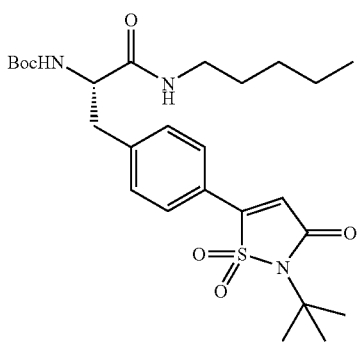

9-D

This compound was prepared according to the procedure of Example 1.1, Step 4, using 9-A and 9-C as the starting materials. $^1$H NMR (500 MHz, $CDCl_3$): δ 7.71 (dd, J=11.7, 3.4 Hz, 2H), 7.37 (dd, J=13.2, 4.9 Hz, 2H), 6.62 (s, 1H), 5.87–5.85 (m, 1H), 5.05–5.00 (m, 1H), 4.32–4.10 (m, 1H), 3.20–3.07 (m, 4H), 1.73 (s, 9H), 1.41 (s, 9H), 1.32–1.24 (m, 6H), 0.87 (t, J=7.3 Hz, 3H); LCMS found for $C_{26}H_{39}N_3O_6SNa$ (M+Na)$^+$: m/z=544.

Step 5. (S)-2-Amino-3-[4-(2-tert-butyl-1,1,3-trioxo-2,3-dihydro-1H-1λ$^6$-isothiazol-5-yl)-phenyl]-N-pentyl-propionamide hydrochloride (9-E)

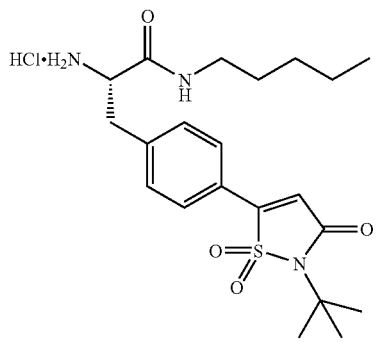

9-E

A solution of 9-D (0.82 g, 1.6 mmol) in 4 N HCl in dioxane (5 mL) was stirred at 25° C. for 16 h. The reaction mixture was concentrated in vacuo to yield 9-E (quantitative) as a light tan solid. $^1$H NMR (500 MHz, $CD_3OD$): δ 8.28 (t, J=5.4 Hz, 0.25H), 7.91 (dd, J=8.3, 2.0 Hz, 2H), 7.50 (dd, J=8.3, 2.0 Hz, 2H), 7.10 (s, 1H), 4.07 (dd, J=7.8, 7.3 Hz, 1H), 3.68 (s, 2H), 3.34–3.19 (m, 3H), 3.17–3.06 (m, 1H), 1.77 (s, 9H), 1.43–1.37 (m, 2H), 1.35–1.27 (m, 2H), 1.22–1.16 (m, 2H), 0.90 (t, J=7.3 Hz, 3H); LCMS found for $C_{21}H_{32}N_3O_4S$ (M+H)$^+$: m/z=422.

Step 6. (S)-2-{(S)-2-[2-(4-Methoxy-phenyl)-acetylamino]-3-phenyl-propionylamino}-N-pentyl-3-[4-(1,1,3-trioxo-2,3-dihydro-1H-1λ$^6$-isothiazol-5-yl)-phenyl]-propionamide This compound was prepared according to the procedure of Example 1.1 using 9-E and other appropriate starting materials. $^1$H NMR (400 MHz, $CD_3OD$): δ8.16 (d, J=8.2 Hz, 0.4H), 7.78 (d, J=8.2 Hz, 2H), 7.37 (d, J=8.0 Hz, 1.6H), 7.23–7.19 (m, 3H), 7.18–7.10 (m, 2H), 7.03–6.98 (m, 3H), 6.77 (d, J=8.6 Hz, 2H), 4.63–4.55 (m, 2H), 3.74 (s, 3H), 3.37 (s, 1H), 3.17–2.90 (m, 5H), 2.88–2.80 (m, 1H), 1.40–1.23 (m, 6H), 1.23–1.17 (m, 2H), 0.88 (t, J=7.2 Hz, 3H); LCMS found for $C_{35}H_{40}N_4O_7S$ (M+H)$^+$: m/z=661.

Example 1.10

(S)-2-(3-{(S)-1-Pentylcarbamoyl-2-[4-(1,1,3-trioxo-2,3-dihydro-1H-1λ⁶-isothiazol-5-yl)-phenyl]-ethyl}-ureido)-3-phenyl-propionic acid

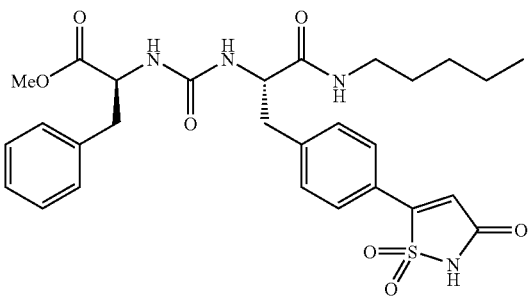

A solution of 9-E (150 mg, 0.33 mmol), methyl (S)-(–)-2-isocyanato-3-phenylpropionate (120 μL, 0.66 mmol), and triethylamine (140 μL, 0.99 mmol) in dimethylformamide (2 mL) was stirred at 25° C. for 16 h. The reaction mixture was treated with Triamine-3 functionalized silica gel (1.2 mmol) and stirred for 1 h. The reaction mixture was filtered through a short plug of silica gel and washed with ethyl acetate (10 mL). The filtrate was concentrated and used without further purification. The crude product was dissolved in trifluoroacetic acid (10 mL) and heated at 70° C. for 16 h. The reaction mixture was concentrated and purified using preparative LCMS to yield the product (29 mg, 15%) as a white solid. $^1$H NMR (500 MHz, CD$_3$OD): δ 7.83 (d, J=8.3 Hz, 2H), 7.42 (d, J=8.3 Hz, 2H), 2H), 7.31–7.28 (m, 2H), 7.25–7.22 (m, 1H), 7.18 (dd, J=8.3, 1.5 Hz, 2H), 7.02 (s, 1H), 4.53 (dd, J=7.8, 5.9 Hz, 1H), 4.44 (dd, J=7.3, 6.8 Hz, 1H), 3.69 (s, 3H), 3.19–3.04 (m, 4H), 3.00–2.94 (m, 2H), 1.42–1.35 (m, 2H), 1.34–1.28 (m, 2H), 1.24–1.19 (m, 2H), 0.90 (t, J=7.3 Hz, 3H); LCMS found for C$_{28}$H$_{35}$N$_4$O$_7$S (M+H)$^+$: m/z=571.

Example 1.11

2-Hydroxy-6-(4-{(S)-2-[3-((S)-1-methoxycarbonyl-2-phenyl-ethyl)-ureido]-3-[4-(trioxo-2,3-dihydro-1H-1λ⁶-isothiazol-5-yl)-phenyl]-propionylamino}-butoxy)-benzoic acid methyl ester

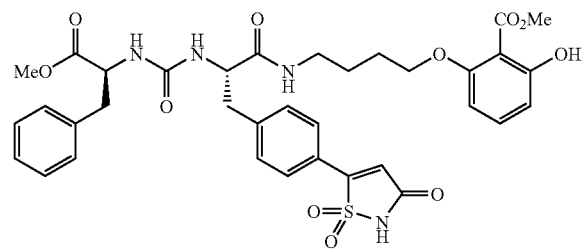

This compound was prepared according to the procedures of Examples 1.9 and 1.10 using 21-B as the starting material. $^1$H NMR (500 MHz, CD$_3$OD): δ 7.81 (d, J=8.3 Hz, 2H), 7.42 (d, J=7.8 Hz, 1.5H), 7.36 (d, J=8.3 Hz, 0.5H), 7.30–7.14 (m, 7H), 6.94 (s, 1H), 6.48 (dd, J=13.2, 8.8 Hz, 2H), 4.53 (dd, J=7.3, 5.4 Hz, 1H), 4.45 (dd, J=6.8, 7.3 Hz, 1H), 3.95–3.90 (m, 2H), 3.87 (s, 3H), 3.69 (s, 3H), 3.30–3.20 (m, 1H), 3.15–3.05 (m, 2H), 3.05–2.94 (m, 2H), 1.65–1.55 (m, 4H); LCMS found for C$_{35}$H$_{39}$N$_4$O$_{11}$S (M+H)$^+$: m/z=723.

Example 1.12

(S)-N-Pentyl-2-((S)-3-phenyl-2-{2-[4-(1,1,3-trioxo-2,3-dihydro-1H-1λ⁶-isothiazol-5-yl)-phenyl]-acetylamino}-propionylamino)-3-[4-(1,1,3-trioxo-2,3-dihydro-1H-1λ⁶-isothiazol-5-yl)-phenyl]-propionamide

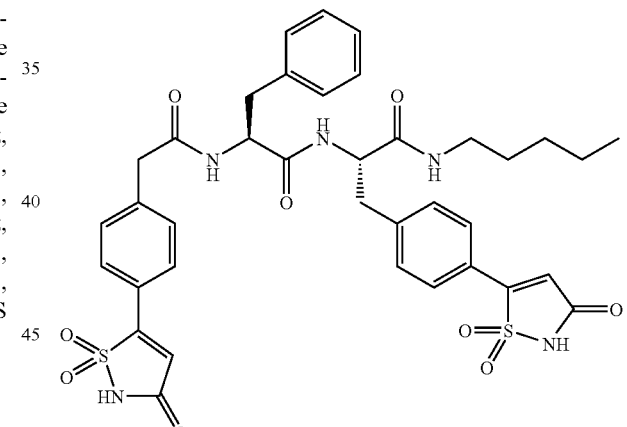

This compound was prepared according to the procedure of Example 1.9 using appropriate starting materials. $^1$H NMR (500 MHz, DMSO-d$_6$): δ 8.38 (d, J=9.8 Hz, 0.5H), 8.17 (d, J=9.8 Hz, 0.5H), 7.93–7.87 (m, 0.5H), 7.81 (d, J=7.3 Hz, 1H), 7.73 (d, J=7.3 Hz, 1H), 7.43 (d, J=7.8 Hz, 1H), 7.38 (d, J=7.8 Hz, 1H), 7.25 (d, J=7.3 Hz, 2H), 7.25–7.13 (m, 6H), 4.60–4.50 (m, 2H), 3.51 (d, J=13.7 Hz, 1H), 3.42 (d, J=14.2 Hz, 1H), 3.10–3.00 (m, 2H), 3.00–2.90 (m, 2H), 2.80–2.68 (m, 2H), 1.40–1.10 (m, 6H), 0.83 (s, 3H); LCMS found for C$_{37}$H$_{38}$N$_5$O$_9$S$_2$ (M–H)$^-$: m/z=760.

Example 1.13

(S)-2-{(S)-2-[2-(4-Methoxy-phenyl)-acetylamino]-3-phenyl-propionylamino}-3-[4-(1,1,3-trioxo-2,3-dihydro-1H-1λ⁶-isothiazol-5-yl)-phenyl]-propionamide

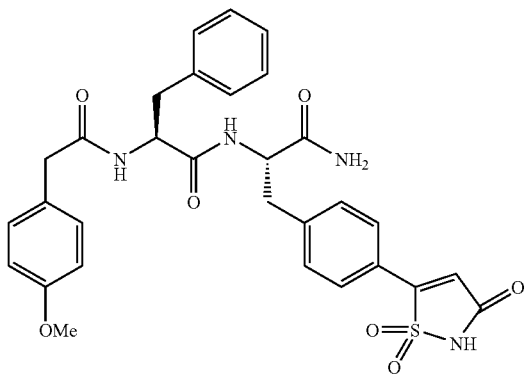

This compound was prepared according to the procedure of Example 1.1 using appropriate starting materials. $^1$H NMR (500 MHz, DMSO-d$_6$): δ 8.20–8.10 (m, 1H), 7.80–7.70 (m, 2H), 7.50–7.30 (m, 3H), 7.30–7.10 (m, 6H), 7.00–6.90 (m, 2H), 6.80–6.70 (m, 2H), 4.60–4.40 (m, 2H), 3.70 (br s, 3H), 3.33 (d, J=13.7 Hz, 1H) 3.24 (d, J=13.2 Hz, 1H), 3.15–3.05 (m, 1H), 3.00–2.80 (m, 2H), 2.80–2.70 (m, 1H); LCMS found for $C_{30}H_{31}N_4O_7S$ (M+H)$^+$: m/z=591.

Example 1.14

(S)-2-{(S)-3-Phenyl-2-[2-(4-trifluoromethyl-phenyl)-acetylamino]-propionylamino}-3-[4-(1,1,3-trioxo-2,3-dihydro-1H-1λ⁶-isothiazol-5-yl)-phenyl]-propionamide

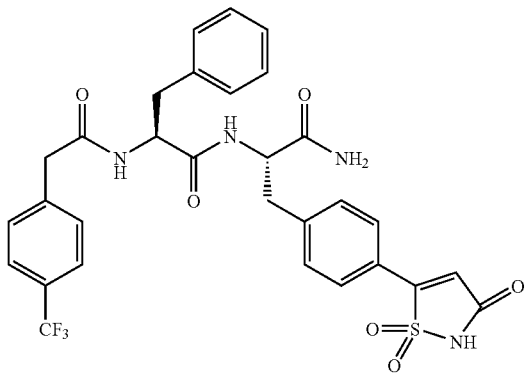

This compound was prepared according to the procedure of Example 1.1 using appropriate starting materials. $^1$H NMR (500 MHz, DMSO-d$_6$): δ 8.39 (d, J=8.3 Hz, 1H), 8.20 (d, J=8.3 Hz, 1H), 7.80 (d, J=8.3 Hz, 2H), 7.55 (d, J=7.8 Hz, 2H), 7.43 (d, J=8.3 Hz, 2H), 7.41 (s, 1H), 7.32 (s, 1H), 7.25 (d, J=8.3 Hz, 2H), 7.22–7.16 (m, 6H), 4.55–4.49 (m, 2H), 3.52 (d, J=14.2 Hz, 1H), 3.43 (d, J=14.2 Hz, 1H), 3.10 (dd, J=13.7, 4.9 Hz, 1H), 2.99 (dd, J=13.7, 4.4 Hz, 1H), 2.92 (dd, J=13.7, 8.3 Hz, 1H), 2.71 (dd, J=14.2, 10.7 Hz, 1H); LCMS found for $C_{30}H_{28}F_3N_4O_6S$ (M+H)$^+$: m/z=629.

Example 1.15

(S)-2-((S)-3-Phenyl-2-phenylacetylamino-propionylamino)-3-[4-(1,1,3-trioxo-2,3-dihydro-1H-1λ⁶-isothiazol-5-yl)-phenyl]-propionamide

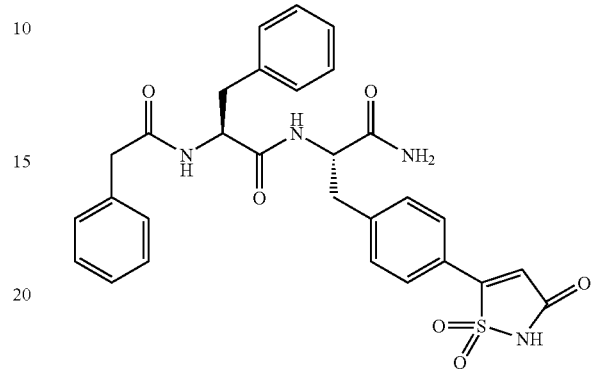

This compound was prepared according to the procedure of Example 1.1 using appropriate starting materials. $^1$H NMR (500 MHz, CD$_3$OD): δ 8.15 (d, J=8.3 Hz, 0.33 H), 7.80 (d, J=8.3 Hz, 2H), 7.42 (d, J=8.3 Hz, 2H), 7.24–7.16 (m, 8H), 7.08 (dd, J=3.9, 1.5 Hz, 2H), 7.05 (s, 1H), 4.63–4.57 (m, 2H), 3.45 (d, J=14.2 Hz, 1H), 3.40 (d, J=14.6 Hz, 1H), 3.21 (dd, J=13.7, 5.4 Hz, 1H), 3.05 (dd, J=14.2, 5.4 Hz, 1H), 2.97 (dd, J=13.7, 8.8 Hz, 1H), 2.82 (dd, J=13.7, 9.3 Hz, 1H); LCMS found for $C_{29}H_{29}N_4O_6S$ (M+H)$^+$: m/z=561.

Example 1.16

(S)-2-[(S)-3-Phenyl-2-(3-phenyl-propionylamino)-propionylamino]-3-[4-(1,1,3-trioxo-2,3-dihydro-1H-1λ⁶-isothiazol-5-yl)-phenyl]-propionamide

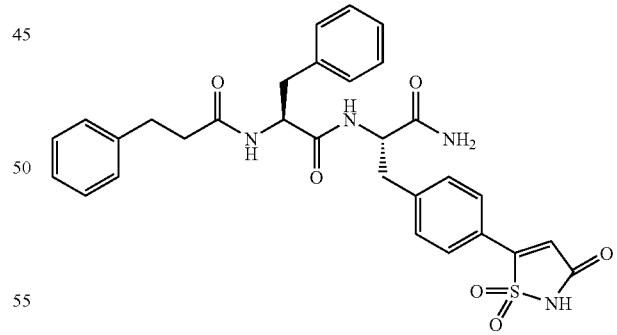

This compound was prepared according to the procedure of Example 1.1 using appropriate starting materials. $^1$H NMR (500 MHz, DMSO-d$_6$): δ 8.10 (dd, J=7.8, 5.9 Hz, 2H), 7.79 (dd, J=8.3, 2.0 Hz, 2H), 7.43 (d, J=8.3 Hz, 2H), 7.35 (s, 1H), 7.29 (s, 1H), 7.24–7.12 (m, 8H), 7.09 (dd, J=8.3 1.5 Hz, 2H), 4.51–4.46 (m, 2H), 3.10 (dd, J=13.7, 4.9 Hz, 1H), 2.96–2.89 (m, 2H), 2.73–2.63 (m, 3H), 2.30 (dd, J=8.3, 7.8 Hz, 2H); LCMS found for $C_{30}H_{31}N_4O_6S$ (M+H)$^+$: m/z=575.

Example 1.17

N-((S)-1-{(S)-1-Carbamoyl-2-[4-(1,1,3-trioxo-2,3-dihydro-1H-1λ⁶-isothiazol-5-yl)-phenyl]-ethylcarbamoyl}-2-phenyl-ethyl)-benzamide

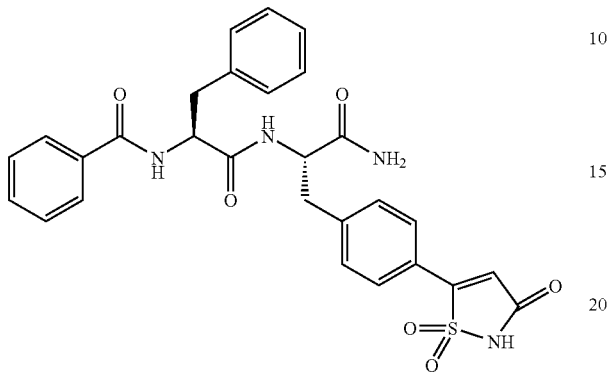

This compound was prepared according to the procedure of Example 1.1 using appropriate starting materials. $^1$H NMR (500 MHz, DMSO-$d_6$): δ 8.58 (d, J=8.3 Hz, 1H), 8.15 (d, J=8.3 Hz, 1H), 7.77–7.71 (m, 4H), 7.52–7.51 (m, 1H), 7.50–7.41 (m, 5H), 7.30 (d, J=6.8 Hz, 2H), 7.25–7.13 (m, 6H), 4.69–4.65 (m, 1H), 4.54–4.50 (m, 1H), 3.11 (dd, J=13.7, 4.9 Hz, 1H), 3.04 (dd, J=13.7, 3.9 Hz, 1H), 2.97–2.91 (m, 2H); LCMS found for $C_{28}H_{27}N_4O_6S$ (M+H)$^+$: m/z=547.

Example 1.18

(S)-2-{(S)-2-[2-(4-Hydroxy-phenyl)-acetylamino]-3-phenyl-propionylamino}-3-[4-(1,1,3-trioxo-2,3-dihydro-1H-1λ⁶-isothiazol-5-yl)-phenyl]-propionamide

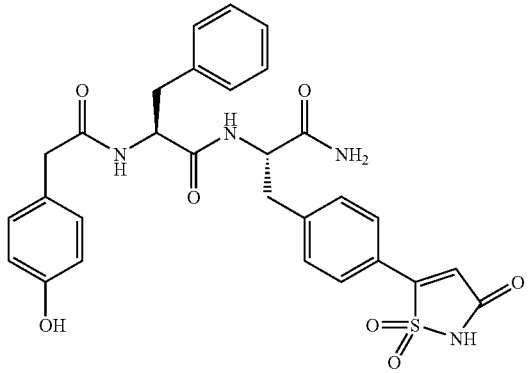

This compound was prepared according to the procedure of Example 1.1 using appropriate starting materials. $^1$H NMR (500 MHz, DMSO-$d_6$): δ 8.12 (dd, J=13.2, 8.3 Hz, 2H), 7.79 (d, J=7.8 Hz, 2H), 7.45–7.39 (m, 4H), 7.27–7.14 (m, 6H), 6.82 (d, J=8.8 Hz, 2H), 6.58 (dd, J=6.3, 2.0 Hz, 2H), 4.51–4.45 (m, 2H), 3.28 (d, J=14.2 Hz, 1H), 3.17 (d, J=14.2 Hz, 1H), 3.13–3.07 (m, 1H), 2.97–2.89 (m, 2H), 2.77–2.69 (m, 2H); LCMS found for $C_{29}H_{29}N_4O_7S$ (M+H)$^+$: m/z=577.

Example 1.19

(S)-2-((S)-2-Acetylamino-3-phenyl-propionylamino)-3-[4-(1,1,3-trioxo-2,3-dihydro-1H-1λ⁶-isothiazol-5-yl)-phenyl]-propionamide

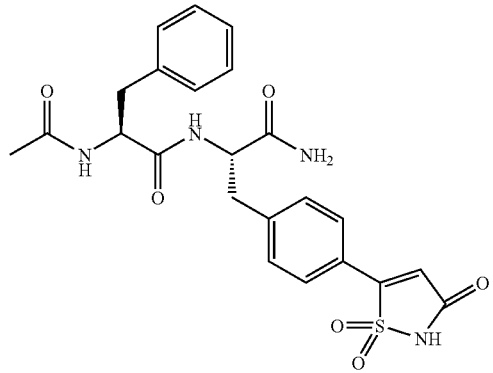

This compound was prepared according to the procedure of Example 1.1 using appropriate starting materials. $^1$H NMR (500 MHz, CD$_3$OD): δ 8.20 (d, J=8.3 Hz, 0.25H), 7.85 (d, J=8.3 Hz, 2H), 7.48 (d, J=8.8 Hz, 2H), 7.31–7.28 (m, 2H), 7.25–7.22 (m, 3H), 7.09 (s, 1H), 4.77–4.64 (m, 1H), 4.60 (dd, J=8.8, 5.9 Hz, 1H), 3.29 (dd, J=13.7, 4.9 Hz, 1H), 3.08–2.98 (m, 2H), 2.84 (dd, J=13.7, 8.8 Hz, 1H), 1.89 (s, 3H); LCMS found for $C_{23}H_{25}N_4O_6S$ (M+H)$^+$: m/z=485.

Example 1.20

4'-[4-(1,1,3-Trioxo-2,3-dihydro-1H-1λ⁶-isothiazol-5-yl)-benzylsulfanylmethyl]-biphenyl-3-sulfonic acid amide

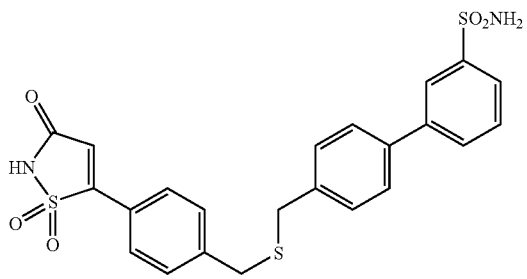

Step 1. 2-tert-Butyl-5-(4-hydroxymethyl-phenyl)-1,1-dioxo-1,2-dihydro-1λ⁶-isothiazol-3-one (20-A)

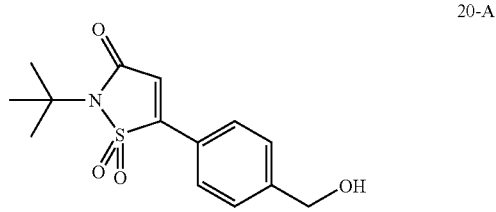

20-A

-continued

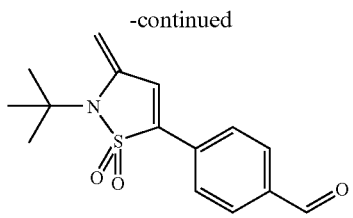

This compound was prepared according to the procedure of Example 1.1, Step 4, using 9-A and 4-(hydroxymethyl) phenylboronic acid as the starting materials. $^1$H NMR (500 MHz, CDCl$_3$): δ 7.77 (d, J=8.3 Hz, 2H), 7.52 (d, J=8.3 Hz, 2H), 6.64 (s, 1H), 4.79 (d, J=5.9 Hz, 2H), 1.86–1.84 (m, 1H), 1.73 (s, 9H); LCMS found for C$_{14}$H$_{17}$NO$_4$SNa (M+Na)$^+$: m/z=318.

Step 2. 4-(2-tert-Butyl-1,1,3-trioxo-2,3-dihydro-1H-1λ$^6$-isothiazol-5-yl)-benzaldehyde (20-B)

20-B

A solution of 20-A (350 mg, 1.2 mmol) in 1,2-dimethoxyethane (11.8 mL) was treated with manganese (IV) oxide (721 mg, 8.3 mmol). The reaction mixture was stirred at 80° C. for 2 h and filtered through celite and washed with ethyl acetate. The filtrate was concentrated in vacuo and the crude residue was purified using flash column chromatography (100% hexane →25% EtOAc/hexane) to yield 20-B as a white solid (267 mg, 77%). $^1$H NMR (400 MHz, CDCl$_3$): δ 10.10 (s, 1H), 8.03 (dd, J=6.6, 1.9 Hz, 2H), 7.95 (dd, J=6.8, 1.9 Hz, 2H), 6.78 (s, 1H), 1.74 (s, 9H); LCMS found for C$_{14}$H$_{16}$NO$_4$S (M+Na)$^+$: m/z=294.

Step 3. Thioacetic acid S-(3'-sulfamoyl-biphenyl-4-ylmethyl) ester (20-C)

20-C

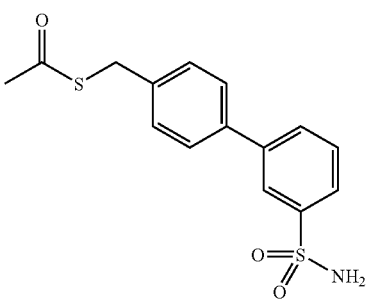

A solution of 4'-(bromomethyl)biphenyl-3-sulfonamide (1.28 g, 3.9 mmol) (WO 01/70753) in acetonitrile (16.4 mL) was treated with sodium bicarbonate (475 mg, 5.7 mmol) and thioacetic acid (0.34 mL, 4.7 mmol). The reaction mixture was stirred at 25° C. for 16 h. Additional sodium bicarbonate and thioacetic acid (0.4 eq. each) were added followed by acetonitrile (5 mL) and the reaction mixture was heated to 50° C. for 30 min. The reaction mixture was washed with water (10 mL) and brine (10 mL), dried with MgSO$_4$, filtered, and concentrated to give a crude residue (quantitative) which was used in the next step without further purification. $^1$H NMR (500 MHz, CDCl$_3$): δ 8.15 (dd, J=2.0, 2.0 Hz, 1H), 7.92 (ddd, J=7.8, 2.0, 1.0 Hz, 1H), 7.80 (ddd, J=7.8, 2.0, 1.0 Hz, 1H), 7.61 (dd, J=7.8, 7.8 Hz, 1H), 7.58–7.55 (m, 2H), 7.44–7.41 (m, 2H), 4.90 (br s, 2H), 4.19 (s, 2H), 2.40 (s, 3H); LCMS found for C$_{15}$H$_{15}$NO$_3$S$_2$Na (M+Na)$^+$: m/z=344.

Step 4. 4'-[4-(2-tert-Butyl-1,1,3-trioxo-2,3-dihydro-1H-1λ$^6$-isothiazol-5-yl)-benzylsulfanylmethyl]-biphenyl-3-sulfonic acid amide (20-D)

20-D

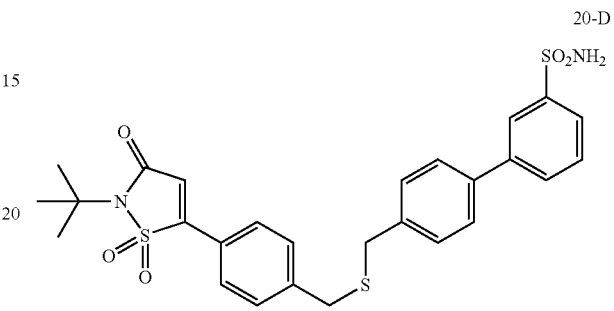

A solution of 20-C (311 mg, 0.98 mmol) in tetrahydrofuran (3 mL) and methanol (3 mL) was cooled to 0° C. and degassed. The reaction mixture was treated with sodium methoxide (25 wt % solution in methanol, 0.58 mL, 6.4 mmol) dropwise. The reaction mixture was stirred at 0° C. for 5 min, diluted with saturated ammonium chloride (20 mL) and extracted with ethyl acetate. The organic layer was separated and washed with brine (10 mL), dried with Na$_2$SO$_4$, filtered, and concentrated to give the desired benzyl mercaptan which was used immediately in the next step. A suspension of the benzyl mercaptan and triethylsilane (0.18 mL, 1.1 mmol) in methylene chloride (5.7 mL) was added to a solution of 20-B (258 mg, 0.9 mmol) in trifluoroacetic acid (4.3 mL). The reaction mixture was degassed and stirred at 25° C. for 16 h. The reaction mixture was concentrated and dissolved in ethyl acetate (50 mL), washed with sodium bicarbonate (50 mL) and brine (20 mL), dried with Na$_2$SO$_4$, filtered, and concentrated to give a crude residue which was purified using flash column chromatography (100% hexane→45% EtOAc/hexane) to yield 20-D as a white solid (236 mg, 48%). $^1$H NMR (500 MHz, CDCl$_3$): δ 8.13 (dd, J=2.0, 1.5 Hz, 1H), 7.90 (ddd, J=7.8, 2.9, 2.0 Hz, 1H), 7.78 (ddd, J=7.8, 2.9, 1.0 Hz, 1H), 7.67 (d, J=8.3 Hz, 2H), 7.59 (dd, J=7.8, 7.8 Hz, 1H), 7.51 (d, J=8.3 Hz, 2H), 7.39 (d, J=8.3 Hz, 2H), 7.34 (d, J=8.3 Hz, 2H), 6.60 (s, 1H), 4.94 (br s, 1H), 4.92 (br s, 0.5H), 3.68 (s, 4H), 1.73 (s, 9H); LCMS found for C$_{27}$H$_{29}$N$_2$O$_5$S$_3$ (M+H)$^+$: m/z=557.

Step 5. 4'-[4-(1,1,3-Trioxo-2,3-dihydro-1H-1λ$^6$-isothiazol-5-yl)-benzylsulfanylmethyl]-biphenyl-3-sulfonic acid amide The final compound was prepared according to the procedure of Example 1.1, Step 12, using 20-D as the starting material. $^1$H NMR (400 MHz, CD$_3$OD): δ 8.14 (br s, 1H), 7.87–7.80 (m, 4H), 7.62–7.58 (m, 3H), 7.47 (d, J=8.4 Hz, 2H), 7.39 (d, J=8.2 Hz, 2H), 6.98 (br s, 1H), 3.73 (d, J=8.2 Hz, 4H); LCMS found for C$_{23}$H$_{21}$N$_2$O$_5$S$_3$ (M+H)$^+$: m/z=501.

Example 1.21

2-[4-({(2S)-2-(acetylamino)-3-[4-(1,1-dioxido-3-oxo-2,3-dihydroisothiazol-5-yl)phenyl]propanoyl}amino)butoxy]-6-hydroxybenzoic acid

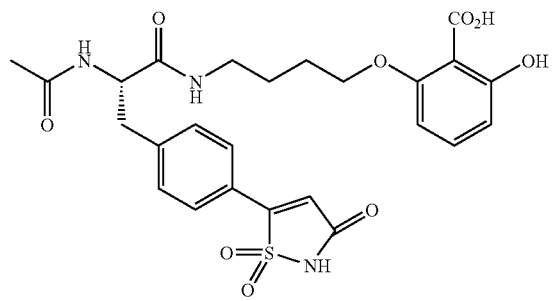

Step 1.
Methyl-2-(4-aminobutoxy)-6-hydroxybenzoate hydrochloride (21-A)

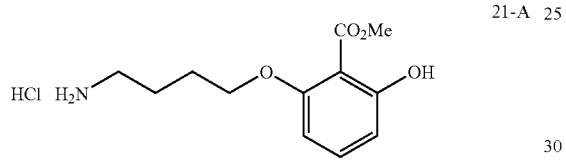
21-A

Amine 21-A was synthesized according to the literature procedure provided in Z. Pei, X. Li, et al. "Discovery and SAR of Novel, Potent, and Selective Protein Tyrosine Phosphatase 1B Inhibitors", *Bioorg. & Medchem. Lett.* 2003, 13, 3129–3132.

Step 2. Methyl-2-[4-({(2S)-2-(acetylamino)-3-[4-(1,1-dioxido-3-oxo-2,3-dihydroisothiazol-5-yl)phenyl]propanoyl}amino)butoxy]-6-hydroxybenzoate (21-B)

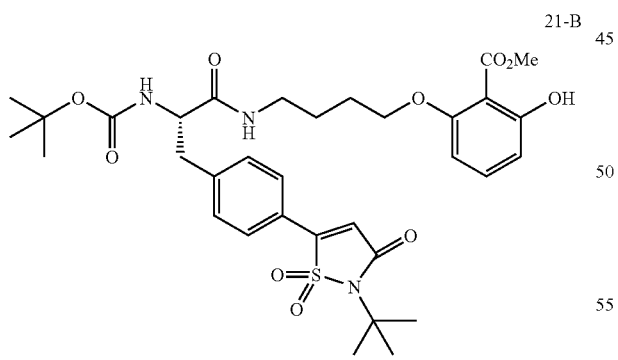
21-B

21-A (*Bioorg. & Medchem. Lett.* (2003), 13, 3129–3132) (8 mg, 0.029 mmol) was added to a DCM (0.1 M) solution of (2S)-2-[(tert-butoxycarbonyl)amino]-3-[4-(2-tert-butyl-1,1-dioxido-3-oxo-2,3-dihydroisothiazol-5-yl)phenyl]propanoic acid (12 mg, 0.027 mmol), EDC (5 mg, 0.027 mmol), HOBt (3.6 mg, 0.027 mmol) and DIEA (10 µL, 0.029 mmol). The reaction was stirred at 40° C. for 4 h and then concentrated. The crude was purified by reverse phase HPLC to afford 21-B (8.1 mg, 44%).

Step 3. 2-[4-({(2S)-2-(acetylamino)-3-[4-(1,1-dioxido-3-oxo-2,3-dihydroisothiazol-5-yl)phenyl]propanoyl}amino)butoxy]-6-hydroxybenzoic acid TFA/DCM (1:1) (1 mL) was added to 21-B (8.1 mg, 0.012 mmol), and stirred for 30 min. The solvent was evaporated in vacuo. The deprotected amine was then treated with $Ac_2O$ and pyridine (1:1) for 30 min. The reaction was then dissolved in anhydrous TFA/triisopropylsilane (97:3) and heated at 70° C. overnight to deprotect the t-butyl group. The solvents were removed in vacuo and purified by reverse phase HPLC to afford Example 1.21 (2.0 mg, 31%). $^1$H NMR (500 MHz, $CD_3OD$): δ 7.84 (d, J=8 Hz, 2H), 7.48 (d, J=8 Hz, 2H), 7.38 (m, 1H), 6.98 (s, 1H), 6.58 (m, 2H), 4.62 (m, 2H), 4.08 (m, 1H), 3.36 (s, 3H), 3.30 (m, 2H), 3.10 (m, 2H), 1.96 (s, 3H), 1.65 (m, 2H), 1.55 (m, 2H); LCMS found for $C_{25}H_{27}N_3O_9S$ $(M+H)^+$: m/z=546.

Example 1.22

2-[(3R)-3-aminopyrrolidin-1-yl]-5-(1,1-dioxido-3-oxo-2,3-dihydro-isothiazol-5-yl)-benzaldehyde trifluoroacetate (salt)

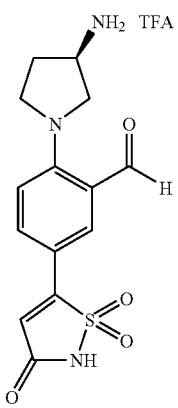

Step 1. tert-butyl [(3R)-1-(4-bromo-2-formylphenyl)pyrrolidin-3-yl]carbamate (22-A)

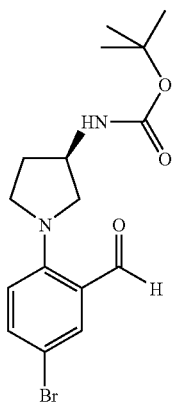

5-Bromo-2-fluorobenzaldehyde (1.55 mL, 13.0 mmol) and tert-butyl-(3R)-pyrrolidin-3-ylcarbamate (2.90 g, 15.6 mmol) in DMF (70 mL) were treated with potassium carbonate (2.25 g, 16.3 mmol). The solution was heated to 120° C. for 18 h under nitrogen. The solution was allowed to cool to ambient temperature and was diluted with ethyl acetate (150 mL) and washed with water (100 mL). The organic phase was separated, dried over sodium sulfate, and concentrated in vacuo. The residue was purified by silica gel chromatography (30% ethyl acetate/hexanes) to afford product 22-A as a yellow solid (4.00 g, 83%). $^1$H NMR (500 MHz, CD$_3$OD): δ 10.02 (s, 1H), 7.81 (d, J=2.9 Hz, 1H), 7.51 (dd, J=11.2, 2.4 Hz, 1H), 6.88 (d, J=9.27 Hz, 1H), 4.20 (m, 1H), 3.60–3.51 (m, 2H), 3.42 (m, 1H), 3.21 (m, 1H), 2.22 (m, 1H), 2.00 (m, 1H), 1.46 (s, 9H); LCMS found for C$_{16}$H$_{21}$N$_2$O$_3$Br (M+H)$^+$: m/z=370.

Step 2. tert-butyl {(3R)-1-[2-formyl-4-(4,4,5,5-tetramethyl-1,3,2-dioxaborolan-2-yl)phenyl]pyrrolidin-3-yl}carbamate (22-B)

22-B

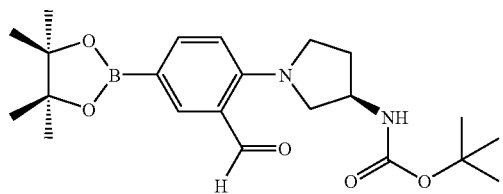

Bromide 22-A (692 mg, 1.87 mmol) in DMF (12 mL) was treated with bis(pinacolato)diboron (713 mg, 2.81 mmol), potassium acetate (550 mg, 5.60 mmol), tricyclohexylphosphine (17 mg, 0.061 mmol) and bis(tricyclohexylphosphine)-palladium(II) chloride (45 mg, 0.061 mmol). The solution was degassed, placed under nitrogen and heated to 95° C. for 65 hours. The solution was cooled to ambient temperature, diluted with ethyl acetate (50 mL) and washed with water (50 mL). The organic phase was separated, dried over sodium sulfate and concentrated in vacuo. The residue was purified by silica gel chromatography (30% ethyl acetate/hexanes) to afford 22-B as a yellow solid (545 mg, 70%). $^1$H NMR (500 MHz, CD$_3$OD): δ 10.04 (s, 1H), 8.11 (d, J=1.46 Hz, 1H), 7.76 (dd, J=10.2, 1.46 Hz, 1H), 6.90 (d, J=8.8 Hz, 1H), 4.21 (m, 1H), 3.61 (m, 2H), 3.44 (m, 1H), 3.24 (m, 1H), 2.24 (m, 1H), 1.46 (s, 9H), 1.36 (s, 12H); LCMS found for C$_{22}$H$_{33}$N$_2$O$_5$B (M+H)$^+$: m/z 417.

Step 3. tert-butyl {(3R)-1-[4-(2-tert-butyl-1,1-dioxido-3-oxo-2,3-dihydroisothiazol-5-yl)-2-formylphenyl]pyrrolidin-3-yl}carbamate (22-C)

22-C

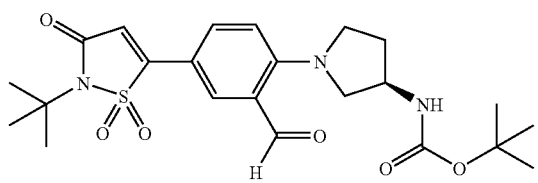

Boronic ester 22-B in dioxane (1 mL) was treated with potassium carbonate (124 mg, 0.901 mmol), heterocycle 9-A (48 mg, 0.21 mmol) and [1,1'-bis(diphenylphosphino)-ferrocene]dichloropalladium(II), complex with dichloromethane (1:1) (17.6 mg, 0.0216 mmol). The solution was degassed, placed under nitrogen and heated to 80° C. for 48 hours. The solution was allowed to cool to ambient temperature, diluted with ethyl acetate (10 mL) and washed with water (10 mL). The organics were separated, dried over sodium sulfate and concentrated in vacuo. The residue was purified by silica gel chromatography (30 ethyl acetate/hexanes) to afford a yellow solid 22-C (63 mg, 73%). $^1$H NMR (500 MHz, CD$_3$OD): δ 10.05 (s, 1H), 8.25 (d, J=1.95 Hz, 1H), 7.87 (dd, J=11.22 Hz, 1H), 7.06 (d, J=9.27 Hz, 1H), 6.84 (s, 1H), 4.24 (m, 1H), 3.70 (m, 2H), 3.65 (m, 1H), 3.19 (m, 1H), 2.28 (m, 1H), 2.26 (m, 1H), 1.72 (s, 9H), 1.46 (s, 9H); LCMS found for C$_{23}$H$_{31}$N$_3$O$_6$S (M+H)$^+$: m/z=478.

Step 4. 2-[(3R)-3-aminopyrrolidin-1-yl]-5-(1,1-dioxido-3-oxo-2,3-dihydro-isothiazol-5-yl)-benzaldehyde 22-C (63 mg, 0.13 mmol) in TFA (0.65 mL) was treated with triisopropylsilane (0.8 μL, 0.004 mmol). The solution was sealed in a microwave tube and heated to 130° C. for 15 min. The solution was concentrated in vacuo. The residue was purified by reverse phase HPLC to afford a yellow solid (10 mg, 17%). $^1$H NMR (500 MHz, CD$_3$OD): δ 10.04 (s, 1H), 8.31 (d, J=2.44 Hz, 1H), 7.97 (dd, J=11.2, 2.4 Hz, 1H), 7.14 (d, J=9.27 Hz, 1H), 4.05 (m, 1H), 3.80–3.75 (m, 2H), 3.65–3.47 (m, 2H), 2.52 (m, 1H), 2.22 (m, 1H); LCMS found for C$_{14}$H$_{15}$N$_3$O$_4$S (M+H)$^+$: m/z=322.

Example 1.23

N-{2-[4-(1,1-dioxido-3-oxo-2,3-dihydroisothiazol-5-yl)phenyl]ethyl}benzamide

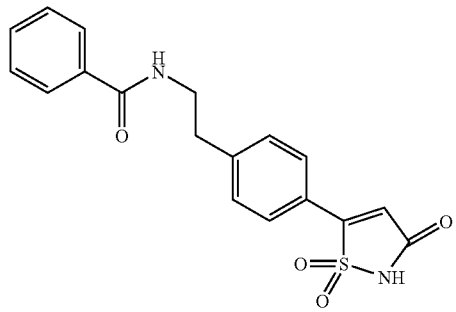

Step 1. Synthesis of [2-(4-Hydroxy-phenyl)-ethyl]-carbamic acid tert-butyl ester (23-A)

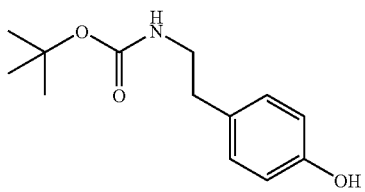

Into the reaction was dissolved 4-(2-amino-ethyl)-phenol hydrochloride (11.62 g, 67 mmol) in water (30 mL) and tetrahydrofuran (30 mL). Sodium bicarbonate (12.52 g, 147 mmol) was added, followed by di-tert-butyl dicarbonate (16.06 g, 74 mmol). The reaction was stirred overnight. Water (100 mL) was added and the mixture was extracted with ethyl acetate (100 mL) three times. The organic phases were combined and dried with MgSO$_4$. The solution was filtered through a glass frit and the solvent concentrated in vacuo to give 15.88 g of a clear oil (100%). $^1$H NMR (400 MHz, CDCl$_3$): δ 7.03 (d, J=8.3 Hz, 2H), 6.77 (d, J=8.3 Hz, 2H), 4.55 (br s, 1H), 3.33 (m, 2H), 2.71 (t, J=7.2Hz, 2H), 1.44 (s, 9H); LCMS found for C$_{13}$H$_{19}$NNaO$_3$ (M+Na)$^+$: m/z=260.

Step 2. Synthesis of Trifluoro-methanesulfonic acid 4-(2-tert-butoxycarbonylamino-ethyl)-phenyl ester (23-B)

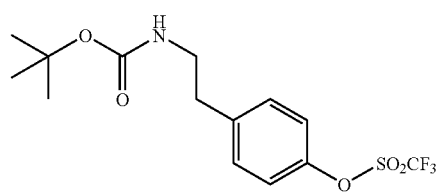

23-A (15.88 g, 67 mmol) was dissolved in methylene chloride (130 mL) and then pyridine (8.2 mL) was added. The reaction was cooled to 0° C. Trifluoro-methanesulfonic anhydride (20.77 g, 74 mmol) was dissolved in methylene chloride (70 mL) and added to the reaction mixture via addition funnel over 30 minutes. The reaction was allowed to slowly come to room temperature overnight. Water (150 mL) was added and the mixture shaken then separated. The aqueous phase was extracted with methylene chloride (100 mL) twice. The organic phases were combined and dried with MgSO$_4$. The solution was filtered through a glass frit and the solvent was evaporated in vacuo. The mixture was loaded on a silica gel column using ethyl acetate and eluted with 1 L 10% ethyl acetate in hexanes then 2 L 30% ethyl acetate in hexanes. Fractions containing the major component were combined, concentrated and place under high vacuum overnight to give a colorless oil (24.72 g, 100%) which gradually crystallized. $^1$H NMR (400 MHz, CDCl$_3$): δ 7.27 (d, J=8.6 Hz, 2H), 7.20 (d, J=8.6 Hz, 2H), 4.55 (br s, 1H), 3.37 (m, 2H), 2.83 (t, J=6.4 Hz, 2H), 1.43 (s, 9H); LCMS found for C$_{10}$H$_{11}$F$_3$NO$_5$S (M+H-isobutylene)$^+$: m/z=314.

Step 3. 1-(2-tert-Butoxycarbonylamino-ethyl)-4,4,5,5-tetramethyl-1,3,2-dioxaborolane (23-C)

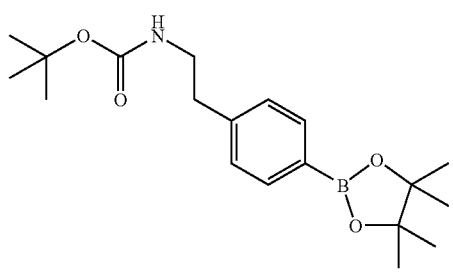

23-B (22.50 g, 61 mmol), bis(tricyclohexylphosphine)palladium(II) chloride (1.35 g, 1.83 mmol), tricyclohexylphosphine (0.513 g, 1.83 mmol), potassium acetate (11.96 g, 122 mmol), and 4,4,5,5,4',4',5',5'-octamethyl-[2,2']bi[[1,3,2]dioxaborolanyl] (17.02 g, 67 mmol) where dissolved in dry N,N-dimethylformamide (370 mL). The reaction was heated in an oil bath at 100° C. overnight. The mixture was diluted with water (1 L) then was extracted with diethyl ether (250 mL) four times. The combined organic phases were combined and dried with MgSO$_4$. The solution was filtered through a glass frit and the solvent evaporated in vacuo. The mixture was loaded on a silica gel column using ethyl acetate/hexanes and eluted with 1 L 10% ethyl acetate in hexanes then 1 L 50% ethyl acetate in hexanes. Fractions containing the major component were combined and rotovaped to give a lavender oil. TLC shows some impurities. The mixture was chromatographed again with 1 L 5% ethyl acetate in hexanes then 1 L 10% ethyl acetate in hexanes. Fractions containing the major component were combined and concentrated to give a pale pink oil (17.13 g, 81%). $^1$H NMR (500 MHz, CDCl$_3$): δ 7.76 (d, J=8.2 Hz, 2H), 7.21 (d, J=8.2 Hz, 2H), 4.51 (br s, 1H), 3.38 (m, 2H), 2.81 (t, J=6.8 Hz, 2H), 1.43 (s, 9H), 1.43 (s, 12H); LCMS found for C$_{19}$H$_{30}$BNNaO$_4$ (M+Na)$^+$: m/z=370.

Step 4. 2-[4-(2-tert-Butyl-1,1,3-trioxo-2,3-dihydro-1H-1λ$^6$-isothiazol-5-yl)-phenyl]-ethyl-carbamic acid tert-butyl ester (23-D)

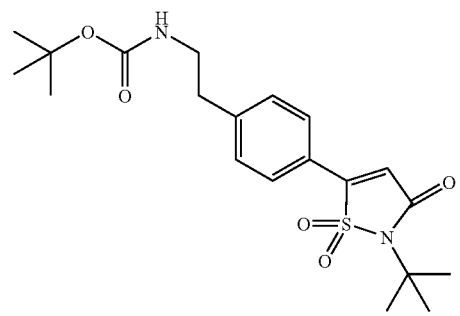

23-C (0.328 g, 0.944 mmol), 9-A (0.253 g, 1.13 mmol), [1,1'-bis(diphenylphosphino)ferrocene]-dichloropalladium (II), complex with dichloromethane (1:1) (0.095 g, 0.12 mmol), and potassium carbonate (0.652 g, 4.72 mmol) in 1,4-dioxane (6 mL) were added to a flask with a reflux condenser. The reaction was degassed and heated to 80° C. for 15 hours. Additional catalyst [1,1'-bis(diphenylphosphino)ferrocene]dichloropalladium(II), complex with dichloromethane (1:1) (0.100 g, 0.122 mmol) was added and the reaction atmosphere was degassed. The reaction was heated overnight. The reaction mixture was diluted with methylene chloride (25 mL) and was rotovaped onto 9 g of silica gel. The mixture was eluted with 500 mL 10% ethyl acetate in hexanes (1000 mL) then 20% ethyl acetate (500 mL). Fractions containing the major component were combined and concentrated to give a light brown oil (0.356 g, 93%). $^1$H NMR (500 MHz, CDCl$_3$): δ 7.72 (d, J=8.3 Hz, 2H), 7.34 (d, J=8.3 Hz, 2H), 6.63 (s, 1H), 4.55 (br s, 1H), 3.40 (m, 2H), 2.87 (t, J=7.0 Hz, 2H), 1.73 (s, 9H), 1.44 (s, 9H); LCMS found for C$_{20}$H$_{28}$N$_2$NaO$_5$S (M+Na)$^+$: m/z=431.

Step 5. 5-[4-(2-Amino-ethyl)-phenyl]-2-tert-butyl-1,1-dioxo-1,2-dihydro-1λ⁶-isothiazol-3-one (23-E)

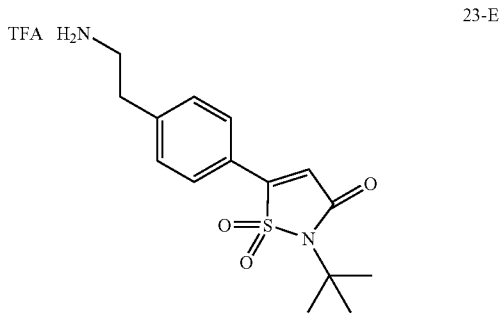

23-D (0.356 g, 0.871 mmol) was dissolved in trifluoroacetic acid (1 mL) and methylene chloride (1 mL) and the reaction was stirred for one hour. The volatiles were evaporated and the crude material chromatographed on a 50 mm Luna C18 column using a 10–90% acetonitrile in water gradient with 0.05% trifluoroacetic acid at 50 mL per minute over a 15 minute period. The major fraction was lyophilized to give an off-white powder (0.262 g, 97%). $^1$H NMR (500 MHz, CD$_3$OD): δ 7.90 (d, J=8.3 Hz, 2H), 7.52 (d, J=8.3 Hz, 2H), 7.08 (s, 1H), 3.25 (t, J=7.5 Hz, 2H), 3.06 (t, J=7.9 Hz, 2H), 1.73 (s, 9H); LCMS found for C$_{15}$H$_{21}$N$_2$O$_3$S (M+H)$^+$: m/z=309.

Step 6. 5-[4-(2-aminoethyl)phenyl]isothiazol-3(2H)-one 1,1-dioxide Trifluoroacetate (23-F)

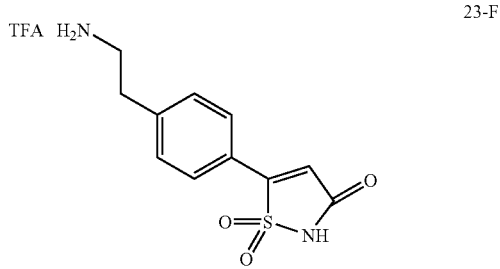

23-E (262 mg, 0.850 mmol) was dissolved in trifluoroacetic acid (10 mL) and triisopropylsilane (1 mL) was added. The reaction was heated to reflux under an atmosphere of nitrogen overnight. The reaction was cooled to room temperature then concentrated via rotovap. The reaction material was chromatographed on a 50 mm Luna C18 column using a 0–30% acetonitrile in water gradient with 0.05% trifluoroacetic acid at 30 mL per minute over a 20 minute period. The major fraction was lyophilized to give a white powder (0.128 g, 60%). $^1$H NMR (500 MHz, CD$_3$OD): δ 7.89 (d, J=9.0 Hz, 2H), 7.51 (d, J=9.0 Hz, 2H), 7.06 (s, 1H), 3.25 (t, J=7.2 Hz, 2H), 3.06 (t, J=7.2 Hz, 2H); LCMS found for C$_{11}$H$_{13}$N$_2$O$_3$S (M+H)$^+$: m/z=253.

Step 7. N-{2-[4-(1,1-dioxido-3-oxo-2,3-dihydroisothiazol-5-yl)phenyl]ethyl}benzamide.

23-F (7.0 mg, 0.019 mmol) and triethylamine (8 µL, 0.0573 mmol) were dissolved in methylene chloride (0.25 mL). Benzoyl chloride (2.8 µL, 0.0239 mmol) was added and the reaction was allowed to stir at room temperature. DMF (0.25 mL) was added and allowed to stir overnight. The reaction was chromatographed on a 21 mm Luna C18 column using a 10–90% acetonitrile in water gradient with 0.05% trifluoroacetic acid at 12.5 mL per minute over a 30 minute period. The major fraction was lyophilized to give a white powder (2.0 mg, 29%). $^1$H NMR (500 MHz, CD$_3$OD): δ 7.91 (d, J=8.7 hz, 2H), 7.81 (d, J=8.9 Hz, 2H), 7.52 (d, J=8.8 Hz, 2H), 7.43 (m, 3H), 6.97 (s, 1H), 6.69 (br s, 1H), 3.47 (t, J=7.0 Hz, 2H), 2.91 (t, J=7.0 Hz, 2H); LCMS found for C$_{18}$H$_{17}$N$_2$O$_4$S (M+H)$^+$: m/z=357.

Example 1.24

2-[4-(benzyloxy)phenyl]-N-{2-[4-(1,1-dioxido-3-oxo-2,3-dihydroisothiazol-5-yl)phenyl]ethyl}acetamide

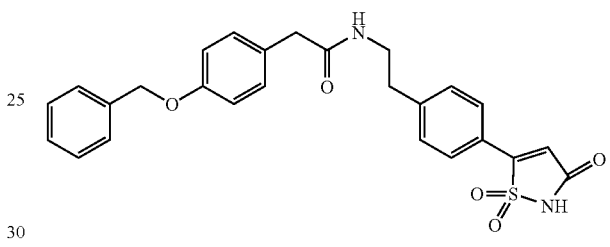

This compound was prepared according to the procedure in Example 1.23 using the appropriate reagents and starting materials. $^1$H NMR (500 MHz, CD$_3$OD): δ 7.89 (d, J=8.6 Hz, 2H), 7.50 (d, J=8.6 Hz, 2H), 7.20 (m, 5H), 6.95 (d, J=9.0 Hz, 2H), 6.90 (s, 1H), 6.72 (d, J=9.0 Hz, 2H), 6.68 (br s, 1H), 5.27 (s, 2H), 3.52 (t, J=6.8 Hz, 2H), 3.44 (s, 2H), 2.93 (t, J=6.8 Hz, 2H); LCMS found for C$_{26}$H$_{25}$N$_2$O$_5$S (M+H)$^+$: m/z=477.

Example 1.25

N-{2-[4-(1,1-dioxido-3-oxo-2,3-dihydroisothiazol-5-yl)phenyl]ethyl}-3-phenoxybenzamide

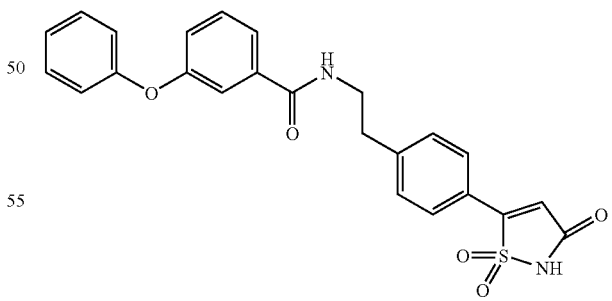

This compound was prepared according to the procedure in Example 1.23 using the appropriate reagents and starting materials. $^1$H NMR (500 MHz, CD$_3$OD): δ 7.90 (d, J=9.0 Hz, 2H), 7.68 (m, 2H), 7.52 (d, J=9.0 Hz, 2H), 7.42 (m, 1H), 7.20 (m, 3H), 6.92 (m, 4H), 6.65 (br s, 1H), 3.51 (t, J=6.8 Hz, 2H), 2.94 (t, J=6.8 Hz, 2H); LCMS found for C$_{26}$H$_{25}$N$_2$O$_5$S (M+H)$^+$: m/z=449.

Example 1.26

4-(Acetylamino)-N-{2-[4-(1,1-dioxido-3-oxo-2,3-dihydroisothiazol-5-yl)phenyl]ethyl}benzamide

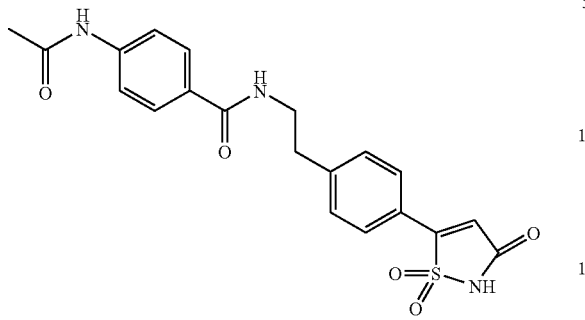

This compound was prepared according to the procedure in Example 1.23 using the appropriate reagents and starting materials. $^1$H NMR (500 MHz, CD$_3$OD): δ 7.89 (d, J=8.9 Hz, 2H), 7.82 (d, J=8.7 Hz, 2H), 7.78 (d, J=8.7 Hz, 2H), 7.52 (d, J=8.9 Hz, 2H), 6.98 (s, 1H), 6.60 (br s, 1H), 6.53 (br s, 1H), 3.51 (t, J=6.8 Hz, 2H), 2.93 (t, J=6.8 Hz, 2H), 2.02 (s, 3H); LCMS found for C$_{20}$H$_{20}$N$_3$O$_5$S (M+H)$^+$: m/z=414.

Example 1.27

N-{2-[4-(1,1-dioxido-3-oxo-2,3-dihydroisothiazol-5-yl)phenyl]ethyl}-N'-(3-phenoxyphenyl)urea

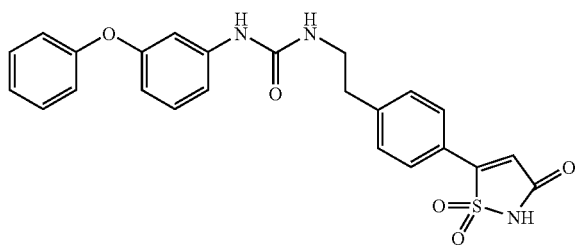

This compound was prepared according to the procedure in Example 1.23 using the appropriate reagents and starting materials. $^1$H NMR (500 MHz, CD$_3$OD): δ 7.89 (d, J=8.9 Hz, 2H), 7.52 (d, J=8.9 Hz, 2H), 7.33 (m, 2H), 7.21 (m, 3H), 6.98 (s, 1H), 6.95 (m, 3H), 6.68 (d, J=8.4 Hz, 1H), 6.62 (br s, 1H), 6.54 (br s, 1H), 3.50 (t, J=7.0 Hz, 2H), 2.94 (t, J=7.0 Hz, 2H); LCMS found for C$_{24}$H$_{22}$N$_3$O$_5$S (M+H)$^+$: m/z=464.

Example 1.28

N-{2-[4-(1,1-dioxido-3-oxo-2,3-dihydroisothiazol-5-yl)phenyl]ethyl}-N'-(4-phenoxyphenyl)urea

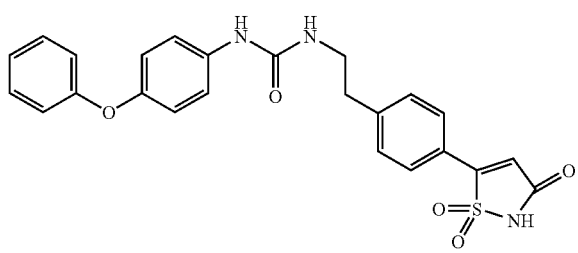

This compound was prepared according to the procedure in Example 1.23 using the appropriate reagents and starting materials. $^1$H NMR (500 MHz, CD$_3$OD): δ 7.77 (d, J=8.9 Hz, 2H), 7.40 (d, J=8.9 Hz, 2H), 7.31 (m, 1H), 7.30 (m, 4H), 7.07 (m, 1H), 6.95 (m, 4H), 6.71 (br s, 1H), 3.50 (t, J=6.8 Hz, 2H), 2.93 (t, J=6.8 Hz, 2H); LCMS found for C$_{24}$H$_{22}$N$_3$O$_5$S (M+H)$^+$: m/z=464.

Example 1.29

N-{2-[4-(1,1-dioxido-3-oxo-2,3-dihydroisothiazol-5-yl)phenyl]ethyl}-4-methylbenzenesulfonamide

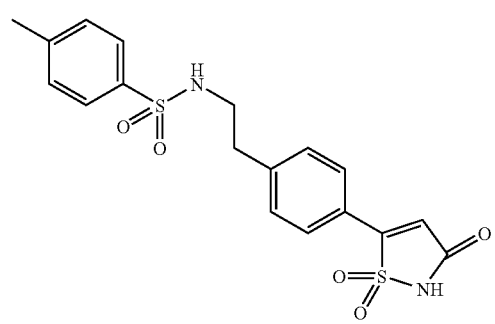

This compound was prepared according to the procedure in Example 1.23 using the appropriate reagents and starting materials. $^1$H NMR (500 MHz, CD$_3$OD): δ 7.92 (d, J=8.9 Hz, 2H), 7.82 (d, J=8.7 Hz, 2H), 7.53 (d, J=8.9 Hz, 2H), 7.34 (d, J=8.7 Hz, 2H), 6.96 (s, 1H), 6.30 (br s, 1H), 3.51 (t, J=7.0 Hz, 2H), 2.93 (t, J=7.0 Hz, 2H), 2.35 (s, 3H); LCMS found for C$_{18}$H$_{19}$N$_2$O$_5$S$_2$ (M+H)$^+$: m/z=407.

Example 1.30

N-{2-[4-(1,1-dioxido-3-oxo-2,3-dihydroisothiazol-5-yl)phenyl]ethyl}-4-phenoxybenzenesulfonamide

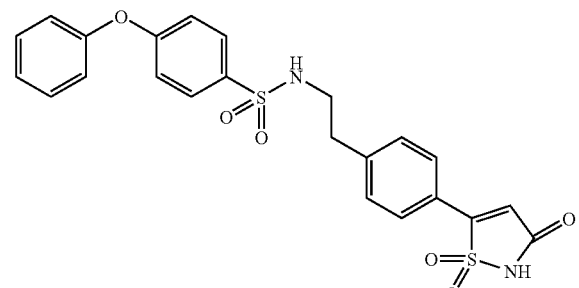

This compound was prepared according to the procedure in Example 1.23 using the appropriate reagents and starting materials. $^1$H NMR (500 MHz, CD$_3$OD): δ 7.89 (d, J=9.0 Hz, 2H), 7.81 (d, J=8.9 Hz, 2H), 7.45 (d, J=9.0 Hz, 2H), 7.25 (m, 2H), 7.21 (d, J=8.9 Hz, 2H), 7.07 (m, 1H), 6.96 (m, 3H), 6.25 (br s, 1H), 3.40 (t, J=6.8 Hz, 2H), 2.96 (t, J=6.8 Hz, 2H); LCMS found for C$_{23}$H$_{21}$N$_2$O$_6$S$_2$ (M+H)$^+$: m/z=485.

Example 1.31

N-{2-[4-(1,1-dioxido-3-oxo-2,3-dihydroisothiazol-5-yl)phenyl]ethyl}-5-fluoro-1H-indole-2-carboxamide

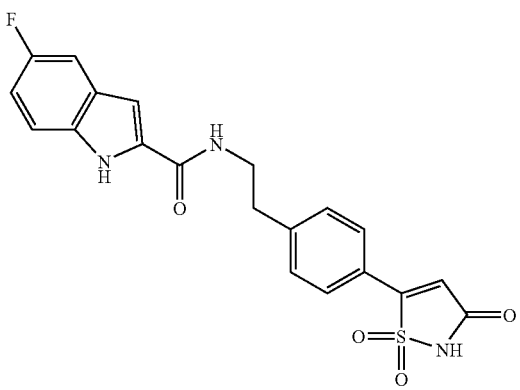

This compound was prepared according to the procedure in Example 1.23 using the appropriate reagents and starting materials. $^1$H NMR (500 MHz, CD$_3$OD): δ 7.89 (d, J=9.0 Hz, 2H), 7.51 (d, J=9.0 Hz, 2H), 7.38 (m, 2H), 7.26 (m, 1H), 7.01 (s, 1H), 6.79 (m, 1H), 3.45 (t, J=7.0 Hz, 2H), 2.89 (t, J=7.0 Hz, 2H); LCMS found for C$_{20}$H$_{17}$FN$_3$O$_4$S (M+H)$^+$: m/z=414.

Example 1.32

{4-[2-({2-[4-(1,1-Dioxido-3-oxo-2,3-dihydroisothiazol-5-yl)phenyl]ethyl}amino)-2-oxoethyl]phenyl}acetic acid

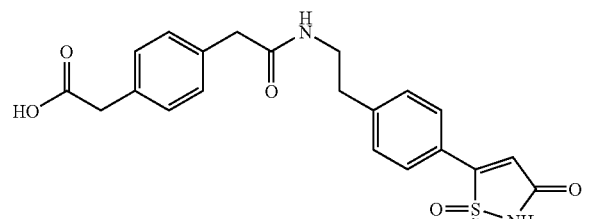

This compound was prepared according to the procedure in Example 1.23 using the appropriate reagents and starting materials. $^1$H NMR (500 MHz, CD$_3$OD): δ 7.92 (d, J=8.9 Hz, 2H), 7.50 (d, J=8.9 Hz, 2H), 7.03 (s, 1H), 6.94 (m, 4H), 3.55 (s, 2H), 3.45 (s, 2H), 3.40 (t, J=6.9 Hz, 2H), 2.87 (t, J=6.9 Hz, 2H); LCMS found for C$_{21}$H$_{21}$N$_2$O$_6$S (M+H)$^+$: m/z=429.

Example 1.33

{4-[2-({2-[4-(1,1-Dioxido-3-oxo-2,3-dihydroisothiazol-5-yl)phenyl]ethyl}amino)-2-oxoethyl]phenyl}acetic acid

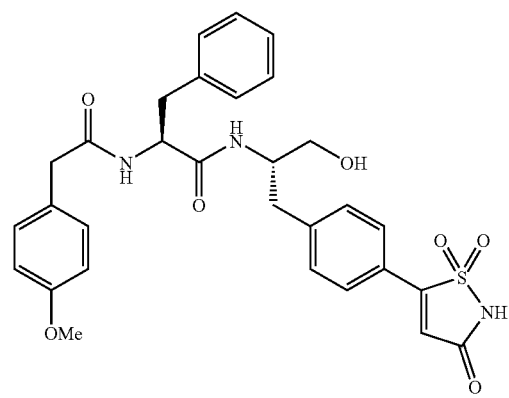

This compound was prepared according to the procedure in Example 1.23 using the appropriate reagents and starting materials. $^1$H NMR (500 MHz, CD$_3$OD): δ 7.89 (d, J=9.0 Hz, 2H), 7.51 (d, J=9.0 Hz, 2H), 7.06 (d, J=8.3 Hz, 1H), 7.00 (s, 1H), 6.87 (m, 3H), 3.59 (s, 2H), 3.45 (t, J=7.0 Hz, 2H), 3.39 (s, 2H), 2.89 (t, J=7.0 Hz, 2H); LCMS found for C$_{21}$H$_{21}$N$_2$O$_6$S (M+H)$^+$: m/z=429.

Example 1.34

N-(1S)-1-[4-(1,1-dioxido-3-oxo-2,3-dihydroisothiazol-5-yl)benzyl]-2-hydroxyethyl-N-α-[(4-methoxyphenyl)acetyl]-L-phenylalaninamide

141

Step 1. tert-butyl {(1R)-2-hydroxy-1-[4-(4,4,5,5-tetramethyl-1,3,2-dioxaborolan-2-yl)benzyl]ethyl}carbamate (34-A)

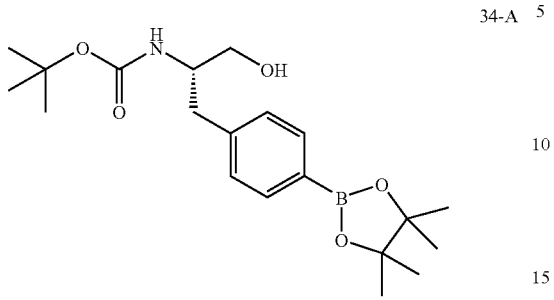

Methyl (2R)-2-[(tert-butoxycarbonyl)amino]-3-[4-(4,4,5,5-tetramethyl-1,3,2-dioxaborolan-2-yl)phenyl]propanoate (9.50 g, 0.0234 mol) was dissolved in tetrahydrofuran (30 mL, 0.37 mol) and cooled to 0° C. 2 M lithium tetrahydroborate in tetrahydrofuran (12.0 mL) was added over 3 minutes. The reaction was allowed to stir in the ice bath for 21 minutes. The bath was removed and the reaction continued stirring for additional 3 hours. The reaction was quenched with saturated aqueous ammonium chloride. The mixture was extracted with ethyl acetate. The combined organic extracts were washed with brine and dried over $Na_2SO_4$. The solution was filtered through a glass frit and the solvent concentrated to give a white solid (8.80 g, 100%). $^1$H NMR (400 MHz, $CDCl_3$): δ 7.75 (d, J=8.8 Hz, 2H), 7.23 (d, J=8.8 Hz, 2H), 4.73 (br s, 1H), 3.86 (br s, 1H), 3.66 (m, 1H), 3.54 (m, 1H), 2.87 (m, 2H), 1.42 (s, 9H), 1.34 (s, 12H).

Step 2. tert-butyl (1S)-1-[4-(2-tert-butyl-1,1-dioxido-3-oxo-2,3-dihydroisothiazol-5-yl)benzyl]-2-hydroxyethylcarbamate (34-B)

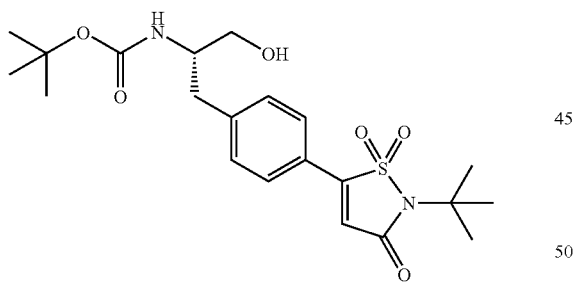

Combined 34-A (6.1 g, 61 mmol), 9-A (3.55 g, 15.9 mmol), potassium carbonate (10.0 g, 72.4 mmol), [1,1'-bis(diphenylphosphino)ferrocene]dichloropalladium(II), complex with dichloromethane (1:1) (2.50 g, 3.06 mmol) in 200 mL dioxane. The reaction was degassed and heated at 90° C. for 48 hours. The crude was extracted with ethyl acetate, washed with water and brine. The combined organic extracts were dried over $Na_2SO_4$, filtered and evaporated to give 11.4 g of a dark glass. The crude was chromatographed on a silica column to afford a dark semi-solid (3.3 g, 90%). $^1$H NMR (500 MHz, $CDCl_3$): δ 7.72 (d, J=8.8 Hz, 2H), 7.38 (d, J=8.8 Hz, 2H), 6.62 (s, 1H), 4.77 (br s, 1H), 3.89 (br s, 1H), 3.69 (m, 1H), 3.58 (m, 1H), 2.93 (d, J=7.2 Hz, 2H) 1.43 (s, 9H), 1.39 (s, 9H).

142

Step 3. 5-4-[(2S)-2-amino-3-hydroxypropyl]phenyl-isothiazol-3(2H)-one 1,1-dioxide bis(trifluoroacetate) salt (34-C)

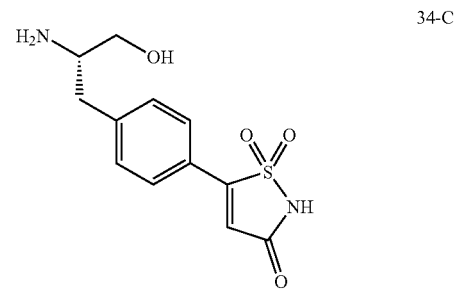

34-B (1.29 g, 2.94 mmol) was dissolved in 20 ml trifluoroacetic acid and heated to 80° C. for 17 hours. Solvent was evaporated to obtain a brown solid (1.46 g, 58%). $^1$H NMR (500 MHz, $CDCl_3$+$CD_3OD$): δ 7.80 (d, J=8.8 Hz, 2H), 7.42 (d, J=8.8 Hz, 2H), 6.72 (s, 1H), 4.22 (m, 1H), 3.55 (m, 1H), 3.46 (br s, 1H), 3.02 (m, 2H).

Step 4. N-(1S)-1-[4-(1,1-dioxido-3-oxo-2,3-dihydroisothiazol-5-yl)benzyl]-2-hydroxyethyl-N-α-[(4-methoxyphenyl)acetyl]-L-phenylalaninamide A solution of 34-C (200 mg, 0.235 mmol) and N-[(4-methoxyphenyl)acetyl]-L-phenylalanine (0.125 g, 0.399 mmol) was dissolved in 2.0 mL N,N-dimethylformamide. Diisopropylethylamine (0.480 mL, 0.2.76 mmol) was then added followed by N-(3-dimethylaminopropyl)-N'-ethylcarbodiimide hydrochloride (141 mg, 0.736 mmol). The reaction was stirred at room temperature for 3 days then heated to 50° C. for 20 h. The crude reaction was extracted with EtOAc, dried over $Na_2SO_4$, filtered, and solvents evaporated in vacuo. The crude oil was purified by reverse phase HPLC and combined fractions lyophilized to give a white powder (24 mg, 18%). $^1$H NMR (500 MHz, $CD_3OD$): δ 7.70 (m, 2H), 7.32 (m, 3H), 7.23 (m, 3H), 7.05 (m, 3H), 6.84 (m, 2H), 6.67 (s, 1H), 4.51 (m, 1H), 4.04 (br m, 2H), 3.80 (s, 3H), 3.53 (m, 1H), 3.43 (m, 2H), 3.40 (m, 1H), 3.38 (m, 1H), 2.91 (m, 1H); LCMS found for $C_{30}H_{32}N_3O_7S$ $(M+H)^+$: m/z=578.

Example 1.35

5-[4-(3'-Methanesulfonyl-biphenyl-4-ylmethylsulfanylmethyl)-phenyl]-1,1-dioxo-1,2-dihydro-1λ$^6$-isothiazol-3-one

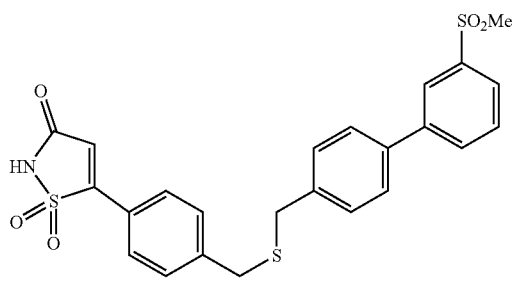

Step 1. Thioacetic acid S-(3'-methanesulfonyl-biphenyl-4-ylmethyl)ester (1.35-A)

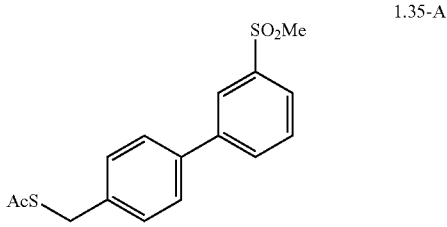

A solution of 4'-bromomethyl-3-methylsulfonylbiphenyl (190 mg, 0.57 mmol) (WO 01/70753) and potassium thioacetate (78 mg, 0.68 mmol) in N,N-dimethylformamide (4 mL) was heated at 150° C. in a microwave for 3 min. The reaction mixture was poured into diethyl ether (30 mL) and washed with water (3×15 mL), brine (15 mL), dried with magnesium sulfate, filtered, and concentrated to give a crude yellow oil. The crude oil was purified by flash column chromatography to yield 1.35-A (180 mg, 89%) as a thick light yellow oil. LCMS found for $C_{16}H_{17}O_3S_2$ $(M+H)^+$: m/z=321.

Step 2. (3'-Methanesulfonyl-biphenyl-4-yl)-methanethiol (1.35-B)

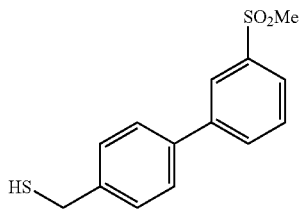

A solution of 1.35-A of Step 1 (160 mg, 0.49 mmol) in tetrahydrofuran (1.5 mL) and methanol (1.5 mL) was cooled to 0° C. and degassed. The reaction mixture was treated with sodium methoxide (0.30 mL, 3.3 mmol, 25 wt % solution in methanol) dropwise and stirred at 0° C. for 5 min. The reaction mixture was quenched with saturated ammonium chloride (20 mL) and extracted with ethyl acetate (30 mL). The organic layer was separated and washed with brine (10 mL), dried with sodium sulfate, filtered, and concentrated to give a white solid which was used in the next step without further purification. LCMS found for $C_{14}H_{15}O_2S_2$ $(M+H)^+$: m/z=279.

Step 3. Methanesulfonic acid 4-(2-tert-butyl-1,1,3-trioxo-2,3-dihydro-1λ⁶-isothiazolidin-5-yl)-benzyl ester (1.35-C)

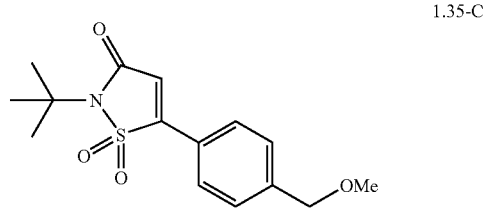

A solution of 20-A of Example 1.20 (120 mg, 0.42 mmol) and triethylamine (87 µL, 0.63 mmol) in methylenechloride (2.5 mL) was cooled to −10° C. and treated with methanesulfonyl chloride (37 µL, 0.48 mmol) dropwise. The reaction mixture was stirred at −10° C. for 10 min, diluted with methylene chloride (5 mL), and washed with water (20 mL), brine (10 mL), dried with sodium sulfate, filtered, and concentrated to give a white solid which was used in the next step without further purification. LCMS found for $C_{15}H_{19}NO_6S_2Na$ $(M+Na)^+$: m/z=396.

Step 4. 2-tert-Butyl-5-[4-(3'-methanesulfonyl-biphenyl-4-ylmethylsulfanylmethyl)-phenyl]-1,1-dioxo-1,2-dihydro-1λ⁶-isothiazol-3-one (1.36-D)

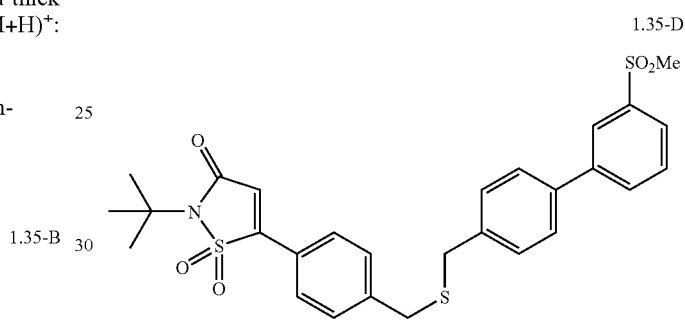

A solution of 1.35-C of Step 3 (153 mg, 0.41 mmol) and cesium carbonate (160 mg, 0.49 mmol) in N,N-dimethylformamide (1.5 mL) was cooled to 0° C. and degassed. The reaction mixture was treated with a solution of 1.35-B of Step 2 (137 mg, 0.49 mmol) in N,N-dimethylformamide (2 mL) and stirred at 0° C. for 45 min. The reaction mixture was diluted with ethyl acetate (50 mL), and washed with 0.1 M HCl (50 mL), brine (20 mL), dried with sodium sulfate, filtered, and concentrated to give a tan oil which was purified by reverse phase HPLC to yield 1.35-D (129 mg, 57%) as a white solid. LCMS found for $C_{28}H_{30}NO_5S_3$ $(M+H)^+$: m/z=556.

Step 5. 5-[4-(3'-Methanesulfonyl-biphenyl-4-ylmethylsulfanylmethyl)-phenyl]-1,1-dioxo-1,2-dihydro-1λ⁶-isothiazol-3-one The final compound was prepared according to the procedure of Example 1.1, Step 12, using 1.35-D of Step 4 as the starting material. $^1$H NMR (400 MHz, DMSO-d$_6$): δ 8.16 (dd, J=1.8, 1.6 Hz, 1H), 8.04 (ddd, J=7.8, 1.8, 1.2 Hz, 1H), 7.90 (ddd, J=8.8, 2.7, 1.0 Hz, 1H), 7.85 (d, J=8.2 Hz, 2H), 7.76–7.72 (m, 3H), 7.53 (d, J=8.4 Hz, 2H), 7.44 (d, J=8.2 Hz, 2H), 7.32 (s, 1H), 3.77 (d, J=9.2 Hz, 4H), 3.30 (s, 3H); LCMS found for $C_{24}H_{22}NO_5S_3$ $(M+H)^+$: m/z=500.

Example 1.36

5-[2-Bromo-4-(3-oxo-2,3-diphenyl-propyl)-phenyl]-1,1-dioxo-1,2-dihydro-1λ⁶-isothiazol-3-one

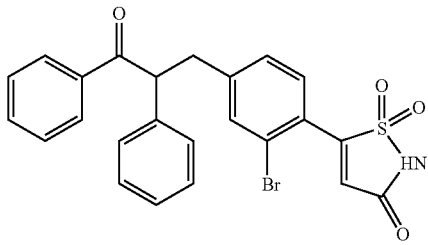

Step 1. 3-(3-Bromo-4-iodo-phenyl)-1,2-diphenyl-propan-1-one (1.36-A)

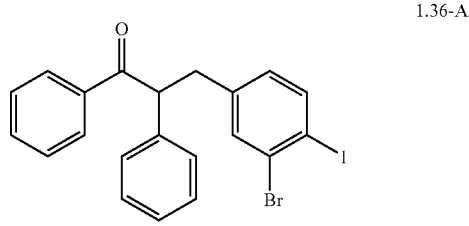

1.36-A

A solution of deoxybenzoin (26.4 mg, 0.134 mmol) in tetrahydrofuran (0.66 mL) was cooled to −78° C. and potassium tert-butoxide (0.15 mL, 0.15 mmol, 1.0 M in tetrahydrofuran) was added dropwise. The reaction mixture was stirred at −78° C. for 10 minutes and 2-bromo-4-(bromomethyl)-1-iodobenzene (50.0 mg, 0.133 mmol) in tetrahydrofuran (1 mL) was added dropwise. The reaction mixture was warmed to 25° C. and quenched with saturated ammonium chloride (5 mL) and extracted with ethyl acetate (2×5 mL). The combined organic extracts were washed with brine (5 mL), dried with magnesium sulfate, filtered, and concentrated to a crude yellow oil which was purified by flash column chromatography to yield the desired product (65 mg, 42%). LCMS found for $C_{21}H_{17}BrIO$ (M+H)⁺: m/z=491, 493.

Step 2. 5-[2-Bromo-4-(3-oxo-2,3-diphenyl-propyl)-phenyl]-2-tert-butyl-1,1-dioxo-1,2-dihydro-1λ⁶-isothiazol-3-one (1.36-B)

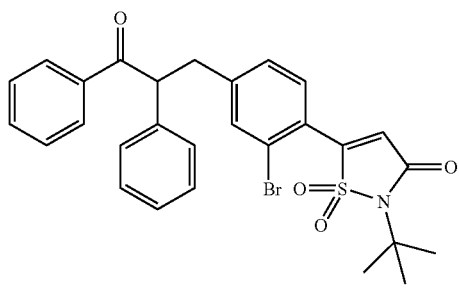

1.36-B

A solution of 1.36-A (25.0 mg, 51 μmol), 2-tert-butyl-isothiazol-3(2H)-one 1,1-dioxide (19.3 mg, 0.102 mmol), tetra-N-butylammonium chloride (21.2 mg, 76 μmol) and palladium acetate (1.71 mg, 7.6 μmol) in N,N-dimethylformamide (0.48 mL, 0.153 mmol). The reaction mixture was degassed by bubbling with a nitrogen balloon for 10 minutes and heated at 70° C. for 1 h. The reaction mixture was diluted with ethyl acetate (5 mL) and washed with water (5 mL) and 1 N HCl (5 mL). The organic extract was dried with magnesium sulfate, filtered, and concentrated to a crude residue which was purified by flash column chromatography to yield the desired product (12 mg, 43%). LCMS found for $C_{28}H_{27}BrNO_4S$ (M+H)⁺: m/z=552, 554.

Step 3. 5-[2-Bromo-4-(3-oxo-2,3-diphenyl-propyl)-phenyl]-1,1-dioxo-1,2-dihydro-1λ⁶-isothiazol-3-one A solution of 1.36-B (12 mg, 22 μmol) in trifluoroacetic acid (2.5 mL) was heated at 150° C. in a microwave for 30 sec. The reaction mixture was concentrated to a crude residue which was purified by preparative LCMS to yield the desired product (7 mg, 65%). ¹H NMR (400 MHz, CDCl₃): δ 7.91 (d, J=7.2 Hz, 2H), 7.75 (d, J=8.0 Hz, 1H), 7.52–7.47 (m, 2H), 7.37 (dd, J=7.8, 7.6 Hz, 2H), 7.32–7.21 (m, 6H), 7.00 (s, 1H), 4.79 (dd, J=7.4, 7.2 Hz, 1H), 3.57 (dd, J=13.7, 7.6 Hz, 1H), 3.10 (dd, J=13.9, 6.8 Hz, 1H); LCMS found for $C_{24}H_{19}BrNO_4S$ (M+H)⁺: m/z=496.

Example 1.37

N-{(S)-1-(4,5-Dihydro-1H-imidazol-2-yl)-2-[4-(1,1,3-trioxo-2,3-dihydro-1H-1λ⁶-isothiazol-5-yl)-phenyl]-ethyl}-3-trifluoromethyl-benzenesulfonamide

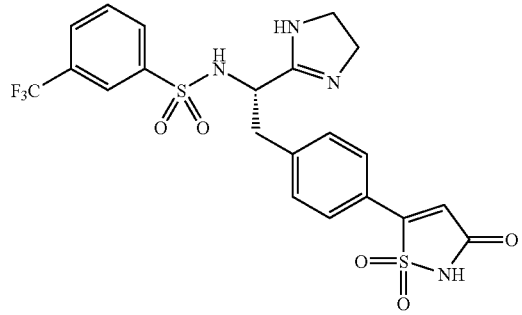

Step 1. (S)-2-Amino-3-[4-(2-tert-butyl-1,1,3-trioxo-2,3-dihydro-1H-1λ⁶-isothiazol-)5-yl)phenyl]-propionamide (1.37-A)

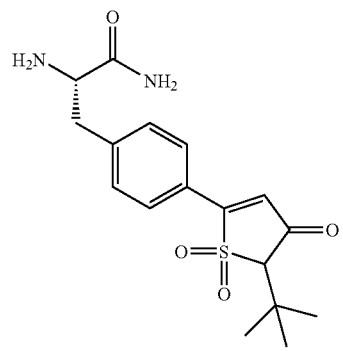

1.37-A

This compound was prepared according to the procedure of Example 1.1, Steps 4–7, using 9-A (Example 1.9) as the starting material. LCMS found for $C_{16}H_{22}N_3O_4S$ (M+H)⁺: m/z=352.

Step 2. (S)-3-[4-(2-tert-Butyl-1,1,3-trioxo-2,3-dihydro-1H-1λ⁶-isothiazol-5-yl)-phenyl]-2-(3-trifluoromethyl-benzenesulfonylamino)-propionamide (1.37-B)

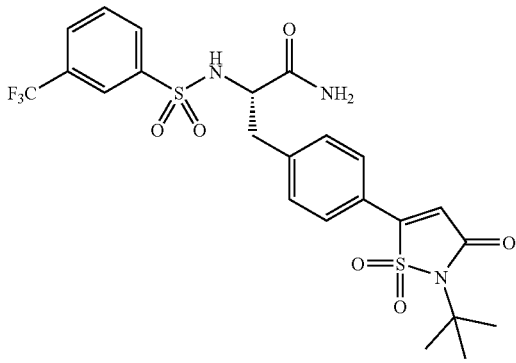

1.37-B

A solution of 1.37-A of Step 1 (1.7 g, 12.9 mmol) and N,N-diisopropylethylamine (2.2 mL, 12.9 mmol) in methylene chloride (23 mL) was treated with m-trifluoromethylbenzenesulfonyl chloride (1.4 mL, 8.6 mmol) dropwise. The reaction mixture was stirred at 25° C. for 30 min, diluted with ethyl acetate (200 mL), washed with 0.1 N HCl (2×80 mL) and brine (80 mL), dried with sodium sulfate, filtered, and concentrated to a crude residue which was purified by flash column chromatography to yield the desired product (1.7 g, 70%). LCMS found for $C_{23}H_{25}F_3N_3O_6S_2$ (M+H)⁺: m/z=560.

Step 3. N-{2-[4-(2-tert-Butyl-1,1,3-trioxo-2,3-dihydro-1H-1λ⁶-isothiazol-5-yl)-phenyl]-1-cyano-ethyl}-3-trifluoromethyl-benzenesulfonamide (1.37-C)

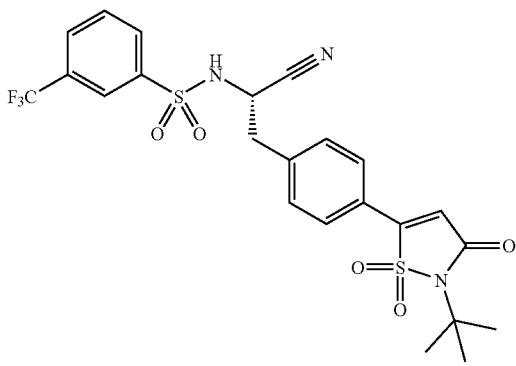

1.37-C

A solution of 1.37-B of Step 2 (367 mg, 0.66 mmol) in methylene chloride (7.6 mL) was treated with triethylamine (274 μL, 2.0 mmol) followed by trichloroacetyl chloride (117 μL, 1.1 mmol) at 0° C. The reaction mixture was stirred at 0° C. for 2 h, diluted with ethyl acetate (25 mL), washed with water (2×20 mL) and brine (20 mL), dried with sodium sulfate, filtered, and concentrated to a crude residue which was purified by flash column chromatography to yield the desired product (158 mg, 45%). LCMS found for $C_{23}H_{26}F_3N_4O_5S_2$ (M+NH₄)⁺: m/z=559.

Step 4. 3-[4-(2-tert-Butyl-1,1,3-trioxo-2,3-dihydro-1H-1λ⁶-isothiazol-5-yl)-phenyl]-2-(3-trifluoromethyl-benzenesulfonylamino)-propionimidic acid ethyl ester hydrochloride (1.37-D)

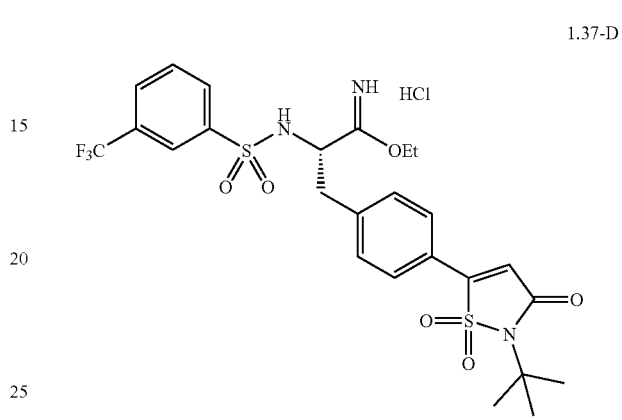

1.37-D

A solution of 1.37-C of Step 3 (87 mg, 0.16 mmol) in methylene chloride (5 mL) and ethanol (0.2 mL) was treated with HCl gas for 1 h. Additional methylene chloride was added during the reaction to replenish the amount which was evaporated during the bubbling of HCl. The reaction mixture was concentrated and used immediately in the next reaction.

Step 5. N-[2-[4-(2-tert-Butyl-1,1,3-trioxo-2,3-dihydro-1H-1λ⁶-isothiazol-5-yl)-phenyl]-1-(4,5-dihydro-1H-imidazol-2-yl)-ethyl]-3-trifluoromethyl-benzenesulfonamide Trifluoroacetate (1.37-E)

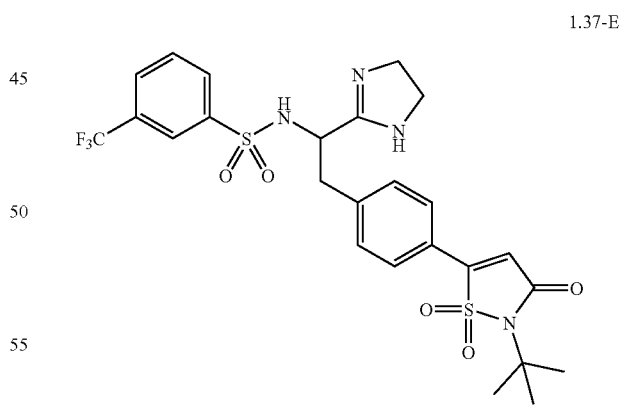

1.37-E

A solution of 1.37-D of Step 4 (160 mg, 0.16 mmol) in ethanol (2 mL) was treated with ethylenediamine (11.3 μL, 0.17 mmol) dropwise at 0° C. The reaction mixture was stirred at 0° C. for 1 h, quenched with trifluoroacetic acid (24.8 μL, 0.322 mmol), and warmed to 25° C. The reaction mixture was concentrated to a brown foam that was purified by preparative LCMS to yield 1.37-E (46 mg, 41%). LCMS found for $C_{25}H_{28}F_3N_4O_5S_2$ (M+H)⁺: m/z=585.

Step 6. N-{1-(4,5-Dihydro-1H-imidazol-2-yl)-2-[4-(1,1,3-trioxo-2,3-dihydro-1H-1λ⁶-isothiazol-5-yl)-phenyl]-ethyl}-3-trifluoromethyl-benzenesulfonamide The final compound was prepared according to the procedure of Example 1.36, Step 3, using 1.37-E of Step 5 as the starting material. ¹H NMR (400 MHz, CD₃OD): δ 7.91 (brs, 1H), 7.84 (d, J=7.6 Hz, 1H), 7.71 (d, J=9.4 Hz, 1H), 7.58–7.51 (m, 3H), 7.18 (d, J=8.2 Hz, 2H), 6.93 (s, 1H), 4.49 (dd, J=10.5, 4.3 Hz, 1H), 4.02–3.97 (m, 4H), 3.15 (dd, J=14.1, 4.3 Hz, 1H), 2.92 (dd, J=14.1, 10.7 Hz, 1H); LCMS found for $C_{21}H_{20}F_3N_4O_5S_2$ (M+H)⁺: m/z=529.

Example 1.38

({4-[((S)-1-{(S)-1-Carbamoyl-2-[4-(1,1,3-trioxo-2,3-dihydro-1H-1λ⁶-isothiazol-5-yl)-phenyl]-ethylcarbamoyl}-2-phenyl-ethylcarbamoyl)-methyl]-phenyl}-difluoro-methyl)-phosphonic acid

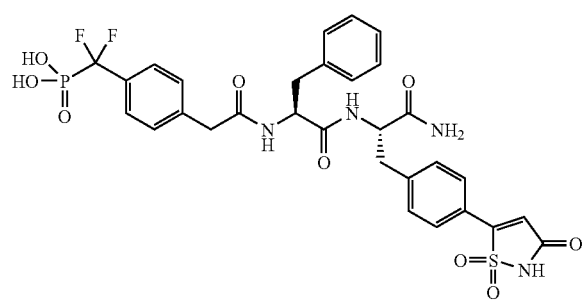

Step 1. ((S)-1-{(S)-2-[4-(2-tert-Butyl-1,1,3-trioxo-2,3-dihydro-1H-1λ⁶-isothiazol-5-yl)-phenyl]-1-carbamoyl-ethylcarbamoyl}-2-phenyl-ethyl)-carbamic acid tert-butyl ester (1.38-A)

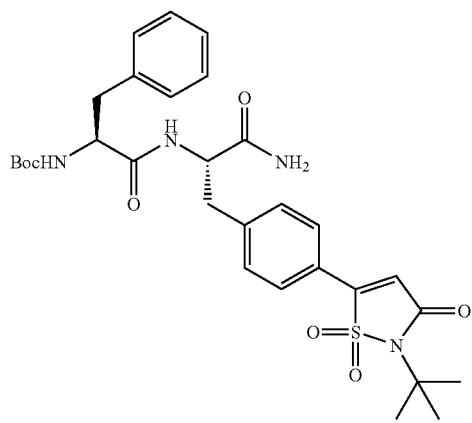

This compound was prepared according to the procedure of Example 1.1, Step 8, using 1.37-A of Example 1.37, Step 1 as the starting material. LCMS found for $C_{25}H_{31}N_4O_5S$ (M(-Boc)+H)⁺: m/z=499.

Step 2. (S)-2-Amino-N-{(S)-1-carbamoyl-2-[4-(1,1,3-trioxo-2,3-dihydro-1H-1λ⁶-isothiazol-5-yl)-phenyl]-ethyl}-3-phenyl-propionamide Trifluoroacetate (1.38-B)

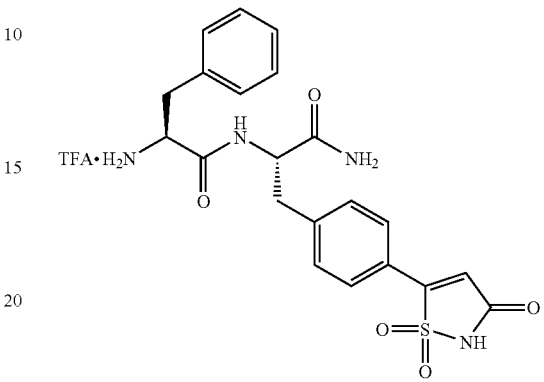

This compound was prepared according to the procedure of Example 1.1, Step 12, using 1.38-A of Step 1 as the starting material. LCMS found for $C_{21}H_{23}N_4O_5S$ (M+H)⁺: m/z=443.

Step 3. ({4-[((S)-1-{(S)-1-Carbamoyl-2-[4-(1,1,3-trioxo-2,3-dihydro-1H-1λ⁶-isothiazol-5-yl)-phenyl]-ethylcarbamoyl}-2-phenyl-ethylcarbamoyl)-methyl]-phenyl}-difluoro-methyl)-phosphonic acid diethyl ester (1.38-C)

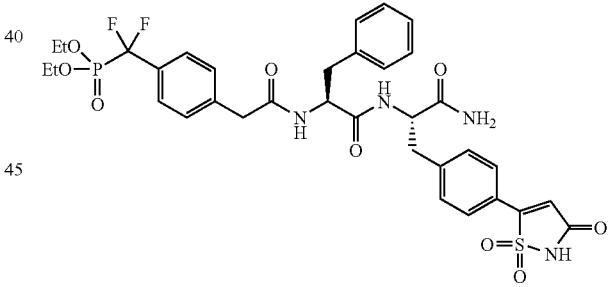

This compound was prepared according to the procedure of Example 1.1, Step 10, using 1.38-B of Step 2 and {4-[(diethoxy-phosphoryl)-difluoro-methyl]-phenyl}-acetic acid (Biochemistry, 2003, 42, 12792) as the starting materials. LCMS found for $C_{34}H_{38}F_2N_4O_9PS$ (M+H)⁺: m/z=747.

Step 4. ({4-[((S)-1-{(S)-1-Carbamoyl-2-[4-(1,1,3-trioxo-2,3-dihydro-1H-1λ⁶-isothiazol-5-yl)-phenyl]-ethylcarbamoyl}-2-phenyl-ethylcarbamoyl)-methyl]-phenyl}-difluoro-methyl)-phosphonic acid 1.38-C of Step 3 (53 mg, 71 µmol) was treated with a solution of trifluoroacetic acid (2.5 mL, 32.5 mmol), trimethylsilyl trifluoromethanesulfonate (0.29 mL, 1.6 mmol), dimethyl sulfide (0.88 mL, 12.0 mmol), and triisopropylsilane (52 µL, 0.26 mmol). The reaction mixture was stirred at 25° C. for 16 h, concentrated, and purified by preparative HPLC to yield 1.38-A (17 mg, 35%). $^1$H NMR (500 MHz, CD$_3$OD): δ 7.88–7.78 (m, 2H), 7.54–7.39 (m, 4H), 7.27–7.12 (m, 7H), 7.01 (brs, 1H), 4.72–4.58 (m, 2H), 3.58–3.45 (m, 2H), 3.30–3.25 (m, 1H), 3.12–3.05 (m, 1H), 3.05–2.97 (m, 1H), 2.90–2.80 (m, 1H); LCMS found for C$_{30}$H$_{30}$F$_2$N$_4$O$_9$PS (M+H)$^+$: m/z=691.

Example 1.39

5-4-[(4-[2-(Methylsulfonyl)phenoxy]benzyloxy)methyl]phenylisothiazol-3(2H)-one 1,1-dioxide

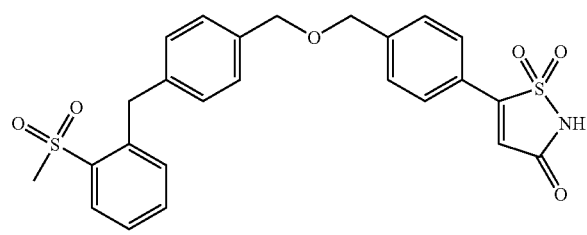

Step 1. Synthesis of 2-(methylthio)phenol

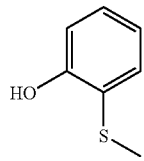

2-Mercaptophenol (0.80 mL, 7.9 mmol) was added to a solution of sodium hydroxide (0.290 g, 7.2 mmol) in methanol (5.0 mL). The resulting light green solution was stirred for 30 minutes before methyl iodide (0.45 mL, 7.2 mmol) was added carefully over 1 minute. The reaction was stirred at ambient temperature for 2 hours, and was evaporated to dryness. The residue was partitioned between ether and water. The combined organic layers were dried over sodium sulfate, filtered, and evaporated to yield an oil (1.08 g, 100%). $^1$H NMR (400 MHz, CDCl$_3$): δ 7.49 (dd, J=7.6 Hz, J'=1.6 Hz, 1H), 7.25 (m, 1H), 6.98 (dd, J=8.2 Hz, J'=1.4 Hz, 1H), 6.88 (td, J=7.4 Hz, J'=1.3 Hz, 1H), 6.65 (bs, 1H), 2.33 (s, 3H).

Step 2. Synthesis of 2-(methylsulfonyl)phenol

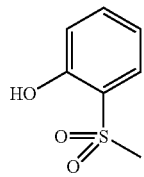

2-(Methylthio)phenol (1.08 g, 7.32 mmol) was dissolved in acetone (20 mL). Oxone® (9.4 g, 15 mmol) was separately dissolved in water (100 mL) and stirred at ambient temperature for 24 h. The acetone was concentrated, extracted with ether, dried over sodium sulfate, filtered, and concentrated to yield a waxy solid (1.2 g, 95%). $^1$H NMR (400 MHz, CDCl$_3$): δ 8.85 (s, 1H), 7.69 (dd, J=8.4 Hz, J'=1.7 Hz, 1H), 7.54 (m, 1H), 7.05 (m, 2H), 3.12 (s, 3H); LCMS found for C$_7$H$_9$O$_3$S (M+H)$^{+:\ m/z}$=173.0.

Step 3. Synthesis of 4-[2-(methylsulfonyl)phenoxy]benzaldehyde

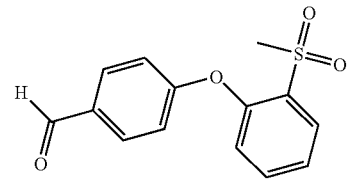

4-Fluorobenzaldehyde (0.690 mL, 6.4 mmol) and 2-(methylsulfonyl)phenol (1.2 g, 7.0 mmol) were dissolved in N,N-dimethylformamide (15 mL), and potassium carbonate (0.85 g, 6.1 mmol) was added. The mixture was heated at 100° C. for 4 days. The reaction was diluted with ethyl acetate and extracted with water three times. The combined aqueous layers were extracted with ethyl acetate twice. The combined organic layers were dried over sodium sulfate, filtered, and evaporated on the rotovap. The residue was chromatographed on silica gel using a 20–40% ethyl acetate in hexanes. The major component was collected to give a solid (0.942 g, 53%). $^1$H NMR (400 MHz, CDCl$_3$): δ 9.97 (s, 1H), 8.12 (dd, J=8.0 Hz, J'=1.6 Hz, 1H), 7.92 (dd, J=6.6 Hz, J'=2.1 Hz, 2H), 7.64 (m, 1H), 7.38 (td, J=7.9 Hz, J'=1.0 Hz, 1H), 7.18 (dd, J=6.7 Hz, J'=1.9 Hz, 2H), 7.07 (dd, J=8.8.2 Hz, J'=1.0 Hz, 1H), 3.28 (s, 3H); LCMS found for C$_{14}$H$_{13}$O$_4$S (M+H)$^+$: m/z=277.0.

Step 4. Synthesis of 5-4-[(4-[2-(methylsulfonyl)phenoxy]benzyloxy)methyl]phenylisothiazol-3(2H)-one 1,1-dioxide

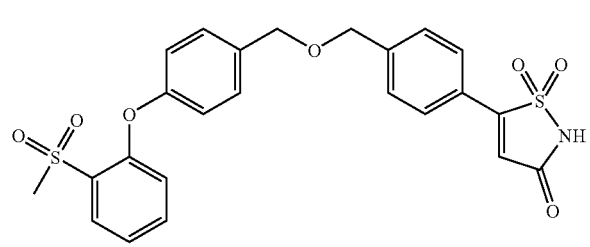

4-[2-(Methylsulfonyl)phenoxy]benzaldehyde (0.132 g, 0.478 mmol) and 5-[4-(hydroxymethyl)phenyl]isothiazol-3(2H)-one 1,1-dioxide (0.100 g, 0.418 mmol) were dissolved in 1,4-dioxane (3 mL). 4 M hydrogen chloride in 1,4-dioxane (1 mL) was added, followed 4 minutes later by triethylsilane (0.1 mL, 0.63 mmol). The reaction was stirred at ambient temperature for 23 h. HPLC analysis indicated only unreacted starting materials. Additional 4 M hydrogen chloride in 1,4-dioxane (2 mL) was added and stirred at ambient temperature 19 h. Crushed 3 Å molecular sieves (0.2 g) were added. After 6 h, the reaction was evaporated. 4 M hydrogen chloride in 1,4-dioxane (3 mL) was added, followed 3 minutes later by triethylsilane (0.1 mL, 0.63 mmol). The reaction was stirred for 3 days at ambient temperature, quenched with acetone, and evaporated. The product was purified on a 50 mm Luna C18 column using a 20–100% acetonitrile in water gradient with 0.05% trifluoroacetic acid at 30 mL per minute over a 30 minute period. The product was lyophilized to give a white powder (37 mg, 18%). $^1$H NMR (500 MHz, CD$_3$OD): δ 8.01 (dd, J=7.8 Hz, J'=1.4 Hz, 1H), 7.89 (d, J=8.3 Hz, 2H), 7.63 (m, 1H), 7.58 (d, J=8.3 Hz, 2H), 7.47 (dd, J=8.3 Hz, J'=6.3 Hz, 2H), 7.31 (m, 1H), 7.14 (dd, J=6.3 Hz, J'=1.9 Hz, 2H), 7.05 (s, 1H), 6.98 (d, J=8.3 Hz, 1H), 4.68 (s, 2H), 4.63 (s, 2H), 3.33 (s, 3H); LCMS found for C$_{24}$H$_{25}$N$_2$O$_7$S$_2$ (M+NH$_4$)$^+$: m/z=517.1.

Example 2.1

(S)-2-{(S)-2-[2-(4-Methoxy-phenyl)-acetylamino]-3-phenyl-propionylamino}-N-pentyl-3-[4-(1,1,3-trioxo-2,3-dihydro-1H-1λ$^6$-isothiazol-4-yl)-phenyl]-propionamide

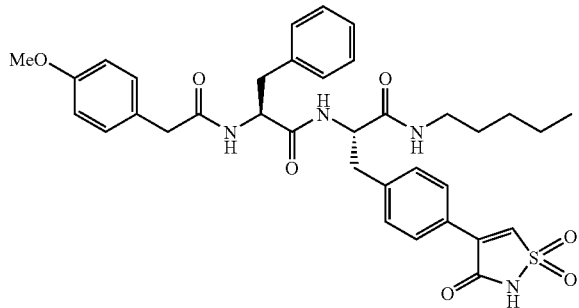

This compound was prepared according to the procedure of Example 1.9 using 4-bromo-2-tert-butyl-1,1-dioxo-1,2-dihydro-1λ$^6$-isothiazol-3-one (Helv. Chim. Acta (1989), 72, 1416) and other appropriate starting materials. $^1$H NMR (500 MHz, CD$_3$OD): δ 8.15 (d, J=7.8 Hz, 1H), 7.99 (d, J=7.8 Hz, 1H), 7.96 (s, 1H), 7.85–7.81 (m, 3H), 7.32 (d, J=8.3 Hz, 2H), 7.25–7.21 (m, 3H), 7.15–7.14 (m, 2H), 7.03 (dd, J=6.8, 2.0 Hz, 2H), 6.81 (dd, J=6.8, 2.0 Hz, 2H), 4.63–4.55 (m, 2H), 3.78 (s, 3H), 3.40 (d, J=2.9 Hz, 2H), 3.20–3.00 (m, 4H), 2.97 (dd, J=13.7, 8.3 Hz, 1H), 2.86 (dd, J=13.7, 8.8 Hz, 1H), 1.42–1.37 (m, 2H), 1.37–1.25 (m, 2H), 1.22–1.18 (m, 2H), 0.90 (t, J=7.3 Hz, 3H); LCMS found for C$_{35}$H$_{40}$N$_4$O$_7$S (M+H)$^+$: m/z=661.

Example 3.1

((S)-1-{(S)-1-Pentylcarbamoyl-2-[4-(1,1,4-trioxo-1λ$^6$-[1,2,5]thiadiazolidin-2-yl)-phenyl]-ethylcarbamoyl}-2-phenyl-ethyl)-carbamic acid tert-butyl ester

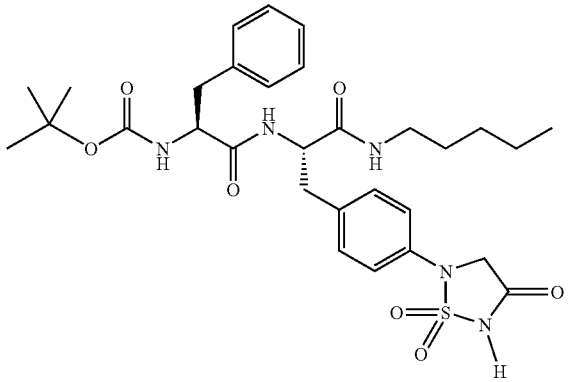

Step 1. {(S)-2-[4-(5-Benzyl-1,1,4-trioxo-1λ$^6$-[1,2,5]thiadiazolidin-2-yl)-phenyl]-1-pentylcarbamoyl-ethyl}-carbamic acid tert-butyl ester (301-A)

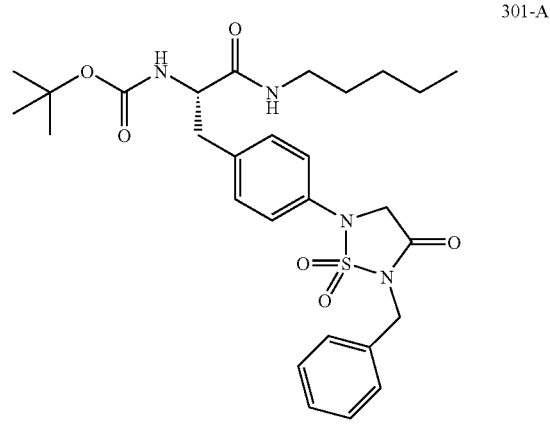

301-A

2-Benzyl-1,1-dioxo-1λ$^6$-[1,2,5]thiadiazolidin-3-one (Tetrahedron (1996), 52, 993) (174 mg, 0.769 mmol), copper(II) acetate (211 mg, 1.16 mmol), 9-C (582 mg, 1.54 mmol), triethylamine (0.322 mL, 2.31 mmol), and 4 Å molecular sieves (500 mg) in methylene chloride (10.0 mL) were stirred at ambient temperature under air for 24 h. The reaction mixture was filtered through celite, concentrated in vacuo, and the residue purified by preparative LCMS to afford product 301-A as a white solid (208 mg, 41%). $^1$H NMR (500 MHz, CD$_3$OD): δ 7.48 (d, J=7.1 Hz, 1H), 7.40–7.33 (m, 7H), 4.88 (s, 2H), 4.62 (s, 2H), 4.26 (dd, J=8.4, 6.8 Hz, 1H), 3.15–3.06 (m, 3H), 2.86 (dd, J=13.0, 8.8 Hz, 1H), 1.47–1.43 (m, 2H), 1.39 (s, 9H), 1.37–1.33 (m, 2H), 1.31–1.25 (m, 2H), 0.92 (t, J=7.0 Hz, 3H). LCMS found for C$_{28}$H$_{38}$N$_4$O$_6$S (M+H)$^+$: m/z=559.

Step 2. ((S)-1-{(S)-2-[4-(5-Benzyl-1,1,4-trioxo-1λ$^6$-[1,2,5]thiadiazolidin-2-yl)-phenyl]-1-pentylcarbamoyl-ethylcarbamoyl}-2-phenyl-ethyl)-carbamic acid tert-butyl ester (301-B)

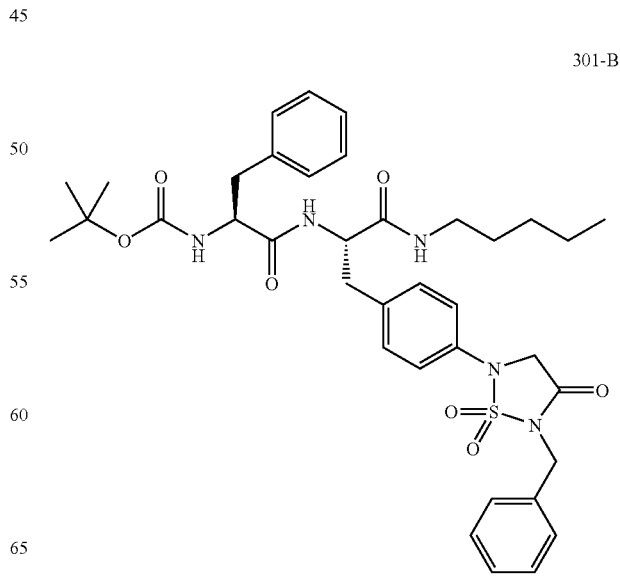

301-B

Amide 301-A (16 mg, 0.029 mmol) in methylene chloride (1.5 mL) was treated with trifluoroacetic acid (0.5 mL). The solution stirred 1 h under nitrogen and was then concentrated in vacuo. 301-C: LCMS found for $C_{23}H_{30}N_4O_4S$ (M+H)$^+$: m/z=459. The residue 301-C in methylene chloride/DMF=5/1 (1.5 mL) was added to a solution of PheBocOH (9.2 mg, 0.0348 mmol) that was pre-treated with EDC (6.7 mg, 0.0348 mmol), diisopropylethylamine (25 μL, 0.145 mmol), and HOAt (5 μL, 0.00348 mmol) in methylene chloride/DMF=5/1 (1.5 mL). The solution stirred under nitrogen for 2 h and was then diluted with methylene chloride (10 mL) washed with aqueous hydrochloric acid solution (0.1 N, 30 mL) and saturated aqueous sodium bicarbonate solution (30 mL). The organic phase was separated, dried over sodium sulfate, and concentrated in vacuo. The residue was purified by silica gel chromatography (75% EtOAc/hexanes) to afford product 301-B as a white solid (15 mg, 73%). $^1$H NMR (500 MHz, CD$_3$OD): δ 7.47 (d, J=6.9 Hz, 2H), 7.36–7.10 (m, 12H), 4.88 (s, 2H), 4.61 (s, 2H), 4.55 (t, J=7.5 Hz, 1H), 4.26 (dd, J=9.4, 5.4 Hz, 1H), 3.13–2.98 (m, 5H), 2.80–2.75 (m, 1H), 1.40–1.38 (m, 2H), 1.38 (s, 9H), 1.34–1.22 (m, 4H), 0.91 (t, J=7.1 Hz, 3H). LCMS found for $C_{16}H_{24}N_4O_4S$ (M(−Boc)−H)$^+$: m/z=606.

Step 3. ((S)-1-{(S)-1-Pentylcarbamoyl-2-[4-(1,1,4-trioxo-1λ$^6$-[1,2,5]thiadiazolidin-2-yl)-phenyl]-ethylcarbamoyl}-2-phenyl-ethyl)-carbamic acid tert-butyl ester Amide 301-B (12 mg, 0.17 mmol) was dissolved in ethanol (1.00 mL) and treated with ammonium formate (12 mg). The suspension was degassed with nitrogen. 10% wt. palladium on activated carbon (12 mg) was added and the solution stirred at 60° C. for 1 h under nitrogen. Filtration of the reaction mixture through celite followed by purification on preparative LCMS afforded Example 3.1 (6.7 mg, 64%). $^1$H NMR (500 MHz, CD$_3$OD): δ 7.28–7.09 (m, 9H), 4.54 (q, J=7.5 Hz, 1H), 4.44 (s, 2H), 4.26 (dd, J=9.1, 5.1 Hz, 1H), 3.17–3.14 (m, 1H), 3.09–3.00 (m, 4H), 2.81–2.77 (m, 1H), 1.44–1.40 (m, 2H), 1.38 (s, 9H), 1.36–1.33 (m, 2H), 1.30–1.26 (m, 2H), 0.92 (t, J=7.5 Hz, 3H). LCMS found for $C_{30}H_{41}N_5O_7S$ (M−H)$^-$: m/z=614.

Example 3.2

(S)-2-{(S)-2-[2-(4-Methoxy-phenyl)-acetylamino]-3-phenyl-propionylamino}-N-pentyl-3-[4(1,1,4-trioxo-1λ$^6$-[1,2,5]thiadiazolidin-2-yl)-phenyl]-propionamide

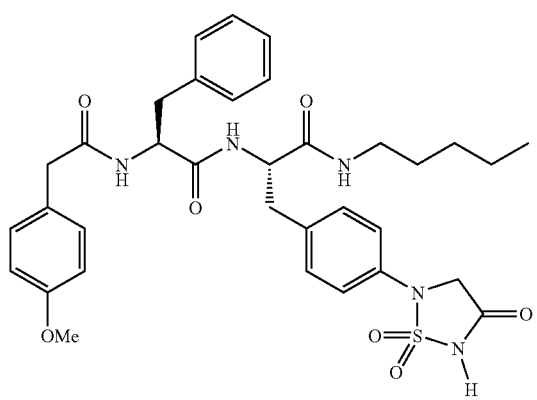

Step 1. (S)-3-[4-(5-Benzyl-1,1,4-trioxo-1λ$^6$-[1,2,5]thiadiazolidin-2-yl)-phenyl]-2-{(S)-2-[2-(4methoxyphenyl(-acetylamino]-3-phenyl-propionylamino}-N-pentyl-propionamide (302-A)

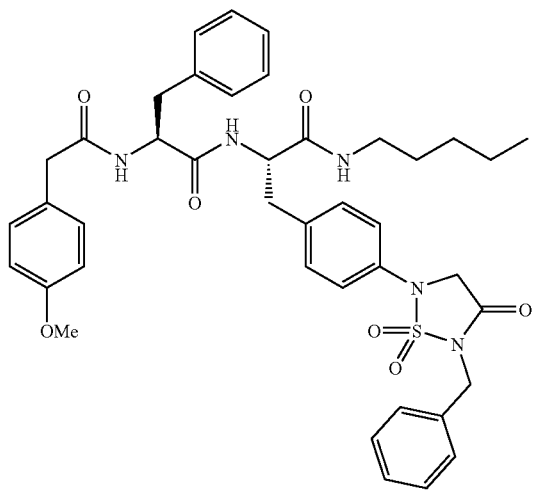

302-A

Following the deprotection/coupling protocol of Example 3.1, Step 2, 301-B (48 mg, 0.68 mmol) was converted to adduct 302-A (13 mg, 25%). $^1$H NMR (500 MHz, CD$_3$OD): δ 8.18 (t, J=8.3 Hz, 2H), 7.87 (t, J=5.7 Hz, 1H), 7.42–7.18 (m, 14H), 6.98 (d, J=8.8 Hz, 2H), 6.76 (d, J=8.8 Hz, 2H), 4.84 (s, 2H), 4.82 (s, 2H), 4.50–4.44 (m, 2H), 3.70 (s, 3H), 3.27 (dd, J=15.5, 8.8 Hz, 2H), 3.03–2.97 (m, 4H), 2.83 (dd, J=14.0, 8.6 Hz, 1H), 2.73 (dd, J=13.9, 9.7 Hz, 1H), 1.41–1.38 (m, 2H), 1.36–1.33 (m, 2H), 1.26–1.20 (m, 2H), 0.86 (t, J=7.2 Hz, 3H). LCMS found for $C_{41}H_{47}N_5O_7S$ (M+H)$^{+: m/z=}$754.

Step 2. (S)-2-{(S)-2-[2-(4-Methoxy-phenyl)-acetylamino]-3-phenyl-propionylamino}-N-pentyl-3-[4-(1,1,4-trioxo-1λ$^6$-[1,2,5]thiadiazolidin-2-yl)-phenyl]-propionamide Following the debenzylation protocol of Example 3.1, Step 3, compound 302-A (11.0 mg, 0.150 mmol) was converted to final product (6.0 mg, 62%). $^1$H NMR (500 MHz, CD$_3$OD): δ 7.31–7.16 (m, 9H), 7.02 (d, J=8.8 Hz, 2H), 6.82 (d, J=8.8 Hz, 2H), 4.62–4.58 (m, 1H), 4.55–4.50 (m, 1H), 4.42 (s, 2H), 3.78 (s, 3H), 3.62–3.59 (m, 2H), 3.17–3.01 (m, 4H), 2.92–2.80 (m, 2H), 1.43–1.37 (m, 2H), 1.38–1.33 (m, 2H), 1.25–1.20 (m, 2H), 0.86 (t, J=7.2 Hz, 3H). LCMS found for $C_{34}H_{41}N_5O_7S$ (M−N)$^-$: m/z=662.

Example 3.3

N-(1S)-2-[4-(1,1-dioxido-4-oxo-1,2,5-thiadiazolidin-2-yl)phenyl]-1-[5-(trifluoromethyl)-1H-benzimidazol-2-yl]ethylbiphenyl-4-sulfonamide

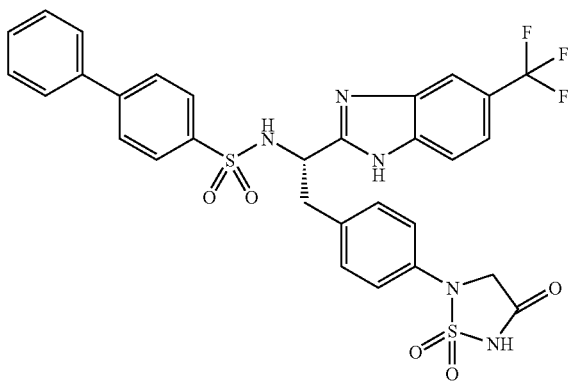

Step 1. Synthesis of benzyl (2S)-2-[(tert-butoxycarbonyl)amino]-3-4-[(2-ethoxy-2-oxoethyl)amino]phenylpropanoate

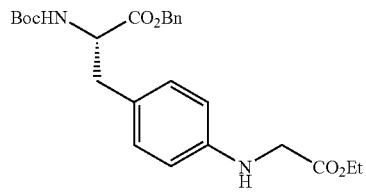

Benzyl (2S)-3-(4-aminophenyl)-2-[(tert-butoxycarbonyl)amino]propanoate (9.89 g, 0.026 mol), ethyl bromoacetate (3.2 mL, 0.028 mol), N,N-diisopropylethylamine (5.4 mL, 0.031 mol) were dissolved in acetonitrile (50 mL) and stirred at 25° C. overnight. The solvent was evaporated. The residue was diluted with ethyl acetate, washed with water and saturated aqueous sodium bicarbonate, then dried with MgSO$_4$. The solvent was evaporated. The mixture was purified by silica gel chromatography, eluting with 50% ethyl acetate in hexanes. Fractions containing the major component were combined and rotavaped to give a yellow oil. The oil was dissolved in ethyl acetate (30 mL) and then hexanes (500 mL) was added, evaporated to slush, which was filtered and washed with hexanes. The solid was placed under high vacuum to remove residual solvent 6.93 g, 58%). $^1$H NMR (400 MHz, CDCl$_3$): δ 7.33 (m, 5H), 6.85 (d, J=8.2 Hz, 2H), 6.48 (d, J=8.3 Hz, 2H), 5.17 (d, J=12.3 Hz, 1H), 5.09 (d, J=12.3 Hz, 1H), 4.94 (d, J=8.2 Hz, 1H), 4.55 (m, 1H), 4.25 (q, J=7.2 Hz, 2H), 3.86 (d, J=4.1 Hz, 2H), 2.98 (d, J=6.2 Hz, 2H), 1.41 (s, 9H), 1.30 (t, J=7.1 Hz, 3H); LCMS found for C$_{25}$H$_{32}$N$_2$NaO$_6$ (M+Na)$^+$: m/z=479.2.

Step 2. Synthesis of benzyl (2S)-2-[(tert-butoxycarbonyl)amino]-3-4-[[(tert-butoxycarbonyl)amino]-3-4-[[(tert-butoxycarbonyl)amino]sulfonyl(2-ethoxy-2-oxoethyl)amino]phenylpropanoate

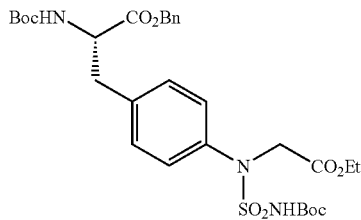

Benzyl (2S)-2-[(tert-butoxycarbonyl)amino]-3-4-[(2-ethoxy-2-oxoethyl)amino]phenylpropanoate (6.93 g, 15.2 mmol) and N,N-diisopropylethylamine (10.6 mL, 60.7 mmol) were dissolved in methylene chloride (45 mL) and cooled to 0° C. Into the reaction was added tert-butyl (chlorosulfonyl)carbamate (5.4 g, 25 mmol) in methylene chloride (30 mL) dropwise. The reaction was stirred at 0° C. for 10 minutes and at 25° C. overnight. The reaction mixture was extracted with dichloromethane, washed with water, 1 N HCl, brine, dried with MgSO$_4$ and the solvent evaporated. The mixture was purified by silica gel chromatography, eluting with 30–100% ethyl acetate in hexanes to give an orange glass (7.3 g, 76%). $^1$H NMR (400 MHz, CD$_3$OD): δ 7.34 (m, 7H), 7.20 (d, J=8.4 Hz, 2H), 5.14 (m, 2H), 4.58 (s, 2H), 4.37 (m, 1H), 4.15 (q, J=7.2 Hz, 2H), 3.10 (m, 1H), 2.92 (m, 1H), 1.50 (s, 9H), 1.37 (s, 9H), 1.23 (t, J=7.1 Hz, 3H); LCMS found for C$_{30}$H$_{41}$N$_3$NaO$_{10}$S (M+Na)$^+$: m/z=658.2.

Step 3. Synthesis of (2S)-2-[(tert-butoxycarbonyl)amino]-3-4-[[(tert-butoxycarbonyl)amino]sulfonyl(2-ethoxy-2-oxoethyl)amino]phenylpropanoic acid

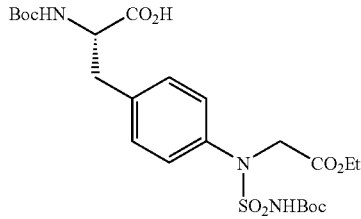

Benzyl (2S)-2-[(tert-butoxycarbonyl)amino]-3-4-[[(tert-butoxycarbonyl)amino]sulfonyl(2-ethoxy-2-oxoethyl)amino]phenylpropanoate (7.30 g, 10.9 mmol) was dissolved in ethanol (100 mL) in a Parr bottle. Palladium (10% by weight on carbon, 3.65 g, 3.43 mol) was added, the mixture degassed and hydrogenated at 60 psi overnight. The suspension was filtered, washed with ethanol and evaporated to give the crude material as a foam (6.36 g, 100%). $^1$H NMR (400 MHz, CDCl$_3$): δ 7.56 (bs, 1H), 7.39 (d, J=8.4 Hz, 2H), 7.22 (d, J=8.4 Hz, 2H), 5.14 (d, J=7.4 Hz, 1H), 4.61 (s, 2H), 4.19 (q, J=7.2 Hz, 2H), 3.14 (m, 2H), 1.50 (s, 9H), 1.43 (bs, 9H), 1.26 (t, J=7.2 Hz, 3H); LCMS found for C$_{23}$H$_{35}$N$_3$NaO$_{10}$S (M+Na)$^+$: m/z=568.0.

Step 4. Synthesis of Ethyl ((4-(2S)-3-[2-amino-5-(trifluoromethyl)phenyl]amino-2-[(tert-butoxycarbonyl)amino]-3-oxopropylphenyl)[(tert-butoxycarbonyl)amino]sulfonylamino)acetate

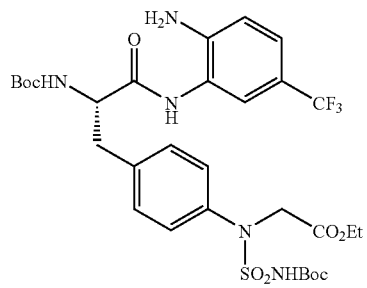

(2S)-2-[(tert-Butoxycarbonyl)amino]-3-4-[[(tert-butoxycarbonyl)amino]sulfonyl(2-ethoxy-2-oxoethyl)amino]phenylpropanoic acid (276 mg, 0.473 mmol), N,N,N',N'-tetramethyl-O-(7-azabenzotriazol-1-yl)uronium hexafluorophosphate (215 mg, 0.565 mmol), N,N-dimethylformamide (1.5 mL), and N,N-diisopropylethylamine (0.390 mL, 2.24 mmol) were combined and stirred at ambient temperature for 7 minutes. 4-(trifluoromethyl)benzene-1,2-diamine (120 mg, 0.681 mmol) was added and stirred at ambient temperature overnight. The reaction mixture was extracted with diethyl ether, dried over sodium sulfate, filtered, and evaporated. The resulting viscous dark oil was chromatographed on silica gel using a 30–75% ethyl acetate in hexanes gradient to give a solid (148 mg, 45%). $^1$H NMR (400 MHz, CDCl$_3$): δ 7.71 (bs, 1H), 7.44 (d, 2H, J=8.2 Hz), 7.36 (s, 1H), 7.31 (d, 2H, J=8.2 Hz), 7.21 (d, 1H, J=8.4 Hz), 6.71 (d, 1H, J=8.4 Hz), 5.31 (bd, 1H, J=7.0 Hz), 4.60 (quart., 2H, J=21.3 Hz), 4.44 (quart., 1H, J=6.9 Hz), 4.19 (quart., 2H, J=7.0 Hz), 3.77 (bs, 1H), 3.09 (m, 2H), 1.48 (s, 9H), 1.46 (s, 9H), 1.26 (t, 3H, J=7.2 Hz); LCMS found for C$_{30}$H$_{41}$F$_3$N$_5$O$_9$S (M+H)$^+$: m/z=704.1.

Step 5. Synthesis of ethyl [[(tert-butoxycarbonyl)amino]sulfonyl(4-(2S)-2-[(tert-butoxycarbonyl)amino]-2-[5-(trifluoromethyl)-1H-benzimidazol-2-yl]ethylphenyl)amino]acetate Trifluoroacetate

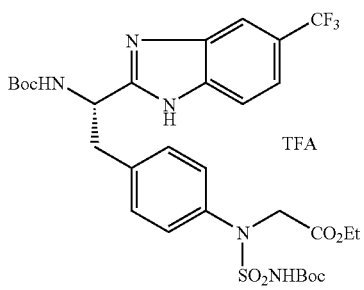

Ethyl ((4-(2S)-3-[2-amino-5-(trifluoromethyl)phenyl]amino-2-[(tert-butoxycarbonyl)amino]-3-oxopropylphenyl)[(tert-butoxycarbonyl)amino]sulfonylamino)acetate (148 mg, 0.210 mmol) was dissolved in acetic acid (1.5 mL) and stirred at ambient temperature for 3 days. The product was purified on a 50 mm Luna C18 column using a 20–90% acetonitrile in water gradient with 0.05% trifluoroacetic acid at 50 mL per minute over a 15 minute period to give a white powder (119 mg, 71%). $^1$H NMR (400 MHz, CDCl$_3$): δ 7.98 (s, 1H), 7.79 (d, 2H, J=8.0 Hz), 7.66 (d, 1H, J=9.6 Hz), 7.34 (d, 2H, J=8.4 Hz), 7.13 (m, 3H), 5.25 (m, 1H), 4.53 (s, 2H), 4.19 (quart., 2H, J=7.0 Hz), 3.43 (m, 1H), 3.34 (m, 1H), 1.48 (s, 9H), 1.39 (s, 9H), 1.26 (t, 3H, J=7.0 Hz); LCMS found for C$_{30}$H$_{39}$F$_3$N$_5$O$_8$S (M+H)$^+$: m/z=686.2.

Step 6. Synthesis of ethyl [(aminosulfonyl)(4-(2S)-2-amino-2-[5-(trifluoromethyl)-1H-benzimidazol-2-yl]ethylphenyl)amino]acetate bistrifluoroacetate

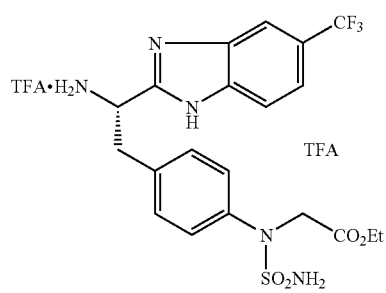

Ethyl [[(tert-butoxycarbonyl)amino]sulfonyl(4-(2S)-2-[(tert-butoxycarbonyl)amino]-2-[5-(trifluoromethyl)-1H-benzimidazol-2-yl]ethylphenyl)amino]acetate trifluoroacetate (213 mg, 0.266 mmol) was dissolved in trifluoroacetic acid (2.0 mL) and stirred at ambient temperature for one hour. The reaction was evaporated and purified on a 50 mm Luna C18 column using a 10–90% acetonitrile in water gradient with 0.05% trifluoroacetic acid at 30 mL per minute over a 30 minute period to give a white powder (146 mg, 77%). $^1$H NMR (400 MHz, CD$_3$OD): δ 7.92 (s, 1H), 7.72 (d, 1H, J=8.4 Hz), 7.55 (dd, 1H, J=8.6 Hz, J'=1.3 Hz), 7.40 (d, 2H, J=8.4 Hz), 7.16 (d, 2H, J=8.4 Hz), 4.87 (m, 1H), 4.37 (s, 2H), 4.15 (quart., 2H, J=7.2 Hz), 3.48 (dd, 1H, J=13.8 Hz, J'=8.2 Hz), 3.38 (dd, 1H, J=13.5 Hz, J'=6.6 Hz), 1.21 (t, 3H, J=7.2 Hz); LCMS found for C$_{20}$H$_{23}$F$_3$N$_5$O$_4$S (M+H)$^+$: m/z=486.1.

Step 7. Synthesis of ethyl [(aminosulfonyl)(4-(2S)-2-[(biphenyl-4-ylsulfonyl)amino]-2-[5-(trifluoromethyl)-1H-benzimidazol-2-yl]ethylphenyl)amino] acetate trifluoroacetate

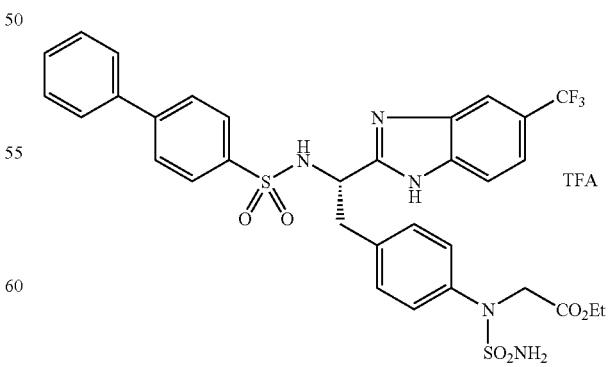

N,N-Diisopropylethylamine (0.022 mL, 0.12 mmol) was added to ethyl [(aminosulfonyl)(4-(2S)-2-amino-2-[5-(trifluoromethyl)-1H-benzimidazol-2-yl]ethylphenyl)amino]acetate trifluoroacetate (25.0 mg, 0.0350 mmol) in methylene chloride (1.0 mL) and stirred at ambient temperature for 1.5 h. Biphenyl-4-sulfonyl chloride (13.9 mg, 0.0550 mmol) was added and stirred at ambient temperature for 4 days. The product was purified on a 50 mm Luna C18 column using a 20–100% acetonitrile in water gradient with 0.05% trifluoroacetic acid at 50 mL per minute over a 30 minute period to give a white powder (22 mg, 77%). $^1$H NMR (400 MHz, CD$_3$OD): δ 7.74 (s, 1H), 7.63 (d, 2H, J=8.6 Hz), 7.57–7.37 (m, 9H), 7.27 (d, 2H, J=8.6 Hz), 7.07 (d, 2H, J=8.4 Hz), 4.85 (m, 1H), 4.26 (s, 2H), 4.11 (quart., 2H, J=7.0 Hz), 3.27 (m, 2H), 1.18 (t, 3H, J=7.2 Hz); LCMS found for C$_{32}$H$_{31}$F$_3$N$_5$O$_6$S$_2$ (M+H)$^+$: m/z=702.0.

Step 8. N-(1S)-2-[4-(1,1-dioxido-4-oxo-1,2,5-thiadiazolidin-2-yl)phenyl]-1-[5-(trifluoromethyl)-1H-benzimidazol-2-yl]ethylbiphenyl-4-sulfonamide

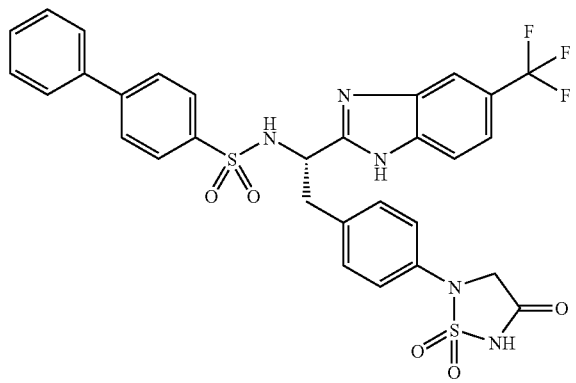

2M trimethylaluminum in toluene (0.015 mL, 0.030 mmol) was added to ethyl [(aminosulfonyl)(4-(2S)-2-[(biphenyl-4-ylsulfonyl)amino]-2-[5-(trifluoromethyl)-1H-benzimidazol-2-yl]ethylphenyl)amino]acetate trifluoroacetate (20 mg, 0.024 mmol) in tetrahydrofuran (0.170 mL) and heated at 50° C. for one hour. Additional 2 M trimethylaluminum in toluene (0.015 mL, 0.030 mmol) was added, followed by tetrahydrofuran (0.100 mL). The reaction was heated at 50° C. for two h and cooled before quenching carefully with 1.0 N hydrochloric acid. The product was purified on a 50 mm Luna C18 column using a 20–100% acetonitrile in water gradient with 0.05% trifluoroacetic acid at 30 mL per minute over a 30 minute period to give a white powder (10 mg, 60%). $^1$H NMR (400 MHz, DMSO-d$_6$): δ 8.73 (d, 1H, J=8.0 Hz), 7.79 (s, 1H), 7.73–7.62 (m, 3H), 7.53 (m, 2H), 7.41 (m, 8H), 7.03 (d, 2H, J=8.6 Hz), 6.89 (d, 2H, J=8.6 Hz), 4.71 (m, 1H), 3.98 (dd, 2H, J=21.5 Hz, J'=14.2 Hz), 3.20–3.06 (m, 2H); LCMS found for C$_{30}$H$_{25}$F$_3$N$_5$O$_5$S$_2$ (M+H)$^+$: m/z=656.0.

Example 3.4

N-(1S)-2-[4-(1,1-dioxido-4-oxo-1,2,5-thiadiazolidin-2-yl)phenyl]-1-[5-(trifluoromethyl)-1H-benzimidazol-2-yl]ethyl-4-(trifluoromethyl)benzenesulfonamide trifluoroacetate

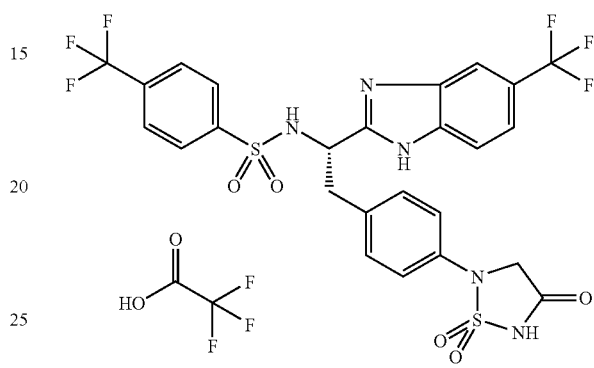

Step 1. Synthesis of ethyl ((aminosulfonyl)4-[(2S)-2-[5-(trifluoromethyl)-1H-benzimidazol-2-yl]-2-([4-(trifluoromethyl)phenyl]sulfonylamino)ethyl]phenylamino)acetate Trifluoroacetate

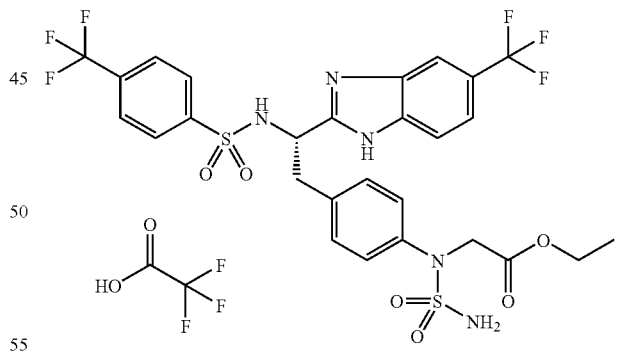

This compound was prepared according to the procedure of Example 3.3, Step 7 (21 mg, 74%). $^1$H NMR (400 MHz, CD$_3$OD): δ 7.72 (m, 3H), 7.55 (m, 2H), 7.47 (d, 2H, J=8.4 Hz), 7.29 (d, 2H, J=8.6 Hz), 7.09 (d, 2H, J=8.4 Hz), 4.87 (t, 1H, J=8.6 Hz), 4.33 (s, 2H), 4.12 (q, 2H, J=7.0 Hz), 3.27 (m, 2H), 1.19 (t, 3H, J=7.0 Hz); LCMS found for C$_{27}$H$_{26}$F$_6$N$_5$O$_6$S$_2$ (M+H)$^+$: m/z=694.0.-

Step 2. N-(1S)-2-[4-(1,1-dioxido-4-oxo-1,2,5-thiadiazolidin-2-yl)phenyl]-1-[5-(trifluoromethyl)-1H-benzimidazol-2-yl]ethyl-4-(trifluoromethyl)benzenesulfonamide trifluoroacetate

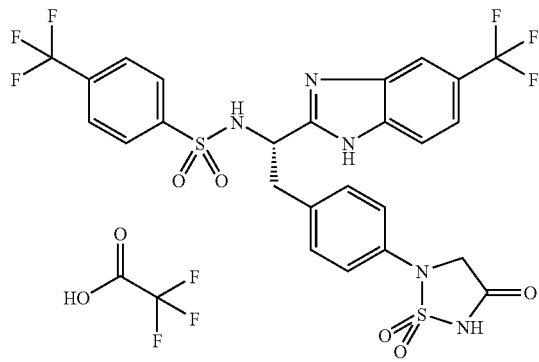

This compound was prepared according to the procedure of Example 3.3, Step 8 (5 mg, 30%). $^1$H NMR (400 MHz, CD$_3$OD): δ 7.93 (s, 1H), 7.75 (m, 4H), 7.61 (d, 2H, J=8.4 Hz), 7.05 (d, 2H, J=8.6 Hz), 6.99 (d, 2H, J=8.8 Hz), 4.90 (m, 1H), 4.26 (s, 2H), 3.24 (m, 2H); LCMS found for C$_{25}$H$_{20}$F$_6$N$_5$O$_5$S$_2$ (M+H)$^+$: m/z=648.0.

Example 3.5

4-Bromo-N-(1S)-2-[4-(1,1-dioxido-4-oxo-1,2,5-thiadiazolidin-2-yl)phenyl]-1-[5-(trifluoromethyl)-1H-benzimidazol-2-yl]ethyl-2-(trifluoromethoxy)benzenesulfonamide trifluoroacetate

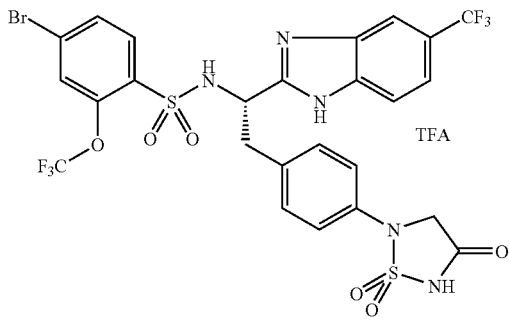

Step 1. Synthesis of ethyl[(aminosulfonyl)(4-(2S)-2-([4-bromo-2-(trifluoromethoxy)-phenyl]sulfonylamino)-2-[5-(trifluoromethyl)-1H-benzimidazol-2-yl]ethylphenyl)amino]acetate trifluoroacetate

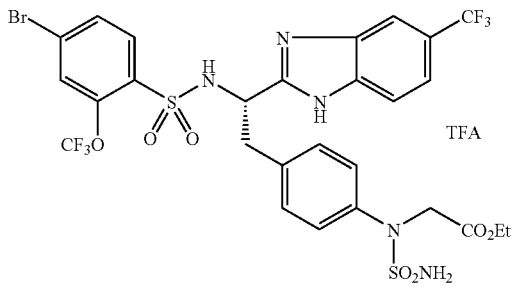

This compound was prepared according to the procedure of Example 3.3, Step 7 (16.5 mg, 65%). $^1$H NMR (400 MHz, CDCl$_3$): δ 8.82 (bs, 1H), 7.93 (s, 1H), 7.79 (d, J=8.6 Hz, 1H), 7.73 (d, J=8.8 Hz, 1H), 7.64 (d, J=8.4 Hz, 1H), 7.24 (m, 1H), 7.19 (d, J=8.4 Hz, 2H), 7.12 (m, 1H), 7.07 (d, J=8.4 Hz, 2H), 5.42 (bs, 1H), 5.31 (m, 1H), 4.32 (bs, 2H), 4.22 (q, J=7.2 Hz, 2H), 3.37 (m, 1H), 3.27 (m, 1H), 1.27 (t, J=7.1 Hz, 3H); LCMS found for C$_{27}$H$_{25}$BrF$_6$N$_5$O$_7$S$_2$ (M+H)$^+$: m/z=788.0.

Step 2. Synthesis of 4-bromo-N-(1S)-2-[4-(1,1-dioxido-4-oxo-1,2,5-thiadiazolidin-2-yl)phenyl]-1-[5-(trifluoromethyl)-1H-benzimidazol-2-yl]ethyl-2-(trifluoromethoxy)benzenesulfonamide trifluoroacetate

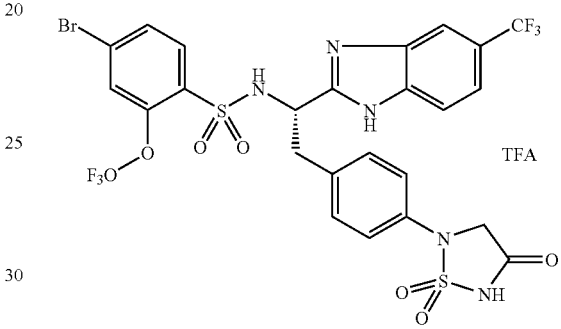

This compound was prepared according to the procedure of Example 1, Step 8 (5 mg, 30%). $^1$H NMR (400 MHz, CD$_3$OD): δ 8.00 (s, 1H), 7.86 (d, 1H, J=8.6 Hz), 7.76 (m, 1H), 7.60 (d, 1H, J=8.8 Hz), 7.45 (m, 2H), 7.09 (d, 2H, J=8.5 Hz), 6.94 (d, 2H, J=8.6 Hz), 4.98 (m, 1H), 4.33 (dd, 2H, J=44.5 Hz, J'=14.5 Hz), 3.33 (m, 1H), 3.12 (m, 1H); LCMS found for C$_{25}$H$_{19}$BrF$_6$N$_5$O$_6$S$_2$ (M+H)$^+$: m/z=742.0.

Example 3.6

N-(1S)-2-[4-(1,1-dioxido-4-oxo-1,2,5-thiadiazolidin-2-yl)phenyl]-1-[5-(trifluoromethyl)-1H-benzimidazol-2-yl]ethyl-3,5-bis(trifluoromethyl)benzenesulfonamide trifluoroacetate

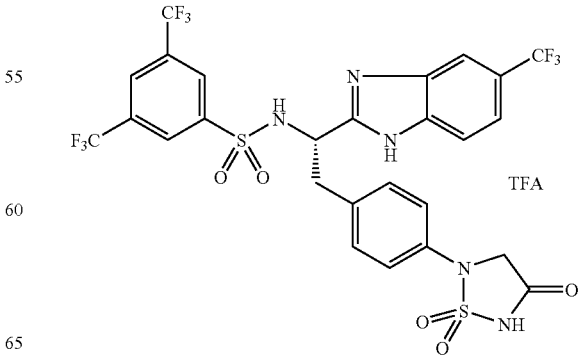

Step 1. Synthesis of Ethyl [(aminosulfonyl)(4-(2S)-2-([3,5-bis(trifluoromethyl)phenyl]sulfonylamino)-2-[5-(trifluoromethyl)-1H-benzimidazol-2-yl]ethylphenyl)amino]acetate trifluoroacetate

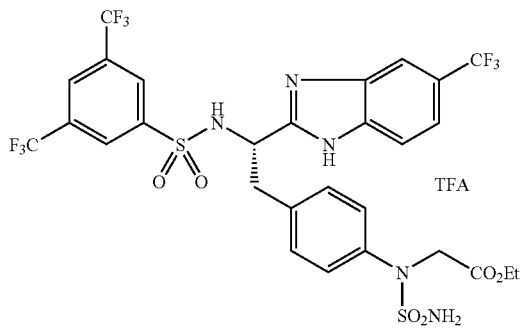

This compound was prepared according to the procedure of Example 3.3, Step 7 (16.5 mg, 65%). $^1$H NMR (400 MHz, CDCl$_3$): δ 9.30 (bm, 1H), 8.07 (s, 2H), 7.83 (s, 1H), 7.68 (m, 2H), 7.60 (s, 1H), 7.27 (d, J=8.4 Hz, 2H), 7.08 (d, J=8.4 Hz, 2H), 5.43 (bs, 1H), 5.31 (m, 1H), 4.35 (s, 2H), 4.24 (q, J=7.2 Hz, 2H), 3.38 (m, 1H), 3.27 (m, 1H), 1.29 (t, J=7.1 Hz, 3H); LCMS found for C$_{28}$H$_{25}$F$_9$N$_5$O$_6$S$_2$ (M+H)$^+$: m/z=762.1.

Step 2. Synthesis of N-(1S)-2-[4-(1,1-dioxido-4-oxo-1,2,5-thiadiazolidin-2-yl)phenyl]-1-[5-(trifluoromethyl)-1H-benzimidazol-2-yl]ethyl-3,5-bis(trifluoromethyl)benzenesulfonamide trifluoroacetate

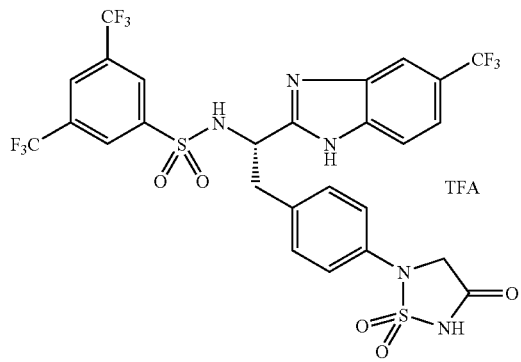

This compound was prepared according to the procedure of Example 3.3, Step 8 (6 mg, 40%). $^1$H NMR (400 MHz, CD$_3$OD): δ 8.10 (s, 2H), 7.92 (s, 1H), 7.84 (s, 1H), 7.66 (m, 3H), 7.06 (d, 2H, J=8.6 Hz), 6.95 (d, 2H, J=8.6 Hz), 5.01 (t, 1H, J=7.0 Hz), 4.30 (s, 2H), 3.25 (m, 2H); LCMS found for C$_{26}$H$_{19}$F$_9$N$_5$O$_5$S$_2$ (M+H)$^+$: m/z=716.0.

Example 3.7

N-(1S)-2-[4-(1,1-dioxido-4-oxo-1,2,5-thiadiazolidin-2-yl)phenyl]-1-[5-(trifluoromethoxy)-1H-benzimidazol-2-yl]ethyl-2-(trifluoromethoxy)benzenesulfonamide trifluoroacetate

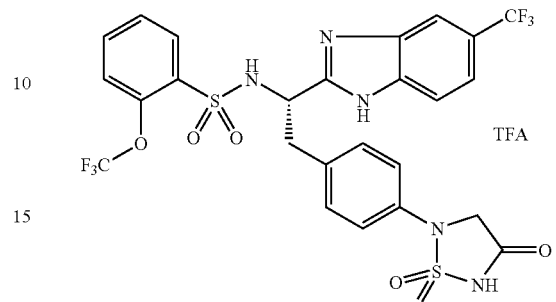

Step 1. Synthesis of ethyl[(aminosulfonyl)(4-(2S-2-([2-(trifluoromethoxy)phenyl]sulfonylamino)-2-[5-(trifluoromethyl)-1H-benzimidazol-2-yl]ethylphenyl)amino]acetate trifluoroacetate

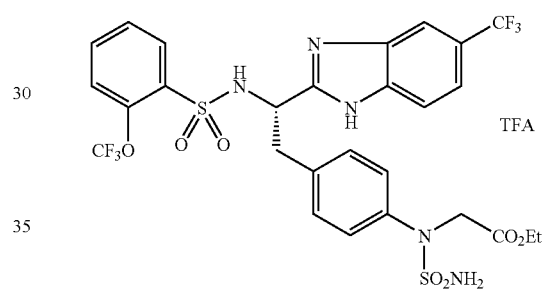

This compound was prepared according to the procedure of Example 3.3, Step 7 (16.5 mg, 65%). $^1$H NMR (400 MHz, CDCl$_3$): δ 8.56 (bm, 1H), 7.90 (s, 1H), 7.77 (m, 2H), 7.68 (d, J=8.4 Hz, 1H), 7.28 (m, 1H), 7.18 (d, J=8.4 Hz, 2H), 7.16 (m, 1H), 7.12 (m, 1H), 7.05 (d, J=8.4 Hz, 2H), 7.00 (m, 1H), 5.42 (bs, 1H), 5.33 (m, 1H), 4.31 (s, 2H), 4.22 (q, J=7.2 Hz, 2H), 3.30 (m, 2H), 1.27 (t, J=7.1 Hz, 3H); LCMS found for C$_{27}$H$_{26}$F$_6$N$_5$O$_7$S$_2$ (M+H)$^+$: m/z=710.1.

Step 2. Synthesis of N-(1S)-2-[4-(1,1-dioxido-4-oxo-1,2,5-thiadiazolidin-2-yl)phenyl]-1-[5-(trifluoromethyl)-1H-benzimidazol-2-yl]ethyl-2-(trifluoromethoxy)benzenesulfonamide trifluoroacetate

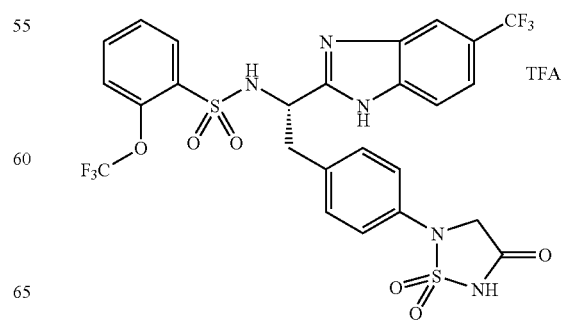

This compound was prepared according to the procedure of Example 3.3, Step 8 (3 mg, 20%). $^1$H NMR (400 MHz, CD$_3$OD): δ 7.94 (s, 1H), 7.74 (m, 3H), 7.50 (m, 1H), 7.25 (m, 2H), 7.02 (d, 2H, J=8.6 Hz), 6.91 (d, 2H, J=8.6 Hz), 4.89 (m, 1H), 4.23 (s, 2H), 3.30 (m, 1H), 3.13 (m, 1H); LCMS found for C$_{25}$H$_{20}$F$_6$N$_5$O$_6$S$_2$ (M+H)$^+$: m/z=664.1.

Example 3.8

Ethyl[(aminosulfonyl)(4-(2S)-2-[(biphenyl-4-ylsulfonyl)amino]-2-[5-(trifluoromethyl)-1H-benzimidazol-2-yl]ethyl-2-chlorophenyl)amino]acetate trifluoroacetate

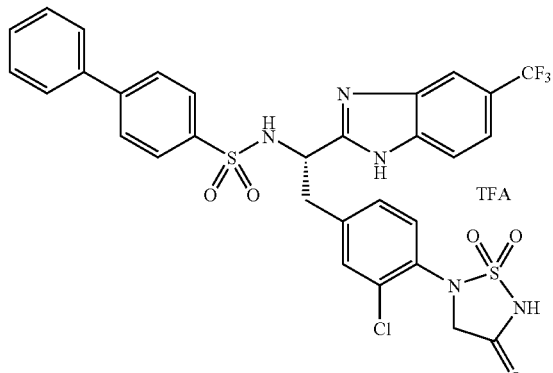

Step 1. Synthesis of benzyl (2S)-3-(4-amino-3-chlorophenyl)-2-[(tert-butoxycarbonyl)amino]propanoate

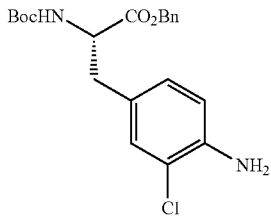

Benzyl (2S)-3-(4-aminophenyl)-2-[(tert-butoxycarbonyl)amino]propanoate (20.8 g, 54.7 mmol) and N-chlorosuccinimide (8.04 g, 60.2 mmol) were dissolved in N,N-dimethylformamide (339 mL) and allowed to stir overnight. The reaction was diluted with water, extracted with diethyl ether, washed with saturated aqueous sodium chloride then dried over MgSO$_4$, filtered and the solvent evaporated. The mixture was purified by silica gel chromatography, eluting with 30% ethyl acetate in hexanes to give an orange oil (13.7 g, 62%). $^1$H NMR (400 MHz, CDCl$_3$): δ 7.34 (m, 5H), 6.95 (s, 1H), 6.72 (d, J=7.8 Hz, 1H), 6.61 (d, J=8.0 Hz, 2H), 5.18 (d, J=12.1 Hz, 1H), 5.10 (d, J=12.3 Hz, 1H), 4.98 (d, J=8.2 Hz, 1H), 4.71 (d, J=5.3 Hz, 1H), 4.54 (m, 1H), 3.97 (m, 2H), 2.96 (m, 2H), 1.43 (s, 9H); LCMS found for C$_{21}$H$_{25}$ClN$_2$NaO$_4$ (M+Na)$^+$: m/z=427.0.

Step 2. Synthesis of benzyl (2S)-2-[(tert-butoxycarbonyl)amino]-3-3-chloro-4-[(2-ethoxy-2-oxoethyl)amino]phenylpropanoate

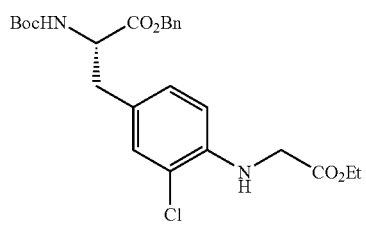

Into a round-bottom flask benzyl (2S)-3-(4-amino-3-chlorophenyl)-2-[(tert-butoxycarbonyl)amino]propanoate (13.67 g, 33.76 mmol), ethyl bromoacetate (4.1 mL, 37 mmol), and N,N-diisopropylethylamine (7.0 mL, 40 mmol) were dissolved in acetonitrile (60 mL) and heated to reflux for 2 h. The mixture was purified by silica gel chromatography, eluting with 20–30% ethyl acetate in hexanes to give a light yellow oil (12.14 g, 73%), which slowly solidified. $^1$H NMR (400 MHz, CDCl$_3$): δ 7.33 (m, 5H), 7.00 (s, 1H), 6.80 (d, J=8.0 Hz, 1H), 6.38 (d, J=8.2 Hz, 2H), 5.17 (d, J=12.3 Hz, 1H), 5.10 (d, J=12.1 Hz, 1H), 4.98 (d, J=8.0 Hz, 1H), 4.88 (m, 1H), 4.54 (m, 1H), 4.26 (q, J=7.2 Hz, 2H), 3.91 (d, J=5.5 Hz, 2H), 2.96 (m, 2H), 1.42 (s, 9H), 1.31 (t, J=7.2 Hz, 3H); LCMS found for C$_{25}$H$_{31}$ClN$_2$NaO$_6$ (M+Na)$^+$: m/z=513.0.

Step 3. Synthesis of benzyl (2S)-2-[(tert-butoxycarbonyl)amino]-3-4-[[(tert-butoxycarbonyl)amino]sulfonyl(2-ethoxy-2-oxoethyl)amino]-3-chlorophenylpropanoate

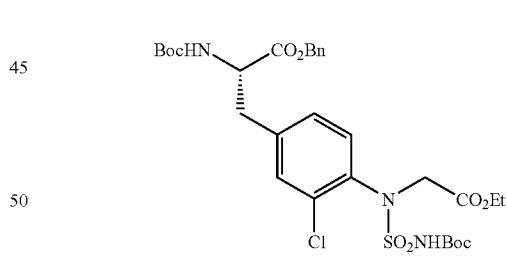

Benzyl (2S)-2-[(tert-butoxycarbonyl)amino]-3-3-chloro-4-[(2-ethoxy-2-oxoethyl)amino]phenyl-propanoate (12.045 g, 24.5 mmol) and N,N-diisopropylethylamine (17.1 mL, 98.1 mmol) were dissolved in methylene chloride (75 mL) and cooled at 0° C. Tert-butyl (chlorosulfonyl)carbamate (8.8 g, 41 mmol) in methylene chloride (50 mL) was added dropwise. The reaction was stirred at 0° C. for 10 minutes and at 25° C. overnight. The reaction mixture was extracted with dichloromethane, washed with water, 1 N HCl, brine, dried (MgSO$_4$) and the solvent evaporated. The mixture was purified by silica gel chromatography, eluting with 50–100% ethyl acetate in hexanes to give a yellow foam (13.9 g, 85%). LCMS found for C$_{30}$H$_{40}$ClN$_3$NaO$_{10}$S (M+Na)$^+$: m/z=692.1.

Step 4. Synthesis of (2S)-2-[(tert-butoxycarbonyl)amino]-3-4-[[(tert-butoxycarbonyl)amino]sulfonyl(2-ethoxy-2-oxoethyl)amino]-3-chlorophenylpropanoic acid

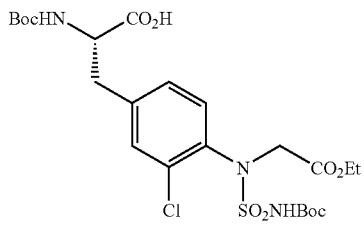

Benzyl (2S)-2-[(tert-butoxycarbonyl)amino]-3-4-[[(tert-butoxycarbonyl)amino]sulfonyl(2-ethoxy-2-oxoethyl)amino]-3-chlorophenylpropanoate (13.90 g, 19.7 mmol) was dissolved in ethanol (200 mL) in a Parr bottle. Palladium (10% by weight on carbon, 6.59 g, 6.20 mmol) was added, the mixture degassed and hydrogenated at 60 psi for 6.5 h. The suspension was filtered, washed with ethanol and evaporated to give the crude material as a foam (8.57 g, 75%). $^1$H NMR (400 MHz, CDCl$_3$): δ 7.78 (d, J=8.2 Hz, 1H), 7.72 (bs, 1H), 7.29 (s, 1H), 7.14 (d, J=7.8 Hz, 1H), 6.34 (bs, 1H), 5.10 (d, J=7.6 Hz, 1H), 4.61 (m, 1H), 4.44 (bs, 1H), 4.19 (q, J=7.0 Hz, 2H), 3.16 (m, 1H), 3.07 (m, 1H), 1.51 (s, 9H), 1.44 (bs, 9H), 1.26 (t, J=7.0 Hz, 3H); LCMS found for $C_{23}H_{34}ClN_3NaO_{10}S$ (M+Na)$^+$: m/z=602.0.

Step 5. Synthesis of Ethyl ((4-(2S)-3-[2-amino-5-(trifluoromethyl)phenyl]amino-2-[(tert-butoxycarbonyl)amino]-3-oxopropyl-2-chlorophenyl)[(tert-butoxycarbonyl160amino]sulfonylamino)acetate

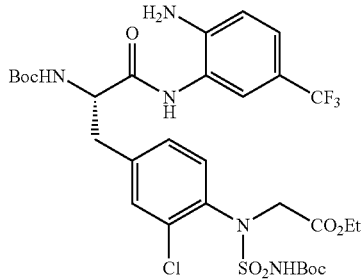

(2S)-2-[(tert-Butoxycarbonyl)amino]-3-4-[[(tert-butoxycarbonyl)amino]sulfonyl(2-ethoxy-2-oxoethyl)amino]-3-chlorophenylpropanoic acid (453 mg, 0.730 mmol), N,N,N',N'-tetramethyl-O-(7-azabenzotriazol-1-yl)uronium hexafluorophosphate (332 mg, 0.873 mmol), N,N-dimethylformamide (3.0 mL), and N,N-diisopropylethylamine (0.640 mL, 3.7 mmol) were combined and stirred at ambient temperature for 16 minutes. 4-(trifluoromethyl)benzene-1,2-diamine (193 mg, 1.10 mmol) was added and stirred at ambient temperature overnight. The reaction mixture was extracted twice with water. The combined aqueous layers were extracted with diethyl ether, dried over sodium sulfate, filtered, and evaporated. The resulting viscous dark oil was chromatographed on silica gel using a 30–75% ethyl acetate in hexanes to give a solid (193 mg, 36%). LCMS found for $C_{30}H_{40}ClF_3N_5O_9S$ (M+H)$^+$: m/z=738.2.

Step 6. Synthesis of ethyl [[(tert-butoxycarbonyl)amino]sulfonyl(4-(2S)-2-[(tert-butoxycarbonyl)amino]-2-[5-(trifluoromethyl)-1H-benzimidazol-2-yl]ethyl-2-chlorophenyl)amino]acetate trifluoroacetate

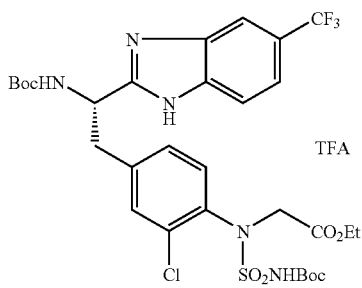

Ethyl ((4-(2S)-3-[2-amino-5-(trifluoromethyl)phenyl]amino-2-[(tert-butoxycarbonyl)amino]-3-oxopropyl-2-chlorophenyl)[(tert-butoxycarbonyl)amino]sulfonylamino)acetate (193 mg, 0.261 mmol) was dissolved in acetic acid (1.5 mL) and stirred at ambient temperature for 4 days. The product was purified on a 50 mm Luna C18 column using a 20–90% acetonitrile in water gradient with 0.05% trifluoroacetic acid at 50 mL per minute over a 15 minute period to give a white powder (140 mg, 64%). LCMS found for $C_{30}H_{38}ClF_3N_5O_8S$ (M+H)$^+$: m/z=720.1.

Step 7. Synthesis of Ethyl [(aminosulfonyl)(4-(2S)-2-amino-2-[5-(trifluoromethyl)-1H-benzimidazol-2-yl]ethyl-2-chlorophenyl)amino]acetate bis(trifluoroacetate)

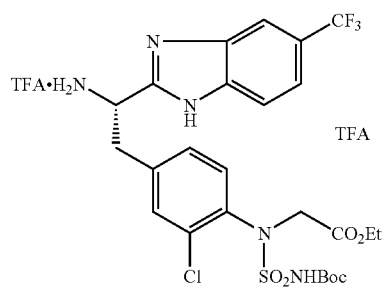

Ethyl [[(tert-butoxycarbonyl)amino]sulfonyl(4-(2S)-2-[(tert-butoxycarbonyl)amino]-2-[5-(trifluoromethyl)-1H-benzimidazol-2-yl]ethyl-2-chlorophenyl)amino]acetate trifluoroacetate (140 mg, 0.17 mmol) was dissolved in trifluoroacetic acid (2.0 mL) and stirred at ambient temperature for 2.5 h. The reaction was evaporated and purified on a 50 mm Luna C18 column using a 10–90% acetonitrile in water gradient with 0.05% trifluoroacetic acid at 30 mL per minute over a 30 minute period to give a white powder (96 mg, 76%). $^1$H NMR (400 MHz, CDCl$_3$): δ 7.87 (s, 1H), 7.72–7.52 (m, 3H), 7.26 (m, 1H), 7.11 (d, 1H, J=6.8 Hz), 5.94 (bs, 1H), 5.24 (bm, 1H), 4.28 (bs, 1H), 4.16 (quart, 2H, J=7.2 Hz), 3.35 (bm, 2H), 1.23 (t, 3H, J=7.1 Hz); LCMS found for $C_{20}H_{22}ClF_3N_5O_4S$ (M+H)$^+$: m/z=520.0.

Step 8. Synthesis of Ethyl [(aminosulfonyl)(4-(2S)-2-[(biphenyl-4-ylsulfonyl)amino]-2-[5-(trifluoromethyl)-1H-benzimidazol-2-yl]ethyl-2-chlorophenyl)amino]acetate trifluoroacetate

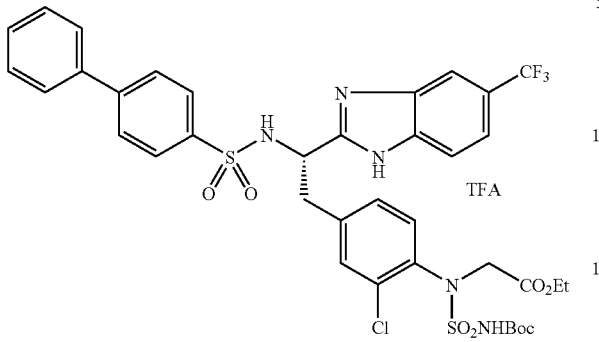

Ethyl [(aminosulfonyl)(4-(2S)-2-amino-2-[5-(trifluoromethyl)-1H-benzimidazol-2-yl]ethyl-2-chlorophenyl)amino] acetate bis(trifluoroacetate) (25 mg, 0.033 mmol) was dissolved in methylene chloride (0.25 mL). N,N-diisopropylethylamine (21 µL, 0.12 mmol) then biphenyl-4-sulfonyl chloride (13.2 mg, 0.0525 mmol) were added. The reaction was allowed to stir at room temperature overnight. The reaction was chromatographed on a 50 mm Luna C18 column using a 10–90% acetonitrile in water gradient with 0.05% trifluoroacetic acid at 50 mL per minute over a 15 minute period to give a white powder. (17 mg, 60%). LCMS found for $C_{32}H_{30}ClF_3N_5O_6S_2$ (M+H)$^+$: m/z=736.0.

Step 9. Synthesis of N-(1S)-2-[3-chloro-4-(1,1-dioxido-4-oxo-1,2,5-thiadiazolidin-2-yl)phenyl]-1[5-(trifluoromethyl)-1H-benzimidazol-2-yl]ethylbiphenyl-4-sulfonamide trifluoroacetate

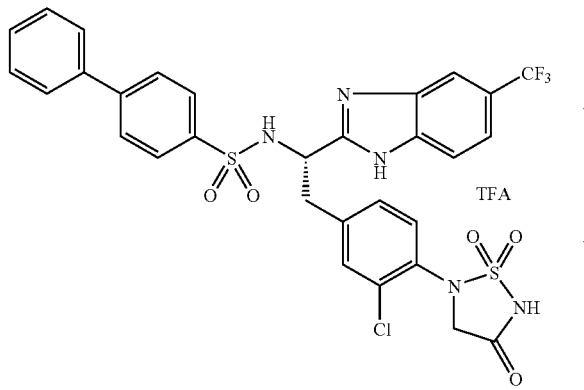

Ethyl [(aminosulfonyl)(4-(2S)-2-[(biphenyl-4-ylsulfonyl)amino]-2-[5-(trifluoromethyl)-1H-benzimidazol-2-yl]ethyl-2-chlorophenyl)amino]acetate trifluoroacetate (17 mg, 0.020 mmol) was dissolved in tetrahydrofuran (140 µL). Added 2 M trimethylaluminum in toluene (20 µL) and heated to 50° C. for 2.5 h. The reaction was quenched with 10 drops 1 N HCl, then diluted with acetonitrile. The reaction was chromatographed on a 50 mm Luna C18 column using a 10–90% acetonitrile in water gradient with 0.05% trifluoroacetic acid at 50 mL per minute over a 15 minute period to give a white powder (2.5 mg, 18%). (17 mg, 60%). $^1$H NMR (400 MHz, CD$_3$OD): δ 7.78 (s, 1H), 7.61 (m, 4H), 7.43 (m, 8H), 7.27 (d, J=1.8 Hz, 1H), 7.07 (dd, J=1.9 Hz, J'=8.3 Hz, 1H), 4.84 (m, 1H), 4.17 (dd, J=14.4 Hz, J'=30.9 Hz, 2H), 3.27 (m, 2H). LCMS found for $C_{30}H_{24}ClF_3N_5O_5S_2$ (M+H)$^+$: m/z=690.0.

Example 3.9

N-(1S)-2-[3-chloro-4-(1,1-dioxido-4-oxo-1,2,5-thiadiazolidin-2-yl)phenyl]-1-[5-(trifluoromethyl)-1H-benzimidazol-2-yl]ethyl-4-(trifluoromethyl)benzenesulfonamide trifluoroacetate

Step 1. Synthesis of Ethyl ((aminosulfonyl)$_2$-chloro-4-[(2S)-2-[5-(trifluoromethyl)-1H-benzimidazol-2-yl]-2-([4-(trifluoromethyl)phenyl]sulfonylamino)ethyl]phenylamino)acetate Trifluoroacetate

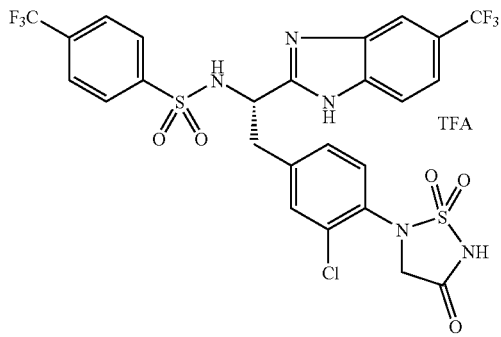

This compound was prepared according to the procedure of Example 3.8, Step 8 (11 mg, 39%). LCMS found for $C_{27}H_{25}ClF_6N_5O_6S_2$ (M+H)$^+$: m/z=728.0.

Step 2. Synthesis of N-(1S)-2-[3-chloro-4-(1,1-dioxido-4-oxo-1,2,5-thiadiazolidin-2-yl)phenyl]-1-[5-(trifluoromethyl)-1H-benzimidazol-2-yl]ethyl-4-(trifluoromethyl)benzenesulfonamide trifluoroacetate

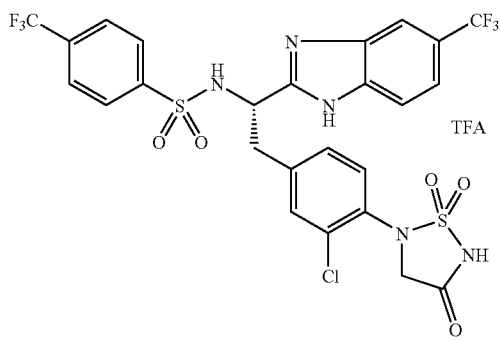

This compound was prepared according to the procedure of Example 3.8, Step 9 (2.3 mg, 12%). $^1$H NMR (400 MHz, CD$_3$OD): δ 7.72 (m, 2H), 7.69 (s, 1H), 7.58 (d, J=8.6 Hz, 1H), 7.49 (m, 4H), 7.31 (d, J=2.0 Hz, 1H), 7.11 (dd, J=2.1 Hz, J'=8.2 Hz, 1H), 4.87 (m, 1H), 4.34 (s, 2H), 3.33 (m, 2H). LCMS found for C$_{25}$H$_{19}$ClF$_6$N$_5$O$_5$S$_2$ (M+H)$^+$: m/z=681.9.

Example 3.10

4-Bromo-N-(1S)-2-[3-chloro-4-(1,1-dioxido-4-oxo-1,2,5-thiadiazolidin-2-yl)phenyl]-1-[5-(trifluoromethyl)-1H-benzimidazol-2-yl]ethyl-2-(trifluoromethoxy)benzenesulfonamide trifluoroacetate

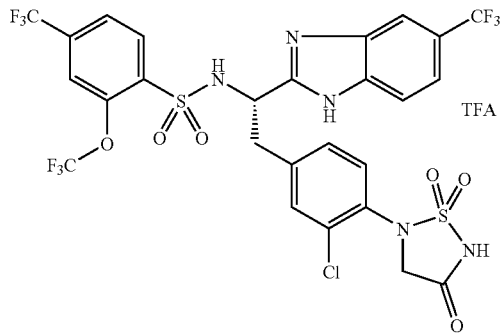

Step 1. Synthesis of Ethyl [(aminosulfonyl)(4-(2S)-2-([4-bromo-2-(trifluoromethoxy)-phenyl]sulfonylamino)-2-[5-(trifluoromethyl)-1H-benzimidazol-2-yl]ethyl-2-chlorophenyl)amino]acetate trifluoroacetate

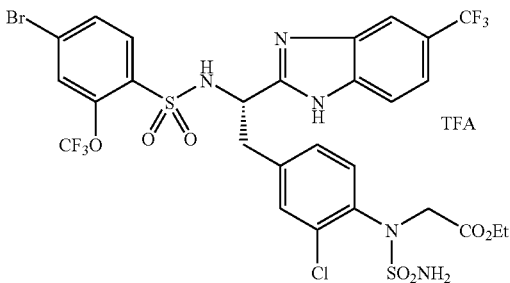

This compound was prepared according to the procedure of Example 3.8, Step 8 (7.5 mg, 30%). $^1$H NMR (400 MHz, CDCl$_3$): δ 8.64 (bs, 1H), 7.93 (s, 1H), 7.78 (d, J=8.6 Hz, 1H), 7.72 (d, J=8.8 Hz, 1H), 7.65 (d, J=8.4 Hz, 1H), 7.54 (d, J=8.0 Hz, 1H), 7.23 (m, 2H), 7.13 (s, 1H), 7.03 (m, 1H), 5.43 (bs, 2H), 5.25 (m, 1H), 4.30 (bs, 1H), 4.19 (q, J=7.0 Hz, 2H), 3.36 (m, 1H), 3.24 (m, 1H), 1.24 (t, J=7.2 Hz, 3H); LCMS found for C$_{27}$H$_{24}$BrClF$_6$N$_5$O$_7$S$_2$ (M+H)$^+$: m/z=823.9.

Step 2. Synthesis of 4-bromo-N-(1S)-2-[3-chloro-4-(1,1-dioxido-4-oxo-1,2,5-thiadiazolidin-2-yl)phenyl]-1-[5-(trifluoromethyl)-1H-benzimidazol-2-yl]ethyl-2-(trifluoromethoxy)benzenesulfonamide trifluoroacetate

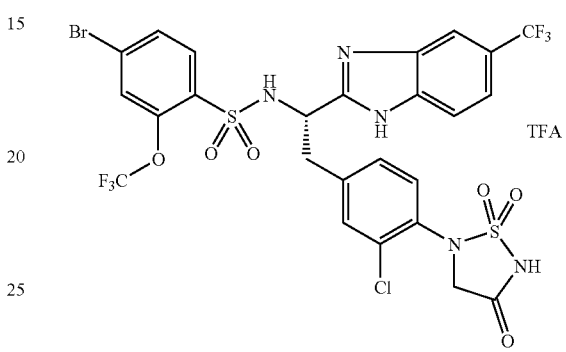

This compound was prepared according to the procedure of Example 3.8, Step 9 (2.6 mg, 42%). $^1$H NMR (400 MHz, CD$_3$OD): δ 7.79 (s, 1H), 7.63 (m, 2H), 7.55 (m, 1H), 7.50 (d, J=8.2 Hz, 1H), 7.33 (m, 2H), 7.28 (m, 1H), 7.13 (dd, J=1.9 Hz, J'=8.2 Hz, 1H), 4.84 (m, 1H), 4.36 (s, 2H), 3.33 (m, 2H); LCMS found for C$_{25}$H$_{18}$BrClF$_6$N$_5$O$_6$S$_2$ (M+H)$^+$: m/z=777.8.

Example 3.11

N-(1S)-2-[3-chloro-4-(1,1-dioxido-4-oxo-1,2,5-thiadiazolidin-2-yl)phenyl]-1-[5-(trifluoromethyl)-1H-benzimidazol-2-yl]ethyl-3,5-bis(trifluoromethyl)benzenesulfonamide trifluoroacetate

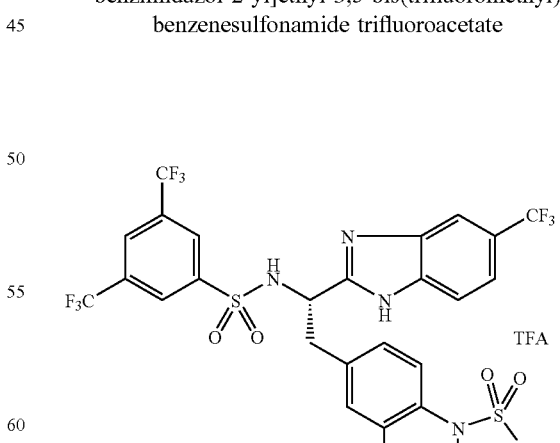

Step 1. Synthesis of Ethyl [(aminosulfonyl)(4-(2S)-2-([3,5-bis(trifluoromethyl)phenyl]sulfonylamino)-2-[5-(trifluoromethyl)-1H-benzimidazol-2-yl]ethyl-2-chlorophenyl)amino]acetate trifluoroacetate

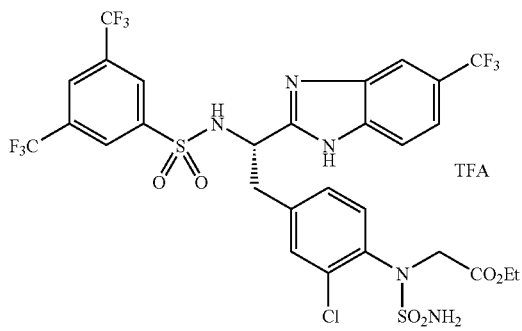

This compound was prepared according to the procedure of Example 3.8, Step 8 (7.2 mg, 30%). $^1$H NMR (400 MHz, CDCl$_3$): δ 9.35 (bs, 1H), 8.06 (s, 2H), 7.83 (s, 1H), 7.67 (m, 2H), 7.59 (m, 2H), 7.23 (m, 2H), 5.44 (bs, 2H), 5.28 (m, 1H), 4.35 (bs, 1H), 4.21 (q, J=7.0 Hz, 2H), 3.37 (m,1H, 3.26 (m, 1H), 1.28 (t, J=7.1 Hz, 3H); LCMS found for C$_{28}$H$_{24}$ClF$_9$N$_5$O$_6$S$_2$ (M+H)$^+$: m/z=796.0.

Step 2. Synthesis of N-(1S)-2-[3-chloro-4-(1,1-dioxido-4-oxo-1,2,5-thiadiazolidin-2-yl)phenyl]-1-[5-(trifluoromethyl)-1H-benzimidazol-2-yl]ethyl-3,5-bis(trifluoromethyl)benzenesulfonamide trifluoroacetate

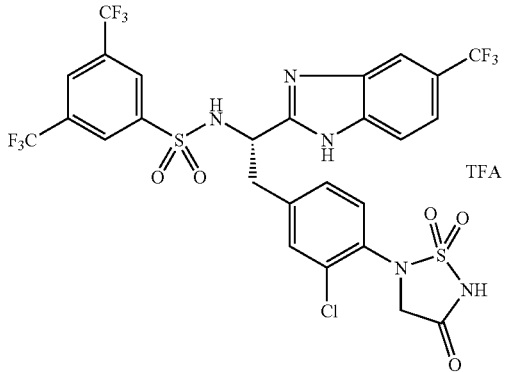

This compound was prepared according to the procedure of Example 3.8, Step 9 (2.1 mg, 35%). $^1$H NMR (400 MHz, CD$_3$OD): δ 8.30 (s, 1H), 8.09 (m, 2H), 7.66 (m, 1H), 7.57 (m, 2H), 7.29 (m, 2H), 7.05 (dd, J=1.9 Hz, J'=8.2 Hz, 1H), 5.11 (m, 1H), 4.26 (s, 2H), 3.26 (m, 2H). LCMS found for C$_{26}$H$_{18}$ClF$_9$N$_5$O$_5$S$_2$ (M+H)$^+$: m/z=750.0.

Example 4.1

(S)-2-{(S)-2-[2-(4-Methoxy-phenyl)-acetylamino]-3-phenyl-propionylamino}-N-pentyl-3-[4-(1,1,3-trioxo-1λ$^6$-isothiazolidin-5-yl)-phenyl]-propionamide

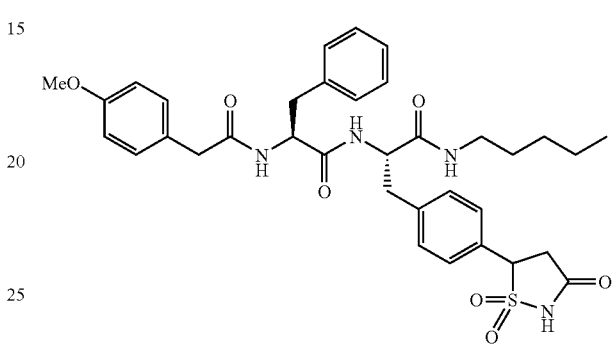

Step 1. (S)-3-[4-(2-tert-Butyl-1,1,3-trioxo-2,3-dihydro-1H-1λ$^6$-isothiazol-5-yl)-phenyl]-2-{(S)-2-[2-(4-methoxy-phenyl)-acetylamino]-3-phenyl-propionylamino}-N-pentyl-propionamide (401-A)

401-A

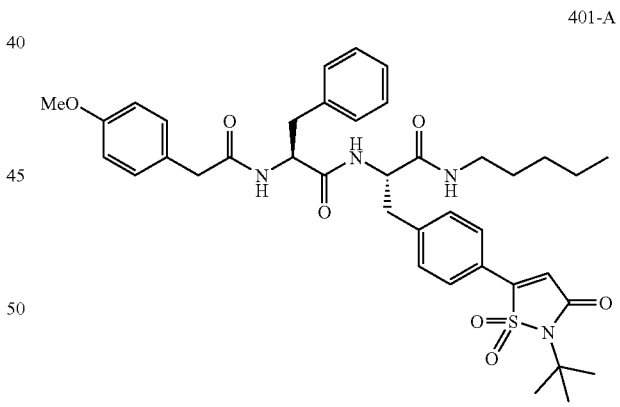

This compound was prepared according to the procedure of Example 1.9 using 9-E as the starting material. $^1$H NMR (500 MHz, CDCl$_3$): δ 7.66 (d, J=8.3 Hz, 2H), 7.24–7.18 (m, 4H), 6.98–6.92 (m, 4H), 6.87–6.86 (m, 2H), 6.61 (s, 1H), 6.42 (d, J=8.5 Hz, 1H), 5.96 (dd, J=5.9, 5.4 Hz, 1H), 5.82 (d, J=6.8 Hz, 1H), 4.61 (dd, J=15.1, 6.8 Hz, 1H), 4.53 (dd, J=13.7, 6.8 Hz, 1H), 3.83 (s, 3H), 3.43 (d, J=16.6 Hz, 1H), 3.36 (d, J=16.6 Hz, 1H), 3.16–3.00 (m, 4H), 2.95–2.91 (m, 2H), 1.73 (s, 9H), 1.42–1.34 (m, 2H), 1.32–1.24 (m, 2H), 1.21–1.14 (m, 2H), 0.87 (t, J=7.3 Hz, 3H); LCMS found for C$_{39}$H$_{49}$N$_4$O$_7$S (M+H)$^+$: m/z=717.

Step 2. (S)-3-[4-(2-tert-Butyl-1,1,3-trioxo-1λ⁶-isothiazolidin-5-yl)-phenyl]-2-{(S)-2-[2-(4-methoxy-phenyl)-acetylamino]-3-phenyl-propionylamino}-N-pentyl-propionamide (401-B)

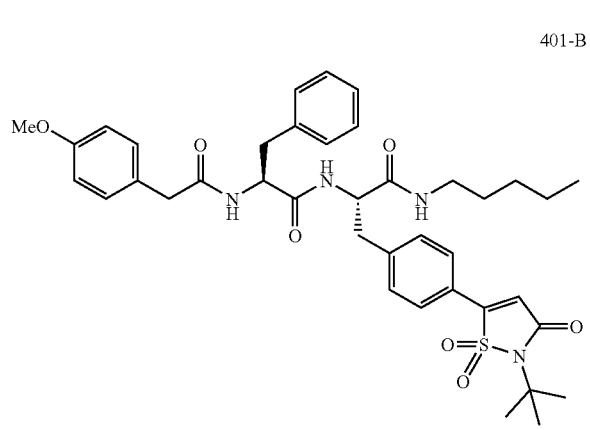

401-B

A solution of 401-A (50 mg, 0.07 mmol) and 5% Pd/BaSO₄ (5 mg, 10 wt %) in ethanol (1.5 mL), methanol (1.0 mL) and dichloromethane (2 drops) was stirred under an atmosphere of hydrogen for 5 h. The reaction mixture was filtered and concentrated to yield the 401-B (48 mg, 96%) as a white solid. $^1$H NMR (500 MHz, CDCl₃): δ 7.30–7.26 (m, 4H), 7.22–7.16 (m, 4H), 7.00–6.94 (m, 4H), 6.85–6.81 (m, 2H), 6.43 (dd, J=8.3, 4.9 Hz, 1H), 5.90–5.84 (m, 1H), 5.79 (dd, J=8.8, 6.8 Hz, 1H), 4.75 (ddd, J=10.7, 9.3, 2.0 Hz, 1H), 4.61–4.57 (m, 1H), 4.50 (dd, J=12.2, 6.3 Hz, 1H), 3.82 (s, 3H), 3.43–3.35 (m, 2H), 3.22–3.09 (m, 4H), 3.05–3.03 (m, 1H), 3.00–2.90 (m, 1H), 2.90–2.80 (m, 1H), 1.66 (s, 9H), 1.40–1.35 (m, 2H), 1.35–1.23 (m, 2H), 1.23–1.17 (m, 2H), 0.88 (t, J=7.1 Hz, 3H); LCMS found for C₃₉H₅₁N₄O₇S (M+H)⁺: m/z=719.

Step 3. (S)-2-{(S)-2-[2-(4-Methoxy-phenyl)-acetylamino]-3-phenyl-propionylamino}-N-pentyl-3-[4-(1,1,3-trioxo-1λ⁶-isothiazolidin-5-yl)-phenyl]-propionamide A solution of 401-B (48 mg, 0.07 mmol) and triisopropylsilane (0.1 mL) in trifluoroacetic acid (3 mL) was heated at 70° C. for 16 h. The reaction mixture was concentrated and purified using preparative LCMS to yield Example 11 (17 mg, 39%) as a white solid. $^1$H NMR (500 MHz, CD₃OD): δ 8.12 (d, J=7.8 Hz, 0.5H), 7.99 (d, J=7.8 Hz, 0.25H), 7.83–7.79 (m, 0.5H), 7.44–7.38 (m, 2H), 7.30 (d, J=7.8 Hz, 2H), 7.26–7.20 (m, 3H), 7.15 (d, J=5.9 Hz, 2H), 7.07–7.02 (m, 2H), 6.82 (d, J=8.3 Hz, 2H), 5.18–5.12 (m, 1H), 4.64–4.58 (m, 1H), 4.58–4.52 (m, 1H), 3.78 (s, 3H), 3.41 (s, 2H), 3.20–3.02 (m, 4H), 2.98–2.92 (m, 1H), 2.88–2.82 (m, 1H), 1.46–1.30 (m, 4H), 1.30–1.20 (m, 2H), 0.93 (t, J=7.3 Hz, 3H); LCMS found for C₃₅H₄₃N₄O₇S (M+H)⁺: m/z=663.

Example 4.2

(S)-2-(3-{(S)-1-Pentylcarbamoyl-2-[4-(1,1,3-trioxo-1λ⁶-isothiazolidin-5-yl)-phenyl]-ethyl}-ureido)-3-phenyl-propionic acid methyl ester

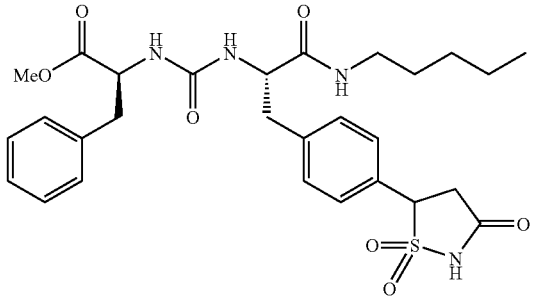

This compound was prepared according to the procedure of Example 4.1, Step 2, using Example 1.10 as the starting material. $^1$H NMR (500 MHz, CD₃OD): δ 7.43 (d, J=7.8 Hz, 2H), 7.33–7.28 (m, 4H), 7.25–7.22 (m, 1H), 7.18 (d, J=7.3 Hz, 2H), 5.17 (dd, J=8.8, 8.8 Hz, 1H), 4.53 (dd, J=7.8, 5.9 Hz, 1H), 4.41–4.37 (m, 1H), 3.69 (s, 3H), 3.40–3.30 (m, 2H), 3.17–3.00 (m, 4H), 3.00–2.92 (m, 2H), 1.48–1.38 (m, 2H), 1.35–1.30 (m, 2H), 1.30–1.23 (m, 2H), 0.92 (t, J=7.0 Hz, 3H); LCMS found for C₂₈H₃₇N₄O₇S (M+H)⁺: m/z=573.

Example 4.3

(S)-2-((S)-2-Acetylamino-3-phenyl-propionylamino)-3-[4-(1,1,3-trioxo-1λ⁶-isothiazolidin-5-yl)-phenyl]-propionamide

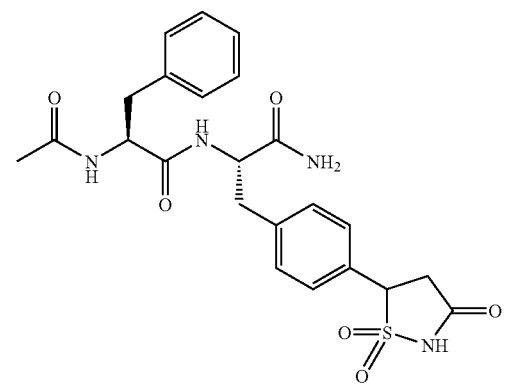

This compound was prepared according to the procedures of Examples 1.1 and 4.1, Step 2, using appropriate starting materials. $^1$H NMR (500 MHz, DMSO-d₆): δ 8.09–8.05 (m, 2H), 7.40 (dd, J=8.3, 2.0 Hz, 2H), 7.33–7.14 (m, 10H), 5.30 (dd, J=9.8, 8.3 Hz, 1H), 4.48–4.41 (m, 2H), 3.43 (ddd, J=17.1, 9.8, 6.8 Hz, 1H), 3.22 (ddd, J=17.1, 8.3, 2.0 Hz, 1H), 3.05 (dd, J=13.7, 4.9, 1H), 2.94 (dd, J=14.2, 4.4 Hz, 1H), 2.87 (dd, J=13.2, 8.3 Hz, 1H), 2.67 (ddd, J=10.2, 2.4, 2.4 Hz, 1H), 1.73 (s, 3H); LCMS found for C₂₃H₂₇N₄O₆S (M+H)⁺: m/z=487.

Example 4.4

(S)-2-((S)-3-Phenyl-2-phenylacetylamino-propionylamino)-3-[4-(1,1,3-trioxo-1λ⁶-isothiazolidin-5-yl)-phenyl]-propionamide

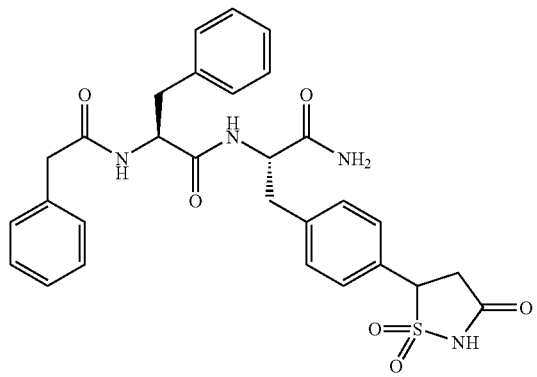

This compound was prepared according to the procedures of Examples 1.1 and 4.1, Step 2, using appropriate starting materials. $^1$H NMR (500 MHz, DMSO-d$_6$): δ 8.27 (dd, J=8.3, 2.0 Hz, 1H), 8.12 (dd, J=7.8, 4.9 Hz, 1H), 7.38 (d, J=8.3 Hz, 2H), 7.29 (dd, J=8.3, 1.5 Hz, 2H), 7.26–7.15 (m, 10H), 7.04 (d, J=8.3 Hz, 2H), 5.29 (dd, J=9.8, 8.3 Hz, 1H), 4.53–4.44 (m, 2H), 3.46–3.39 (m, 1H), 3.41 (d, J=13.7 Hz, 1H), 3.31 (d, J=14.2 Hz, 1H), 3.24–3.18 (m, 1H), 3.04 (dd, J=14.2, 4.9 Hz, 1H), 2.98 (dd, J=14.2, 4.4 Hz, 1H), 2.89–2.85 (m, 1H), 2.75–2.69 (m, 1H); LCMS found for C$_{29}$H$_{31}$N$_4$O$_6$S (M+H)$^+$: m/z=563.

Example 4.5

(S)-2-[(S)-3-Phenyl-2-(3-phenyl-propionylamino)-propionylamino]-3-[4-(1,1,3-trioxo-1λ⁶-isothiazolidin-5-yl)-phenyl]-propionamide

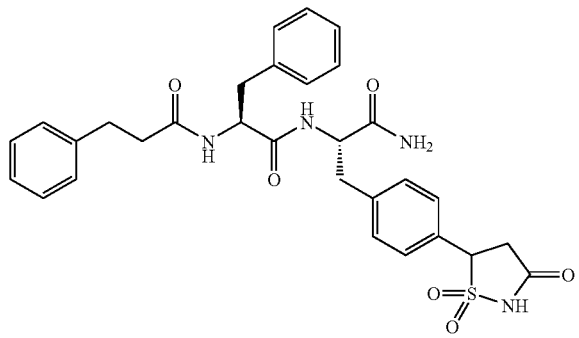

This compound was prepared according to the procedures of Examples 1.1 and 4.1, Step 2, using appropriate starting materials. $^1$H NMR (500 MHz, DMSO-d$_6$): δ 8.09–8.06 (m, 0.25H), 7.40 (d, J=6.8 Hz, 2H), 7.35 (s, 0.5H), 7.31 (d, J=6.8 Hz, 2H), 7.25–7.14 (m, 8H), 7.13–7.10 (m, 2H), 5.31–5.27 (m, 1H), 4.51–4.43 (m, 2H), 3.42 (ddd, J=9.8, 6.8, 6.3 Hz, 1H), 3.23–3.16 (m, 1H), 3.05 (dd, J=14.2, 5.4 Hz, 1H), 2.96 (dd, J=14.2, 4.4 Hz, 1H), 2.92–2.81 (m, 1H), 2.73–2.65 (m, 3H), 2.32 (dd, J=8.8, 6.8 Hz, 2H); LCMS found for C$_{30}$H$_{32}$N$_4$O$_6$S (M+H)$^+$: m/z=577.

Example 4.6

N-((S)-1-{(S)-1-Carbamoyl-2-[4-(1,1,3-trioxo-1λ⁶-isothiazolidin-5-yl)-phenyl]-ethyl]-ethylcarbamoyl}-2-phenyl-ethyl)-benzamide

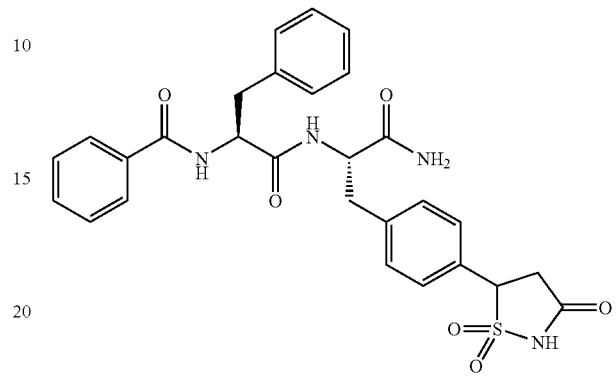

This compound was prepared according to the procedures of Examples 1.1 and 4.1, Step 2, using appropriate starting materials. $^1$H NMR (500 MHz, DMSO-d$_6$): δ 9.60–9.58 (m, 0.2H), 8.58 (d, J=8.3 Hz, 1H), 8.45 (d, J=5.0 Hz, 0.2H), 8.13 (d, J=8.3 Hz, 1H), 7.78–7.76 (m, 2H), 7.52–7.50 (m, 1H), 7.50–7.43 (m, 3H), 7.35–7.28 (m, 6H), 7.27–7.20 (m, 2H), 7.16–7.13 (m, 2H), 5.30–5.26 (m, 0.2H), 5.24 (dd, J=18.1, 8.8 Hz, 0.25H), 4.68–4.66 (m, 0.25H), 4.65–4.63 (m, 0.2H), 4.50–4.47 (m, 0.25H), 4.46–4.40 (m, 0.2H), 3.37 (dd, J=17.1, 9.8 Hz, 0.5H), 3.31 (dd, J=17.1, 9.8 Hz, 0.5H), 3.20–3.12 (m, 1H), 3.08–3.04 (m, 2H), 2.98–2.87 (m, 2H); LCMS found for C$_{28}$H$_{29}$N$_4$O$_6$S (M+H)$^+$: m/z=549.

Example 4.7

(S)-2-{(S)-3-Phenyl-2-[2-(4-trifluoromethyl-phenyl)-acetylamino]-propionylamino)-3-[4-(1,1,3-trioxo-1λ⁶-isothiazolidin-5-yl)-phenyl]-propionamide

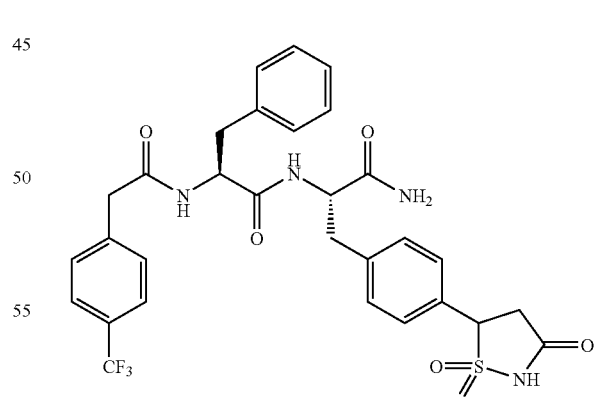

This compound was prepared according to the procedures of Examples 1.1 and 4.1, Step 2, using appropriate starting materials. $^1$H NMR (500 MHz, DMSO-d$_6$): δ 8.38 (dd, J=8.8, 2.0 Hz, 1H), 8.17 (dd, J=8.3, 5.9 Hz, 1H), 7.67 (dd, J=9.8, 8.3 Hz, 0.5H), 7.55 (d, J=7.8 Hz, 2H), 7.50–7.40 (m, 0.5H), 7.39 (d, J=8.3 Hz, 2H), 7.30 (dd, J=8.3, 2.0 Hz, 2H), 7.25 (d, J=7.8 Hz, 2H), 7.20–7.15 (m, 4H), 5.28 (dd, J=9.8, 8.3 Hz, 1H), 4.54–4.49 (m, 1H), 4.48–4.45 (m, 1H), 3.53–3.40 (m,6H), 3.21 (ddd, J=8.3, 7.8, 3.4 Hz, 1H), 3.04 (dd, J=14.2, 4.9 Hz, 1H), 2.99 (dd, J=14.2, 4.4 Hz, 1H), 2.89–2.84 (m, 1H), 2.70 (ddd, J=11.2, 10.2 Hz, 7.8 Hz, 1H); LCMS found for $C_{30}H_{30}F_3N_4O_6S$ (M+H)$^+$: m/z=631.

Example 4.8

2-Hydroxy-6-{3-[3-(1,1,3-trioxo-1$\lambda^6$-isothiazolidin-5-yl)-phenoxy]-propoxy}-benzoic acid

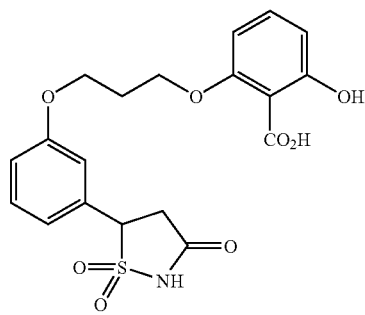

Step 1. 2-tert-Butyl-5-[3-(tert-butyl-dimethyl-silanyloxy)-phenyl]-1,1-dioxo-1,2-dihydro-1$\lambda^6$-isothiazol-3-one (4.08-A)

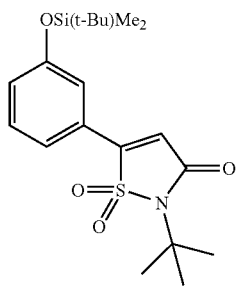

4.08-A

This compound was prepared according to the procedure of Example 1.1, Step 4, using 9-A and 3-(t-butyldimethylsilyoxy)phenylboronic acid as the starting materials. $^1$H NMR (500 MHz, CDCl$_3$): δ 7.37–7.36 (m, 2H), 7.25–7.24 (m, 1H), 7.03–7.01 (m, 1H), 6.61 (s, 1H), 1.73 (s, 9H), 0.99 (s, 9H), 0.23 (s, 6H); LCMS found for $C_{19}H_{29}NO_4SSi$ (M+H)$^+$: m/z=418.

Step 2. 2-tert-Butyl-5-(3-hydroxy-phenyl)-1,1-dioxo-1,2-dihydro-1$\lambda^6$-isothiazol-3-one (4.08-B)

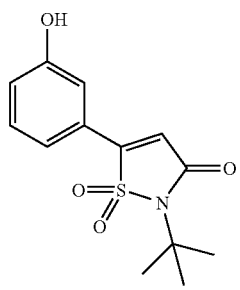

4.08-B

A solution of 4.08-A (1.39 g, 3.5 mmol) in tetrahydrofuran (14 mL) at 0° C. was treated with tetra-n-butylammonium fluoride (1.1 g, 4.2 mmol) dropwise. The reaction mixture was stirred at 25° C. for 30 min and diluted with ethyl acetate (150 mL) and washed with 0.1 N HCl (100 mL) and brine (50 mL). The organic layer was dried with Na$_2$SO$_4$, filtered, and concentrated to give a crude residue which was purified using flash column chromatography (100% hexane to 30% ethyl acetate/hexane) to yield 4.08-B as a white solid (0.95 g, 96%). $^1$H NMR (500 MHz, CDCl$_3$): δ 7.39 (dd, J=7.8, 7.8 Hz, 1H), 7.34–7.32 (m, 1H), 7.26–7.24 (m, 1H), 7.05–7.02 (m, 1H), 6.63 (s, 1H), 5.3 (br s, 1H), 1.73 (s, 9H); LCMS found for $C_{13}H_{16}NO_4S$ (M+H)$^+$: m/z=282.

Step 3. 2-tert-Butyl-5-[3-(3-hydroxy-propoxy)-phenyl]-1,1-dioxo-1,2-dihydro-1$\lambda^6$-isothiazol-3-one (4.08-C)

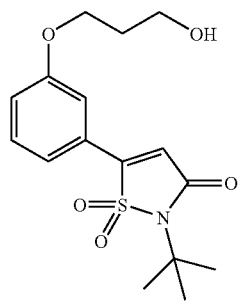

4.08-C

A solution of 4.08-B (0.2 g, 0.7 mmol), 3-bromo-1-propanol (0.1 mL, 1.1 mmol), and potassium carbonate (147 mg, 1.1 mmol) in N,N-dimethylformamide (3 mL) was heated at 80° C. for 1 h. The reaction mixture was diluted with ethyl acetate (75 mL) and washed with 0.5 N HCl (50 mL) and brine (50 mL), dried with Na$_2$SO$_4$, filtered, and concentrated to give a crude residue which was purified using flash column chromatography (100% hexane to 50% ethyl acetate/hexane) to yield 4.08-C as a white solid (0.21 g, 88%). $^1$H NMR (500 MHz, CDCl$_3$): δ 7.42 (dd, J=7.8, 7.8 Hz, 1H), 7.36–7.34 (m, 1H), 7.30 (dd, J=2.0, 2.0 Hz, 1H), 7.11–7.09 (m, 1H), 6.63 (s, 1H), 4.18–4.12 (m, 2H), 3.90–3.86 (m, 2H), 2.10–2.05 (m, 2H), 1.73 (s, 9H); LCMS found for $C_{16}H_{22}NO_5S$ (M+H)$^+$: m/z=340.

Step 4. 2-{3-[3-(2-tert-Butyl-1,1,3-trioxo-2,3-dihydro-1H-1$\lambda^6$-isothiazol-5-yl)-phenyl]-propoxy}-6-hydroxy-benzoic acid methyl ester (408-D)

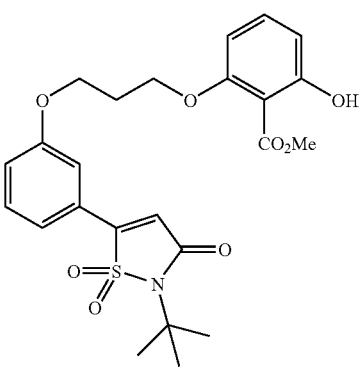

4.08-D

A solution of 4.08-C (0.21 g, 0.6 mmol), methyl 2,6-dihydroxybenzoate (0.13 g, 0.8 mmol), and triphenylphosphine (0.22 g, 0.8 mmol) in tetrahydrofuran (1.5 mL) was treated with diisopropyl azodicarboxylate (0.18 mL, 0.9 mmol) dropwise at 0° C. The reaction mixture was stirred at 25° C. for 2 h. The reaction mixture was concentrated to give a crude residue which was purified using flash column chromatography (100% hexane to 25% ethyl acetate/hexane) to yield 4.08-D as a white solid (0.18 g, 60%). $^1$H NMR (500 MHz, CDCl$_3$): δ 11.47 (s, 1H), 7.42 (dd, J=8.3, 8.3 Hz, 1H), 7.34–7.31 (m, 3H), 7.11–7.08 (m, 1H), 6.62 (s, 1H), 6.60 (dd, J=8.3, 1.0 Hz, 1H), 6.43 (dd, J=8.3, 1.0 Hz, 1H), 4.27–4.25 (m, 2H), 4.21–4.19 (m, 2H), 3.91 (s, 3H), 2.33–2.30 (m, 2H), 1.73 (s, 9H); LCMS found for C$_{24}$H$_{27}$NO$_8$SNa (M+Na)$^+$: m/z=512.

Step 5. 2-{3-[3-(2-tert-Butyl-1,1,3-trioxo-1λ$^6$-isothiazolidin-5-yl)-phenoxy]-propoxy}-6-hydroxy-benzoic acid methyl ester (4.08-E)

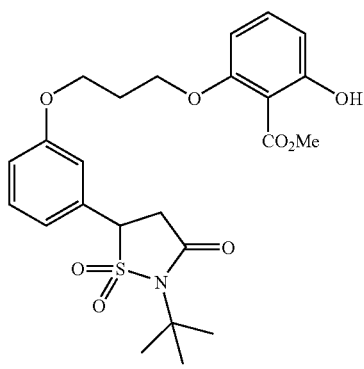

4.08-E

This compound was prepared according to the procedure of Example 4.1, Step 2, using 4.08-D as the starting material. $^1$H NMR (500 MHz, CDCl$_3$): δ 11.47 (s, 1H), 7.37–7.31 (m, 2H), 7.00–6.94 (m, 3H), 6.60 (dd, J=8.3, 1.0 Hz, 1H), 6.43 (d, J=7.8 Hz, 1H), 4.74 (dd, J=8.8, 8.8 Hz, 1H), 4.24–4.22 (m, 2H), 4.20–4.18 (m, 2H), 3.90 (s, 3H), 3.24–3.13 (m, 2H), 2.32–2.28 (m, 2H), 1.66 (s, 9H); LCMS found for C$_{24}$H$_{29}$NO$_8$SNa (M+Na)$^+$: m/z=514.

Step 6. 2-Hydroxy-6-{3-[3-(1,1,3-trioxo-1λ$^6$-isothiazolidin-5-yl)-phenoxy]-propoxy}-benzoic acid The final compound was prepared according to the procedure of Example 1.1, Step 12, using 4.08-E as the starting material. $^1$H NMR (500 MHz, CD$_3$OD): δ 7.39 (dd, J=8.3, 8.3 Hz, 1H), 7.37 (dd, J=7.8, 7.8 Hz, 1H), 7.10–7.05 (m, 3H), 6.63 (d, J=8.3 Hz, 1H), 6.59 (d, J=8.3 Hz, 1H), 5.13 (dd, J=8.8, 8.8 Hz, 1H), 4.36 (dd, J=5.9, 5.9 Hz, 2H), 4.29 (dd, J=5.9, 5.9 Hz, 2H), 3.40–3.30 (m, 2H), 2.37–2.33 (m, 2H); LCMS found for C$_{19}$H$_{18}$NO$_8$S (M–H)$^-$: m/z=420.

Example 4.9

2-Hydroxy-6-{3-[3-(1,1,3-trioxo-1λ$^6$-isothiazolidin-5-yl)-phenoxy]-propoxy}-benzoic acid methyl ester

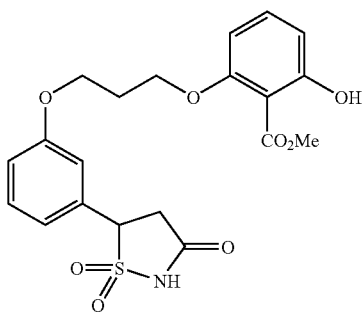

During the synthesis of Example 4.8 this compound was also isolated in Step 6. $^1$H NMR (500 MHz, CD$_3$OD): δ 7.37 (dd, J=8.3, 7.8 Hz, 1H), 7.28 (dd, J=8.3, 8.3 Hz, 1H), 7.10–7.03 (m, 3H), 6.57 (d, J=8.3 Hz, 1H), 6.51 (d, J=8.3 Hz, 1H), 5.13 (dd, J=8.8, 8.3 Hz, 1H), 4.26 (dd, J=6.3, 5.9 Hz, 2H), 4.22 (dd, J=5.9, 5.9 Hz, 2H), 3.85 (s, 3H), 3.38 (dd, J=17.1, 9.3 Hz, 1H), 3.31 (dd, J=17.1, 7.8 Hz, 1H), 2.28–2.25 (m, 2H); LCMS found for C$_{20}$H$_{20}$NO$_8$S (M–H)$^-$: m/z=434.

Example 4.10

4'-[4-(1,1,3-Trioxo-1λ$^6$-isothiazolidin-5-yl)-benzyl-sulfanylmethyl]-biphenyl-3-sulfonic acid amide

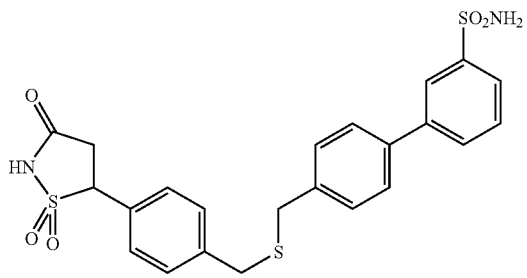

Step 1. 4'-[4-(2-tert-Butyl-1,1,3-trioxo-1λ$^6$-isothia-zolidin-5-yl)-benzylsulfanylmethyl]-biphenyl-3-sulfonic acid amide (4.10-A)

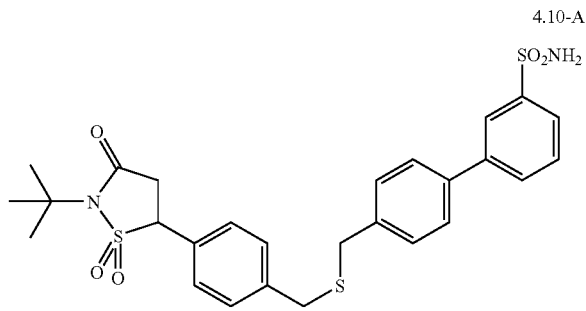

4.10-A

A solution of 20-D (80 mg, 0.14 mmol) in tetrahydrofuran (1.5 mL) at 0° C. was treated with lithium borohydride (2 M in THF, 3.1 mg, 0.14 mmol) dropwise. The reaction mixture was warmed to 25° C., stirred for 30 min and poured into water (25 mL). The reaction mixture was diluted with ethyl acetate (30 mL) and 1 M HCl until the solids dissolved. The organic layer was extracted and washed with brine (10 mL), dried with $Na_2SO_4$, filtered, and concentrated to give a crude residue which was purified using flash column chromatography (5% ethyl acetate/hexane →45% EtOAc/hexane) to yield 4.10-A as a colorless hard foam (64 mg, 80%). $^1$H NMR (500 MHz, $CDCl_3$): δ 8.13 (dd, J=2.0, 1.5 Hz, 1H), 7.90 (ddd, J=7.8, 2.9, 1.9 Hz, 1H), 7.80 (ddd, J=7.8, 2.9, 1.5 Hz, 1H), 7.60 (dd, J=7.8, 7.8 Hz, 1H), 7.52 (dd, J=8.3, 2.0 Hz, 2H), 7.35–7.30 (m, 6H), 4.95 (br s, 1H), 4.93 (br s, 0.5H), 4.76 (dd, J=9.3, 8.8 Hz, 1H), 3.67 (dd, J=7.3, 1.5 Hz, 4H), 3.21 (dd, J=17.1, 8.3 Hz, 1H), 3.13 (dd, J=17.1, 9.3 Hz, 1H), 1.66 (s, 9H); LCMS found for $C_{27}H_{31}N_2O_5S_3$ (M+H)$^+$: m/z=559.

Step 2. 4'-[4-(1,1,3-Trioxo-1λ$^6$-isothiazolidin-5-yl)-benzylsulfanylmethyl]-biphenyl-3-sulfonic acid amide The final compound was prepared according to the procedure of Example 1.1, Step 12, using 4.10-A as the starting material. $^1$H NMR (500 MHz, $CD_3OD$): δ 8.17 (dd, J=2.0, 1.5 Hz, 1H), 7.89 (dd, J=8.3, 8.3 Hz, 2H), 7.87–7.63 (m, 3H), 7.47 (d, J=8.3 Hz, 2H), 7.41 (d, J=7.8 Hz, 4H), 5.19 (dd, J=8.8, 8.8 Hz, 1H), 3.72 (s, 4H), 3.42–3.29 (m, 2H); LCMS found for $C_{23}H_{21}N_2O_5S_3$ (M−H)$^-$: m/z=501.

Example 4.11

5-Fluoro-1H-indole-2-carboxylic acid [6-(4-methoxy-benzyl)-2-(1,1,3-trioxo-1λ$^6$-isothiazolidin-5-yl)-4,5,6,7-tetrahydro-thieno[2,3-c]pyridin-7-ylmethyl]-amide trifluoroacetate

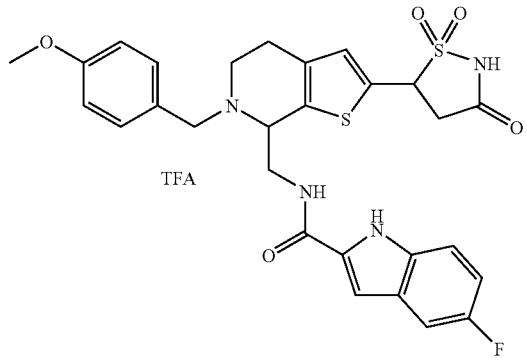

Step 1. (4-Methoxy-benzyl)-(2-thiophen-3-yl-ethyl)-amine Hydrochloride (4.11-A)

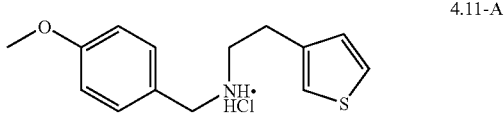

4.11-A

A solution of 2-(3-thienyl)ethanamine hydrochloride (1.0 g, 6.1 mmol), 4-methoxybenzaldehyde (0.74 mL, 6.1 mmol), and triethylamine (1.7 mL, 12.2 mmol) in ethanol (60 mL) was stirred at 25° C. for 5 h. The reaction mixture was cooled to 0° C. and sodium borohydride (289 mg, 7.6 mmol) was added portionwise over 30 min. The reaction mixture was warmed to 25° C. and stirred for 1 h. The reaction mixture was diluted with acetone (5 mL) dropwise and concentrated to a residue that was dissolved in $CH_2Cl_2$ (10 mL) and 1.0 N NaOH (10 mL). The aqueous layer was separated and extracted with $CH_2Cl_2$ (10 mL). The combined organic extracts were washed with brine (10 mL), dried with $Na_2SO_4$, filtered, and concentrated to give a crude oil which was purified using flash column chromatography (30% ethyl acetate/hexane →90% EtOAc/hexane). The fractions containing the amine were acidified with 2 N HCl in 1,4-dioxane to yield 4.11-A as a white solid (1.3 g, 78%). $^1$H NMR (500 MHz, $CD_3OD$): δ 7.46–7.43 (m, 3H), 7.26–7.25 (m, 1H), 7.07–7.06 (m, 1H), 7.05–7.02 (m, 2H), 4.18 (s, 2H), 3.85 (s, 3H), 3.31–3.28 (m, 2H), 3.08 (dd, J=8.3, 7.8 Hz, 2H); LCMS found for $C_{14}H_{18}NOS$ (M+H)$^+$: m/z=248.

Step 2. [6-(4-Methoxy-benzyl)-4,5,6,7-tetrahydro-thieno[2,3-c]pyridin-7-ylmethyl]-carbamic acid tert-butyl ester (4.11-B)

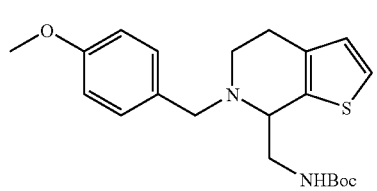

4.11-B

A solution of 4.11-A (5.6 g, 19.7 mmol) and t-butyl (2-oxoethyl)carbamate (12.6 g, 78.9 mmol) in butanol (118 mL) was heated to 140° C. for 16 h in a reaction vessel equiped with a Dean-Stark trap. The reaction mixture was cooled to 25° C. and diluted with ethyl acetate. The starting material 4.11-A precipitates as a white solid which was collected. The ethyl acetate filtrate was washed with saturated sodium bicarbonate (2×100 mL) and brine (100 mL), dried with $Na_2SO_4$, filtered, and concentrated to give a crude oil which was purified using flash column chromatography (100% hexane →30% EtOAc/hexane) to yield 4.11-B as an amber oil (3.4 g, 44%). $^1$H NMR (500 MHz, $CDCl_3$): δ 7.26–7.25 (m, 2H), 7.18 (d, J=4.9 Hz, 1H), 6.88–6.85 (m, 2H), 6.81 (d, J=4.9 Hz, 1H), 5.05–5.00 (M, 1H), 3.81 (s, 3H), 3.80–3.78 (m, 1H), 3.72–3.64 (m, 2H), 3.57–3.53 (m, 1H), 3.20–3.15 (m, 1H), 3.15–3.08 (m, 1H), 2.90–2.78 (m, 2H), 2.48–2.45 (m, 1H), 1.42 (s, 9H); LCMS found for $C_{21}H_{29}N_2O_3S$ (M+H)$^+$: m/z=389.

Step 3. [7-{[(tert-butoxycarbonyl)amino]methyl}-6-(4-methoxybenzyl)-4,5,6,7-tetrahydrothieno[2,3-c]pyridin-2-yl]boronic acid trifluoroacetate (4.11-C)

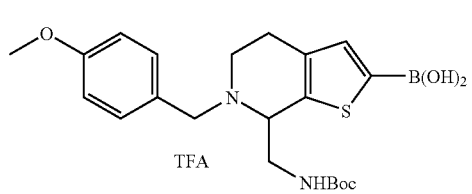

4.11-C

A solution of 4.11-B (1.1 g, 2.8 mmol) in tetrahydrofuran (24 mL) was treated with a solution of t-butyllithium (1.7 M in pentane, 4.1 mL, 7 mmol) at −78° C. The reaction mixture was stirred at −78° C. for 1 h and trimethylborate (0.96 mL, 8.4 mmol) was added. The reaction mixture was stirred at −78° C. for 15 min, warmed to 25° C. and stirred for 3 h. The reaction mixture was diluted with saturated ammonium chloride (15 mL) and extracted with ethyl acetate (30 mL). The organic layer was separated and washed with water (20 mL), dried with $Na_2SO_4$, filtered, and concentrated to give a crude residue which was purified using preparative HPLC to yield 4.11-C as a colorless solid (400 mg, 33%). $^1$H NMR (500 MHz, $CDCl_3$): δ 10.66 (br s, 1H), 7.47–7.27 (m, 3H), 6.97–6.92 (m, 3H), 6.38 (br s, 1H), 4.73–4.65 (m, 1H), 4.33–4.27 (m, 1H), 4.20–4.15 (m, 1H), 3.81 (s, 3H), 3.77–3.60 (m, 2H), 3.58–3.43 (m, 2H), 3.10–2.98 (m, 2H), 1.35 (s, 9H); LCMS found for $C_{21}H_{30}BN_2O_5S$ (M+H)$^+$: m/z=433.

Step 4. [2-(2-tert-Butyl-1,1,3-trioxo-2,3-dihydro-1H-1λ$^6$-isothiazol-5-yl)-6-(4-methoxy-benzyl)-4,5,6,7-tetrahydro-thieno[2,3-c]pyridin-7-ylmethyl]-carbamic acid tert-butyl ester trifluoroacetate (4.11-D)

4.11-D

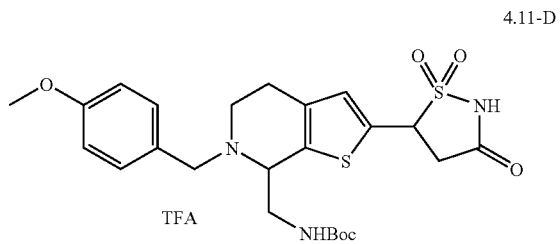

This compound was prepared according to the procedure of Example 1.1, Step 4, using 9-A and 4.11-C as the starting materials. $^1$H NMR (500 MHz, $CDCl_3$): δ 7.56 (s, 1H), 7.36 (d, J=8.4 Hz, 2H), 6.96 (d, J=8.4 Hz, 2H), 6.46 (s, 1H), 4.75–4.65 (m, 1H), 4.58–4.50 (m, 1H), (m, 1H), 4.08–4.00 (m, 1H), 3.83 (s, 3H), 3.80–3.65 (m, 3H), 3.55–3.48 (m, 1H), 3.18–3.10 (m, 2H), 1.75 (s, 9H), 1.36 (s, 9H); LCMS found for $C_{28}H_{38}N_3O_6S_2$ (M+H)$^+$: m/z=576.

Step 5. 5-[7-Aminomethyl-6-(4-methoxy-benzyl)-4,5,6,7-tetrahydro-thieno[2,3-c]pyridin-2-yl]-2tert-butyl-1,1-dioxo-1,2-dihydro-1λ$^6$-isothiazol-3-one bistrifluoroacetate (4.11-E)

4.11-E

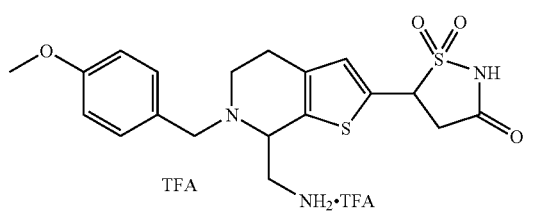

This compound was prepared according to the procedure of Example 1.9, Step 5, using 4.11-D as the starting material. $^1$H NMR (400 MHz, $CD_3OD$): δ 7.53 (s, 1H), 7.33 (d, J=8.4 Hz, 2H), 6.91 (d, J=8.4 Hz, 2H), 6.74 (s, 1H), 4.25–4.18 (m, 1H), 3.87–3.84 (m, 1H), 3.78 (s, 3H), 3.77–3.75 (m, 1H), 3.28–3.21 (m, 3H), 3.08–2.95 (m, 2H), 2.61–2.56 (m, 1H), 1.68 (s, 9H); LCMS found for $C_{23}H_{30}N_3O_4S_2$ (M+H)$^+$: m/z=476.

Step 6. 5-Fluoro-1H-indole-2-carboxylic acid [2-(2-tert-butyl-1,1,3-trioxo-2,3-dihydro-1H-1λ$^6$-isothiazol-5-yl)-6-(4-methoxy-benzyl)-4,5,6,7-tetrahydro-thieno[2,3-c]pyridin-7-ylmethyl]-amide trifluoroacetate (4.11-F)

4.11-F

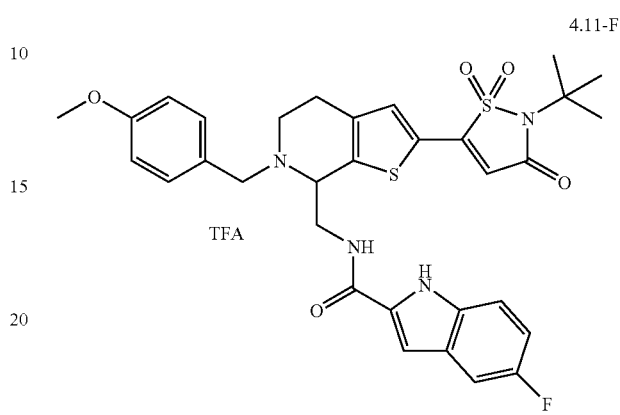

This compound was prepared according to the procedure of Example 1.1, Step 8, using 4.11-E and 5-fluoroindole-2-carboxylic acid as the starting materials. $^1$H NMR (500 MHz, $CDCl_3$): δ 9.53 (br s, 1H), 9.24 (br s, 1H), 7.57 (s, 1H), 7.47–7.33 (m, 2H), 7.19–7.15 (m, 3H), 7.11–7.04 (m, 2H), 6.53–6.47 (m, 2H), 4.94–4.92 (m, 1H), 4.47 (d, J=13.2 Hz, 1H), 4.14–4.10 (m, 1H), 3.94–3.82 (m, 2H), 3.74–3.65 (m, 1H), 3.60–3.50 (m, 1H), 3.28 (s, 3H), 3.20–3.10 (m, 2H), 1.74 (s, 9H); LCMS found for $C_{32}H_{34}FN_4O_5S_2$ (M+H)$^+$: m/z=637.

Step 7. 5-Fluoro-1H-indole-2-carboxylic acid [2-(2-tert-butyl-1,1,3-trioxo-1λ$^6$-isothiazolidin-5-yl)-6-(4-methoxy-benzyl)-4,5,6,7-tetrahydro-thieno[2,3-c]pyridin-7-ylmethyl]-amide trifluoroacetate (4.11-G)

4.11-G

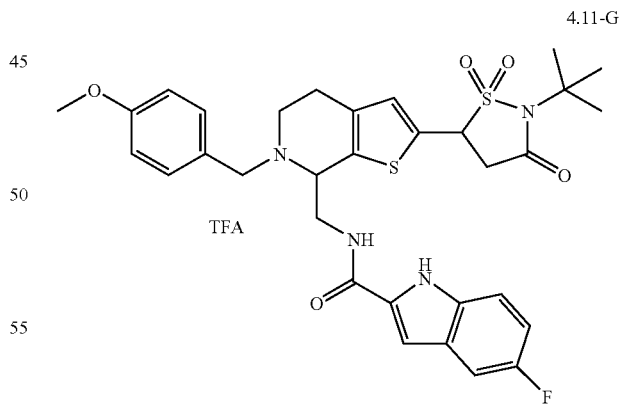

A solution of 4.11-F (54 mg, 0.08 mmol) and 10% palladium on carbon (20 mg, 0.2 mmol) was treated with hydrogen (50 psi) in a Parr reaction vessel. The reaction mixture was shaken for 48 h. The incomplete reaction mixture was filtered and dissolved in 4:1 tetrahydrofuran/methanol (5 mL). The reaction mixture was cooled to 0° C., treated with sodium borohydride (10 mg, 0.3 mmol) and stirred at 25° C. for 1 h. The reaction mixture was quenched with acetone (1 mL), diluted with ethyl acetate (5 mL) and washed with water (5 mL) and brine (5 mL), dried with Na$_2$SO$_4$, filtered, and concentrated to give a crude residue which was purified using preparative LCMS to yield 4.11-G as a white solid (19 mg, 35%). $^1$H NMR (500 MHz, CDCl$_3$): δ 9.72 (br s, 1H), 9.05 (br s, 1H), 7.39 (dd, J=9.3, 4.4 Hz, 1H), 7.33 (dd, J=9.3, 2.4 Hz, 1H), 7.19 (d, J=8.3 Hz, 2H), 7.11–7.07 (m, 2H), 7.02 (s, 1H), 6.51–6.49 (m, 2H), 5.04–5.00 (m, 1H), 4.99–4.89 (m, 1H), 4.46 (d, J=12.7 Hz, 1H), 4.14–4.08 (m, 1H), 3.98–3.94 (m, 1H), 3.89–3.85 (m, 1H), 3.72–3.65 (m, 1H), 3.52 (s, 3H), 3.37–3.30 (m, 2H), 3.15–3.05 (m, 3H), 1.68 (s, 9H); LCMS found for C$_{32}$H$_{36}$FN$_4$O$_5$S$_2$ (M+H)$^+$: m/z=639.

Step 8. 5-Fluoro-1H-indole-2-carboxylic acid [6-(4-methoxy-benzyl)-2-(1,1,3-trioxo-1λ$^6$-isothiazolidin-5-yl)-4,5,6,7-tetrahydro-thieno[2,3-c]pyridin-7-ylmethyl]-amide The final compound was prepared according to the procedure of Example 1.1, Step 12, using 4.11-G as the starting material. $^1$H NMR (500 MHz, CD$_3$OD): δ 11.41 (s, 0.5H), 7.50–7.47 (m, 3H), 7.33–7.31 (m, 1H), 7.22 (s, 1H), 7.09 (ddd, J=9.3, 9.3, 2.4 Hz, 1H), 7.05 (s, 1H), 6.91 (d, J=8.3 Hz, 2H), 5.50–5.46 (m, 1H), 4.56–4.51 (m, 2H), 4.19–4.14 (m, 1H), 3.96–3.86 (m, 2H), 3.70–3.60 (m, 4H), 3.47–3.41 (m, 1H), 3.23–3.13 (m, 1H), 3.10–3.00 (m, 1H); LCMS found for C$_{28}$H$_{28}$FN$_4$O$_5$S$_2$ (M+H)$^+$: m/z=583.

Example 4.12

5-{5-[(4-benzyl-4-hydroxypiperidin-1-yl)methyl]2-thienyl}-isothiazolidin-3-one 1,1-dioxide trifluoroacetate

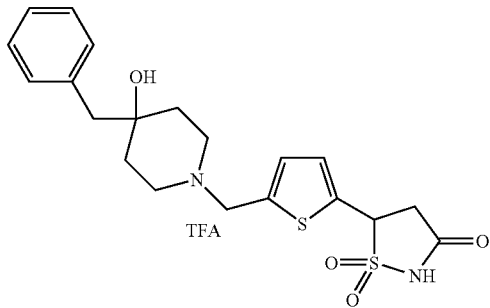

Step 1. {5-[(4-benzyl-4-hydroxypiperidin-1-yl)methyl]-2-thienyl}boronic acid trifluoroacetate (4.12-A)

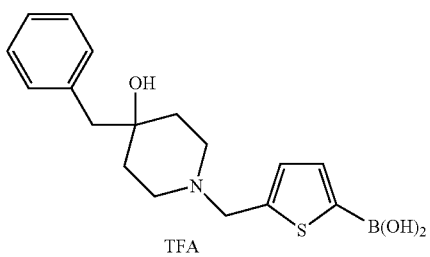

4.12-A

To a solution of (5-formyl-2-thienyl)boronic acid (150 mg, 0.96 mmol) in THF (3.0 mL) was added 4-benzylpiperidin-4-ol (202 mg, 1.06 mmol) followed by sodium triacetoxyborohydride (410 mg, 1.9 mmol) and acetic acid (0.050 mL). The reaction was stirred overnight at room temperature. The mixture was quenched with MeOH and the solvents were evaporated in vacuo. The crude was purified by reverse phase HPLC to afford 4.12-A (164 mg, 38%). LCMS found for C$_{17}$H$_{22}$BNO$_3$S (M+H)$^+$: m/z=332.

Step 2. 5-{5-[(4-benzyl-4-hydroxypiperidin-1-yl)methyl]2-thienyl}2-tertbutylisothiazol-3(2H)-one 1,1-dioxide trifluoroacetate (4.12-B)

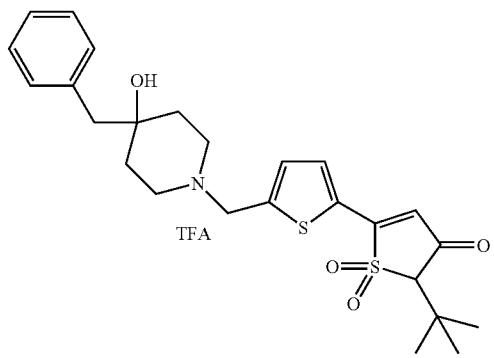

4.12-B

A solution of 4.12-A (100 mg, 0.2 mmol), 9-A (55 mg, 0.25 mmol), potassium carbonate (190 mg, 1.3 mmol) in 1,4-dioxane (1.5 mL) was added to a vial and degassed with nitrogen. Then [1,1'-Bis(diphenylphosphino)ferrocene]dichloropalladium(II), complex with dichloromethane (1:1) (28 mg, 0.034 mmol) was added, degassed with nitrogen and the vial capped and heated at 80° C. overnight. The reaction mixture was filtered through silica gel and eluted with copious amounts of EtOAc. The solvent was concentrated and crude sample purified by reverse phase HPLC to afford 20 mg (15%) of 4.12-B. LCMS found for C$_{24}$H$_{30}$N$_2$O$_4$S$_2$ (M+H)$^+$: m/z=475.

Step 3. 5-{5-[(4-benzyl-4-hydroxypiperidin-1-yl)methyl]2-thienyl}-isothiazol-3(2H)-one 1,1-dioxide trifluoroacetate (4.12-C)

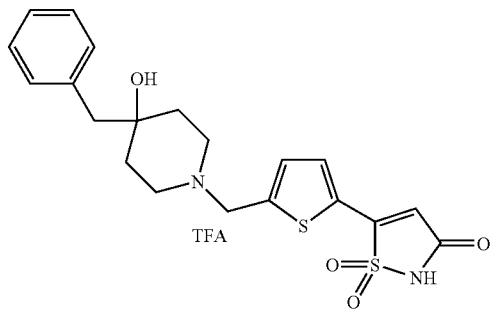

4.12-C

To 4.12-B in a microwave vial was added TFA (1.9 mL) and triisopropylsilane (0.06 mL). The reaction was microwave irradiated at 130° C. for 15 min. The solvents were evaporated and crude purified by reverse phase HPLC to afford 4.12-C (11 mg, 61%). $^1$H NMR (500 MHz, DMSO-d$_6$): δ 9.24 (br s, 1H), 7.52 (d, J=8 Hz, 1H), 7.31 (d, J=8 Hz, 1H), 7.23 (m, 2H), 7.17 (m, 1H), 7.14 (m, 2H), 6.67 (s, 1H), 4.80 (br s, 1H), 4.55 (d, J=7 Hz, 2H), 3.18 (m, 2H), 3.08 (m, 2H), 2.67 (s, 2H), 1.63 (m, 2H), 1.56 (m, 2H); LCMS found for $C_{20}H_{22}N_2O_4S_2$ (M+H)$^+$: m/z=419.

Step 4. 5-{5-[(4-benzyl-4-hydroxypiperidin-1-yl) methyl]2-thienyl}-isothiazolidin-3-one 1,1-dioxide trifluoroacetate To 4.12-C (5.2 mg, 0.0098 mmol) and palladium (10 wt % on activated carbon) in a vial was added MeOH. The reaction was degassed and then hydrogenated overnight under an atmosphere of hydrogen. The reaction mixture was filtered through celite and washed with MeOH and concentrated. The crude was purified by reverse phase HPLC to afford Example 4.12 (3.1 mg, 59%). $^1$H NMR (500 MHz, DMSO-d$_6$): δ 9.37 (br s, 1H), 7.30 (m, 4H), 7.22 (m, 2H), 5.52 (m, 1H), 4.90 (s, 1H), 4.56 (d, J=7 Hz, 2H), 3.30 (m, 2H), 3.24 (m, 2H), 3.15 (m, 2H), 2.74 (s, 2H), 1.70 (m, 2H), 1.65 (m, 2H); LCMS found for $C_{20}H_{24}N_2O_4S_2$ (M+H)$^+$: m/z=421.

Example 4.14

5-[4-(3'-Methanesulfonyl-biphenyl-4-ylmethylsulfa-nylmethyl)-phenyl]-1,1-dioxo-1λ$^6$-isothiazolidin-3-one

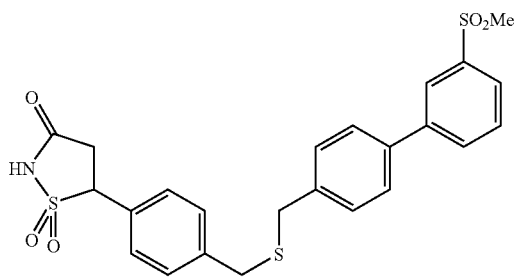

Step 1. 2-tert-Butyl-5-[4-(3'-methanesulfonyl-biphenyl-4-ylmethylsulfanylmethyl)-phenyl]-1,1-dioxo-1λ$^6$-isothiazolidin-3-one (4.14-A)

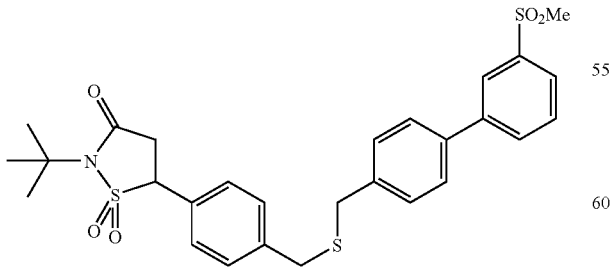

4.14-A

This intermediate was prepared according to the procedure of Example 4.10, Step 1. LCMS found for $C_{28}H_{32}NO_5S_3$ (M+H)$^+$: m/z=558.

Step 2. 5-[4-(3'-Methanesulfonyl-biphenyl-4-ylm-ethylsulfanylmethyl)-phenyl]-1,1-dioxo-1λ$^6$-isothia-zolidin-3-one The final compound was prepared according to the procedure of Example 1.1, Step 12, using 4.14-A of Step 1 as the starting material. $^1$H NMR (400 MHz, CD$_3$OD): δ 8.17 (dd, J=1.8, 1.6 Hz, 1H), 7.98 (d, J=8.0 Hz, 1H), 7.93 (d, J=7.8 Hz, 1H), 7.71 (dd, J=7.8, 7.8 Hz, 1H), 7.63 (d, J=8.2 Hz, 2H), 7.44 (d, J=8.4 Hz, 2H), 7.40–7.37 (m, 4H), 5.17 (dd, J=9.0, 8.6 Hz, 1H), 3.69 (s, 4H), 3.37 (dd, J=17.4, 9.4 Hz, 1H), 3.31–3.25 (m, 1H), 3.18 (s, 3H); LCMS found for $C_{24}H_{24}NO_5S_3$ (M+H)$^+$: m/z=502.

Example 4.15

5-[4-(4'-Methanesulfonyl-biphenyl-4-ylmethylsulfa-nylmethyl)-phenyl]-1,1-dioxo-1λ$^6$-isothiazolidin-3-one

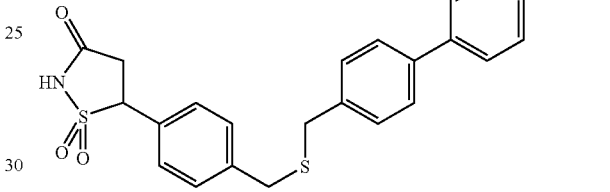

Step 1. (4'-Methanesulfonyl-biphenyl-4-yl)-metha-nol (4.15-A)

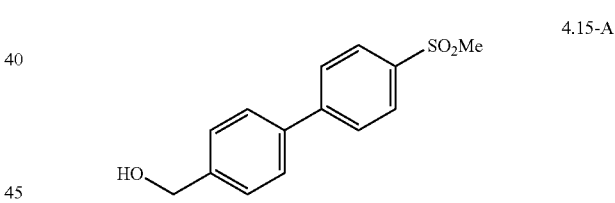

4.15-A

This compound was prepared in a manner analogous to the preparation of (3'-methanesulfonyl-biphenyl-4-yl)-methanol (WO 01/70753, Example 27) using 1-bromo-4-methanesulfonyl-benzene as the starting material. LCMS found for $C_{14}H_{15}O_3S$ (M+H)$^+$: m/z=263.

Step 2. 4'-Bromomethyl-4-methanesulfonyl-biphenyl (4.15-B)

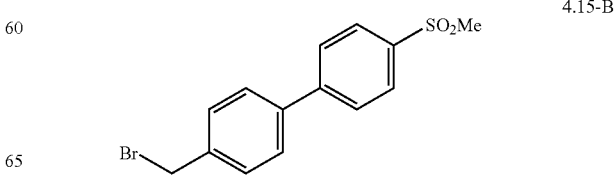

4.15-B

A solution of (4'-methanesulfonyl-biphenyl-4-yl)-methanol (129 mg, 0.49 mmol) in 1,4-dioxane (5 mL) was treated with bromotrimethylsilane (0.2 mL, 1.5 mmol) and stirred at 25° C. for 16 h. The reaction mixture was concentrated and purified by flash column chromatography to yield 4.15-B (152 mg, 95%) as a yellow solid. LCMS found for $C_{14}H_{14}BrO_2S$ (M+H)$^+$: m/z=326.

Step 3. 2-tert-Butyl-5-(4-hydroxymethyl-phenyl)-1,1-dioxo-1λ$^6$-isothiazolidin-3-one (4.15-C)

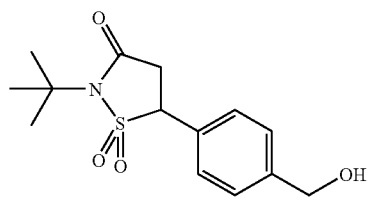

4.15-C

A solution of 20-A of Example 1.20 (420 mg, 1.4 mmol) in tetrahydrofuran (8.4 mL) at 0° C. was treated with lithium tetrahydroborate (0.71 mL, 1.4 mmol, 2 M in tetrahydrofuran). The reaction mixture was stirred at 0° C. for 30 min and quenched with acetic acid (1 mL). The reaction mixture was concentrated and purified by preparative LCMS to yield 4.15-C (359 mg, 85%). LCMS found for $C_{14}H_{20}NO_4S$ (M+H)$^+$: m/z=298.

Step 4. Methanesulfonic acid 4-(2-tert-butyl-1,1,3-trioxo-1λ$^6$-isothiazolidin-5-yl)-benzyl ester (4.15-D)

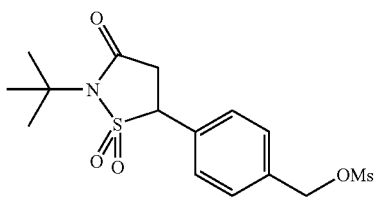

4.15-D

This compound was prepared according to the procedure of Example 1.35, Step 3, using 4.15-C of Step 3 as the starting material. LCMS found for $C_{15}H_{22}NO_6S_2$ (M+H)$^+$: m/z=376.

Step 5. Thioacetic acid S-[4-(2-tert-butyl-1,1,3-trioxo-1λ$^6$-isothiazolidin-5-yl)-benzyl] ester (4.15-E)

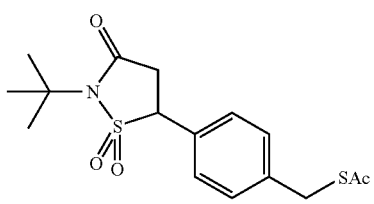

4.15-E

This compound was prepared according to the procedure of Example 1.35, Step 1, using 4.15-D of Step 4 as the starting material. LCMS found for $C_{16}H_{21}NO_4S_2Na$ (M+Na)$^+$: m/z=378.

Step 6. 2-tert-Butyl-5-(4-mercaptomethyl-phenyl)-1,1-dioxo-1λ$^6$-isothiazolidin-3-one (4.15-F)

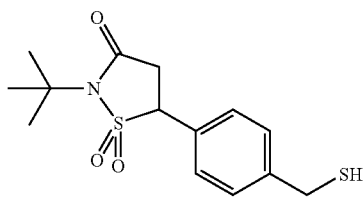

4.15-F

This compound was prepared according to the procedure of Example 1.35, Step 2, using 4.15-E of Step 5 as the starting material. LCMS found for $C_{14}H_{19}NO_3S_2Na$ (M+Na)$^+$: m/z=336.

Step 7. 2-tert-Butyl-5-[4-(4'-methanesulfonyl-biphenyl-4-ylmethylsulfanylmethyl)-phenyl]-1,1-dioxo-1λ$^6$-isothiazolidin-3-one (4.15-G)

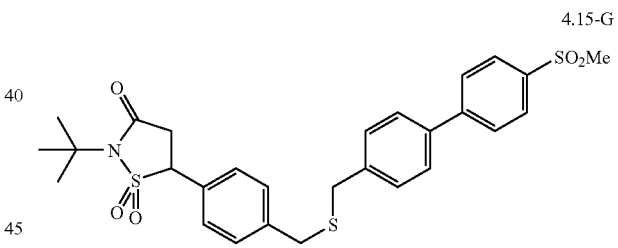

4.15-G

This compound was prepared according to the procedure of Example 1.35, Step 4, using 4.15-D of Step 4 and 4.15-F of Step 6 as the starting materials. LCMS found for $C_{28}H_{31}NO_5S_3Na$ (M+Na)$^+$: m/z=580.

Step 8. 5-[4-(4'-Methanesulfonyl-biphenyl-4-ylmethylsulfanylmethyl)-phenyl]-1,1-dioxo-1λ$^6$-isothiazolidin-3-one The final compound was prepared according to the procedure of Example 1.1, Step 12, using 4.15-G of Step 7 as the starting material. $^1$H NMR (400 MHz, DMSO-d$_6$): δ 8.00 (d, J=8.6 Hz, 2H), 7.95 (d, J=8.6 Hz, 2H), 7.72 (d, J=8.2 Hz, 2H), 7.47–7.38 (m, 6H), 5.31 (dd, J=9.0, 8.8 Hz, 1H), 3.74 (d, J=5.3 Hz, 4H), 3.45 (dd, J=17.2, 9.6 Hz, 1H), 3.28–3.21 (m, 1H), 3.26 (s, 3H); LCMS found for $C_{24}H_{24}NO_5S_3$ (M+H)$^+$: m/z=502.

Example 4.16

4'-[4-(1,1,3-Trioxo-1λ⁶-isothiazolidin-5-yl)-benzyl-sulfanylmethyl]-biphenyl-4-sulfonic acid amide

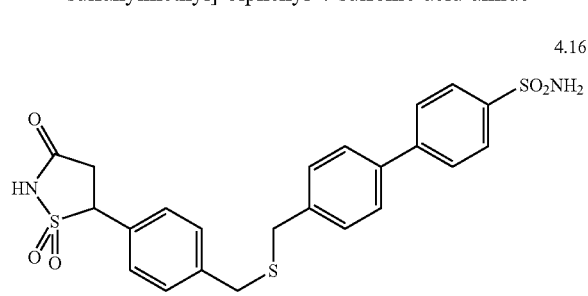

4.16

Step 1. 4'-Hydroxymethyl-biphenyl-4-sulfonic acid amide (4.16-A)

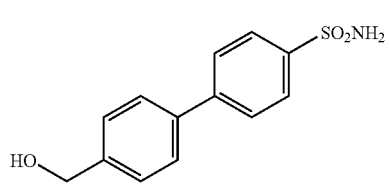

4.16-A

This compound was prepared in a manner analogous to the preparation of (3'-methanesulfonyl-biphenyl-4-yl)-methanol (WO 01/70753, Example 27) using 4-bromo-benzenesulfonamide as the starting material. LCMS found for $C_{13}H_{13}NO_3SNa$ (M+Na)⁺: m/z=286.

Step 2. 4'-Bromomethyl-biphenyl-4-sulfonic acid amide (4.16-B)

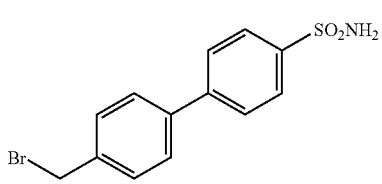

4.16-B

This compound was prepared according to the procedure of Example 4.15, Step 2, using 4.16-A of Step 1 as the starting material.

Step 3. Thioacetic acid S-(4'-sulfamoyl-biphenyl-4-ylmethyl) ester (4.16-C)

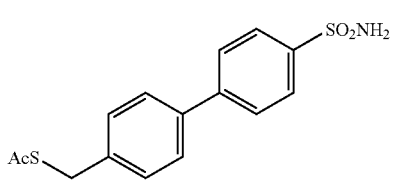

4.16-C

This compound was prepared according to the procedure of Example 1.35, Step 1, using 4.16-B of Step 2 as the starting material. LCMS found for $C_{15}H_{15}NO_3S_2Na$ (M+Na)⁺: m/z=344.

Step 4. 4'-Mercaptomethyl-biphenyl-4-sulfonic acid amide (4.16-D)

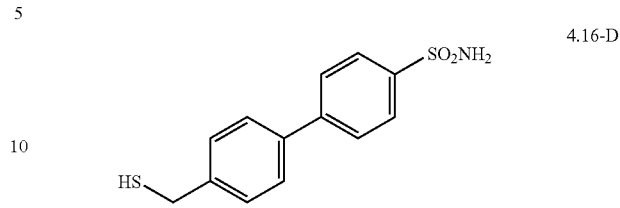

4.16-D

This compound was prepared according to the procedure of Example 1.35, Step 2, using 4.16-C of Step 3 as the starting material.

Step 5. 4'-[4-(2-tert-Butyl-1,1,3-trioxo-1λ⁶-isothiazolidin-5-yl)-benzylsulfanylmethyl]-biphenyl-4-sulfonic acid amide (4.16-E)

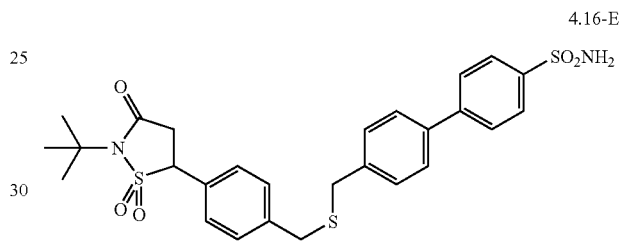

4.16-E

This compound was prepared according to the procedure of Example 1.35, Step 4, using 4.16-D of Step 4 and 4.15-D of Example 4.15, Step 4 as the starting materials. LCMS found for $C_{27}H_{30}N_2O_5S_3Na$ (M+Na)⁺: m/z=581.

Step 6. 4'-[4-(1,1,3-Trioxo-1λ⁶-isothiazolidin-5-yl)-benzylsulfanylmethyl]-biphenyl-4-sulfonic acid amide The final compound was prepared according to the procedure of Example 1.1, Step 12, using 4.16-E of Step 5 as the starting material. ¹H NMR (400 MHz, CD₃OD): δ 7.96 (d, J=8.6 Hz, 2H), 7.80 (d, J=8.6 Hz, 2H), 7.62 (d, J=8.4 Hz, 2H), 7.44 (d, J=8.2 Hz, 2H), 7.39–7.37 (m, 4H), 5.16 (dd, J=9.0, 8.6 Hz, 1H), 3.69 (s, 4H), 3.37 (dd, J=17.2, 9.4 Hz, 1H), 3.30–3.25 (m, 1H); LCMS found for $C_{23}H_{23}N_2O_5S_3$ (M+H)⁺: m/z=503.

Example 4.17

4'-[4-(1,1,3-Trioxo-1λ⁶-isothiazolidin-5-yl)-benzyl-sulfanylmethyl]-biphenyl-4-carboxylic acid methyl ester

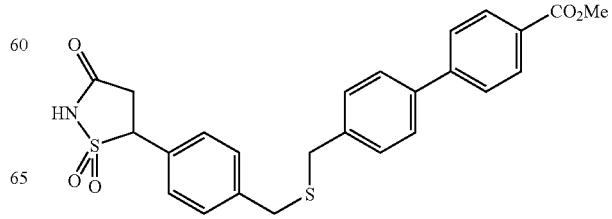

Step 1. 4'-Methanesulfonyloxymethyl-biphenyl-4-carboxylic acid methyl ester (4.17-A)

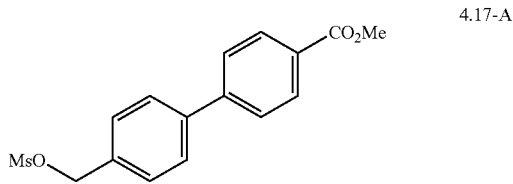

This compound was prepared according to the procedure of Example 1.35, Step 3, using 4'-hydroxymethyl-biphenyl-4-carboxylic acid methyl ester (JOC, 2001, 66, 8815) as the starting material. LCMS found for $C_{16}H_{17}O_5S$ (M+H)$^+$: m/z=321.

Step 2. 4'-[4-(2-tert-Butyl-1,1,3-trioxo-1λ$^6$-isothiazolidin-5-yl)-benzylsulfanylmethyl]-biphenyl-4-carboxylic acid methyl ester (4.17-B)

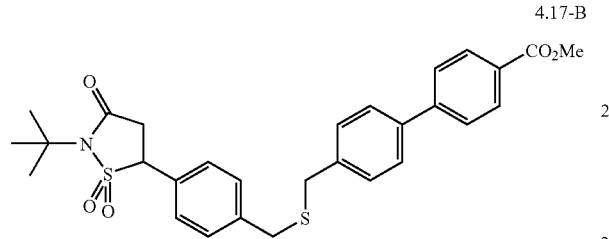

This compound was prepared according to the procedure of Example 1.35, Step 4, using 4.17-A of Step 1 and 4.15-F of Example 4.15, Step 6 as the starting materials. LCMS found for $C_{29}H_{32}NO_5S_2$ (M+H)$^+$: m/z=538.

Step 3. 4'-[4-(1,1,3-Trioxo-1λ$^6$-isothiazolidin-5-yl)-benzylsulfanylmethyl]-biphenyl-4-carboxylic acid methyl ester The final compound was prepared according to the procedure of Example 1.1, Step 12, using 4.17-B of Step 2 as the starting material. $^1$H NMR (400 MHz, DMSO-d$_6$): δ 8.01 (d, J=8.4 Hz, 2H), 7.82 (d, J=8.6 Hz, 2H), 7.69 (d, J=8.2 Hz, 2H), 7.44–7.35 (m, 6H), 5.29 (dd, J=9.2, 8.6 Hz, 1H), 3.85 (s, 3H), 3.71 (d, J=5.7 Hz, 4H), 3.42 (dd, J=17.2, 9.8 Hz, 1H), 3.22 (dd, J=17.2, 8.2 Hz, 1H); LCMS found for $C_{25}H_{24}NO_5S_2$ (M+H)$^+$: m/z=482.

Example 4.18

5-[4-(2',4'-Dimethoxy-biphenyl-4-ylmethylsulfanylmethyl)-phenyl]-1,1-dioxo-1λ$^6$-isothiazolidin-3-one

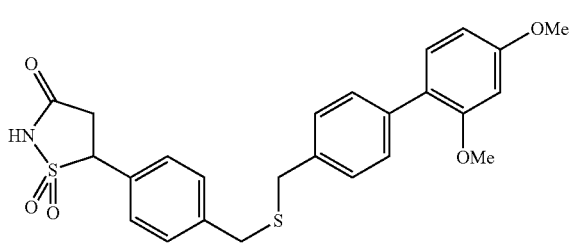

Step 1. (2,4'-Dimethoxy-biphenyl-4-yl)-methanol (4.18-A)

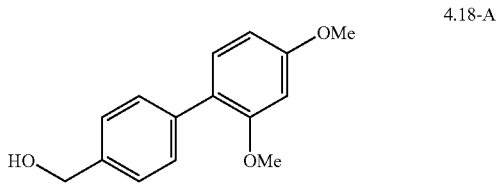

This compound was prepared in a manner analogous to the preparation of (3'-methanesulfonyl-biphenyl-4-yl)-methanol (WO 01/70753, Example 27) using 2,4-dimethoxyiodobenzene as the starting material. LCMS found for $C_{15}H_{15}O_2$ (M–OH)$^+$: m/z=227.

Step 2. 4'-Bromomethyl-2,4-dimethoxy-biphenyl (4.18-B)

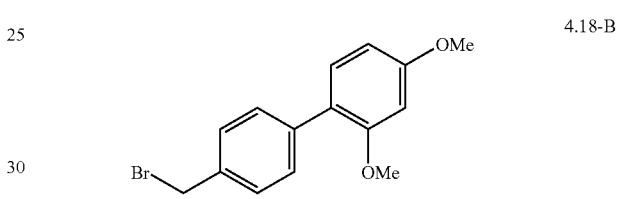

This compound was prepared according to the procedure of Example 4.15, Step 2, using 4.18-A of Step 1 as the starting material. LCMS found for $Cl_{15}H_{16}BrO_2$ (M+H)$^+$: m/z=307, 309.

Step 3. 2-tert-Butyl-5-[4-(2',4'-dimethoxy-biphenyl-4-ylmethylsulfanylmethyl)-phenyl]-1,1-dioxo-1λ$^6$-isothiazolidin-3-one (4.18-C)

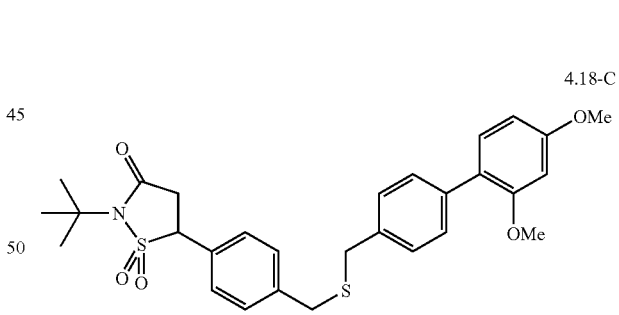

This compound was prepared according to the procedure of Example 1.35, Step 4, using 4.18-B of Step 2 and 4.15-F of Example 4.15, Step 6 as the starting materials. LCMS found for $C_{29}H_{34}NO_5S_2$ (M+H)$^+$: m/z=539.

Step 4. 5-[4-(2,4'-Dimethoxy-biphenyl-4-ylmethylsulfanylmethyl)-phenyl]-1,1-dioxo-1λ$^6$-isothiazolidin-3-one The final compound was prepared according to the procedure of Example 1.1, Step 12, using 4.18-C of Step 3 as the starting material. $^1$H NMR (400 MHz, CD$_3$OD): δ 7.45–7.40 (m, 2H), 7.40–7.37 (m, 4H), 7.25 (d, J=8.4 Hz, 2H), 7.20 (d, J=8.4 Hz, 1H), 6.61–6.57 (m, 2H), 5.16 (dd, J=9.0, 8.6 Hz, 1H), 3.82 (s, 3H), 3.78 (s, 3H), 3.68 (s, 2H), 3.64 (s, 2H), 3.38 (dd, J=17.4, 9.6 Hz, 1H), 3.31–3.26 (m, 1H); LCMS found for $C_{25}H_{26}NO_5S_2$ (M+H)$^+$: m/z=484.

Example 4.19

1,1-Dioxo-5-[4-(3-oxo-2,3-diphenyl-propyl)-phenyl]-1λ$^6$-isothiazolidin-3-one

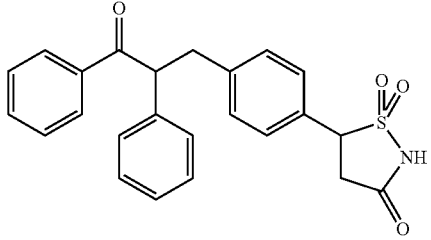

Step 1. 5-(4-Bromomethyl-phenyl)-2-tert-butyl-1,1-dioxo-1λ$^6$-isothiazolidin-3-one (4.19-A)

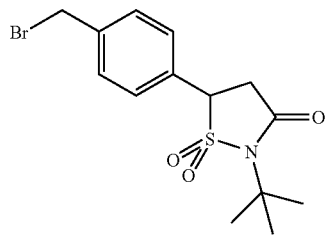

4.19

A solution of 4.15-D of Example 4.15, Step 4 (62.6 mg, 0.32 mmol) in N,N-dimethylacetamide (2 mL) was treated with sodium bromide (150 mg, 1.4 mmol) and stirred at 25° C. for 45 min. The reaction mixture was diluted with ethyl acetate (50 mL), washed with water (2×25 mL) and brine (25 mL), dried with sodium sulfate, filtered, and concentrated to a white solid (258 mg, 99%). This material was used in the next step without further purification. LCMS found for $C_{14}H_{19}BrNO_3S$ (M+H)$^+$: m/z=360, 362.

Step 2. 2-tert-Butyl-1,1-dioxo-5-[4-(3-oxo-2,3-diphenyl-propyl)-phenyl]-1λ$^6$-isothiazolidin-3-one (4.19-B)

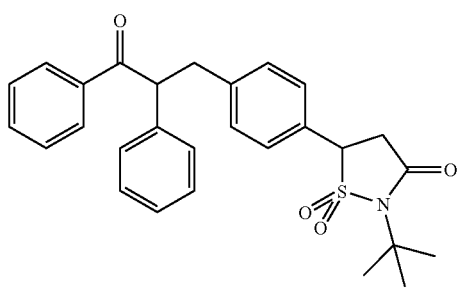

4.19-B

A solution of deoxybenzoin (62.6 mg, 0.32 mmol) in tetrahydrofuran (1.3 mL) was cooled to −78° C. and potassium tert-butoxide (0.15 mL, 0.15 mmol, 1.0 M in tetrahydrofuran) was added dropwise. The reaction mixture was stirred at −78° C. for 10 minutes and 4.19-A of Step 1 (115 mg, 0.32 mmol) in tetrahydrofuran (1.5 mL) was added dropwise. The reaction mixture was warmed to 25° C. and quenched with saturated ammonium chloride (15 mL) and extracted with ethyl acetate (2×30 mL). The combined organic extracts were washed with brine (15 mL), dried with sodium sulfate, filtered, and concentrated to a crude yellow oil which was purified by flash column chromatography to yield the desired product (75 mg, 50%). LCMS found for $C_{28}H_{29}NO_4SNa$ (M+Na)$^+$: m/z=498.

Step 3. 1,1-Dioxo-5-[4-(3-oxo-2,3-diphenyl-propyl)-phenyl]-1λ$^6$-isothiazolidin-3-one The final compound was prepared according to the procedure of Example 1.36, Step 3, using 4.19-B as the starting material. $^1$H NMR (400 MHz, CDCl$_3$): δ 7.90 (d, J=7.4 Hz, 2H), 7.46 (dd, J=7.4, 7.2 Hz, 1H), 7.35 (dd, J=8.0, 7.4 Hz, 2H), 7.30–7.18 (m, 9H), 4.90 (dd, J=8.6, 8.4 Hz, 1H), 4.80 (dd, J=7.4, 7.2 Hz, 1H), 3.60 (ddd, J=13.9, 7.8, 2.9 Hz, 1H), 3.32–3.29 (m, 2H), 3.09 (ddd, J=13.7, 6.8, 2.1 Hz, 1H); LCMS found for $C_{24}H_{22}NO_4S$ (M+H)$^+$: m/z=420.

Example 4.20

N-{1-(4,5-Dihydro-1H-imidazol-2-yl)-2-[4-(1,1,3-trioxo-1λ$^6$-isothiazolidin-5-yl)-phenyl]-ethyl}-3-trifluoromethyl-benzenesulfonamide trifluoroacetate

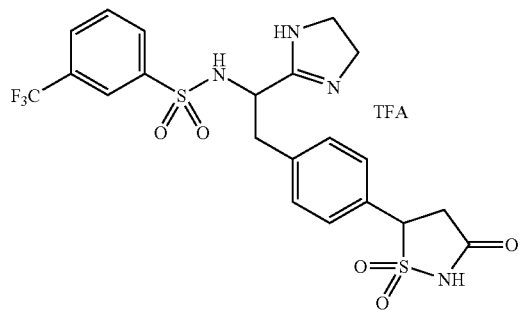

This compound was prepared according to the procedure of Example 4.11, Step 7, using the compound of Example 1.37 as the starting material. $^1$H NMR (400 MHz, CD$_3$OD): δ 8.02 (brs, 1H), 7.94 (dd, J=7.8, 7.6 Hz, 1H), 7.78 (dd, J=13.3, 8.0 Hz, 1H), 7.64 (dd, J=8.0, 7.6 Hz, 1H), 7.27 (dd, J=8.0, 5.1 Hz, 2H), 7.10 (dd, J=8.2, 4.9 Hz, 2H), 5.05 (dd, J=8.8, 8.4 Hz, 1H), 4.39 (dd, J=9.4, 6.1 Hz, 1H), 3.96–3.85 (m, 4H), 3.27–3.25 (m, 2H), 3.08–3.04 (m, 1H), 2.99–2.93 (m, 1H); LCMS found for $C_{21}H_{22}F_3N_4O_5S_2$ (M+H)$^+$: m/z=531.

Example 4.21

N-1{-(1H-Imidazol-2-yl)-2-[4-(1,1,3-trioxo-1λ$^6$-isothiazolidin-5-yl)-phenyl]-ethyl}-benzenesulfonamide trifluoroacetate

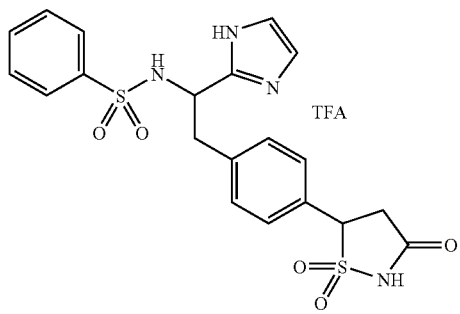

Step 1. {2-[4-(2-tert-Butyl-1,1,3-trioxo-2,3-dihydro-1H-1λ$^6$-isothiazol-5-yl)-phenyl]-1-carbamoyl-ethyl}-carbamic acid 9H-fluoren-9-ylmethyl ester (4.21-A)

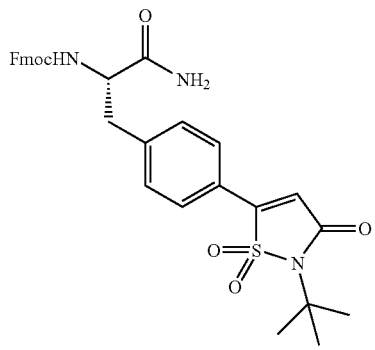

A solution of 1.37-A of Example 1.37, Step 1 (600 mg, 2 mmol) and N,N-diisopropylethylamine (0.53 mL, 3.1 mmol) in acetonitrile (11 mL) was treated with succinimidyl 9-fluorenylmethyl carbonate (646 mg, 1.9 mmol) in one portion. The reaction mixture was stirred at 25° C. for 16 h and concentrated to remove the acetonitrile. The crude material was diluted with chloroform (200 mL) and washed with 1 N HCl (100 mL). The aqueous was separated and extracted with more chloroform (200 mL). The combined organic layers were dried with sodium sulfate, filtered, and concentrated to a crude residue which was triturated with diethyl ether to yield the desired product (617 mg, 70%). LCMS found for $C_{31}H_{32}N_3O_6S$ (M+H)$^+$: m/z=574.

Step 2. {2-[4-(2-tert-Butyl-1,1,3-trioxo-2,3-dihydro-1H-1λ$^6$-isothiazol-5-yl)-phenyl]-1-cyano-ethyl}-carbamic acid 9H-fluoren-9-ylmethyl ester (4.21-B)

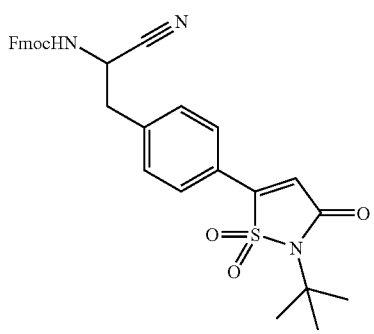

This compound was prepared according to the procedure of Example 1.37, Step 3, using 4.21-A of Step 1 as the starting material. LCMS found for $C_{31}H_{33}N_4O_5S$ (M+NH$_4$)$^+$: m/z=573.

Step 3. 3-[4-(2-tert-Butyl-1,1,3-trioxo-2,3-dihydro-1H-1λ$^6$-isothiazol-5-yl)-phenyl]-2-(9H-fluoren-9-ylmethoxycarbonylamino)-propionimidic acid ethyl ester hydrochloride (4.21-C)

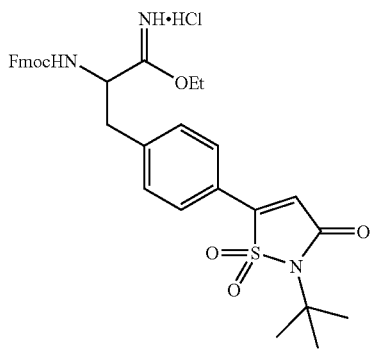

This compound was prepared according to the procedure of Example 1.37, Step 4, using 4.21-B of Step 2 as the starting material. This was used immediately in the next reaction.

203

Step 4. 5-{4-[2-Amino-2-(1H-imidazol-2-yl)-ethyl]-phenyl}-1,1-dioxo-1,2-dihydro-1λ⁶-isothiazol-3-one bistrifluoroacetate (4.21-D)

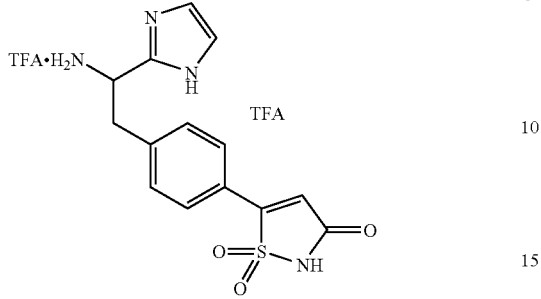

4.21-D

A solution of 4.21-C (260 mg, 0.40 mmol) in ethanol (6.5 mL) was treated with 2,2-diethoxyethanamine (95 μL, 0.65 mmol). The reaction mixture was heated at 90° C. for 16 h, concentrated and treated with 2 M HCl (30 mL). The reaction mixtre was heated to 100° C. for 5 h. The solid which formed was filtered and the filtrate was concentrated to a crude solid which was purified by preparative LCMS to yield 4.21-D (34 mg, 14%). LCMS found for $C_{14}H_{15}N_4O_3S$ (M+H)⁺: m/z=319.

Step 5. N-1-(1H-Imidazol-2-yl)-2-[4-(1,1,3-trioxo-2,3-dihydro-1H-1λ⁶-isothiazol-5-yl)-phenyl]-ethyl}-benzenesulfonamide trifluoroacetate (4.21-E)

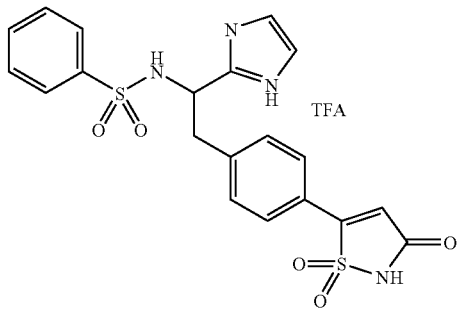

4.21-E

This compound was prepared according to the procedure of Example 1.37, Step 2, using 4.21-D of Step 4 and benzenesulfonyl chloride as the starting materials. LCMS found for $C_{20}H_{19}N_4O_5S_2$ (M+H)⁺: m/z=459.

Step 6. N-{1-(1H-Imidazol-2-yl)-2-[4-(1,1,3-trioxo-1λ⁶-isothiazolidin-5-yl)-phenyl]-ethyl}-benzenesulfonamide trifluoroacetate The final compound was prepared according to the procedure of Example 4.11, Step 7, using 4.21-E of Step 5 as the starting material. ¹H NMR (400 MHz, CD₃OD): δ 7.70–7.60 (m, 3H), 7.52–7.47 (m, 2H), 7.42 (d, J=5.3 Hz, 2H), 7.28 (dd, J=8.2, 1.4 Hz, 2H), 7.00 (d, J=8.0 Hz, 2H), 5.09 (ddd, J=8.8, 8.8, 2.1 Hz, 1H), 4.75 (dd, J=7.8, 7.8 Hz, 1H), 3.15 (d, J=7.8 Hz, 2H); LCMS found for $C_{20}H_{21}N_4O_5S_2$ (M+H)⁺: m/z=461.

204

Example 4.22

N-{1-(5-Phenyl-1H-imidazol-2-yl)-2-[4-(1,1,3-trioxo-1λ⁶-isothiazolidin-5-yl)-phenyl]-ethyl}-3-trifluoromethyl-benzenesulfonamide trifluoroacetate

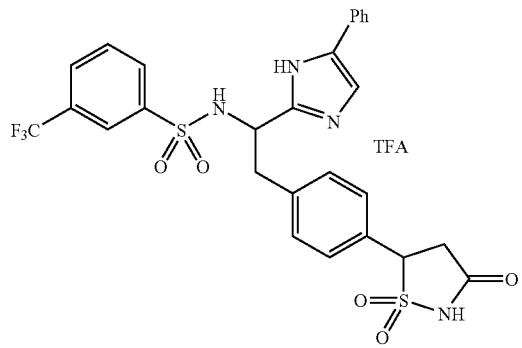

Step 1. 3-[4-(2-tert-Butyl-1,1,3-trioxo-1λ⁶-isothiazolidin-5-yl)-phenyl]-2-(3-trifluoromethyl-benzenesulfonylamino)-propionamide (4.22-A)

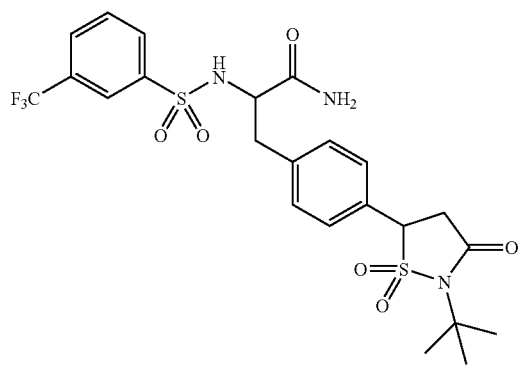

4.22-A

This compound was prepared according to the procedure of Example 4.15, Step 3, using 1.37-B of Example 1.37, Step 2 as the starting material. LCMS found for $C_{23}H_{27}F_3N_3O_6S_2$ (M+H)⁺: m/z=562.

Step 2. N-{2-[4-(2-tert-Butyl-1,1,3-trioxo-1λ⁶-isothiazolidin-5-yl)-phenyl]-1-cyano-ethyl}-3-trifluoromethyl-benzenesulfonamide (4.22-B)

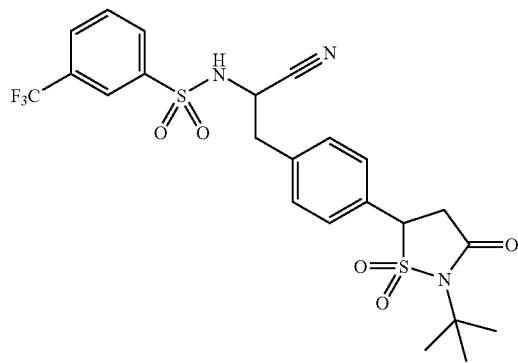

4.22-B

This compound was prepared according to the procedure of Example 1.37, Step 3, using 4.22-A of Step 1 as the starting material. LCMS found for $C_{23}H_{28}F_3N_4O_5S_2$ $(M+NH_4)^+$: m/z=561.

Step 3. 3-[4-(2-tert-Butyl-1,1,3-trioxo-1λ⁶-isothiazolidin-5-yl)-phenyl]-2-(3-trifluoromethyl-benzenesulfonylamino)-propionamide acid ethyl ester hydrochloride (4.22-C)

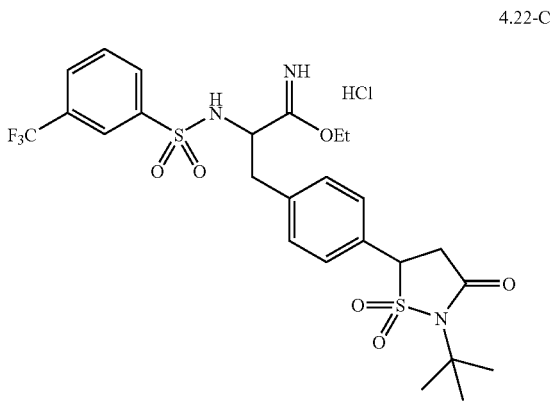

4.22-C

This compound was prepared according to the procedure of Example 1.37, Step 4, using 4.22-B of Step 2 as the starting material. LCMS found for $C_{25}H_{33}F_3N_3O_7S_2$ $(M+(H_2O)+H)^+$: m/z=608.

Step 4. N-[2-[4-(2-tert-Butyl-1,1,3-trioxo-1λ⁶-isothiazolidin-5-yl)-phenyl]-1-(4phenyl-1H-imidazol-2-yl)-ethyl]-3-trifluoromethyl-benzenesulfonamide trifluoroacetate (4.22-D)

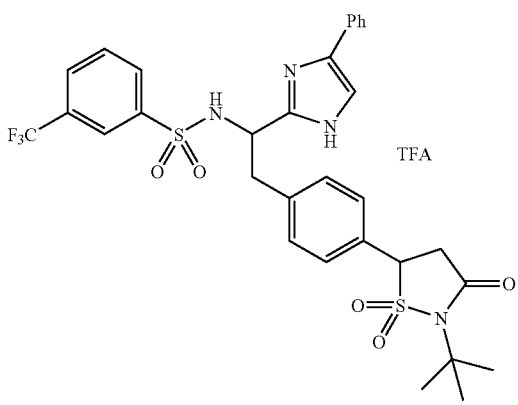

4.22-D

A solution of 4.22-C of Step 3 (80 mg, 0.13 mmol) and potassium acetate (0.5 mg, 0.51 mmol) in methanol (1.1 mL) was heated to 65° C. and treated with a solution of 2-amino-1-phenylethanone hydrochloride (44 mg, 0.26 mmol) in methanol (0.5 mL). The reaction mixture was heated at 65° C. for 16 h, cooled and the solid was filtered. The solid was washed with methanol and the filtrate concentrated to a crude solid which was purified by preparative LCMS to yield 4.22-D (43 mg, 51%). LCMS found for $C_{31}H_{32}F_3N_4O_5S_2$ $(M+H)^+$: m/z=661.

Step 5. N-{1-(5-Phenyl-1H-imidazol-2-yl)-2-[4-(1,1,3-trioxo-1λ⁶-isothiazolidin-5yl)-phenyl]-ethyl}-3-trifluoromethyl-benzenesulfonamide trifluoroacetate A solution of 4.22-D of Step 4 (50 mg, 65 µmol) in trifluoroacetic acid (3 mL) was heated at 120° C. for 5 min in a microwave. The trifluoroacetic acid was concentrated and the crude solid was purified by preparative LCMS to yield the desired product (19 mg, 49%). $^1$H NMR (400 MHz, CD$_3$OD): δ 8.01 (brs, 1H), 7.91–7.85 (m, 2H), 7.69–7.60 (m, 2H), 7.59–7.53 (m, 2H), 7.51–7.40 (m, 3H), 7.29 (d, J=7.6 Hz, 2H), 7.07 (d, J=7.8 Hz, 2H), 5.05–4.95 (m, 1H), 4.89–4.81 (m, 1H), 3.30–3.20 (m, 4H); LCMS found for $C_{27}H_{24}F_3N_4O_5S_2$ $(M+H)^+$: m/z=605.

Example 4.23

({4-[((S)-1-{(S)-1-Carbamoyl-2-[4-(1,1,3-trioxo-1λ⁶-isothiazolidin-5-yl)-phenyl]-ethylcarbamoyl}-2-phenyl-ethylcarbamoyl)-methyl]-phenyl}-difluoromethyl)-phosphonic acid

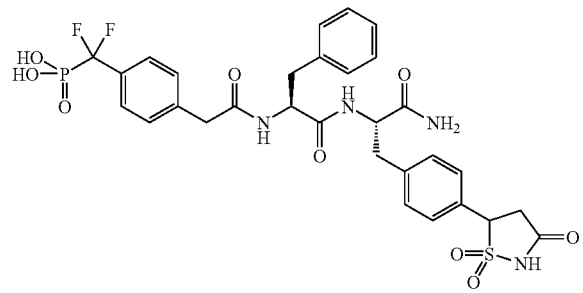

Step 1. ((S)-1-{(S)-2-[4-(2-tert-Butyl-1,1,3-trioxo-1λ⁶-isothiazolidin-5-yl)-phenyl]-1carbamoyl-ethylcarbamoyl}-2-phenyl-ethyl)-carbamic acid tert-butyl ester (4.23-A)

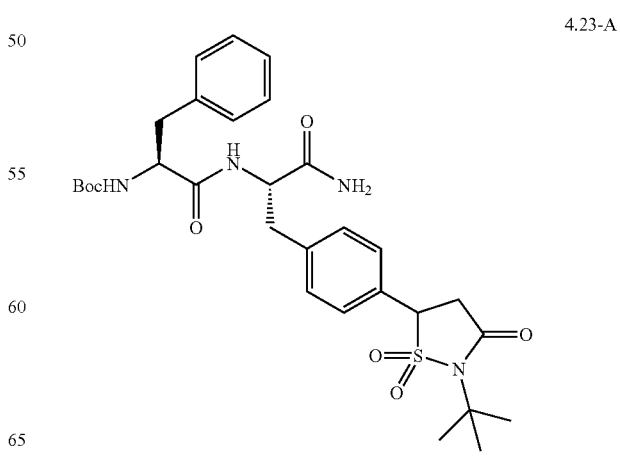

4.23-A

This compound was prepared according to the procedure of Example 4.11, Step 7, using 1.38-A of Example 1.38, Step 1 as the starting material. LCMS found for $C_{25}H_{33}N_4O_5S$ $(M(-Boc)+H)^+$: m/z=501.

Step 2. (S)-2-Amino-N-{(S)-1-carbamoyl-2-[4-(1,1,3-trioxo-1λ⁶-isothiazolidin-5-yl)-phenyl]-ethyl}-3-phenyl-propionamide trifluoroacetate (4.23-B)

4.23-B

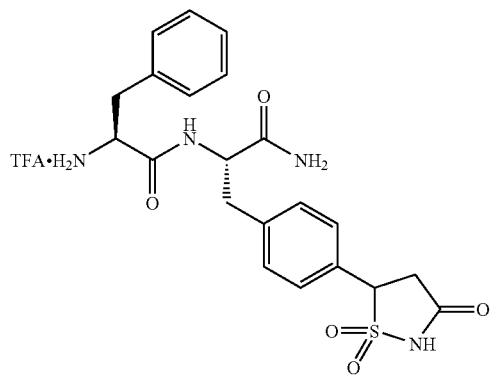

This compound was prepared according to the procedure of Example 1.1, Step 12, using 4.23-A of Step 1 as the starting material. LCMS found for $C_{21}H_{25}N_4O_5S$ $(M+H)^+$: m/z=445.

Step 3. ({4-[((S)-1-{(S)-1-Carbamoyl-2-[4-(1,1,3-trioxo-1λ⁶-isothiazolidin-5-yl)-phenyl]-ethylcarbamoyl}-2-phenyl-ethylcarbamoyl)-methyl]-phenyl}-difluoro-methyl)-phosphonic acid diethyl ester (4.23-C)

4.23-C

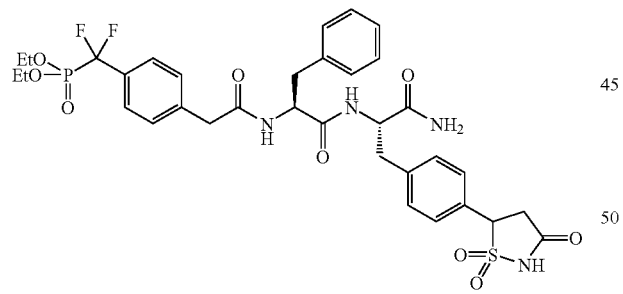

This compound was prepared according to the procedure of Example 1.1, Step 10, using 4.23-B of Step 2 and {4-[(diethoxy-phosphoryl)-difluoro-methyl]-phenyl}-acetic acid (*Biochemistry*, (2003), 42, 12792) as the starting materials. LCMS found for $C_{34}H_{40}F_2N_4O_9PS$ $(M+H)^+$: m/z=749.

Step 4. ({4-[((S)-1-{(S)-1-Carbamoyl-2-[4-(1,1,3-trioxo-1λ⁶-isothiazolidin-5-yl)-phenyl]-ethylcarbamoyl}-2-phenyl-ethylcarbamoyl)-methyl]-phenyl}-difluoro-methyl)-phosphonic acid The final compound was prepared according to the procedure of Example 1.38, Step 4, using 4.23-C of Step 3 as the starting material. ¹H NMR (500 MHz, CD₃OD): δ 7.49 (d, J=8.3 Hz, 2H), 7.41–7.36 (m, 2H), 7.28–7.18 (m, 9H), 4.64–4.58 (m, 3H), 3.56–3.49 (m, 2H), 3.18 (dd, J=14.2, 5.4 Hz, 1H), 3.13–3.07 (m, 2H), 2.95–2.90 (m, 1H), 2.86–2.81 (m, 1H); LCMS found for $C_{30}H_{32}F_2N_4O_9PS$ $(M+H)^+$: m/z=693.

Example 4.24

(S)-2-{(S)-2-[2-(4-Methoxy-phenyl)-acetylamino]-3-phenyl-propionylamino}-3-[4-(1,1,3-trioxo-1λ⁶-isothiazolidin-5-yl)-phenyl]-propionamide

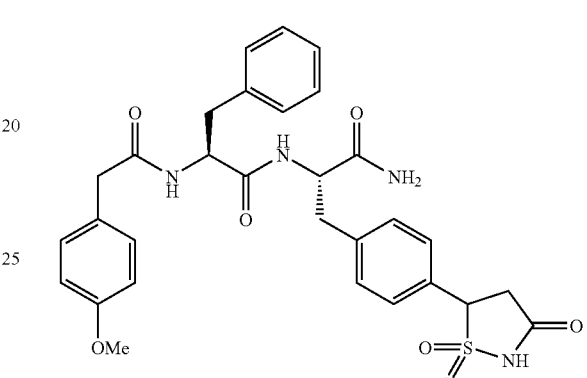

This compound was prepared according to the procedures of Example 1.1 and 4.1, Step 2, using appropriate starting materials. ¹H NMR (500 MHz, CD₃OD): δ 8.11 (d, J=7.3 Hz, 1H), 7.40 (dd, J=7.8, 5.9 Hz, 2H), 7.32 (d, J=8.3 Hz, 2H), 7.25–7.19 (m, 2H), 7.17–7.14 (m, 2H), 7.05–7.02 (m, 2H), 6.81 (d, J=8.3 Hz, 2H), 5.15–5.11 (m, 1H), 4.63–4.60 (m, 2H), 3.78 (s, 3H), 3.43–3.37 (m, 2H), 3.30–3.25 (m, 2H), 3.21–3.16 (m, 1H), 3.09–3.02 (m, 1H), 2.98–2.90 (m, 1H), 2.86–2.81 (m, 1H); LCMS found for $C_{30}H_{33}N_4O_7S$ $(M+H)^+$: m/z=593.

Example 4.25

(S)-2-{(S)-2-[2-(4-Hydroxy-phenyl)-acetylamino]-3-phenyl-propionylamino}-3-[4-(1,1,3-trioxo-1λ⁶-isothiazolidin-5-yl)-phenyl]-propionamide

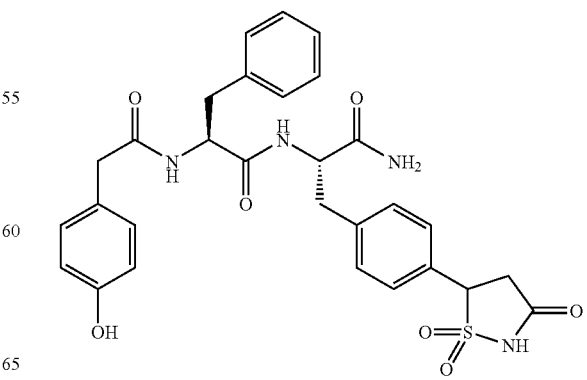

This compound was prepared according to the procedures of Example 1.1 and 4.1, Step 2, using appropriate starting materials. LCMS found for $C_{29}H_{31}N_4O_7S$ (M+H)$^+$: m/z=579.

Example 4.26

5-[4-(2-Benzotriazol-1-yl-3-biphenyl-4-yl-2-phenyl-propyl)-phenyl]-1,1-dioxo-1λ$^6$-isothiazolidin-3-one trifluoroacetate

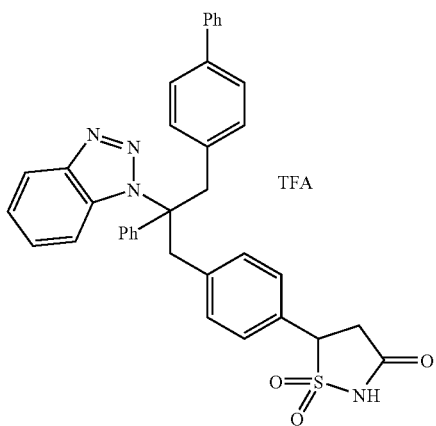

Step 1. 1-(2-Biphenyl-4-yl-1-phenyl-ethyl)-1H-benzotriazole (4.26-A)

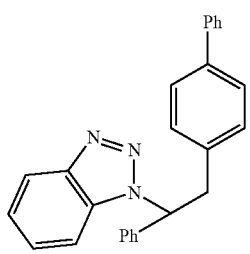

4.26-A

A solution of 1-benzyl-1H-1,2,3-benzotriazole (750 mg, 3.6 mmol) in tetrahydrofuran (36 mL) was cooled to −78° C. and treated with n-butyllithium (2.8 mL, 1.6 M in hexanes) dropwise. The reaction mixture was stirred at −78° C. for 10 min and 4-bromomethyl-biphenyl (1.0 g, 4.1 mmol) in tetrahydrofuran (4 mL) was added dropwise. The reaction mixture was stirred at −78° C. for 1 h, quenched with sat. ammonium chloride (100 mL), and extracted with ethyl acetate (150 mL). The organic layer was separated and washed with brine (50 mL), dried with sodium sulfate, filtered, and concentrated to a white solid. This material was triturated with diethyl ether (2×50 mL) to yield the desired product (1.12 g, 83%). LCMS found for $C_{26}H_{22}N_3$ (M+H)$^+$: m/z=376.

Step 2. 1-{2-Biphenyl-4-yl-1-phenyl-1-[4-(4,4,5,5-tetramethyl-[1,3,2]dioxaborolan-2-yl)-benzyl]-ethyl}-1H-benzotriazole (4.26-B)

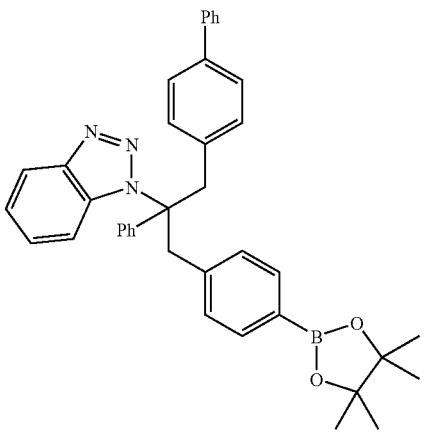

4.26-B

A solution of 4.26-A of Step 1 (450 mg, 1.2 mmol) in tetrahydrofuran (14 mL) was cooled to −78° C. and treated with n-butyllithium (0.62 mL, 2.5 M in hexanes) dropwise. The reaction mixture was stirred at −78° C. for 10 min and 2-[4-(bromomethyl)phenyl]-4,4,5,5-tetramethyl-1,3,2-dioxaborolane (410 mg, 1.4 mmol) in tetrahydrofuran (2 mL) was added dropwise. The reaction mixture was stirred at −78° C. for 1 h, quenched with sat. ammonium chloride (2 mL), and extracted with ethyl acetate (15 mL). The organic layer was separated and washed with brine (5 mL), dried with sodium sulfate, filtered, and concentrated to a crude residue which was purified by flash column chromatography to yield the desired product (350 mg, 50%). LCMS found for $C_{39}H_{38}BN_3O_2Na$ (M+Na)$^+$: m/z=614.

Step 3. 5-[4-(2-Benzotriazol-1-yl-3-biphenyl-4-yl-2-phenyl-propyl)-phenyl]-2-tert-butyl-1,1-dioxo-1,2-dihydro-1λ$^6$-isothiazol-3-one (4.26-C)

4.26-C

This compound was prepared according to the procedure of Example 1.1, Step 4, using 4.26-B of Example 2 and 9-A of Example 1.9 as the starting materials. LCMS found for C$_{40}$H$_{37}$N$_4$O$_3$S (M+H)$^+$: m/z=653.

Step 4. 5-[4-(2-Benzotriazol-1-yl-3-biphenyl-4-yl-2-phenyl-propyl)-phenyl]-2-tert-butyl-1,1-dioxo-1λ$^6$-isothiazolidin-3-one (4.26-D)

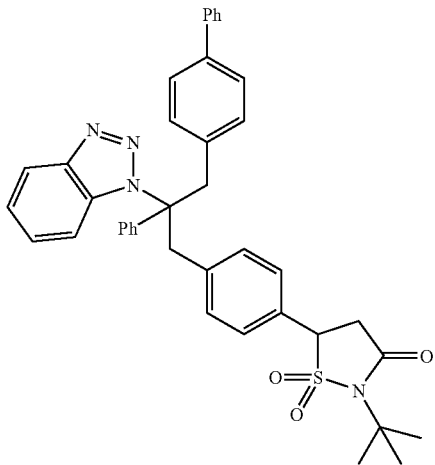

4.26-C

A solution of 4.26-D of Step 3 (75 mg, 0.12 mmol) in tetrahydrofuran (4.5 mL) was cooled to −78° C. and treated with L-selectride (0.11 mL, 1 M in tetrahydrofuran). The reaction mixture was stirred at −78° C. for 15 min, quenched with glacial acetic acid (0.5 mL), diluted with ethyl acetate (25 mL), and washed with water (2×20 mL) and brine (20 mL). The organic layer was separated, dried with sodium sulfate, filtered, and concentrated to a crude residue which was purified by by preparative LCMS to yield the desired product (7 mg, 9%). LCMS found for C$_{40}$H$_{39}$N$_4$O$_3$S (M+H)$^+$: m/z=655.

Step 5. 5-[4-(2-Benzotriazol-1-yl-3-biphenyl-4-yl-2-phenyl-propyl)-phenyl]-1,1-dioxo-1λ$^6$-isothiazolidin-3-on trifluoroacetate The final compound was prepared according to the procedure of Example 1.1, Step 12, using 4.26-D of Step 4 as the starting material. $^1$H NMR (400 MHz, CD$_3$OD): δ 8.01 (dd, J=8.6, 2.9 Hz, 1H), 7.50 (d, J=7.4 Hz, 2H), 7.40–7.37 (m, 4H), 7.36–7.30 (m, 4H), 7.30–7.16 (m, 4H), 7.08 (d, J=8.2 Hz, 2H), 6.77 (dd, J=8.4, 2.0 Hz, 2H), 6.70–6.65 (m, 3H), 5.06 (dd, J=17.0, 8.4 Hz, 1H), 4.12 (dd, J=13.9, 5.5 Hz, 1H), 4.05 (d, J=14.1 Hz, 1H), 3.97–3.91 (m, 2H), 3.28–3.20 (m, 2H); LCMS found for C$_{36}$H$_{31}$N$_4$O$_3$S (M+H)$^+$: m/z=599.

Example 4.27

2-Hydroxy-6-{4-[3-(1,1,3-trioxo-1λ$^6$-isothiazolidin-5-yl)-phenoxy]-butoxy}-benzoic acid methyl ester

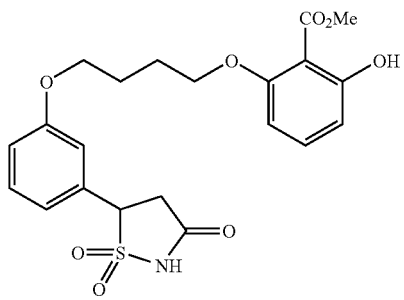

This compound was prepared according to the procedures of Example 4.8 and 4.9 using appropriate starting materials. $^1$H NMR (400 MHz, CD$_3$OD): δ 7.33 (dd, J=8.2, 8.0 Hz, 1H), 7.25 (dd, J=8.4, 8.2 Hz, 1H), 7.05–7.02 (m, 2H), 6.98 (ddd, J=9.2, 3.3, 0.8 Hz, 1H), 6.52–6.47 (m, 2H), 5.12–5.06 (m, 1H), 4.11–4.06 (m, 4H), 3.84 (s, 3H), 3.38–3.25 (m, 2H), 2.03–1.93 (m, 4H); LCMS found for C$_{21}$H$_{23}$NO$_8$SNa (M+Na)$^+$: m/z=472.

Example 4.28

2-Hydroxy-6-{4-[3-(1,1,3-trioxo-1λ$^6$-isothiazolidin-5-yl)-phenoxy]-butoxy}-benzoic acid

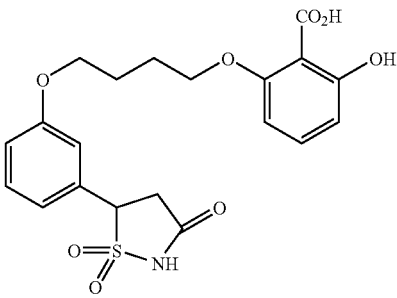

This compound was prepared according to the procedures of Example 4.8 using appropriate starting materials. $^1$H NMR (400 MHz, CD$_3$OD): δ 7.39–7.31 (m, 2H), 7.04–6.97 (m, 3H), 6.61–6.55 (m, 2H), 5.11 (dd, J=8.8, 8.6 Hz, 1H), 4.24 (t, J=6.0 Hz, 2H), 4.10 (t, J=5.9 Hz, 2H), 3.35–3.26 (m, 2H), 2.10–1.98 (m, 4H); LCMS found for C$_{20}$H$_{22}$NO$_8$S (M+H)$^+$: m/z=436.

Example 4.29

2-Hydroxy-6-{5-[3-(1,1,3-trioxo-1λ$^6$-isothiazolidin-5-yl)-phenoxy]-pentyloxy}-benzoic acid methyl ester

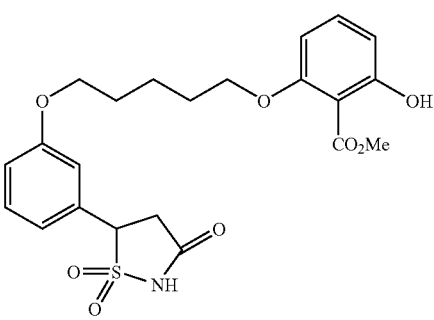

This compound was prepared according to the procedures of Example 4.8 and 4.9 using appropriate starting materials. $^1$H NMR (400 MHz, CD$_3$OD): δ 7.33 (dd, J=8.2, 8.2 Hz, 1H), 7.24 (dd, J=8.4, 8.2 Hz, 1H), 7.04–6.98 (m, 3H), 6.51–6.46 (m, 2H), 5.13 (dd, J=8.8, 8.6 Hz, 1H), 4.06–4.01 (m, 4H), 3.85 (s, 3H), 3.37 (dd, J=17.2, 9.2 Hz, 1H), 3.32–3.26 (m, 1H), 1.88–1.80 (m, 4H), 1.72–1.67 (m, 2H); LCMS found for C$_{22}$H$_{25}$NO$_8$SNa (M+Na)$^+$: m/z=486.

Example 4.30

2-Hydroxy-6-{5-[3-(1,1,3-trioxo-1$\lambda^6$-isothiazolidin-5-yl)-phenoxy]-pentyloxy}-benzoic acid

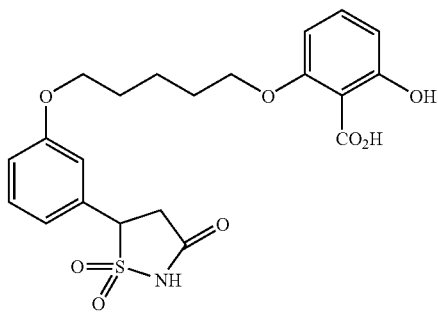

This compound was prepared according to the procedures of Example 4.8 using appropriate starting materials. $^1$H NMR (400 MHz, CD$_3$OD): δ 7.39–7.31 (m, 2H), 7.04–6.97 (m, 3H), 6.58 (dd, J=9.0, 8.6 Hz, 2H), 5.13 (dd, J=9.0, 8.6 Hz, 1H), 4.19 (dd, J=6.4, 6.2 Hz, 2H), 4.04 (dd, J=6.2, 6.2 Hz, 2H), 3.38 (dd, J=17.4, 9.4 Hz, 1H), 3.31–3.26 (m, 1H), 1.96–1.85 (m, 4H), 1.73–1.67 (m, 2H); LCMS found for C$_{21}$H$_{24}$NO$_8$S (M+H)$^+$: m/z=450.

Example 4.31

2-Hydroxy-6-{6-[3-(1,1,3-trioxo-1$\lambda^6$-isothiazolidin-5-yl)-phenoxy]-hexyloxy}-benzoic acid methyl ester

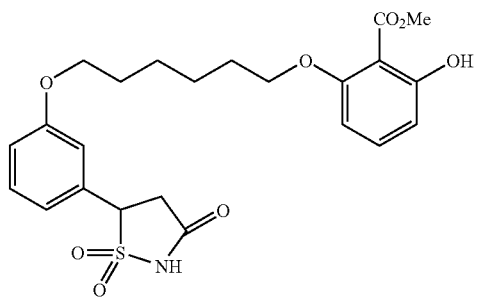

This compound was prepared according to the procedures of Example 4.8 and 4.9 using appropriate starting materials. $^1$H NMR (400 MHz, CD$_3$OD): δ 7.34 (dd, J=8.2, 8.0 Hz, 1H), 7.24 (dd, J=8.4, 8.4 Hz, 1H), 7.03–7.01 (m, 2H), 6.97 (dd, J=7.6, 1.8 Hz, 1H), 6.48 (dd, J=9.4, 9.2 Hz, 2H), 5.07 (dd, J=8.6, 8.6 Hz, 1H), 4.04–3.98 (m, 4H), 3.83 (s, 3H), 3.33–3.25 (m, 2H), 1.84–1.79 (m, 4H), 1.60–1.52 (m, 4H); LCMS found for C$_{23}$H$_{27}$NO$_8$SNa (M+Na)$^+$: m/z=500.

Example 4.32

2-Hydroxy-6-{6-[3-(1,1,3-trioxo-1$\lambda^6$-isothiazolidin-5-yl)-phenoxy]-hexyloxy}-benzoic acid

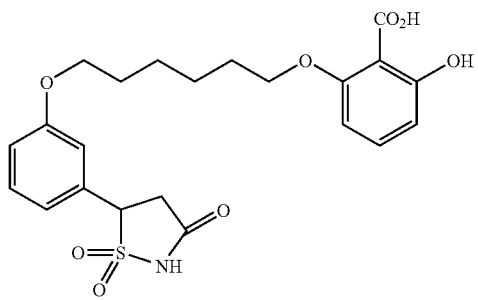

This compound was prepared according to the procedures of Example 4.8 using appropriate starting materials. $^1$H NMR (400 MHz, CD$_3$OD): δ 7.39–7.31 (m, 2H), 7.04–7.02 (m, 2H), 6.99–6.96 (m, 1H), 6.58 (dd, J=8.6, 8.4 Hz, 2H), 5.14 (dd, J=8.8, 8.6 Hz, 1H), 4.18 (t, J=6.3 Hz, 2H), 4.02 (t, J=6.3 Hz, 2H), 3.38 (dd, J=17.2, 9.2 Hz, 1H), 3.33–3.26 (m, 1H), 1.90–1.85 (m, 2H), 1.85–1.78 (m, 2H), 1.62–1.52 (m, 4H); LCMS found for C$_{22}$H$_{26}$NO$_8$S (M+H)$^+$: m/z=464.

Example 4.33

5-Fluoro-1H-indole-2-carboxylic acid [2-(1,1,3-trioxo-1$\lambda^6$-isothiazolidin-5-yl)-4,5,6,7-tetrahydro-thieno[2,3-c]pyridin-7-ylmethyl]-amide trifluoroacetate

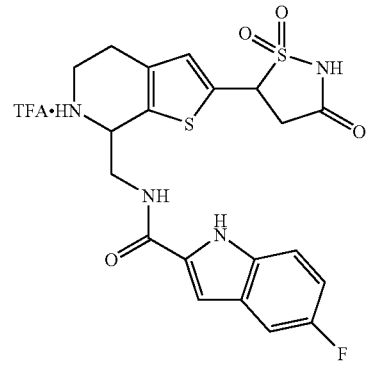

A solution of 411-G of Example 4.11 (11 mg, 13 μmol) and triisopropylsilane (250 mL, 1.2 mmol) in trifluoroacetic acid (1.3 mL) was heated in a microwave at 170° C. for four minutes. The reaction mixture was diluted with toluene (5 mL) and evaporated. This was repeated until a residue appeared which was purified by preparative LCMS to yield the desired product (1.6 mg, 18%). $^1$H NMR (500 MHz, CD$_3$OD): δ 7.46 (dd, J=8.8, 4.4 Hz, 1H), 7.32 (dd, J=9.3, 2.0 Hz, 1H), 7.19 (s, 1H), 7.14 (s, 1H), 7.08–7.04 (s, 1H), 5.44 (dd, J=8.8, 8.3 Hz, 1H), 4.03–3.98 (m, 1H), 3.98–3.84 (m, 2H), 3.79–3.70 (m, 1H), 3.52–3.42 (m, 1H), 3.41–3.39 (m, 1H), 3.33–3.27 (m, 1H), 3.13–3.01 (m, 3H); LCMS found for C$_{20}$H$_{20}$FN$_4$O$_4$S$_2$ (M+H)$^+$: m/z=463.

Example 4.34

(2S)-2-(acetylamino)-3-[4-(1,1-dioxido-3-oxoisothiazolidin-5-yl)phenyl]-N-(4-phenylbutyl)propanamide

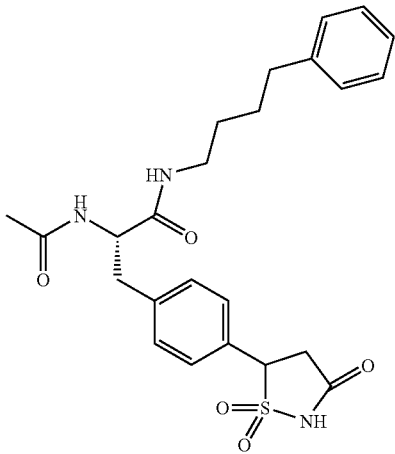

Step 1. (2S)-2-(acetylamino)-3-[4-(1,1-dioxido-3-oxo-2,3-dihydroisothiazol-5-yl)phenyl]propanoic acid

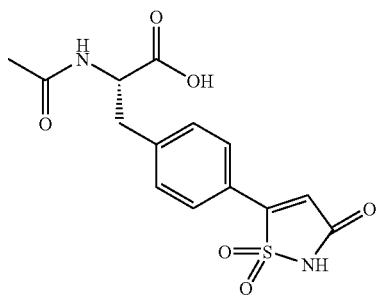

(2S)-2-amino-3-[4-(1,1-dioxido-3-oxo-2,3-dihydroisothiazol-5-yl)phenyl]propanoic acid (45 mg, 0.15 mmol) was dissolved in N-methylpyrrolidinone (1.0 mL) with 20 drops of DMSO added to fully dissolve. To the solution was added acetic anhydride (14 μL, 0.15 mmol) and N,N-diisopropylethylamine (79 μL, 0.46 mmol). The solution was stirred at room temperature for 2 h. The product was purified by preparative LCMS to afford the desired product (61 mg, 96%). LCMS found for $C_{14}H_{15}N_2O_6S$ (M+H)$^+$: m/z=339.1

Step 2. (2S)-2-[(tert-butoxycarbonyl)amino]-3-[4-(2-tert-butyl-1,1-dioxido-3-oxoisothiazolidin-5-yl)phenyl]propanoic acid

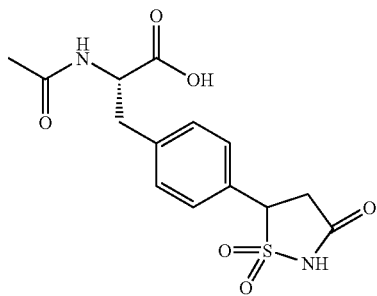

To a solution of (2S)-2-(acetylamino)-3-[4-(1,1-dioxido-3-oxo-2,3-dihydroisothiazol-5-yl)phenyl]propanoic acid (61 mg, 0.18 mmol) in methanol (2.0 mL) was added 5% palladium on carbon (10 mg, 0.1 mmol). The vessel was charged with hydrogen and heated to 60° C. overnight with a hydrogen balloon. Product was filtered through a short plug of silica gel and dried down in vacuo to afford the desired product. LCMS found for $C_{14}H_{17}N_2O_6S$ (M+H)$^+$: m/z=341.0

Step 3. 2S)-2-(acetylamino)-3-[4-(1,1-dioxido-3-oxoisothiazolidin-5-yl)phenyl]-N-(4-phenylbutyl)propanamide To a solution of (2S)-2-[(tert-butoxycarbonyl)amino]-3-[4-(2-tert-butyl-1,1-dioxido-3-oxoisothiazolidin-5-yl)phenyl]propanoic acid (12 mg, 0.035 mmol) in N,N-dimethylformamide (1.0 mL) was added N,N-diisopropylethylamine (0.018 mL, 0.10 mmol) and N,N,N',N'-tetramethyl-O-(7-azabenzotriazol-1-yl)uronium hexafluorophosphate (16 mg, 0.042 mmol) and premixed for 5 minutes. 4-phenylbutan-1-amine (6.3 mg, 0.042 mmol) was added and the mixture was stirred for 2 h. The product was purified by preparative LCMS to afford the final product (6.8 mg, 41%). $^1$H NMR (500 MHz, CD$_3$OD): δ 7.41 (d, J=8.3 Hz, 2H), 7.33 (d, J=8.3 Hz, 2H), 7.25–7.27 (m, 2H), 7.15–7.20 (m, 4H), 5.08–5.12 (m, 1H), 4.54–4.58 (m, 1H), 3.18–3.31 (m, 1H), 3.07–3.17 (m, 3H), 2.93–2.97 (m, 1H), 2.59–2.68 (m, 2H), 1.94 (s, 3H), 1.51–1.59 (m, 2H), 1.41–1.46 (m, 2H); LCMS found for $C_{24}H_{30}N_3O_5S$ (M+H)$^+$: m/z=472.2

Example 4.35

Methyl 2-[4-((2S)-2-(acetylamino)-3-[4-(1,1-dioxido-3-oxoisothiazolidin-5-yl)phenyl]propanoylamino)butoxy]-6-hydroxybenzoate

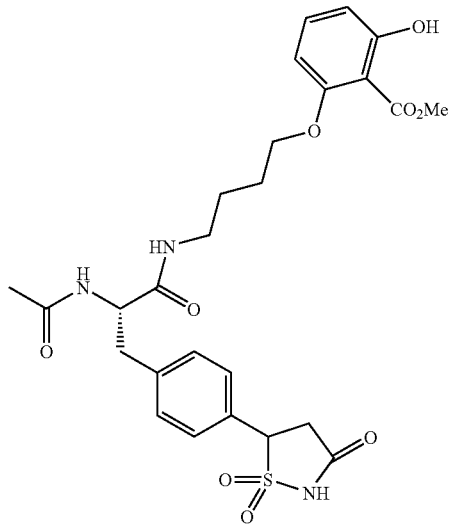

To a solution of (2S)-2-[(tert-butoxycarbonyl)amino]-3-[4-(2-tert-butyl-1,1-dioxido-3-oxoisothiazolidin-5-yl)phenyl]propanoic acid (12 mg, 0.035 mmol) in N,N-dimethylformamide (1.0 mL,) was added N,N-diisopropylethylamine (0.018 mL, 0.10 mmol) and N,N,N',N'-tetramethyl-O-(7-azabenzotriazol-1-yl)uronium hexafluorophosphate (16 mg, 0.042 mmol) and premixed for 5 minutes. Methyl 2-(4-aminobutoxy)-6-hydroxybenzoate hydrochloride (12 mg, 0.042 mmol) was added and the mixture was stirred for 2 h.

The product was purified by preparative LCMS to afford the desired product (4.0 mg, 20%). $^1$H NMR (500 MHz, CD$_3$OD): δ 7.43–7.45 (m, 2H), 7.35–7.36 (m, 2H), 7.27(t, J=8.3 Hz), 6.49–6.53 (m, 2H), 5.12–5.17 (m, 1H), 4.55–4.59 (m, 1H), 3.96–3.99 (m, 2H), 3.90 (s, 3H), 2.89–3.89 (m, 4H), 1.95 (s, 3H), 1.64–1.68 (m, 2H), 1.57–1.61 (m, 2H); LCMS found for C$_{26}$H$_{32}$N$_3$O$_9$S (M+H)$^+$: m/z=562.2.

Example 4.36

(2S)-2-(acetylamino)-N-{(1R)-1-(1H-benzimidazol-2-yl)-2-[4-(1,1-dioxido-3-3-oxoisothiazolidin-5-yl)phenyl]ethyl}-3-phenylpropanamide trifluoroacetate

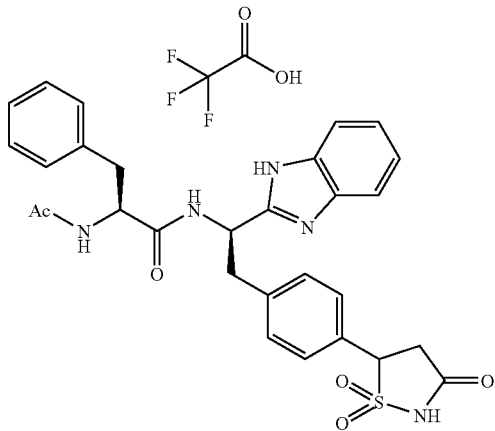

Step 1. (2S)-2-((2S)-2-[(tert-Butoxycarbonyl)amino]-3-phenylpropanoylamino)-3-[4-(1,1-dioxido-3oxo-2,3-dihydroisothiazol-5-yl)phenyl]propanoic acid

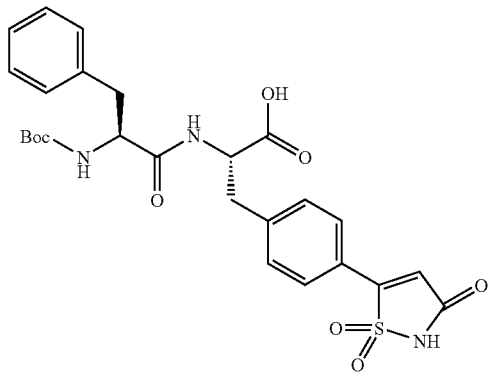

To a solution of N-(tert-butoxycarbonyl)-L-phenylalanine (98.5 mg, 0.371 mmol) in N-methylpyrrolidinone (2.2 mL) was added N,N,N',N'-tetramethyl-O-(7-azabenzotriazol-1-yl)uronium hexafluorophosphate (128 mg, 0.337 mmol) and N,N-diisopropylethylamine (180 μL, 0.001 mol) and pre-mixed for 5 minutes. To the solution was added (2S)-2-amino-3-[4-(1,1-dioxido-3-oxo-2,3-dihydroisothiazol-5-yl)phenyl]propanoic acid (100 mg, 0.338 mmol) with several drops of DMSO to dissolve and the mixture was stirred overnight. The product was purified by preparative LCMS to afford the desired product (96 mg, 52%). $^1$H NMR (400 MHz, CD$_3$OD): δ 7.81 (d, J=8.2, 2H), 7.42 (d, J=8.2, 2H), 7.18–7.36 (m, 5H), 6.98 (s, 1H), 4.70–4.73 (m, 1H), 4.26–4.30 (m, 1H), 3.02–3.13 (m, 3H), 2.71–2.76 (m, 1H), 1.33 (s, 9H); LCMS found for C$_{26}$H$_9$N$_3$O$_8$SNa (M+Na)$^+$: m/z=566.0.

Step 2. tert-Butyl [(1S)-2-({2-[(2-aminophenyl)amino]-1-[4-(1,1-dioxido-3-oxo-2,3dihydroisothiazol-5-yl)benzyl]-2-oxoethyl}amino)-1-benzyl-2-oxoethyl]carbamate

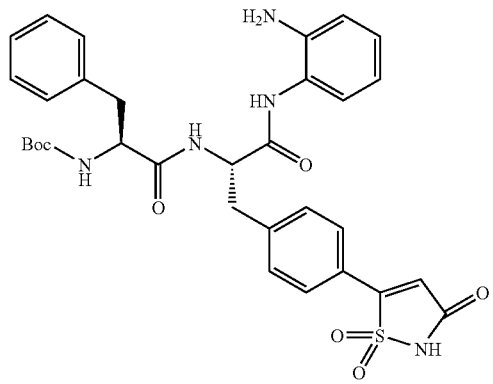

To a solution of (2S)-2-((2S)-2-[(tert-butoxycarbonyl)amino]-3-phenylpropanoylamino)-3-[4-(1,1-dioxido-3-oxo-2,3-dihydroisothiazol-5-yl)phenyl]-propanoic acid (15.0 mg, 0.0276 mmol) in N,N-dimethylformamide (3 mL) was added N,N,N',N'-tetramethyl-O-(7-azabenzotriazol-1-yl) uronium hexafluorophosphate (10.5 mg, 0.027 mmol) and N,N-diisopropylethylamine (24 μL, 0.14 mmol) and pre-mixed for 5 minutes. To the solution was added 1,2-benzenediamine (4.2 mg, 0.04 mmol) and stirred at room temperature overnight. Preformed ester was yellow in color and upon addition of the diamine continued to darken over several minutes. Product was purified by preparative LCMS to afford the desired product (7.3 mg, 42%). LCMS found for C$_{32}$H$_{36}$N$_5$O$_7$S (M+H)$^+$: m/z=634.2.

Step 3. tert-Butyl[(1S)-2-({1-(1H-benzimidazol-2-yl)-2-[4-(1,1-dioxido-3-oxo-2,3-dihydroisothiazol-5-yl)phenyl]ethyl}amino)-1-benzyl-2-oxoethyl]carbamate trifluoroacetate

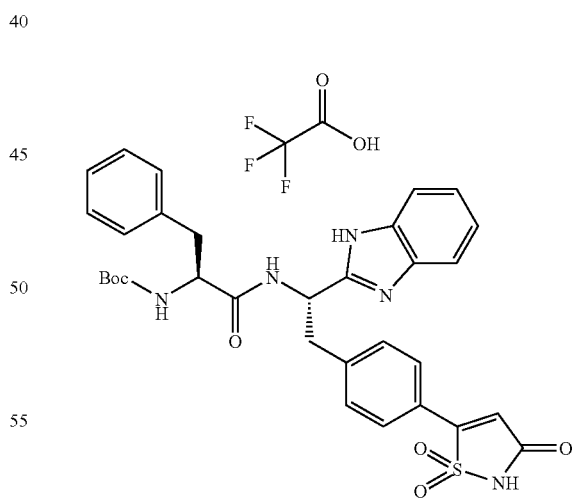

Tert-butyl [(1S)-2-((1S)-2-[(2-aminophenyl)amino]-1-[4-(1,1-dioxido-3-oxo-2,3-dihydroisothiazol-5-yl)benzyl]-2-oxoethylamino)-1-benzyl-2-oxoethyl]carbamate (7.3 mg, 0.012 mmol) was dissolved in glacial acetic acid (1 mL) and heated to 65° C. for 1.5 h. The acetic acid was removed in vacuo and the product was purified by preparative LCMS to afford the desired product (4.6 mg, 65%). LCMS found for C$_{32}$H$_{34}$N$_5$O$_6$S (M+H)$^+$: m/z=616.1.

Step 4. (2S)-2-Amino-N-{1-(1H-benzimidazol-2-yl)-2-[4-(1,1-dioxido-3-oxo-2,3-dihydroisothiazol-5-yl)phenyl]ethyl}-3-phenylpropanamide trifluoroacetate

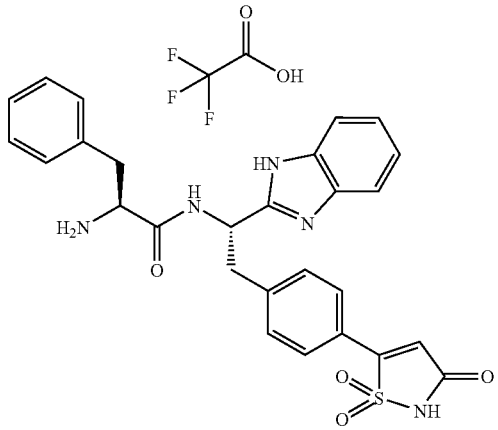

Tert-butyl [(1S)-2-({1-(1H-benzimidazol-2-yl)-2-[4-(1,1-dioxido-3-oxo-2,3-dihydroisothiazol-5-yl)phenyl]ethyl}amino)-1-benzyl-2-oxoethyl]carbamate (10 mg, 0.016 mmol) was dissolved in a mixture of trifluoroacetic acid (1 mL) and methylene chloride (1 mL) and stirred for 45 minutes. The solvent was removed in vacuo. The diastereomers alpha to the benzimidazole were resolved through preparative LCMS purification to yield 5.5 mg (95%) of (2S)-2-amino-N-{(1R)-1-(1H-benzimidazol-2-yl)-2-[4-({1-dioxido-3-oxo-2,3-dihydroisothiazol-5-yl)phenyl]ethyl}-3-phenylpropanamide (Peak A) and 5.5 mg (95%) of (2S)-2-amino-N-{(1S)-1-(1H-benzimidazol-2-yl)-2-[4-(1,1-dioxido-3-oxo-2,3-dihydroisothiazol-5-yl)phenyl]ethyl}-3-phenylpropanamide (Peak B). Peak A: $^1$H NMR (500 MHz, CD$_3$OD): δ 7.84 (d, J=8.4 Hz, 2H), 7.76–7.79 (m, 2H), 7.56–7.59 (m, 2H), 7.43 (d, J=8.4 Hz, 2H), 7.28–7.31 (m, 3H), 7.10–7.13 (m, 2H), 6.93 (s, 1H), 5.59–5.63 (m, 1H), 4.19–4.22 (m, 1H), 3.50–3.55 (m, 1H), 3.32–3.41 (m, 1H), 3.08–3.13 (m, 1H), 2.86–2.91 (m, 1H); LCMS found for C$_{27}$H$_{25}$N$_5$O$_4$S (M+H)$^+$: m/z=516.0 Peak B: $^1$H NMR (500 MHz, CD$_3$OD): δ 7.77–7.82 (m, 4H), 7.62–7.64 (m, 2H), 7.41 (d, J=8.4 Hz, 2H), 6.88–7.01 (m, 6H), 5.61–5.65 (m, 1H), 4.14–4.18 (m, 1H), 3.48–3.53 (m, 2H), 2.97–3.25 (m, 2H); LCMS found for C$_{27}$H$_{26}$N$_5$O$_4$S (M+H)$^+$: m/z=516.0

Step 5. (2S)-2-(acetylamino)-N-{(1S)-1-(1H-benzimidazol-2-yl)-2-[4-(1,1-dioxido-3-oxo-2,3-dihydroisothiazol-5-yl)phenyl]ethyl}-3-phenylpropanamid trifluoroacetate

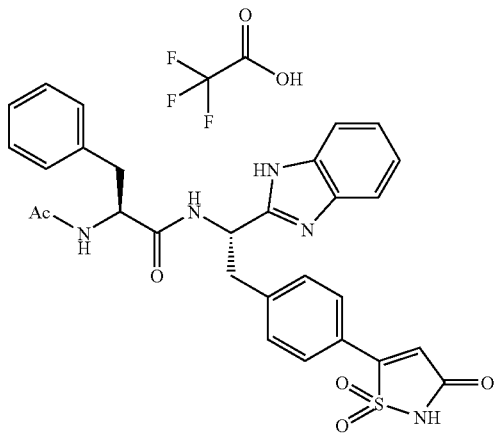

To a solution of (2S)-2-amino-N-{(1R)-1-(1H-benzimidazol-2-yl)-2-[4-(1,1-dioxido-3-oxo-2,3-dihydroisothiazol-5-yl)phenyl]ethyl}-3-phenylpropanamide (5.5 mg, 0.0087 mmol) in methylene chloride (1.0 mL) was added N,N-diisopropylethylamine (4.6 µL, 0.026 mmol) and acetic anhydride (1.1 µL, 0.011 mmol). The mixture was stirred for 1 hour. The reaction was quenched with methanol/water and the solvents were stripped off in vacuo. Product was used directly in the next step without purification. LCMS found for C$_{29}$H$_{28}$N$_5$O$_5$S (M+H)$^+$: m/z=558.1.

Step 6. (2S)-2-(Acetylamino)-N-{(1R)-1-(1H-benzimidazol-2-yl)-2-[4-(1,1-dioxido-3-oxoisothiazolidin-5-yl)phenyl]ethyl}-3-phenylpropanamide To a solution of (2S)-2-(acetylamino)-N-{(1R)-1-(1H-benzimidazol-2-yl)-2-[4-(1,1-dioxido-3-oxo-2,3-dihydroisothiazol-5-yl)phenyl]ethyl}-3-phenylpropanamide (5.0 mg, 0.009 mmol) in methanol (1.5 mL) was added 5% palladium on carbon (3 mg, 0.03 mmol), and mixed for 1.5 h under hydrogen gas (50 psi). Product was filtered and purified by preparative LCMS to afford the final product (1.9 mg, 38%). $^1$H NMR (500 MHz, CD$_3$OD): δ 7.73–7.76 (m, 2H), 7.58–7.60 (m, 2H), 7.43 (d, J=7.0 Hz, 2H), 7.23–7.26 (m, 5H), 7.14–7.16 (m, 2H), 5.42–5.47 (m, 1H), 5.11–5.16 (m, 1H), 4.52–4.56 (m, 1H), 3.40–3.46 (m, 2H), 2.76–2.92 (m, 4H), 1.90 (s, 3H); LCMS found for C$_{29}$H$_{30}$N$_5$O$_5$S (M+H)$^+$: m/z=560.1

Example 4.37

(2S)-2-(Acetylamino)-N-{(1S)-1-(1H-benzimidazol-2-yl)-2-[4-(1,1-dioxido-3-oxoisothiazolidin-5-yl)phenyl]ethyl}-3-phenylpropanamide trifluoroacetate

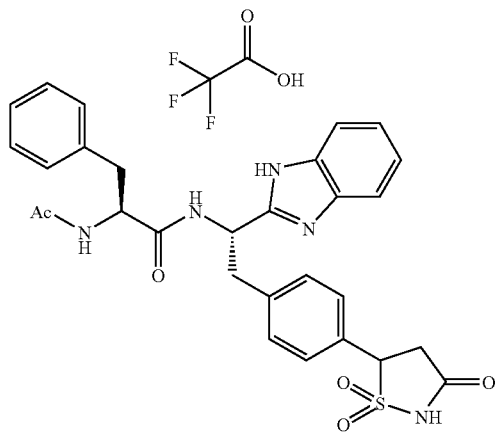

To a solution of (2S)-2-(acetylamino)-N-{(1S)-1-(1H-benzimidazol-2-yl)-2-[4-(1,1-dioxido-3-oxo-2,3-dihydroisothiazol-5-yl)phenyl]ethyl}-3-phenylpropanamide (5.0 mg, 0.0090 mmol) in methanol (1.5 mL) was added 5% palladium on carbon (3 mg, 0.03 mmol), and mixed for 1.5 h under hydrogen gas (50 psi). Product was filtered and purified by preparative LCMS to afford the desired product (2.1 mg, 42%). $^1$H NMR (500 MHz, CD$_3$OD): δ 7.71–7.75 (m, 2H), 7.60–7.63 (m, 2H), 7.41–7.43 (m, 2H), 7.27–7.30 (m, 2H), 7.03–7.08 (m, 5H), 5.44–5.49 (m, 1H), 5.09–5.14 (m, 1H), 4.54–4.58 (m, 1H), 3.43–3.49 (m, 2H), 2.96–3.01 (m, 2H), 2.77–2.86 (m, 2H), 1.89 (s, 3H); LCMS found for C$_{29}$H$_{30}$N$_5$O$_5$S (M+H)$^+$: m/z=560.1.

Example 4.38

Methyl 2-({[(7S,11S)-11-benzyl-7-[4-(1,1-dioxido-3-oxoisothiazolidin-5-yl)benzyl]-6,9,12-trioxo-13-oxa-5,8,10-triazatetradec-1-yl}oxy)-6-hydroxybenzoate

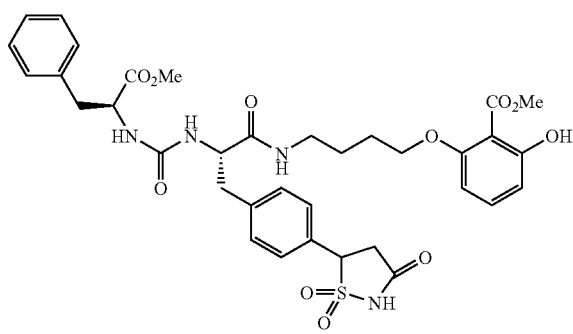

To a solution of methyl 2-[4-({(2S)-2-amino-3-[4-(1,1-dioxido-3-oxoisothiazolidin-5-yl)phenyl]propanoyl}amino)butoxy]-6-hydroxybenzoate (8.0 mg, 0.015 mmol) in N,N-dimethylformamide (0.5 mL) was added N,N-diisopropylethylamine (0.008 mL, 0.045 mmol) and (S)-2-isocyanato-3-phenyl-propionic acid methyl ester (3.5 mg, 0.017 mmol) and stirred overnight at room temperature. The product was purified by preparative LCMS to afford the desired product (1.9 mg, 17%). LCMS found for $C_{35}H_{41}N_4O_{11}S$ $(M+H)^+$: m/z=725.1

Example 4.39

Methyl 2-(4-{[(2S)-3-[4-(1,1-dioxido-3-oxoisothiazolidin-5-yl)phenyl]-2-({[(2S)-5oxopyrrolidin-2-yl]carbonyl}amino)propanoyl]amino}butoxy)-6-hydroxybenzoate

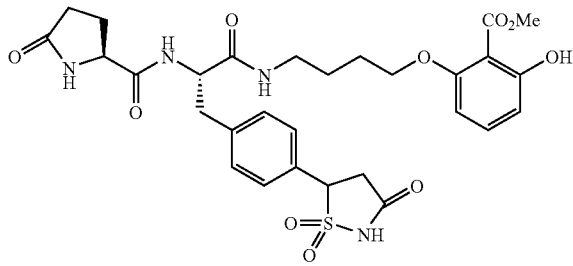

To a solution of (2S)-5-oxopyrrolidine-2-carboxylic acid (2.0 mg, 0.015 mmol) in DMF (0.5 mL) was added N,N,N',N'-tetramethyl-O-(7-azabenzotriazol-1-yl)uronium hexafluorophosphate (5.8 mg, 0.015 mmol) and N,N-diisopropylethylamine (0.008 mL, 0.045 mmol) and premixed for 5 minutes. To the solution was added methyl 2-[4-({(2S)-2-amino-3-[4-(1,1-dioxido-3-oxoisothiazolidin-5-yl)phenyl]propanoyl}amino)-butoxy]-6-hydroxybenzoate (8.0 mg, 0.015 mmol) and stirred overnight at room temperature. The product was purified by preparative LCMS to afford the desired product (1.4 mg). LCMS found for $C_{29}H_{35}N_4O_{10}S$ $(M+H)^+$: m/z=631.0

Example 4.40

Methyl 2-[4-({(2S)-2-{[(2-benzyl-5-oxopyrrolidin-2-yl)carbonyl]amino}-3-[4-(1,1-dioxido-3-oxoisothiazolidin-5-yl)phenyl]propanoyl}amino)butoxy]-6-hydroxybenzoate

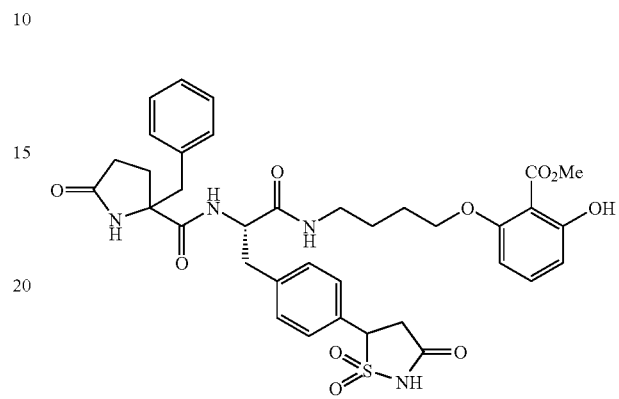

This compound was prepared according to the procedure of Example 4.39 using using 2-benzyl-5-oxopyrrolidine-2-carboxylic acid. LCMS found for $C_{36}H_{41}N_4O_{10}S$ $(M+H)^+$: m/z=721.1

Example 4.41

Methyl 2-[4-({(2S)-3-[4-(1,1-dioxido-3-oxoisothiazolidin-5-yl)phenyl]-2-[(morpholin-4-ylcarbonyl)amino]propanoyl}amino)butoxy]-6-hydroxybenzoate

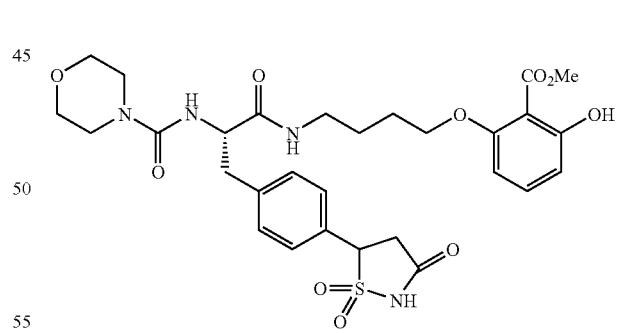

This compound was prepared according to the procedure of Example 4.38 using morpholine-4-carbonyl chloride. $^1$H NMR (500 MHz, $CD_3OD$): δ 7.40–7.43 (m, 2H), 7.32–7.34 (m, 2H), 7.24 (t, J=8.4 Hz, 1H), 6.46–6.51 (m, 2H), 5.10–5.15 (m, 1H), 4.43–4.48 (m, 1H), 3.95–3.98 (m, 2H), 3.87 (s, 3H), 3.52–3.59 (m, 4H), 2.93–3.30 (m, 8H), 1.57–1.68 (m, 4H); LCMS found for $C_{29}H_{37}N_4O_{10}S$ $(M+H)^+$: m/z=633.2

Example 4.42

N-(1S)-1-(1H-benzimidazol-2-yl)-2-[4-(1,1-dioxido-3-oxoisothiazolidin-5-yl)phenyl]ethylacetamide trifluroacetate

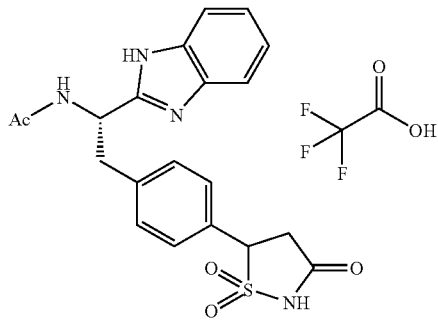

Step 1. tert-Butyl (1S)-1-(1H-benzimidazol-2-yl)-2-[4-(1,1-dioxido-3-oxoisothiazolidin-5-yl)phenyl]ethylcarbamate bis(trifluoroacetate)

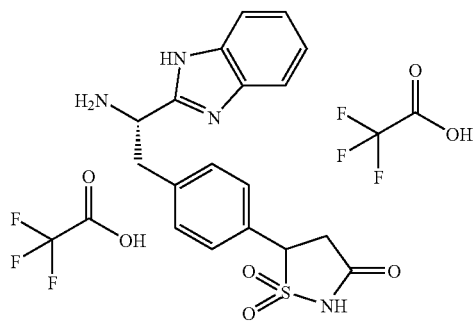

(2S)-2-[(tert-Butoxycarbonyl)amino]-3-[4-(1,1-dioxido-3-oxoisothiazolidin-5-yl)phenyl]propanoic acid (50.0 mg, 0.125 mmol) was preactivated with N,N,N',N'-tetramethyl-O-(7-azabenzotriazol-1-yl)uronium hexafluorophosphate (47 mg, 0.13 mmol) in N,N-dimethylformamide (1 mL). N,N-diisopropylethylamine (66 µL, 0.38 mmol) was added and stirred for 5 minutes. To the solution was then added a slight excess of 1,2-benzenediamine (19 mg, 0.18 mmol) and mixed for 4 h. The solution was dried down in vacuo and purified by preparative LCMS. The purified material was dried down in vacuo, dissolved in acetic acid (1.5 mL) and heated at 65° C. for 1 hour. The acetic acid was removed in vacuo and the material was redissolved in 50% TFA/DCM and stirred for 40 minutes. The TFA was removed in vacuo to afford the desired product (46 mg, 54%). LCMS found for $C_{18}H_{19}N_4O_3S$ (M+H)$^+$: m/z=371.0

Step 2. N-(1S)-1-(1H-Benzimidazol-2-yl)-2-[4-(1,1-dioxido-3-oxoisothiazolidin-5-yl)phenyl]ethylacetamide trifluoroacetate To a solution of tert-butyl (1S)-1-(1H-benzimidazol-2-yl)-2-[4-(1,1-dioxido-3-oxoisothiazolidin-5-yl)phenyl]ethylcarbamate (6.0 mg, 0.016 mmol) in methylene chloride (1.0 mL) with a couple drops of DMF was added N,N-diisopropylethylamine (8.5 µL, 0.05 mmol) and acetic anhydride (1.5 µL, 0.016 mmol) and mixed for 1 hour. The volatiles were removed in vacuo and crude material purified by preparative LCMS to afford the desired product (3.3 mg, 49%). LCMS found for $C_{20}H_{21}N_4O_4S$ (M+H)$^+$: m/z=413.0

Example 4.43

N-(1S)-1-(1H-Benzimidazol-2-yl)-2-[4-(1,1-dioxido-3-oxoisothiazolidin-5-yl)phenyl]ethyl-2-benzyl-5-oxopyrrolidine-2-carboxamide trifluoroacetate

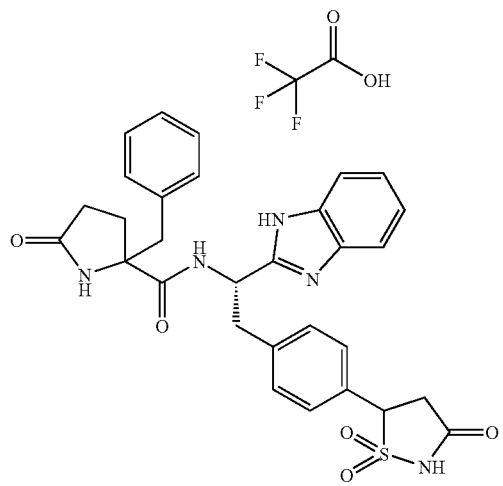

2-Benzyl-5-oxopyrrolidine-2-carboxylic acid (14.8 mg, 0.068 mmol) was preactivated with N,N,N',N'-tetramethyl-O-(7-azabenzotriazol-1-yl)uronium hexafluorophosphate (25.7 mg, 0.0675 mmol) and N,N-diisopropylethylamine (35.3 µL, 0.2 mmol) in N,N-dimethylformamide (2 mL) for 5 minutes. To the solution was added tert-butyl (1S)-1-(1H-benzimidazol-2-yl)-2-[4-(1,1-dioxido-3-oxoisothiazolidin-5-yl)phenyl]ethylcarbamate (25 mg, 0.068 mmol) and mixed overnight. The product was purified by preparative LCMS to afford the desired product (20 mg, 52%). LCMS found for $C_{30}H_{30}N_5O_5S$ (M+H)$^+$: m/z=572.1

Example 4.44

N-[(1S)-2-[4-(1,1-dioxido-3-oxoisothiazolidin-5-yl)phenyl]-1-(6-methoxy-1H-benzimidazol-2-yl)ethyl]morpholine-4-carboxamide trifluoroacetate

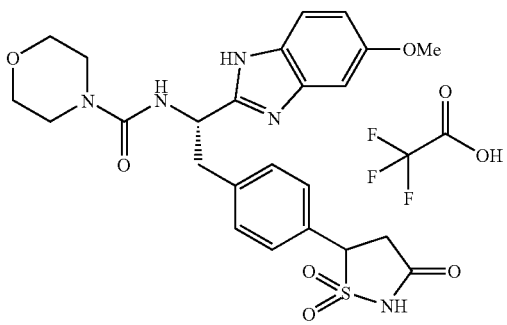

This compound was prepared according to the procedure of Example 4.42 using 4-methoxybenzene-1,2-diamine and morpholine-4-carbonyl chloride. LCMS found for $C_{24}H_{28}N_5O_6S$ (M+H)⁺: m/z=514.1

Example 4.45

N-{(1S)-1-(6-chloro-1H-benzimidazol-2-yl)-2-[4-(1,1-dioxido-3-oxoisothiazolidin-5-yl)phenyl]ethyl}morpholine-4-carboxamide trifluoroacetate

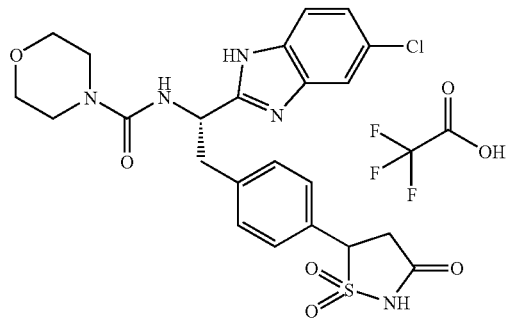

This compound was prepared according to the procedure of Example 4.42 using 4-chlorobenzene-1,2-diamine and morpholine-4-carbonyl chloride. LCMS found for $C_{23}H_{25}ClN_5O_5S$ (M+H)⁺: m/z=518.0

Example 4.46

N-[(1S)-2-[4-(1,1-dioxido-3-oxoisothiazolidin-5-yl)phenyl]-1-(7-methyl-1H-benzimidazol-2-yl)ethyl]morpholine-4-carboxamide trifluoroacetate

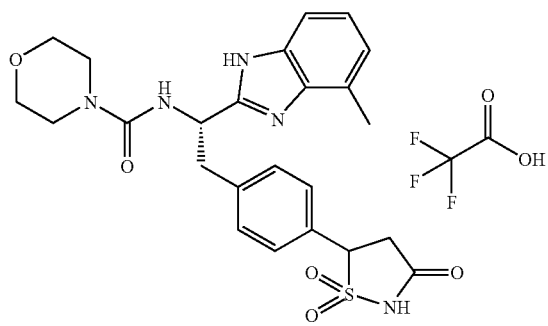

This compound was prepared according to the procedure of Example 4.42 using 3-methylbenzene-1,2-diamine and morpholine-4-carbonyl chloride. LCMS found for $C_{24}H_{28}N_5O_5S$ (M+H)⁺: m/z=498.1

Example 4.47A

Methyl (2R)-2-[({2-[4-(1,1-dioxido-3-oxoisothiazolidin-5-yl)phenyl]-1-(3H-imidazo[4,5-c]pyridin-2-yl)ethyl]amino}carbonyl)amino]-3-phenylpropanoate trifluoroacetate

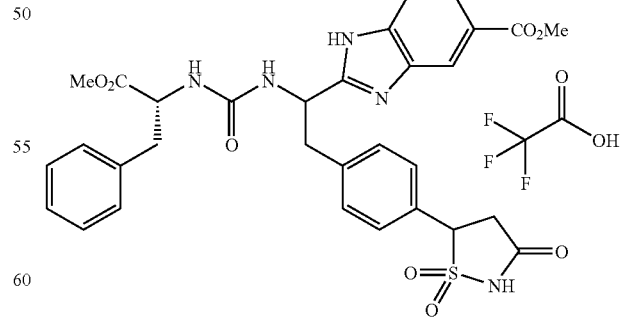

This compound was prepared according to the procedure of Example 4.42 using pyridine-3,4-diamine and (S)-2-isocyanato-3-phenyl-propionic acid methyl ester. LCMS found for $C_{28}H_{29}N_6O_6S$ (M+H)⁺: m/z=577.1

Example 4.47B

Methyl 2-{1-[(1[(1R)-1-benzyl-2-methoxy-2-oxoethyl]amino}carbonyl)amino]-2-[4-(1,1-dioxido-3-oxoisothiazolidin-5-yl)phenyl]ethyl}-1H-benzimidazole-6-carboxylate trifluoroacetate This compound was prepared according to the procedure of Example 4.42 using methyl 3,4-diaminobenzoate and (S)-2-isocyanato-3-phenyl-propionic acid methyl ester. LCMS found for $C_{31}H_{32}N_5O_8S$ (M+H)⁺: m/z=634.1

Example 4.48

Methyl (2S)-2-[((1S)-1-(1H-benzimidazol-2-yl)-2-[4-(1,1-dioxido-3-oxoisothiazolidin-5-yl)phenyl]ethylamino)carbonyl]amino-3-phenylpropanoate trifluoroacetate

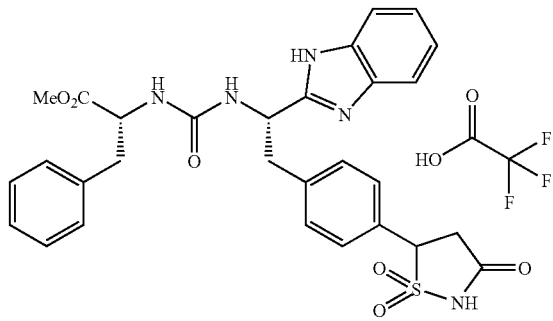

To a solution of tert-butyl (1S)-1-(1H-benzimidazol-2-yl)-2-[4-(1,1-dioxido-3-oxoisothiazolidin-5-yl)phenyl]ethylcarbamate (10.0 mg, 0.0270 mmol) in methylene chloride (1 mL) with a few drops of DMF was added N,N-diisopropylethylamine (14 μL, 0.081 mmol) and (S)-2-isocyanato-3-phenyl-propionic acid methyl ester (5.5 mg, 0.027 mmol) and stirred at room temperature for 2 h. The solvent was removed under vacuum and the product was purified by preparative LCMS to afford the desired product (4.1 mg, 26%). $^1$H NMR (500 MHz, CD$_3$OD): δ 7.69–7.72 (m, 2H), 7.56–7.59 (m, 2H), 7.40 (d, J=8.0 Hz, 2H), 7.13–7.28 (m, 7H), 5.20–5.26 (m, 1H), 5.07–5.12 (m, 1H), 4.47–4.50 (m, 1H), 3.66 (s, 3H), 3.32–3.45 (m, 2H), 2.84–3.11 (m, 4H); LCMS found for C$_{29}$H$_{30}$N$_5$O$_6$S (M+H)$^+$: m/z=576.1

Example 4.49

Methyl 2-{4-[({2-[4-(1,1-dioxido-3-oxoisothiazolidin-5-yl)benzyl]-5-oxopyrrolidin-2-yl}carbonyl)amino]butoxy}-6-hydroxybenzoate

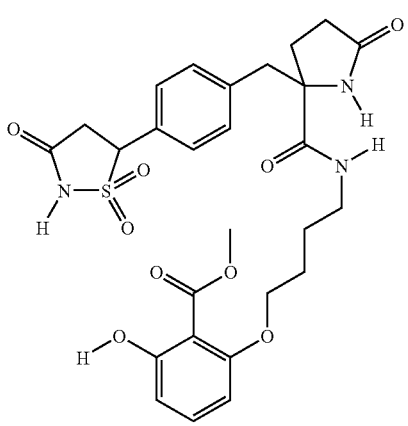

Step 1. Synthesis of ethyl 5-oxo-2-[4-(4,4,5,5-tetramethyl-1,3,2-dioxaborolan-2-yl)benzyl]pyrrolidine-2-carboxylate

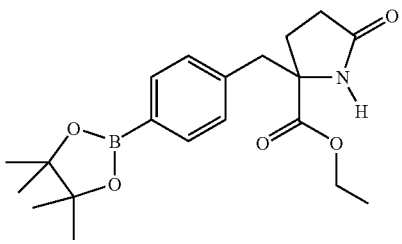

Ethyl (2S)-5-oxopyrrolidine-2-carboxylate (0.200 g, 1.27 mmol) was azeotroped three times from toluene (25 mL each), dissolved in tetrahydrofuran (4.4 mL) and cooled to −78° C. 1 M lithium hexamethyldisilazide in tetrahydrofuran (1 M, 3.75 mL) was added via syringe and the colorless solution was stirred 30 min before addition of 2-[4-(bromomethyl)phenyl]-4,4,5,5-tetramethyl-1,3,2-dioxaborolane (0.4 g, 1.0 mmol) in tetrahydrofuran (2.0 mL). The slightly yellow solution was stirred at −78° C. for 30 min and then at −10° C. for 1 h and warmed to rt for an additional 1 h before it was cooled back to −78° C. and quenched with acetic acid (1.00 mL, 17.6 mmol). Evaporation and purification by preparative LCMS gave the desired product as a colorless glass, (296 mg, 62%). $^1$H NMR (400 MHz, CD$_3$OD): δ 7.67 (d, J=7.4 Hz, 2H), 7.22 (d, J=7.4 Hz, 2H), 4.20 (q, J=7.2 Hz, 2H), 3.08 (d, J=13.0 Hz, 1H), 3.05 (d, J=13.0 Hz, 1H), 2.35 (m, 1H), 2.23 (m, 1H), 2.15 (m, 1H), 1.79 (m, 1H), 1.35 (s, 12H), 1.25 (t, J=7.0 Hz, 3H); LCMS found for C$_{20}$H$_{29}$BNO$_5$ (M+H)$^+$: m/z=374.

Step 2. Synthesis of ethyl 5-oxo-2-[4-(4,4,5,5-tetramethyl-1,3,2-dioxaborolan-2-yl)benzyl]pyrrolidine-2-carboxylate

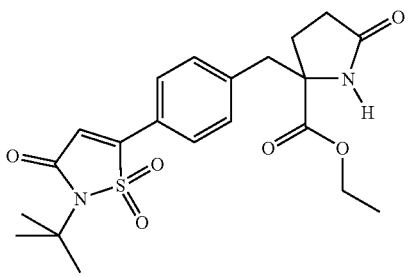

Ethyl 5-oxo-2-[4-(4,4,5,5-tetramethyl-1,3,2-dioxaborolan-2-yl)benzyl]pyrrolidine-2-carboxylate (5.10 g, 13.7 mmol), 2-tert-butyl-5-chloro-1,1-dioxo-1,2-dihydro-1λ$^6$-isothiazol-3-one (6.11 g, 27.3 mmol), potassium carbonate (9.44 g, 68.3 mmol), and 1,4-dioxane (42.6 mL) were combined and degassed with nitrogen gas for ten min before [1,1'-bis(diphenylphosphino)ferrocene]dichloropalladium (II), complex with dichloromethane (1:1) (2.23 g, 2.73 mmol) was added and degassing continued for another ten min. The orange suspension was heated to 80° C. overnight. Purification by flash chromatography on silica gel followed by preparative LCMS gave the desired product as a colorless glass (1.9 g, 32%). $^1$H NMR (400 MHz, CDCl$_3$): δ 7.81 (d, J=8.2 Hz, 2H), 7.42 (d, J=8.2 Hz, 2H), 7.03 (s, 1H), 4.20 (q, J=7.2 Hz, 2H), 3.22 (d, J=13.7 Hz, 1H), 3.17 (d, J=13.7 Hz, 1H), 2.38 (m, 1H), 2.21 (m, 2H), 1.95 (m, 1H), 1.65 (s, 9H), 1.25 (t, J=7.1 Hz, 3H); LCMS found for $C_{21}H_{27}N_2O_6S$ $(M+H)^+$: m/z=435.

Step 3. Synthesis of ethyl 2-[4-(2-tert-butyl-1,1-dioxido-3-oxoisothiazolidin-5-yl)benzyl]-5-oxopyrrolidine-2-carboxylate

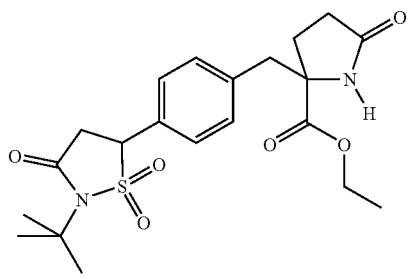

Ethyl 2-[4-(2-tert-butyl-1,1-dioxido-3-oxo-2,3-dihydroisothiazol-5-yl)benzyl]-5-oxopyrrolidine-2-carboxylate (24 mg, 0.055 mmol) was dissolved in ethanol (2.5 mL) and 10% Pd/C (10 mg, 0.09 mmol) was added. Hydrogen was added to a Parr shaker (58 psi) and shaken overnight. Purification by preparative LCMS gave the desired product as a colorless glass (23 mg, 95%). $^1$H NMR (400 MHz, CD$_3$OD): δ 7.42 (d, J=8.2 Hz, 2H), 7.32 (d, J=8.2 Hz, 2H), 5.12 (t, J=8.9 Hz, 1H), 4.20 (q, J=7.2 Hz, 2H), 3.30 (m, 2H), 3.22 (d, J=13.6 Hz, 1H), 3.13 (d, J=13.6 Hz, 1H), 2.38 (m, 1H), 2.21 (m, 2H), 1.92 (m, 1H), 1.61 (s, 9H), 1.28 (t, J=7.0 Hz, 3H); LCMS found for $C_{21}H_{29}N_2O_6S$ $(M+H)^+$: m/z=437.

Step 4. Synthesis of ethyl 2-[4-(1,1-dioxido-3-oxoisothiazolidin-5-yl)benzyl]-5-oxopyrrolidine-2-carboxylate

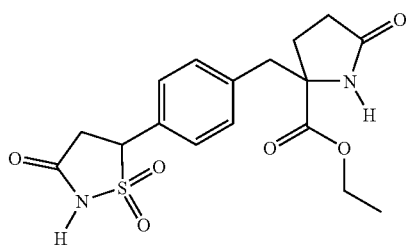

Ethyl 2-[4-(2-tert-butyl-1,1-dioxido-3-oxoisothiazolidin-5-yl)benzyl]-5-oxopyrrolidine-2-carboxylate (34 mg, 0.078 mmol) was stirred in trifluoroacetic acid (3.0 mL, 40.0 mmol) in a small microwave tube and heated to 130° C. for 60 seconds. Trifluoroacetic acid was evaporated and the residue was purified by preparative LCMS to give the desired compound as a white solid (25 mg, 84%). $^1$H NMR (400 MHz, CD$_3$OD): δ 7.45 (d, J=8.2 Hz, 2H), 7.32 (d, J=8.2 Hz, 2H), 5.17 (t, J=8.9 Hz, 1H), 4.20 (q, J=7.2 Hz, 2H), 3.30 (m, 2H), 3.20 (d, J=13.6 Hz, 1H), 3.10 (d, J=13.6 Hz, 1H), 2.38 (m, 1H), 2.21 (m, 2H), 1.95 (m, 1H), 1.23 (t, J=7.0 Hz, 3H); LCMS found for $C_{17}H_{21}N_2O_6S$ $(M+H)^+$: m/z=381.

Step 5. Synthesis of 2-[4-(1,1-dioxido-3-oxoisothiazolidin-5-yl)benzyl]-5-oxopyrrolidine-2-carboxylic acid

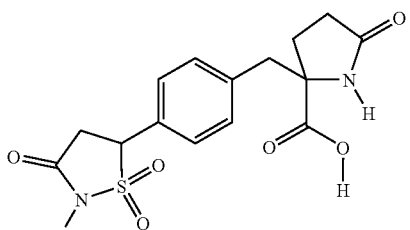

Ethyl 2-[4-(1,1-dioxido-3-oxoisothiazolidin-5-yl)benzyl]-5-oxopyrrolidine-2-carboxylate (30.0 mg, 0.0631 mmol) lithium hydroxide (9.06 mg, 0.378 mmol) was stirred in methanol (200 µL, 0.005 mmol) tetrahydrofuran (800 µL) and water (200 µL, 0.01 mmol). The solution was heated to 120° C. for 1 min in a microwave. The mixture was acidified with acetic acid and purified by preparative LCMS to give the desired compound as a white powder, (18.9 mg, 85%). $^1$H NMR (400 MHz, CD$_3$OD): δ 7.42 (d, J=8.0 Hz, 2H), 7.37 (d, J=8.0 Hz, 2H), 5.17 (t, J=8.5 Hz, 1H), 3.30 (m, 2H), 3.21 (d, J=13.9 Hz, 1H), 3.10 (d, J=13.9 Hz, 1H), 2.39 (m, 1H), 2.21 (m, 2H), 1.90 (m, 1H); LCMS found for $C_{15}H_{17}N_2O_6S$ $(M+H)^+$: m/z=353.

Step 6. Synthesis of methyl 2-{4-[({2-[4-(1,1-dioxido-3-oxoisothiazolidin-5-yl)benzyl]-5oxopyrrolidin-2-yl}carbonyl)amino]butoxy}-6-hydroxybenzoate 2-[4-(1,1-dioxido-3-oxoisothiazolidin-5-yl)benzyl]-5-oxopyrrolidine-2-carboxylic acid (4.5 mg, 0.013 mmol) was stirred in methylene chloride (150 µL) with N-(3-dimethylaminopropyl)-N'-ethylcarbodiimide hydrochloride (2.7 mg, 0.014 mmol), 1-hydroxybenzotriazole hydrate (1.96 mg, 0.0128 mmol) and N,N-diisopropylethylamine (4.7 µL, 0.027 mmol) for 20 min before transfer to a solution of an appropriate amine (0.0128 mmol) in dichloromethane (150 µL). The amines that were hydrochloride salts were neutralized with an additional equiv of N,N-diisopropylethylamine. The salicylate amine was coupled using HATU as the coupling reagent instead of EDC/HOBt. The reactions were stirred at rt overnight. Methanol was then added and the crude mixtures were purified directly on preparative LCMS to afford a white powder (3.5 mg, 31%), $^1$H-NMR (400 MHz, CD$_3$OD): δ 7.42 (m, 2H), 7.33 (m, 2H), 7.22 (m, 1H), 6.50 (m, 2H), 5.17 (m, 1H), 4.00 (m, 2H), 3.87 (s, 3H), 3.30 (m, 2H), 3.01 (d, J=13.5 Hz, 1H), 2.98 (d, J=13.5 Hz, 1H), 2.32–2.18 (m, 4H), 2.03–1.90 (m, 2H), 1.68 (m, 4H); LCMS found for $C_{27}H_{32}N_3O_9S$ $(M+H)^+$: m/z=574.

Example 4.50

N-[4-(Aminosulfonyl)benzyl]-2-[4-(1,1-dioxido-3-oxoisothiazolidin-5-yl)benzyl]-5-oxopyrrolidine-2-carboxamide

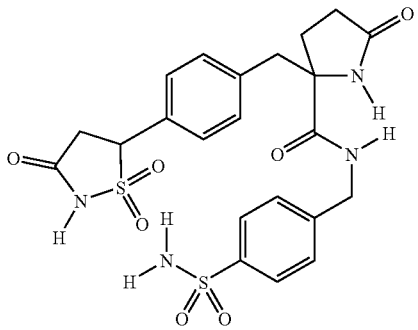

Title compound was prepared according to a procedure analgous to Example 4.49 using 4-(aminomethyl)benzenesulfonamide hydrochloride. White solid (4.6 mg, 63%), $^1$H-NMR (400 MHz, CD$_3$OD): δ 7.82 (d, J=8.2 Hz, 2H), 7.38 (m, 4H), 7.22 (m, 2H), 5.17 (t, J=8.7 Hz, 1H), 4.60–4.30 (m, 2H), 3.30 (m, 2H), 3.03 (d, J=13.4 Hz, 1H), 3.00 (d, J=13.4 Hz, 1H), 2.30 (m, 1H), 2.21 (m, 2H), 1.95 (m, 1H). LCMS found for C$_{22}$H$_{25}$N$_4$O$_7$S$_2$ (M+H)$^+$: m/z=521.

Example 4.51

5-(4-{[2-(1H-benzimidazol-2-yl)-5-oxopyrrolidin-2-yl]methyl}phenyl)isothiazolidin-3-one 1,1-dioxide trifluoroacetate

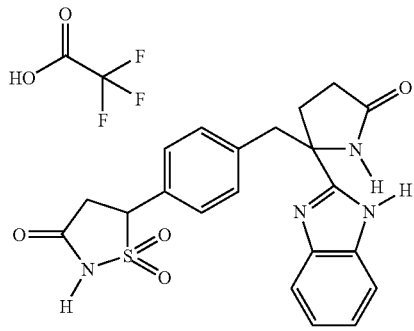

Step 1. Synthesis of N-(2-aminophenyl)-2-[4-(1,1-dioxido-3-oxoisothiazolidin-5-yl)benzyl]-5-oxopyrrolidine-2-carboxamide

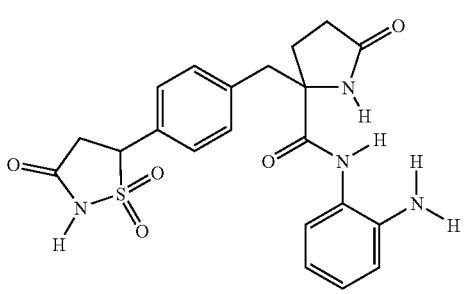

Title compound was prepared according to a procedure analogous to Example 4.49 using 1,2-benzenediamine. White solid, (8.5 mg, 62%), $^1$H NMR (400 MHz, CD$_3$OD): δ 7.48 (d, J=8.2 Hz, 2H), 7.35 (d, J=8.2 Hz, 2H), 7.25 (t, J=7.5 Hz, 1H), 7.15 (d, J=8.8 Hz, 1H), 7.10 (d, J=7.5 Hz, 1H), 7.02 (t, J=7.6 Hz, 1H), 5.19 (m, 1H), 3.40–3.18 (m, 2H), 3.16 (m, 2H), 2.55 (m, 1H), 2.40 (m, 1H), 2.30 (m, 1H), 2.02 (m, 1H); LCMS found for C$_{21}$H$_{22}$N$_4$O$_5$S (M+H)$^+$: m/z=443.

Step 2. 5-(4-{[2-(1H-Benzimidazol-2-yl)-5-oxopyrrolidin-2-yl]methyl}phenyl)isothiazolidin-3-one 1,1-dioxide N-(2-aminophenyl)-2-[4-(1,1-dioxido-3-oxoisothiazolidin-5-yl)benzyl]-5-oxopyrrolidine-2-carboxamide (6.6 mg, 0.01 mmol) was stirred in acetic acid (0.5 mL) and heated to 120° C. for 60 seconds in a microwave. Purification by preparative LCMS gave the title compound as a white solid, (2.5 mg, 42%), $^1$H NMR (400 MHz, CD$_3$OD): δ 7.80 (m, 2H), 7.62 (m, 2H), 7.50 (d, J=8.8 Hz, 2H), 7.38 (d, J=8.3 Hz, 2H, 5.20 (m, 1H), 3.50 (m, 2H), 2.65 (m, 1H), 2.50 (m, 1H), 2.35 (m, 1H), 2.26 (m, 1H), 2.03 (m, 1H), 1.70 (m, 1H); LCMS found for C$_{21}$H$_{20}$N$_2$O$_4$S (M+H)$^+$: m/z=425.

Example 4.52

Methyl 2-4-[(2-[4-(1,1-dioxido-3-oxoisothiazolidin-5-yl)benzyl]-5-oxopyrrolidin-2-ylmethyl)amino]butoxy-6-hydroxybenzoate trifluoroacetate

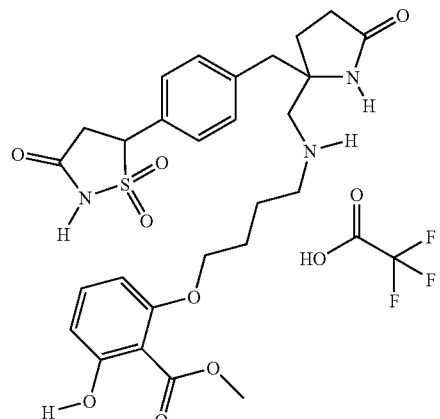

Step 1. Synthesis of 2-tert-butyl-5-(4-[2-(hydroxymethyl)-5-oxopyrrolidin-2-yl]methylphenyl)isothiazolidin-3-one 1,1-dioxide

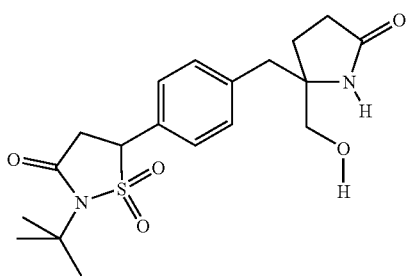

Ethyl 2-benzyl-5-oxopyrrolidine-2-carboxylate (1.70 g, 3.91 mmol) was stirred in tetrahydrofuran (50 mL) at −15° C. while 2 M LiBH$_4$ in tetrahydrofuran (4 mL) was added.

The reaction was stirred at 0° C. for 75 minutes before the mixture was cooled back to −15° C. and quenched with acetic acid (10 mL) followed by methanol (20 mL). Evaporation and purification on preparative LCMS gave the desired product as a white powder (850 mg, 55%). $^1$H NMR (400 MHz, CD$_3$OD): δ 7.40 (m, 4H), 5.10 (t, J=9.1 Hz, 1H), 3.50 (m, 2H), 3.30 (m, 2H), 2.92 (d, J=13.4 Hz, 1H), 2.85 (d, J=13.4 Hz, 1H), 2.38 (m, 1H), 2.21 (m, 2H), 1.95 (m, 1H), 1.61 (s, 9H); LCMS found for C$_{19}$H$_{27}$N$_2$O$_5$S (M+H)$^+$: m/z=395.

Step 2. Synthesis of 2-[4-(2-tert-butyl-1,1-dioxido-3-oxoisothiazolidin-5-yl)benzyl]-5-oxopyrrolidine-2-carbaldehyde

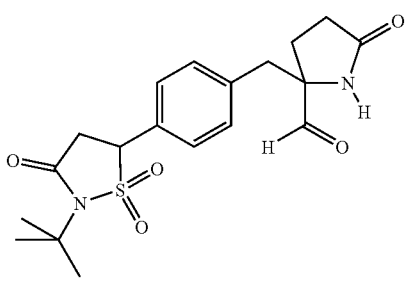

Oxalyl chloride (74.3 μL, 0.878 mmol) was stirred in methylene chloride (2.6 mL), and the resulting solution was cooled to −78° C., whereupon dimethyl sulfoxide (142 μL, 2.00 mmol) was added. Then to the mixture, a solution of 2-tert-butyl-5-(4-[2-(hydroxymethyl)-5-oxopyrrolidin-2-yl]methylphenyl)isothiazolidin-3-one 1,1-dioxide (105 mg, 0.266 mmol) in dichloromethane (2.0 mL) was added dropwise, within five minutes. The mixture was stirred for fifteen minutes at −78° C.; after addition of N,N-diisopropylethylamine (695 μL, 3.99 mmol) the mixture was allowed to reach room temperature, and poured into water (1 mL). The aqueous phase was extracted twice with dichloromethane (5 mL) and the combined extracts were evaporated to give the crude aldehyde as a yellow oil. Purification on the preparative LCMS gave the desired aldehyde as a tan solid (30 mg, 30%). $^1$H NMR (400 MHz, CDCl$_3$): δ 9.60 (s, 1H), 7.38 (m, 2H), 7.25 (m, 2H), 6.70 (s, 1H), 4.76 (m, 1H), 3.17 (m, 1H), 2.92 (m, 1H), 2.30 (m, 2H), 2.18 (m, 2H), 1.65 (s, 9H); LCMS found for C$_{19}$H$_{25}$N$_2$O$_5$S (M+H)$^+$: m/z=393

Step 3. Synthesis of 2-[4-(1,1-dioxido-3-oxoisothiazolidin-5-yl)benzyl]-5-oxopyrrolidine-2-carbaldehyde

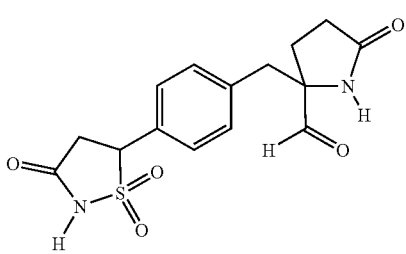

2-[4-(2-tert-butyl-1,1-dioxido-3-oxoisothiazolidin-5-yl)benzyl]-5-oxopyrrolidine-2-carbaldehyde (4.5 mg, 0.011 mmol) was stirred in trifluoroacetic acid (1 mL, 10 mmol) in a small microwave tube and heated to 130° C. for 60 seconds. The mixture was evaporated and used directly. LCMS found for C$_{15}$H$_{17}$N$_2$O$_5$S (M+H)$^+$: m/z=337.

Step 4. Synthesis of methyl 2-4-[(2-[4-(1,1-dioxido-3-oxoisothiazolidin-5-yl)benzyl]-5-oxopyrrolidin-2-ylmethyl)amino]butoxy-6-hydroxybenzoate trifluoroacetate Methyl 2-(4-aminobutoxy)-6-hydroxybenzoate hydrochloride (3.8 mg, 0.014 mmol) 2-[4-(1,1-dioxido-3-oxoisothiazolidin-5-yl)benzyl]-5-oxopyrrolidine-2-carbaldehyde (2.3 mg, 0.0068 mmol), DIEA (6 μL, 0.03 mmol) and acetic acid (50 μL) were stirred in THF at rt. Sodium triacetoxyborohydride (5.80 mg, 0.0274 mmol) was added and the mixture stirred at 50° C. for 1 h. Methanol was added and the mixture was purified by preparative LCMS to give the desired compound as a white solid (1.0 mg, 26%) LCMS found for C$_{27}$H$_{34}$N$_3$O$_8$S (M+H)$^+$: m/z=560.

Example 4.53

5-(4-[(biphenyl-4-ylmethyl)(pyridin-2-ylmethyl)amino]methylphenyl)isothiazolidin-3-one 1,1-dioxide trifluoroacetate

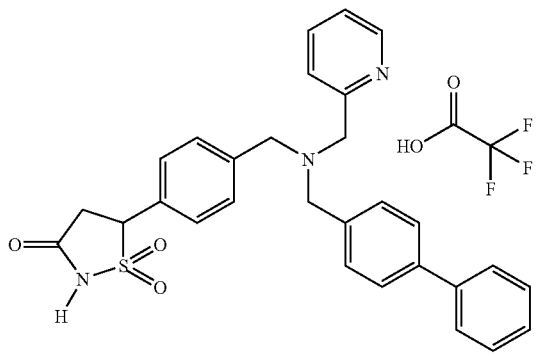

1-Biphenyl-4-yl-N-(pyridin-2-ylmethyl)methanamine (10 mg, 0.05 mmol), 4-(1,1-dioxido-3-oxoisothiazolidin-5-yl)benzaldehyde (6 mg, 0.02 mmol) were stirred in tetrahydrofuran at 50° C. overnight. Sodium triacetoxyborohydride (10 mg, 0.05 mmol) was added and the mixture stirred at rt for 1 h. Acetic acid (10 μL) was added and the mixture was stirred for an additional 1 h. Tetrahydrofuran was evaporated and the mixture was purified on the preparative LCMS to give the desired compound as a white powder (4.0 mg, 29%) $^1$H NMR (400 MHz, CD3OD): δ 8.64 (s, 1H), 8.56 (d, J=5.7 Hz, 1H), 8.38 (d, J=8.2 Hz, 1H), 7.78 (dd, J=5.9 Hz, J=8.1 Hz, 1H), 7.61 (m, 4H), 7.46 (m, 8H), 7.23 (m, 1H), 5.17 (t, J=8.7 Hz, 1H), 4.00 (m, 6H), 3.30 (m, 2H). LCMS found for C$_{29}$H$_{27}$N$_3$O$_3$S (M+H)$^+$: m/z=498.

Example 4.54

N-[4-(1,1-dioxido-3-oxoisothiazolidin-5-yl)benzyl]-
N-[2-(4-phenoxyphenyl)ethyl]isonicotinamide

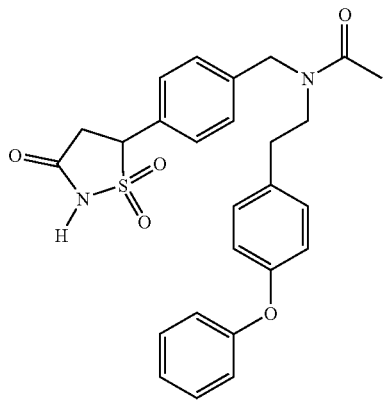

5-[4-([2-(4-phenoxyphenyl)ethyl]aminomethyl)phenyl] isothiazolidin-3-one 1,1-dioxide trifluoroacetate of (6.5 mg, 0.012 mmol) was dissolved in N-methyl-pyrrolidinone (100 μL) with N,N-diisopropylethylamine (10 μL). A solution of acetic anhydride in N-methyl-pyrrolidinone (100 mL) was added and the mixture stirred for 1 h. The mixture was purified by preparative LCMS to give the desired product. White solid, (5.0 mg, 87%). LCMS found for $C_{26}H_{27}N_2O_5S$ (M+H)$^+$: m/z=479.

Example 4.55

N-[4-(1,1-dioxido-3-oxoisothiazolidin-5-yl)benzyl]-
N-[2-(4-phenoxyphenyl)ethyl]-N'-phenylurea

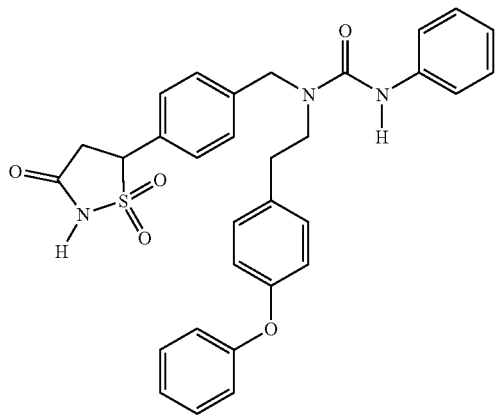

5-[4-([2-(4-Phenoxyphenyl)ethyl]aminomethyl)phenyl] isothiazolidin-3one 1,1-dioxide trifluoroacetate (6.5 mg, 0.012 mmol) was dissolved in N-methyl-pyrrolidinone (100 μL) with N,N-diisopropylethylamine (10 μL). A solution of phenyhlisocyanate in N-methyl-pyrrolidinone (100 μL) was added and the mixture stirred for 1 h. The mixture was purified by preparative LCMS to give the desired product. White solid, (5.0 mg, 74%). LCMS found for $C_{31}H_{29}N_3O_5S$ (M+H)$^+$: m/z=556.

Example 4.56

N'-(tert-butyl)-N-[4-(1,1-dioxido-3-oxoisothiazolidin-5-yl)benzyl]-N-[2-(4-phenoxyphenyl)ethyl]urea

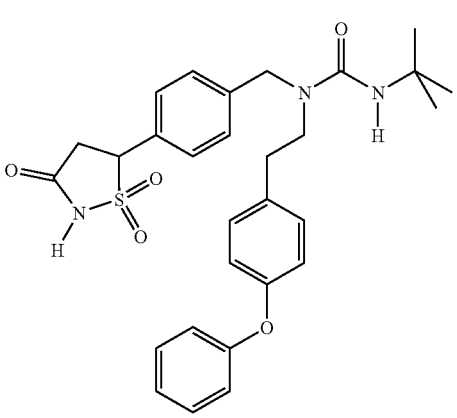

5-[4-([2-(4-Phenoxyphenyl)ethyl]aminomethyl)phenyl] isothiazolidin-3-one 1,1-dioxide trifluoroacetate (6.5 mg, 0.012 mmol) was dissolved in N-methyl-pyrrolidinone (100 μL) with N,N-diisopropylethylamine (10 μL). A solution of t-butylisocyanate in N-methyl-pyrrolidinone (100 μL) was added and the mixture stirred for 1 h. The mixture was purified by preparative LCMS to give the desired product. White solid, (6.5 mg, 100%). LCMS found for $C_{22}H_{21}N_2O_5S$ (M+H)$^+$: m/z=536.

Example 4.57

N-[4-(1,1-dioxido-3-oxoisothiazolidin-5-yl)benzyl]-
N-[2-(4-phenoxyphenyl)ethyl]urea

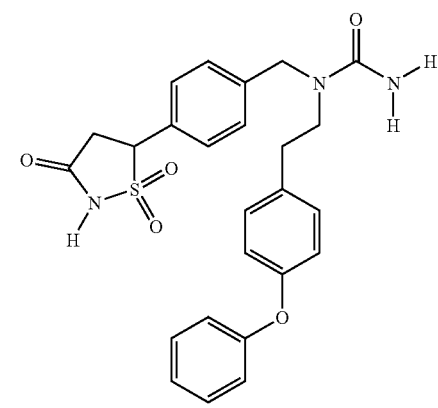

N'-(tert-butyl)-N-[4-(1,1-dioxido-3-oxoisothiazolidin-5-yl)benzyl]-N-[2-(4-phenoxyphenyl)ethyl]urea (4.5 mg, 0.008 mmol) was heated in trifluoroacetic acid (1 mL) at 100° C. for 5 min in a microwave. The mixture was concentrated and purified by preparative LCMS to give the title compound as a white solid, (3.0 mg, 75%). LCMS found for $C_{25}H_{26}N_3O_5S$ (M+H)$^+$: m/z=480.

Example 4.58

5-(4-{[(4-phenoxyphenyl)amino]methyl}phenyl)isothiazolidin-3-one 1,1-dioxide trifluoroacetate

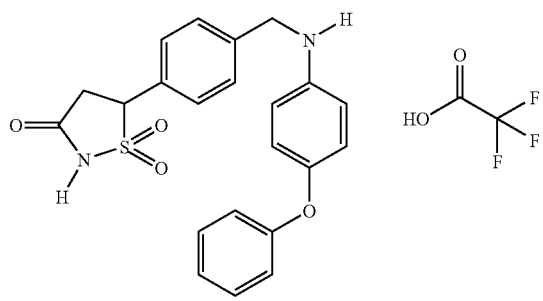

To 4-(1,1-dioxido-3-oxo-2,3-dihydroisothiazol-5-yl)benzaldehyde (6.2 mg, 0.026 mmol) in methanol (300 μL, 7.0 mmol), 4-phenoxyaniline (12 mg, 0.13 mmol) was added. The solution was heated to 50° C. for 16 h. The cooled orange solution was concentrated to an orange glass and redissolved in tetrahydrofuran (250 μL) and lithium borohydride in tetrahydrofuran (2 M, 75 μL) was added with stirring. The reaction was heated to 50° C. for 2 h. All reactions were quenched with a few drops of 1 N HCl and 2 mL methanol. The mixture was purified by preparative LCMS to give the desired product. (5.1 mg, 38%). LCMS found for $C_{22}H_{20}N_2O_4S$ (M+H)$^+$: m/z=409.

Example 4.59

(4-{[4-(1,1-dioxido-3-oxo-2,3-dihydroisothiazol-5-yl)benzyl]amino}phenyl)acetic acid trifluoroacetate

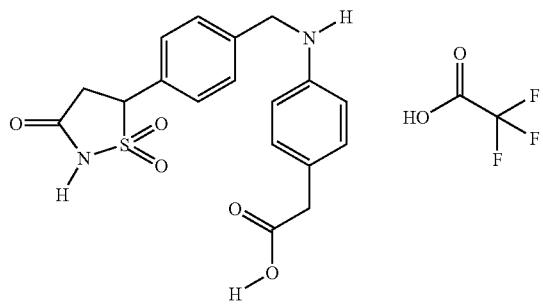

To 4-(1,1-dioxido-3-oxo-2,3-dihydroisothiazol-5-yl)benzaldehyde (6.2 mg, 0.026 mmol) in methanol (300 μL, 7.0 mmol), 4-aminophenylacetic acid (12 mg, 0.13 mmol) was added. The solution was heated to 50° C. for 16 h. The cooled orange solution was concentrated to an orange glass and redissolved in tetrahydrofuran (250 μL) and 2 M lithium borohydride in tetrahydrofuran (75 μL) was added with stirring. The reaction was heated to 50° C. for 2 h. All reactions were quenched with a few drops of 1 N HCl and 2 mL methanol. The mixture was purified by preparative LCMS to give the desired product. (3.5 mg, 28%). LCMS found for $C_{18}H_{16}N_2O_5S$ (M+H)$^+$: m/z=373.

Example 4.60

N-(4-{[4-(1,1-dioxido-3-oxoisothiazolidin-5-yl)benzyl]amino}phenyl)-4-methylbenzenesulfonamide trifluoroacetate

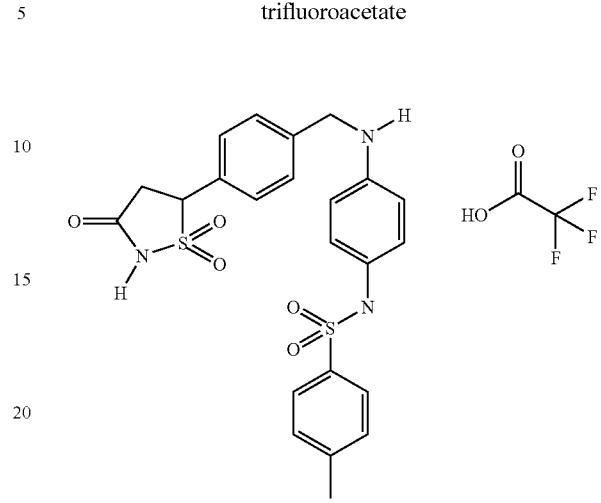

To 4-(1,1-dioxido-3-oxo-2,3-dihydroisothiazol-5-yl)benzaldehyde (6.2 mg, 0.026 mmol) in methanol (300 μL, 7.0 mmol), N-(4'-aminophenyl)-4-methylbenzenesulfonamide (12 mg, 0.13 mmol) was added. The solution was heated to 50° C. for 16 h. The cooled orange solution was concentrated to an orange glass and redissolved in tetrahydrofuran (250 μL) and 2 M lithium borohydride in tetrahydrofuran (75 μL) was added with stirring. The reaction was heated to 50° C. for 2 h. All reactions were quenched with a few drops of 1 N HCl and 2 mL methanol. The mixture was purified by preparative LCMS to give the desired product. (5.3 mg, 33%). LCMS found for $C_{23}H_{23}N_3O_5S_2$ (M+H)$^+$: m/z=486.

Example 4.61

5-[4-({[3-(1H-tetrazol-5-yl)phenyl]amino}methyl)phenyl]isothiazolidin-3-one 1,1-dioxide trifluoroacetate

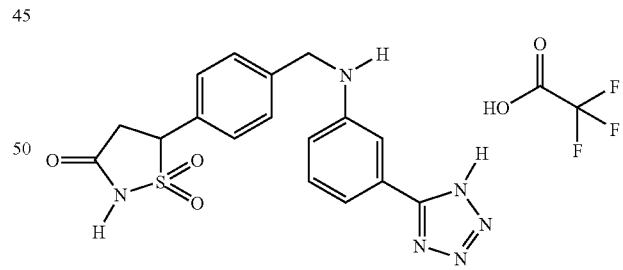

To 4-(1,1-dioxido-3-oxo-2,3-dihydroisothiazol-5-yl)benzaldehyde (6.2 mg, 0.026 mmol) in methanol (300 μL, 7.0 mmol), 3-(1H-tetrazol-5-yl)aniline (12 mg, 0.13 mmol) was added. The solution was heated to 50° C. for 16 h. The cooled orange solution was concentrated to an orange glass and redissolved in tetrahydrofuran (250 μL) and lithium borohydride in tetrahydrofuran (2 M, 75 μL) was added with stirring. The reaction was heated to 50° C. for 2 h. All reactions were quenched with a few drops of 1 N HCl and 2 mL methanol. The mixture was purified by preparative LCMS to give the desired product. (5.1 mg, 38%). LCMS found for $C_{17}H_{16}N_6O_3S$ (M+H)$^+$: m/z=385.

Example 4.62

Methyl 2-[4-((2S)-2-[(benzyloxy)carbonyl]amino-3-[3-bromo-4-(1,1-dioxido-3-oxoisothiazolidin-5-yl)phenyl]propanoylamino)butoxy]-6-hydroxybenzoate

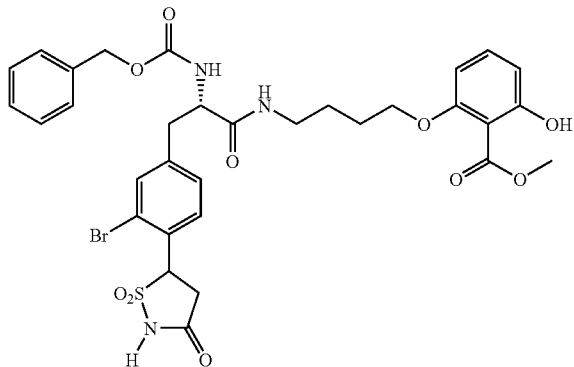

Step 1. Methyl (2S)-2-[(tert-butoxycarbonyl)amino]-3-(4-nitrophenyl)propanoate

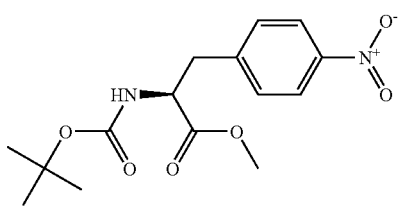

(2S)-2-[(tert-Butoxycarbonyl)amino]-3-(4-nitrophenyl)propanoic acid (45.0 g, 145 mmol) was dissolved in DMF (425 mL) and treated with sodium bicarbonate (24.4 g, 290 mmol) followed by methyl iodide (36.1 mL, 580 mmol). The solution stirred at rt for 16 h. The solution was diluted with ethyl acetate (500 mL), washed with water (500 mL), saturated aqueous sodium bicarbonate solution (300 mL), aqueous hydrochloric acid solution (1.0 N, 500 mL), and the organic phase dried over sodium sulfate. The solvent was removed in vacuo to afford product as a slightly yellow solid (46.2 g, 98%). $^1$H NMR (400 MHz, CDCl$_3$): δ 8.16 (d, J=8.6 Hz, 2H), 7.46 (d, J=8.6 Hz, 2H), 4.45–4.41 (m, 1H), 3.71 (s, 3H), 3.30–3.26 (m, 1H), 3.05–2.99 (m, 1H), 1.36 (s, 9H); LCMS found for C$_{15}$H$_{20}$N$_2$O$_6$Na (M+Na)$^+$: m/z=347.

Step 2. Methyl (2S)-3-(4-aminophenyl)-2-[(tert-butoxycarbonyl)amino]propanoate

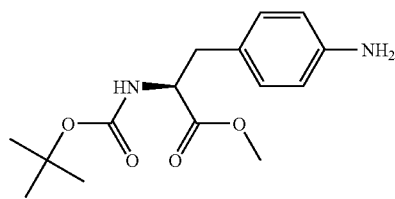

Methyl (2S)-2-[(tert-butoxycarbonyl)amino]-3-(4-nitrophenyl)propanoate (44.0 g, 136 mmol) in methanol (750 mL) and water (75 mL) was treated with ammonium chloride (10.9 g, 203 mmol) and then zinc (71 g, 1.1 mol). The solution was stirred at reflux for 1 h. The solution was filtered through celite, the residue concentrated under vacuum to remove methanol, the water solution extracted with ethyl acetate (500 mL) and dried over sodium sulfate. The product was a yellow foam (38.2 g, 96%). $^1$H NMR (400 MHz, CD$_3$OD): δ 6.91 (d, J=8.4 Hz, 2H), 6.65 (d, J=8.3 Hz, 2H), 4.28–4.22 (m, 1H), 3.66 (s, 3H), 2.98–2.90 (m, 1H), 2.86–2.78 (m, 1H), 1.39 (s, 9H). LCMS found for C$_{15}$H$_{22}$N$_2$O$_4$Na (M+Na)$^+$: m/z=317.

Step 3. Methyl (2S)-3-(4-amino-3-bromophenyl)-2-[(tert-butoxycarbonyl)amino]-propanoate

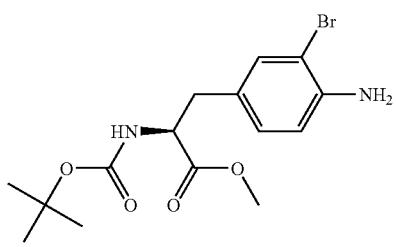

Methyl (2S)-3-(4-aminophenyl)-2-[(tert-butoxycarbonyl)amino]propanoate (17.2 g, 58.4 mmol) in DMF (400 mL) was treated with N-bromosuccinimide (11.4 g, 64.3 mmol). The solution stirred at rt overnight. The solution was diluted with ethyl acetate (500 mL), washed with water (500 mL), saturated aqueous sodium bicarbonate solution (500 mL), and aqueous hydrochloric acid solution (1.0 N, 500 mL). The organic phase was dried over sodium sulfate and conc. in vacuo. Silica gel chromatography (10-50% gradient, ethyl acetate/hexanes) afforded product as a viscous slightly yellow gel (20.1 g, 92%). $^1$H NMR (400 MHz, CD$_3$OD): δ 7.21 (d, J=1.7 Hz, 1H), 6.92 (dd, J=8.2, 1.8 Hz), 6.75 (d, J=8.2 Hz, 1H), 4.27–4.23 (m, 1H), 3.68 (s, 3H), 2.97–2.92 (m, 1H), 2.77–2.72 (m, 1H), 1.39 (s, 9H); LCMS found for C$_{15}$H$_{21}$BrN$_2$O$_4$Na (M+Na)$^+$: m/z=396.

Step 4. Methyl (2S)-3-(3-bromo-4-iodophenyl)-2-[(tert-butoxycarbonyl)amino-]propanoate

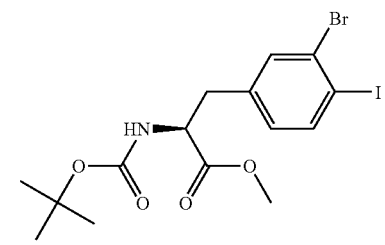

Methyl (2S)-3-(4-amino-3-bromophenyl)-2-[(tert-butoxycarbonyl)amino]-propanoate (19.8 g, 53.0 mmol) suspended in 1 N aqueous hydrogen chloride (500 mL) was treated sequentially at 0° C. with sodium nitrite (3.66 g, 53.0 mmol) in water (75 mL) dropwise. After 15 minutes at 0° C., potassium iodide (8.81 g, 53.1 mmol) in water (75 mL) was added and the solution was heated at 40° C. for 15 minutes. The solution was quenched with saturated aqueous sodium thiosulfate solution (100 mL), and extracted with ethyl acetate (500 mL). The organic phase was washed with 0.1 N Hydrochloric acid solution (500 mL), saturated aqueous sodium bicarbonate solution (500 mL), and dried over sodium sulfate. Purification by silica gel chromatography (10–40% ethyl acetate/hexanes) afforded product as slightly yellow solid (18.7 g, 73%). $^1$H NMR (400 MHz, CD$_3$OD): δ 7.80 (d, J=8.0 Hz, 1H), 7.55 (d, J=1.8 Hz, 1H), 6.92 (dd, J=8.0, 1.9 Hz), 4.36–4.29 (m, 1H), 3.71 (s, 3H), 3.10–2.79 (m, 1H), 1.37 (s, 9H); LCMS found for C$_{15}$H$_{19}$BrINO$_4$Na (M+Na)$^+$: m/z=506.

Step 5. Methyl (2S)-3-[3-bromo-4-(2-tert-butyl-1,1-dioxido-3-oxo-2,3-dihydroisothiazol-5-yl)phenyl]-2-[(tert-butoxycarbonyl)amino]propanoate

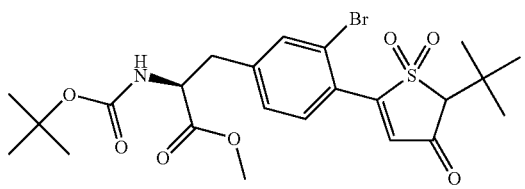

Methyl (2S)-3-(3-bromo-4-iodophenyl)-2-[(tert-butoxycarbonyl)amino]-propanoate (2.35 g, 4.85 mmol), 2-tert-butylisothiazol-3(2H)-one 1,1-dioxide (1.61 g, 8.49 mmol), palladium acetate (218 mg, 0.971 mmol), tetra-N-butylammonium chloride (1.35 g, 4.85 mmol), and then triethylamine (2.03 mL, 14.6 mmol) were dissolved in DMF (40.0 mL, 0.516 mmol). The solution was degassed and then stirred with heating at 70° C. under nitrogen for 120 minutes. LCMS indicated an absence of starting material. The solution was diluted with ethyl acetate (150 mL) and washed with water (150 mL) and aqueous hydrochloric acid solution (1.0 N, 150 mL). The organic phase was filtered through celite with ethyl acetate washing. The organic solution was dried over sodium sulfate, concentrated in vacuo, and then purified by silica gel chromatography (slow gradient, 10–25% ethyl acetate/hexanes) to afford product as a yellow solid (1.38 g, 52%). $^1$H NMR (500 MHz, CD$_3$OD): δ 7.80 (d, J=8.2 Hz, 1H), 7.55 (s, 1H), 7.23 (d, J=8.2 Hz, 1H), 6.89 (s, 1H), 5.08–5.05 (m, 1H), 4.62–4.59 (m, 1H), 3.76 (s, 3H), 3.23–3.20 (m, 1H), 3.06–3.02 (m, 1H), 1.79 (s, 9H), 1.43 (s, 9H). LCMS found for C$_{22}$H$_{29}$BrN$_2$O$_7$SNa (M+Na)$^+$: m/z=567.

Step 6. Methyl (2S)-3-[3-bromo-4-(2-tert-butyl-1,1-dioxido-3-oxoisothiazolidin-5-yl)phenyl]-2-[(tert-butoxycarbonyl)amino]propanoate

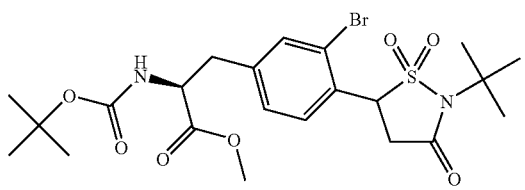

Methyl (2S)-3-[3-bromo-4-(2-tert-butyl-1,1-dioxido-3-oxo-2,3-dihydroisothiazol-5-yl)phenyl]-2-[(tert-butoxycarbonyl)-amino]propanoate (834 mg, 1.53 mmol) in tetrahydrofuran (20 mL,) was chilled to 0° C. and treated dropwise with 2 M lithium tetrahydroborate in tetrahydrofuran (0.801 mL). The solution was stirred at 0° C. for 30 minutes. After ten drops of acetic acid were added, the solution diluted with ethyl acetate (150 mL), washed with water (150 mL), and dried over sodium sulfate. Silica gel chromatography (10–40% ethyl acetate hexanes) afforded product as a slightly yellow foam (682 mg, 82%). $^1$H NMR (400 MHz, CDCl$_3$): δ 7.49–7.45 (m, 1H), 7.32–7.29 (m, 1H), 7.24–7.18 (m, 1H), 5.46–5.42 (m, 1H), 5.05–5.00 (m, 1H), 4.60–4.54 (m, 1H), 3.35–3.30 (m, 1H), 3.20–3.16 (m, 1H), 3.08–3.00 (m, 2H), 1.68 (s, 9H), 1.43 (s, 9H); LCMS found for C$_{22}$H$_{31}$BrN$_2$O$_7$S (M+Na)$^+$: m/z=569.

Step 7. Methyl (2S)-2-amino-3-[3-bromo-4-(1,1-dioxido-3-oxoisothiazolidin-5-yl)phenyl]-propanoate trifluoroacetate

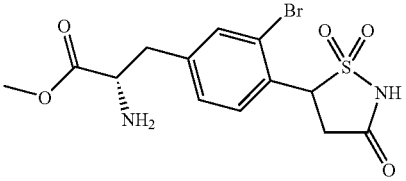

Methyl (2S)-3-[3-bromo-4-(2-tert-butyl-1,1-dioxido-3-oxoisothiazolidin-5-yl)phenyl]-2-[(tert-butoxycarbonyl)amino]propanoate (458 mg, 0.654 mmol) was dissolved in trifluoroacetic acid (10 mL) and heated at 130° C. in the microwave for 2 minutes. The solution was concentrated in vacuo to a white foam (420 mg, 99%). The product was used in subsequent steps without purification. $^1$H NMR (500 MHz, CDCl$_3$): δ 7.68 (dd, J=14.2, 1.6 Hz, 1H), 7.56–7.51 (m, 1H), 7.40–7.36 (m, 1H), 5.65 (t, J=7.4 Hz, 1H), 4.39 (t, J=6.8 Hz, 1H), 3.82 (s, 3H), 3.47–3.42 (m, 1H), 3.36–3.25 (m, 2H), 2.18–3.11 (m, 1H); LCMS found for C$_{13}$H$_{16}$BrN$_2$O$_5$S (M+Na)$^+$: m/z=391.

Step 8. (2S)-2-[(benzyloxy)carbonyl]amino-3-[3-bromo-4-(1,1-dioxido-3-oxoisothiazolidin-5-yl)phenyl]propanoic acid

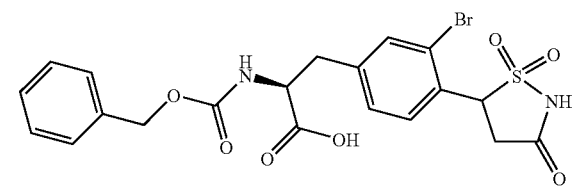

Methyl (2S)-2-amino-3-[3-bromo-4-(1,1-dioxido-3-oxoisothiazolidin-5-yl)phenyl]-propanoate trifluoroacetate (83.8 mg, 0.166 mmol) in methanol (2.0 mL) was treated with triethylamine (92.5 µL, 0.663 mmol) and chilled to 0° C. Benzyl chloroformate (20.8 µL, 0.146 mmol) was added and the solution stirred 2 h at 0° C. Aqueous lithium hydroxide solution (4.0 M, 0.21 mL) was added and the solution stirred 2 h. Purification by preparative LCMS afford product as a white solid (69 mg, 81%). $^1$H NMR (400 MHz, CDCl$_3$): δ 7.48 (brs, 1H), 7.46–7.43 (m, 1H), 7.31–7.26 (m, 6H), 5.65 (t, J=8.2 Hz, 1H), 5.03 (s, 2H), 4.45–4.41 (m, 1H), 3.45 (dd, J=17.5, 8.5 Hz, 1H), 3.36–3.19 (m, 2H), (2.94 dd, J=14.2, 9.7 Hz, 1H); LCMS found for C$_{20}$H$_{20}$BrN$_2$O$_7$S (M+H)$^+$: m/z=511.

243

Step 9. Methyl 2-[4-((2S)-2-[(benzyloxy)carbonyl]amino-3-[3-bromo-4-(1,1-dioxido-3oxoisothiazolidin-5-yl)phenyl]propanoylamino)butoxy]-6-hydroxybenzoate (2S)-2-[(Benzyloxy)carbonyl]amino-3-[3-bromo-4-(1,1-dioxido-3-oxoisothiazolidin-5-yl)phenyl]propanoic acid (10.2 mg, 0.020 mmol) in DMF (2.00 mL) was treated with benzotriazol-1-yloxytris(dimethylamino)phosphonium hexafluorophosphate (10.6 mg, 0.0240 mmol). After five minutes methyl 2-(4-aminobutoxy)-6-hydroxybenzoate hydrochloride (8.27 mg, 0.030 mmol) and N,N-diisopropylethylamine (17.4 µL, 0.100 mmol) were added and the solution stirred at rt for 2 h. Purification by preparative LCMS afforded product as a white solid (8.9 mg, 61%). $^1$H NMR (400 MHz, CD$_3$OD): δ 8.07 (brs, 1H), 7.63 (s, 1H), 7.41 (d, J=8.1 Hz, 1H), 7.31–7.23 (m, 7H), 6.49–6.46 (m, 2H), 5.43 (t, J=6.1 Hz, 1H), 5.02 (s, 2H), 4.33–4.29 (m, 1H), 3.97–3.92 (m, 2H), 3.85 (s, 3H), 3.47–3.36 (m, 2H), 3.29–2.82 (m, 4H), 1.68–1.60 (m, 4H); LCMS found for C$_{32}$H$_{35}$BrN$_3$O$_{10}$S (M+H)$^+$: m/z=734.

Example 4.63

Benzyl (1S)-1-[3-bromo-4-(1,1-dioxido-3-oxoisothiazolidin-5-yl)benzyl]-2-oxo-2-[(4-phenylbutyl)amino]ethylcarbamate

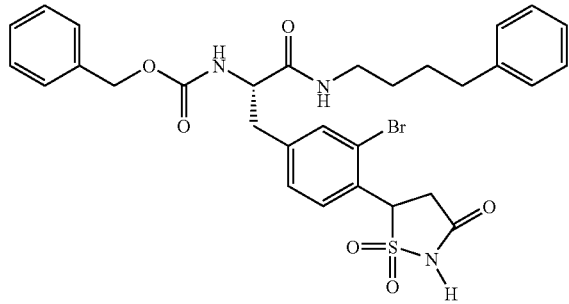

This compound was prepared according to the procedures of Example 4.62 using appropriate starting materials. $^1$H NMR (400 MHz, CD$_3$OD): δ 8.02 (brs, 1H), 7.62 (brs, 1H), 7.42–7.35 (m, 1H), 7.31–7.12 (m, 10H), 5.57–5.53 (m, 1H), 5.05–5.03 (m, 2H), 4.31–4.28 (m, 1H), 3.45–3.31 (m, 1H), 3.20–3.05 (m, 4H), 2.91–2.87 (m, 1H), 2.60 (t, J=7.6 Hz, 2H), 1.57–1.52 (m, 2H), 1.47–1.43 (m, 2H); LCMS found for C$_{30}$H$_{33}$BrN$_3$O$_6$S (M+H)$^+$: m/z=644.

Example 4.64

Methyl 2-[3-((2S)-2-[(benzyloxy)carbonyl]amino-3-[3-bromo-4-(1,1-dioxido-3-oxoisothiazolidin-5-yl)phenyl]propanoylamino)propoxy]-6-hydroxybenzoate

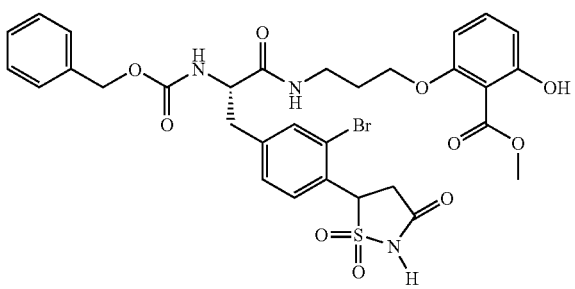

244

This compound was prepared according to the procedures of Example 4.62 using appropriate starting materials. $^1$H NMR (400 MHz, CD$_3$OD): δ 7.64 (s, 1H), 7.41 (d, J=8.1 Hz, 1H), 7.31–7.23 (m, 7H), 6.48 (d, J=8.2 Hz, 2H), 5.43 (t, J=6.1 Hz, 1H), 5.02–5.00 (m, 2H), 4.33 (t, J=5.2 Hz, 1H), 3.89–3.80 (m, 2H), 3.86 (s, 3H), 3.47–3.20 (m, 4H), 3.14–3.06 (m, 1H), 2.95–2.89 (m, 1H), 1.93–1.84 (m, 2H); LCMS found for C$_{31}$H$_{33}$BrN$_3$O$_{10}$S (M+H)$^+$: m/z=720.

Example 4.65

Methyl 2-[5-((2S)-2-[(benzyloxy)carbonyl]amino-3-[3-bromo-4-(1,1-dioxido-3-oxoisothiazolidin-5-yl)phenyl]propanoylamino)pentyl]oxy-6-hydroxybenzoate

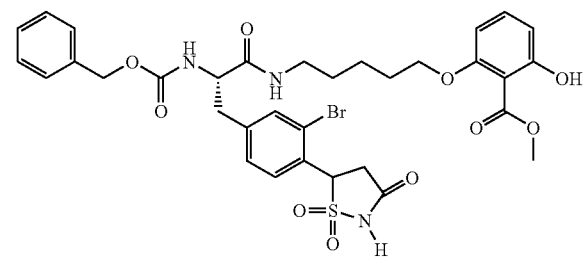

This compound was prepared according to the procedures of Example 4.62 using appropriate starting materials. $^1$H NMR (400 MHz, CD$_3$OD): δ 8.03 (brs, 1H), 7.62 (s, 1H), 7.45 (d, J=8.0 Hz, 1H), 7.31–7.23 (m, 7H), 6.48 (t, J=8.5 Hz, 2H), 5.41 (t, J=6.5 Hz, 1H), 5.02–5.00 (m, 2H), 4.30 (t, J=5.2 Hz, 1H), 3.95–3.90 (m, 2H), 3.86 (s, 3H), 3.47–3.39 (m, 1H), 3.27–3.02 (m, 4H), 2.95–2.89 (m, 1H), 1.82–1.74 (m, 2H), 1.50–1.38 (m, 4H); LCMS found for C$_{33}$H$_{37}$BrN$_3$O$_{10}$S (M+H)$^+$: m/z=746.

Example 4.66

Benzyl (1S)-1-(1H-benzimidazol-2-yl)-2-[3-bromo-4-(1,1-dioxido-3-oxoisothiazolidin-5-yl)phenyl]ethylcarbamate trifluoroacetate

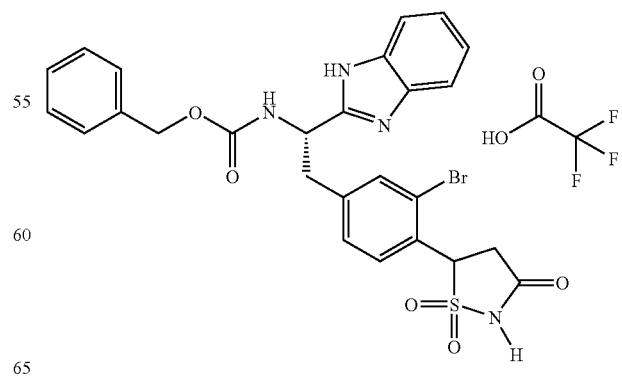

Step 1. Benzyl (1S)-2-[(2-aminophenyl)amino]-1-[3-bromo-4-(1,1-dioxido-3-oxoisothiazolidin-5-yl)benzyl]-2-oxoethylcarbamate

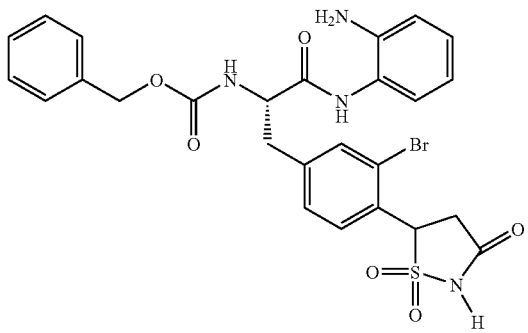

(2S)-2-[(Benzyloxy)-carbonyl]amino-3-[3-bromo-4-(1,1-dioxido-3-oxoisothiazolidin-5-yl)phenyl]propanoic acid (65.3 mg, 0.128 mmol) in DMF (4 mL) was treated with benzotriazol-1-yloxytris(dimethylamino)phosphonium hexafluorophosphate (67.8 mg, 0.153 mmol). After 5 minutes 1,2-benzenediamine (20.7 mg, 0.192 mmol) and N,N-diisopropylethylamine (111 μL, 0.638 mmol) were added and the solution stirred at rt for 2 h. Purification by preparative LCMS afforded product as a white solid (58 mg, 76%). $^1$H NMR (400 MHz, CD$_3$OD): δ 7.72 (s, 1H), 7.56–7.23 (m, 10H), 6.91–6.85 (m, 1H), 5.67 (t, J=7.7 Hz, 1H), 5.09 (s, 2H), 4.50–4.47 (m, 1H), 3.46 (dd, J=16.5, 8.8 Hz, 1H), 3.34–3.24 (m, 1H), 3.26–3.08 (m, 2H); LCMS found for C$_{26}$H$_{26}$BrN$_4$O$_6$S (M+H)$^+$: m/z=601.

Step 2. Benzyl (1S)-1-(1H-benzimidazol-2-yl)-2-[3-bromo-4-(1,1-dioxido-3-oxoisothiazolidin-5-yl)phenyl]ethylcarbamate Benzyl (1S)-2-[(2-aminophenyl)amino]-1-[3-bromo-4-(1,1-dioxido-3-oxoisothiazolidin-5-yl)benzyl]-2-oxoethylcarbamate (28.2 mg, 0.0469 mmol) was dissolved in acetic acid (2.76 mL) and stirred at 60° C. for 1 h. The solution was concentrated and purified by preparative LCMS to afford product as a white solid (26.1 mg, 95%). $^1$H NMR (400 MHz, CD$_3$OD): δ 7.79–7.56 (m, 5H), 7.42–7.12 (m, 7H), 5.61–5.57 (m, 1H), 5.35–5.31 (m, 1H), 5.03 (s, 2H), 3.47–3.28 (m, 1H); LCMS found for C$_{26}$H$_{24}$BrN$_4$O$_5$S (M+H)$^+$: m/z=583.

Example 4.67

Benzyl (1S)-1-(1H-benzimidazol-2-yl)-2-[3-cyano-4-(1,1-dioxido-3-oxoisothiazolidin-5-yl)phenyl]ethylcarbamate trifluoroacetate

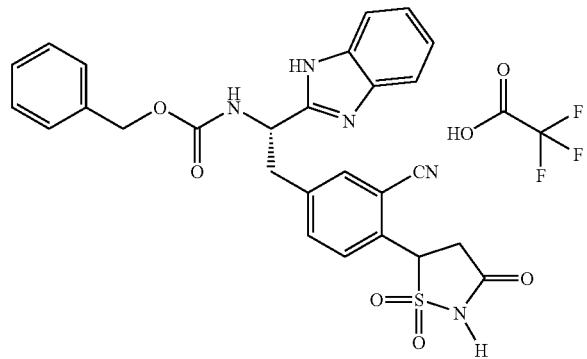

Benzyl (1S)-1-(1H-benzimidazol-2-yl)-2-[3-bromo-4-(1,1-dioxido-3-oxoisothiazolidin-5-yl)phenyl]ethylcarbamate (11.2 mg, 0.0192 mmol), zinc cyanide (6.76 mg, 0.0576 mmol), and tetrakis(triphenylphosphine)palladium(0) (4.44 mg, 0.00384 mmol) were dissolved in DMF (1.00 mL) and the solution was degassed. The reaction was stirred in the microwave for 4 minutes at 175° C. The solution was diluted with methanol, filtered, and purified by preparative LCMS to afford product as a white solid (6.5 mg, 64%). $^1$H NMR (400 MHz, CD$_3$OD): δ 7.80–7.75 (m, 3H), 7.62–7.57 (m, 5H), 7.34–7.30 (m, 4H), 5.43–5.39 (m, 1H), 5.04 (s, 2H), 4.95–4.90 (m, 1H), 3.52–3.35 (m, 4H), 3.29–3.25 (m, 1H); LCMS found for C$_{27}$H$_{24}$N$_5$O$_5$S (M+H)$^+$: m/z=530.

Example 4.68

Methyl 2-[3-((2S)-2-[(benzyloxy)carbonyl]amino-3-[3-cyano-4-(1,1-dioxido-3-oxoisothiazolidin-5-yl)phenyl]propanoylamino)propyl]oxy-6-hydroxybenzoate

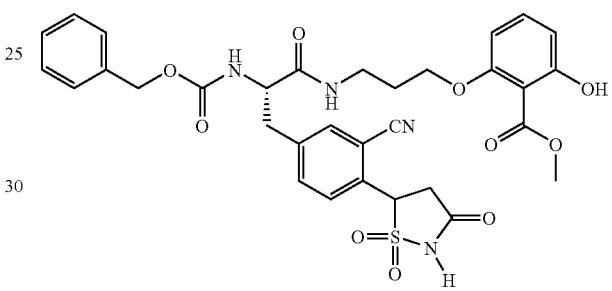

This compound was prepared by cyanation of Example 4.65 according to the procedure of Example 4.67 using appropriate starting materials. $^1$H NMR (400 MHz, CD$_3$OD): δ 7.75 (s, 1H), 7.60–7.57 (m, 2H), 7.32–7.20 (m, 6H), 6.48 (t, J=8.5 Hz, 2H), 5.44–5.40 (t, J=6.5 Hz, 1H), 5.02 (d, J=7.4 Hz, 2H), 4.35 (t, J=5.2 Hz, 1H), 3.95–3.90 (m, 2H), 3.89 (s, 3H), 3.47–3.30 (m, 4H), 3.16–3.12 (m, 1H), 3.00–2.94 (m, 1H), 1.86–1.83 (m, 2H); LCMS found for C$_{32}$H$_{33}$N$_4$O$_{10}$S (M+H)$^+$: m/z=665.

Example 4.69

Methyl 2-[5-((2S)-2-[(benzyloxy)carbonyl]amino-3-[3-cyano-4-(1,1-dioxido-3-oxoisothiazolidin-5-yl)phenyl]propanoylamino)pentyl]oxy-6-hydroxybenzoate

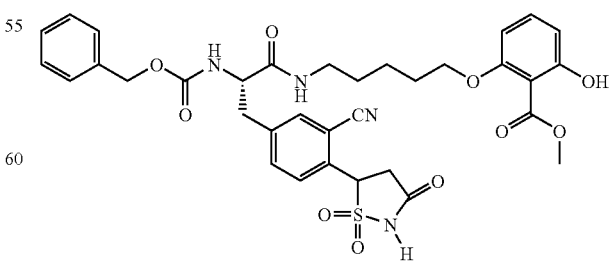

This compound was prepared by cyanation of Example 4.65 according to the procedure of Example 4.67 using appropriate starting materials. ¹H NMR (400 MHz, CD₃OD): δ 7.74 (s, 1H), 7.60–7.57 (m, 2H), 7.32–7.20 (m, 6H), 6.47 (t, J=8.9 Hz, 2H), 5.45–5.40 (m, 1H), 5.02–5.00 (m, 2H), 4.35–4.31 (m, 1H), 3.98–3.95 (m, 2H), 3.86 (s, 3H), 3.47–3.35 (m, 2H), 3.16–3.10 (m, 3H), 3.00–2.94 (m, 1H), 1.77–1.73 (m, 2H), 1.49–1.42 (m, 2H); LCMS found for $C_{34}H_{37}N_4O_{10}S$ (M+H)⁺: m/z=693

Example 4.70

Methyl 2-[4-((2S)-3-[3-bromo-4-(1,1-dioxido-3-oxoisothiazolidin-5-yl)phenyl]-2-[(phenylsulfonyl)-amino]propanoylamino)butoxy]-6-hydroxybenzoate

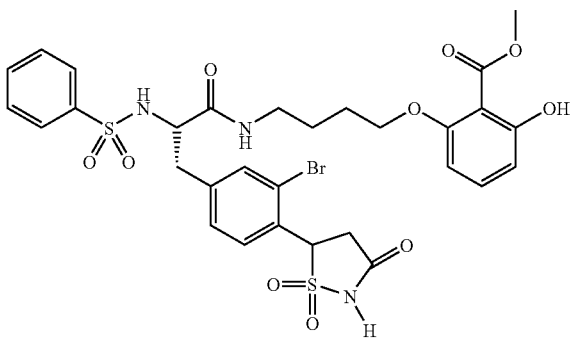

Step 1. (2R)-3-[3-bromo-4-(1,1-dioxido-3-oxoisothiazolidin-5-yl)phenyl]-2-[(phenylsulfonyl)-amino]propanoic acid

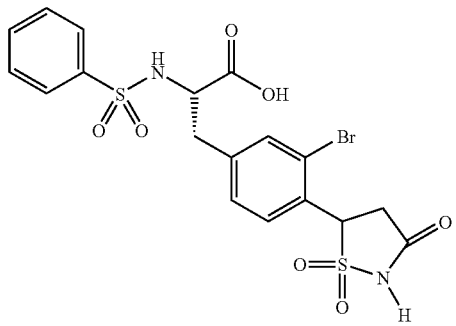

Methyl (2S)-2-amino-3-[3-bromo-4-(1,1-dioxido-3-oxoisothiazolidin-5-yl)-phenyl]-propanoate trifluoroacetate (77.1 mg, 0.152 mmol) in methanol (1.7 mL,) was treated with triethylamine (85.0 μL, 0.610 mmol) and then benzenesulfonyl chloride (29.2 μL, 0.228 mmol). The solution was stirred at rt for 2 h. 4 M lithium hydroxide in water (0.38 mL) was added and stirred for 3 h at rt. The solution was acidified with aqueous 1 N hydrochloric acid solution (4 mL), diluted with methanol (1.5 mL) and purified by preparative LCMS to afford product as a white solid (55.4 mg, 70%). ¹H NMR (400 MHz, CD₃OD): δ 7.65–7.62 (m, 2H), 7.53–7.36 (m, 4H), 7.25–7.20 (m, 1H), 5.65 (t, J=6.8 Hz, 1H), 4.06–5.01 (m, 1H), 3.48 (dd, J=16.2, 8.0 Hz, 1H), 3.38–3.28 (m, 1H), 3.11–3.06 (m, 1H), 2.87–2.83 (m, 1H); LCMS found for $C_{18}H_{18}BrN_2O_7S_2$ (M+H)⁺: m/z=517.

Step 2. Methyl 2-[4-((2S)-3-[3-bromo-4-(1,1-dioxido-3-oxoisothiazolidin-5-yl)phenyl]-2-[(phenylsulfonyl)-amino]propanoylamino)butoxy]-6-hydroxybenzoate (2S)-3-[3-bromo-4-(1,1-dioxido-3-oxoisothiazolidin-5-yl)phenyl]-2-[(phenylsulfonyl)-amino]-propanoic acid (10.3 mg, 0.020 mmol) in DMF (1 mL) was treated with benzotriazol-1-yloxytris(dimethylamino)phosphonium hexafluorophosphate (10.6 mg, 0.024 mmol). After stirring 5 minutes at rt a solution of N,N-diisopropylethylamine (17.4 L, 0.10 mmol) and methyl 2-(4-aminobutoxy)-6-hydroxybenzoate hydrochloride (8.27 mg, 0.030 mmol) in DMF (1 mL) was added. The solution stirred at rt for 2 h. Purification by preparative LCMS afforded product as a white solid (9.2 mg, 62%). ¹H NMR (400 MHz, CD₃OD): δ 7.96 (brs, 1H), 7.69–7.65 (m, 2H), 7.52–7.14 (m, 7H), 6.51–6.46 (m, 2H), 5.62–5.59 (m, 1H), 4.00–3.94 (m, 13H), 3.87 (s, 3H), 3.44–3.38 (m, 1H), 3.36–3.30 (m. 1H), 3.06–3.00 (m, 1H), 2.98–2.91 (m, 2H), 2.81–2.72 (m, 1H), 1.64–1.60 (m, 2H), 1.51–1.47 (m, 2H); LCMS found for $C_{30}H_{33}BrN_3O_{10}S_2$ (M+H)⁺: m/z=738.

Example 4.71

Methyl 2-[3-(3-[3-bromo-4-(1,1-dioxido-3-oxoisothiazolidin-5-yl)phenyl]-2-[(phenylsulfonyl)-amino]-propanoylamino)propoxy]-6-hydroxybenzoate

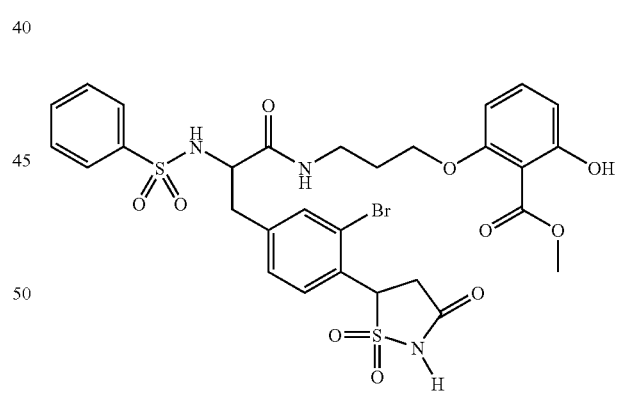

This compound was prepared according to the procedures of Example 4.70 using appropriate starting materials. ¹H NMR (400 MHz, CD₃OD): δ 7.99 (brs, 1H), 7.65 (t, J=7.3 Hz, 2H), 7.54–7.17 (m, 7H), 6.51–6.46 (m, 2H), 5.60 (t, J=6.2 Hz, 1H), 4.03–3.94 (m, 1H), 3.89 (s, 3H), 3.89–3.85 (m, 2H), 3.47–3.38 (m, 1H), 3.30–2.88 (m, 5H) 3.04–2.75 (m, 4H), 1.74–1.70 (m, 2H); LCMS found for $C_{29}H_{31}BrN_3O_{10}S_2$ (M+H)⁺: m/z=726.

Example 4.72

Methyl 2-[5-(3-[3-bromo-4-(1,1-dioxido-3-ox-oisothiazolidin-5-yl)phenyl]-2-[(phenylsulfonyl)-amino]propanoylamino)pentyl]oxy-6-hydroxybenzoate

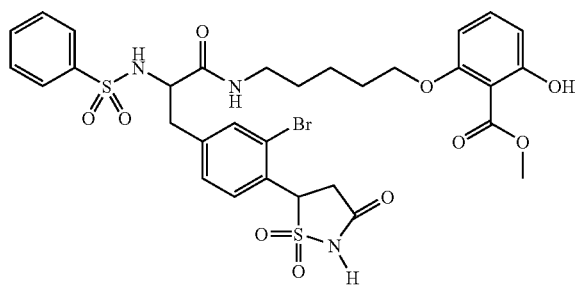

This compound was prepared according to the procedures of Example 4.70 using appropriate starting materials. $^1$H NMR (400 MHz, CD$_3$OD): δ 7.93 (brs, 1H), 7.67 (t, J=7.0 Hz, 2H), 7.58–7.16 (m, 6H), 6.51–6.46 (m, 2H), 5.61–5.58 (m, 1H), 3.97–3.88 (m, 3H), 3.86 (s, 3H), 3.47–3.38 (m, 1H), 3.32–3.23 (m, 1H) 3.04–2.75 (m, 4H), 1.74–1.70 (m, 2H), 1.40–1.32 (m, 4H); LCMS found for C$_{31}$H$_{35}$BrN$_3$O$_{10}$S$_2$ (M+H)$^+$: m/z=752.

Example 4.73

3-[3-bromo-4-(1,1-dioxido-3-oxoisothiazolidin-5-yl)phenyl]-N-(4-phenylbutyl)-2-[(phenylsulfonyl)-amino]propanamide

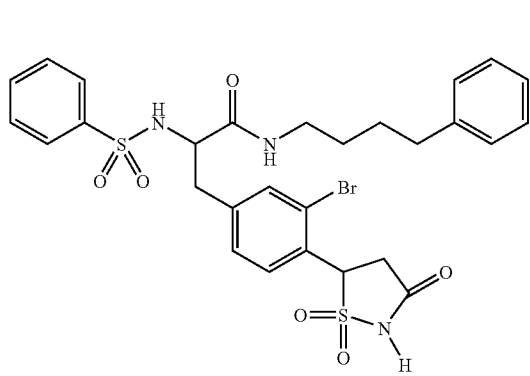

This compound was prepared according to the procedures of Example 4.70 using appropriate starting materials. $^1$H NMR (400 MHz, CD$_3$OD): δ 7.91 (brs, 1H), 7.67–7.62 (m, 2H), 7.52–7.27 (m, 5H), 7.24–7.15 (m, 6H), 5.59–5.56 (m, 1H), 3.91–3.88 (m, 1H), 3.41–3.20 (m, 3H), 3.02–2.84 (m, 2H), 2.77–2.72 (m, 1H), 2.56 (t, J=7.6 Hz, 2H), 1.51–1.47 (m, 2H), 1.33–1.29 (m, 2H); LCMS found for C$_{28}$H$_{31}$BrN$_3$O$_6$S$_2$ (M+H)$^+$: m/z=648.

Example 4.74

3-[3-Bromo-4-(1,1-dioxido-3-oxoisothiazolidin-5-yl)phenyl]-N-(4-phenoxybutyl)-2-[(phenylsulfonyl)-amino]propanamide

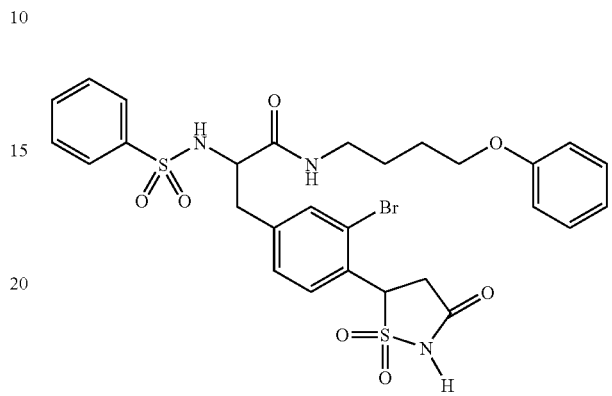

This compound was prepared according to the procedures of Example 4.70 using appropriate starting materials. $^1$H NMR (400 MHz, CD$_3$OD): δ 7.71–7.67 (m, 2H), 7.54–7.34 (m, 3H), 7.26–7.15 (m, 2H), 6.90–6.88 (d, J=8.2 Hz, 1H), 5.62–5.59 (m, 1H), 3.92–3.87 (m, 3H), 3.44–3.37 (m, 1H), 3.35–3.25 (m, 1H), 3.10–2.77 (m, 4H), 1.63–1.57 (m, 2H), 1.47–1.43 (m, 2H); LCMS found for C$_{28}$H$_{31}$BrN$_3$O$_7$S$_2$ (M+H)$^+$: m/z=664.

Example 4.75

Methyl 2-[4-(3-[3-bromo-4-(1,1-dioxido-3-ox-oisothiazolidin-5-yl)phenyl]-2-[(phenylsulfonyl)-amino]propanoylamino)butoxy]benzoate

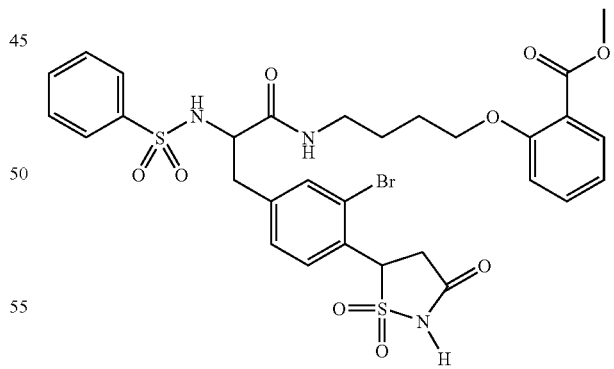

This compound was prepared according to the procedures of Example 4.70 using appropriate starting materials. $^1$H NMR (400 MHz, CD$_3$OD): δ 7.76–7.67 (m, 3H), 7.53–7.35 (m, 6H), 7.21 (dd, J=8.0, 2.0 Hz, 1H), 7.05 (d, J=8.0 Hz, 1H), 6.98 (t, J=7.2 Hz, 1H), 5.62–5.59 (m, 1H), 4.01–3.92 (m, 3H), 3.86 (s, 3H), 3.42–3.37 (m, 1H), 3.35–3.25 (m, 1H), 3.07–2.79 (m, 4H), 1.64–1.48 (m, 4H); LCMS found for C$_{30}$H$_{33}$BrN$_3$O$_9$S$_2$ (M+H)$^+$: m/z=722.

Example 4.76

3-[3-Bromo-4-(1,1-dioxido-3-oxoisothiazolidin-5-yl)phenyl]-N-[4-(3-hydroxyphenoxy)-butyl]-2-[(phenylsulfonyl)-amino]propanamide (1a)

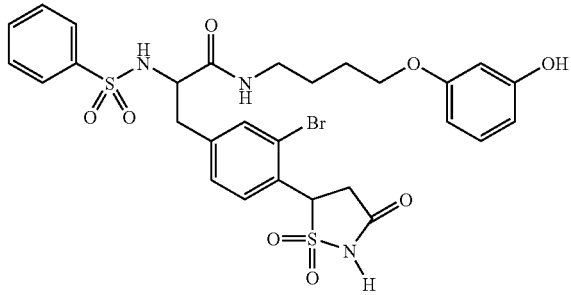

This compound was prepared according to the procedures of Example 4.70 using appropriate starting materials. $^1$H NMR (400 MHz, CD$_3$OD): δ 7.69–7.67 (m, 2H), 7.52–7.35 (m, 5H), 7.21 (dd, J=5.0, 2.0 Hz, 1H), 7.03 (t, J=8.1 Hz, 1H), 6.39–6.34 (m, 3H), 5.62–5.59 (m, 1H, 3.93–3.83 (m, 3H), 3.47–3.37 (m, 1H), 3.30–3.22 (m, 1H), 3.05–2.77 (m, 4H), 1.60–1.56 (m, 2H), 1.46–1.41 (m, 2H); LCMS found for C$_{28}$H$_{31}$BrN$_3$O$_8$S$_2$ (M+H)$^+$: m/z=679.

Example 4.77

N-1-(1H-benzimidazol-2-yl)-2-[3-bromo-4-(1,1-dioxido-3-oxoisothiazolidin-5-yl)phenyl]ethylbenzenesulfonamide trifluroacetate

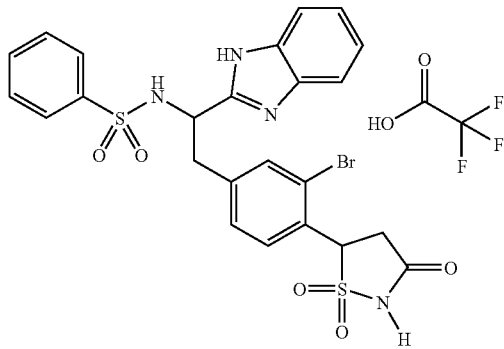

Step 1. N-(2-aminophenyl)-3-[3-bromo-4-(1,1-dioxido-3-oxoisothiazolidin-5-yl)phenyl]-2-[(phenylsulfonyl)-amino]propanamide

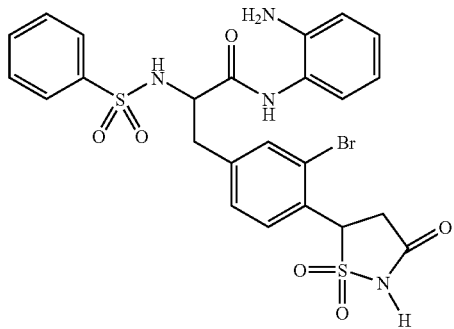

(2S)-3-[3-Bromo-4-(1,1-dioxido-3-oxoisothiazolidin-5-yl)phenyl]-2-[(phenylsulfonyl)-amino]propanoic acid (20.7 mg, 0.040 mmol) in DMF (1 mL) was treated with benzotriazol-1-yloxytris(dimethylamino)phosphonium hexafluorophosphate (21.2 mg, 0.0480 mmol). After stirring 5 minutes at rt a solution of N,N-diisopropylethylamine (34.8 μL, 0.200 mmol) and 1,2-benzenediamine (6.49 mg, 0.0600 mmol) in DMF (1.0 mL) was added. The solution stirred at rt for 2 h. Purification by preparative LCMS afforded product as a white solid (18.1 mg, 75%).

Step 2. N-1-(1H-benzimidazol-2-yl)-2-[3-bromo-4-(1,1-dioxido-3-oxoisothiazolidin-5-yl)phenyl]ethylbenzenesulfonamide trifluroacetate N-(2-Aminophenyl)-3-[3-bromo-4-(1,1-dioxido-3-oxoisothiazolidin-5-yl)phenyl]-2-[(phenylsulfonyl)-amino]propanamide (15.2 mg, 0.0250 mmol) was heated in acetic acid (1 mL) at 60° C. for 1 h. The solution was concentrated in vacuo. Purification by preparative LCMS afforded product as a white solid (10.8 mg, 73%). $^1$H NMR (400 MHz, CD$_3$OD): δ 7.77–7.74 (m, 2H), 7.64–7.52 (m, 5H), 7.45–7.25 (m, 5H), 5.56–5.52 (m, 1H), 4.98–5.90 (m, 1H), 3.46–3.40 (m, 2H), 3.26–3.15 (m, 2H); LCMS found for C$_{24}$H$_{22}$BrN$_4$O$_5$S$_2$ (M+H)$^+$: m/z=591.

Example 4.78

N-1-(1H-Benzimidazol-2-yl)-2-[3-cyano-4-(1,1-dioxido-3-oxoisothiazolidin-5-yl)phenyl]ethylbenzenesulfonamide trifluroacetate

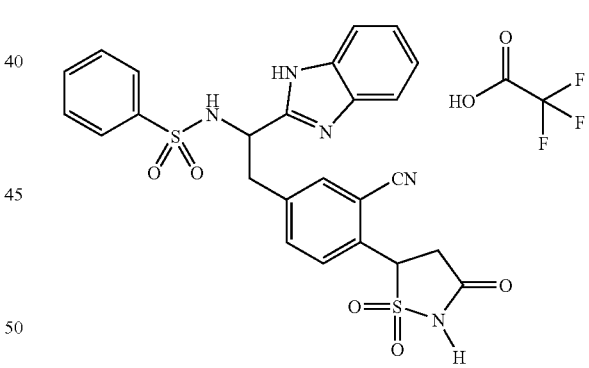

N-1-(1H-benzimidazol-2-yl)-2-[3-bromo-4-(1,1-dioxido-3-oxoisothiazolidin-5-yl)phenyl]ethylbenzenesulfonamide (6.2 mg, 0.010 mmol) was dissolved in DMF (1.0 mL) and treated with zinc cyanide (3.7 mg, 0.032 mmol) and tetrakis(triphenylphosphine)palladium(0) (2.4 mg, 0.002 mmol). The solution was degassed and heated under nitrogen at 170° C. for 3 minutes. The solution was cooled, diluted with methanol (1 mL), filtered, and purified by preparative LCMS. This afforded product as a white solid (4.4 mg, 78%). $^1$H NMR (400 MHz, CD$_3$OD): δ 7.79–7.77 (m, 2H), 7.62–7.39 (m, 10H), 5.35 (t, J=6.6 Hz, 1H), 5.06–5.01 (m, 1H), 3.52–3.20 (m, 4H); LCMS found for C$_{25}$H$_{22}$N$_5$O$_5$S$_2$ (M+H)$^+$: m/z=536.

Example 4.79

3-[3-Cyano-4-(1,1-dioxido-3-oxoisothiazolidin-5-yl)phenyl]-N-(4-phenylbutyl)-2-[(phenylsulfonyl)amino]propanamide

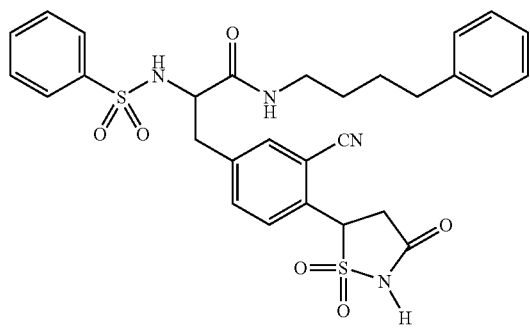

This compound was prepared according to the procedures of Example 4.78 using appropriate starting materials. $^1$H NMR (400 MHz, CD$_3$OD): δ 7.67–7.63 (m, 2H), 7.56–7.38 (m, 5H), 7.27–7.23 (m, 2H), 7.16–7.13 (m, 3H), 5.41–5.39 (m, 1H), 3.96–3.92 (m, 1H), 3.47–3.37 (m, 2H), 3.02–2.82 (m, 4H), 2.57 (t, J=7.6 Hz, 2H), 2.56 (t, J=7.5 Hz, 2H), 1.52–1.48 (m, 2H), 1.35–1.31 (m, 2H); LCMS found for C$_{29}$H$_{31}$N$_4$O$_6$S$_2$ (M+H)$^+$: m/z=595.

Example 4.80

Methyl 2-[4-((2S)-2-[(benzyloxy)carbonyl]amino-3-[3-chloro-4-(1,1-dioxido-3-oxoisothiazolidin-5-yl)phenyl]propanoylamino)butoxy]-6-hydroxybenzoate

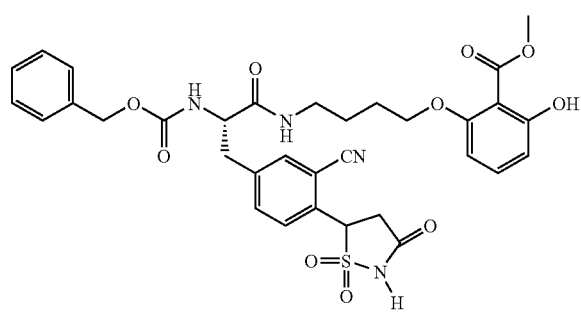

Step 1. Methyl (2S)-3-(4-amino-3-chlorophenyl)-2-[(tert-butoxycarbonyl-)amino]propanoate

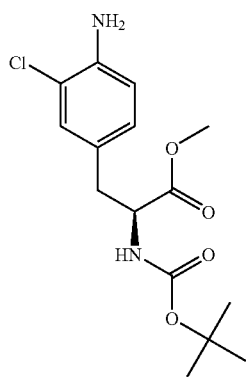

Methyl (2S)-3-(4-aminophenyl)-2-[(tert-butoxycarbonyl)amino]propanoate (1.0 g, 3.22 mmol) and N-chlorosuccinimide (474 mg, 3.55 mmol) were dissolved in DMF (20 mL) and allowed to stir under an atmosphere of nitrogen for 24 h. The reaction was quenched with water and diluted with ethyl acetate (100 mL). The organic phase was separated, dried over sodium sulfate, filtered and concentrated in vacuo. The crude material was purified by silica gel column (5–20% ethyl acetate/hexanes) to afford the product as a clear oil (645 mg, 61%). $^1$H NMR (400 MHz, CD$_3$OD): δ 7.05 (s, 1H), 6.90–6.87 (m, 1H), 6.76–6.74 (m, 1H), 4.27–4.23 (m, 1H), 3.68 (s, 3H), 2.97–2.92 (m, 1H), 2.78–2.72 (m, 1H), 1.39 (s, 9H); LCMS found for C$_{10}$H$_{14}$ClN$_2$O$_2$ (M+H)$^+$: m/z=229.

Step 2. Methyl (2S)-2-[(tert-butoxycarbonyl)amino]-3-(3-chloro-4-iodophenyl)propanoate

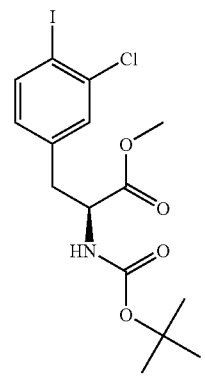

Methyl (2S)-3-(4-amino-3-chlorophenyl)-2-[(tert-butoxycarbonyl)amino]propanoate (3.00 g, 9.12 mmol) in aqueous hydrochloric acid solution (1.0 N, 100.0 mL) at 0° C. was treated with a solution of sodium nitrite (692 mg, 10.0 mmol) in water (10 mL). The solution was stirred at 0° C. for 30 minutes. A solution of potassium iodide (1.89 g, 11.4 mmol) in water (10 mL) was added and the solution stirred 30 minutes at rt and then 10 minutes at 35° C. The solution was diluted with ethyl acetate (200 mL), quenched with aqueous sodium thiosulfate solution (1.0 N, 500 mL), and the organic phase separated. The organic layer was washed with aqueous hydrochloric acid solution (1.0 N, 100 mL), brine (100 mL), and after drying over sodium sulfate was concentrated in vacuo. Purification by silica gel chromatography (10–40% ethyl acetate/hexanes) afforded product as a yellow solid (2.1 g, 53%). $^1$H NMR (400 MHz, CD$_3$OD): δ 7.80 (d, J=8.0 Hz, 1H), 7.37 (s, 1H), 6.90 (d, J=8.2 Hz, 1H), 4.36–4.33 (m, 1H), 3.70 (s, 3H), 3.12–3.07 (m, 1H), 2.86–2.80 (m, 1H), 1.37 (s, 9H); LCMS found for C$_{10}$H$_{12}$ClINO$_2$ (M+H)$^+$: m/z=340.

Step 3. Methyl (2S)-2-[(tert-butoxycarbonyl)amino]-3-[4-(2-tert-butyl-1,1-dioxido-3-oxo-2,3-dihydroisothiazol-5-yl)-3-chlorophenyl]propanoate

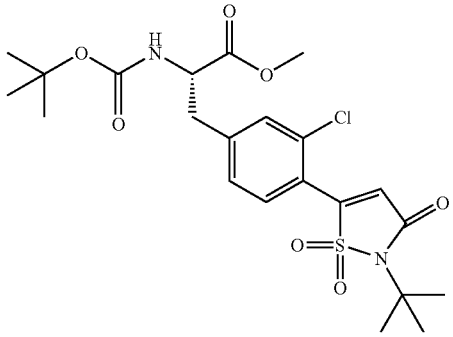

2-tert-Butylisothiazol-3(2H)-one 1,1-dioxide (284 mg, 1.50 mmol), palladium acetate (48 mg, 0.21 mmol) and tetra-N-butylammonium chloride (238 mg, 0.858 mmol) were combined. To this mixture was added methyl (2S)-2-[(tert-butoxycarbonyl)amino]-3-(3-chloro-4-iodophenyl)propanoate (377.2 mg, 0.8579 mmol) in DMF (4.00 mL). The reaction was treated with triethylamine (0.598 mL, 4.29 mmol). The reaction was then degassed and then allowed to stir under an atmosphere of nitrogen at 65° C. for 2 h. The reaction was quenched with water (50 mL), diluted with ethyl acetate (100 mL) and washed with aqueous hydrochloric acid solution (1.0 N, 100 mL). The organic was dried over sodium sulfate, filtered and was concentrated in vacuo. The crude material was purified by silica gel chromatography (5–25% ethyl acetate/hexanes) to afford the product as a white solid (100 mg, 23%). $^1$H NMR (400 MHz, CD$_3$OD): δ 7.80 (d, J=8.2 Hz, 1H), 7.54 (s, 1H), 7.35 (d, J=8.0 Hz, 1H), 7.03 (s, 1H), 4.44–4.40 (m, 1H), 3.73 (s, 3H), 3.25–3.20 (m, 1H), 2.95 (dd, J1=10.0 Hz, J2=13.7 Hz, 1H), 1.70 (s, 9H), 1.37 (s, 9H); LCMS found for C$_{17}$H$_{22}$ClN$_2$O$_5$S (M+H)$^+$: m/z=401.

Step 4. methyl (2S)-2-[(tert-butoxycarbonyl)amino]-3-[4-(2-tert-butyl-1,1-dioxido-3-oxoisothiazolidin-5-yl)-3-chlorophenyl]propanoate

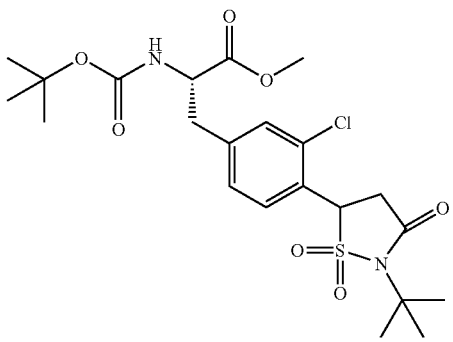

Methyl (2S)-2-[(tert-butoxycarbonyl)amino]-3-[4-(2-tert-butyl-1,1-dioxido-3-oxo-2,3-dihydroisothiazol-5-yl)-3-chlorophenyl]propanoate (300 mg, 0.598 mmol) in tetrahydrofuran (6.00 mL) was cooled to 0° C. and treated with lithium tetrahydroborate solution in tetrahydrofuran (2.0 M, 0.329 mL). The reaction was allowed to stir for 0.5 h at rt. After addition of acetic acid (0.5 mL), the solution was diluted with ethyl acetate (100 mL), washed with water (100 mL), separated, dried over sodium sulfate, filtered and was concentrated in vacuo. The crude material was purified by silica gel chromatography (5–30% ethyl acetate/hexanes) to afford the product as a white solid (162 mg, 54%). $^1$H NMR (400 MHz, CD$_3$OD): δ 7.45–7.42 (m, 2H), 7.31–7.27 (m, 1H), 5.59 (t, J=8.0 Hz, 1H), 4.39–4.36 (m, 1H), 3.70 (s, 3H), 3.38–3.33 (m, 1H), 3.25–3.14 (m, 2H), 2.95–2.92 (m, 1H), 1.67 (s, 9H), 1.37 (s, 9H); LCMS found for C$_{17}$H$_{24}$ClN$_2$O$_5$S (M+H)$^+$: m/z=403.

Step 5. (2S)-2-[(benzyloxy)carbonyl]amino-3-[3-chloro-4-(1,1-dioxido-3-oxoisothiazolidin-5-yl)phenyl]propanoic acid

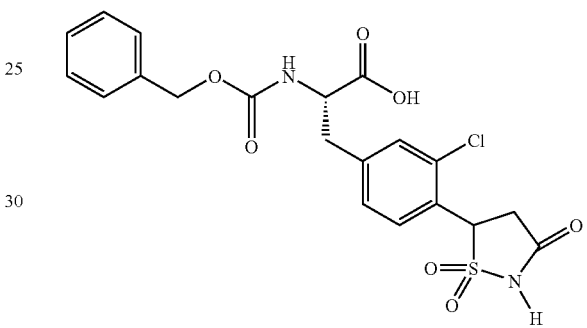

Methyl (2S)-2-amino-3-[3-chloro-4-(1,1-dioxido-3-oxoisothiazolidin-5-yl)phenyl]-propanoate trifluoroacetate (50.0 mg, 0.108 mmol) was dissolved in trifluoroacetic acid (3 mL) and heated in the microwave at 130° C. for 180 s. The reaction was concentrated in vacuo and then dissolved in methanol (1.0 mL). The solution was treated with triethylamine (75.6 µL, 0.542 mmol) and benzyl chloroformate (21.7 µL, 0.152 mmol). The reaction stirred at rt for 2 h. The reaction was then treated with aqueous lithium hydroxide solution (4.0 M, 0.14 mL) and allowed to stir for 2 h. The reaction was quenched with aqueous hydrochloric acid solution (1.0 N, 1.0 mL) and purified by reverse phase HPLC to afford the product as a white solid (26 mg, 51%). LCMS found for C$_{20}$H$_{20}$ClN$_2$O$_7$S (M+H)$^+$: m/z=467.

Step 6. Methyl 2-[4-((2S)-2-[(benzyloxy)carbonyl]amino-3-[3-chloro-4-(1,1-dioxido-3-oxoisothiazolidin-5-yl)phenyl]propanoylamino)butoxy]-6-hydroxybenzoate This compound was prepared according to the procedures of Example 4.71 using appropriate starting materials. $^1$H NMR (400 MHz, CD$_3$OD): δ 7.52–7.42 (m, 1H), 7.35–7.20 (m, 8H), 6.54–6.46 (m, 2H), 5.67–5.62 (m, 1H), 5.03 (s, 2H), 4.35–4.28 (m, 1H), 3.98–3.94 (m, 2H), 3.85 (s, 3H), 3.48–3.37 (m, 2H), 3.26–2.85 (m, 4H), 1.70–1.55 (m, 4H); LCMS found for C$_{32}$H$_{35}$ClN$_3$O$_{10}$S (M+H)$^+$ m/z=688.

Example 4.81

Benzyl (1S)-1-(1H-benzimidazol-2-yl)-2-[3-chloro-4-(1,1-dioxido-3-oxoisothiazolidin-5-yl)phenyl]ethylcarbamate trifluoroacetate

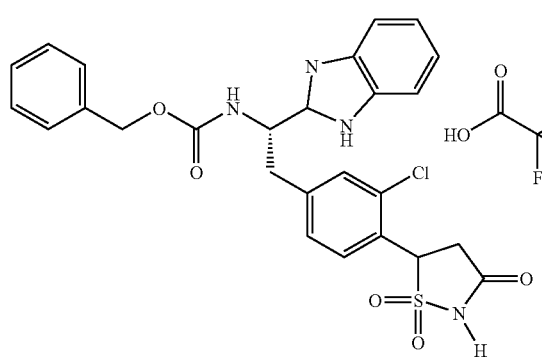

Step 1. Benzyl (1R)-2-[(2-aminophenyl)amino]-1-[3-chloro-4-(1,1-dioxido-3-oxoisothiazolidin-5-yl)benzyl]-2-oxoethylcarbamate

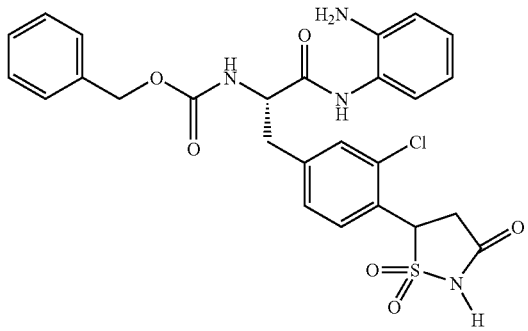

This compound was prepared according to the procedures of Example 4.77, Step 1, using appropriate starting materials. The crude product was used without purification. LCMS found for $C_{26}H_{26}ClN_4O_6S$ (M+H)$^+$: m/z=557

Step 2. Benzyl (1S)-1-(1H-benzimidazol-2-yl)-2-[3-chloro-4-(1,1-dioxido-3-oxoisothiazolidin-5-yl)phenyl]ethylcarbamate trifluroacetate Benzyl (1S)-2-[(2-aminophenyl)amino]-1-[3-chloro-4-(1,1-dioxido-3-oxo-isothiazolidin-5-yl)benzyl]-2-oxoethylcarbamate (10.0 mg, 0.0180 mmol) was heated in acetic acid (1 mL) at 60° C. for 1 h. The solution was concentrated in vacuo. Purification by preparative LCMS afforded product as a white solid (7.6 mg, 78%). $^1$H NMR (400 MHz, CD$_3$OD): δ 7.76–7.74 (m, 2H), 7.65–7.55 (m, 2H), 7.50–7.42 (m, 6H), 5.63 (t, J=7.6, 1H), 5.40–5.30 (m, 1H), 5.05 (s, 2H), 3.47–3.35 (m, 4H), 3.27–3.20 (m, 2H); LCMS found for $C_{26}H_{24}ClN_4O_5S$ (M+H)$^+$: m/z=539.

Example 4.82

3-[3-Chloro-4-(1,1-dioxido-3-oxoisothiazolidin-5-yl)phenyl]-N-(4-phenylbutyl)-2-[(phenylsulfonyl)-amino]propanamide

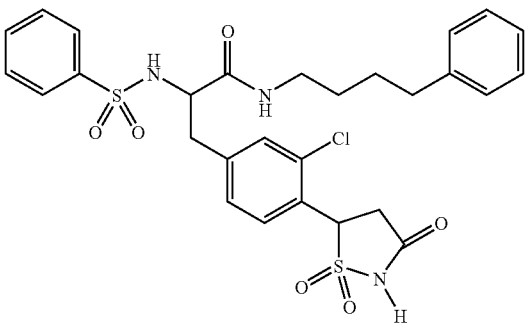

Step 1. (2S)-3-[3-Chloro-4-(1,1-dioxido-3-oxoisothiazolidin-5-yl)phenyl]-2-[(phenylsulfonyl)-amino]-propanoic acid)

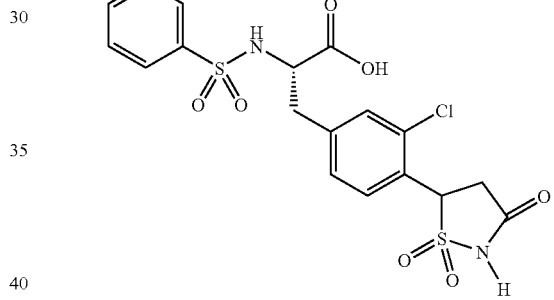

Methyl (2S)-2-amino-3-[3-chloro-4-(1,1-dioxido-3-oxoisothiazolidin-5-yl)-phenyl]-propanoate trifluoroacetate (145 mg, 0.314 mmol) was dissolved in trifluoroacetic acid (3 mL) and heated in the microwave at 130° C. for 180 s. The reaction was concentrated in vacuo and azetroped with toluene (5 mL). The product was dissolved in methanol (2 mL), was treated with triethylamine (170 µL, 1.2 mmol) and then benzenesulfonyl chloride (60 µL, 0.47 mmol). The solution stirred at rt for 1 h. 4 M aqueous lithium hydroxide solution (0.782 mL) was added and the solution stirred 3 h at rt. The solution was acidified with aqueous hydrochloric acid solution (1.0 N, 4.0 mL), diluted with methanol to 10 mL volume, and then purified by reverse phase HPLC to afford product as a white solid (108 mg, 73%). $^1$H NMR (400 MHz, CD$_3$OD): δ 7.66–7.64 (m, 2H), 7.63–7.51 (m, 1H), 7.44–7.38 (m, 3H), 7.31–7.16 (m, 2H), 5.65–5.61 (m, 1H), 4.10–4.03 (m, 1H), 3.48–3.42 (m, 1H), 3.29–3.27 (m, 1H), 3.12–3.07 (m, 1H), 2.88–2.81 (m, 1H); LCMS found for $C_{18}H_{21}ClN_3O_7S_2$ (M+H)$^+$: m/z=490.

Step 2. 3-[3-chloro-4-(1,1-dioxido-3-oxoisothiazolidin-5-yl)phenyl]-N-(4-phenylbutyl)-2-[(phenylsulfonyl)-amino]propanamide (2S)-3-[3-chloro-4-(1,1-dioxido-3-oxoisothiazolidin-5-yl)phenyl]-2-[(phenylsulfonyl)-amino]propanoic acid (15.0 mg, 0.0317 mmol) in DMF (1 mL) was treated with benzotriazol-1-yloxytris(dimethylamino)phosphonium hexafluorophosphate (16.8 mg, 0.0381 mmol) and stirred at rt for 5 minutes. A solution of 4-phenylbutan-1-amine (10 μL, 0.0634 mmol) and N,N-diisopropylethylamine (28 μL, 0.16 mmol) in DMF (1 mL) was added and the reaction stirred at rt for 1 h. Purification by preparative LCMS afforded product as a white solid (12.9 mg, 67%). $^1$H NMR (400 MHz, CD$_3$OD): δ 7.68–7.64 (m, 2H), 7.54–7.34 (m, 4H), 7.27–7.11 (m, 7H), 5.59–5.57 (m, 1H), 3.92–3.87 (m, 1H), 3.42–3.35 (m, 1H), 3.35–3.28 (m, 1H), 2.99–2.84 (m, 3H), 2.79–2.74 (m, 1H), 2.56 (t, J=7.5 Hz, 2H), 1.53–1.47 (m, 2H), 1.33–1.29 (m, 2H); LCMS found for C$_{28}$H$_{31}$ClN$_3$O$_6$S$_2$ (M+H)$^+$: m/z=604.

Example 4.83

3-[3-Chloro-4-(1,1-dioxido-3-oxoisothiazolidin-5-yl)phenyl]-N-(4-phenoxybutyl)-2-[(phenylsulfonyl)-amino]propanamide

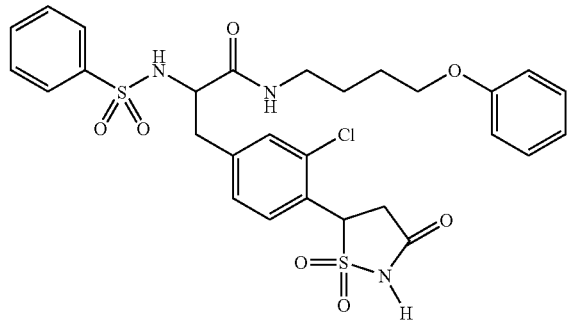

This compound was prepared according to the procedures of Example 4.82 using appropriate starting materials. $^1$H NMR (400 MHz, CD$_3$OD): δ 7.96 (brs, 1H), 7.71–7.68 (m, 2H), 7.54–7.38 (m, 4H), 7.35–7.12 (m, 4H), 6.90–6.88 (m, 2H), 5.63–5.58 (m, 1H), 3.95–3.88 (m, 3H), 3.41–3.34 (m, 2H), 3.03–2.76 (m, 4H), 1.63–1.58 (m, 2H), 1.47–1.42 (m, 2H); LCMS found for C$_{28}$H$_{31}$ClN$_3$O$_7$S$_2$ (M+H)$^+$: m/z=620.

Example 4.84

Methyl 2-[4-(3-[3-chloro-4-(1,1-dioxido-3-oxoisothiazolidin-5-yl)phenyl]-2-[(phenylsulfonyl)-amino]propanoylamino)butoxy]benzoate

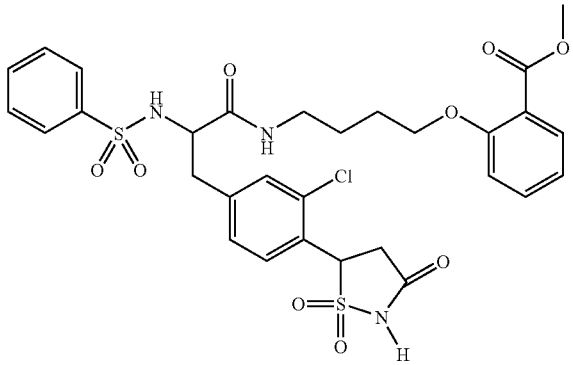

This compound was prepared according to the procedures of Example 4.82 using appropriate starting materials. $^1$H NMR (400 MHz, CD$_3$OD): δ 8.01 (brs, 1H), 7.75 (d, J=7.8 Hz, 1H), 7.70–7.66 (m, 2H), 7.53–7.29 (m, 5H), 7.23–6.97 (m, 4H), 5.62–5.58 (m, 1H), 4.06–4.00 (m, 3H), 3.86 (s, 3H), 3.40–3.35 (m, 1H), 3.34–3.29 (m, 1H), 3.08–2.81 (m, 4H), 1.64–1.49 (m, 4H); LCMS founder for C$_{30}$H$_{33}$ClN$_3$O$_9$S$_2$ (M+H)$^+$: m/z=678.

Example 4.85

3-[3-Chloro-4-(1,1-dioxido-3-oxoisothiazolidin-5-yl)phenyl]-N-[4-(3-hydroxyphenoxy)-butyl]-2-[(phenylsulfonyl)-amino]propanamide

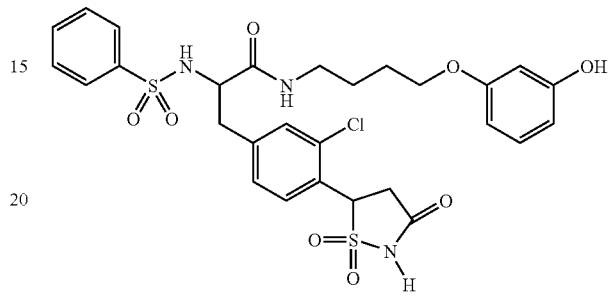

This compound was prepared according to the procedures of Example 4.82 using appropriate starting materials. $^1$H NMR (400 MHz, CD$_3$OD): δ 7.69 (t, J=6.0 Hz, 2H), 7.52–7.38 (m, 4H), 7.34–7.02 (m, 3H), 6.39–6.34 (m, 3H), 5.62–5.56 (m, 1H), 3.95–3.92 (m, 1H), 3.87–3.85 (m, 2H), 3.40–3.36 (m, 1H), 3.34–3.30 (m, 1H), 3.00–2.78 (m, 4H), 1.60–1.56 (m, 2H), 1.46–1.41 (m, 2H); LCMS found for C$_{28}$H$_{31}$ClN$_3$O$_8$S$_2$ (M+H)$^+$: m/z=636.

Example 4.86

Methyl 3-[4-(3-[3-chloro-4-(1,1-dioxido-3-oxoisothiazolidin-5-yl)phenyl]-2-[(phenylsulfonyl)amino]propanoylamino)butoxy]-2-naphthoate

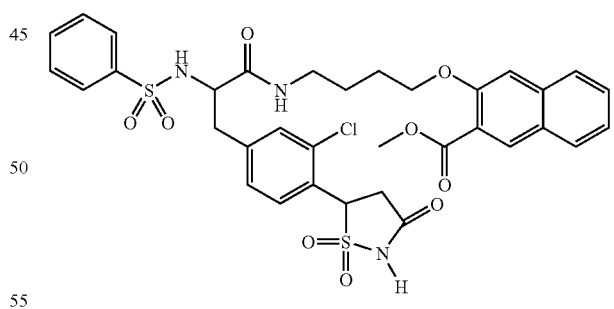

This compound was prepared according to the procedures of Example 4.82 using appropriate starting materials. $^1$H NMR (400 MHz, CD$_3$OD): δ 8.27 (s, 1H), 7.81 (dd, J=18.3, 8.0 Hz, 2H), 7.68–7.65 (m, 2H), 7.53–7.47 (m, 2H), 7.40–7.35 (m, 4H), 7.26–7.20 (m, 1H), 7.10 (dd, J=15.2, 6.4 Hz, 1H), 5.63–5.57 (m, 1H), 4.09–4.05 (m, 2H), 3.99–3.94 (m, 1H), 3.92 (s, 3H), 3.50–3.44 (m, 1H), 3.30–3.23 (m, 1H), 3.12–3.08 (m, 1H), 2.98–2.89 (m, 2H), 2.81–2.77 (m, 1H), 1.71–1.65 (m, 2H), 1.58–1.53 (m, 2H); LCMS found for C$_{34}$H$_{35}$ClN$_3$O$_9$S$_2$ (M+H)$^+$: m/z=728.

Example 4.87

Methyl 3-[5-(3-[3-chloro-4-(1,1-dioxido-3-ox-oisothiazolidin-5-yl)phenyl]-2-[(phenylsulfonyl)amino]propanoylamino)pentyl]oxy-2-naphthoate

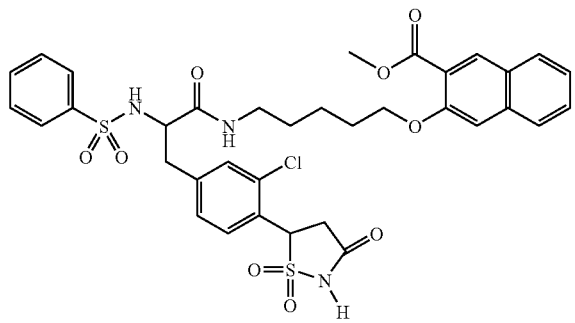

This compound was prepared according to the procedures of Example 4.82 using appropriate starting materials. $^1$H NMR (400 MHz, CD$_3$OD): δ 8.20 (s, 1H), 7.81 (dd, J=16.4, 8.2 Hz, 2H), 7.68–7.65 (m, 2H), 7.53–7.47 (m, 2H), 7.40–7.35 (m, 4H), 7.26–7.20 (m, 1H), 7.14–7.06 (m, 1H), 5.61–5.57 (m, 1H), 4.13–4.07 (m, 2H), 3.97–3.93 (m, 1H), 3.91 (s, 3H), 3.45 (dd, J=14.8, 8.4 Hz, 1H), 3.30–3.23 (m, 1H), 3.09–3.00 (m, 1H), 2.95–2.87 (m, 2H), 2.78–2.71 (m, 1H), 1.84–1.79 (m, 2H), 1.44–1.36 (m, 4H); LCMS found for C$_{35}$H$_{37}$ClN$_3$O$_9$S$_2$ (M+H)$^+$: m/z=742.

Example 4.88

Methyl 2-[5-((2S)-3-[3-chloro-4-(1,1-dioxido-3-oxoisothiazolidin-5-yl)phenyl]-2-[(phenylsulfonyl)-amino]propanoylamino)pentyl]oxy-6-hydroxybenzoate

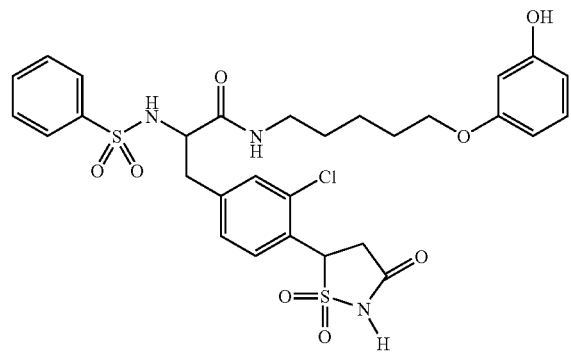

This compound was prepared according to the procedures of Example 4.82 using appropriate starting materials. $^1$H NMR (400 MHz, CD$_3$OD): δ 7.92 (bs, 1H), 7.69–7.65 (m, 2H), 7.53–7.51 (m, 1H), 7.45–7.34 (m, 3H), 7.28–7.21 (m, 3H), 6.48 (dd, J$_1$=8.6, J$_2$=11.3 Hz, 2H), 5.61–5.59 (m, 1H), 3.97–3.91 (m, 3H), 3.87 (s, 3H), 3.50–3.35 (m, 1H), 2.97–2.75 (m, 5H), 1.72 (m, 2H), 1.36 (m, 4H); LCMS found for C$_{31}$H$_{35}$ClN$_3$O$_{10}$S$_2$ (M+H)$^+$: m/z=708.

Example 4.89

3-[3-Chloro-4-(1,1-dioxido-3-oxoisothiazolidin-5-yl)phenyl]-N-[4-(3-chlorophenoxy)butyl]-2-[(phenylsulfonyl)-amino]propanamide

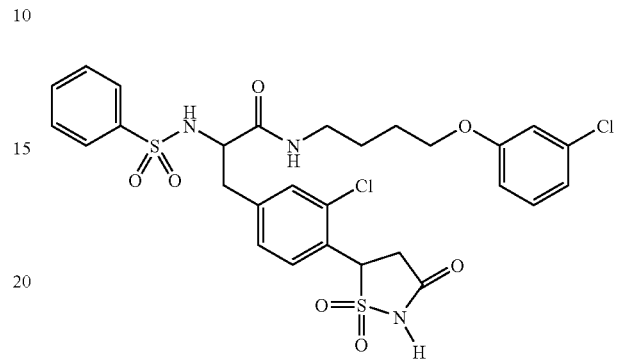

This compound was prepared according to the procedures of Example 4.82 using appropriate starting materials. $^1$H NMR (400 MHz, CD$_3$OD): δ 7.70–7.67 (m, 2H), 7.52–7.45 (m, 1H), 7.45–7.36 (m, 3H), 7.29–7.13 (m, 3H), 6.92–6.83 (m, 3H), 5.62–5.60 (m, 1H), 3.93–3.90 (m, 3H), 3.40–3.37 (m, 1H), 3.34–3.25 (m, 1H), 3.03–2.78 (m, 5H), 1.62–1.59 (m, 2H), 1.47–1.43 (m, 2H); LCMS found for C$_{28}$H$_{30}$Cl$_2$N$_3$O$_7$S$_2$ (M+H)$^+$: m/z=654.

Example 4.90

3-[3-Chloro-4-(1,1-dioxido-3-oxoisothiazolidin-5-yl)phenyl]-N-[4-(3-fluorophenoxy)butyl]-2-[(phenylsulfonyl)-amino]propanamide

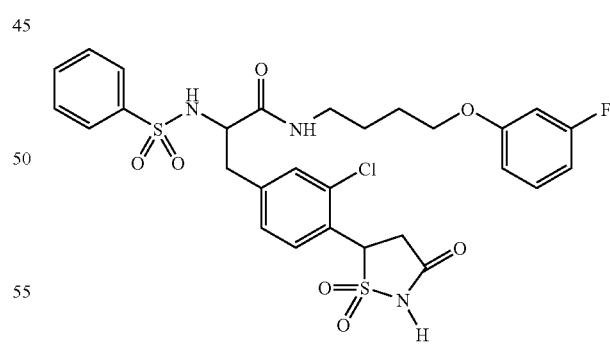

This compound was prepared according to the procedures of Example 4.82 using appropriate starting materials. $^1$H NMR (400 MHz, CD$_3$OD): δ 7.70–7.67 (m, 2H), 7.52–7.50 (m, 1H), 7.45–7.36 (m, 3H), 7.29–7.13 (m, 3H), 6.73–6.63 (m, 3H), 5.63–5.60 (m, 1H), 3.93–3.89 (m, 3H), 3.40–3.37 (m, 1H), 3.04–2.78 (m, 5H), 1.62–1.59 (m, 2H), 1.47–1.43 (m, 2H); LCMS found for C$_{28}$H$_{30}$ClFN$_3$O$_7$S$_2$ (M+H)$^+$: m/z=638.

Example 4.91

3-[3-Chloro-4-(1,1-dioxido-3-oxoisothiazolidin-5-yl)phenyl]-N-[4-(3-methylphenoxy)butyl]-2-[(phenylsulfonyl)-amino]propanamide

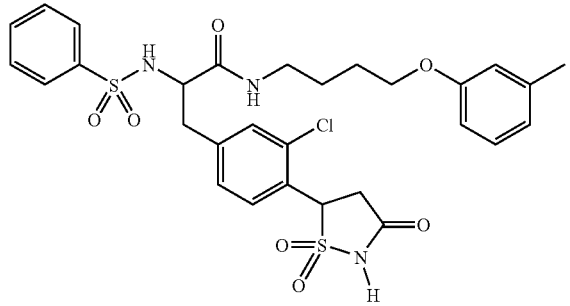

This compound was prepared according to the procedures of Example 4.82 using appropriate starting materials. $^1$H NMR (400 MHz, CD$_3$OD): δ 7.71–7.69 (m, 2H), 7.52–7.50 (m, 1H), 7.45–7.35 (m, 3H), 7.28–7.10 (m, 3H), 6.72–6.67 (m, 3H), 5.60–5.56 (m, 1H), 3.93–3.88 (m, 3H), 3.40–3.33 (m, 1H), 3.06–2.78 (m, 5H), 1.59–1.46 (m, 2H), 1.45–1.41 (m, 2H); LCMS found for C$_{29}$H$_{33}$ClN$_3$O$_7$S$_2$ (M+H$^+$: m/z=634.

Example 4.92

3-[3-Chloro-4-(1,1-dioxido-3-oxoisothiazolidin-5-yl)phenyl]-N-[4-(3-methoxyphenoxy)buytl]-2-[(phenylsulfonyl)-amino]propanamide

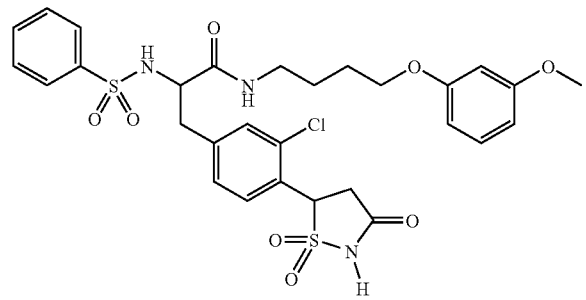

This compound was prepared according to the procedures of Example 4.82 using appropriate starting materials. $^1$H NMR (400 MHz, CD$_3$OD): 567.71–7.67 (m, 2H), 7.52–7.50 (m, 1H), 7.45–7.36 (m, 3H), 7.28–7.12 (m, 3H), 6.49–6.45 (m, 3H), 5.62–5.58 (m, 1H), 3.93–3.88 (m, 3H), 3.75 (s, 3H), 3.38–3.34 (m, 1H), 3.28–3.24 (m, 2H), 3.05–2.78 (m, 5H), 1.60–1.55 (m, 2H), 1.46–1.43 (m, 2H); LCMS found for C$_{29}$H$_{33}$ClN$_3$O$_8$S$_2$ (M+H)$^+$: m/z=650.

Example 4.93

3-[3-Chloro-4-(1,1-dioxido-3-oxoisothiazolidin-5-yl)phenyl]-2-[(phenylsulfonyl)-amino]-N-4-[2-(1H-pyrazol-5-yl)phenoxy]butylpropanamide trifluoroacetate

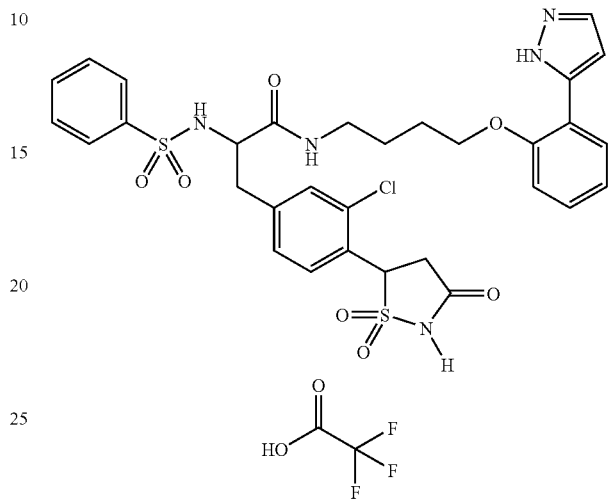

This compound was prepared according to the procedures of Example 4.82 using appropriate starting materials. $^1$H NMR (400 MHz, CD$_3$OD): δ 7.99 (bs, 1H), 7.87 (bs, 1H), 7.71–7.56 (m, 3H), 7.51–7.47 (m, 1H), 7.42–7.25 (m, 4H), 7.18–7.13 (m, 2H), 7.06–7.03 (m, 2H), 6.90 (bs, 1H), 5.62–5.55 (m, 1H), 4.12–4.09 (m, 2H), 3.93–3.88 (m, 1H), 3.40–3.33 (m, 1H), 3.27–3.19 (m, 1H), 3.06–2.99 (m, 1H), 2.95–2.90 (m, 2H), 2.78–2.73 (m, 1H), 1.71–1.70 (m, 2H), 1.50–1.40 (m, 2H); LCMS founder for C$_{31}$,H$_{33}$ClN$_5$O$_7$S$_2$ (M+H)$^+$: m/z=686.

Example 4.94

3-[3-Chloro-4-(1,1-dioxido-3-oxoisothiazolidin-5-yl)phenyl]-N-[4-(2-isoxazol-5-ylphenoxy)butyl]-2-[(phenylsulfonyl)-amino]propanamide

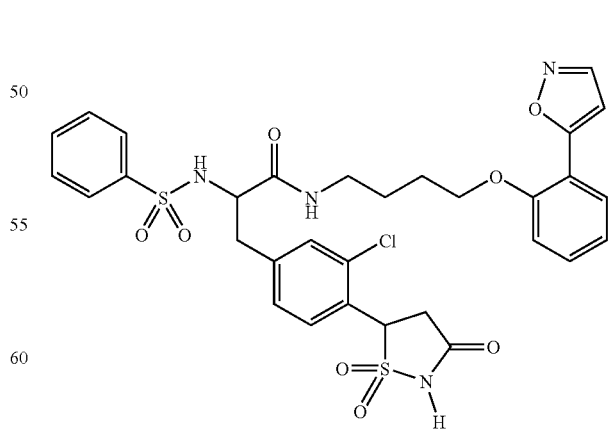

This compound was prepared according to the procedures of Example 4.82 using appropriate starting materials. $^1$H NMR (400 MHz, CD$_3$OD): δ 8.44 (bs, 1H), 8.01 (m, 1H), 7.90 (d, J=7.8 Hz, 1H), 7.69–7.67 (m, 2H), 7.52–7.27 (m, 5H), 7.19–7.05 (m, 3H), 6.86 (bs, 1H), 5.60–5.57 (m, 1H), 4.12 (t, J=6.2 Hz, 2H), 3.94–3.90 (m, 1H), 3.38–3.34 (m, 1H), 3.27–3.23 (m, 1H), 3.08–3.04 (m, 1H), 2.99–2.92 (m, 2H), 2.79–2.74 (m, 1H), 1.78–1.75 (m, 2H), 1.55–1.49 (m, 2H); LCMS found for $C_{31}H_{32}ClN_4O_8S_2$ (M+H)$^+$: m/z=687.

Example 4.95

Methyl 2-[4-(3-[3-Chloro-4-(1,1-dioxido-3-oxoisothiazolidin-5-yl)phenyl]-2-[(phenylsulfonyl)amino]propanoylamino)butoxy]-6-hydroxybenzoate

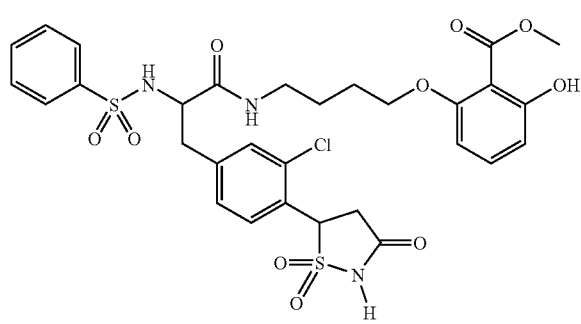

This compound was prepared according to the procedures of Example 4.82 using appropriate starting materials. $^1$H NMR (400 MHz, CD$_3$OD): δ 7.95 (bs, 1H), 7.69–7.66 (m, 2H), 7.52–7.50 (m, 1H), 7.45–7.34 (m, 3H), 7.27–7.10 (m, 3H), 6.50–6.46 (m, 2H), 5.62–5.56 (m, 1H), 3.84–3.89 (m, 3H), 3.87 (s, 3H), 3.43–3.37 (m, 1H), 3.28–3.23 (m, 1H), 3.08–3.03 (m, 1H), 2.99–2.92 (m, 2H), 2.79–2.77 (m, 1H), 1.65–1.58 (m, 2H), 1.53–1.47 (m, 2H); LCMS found for $C_{30}H_{33}ClN_3O_{10}S_2$ (M+H)$^+$: m/z=694.

Example 4.96

Methyl 2-[2-(3-[3-chloro-4-(1,1-dioxido-3-oxoisothiazolidin-5-yl)phenyl]-2-[(phenylsulfonyl)amino]propanoylamino)ethoxy]-6-hydroxybenzoate

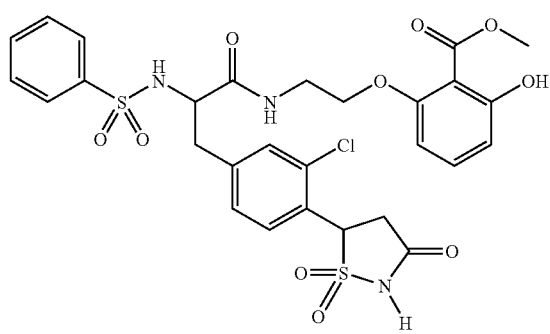

This compound was prepared according to the procedures of Example 4.92 using appropriate starting materials. $^1$H NMR (400 MHz, CD$_3$OD): δ 8.03 (bs, 1H), 7.66 (t, J=8.4 Hz, 2H), 7.49–7.48 (m, 1H), 7.41–7.37 (m, 2H), 7.33–7.23 (m, 3H), 7.17–7.11 (m, 1H), 6.52 (d, J=8.2 Hz, 1H), 6.48–6.44 (m, 1H), 5.58–5.50 (m, 1H), 3.99–3.94 (m, 1H), 3.90 (s, 3H), 3.89–3.83 (m, 2H), 3.43–3.35 (m, 3H), 3.26–3.23 (m, 1H), 2.99–2.94 (m, 1H), 2.81–2.77 (m, 1H); LCMS found for $C_{28}H_{29}ClN_3O_{10}S_2$ (M+H)$^+$: m/z=666.

Example 4.97

3-[3-Chloro-4-(1,1-dioxido-3-oxoisothiazolidin-5-yl)phenyl]-N-(5-phenoxypentyl)-2-[(phenylsulfonyl)amino]propanamide

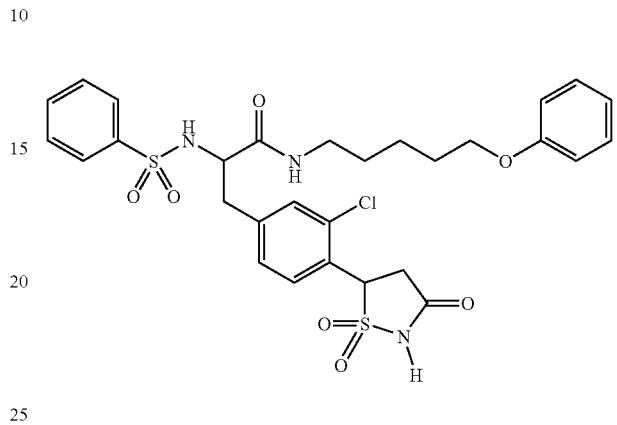

This compound was prepared according to the procedures of Example 4.82 using appropriate starting materials. $^1$H NMR (400 MHz, CD$_3$OD): δ 7.95–7.93 (m, 1H), 7.69–7.66 (m, 2H), 7.55–7.51 (m, 1H), 7.44–7.35 (m, 3H), 7.28–7.10 (m, 4H), 6.89–6.87 (m, 2H), 5.62–5.58 (m, 1H), 3.95–3.90 (m, 3H), 3.44–3.38 (m, 1H), 3.27–3.23 (m, 1H), 3.03–2.86 (m, 4H), 2.79–2.74 (m, 1H), 1.73–1.72 (m, 2H), 1.36–1.35 (m, 4H); LCMS found for $C_{29}H_{33}ClN_3O_7S_2$ (M+H)$^+$: m/z=634.

Example 4.98

Methyl 2-[5-(3-[3-chloro-4-(1,1-dioxido-3-oxoisothiazolidin-5-yl)phenyl]-2-[(phenylsulfonyl)amino]propanoylamino)pentyl]oxybenzoate

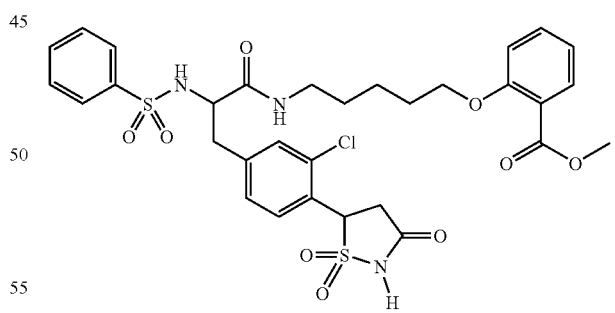

This compound was prepared according to the procedures of Example 4.82 using appropriate starting materials. $^1$H NMR (400 MHz, CD$_3$OD): δ 7.91–7.90 (m, 1H), 7.71–7.65 (m, 3H), 7.55–7.34 (m, 5H), 7.27–7.07 (m, 3H), 6.98–6.95 (m, 1H), 5.62–5.58 (m, 1H), 4.04–4.02 (m, 2H), 3.97–3.91 (m, 1H), 3.83 (s, 3H), 3.45–3.38 (m, 1H), 3.27–3.23 (m, 1H), 3.03–2.86 (m, 3H), 2.80–2.76 (m, 1H), 1.76–1.73 (m, 2H), 1.38–1.37 (m, 4H); LCMS found for $C_{31}H_{35}ClN_3O_9S_2$ (M+H)$^+$: m/z=692.

Example 4.99

3-[3-Chloro-4-(1,1-dioxido-3-oxoisothiazolidin-5-yl)phenyl]-N-[5-(3-hydroxyphenoxy)pentyl]-2-[(phenylsulfonyl)-amino]propanamide

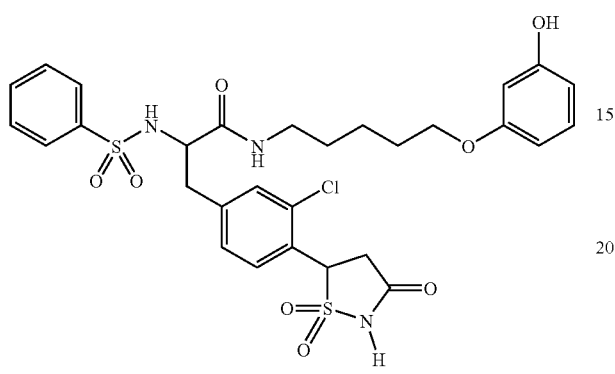

This compound was prepared according to the procedures of Example 4.82 using appropriate starting materials. $^1$H NMR (400 MHz, CD$_3$OD): δ 7.68–7.67 (m, 2H), 7.54–7.51 (m, 1H), 7.45–7.43 (m, 2H), 7.36–7.02 (m, 6H), 6.38–6.33 (m, 2H), 5.50–5.49 (m, 1H), 3.95–3.88 (m, 3H), 3.48–3.35 (m, 1H), 3.20–3.12 (m, 1H), 2.99–2.86 (m, 3H), 2.79–2.77 (m, 1H), 1.70–1.60 (m, 2H), 1.35–1.34 (m, 4H); LCMS found for C$_{29}$H$_{33}$ClN$_3$O$_8$S$_2$ (M+H)$^+$: m/z=650.

Example 4.100

Methyl 2-[3-(3-[3-chloro-4-(1,1-dioxido-3-oxoisothiazolidin-5-yl)phenyl]-2-[(phenylsulfonyl)amino]propanoylamino)propoxy]-6-hydroxybenzoate

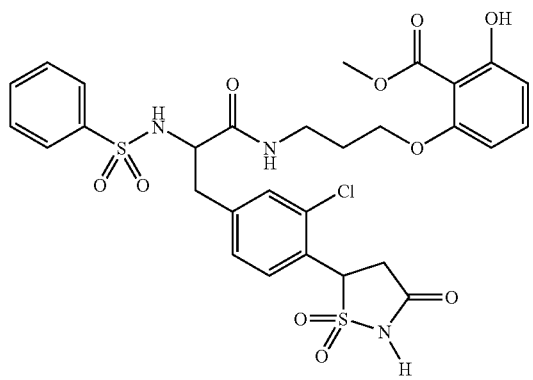

This compound was prepared according to the procedures of Example 4.82 using appropriate starting materials. $^1$H NMR (400 MHz, CD$_3$OD): δ 7.67–7.64 (m, 2H), 7.53–7.50 (m, 1H), 7.37–7.11 (m, 6H), 6.51–6.48 (m, 2H), 5.62–5.58 (m, 1H), 3.99–3.95 (m, 1H), 3.89 (s, 3H), 3.87–3.82 (m, 2H), 3.41–2.78 (m, 6H), 1.74–1.69 (m, 2H); LCMS found for C$_{29}$H$_{31}$ClN$_3$O$_{10}$S$_2$ (M+H)$^+$: m/z=680.

Example 4.101

Methyl 2-[6-(3-[3-chloro-4-(1,1-dioxido-3-oxoisothiazolidin-5-yl)phenyl]-2-[(phenylsulfonyl)amino]propanoylamino)hexyl-oxy]-6-hydroxybenzoate

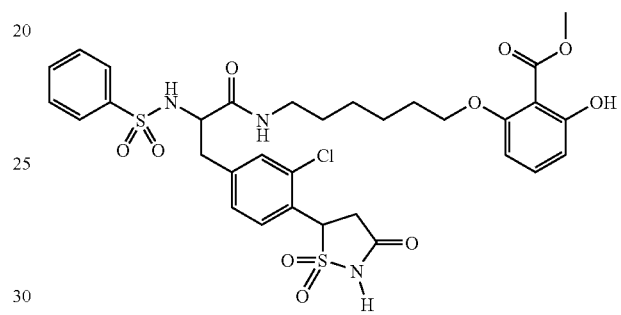

This compound was prepared according to the procedures of Example 4.82 using appropriate starting materials. $^1$H NMR (400 MHz, CD$_3$OD): δ 7.95–7.91 (m, 1H), 7.67–7.65 (m, 2H), 7.44–7.26 (m, 4H), 7.23–7.09 (m, 3H), 6.50–6.44 (m, 2H), 5.62–5.60 (m, 1H), 3.99–3.97 (m, 2H), 3.92–3.90 (m, 1H), 3.87 (s, 3H), 3.42 (dd, J=17.4, 8.4 Hz, 1H), 3.33–3.27 (m, 1H), 3.02–2.89 (m, 3H), 2.76–2.72 (m, 1H), 1.77–1.73 (m, 2H), 1.48–1.46 (m, 2H), 1.34–1.27 (m, 4H); LCMS found for C$_{29}$H$_{31}$ClN$_3$O$_{10}$S$_2$ (M+H)$^+$: m/z=722.

Example 4.102

N-(1S)-1-(1H-Benzimidazol-2-yl)-2-[3-chloro-4-(1,1-dioxido-3-oxoisothiazolidin-5-yl)phenyl]ethylbenzenesulfonamide trifluoroacetate

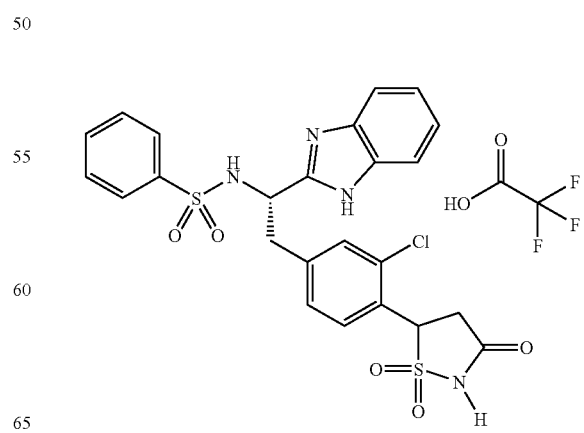

Step 1. N-(2-aminophenyl)-3-[3-chloro-4-(1,1-dioxido-3-oxoisothiazolidin-5-yl)phenyl]-2-[(phenylsulfonyl)amino]propanamide

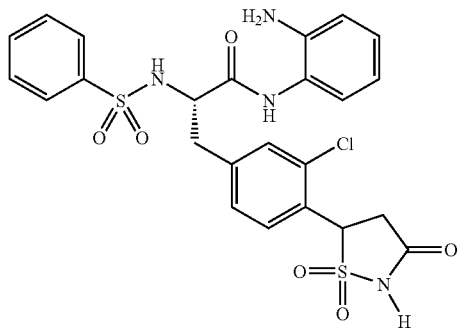

This compound was prepared according to the procedures of Example 4.77, Step 1, using appropriate starting materials. The crude product was used without purification. LCMS found for $C_{24}H_{24}ClN_4O_6S_2$ (M+H)$^+$: m/z=563

Step 2. N-(1S)-1-(1H-benzimidazol-2-yl)-2-[3-chloro-4-(1,1-dioxido-3-oxoisothiazolidin-5-yl)phenyl]ethylbenzenesulfonamide trifluoroacetate (2S)-N-(2-aminophenyl)-3-[3-chloro-4-(1,1-dioxido-3-oxoisothiazolidin-5-yl)phenyl]-2-[(phenylsulfonyl)-amino]propanamide (13.5 mg, 0.0240 mmol) was heated in acetic acid (2.0 mL) at 60° C. for 1 h. The solution was concentrated in vacuo. Purification by preparative LCMS afforded product as a white solid (7.5 mg, 57%). $^1$H NMR (400 MHz, CD$_3$OD): δ 7.78–7.75 (m, 2H), 7.64–7.60 (m, 4H), 7.55–7.51 (m, 1H), 7.42–7.37 (m, 2H), 7.30–7.28 (m, 1H), 7.18–7.00 (m, 2H), 5.62–5.56 (m, 1H), 5.00–4.99 (m, 1H), 3.48–3.39 (m, 2H), 3.26–3.17 (m, 2H); LCMS found for $C_{24}H_{22}ClN_4O_5S_2$ (M+H)$^+$: m/z=545.

Example 4.103 tert-Butyl (1S)-1-[4-(1,1-dioxido-3-oxoisothiazolidin-5-yl)benzyl]-2-oxo-2-[(4-phenylbutyl)amino]ethylcarbamate

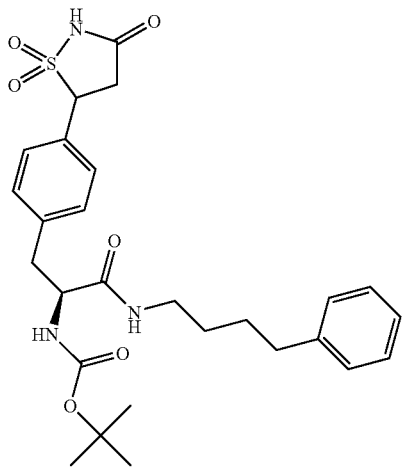

This compound was prepared according to the procedures of Example 4.82 using appropriate starting materials. $^1$H NMR (400 MHz, CD$_3$OD): δ 7.39–7.37 (m, 2H), 7.31–7.29 (m, 2H), 7.26–7.24 (m, 2H), 7.23–7.18 (m, 2H), 7.17–7.12 (m, 3H), 5.05–5.01 (m, 1H), 4.25–4.20 (m, 1H), 3.27–3.04 (m, 5H), 2.89–2.85 (m, 1H), 2.61–2.58 (m, 2H), 1.58–1.53 (m, 2H), 1.45–1.44 (m, 2H), 1.37 (s, 9H); LCMS found for $C_{22}H_{28}N_3O_4S$ (M+H)$^+$: m/z=530.

Example 4.104

Methyl 2-[4-((2S)-2-[(tert-butoxycarbonyl)amino]-3-[4-(1,1-dioxido-3-oxoisothiazolidin-5-yl)phenyl]propanoylamino)butoxy]-6-hydroxybenzoate

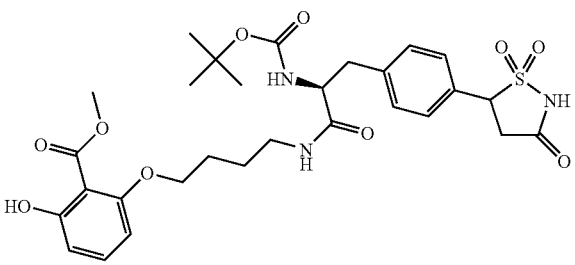

This compound was prepared according to the procedures of Example 4.82 using appropriate starting materials. $^1$H NMR (400 MHz, CD$_3$OD): δ 7.40 (d, J=7.8 Hz, 2H), 7.31 (d, J=8.3 Hz, 2H), 7.25 (t, J=8.3 Hz, 1H), 6.51–6.46 (m, 2H), 5.04–4.98 (m, 1H), 4.25–4.23 (m, 1H), 3.98–3.95 (m, 2H), 3.89 (s, 3H), 3.27–2.78 (m, 6H), 1.70–1.60 (m, 4H), 1.38 (s, 9H); LCMS found for $C_{29}H_{38}N_3O_{10}S$ (M+H)$^+$: m/z=620.

Example 4.105

Methyl 2-((7S,10S)-10-benzyl-7-[4-(1,1-dioxido-3-oxoisothiazolidin-5-yl)benzyl]-14,14-dimethyl-6,9,12-trioxo-13-oxa-5,8,11-triazapentadec-1-yloxy)-6-hydroxybenzoate

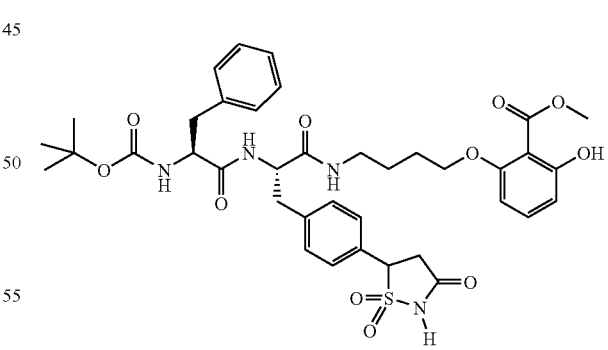

This compound was prepared according to the procedures of Example 4.71 using appropriate starting materials. $^1$H NMR (400 MHz, CD$_3$OD): δ 7.41 (d, J=8.3 Hz, 2H), 7.31–7.17 (m, 8H), 6.15–6.46 (m, 2H), 6.48 (t, J=8.8 Hz, 1H), 4.56–4.54 (m, 1H), 4.25–4.22 (m, 1H), 3.95 (t, J=5.8 Hz, 2H), 3.87 (s, 3H), 3.28–2.74 (m, 8H), 1.64–1.56 (m, 4H), 1.38 (s, 9H); LCMS found for $C_{38}H_{47}N_4O_{11}S$ (M+H)$^+$: m/z=767.

Example 4.106

4'-([3-bromo-4-(1,1-dioxido-3-oxo-2,3-dihydroisothiazol-5-yl)benzyl]thiomethyl)-biphenyl-3-sulfonamide

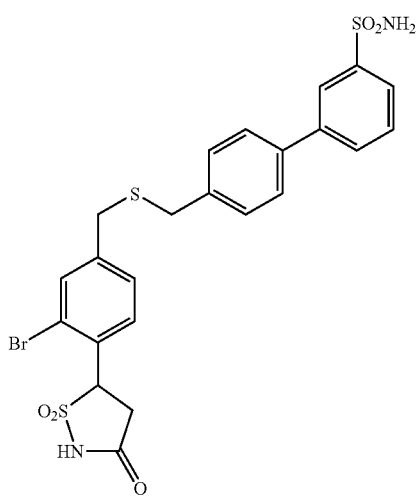

Step 1. Synthesis of methyl 3-bromo-4-[(1E)-3-methoxy-3-oxoprop-1-en-1-yl]benzoate

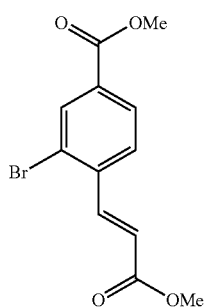

A mixture of methyl 3-bromo-4-iodobenzoate (5.9 g, 17 mmol), methyl acrylate (2.01 mL, 22.3 mmol), tetra-N-butylammonium chloride (4.8 g, 17 mmol), palladium acetate (80 mg, 0.3 mmol) and finely ground potassium carbonate (5.98 g, 43.3 mmol) in N,N-dimethylformamide (21 mL) was stirred at 50° C. for 20 h. The reaction mixture was cooled to room temperature. Ethyl acetate (200 mL) and brine (50 mL) were added, and the mixture was filtered under suction. The filtrate was collected, and aqueous layer was extracted with ethyl acetate twice. The combined organic layers were dried over NaSO₄, filtered, and concentrated. The product was crashed out after concentration, filtered and washed with ethyl acetate to give product. The remained residue was purified with silica gel chromatography (10% ethyl acetate/hexanes) to provide white solid (3.5 g, 67%). $^1$H NMR (400 MHz, CDCl$_3$): δ 8.27 (d, J=1.7 Hz, 1H), 8.04 (d, J=16.0 Hz, 1H), 7.98 (m, 1H), 7.65 (d, J=8.2 Hz, 1H), 6.46 (d, J=15.8 Hz, 1H), 3.94 (s, 3H), 3.84 (s, 3H). LCMS found for C$_{12}$H$_{12}$BrO$_4$ (M+H)$^+$: m/z=299, 301.

Step 2. Synthesis of 1-[2-bromo-4-(methoxycarbonyl)phenyl]-3-methoxy-3-oxopropane-1-sulfonic acid

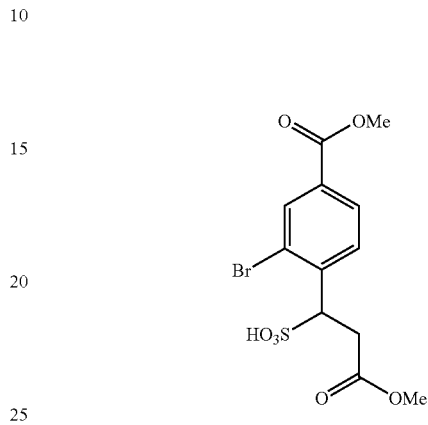

Methyl 3-bromo-4-[(1E)-3-methoxy-3-oxoprop-1-en-1-yl]benzoate (300 mg, 1.00 mmol) dissolved in ethanol (2.0 mL) was added to sodium bisulfite (209 mg, 2.00 mmol) in water (2.0 mL). The reaction mixture was heated in the microwave at 165° C. with stirring for 30 minutes. The colorless solution was purified by preparative LCMS to afford product as a white solid (0.26 g, 68%). $^1$H NMR (400 MHz, CDCl$_3$): δ 8.19 (d, J=1.5 Hz, 1H), 7.93 (dd, J=8.2, 1.8 Hz, 1H), 7.74 (d, J=8.2 Hz, 1H), 5.18 (dd, J=10.0, 5.1 Hz, 1H), 3.88 (s, 3H), 3.55 (s, 3H), 3.38 (dd, J=16.5, 5.1 Hz, 1H), 3.08 (dd, J=16.5, 10.0 Hz, 1H). LCMS found for C$_{12}$H$_{12}$BrO$_7$S (M–H)$^-$: m/z=378, 380.

Step 3. Synthesis of 1-[2-bromo-4-(methoxycarbonyl)phenyl]-3-methoxy-3-oxopropane-1-sulfonic acid—pyridine (1:1)

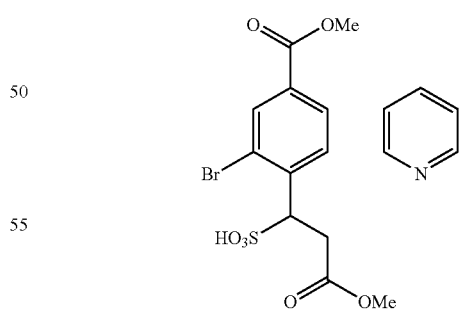

To a flask contained 1-[2-bromo-4-(methoxycarbonyl)phenyl]-3-methoxy-3-oxopropane-1-sulfonic acid (0.78 g, 2.0 mmol) was added acetic anhydride (0.965 mL, 10.2 mmol) and pyridine (0.496 mL) at room temperature. The mixture was stirred at room temperature overnight. The salt was precipitated by addition of diethyl ether, isolated by filtration. The crude product was used in next step.

Step 4. Synthesis of methyl 4-[1-(aminosulfonyl)-3-methoxy-3-oxopropyl]-3-bromobenzoate

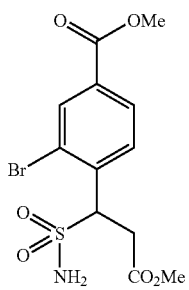

1-[2-bromo-4-(methoxycarbonyl)phenyl]-3-methoxy-3-oxopropane-1-sulfonic acid—pyridine (1:1) (0.220 g, 0.478 mmol) was dissolved in methylene chloride (2 mL) at room temperature, and phosphorus pentachloride (0.199 g, 0.956 mmol) were added. The mixture was stirred overnight. The reaction solution was cannulated into a 2 mL ammonia hydroxide solution at 0° C. dropwise. After stirring for 1 h, the organic layer was isolated, aqueous layer was extracted with methylene chloride twice. The combined organic solutions were dried over sodium sulfate, filtered, concentrated. The residue was purified by preparative LCMS to afford product as slight yellow solid (114 mg, 63%). $^1$H NMR (400 MHz, CD$_3$OD): δ 8.24 (d, J=1.5 Hz, 1H), 7.99 (dd, J=8.2, 1.5 Hz, 1H), 7.70 (d, J=8.2 Hz, 1H), 5.39 (dd, J=10.1, 4.9 Hz, 1H), 3.91 (s, 3H), 3.58 (s, 3H), 3.43 (dd, J=16.6, 4.9 Hz, 1H), 3.18 (dd, J=16.6, 10.1 Hz, 1H). LCMS found for C$_{12}$H$_{14}$BrNO$_6$SNa (M+Na)$^+$: m/z=401, 403.

Step 5. Synthesis of methyl 3-bromo-4-(1,1-dioxido-3-oxoisothiazolidin-5-yl)benzoate

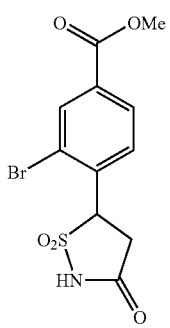

Methyl 4-[1-(aminosulfonyl)-3-methoxy-3-oxopropyl]-3-bromobenzoate (187 mg, 0.492 mmol) in methanol (16 mL) was treated with sodium methoxide (281 μL, 4.92 mmol) at 0° C. The solution stirred at room temperature for 3 h and 30 minutes. The reaction mixture was purified by preparative LCMS to afford product as a white solid (66 mg, 38%). $^1$H NMR (400 MHz, CD$_3$OD): δ 8.31 (d, J=1.8 Hz, 1H), 8.07 (dd, J=8.2, 1.8 Hz, 1H), 7.67 (d, J=8.2 Hz, 1H), 5.71 (dd, J=8.7, 6.7 Hz, 1H), 3.94 (s, 3H), 3.52 (dd, J=17.5, 8.6 Hz, 1H), 3.27 (m, 1H). LCMS found for C$_{11}$H$_{10}$BrNO$_5$SNa (M+Na)$^{30}$: m/z=370, 372.

Step 6. Synthesis of 5-[2-bromo-4-(hydroxymethyl)phenyl]isothiazolidin-3-one 1,1-dioxide

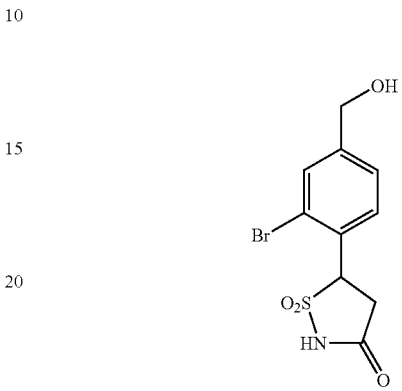

To a solution of methyl 3-bromo-4-(1,1-dioxido-3-oxoisothiazolidin-5-yl)benzoate (77.0 mg, 0.221 mmol) in tetrahydrofuran (6 mL) was added 2 M lithium tetrahydroborate in tetrahydrofuran (332 μL) at room temperature. The resulting solution was stirred at room temperature overnight. The reaction solution was diluted with methanol, and stirred for 0.5 h. The crude material was purified by preparative LCMS to give a white solid (65 mg, 92%). $^1$H NMR (400 MHz, CD$_3$OD): δ 7.57 (s, 1H), 7.46 (m, 2H), 5.30 (dd, J=9.0, 5.9 Hz, 1H), 4.49 (s, 2H), 3.26 (m, 1H), 2.97 (dd, J=17.2, 5.7 Hz, 1H). LCMS found for C$_{10}$H$_{10}$BrNO$_4$SNa (M+Na)$^+$: m/z=342, 344.

Step 7. Synthesis of 5-[2-bromo-4-(bromomethyl)phenyl]isothiazolidin-3-one 1,1-dioxide

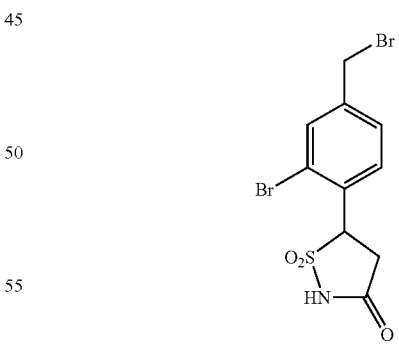

To a solution of 5-[2-bromo-4-(hydroxymethyl)phenyl]isothiazolidin-3-one 1,1-dioxide (54.0 mg, 0.169 mmol) in 1,4-dioxane (5 mL) was added triphenylphosphine (49 mg, 0.18 mmol) and carbon tetrabromide (62 mg, 0.18 mmol) at room temperature. The resulting mixture was stirred at room temperature overnight. The reaction was diluted with acetonitrile and purified by preparative LCMS to give the product as a white solid.

Step 8. Synthesis of 4'-([3-bromo-4-(1,1-dioxido-3-oxo-2,3-dihydroisothiazol-5-yl)benzyl]thiomethyl)biphenyl-3-sulfonamide

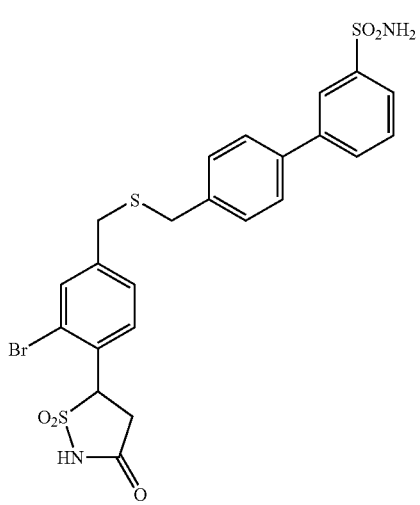

Into a 50 mL round bottom flask was placed benzyl bromide of Step 7 (17 mg, 0.045 mmol) and cesium carbonate (0.017 g, 0.054 mmol) under an atmosphere of nitrogen in anhydrous DMF (0.68 mL). The solution was cooled to 0° C., evacuated and refilled with nitrogen several times. 4'-(Mercaptomethyl)biphenyl-3-sulfonamide (15 mg, 0.054 mmol) in 2 mL anhydrous DMF was added to reaction solution dropwise. The resulting solution was stirred at 0° C. for 1 h. The crude material was purified by preparative LCMS to give product as a white solid (4.6 mg 17%). $^1$H NMR (400 MHz, CD$_3$OD): δ 8.15 (m, 1H), 7.86 (m, 2H), 7.59 (m, 4H), 7.38 (m, 4H), 5.54 (dd, J=18.6, 6.8 Hz, 1H), 3.72 (s, 2H), 3.68 (s, 2H), 3.42 (m, 1H), 3.35 (m, 1H). LCMS found for C$_{23}$H$_{22}$BrN$_2$O$_5$S$_3$ (M+H)$^+$: m/z=581, 583.

Example 4.107

Methyl 2-[4-((2S)-2-[(benzyloxy)carbonyl]amino-3-[3-bromo-4-(1,1-dioxido-3-oxoisothiazolidin-5-yl)phenyl]propanoylamino)butoxy]-6-hydroxybenzoate

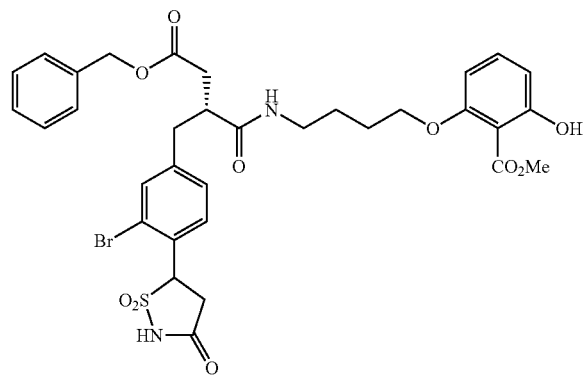

Step 1. Synthesis (3-bromo-4-iodophenyl)methanol

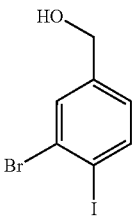

To a solution of methyl 3-bromo-4-iodobenzoate (110.0 mg, 0.322 mmol) in tetrahydrofuran (2 mL) was added 2 M lithium tetrahydroborate in tetrahydrofuran (0.161 mL) at room temperature. After stirring for 36 h, the reaction was quenched with sat. ammonium chloride solution, diluted with diethyl ether. The aqueous phase was extract with diethyl ether once. The combined organic solutions were dried over sodium sulfate, filtered and concentrated under reduced pressure. The residue was purified with silica gel chromatography (5% to 20% ethyl acetate/hexane) to give a white solid (66 mg, 65%). $^1$H NMR (400 MHz, CDCl$_3$): δ 7.82 (d, J=8.2 Hz, 1H), 7.63 (m, 1H), 6.98 (m, 1H), 4.63 (s, 2H). LCMS found for C$_7$H$_5$BrI (M+H−H$_2$O)$^+$: m/z=295, 297.

Step 2. Synthesis methyl (2E)-3-[2-bromo-4-(hydroxymethyl)phenyl]acrylate

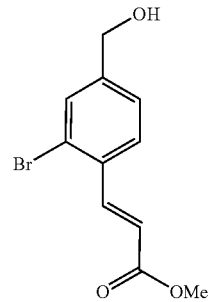

A mixture of (3-bromo-4-iodophenyl)methanol (5.3 g, 17 mmol), methyl acrylate (1.97 mL, 21.8 mmol), tetra-N-butylammonium chloride (4.7 g, 17 mmol), palladium acetate (80 mg, 0.03 mmol) and finely grounded potassium carbonate (5.85 g, 42.3 mmol) in N,N-dimethylformamide (20 mL) was stirred at 50° C. for 20 h. The reaction mixture was cooled to room temperature. Ethyl acetate (200 mL) and brine (50 mL) were added, and the mixture was filtered under suction. The filtrate was collected, and aqueous layer was extracted with ethyl acetate twice. The combined organic layers were dried over sodium sulfate, filtered, and concentrated. The residue was purified by silica gel chromatography (5% to 40% ethyl acetate/hexane) to give oil (3.6 g, 90% purity, 70%). $^1$H NMR (400 MHz, CDCl$_3$): δ 8.03 (d, J=18.2 Hz, 1H), 7.60 (m, 2H), 7.32 (d, J=8.0 Hz, 1H), 6.39 (d, J=16.0 Hz, 1H), 4.71 (d, J=5.5 Hz, 1H). LCMS found for C$_{11}$H$_{12}$BrO$_3$ (M+H)$^+$: m/z=271, 273.

Step 3. Synthesis of 1-4-[(acetyloxy)methyl]-2-bromophenyl-3-methoxy-3-oxopropane-1-sulfonic acid

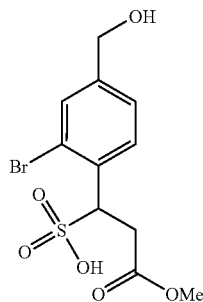

Methyl (2E)-3-[2-bromo-4-(hydroxymethyl)phenyl]acrylate (300 mg, 1.11 mmol) dissolved in ethanol (2.00 mL) was added to sodium bisulfite (0.230 g, 2.21 mmol) in water (2.00 mL). The reaction mixture was heated in the microwave at 165° C. with stirring for 30 minutes. The colorless solution was purified by preparative LCMS to afford product as a glass (245 mg, 65%). $^1$H NMR (400 MHz, CD$_3$OD): δ 7.59 (m, 2H), 7.28 (m, 1H), 5.13 (dd, J=10.4, 4.9 Hz, 1H), 4.55 (s, 2H), 3.54 (s, 3H), 3.35 (m, 1H), 3.03 (m, 1H). LCMS found for C$_{11}$H$_{12}$BrO$_6$S (M−H)$^-$: m/z=351, 353.

Step 4. Synthesis of 1-4-[(acetyloxy)methyl]-2-bromophenyl-3-methoxy-3-oxopropane-1-sulfonic acid—pyridine (1:1)

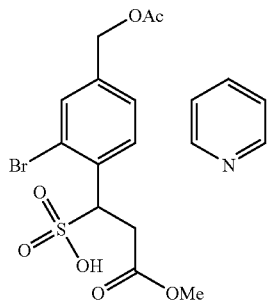

To a flask contained 1-4-[(acetyloxy)methyl]-2-bromophenyl-3-methoxy-3-oxopropane-1-sulfonic acid (0.56 g, 1.6 mmol) was added acetic anhydride (0.9 mL, 9.51 mmol) and pyridine (0.513 mL, 6.34 mmol) at room temperature. The mixture was stirred at room temperature for 8 h. The salt was precipitated by addition of diethyl ether, isolated by filtration. The crude product was used in the next step without further purification.

Step 5. Synthesis of methyl 3-4-[(acetyloxy)methyl]-2-bromophenyl-3-(aminosulfonyl)propanoate

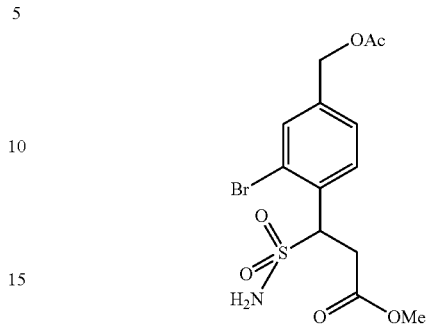

1-4-[(Acetyloxy)methyl]-2-bromophenyl-3-methoxy-3-oxopropane-1-sulfonic acid—pyridine (1:1) (0.71 g, 1.5 mmol) was dissolved in methylene chloride (6 mL) at room temperature, and DMF (30 µL, 0.04 mmol) and phosphorus pentachloride (0.343 g, 1.65 mmol) were added. After stirring for 6 h, the reaction mixture was cannulated into a ammonium hydroxide (5.7 mL) at 0° C. dropwise. After stirring for 45 min, the organic layer was isolated, aqueous layer was extracted with methylene chloride twice. The combined organic solutions were dried over sodium sulfate, filtered, concentrated. The crude material was used for next step without purification.

Step 6. Synthesis of 3-bromo-4-(1,1-dioxido-3-oxoisothiazolidin-5-yl)benzyl acetate

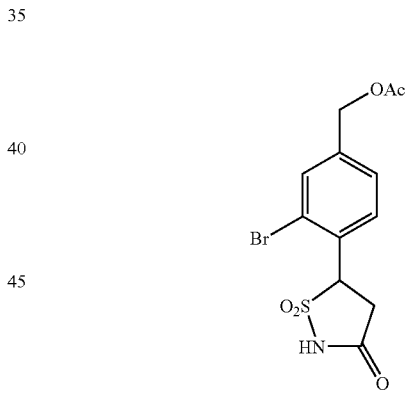

To a solution of methyl 3-4-[(acetyloxy)methyl]-2-bromophenyl-3-(aminosulfonyl)propanoate (0.50 g, 1.3 mmol) in tetrahydrofuran (8 mL) was added 2 M trimethylaluminum in toluene (0.698 mL) at room temperature. The resulting yellow solution was heat at 50° C. for 2 h. The reaction solution was cooled to room temperature, quenched with 1 N HCl solution. The aqueous layer was extracted with ethyl acetate twice. The combined organic solutions were washed with brine, dried over sodium sulfate, filtered, concentrated. The residue was purified by preparative LCMS to give a white solid (175 mg, 38% for two steps). $^1$H NMR (400 MHz, CD$_3$OD): δ7.73 (d, J=1.6 Hz, 1H), 7.54 (dd, J=8.2, 1.6 Hz, 1H), 7.47 (dd, J=8.2, 1.6 Hz, 1H), 5.66 (dd, J=8.4, 7.0 Hz, 1H), 5.11 (s, 2H), 3.48 (dd, J=17.6, 8.4 Hz, 1H), 3.31 (dd, J=17.6, 7.0 Hz, 1H), 2.10 (s, 3H). LCMS found for C$_{12}$H$_{11}$BrNO$_5$S (M−H)$^-$: m/z=360, 362.

Step 7. Synthesis of 3-bromo-4-(1,1-dioxido-3-oxo-2-[2-(trimethylsilyl)ethoxy]-methylisothiazolidin-5-yl)benzyl acetate

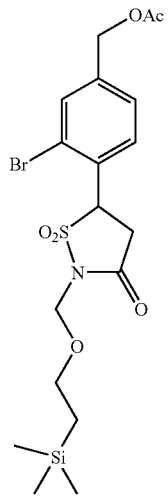

3-Bromo-4-(1,1-dioxido-3-oxoisothiazolidin-5-yl)benzyl acetate (175 mg, 0.483 mmol) was dissolved in acetonitrile (1.0 mL) and N,N-diisopropylethylamine (126 μL, 0.725 mmol) was added followed by [β-(trimethylsilyl)ethoxy]methyl chloride (103 μL, 0.580 mmol), and the reaction was heated at 50° C. for 1 h. Reaction solution was cooled to room temperature and transferred to separatory funnel, partitioned between 0.1 N HCl solution and ethyl acetate, aqueous phase was washed with ethyl acetate. The combined organic phase was washed with saturated sodium chloride, dried over sodium sulfate and concentrated to give a yellow oil. This material was chromatographed (12 g column, 0–20% ethyl acetate/hexanes) to give the product as an oil (193 mg, 81%). $^1$H NMR (400 MHz, CDCl$_3$): δ 7.70 (s, 1H), 7.37 (m, 2H), 5.53 (dd, J=8.0, 6.5 Hz, 1H), 5.06 (m, 4H), 3.65 (m, 2H), 3.49 (dd, J=17.4, 8.0 Hz, 1H), 3.23 (dd, J=17.4, 6.5 Hz, 1H), 2.13 (s, 3H), 0.95 (m, 2H), 0.0 (s, 9H).

Step 8. Synthesis of 5-[2-bromo-4-(hydroxymethyl)phenyl]-2-[2-(trimethylsilyl)ethoxy]-methylisothiazolidin-3-one 1,1-dioxide

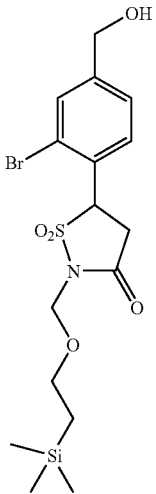

To a solution of 3-bromo-4-(1,1-dioxido-3-oxo-2-[2-(trimethylsilyl)ethoxy]-methylisothiazolidin-5-yl)benzyl acetate (10 mg, 0.02 mmol) in acetonitrile (0.5 mL) and methanol (0.5 mL) was added acetyl chloride (2.9 μL, 0.041 mmol) at room temperature. The resulting solution was stirred for 24 h and then the reaction was concentrated. The residue was purified by silica gel chromatography (5%–40% ethyl acetate/hexanes) to afford product as oil (8.0 mg, 87%). $^1$H NMR (400 MHz, CDCl$_3$): δ 7.74 (m, 1H), 7.36 (m, 2H), 5.54 (dd, J=8.0, 6.3 Hz, 1H), 5.07 (dd, J=16.4, 11.3 Hz, 2H), 4.73 (d, J=5.6 Hz, 2H), 3.66 (dd, J=9.4, 7.4 Hz, 2H), 3.50 (dd, J=17.6, 8.0 Hz, 1H), 3.24 (dd, J=17.6, 6.3 Hz, 1H), 1.82 (t, J=5.6 Hz, 1H), 0.96 (dd, J=9.4, 7.4 Hz, 2H), 0.01 (s, 9H). LCMS found for C$_{16}$H$_{24}$BrNO$_5$SSiNa (M+Na)$^+$: m/z=472, 474.

Step 9. Synthesis of 3-bromo-4-(1,1-dioxido-3-oxo-2-[2-(trimethylsilyl)ethoxy]-methylisothiazolidin-5-yl)benzaldehyde

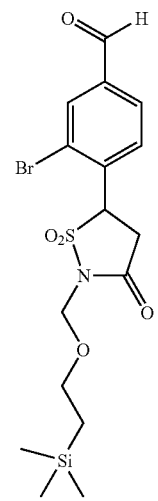

To a solution of 5-[2-bromo-4-(hydroxymethyl)phenyl]-2-[2-(trimethylsilyl)ethoxy]-methylisothiazolidin-3-one 1,1-dioxide (0.70 g, 1.6 mmol) in methylene chloride (15 mL) was added Dess-Martin periodinane (725 mg, 1.71 mmol) at room temperature. After stirring for 1 h, reaction solution was diluted with diethyl ether, quenched with saturated sodium bicarbonate solution. The aqueous phase was extracted with diethyl ether once. The combined organic solutions were washed with brine, dried over sodium sulfate, filtered, and concentrated. The residue was purified with silica gel chromatography (5%–50% ethyl acetate/hexanes) to afford product as oil (0.69 g, 99%). $^1$H NMR (400 MHz, CDCl$_3$): δ 10.01 (s, 1H), 8.21 (d, J=1.6 Hz, 1H), 7.92 (dd, J=8.2, 1.6 Hz, 1H), 7.57 (d, J=8.2 Hz, 1H), 7.38 (m, 4H), 5.60 (dd, J=8.2, 6.2 Hz, 1H), 5.09 (dd, J=15.0, 11.3 Hz, 2H), 3.66 (dd, J=9.2, 7.4 Hz, 2H), 3.56 (dd, J=17.6, 8.2 Hz, 1H), 3.28 (dd, J=17.6, 6.2 Hz, 1H), 0.96 (dd, J=8.6, 7.0 Hz, 2H), 0.01 (s, 9H). LCMS found for C$_{16}$H$_{23}$BrNO$_5$SSi (M+H)$^+$: m/z=448, 450.

Step 10. Synthesis of 3-methyl (2Z)-2-[(benzyloxy)
carbonyl]amino-3-[3-bromo-4-(1,1-dioxido-3-oxo-2-
[2-(trimethylsilyl)ethoxy]methylisothiazolidin-5-yl)
phenyl]acrylate

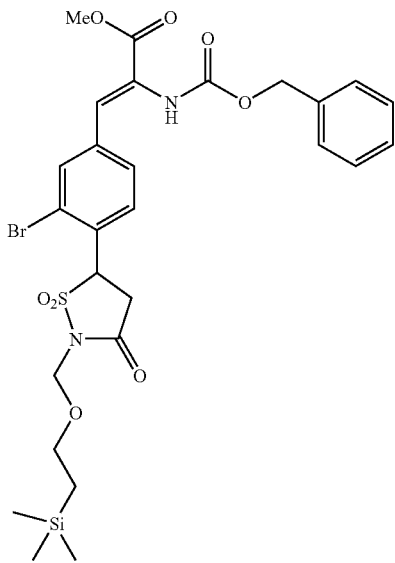

To a solution of N-(benzyloxycarbonyl)phosphonoglycine trimethyl ester (0.303 g, 0.914 mmol) in methylen chloride (2 mL) was added 1,8-diazabicyclo[5.4.0]undec-7-ene (0.150 mL, 1.00 mmol) at room temperature under an atmosphere of nitrogen. The resulting solution was stirred for 10 min, a solution of 3-bromo-4-(1,1-dioxido-3-oxo-2-[2-(trimethylsilyl)ethoxy]methylisothiazolidin-5-yl)benzaldehyde (0.410 g, 0.914 mmol) in methylen chloride (1.5 mL) was cannulated into the reaction solution. The resulting solution was stirred at room temperature for 1.5 h. The reaction was diluted with ethyl acetate and quenched with 1.0 N HCl solution. The aqueous layer was extracted with ethyl acetate twice. The combined organic solutions were washed with brine, dried over sodium sulfate, filtered, concentrated. The residue was purified with silica gel chromatography (5%–50% ethyl acetate/hexanes) to afford product as an oil (0.50 g, 84%). $^1$H NMR (400 MHz, CDCl$_3$): δ 7.79 (d, J=1.6 Hz, 1H), 7.48 (d, J=8.2 Hz, 1H), 7.34 (m, 7H), 6.64 (brs, 1H), 5.50 (dd, J=8.0, 6.7 Hz, 1H), 3.85 (s, 3H), 3.66 (dd, J=9.1, 7.6 Hz, 2H), 3.48 (dd, J=17.6, 8.2 Hz, 1H), 3.22 (dd, J=17.6, 6.4 Hz, 1H), 0.96 (dd, J=8.4, 7.2 Hz, 2H), 0.01 (s, 9H). LCMS found for C$_{27}$H$_{33}$BrN$_2$O$_8$SSiNa(M+Na)$^+$: m/z=675, 677.

Step 11. Synthesis of methyl (2S)-2-[(benzyloxy)
carbonyl]amino-3-[3-bromo-4-(1,1-dioxido-3-oxo-2-
[2-(trimethylsilyl)ethoxy]methylisothiazolidin-5-yl)
phenyl]propanoate

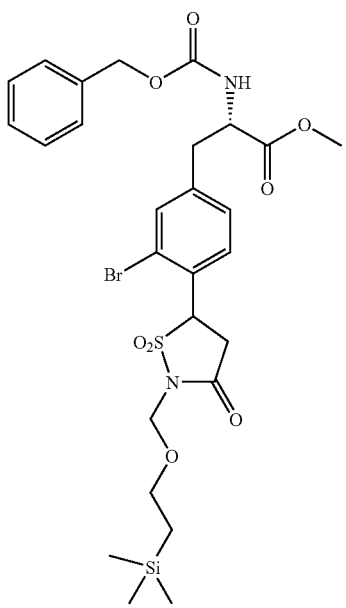

A solution of methyl (2Z)-2-[(benzyloxy)carbonyl]amino-3-[3-bromo-4-(1,1-dioxido-3-oxo-2-[2-(trimethylsilyl)ethoxy]methylisothiazolidin-5-yl)phenyl]acrylate (0.24 g, 0.37 mmol) in ethanol (10 mL) was bubble with nitrogen. (R,R)-(−)-1,2-bis[(o-methoxyphenyl)(phenyl)phosphino]ethane (1,5-cyclooctadiene) rhodium (I) tetrafluroborate (3 mg, 0.004 mmol) was added to the reaction solution and nitrogen was bubble through. After five cycles of vacuum/H$_2$, the reaction was processed at a H$_2$ pressure of 50 psi at room temperature. After 18 h, the solvent was removed under reduced pressure and the residue was purified with silica gel chromatography (5%–50% ethyl acetate/hexanes) to afford product as a white solid (0.22 g, 91%). $^1$H NMR (400 MHz, CDCl$_3$): δ 7.47 (dd, J=13.3, 1.4 Hz, 1H), 7.33 (m, 5H), 7.24 (m, 1H), 7.14 (m, 1H), 5.47 (m, 1H), 5.06 (m, 4H), 4.10 (m, 1H), 3.72 (s, 3H), 3.65 (t, J=8.0 Hz, 2H), 3.43 (dd, J=17.5, 8.2 Hz, 1H), 3.18 (m, 2H), 3.04 (dd, J=17.5, 6.4 Hz, 1H), 0.97 (dd, J=8.4, 7.2 Hz, 2H), 0.01 (s, 9H). LCMS found for C$_{27}$H$_{35}$BrN$_2$O$_8$SSiNa (M+Na)$^+$: m/z=677, 679.

Step 12. Synthesis of methyl (2S)-2-[(benzyloxy)carbonyl]amino-3-[3-bromo-4-(1,1-dioxido-3-oxoisothiazolidin-5-yl)phenyl]propanoate

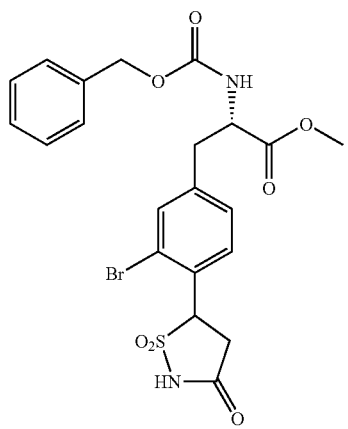

Into a round-bottom flask was added methyl (2S)-2-[(benzyloxy)carbonyl]amino-3-[3-bromo-4-(1,1-dioxido-3-oxo-2-[2-(trimethylsilyl)ethoxy]methylisothiazolidin-5-yl)phenyl]-propanoate (165 mg, 0.252 mmol), dichloromethane (5 mL), and trifluoroacetic acid (2.5 mL). After stirring at room temperature for 30 minutes, the solvent was removed. The resulting residue was used in the next step without purification.

Step 13. Synthesis of (2S)-2-[(benzyloxy)carbonyl]amino-3-[3-bromo-4-(1,1-dioxido-3-oxoisothiazolidin-5-yl)phenyl]propanoic acid

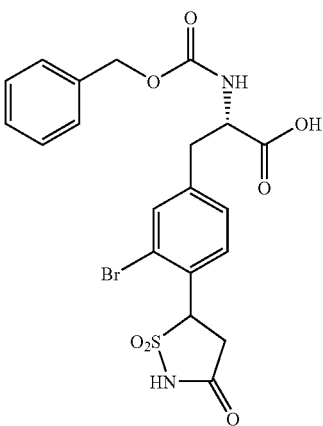

Methyl (2S)-2-[(benzyloxy)carbonyl]amino-3-[3-bromo-4-(1,1-dioxido-3-oxoisothiazolidin-5-yl)phenyl]propanoate (132 mg, 0.251 mmol) was dissolved in tetrahydrofuran (1.0 mL) and methanol (2.0 mL). Lithium hydroxide (60.2 mg, 2.51 mmol) in water was added and the reaction was allowed to stir for 1 h at room temperature. The organics were removed and the aqueous was acidified with 1 N HCl. The aqueous was extracted with ethyl acetate, dried over sodium sulfate, filtered and concentrated in vacuo. The residue was purified by preparative LCMS to afford product as a white solid (108 mg, 84% two steps). $^1$H NMR (400 MHz, CD$_3$OD): δ 7.62 (s, 1H), 7.43 (t, J=7.6 Hz, 1H), 7.31 (m, 6H), 5.65 (m, 1H), 5.03 (s, 2H), 4.43 (dd, J=9.6, 4.7 Hz, 1H), 3.45 (dd, J=7.7, 8.4 Hz, 1H), 3.30 (m, 2H), 2.95 (dd, J=13.7, 9.6 Hz, 1H). LCMS found for C$_{20}$H$_{19}$BrN$_2$O$_7$SNa (M+Na)$^+$: m/z=511, 513.

Step 14. Synthesis of methyl 2-[4-((2S)-2-[(benzyloxy)carbonyl]amino-3-[3-bromo-4-(1,1-dioxido-3-oxoisothiazolidin-5-yl)phenyl]propanoylamino)butoxy]-6-hydroxybenzoate

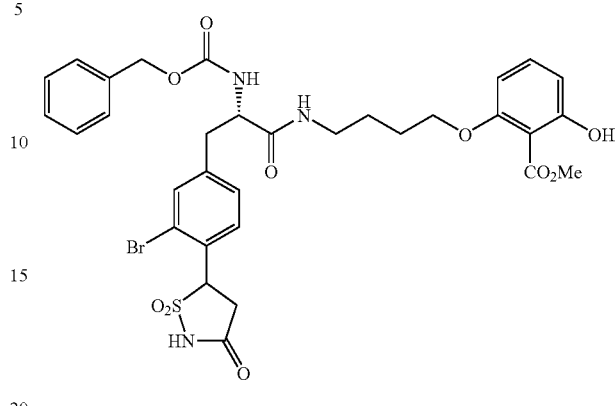

To a solution of (2S)-2-[(benzyloxy)carbonyl]amino-3-[3-bromo-4-(1,1-dioxido-3-oxoisothiazolidin-5-yl)phenyl] propanoic acid (350 mg, 0.68 mmol) in N,N-dimethylformamide (6.54 mL) was added benzotriazol-1-yloxytris(dimethylamino)phosphonium hexafluorophosphate (318 mg, 0.719 mmol) at 0° C. under an atmosphere of nitrogen. After stirring for 15 min, methyl 2-(4-aminobutoxy)-6-hydroxybenzoate (196 mg, 0.821 mmol) and N,N-diisopropylethylamine (358 µL, 2.05 mmol) was added. The reaction mixture was warmed to room temperature and stirred for 2 h. The reaction was diluted with ethyl acetate and quenched with sat. sodium bicarbonate solution. The aqueous phase was extracted with ethyl acetate once. The combined organic solutions were washed with brine, dried over sodium sulfate, filtered and concentrated in vacuo. The residue was purified by preparative LCMS to afford product as a white solid (361 mg, 72% two steps). $^1$H NMR (500 MHz, CD$_3$OD): δ 7.63 (d, J=15.6 Hz, 1H), 7.44 (m, 1H), 7.31 (m, 7H), 6.48 (t, J=8.0 Hz, 2H), 5.56 (m, 1H), 5.03 (d, J=13.9 Hz, 2H), 4.31 (m, 1H), 3.97 (t, J=5.6 Hz, 2H), 3.86 (s, 3H), 3.44 (m, 1H), 3.25 (m, 3H), 2.95 (m, 1H), 1.66 (m, 4H). LCMS found for C$_{32}$H$_{35}$BrN$_3$O$_{10}$S (M+H)$^+$: m/z=732, 734.

Example 4.108

Methyl 2-[4-((2S)-2-[(benzyloxy)carbonyl]amino-3-[3-cyano-4-(1,1-dioxido-3-oxoisthiazolidin-5-yl)phenyl]propanoylamino)butoxy]-6-hydroxybenzoate

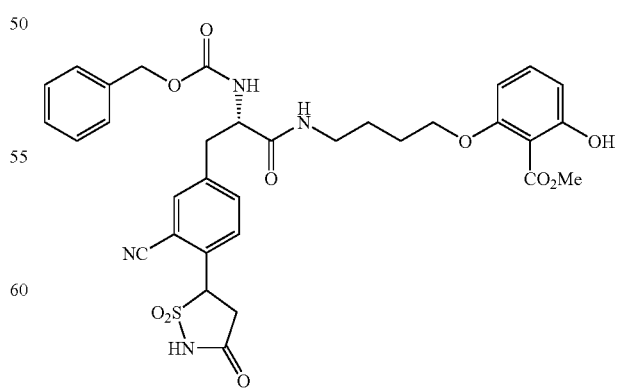

Methyl 2-[4-((2S)-2-[(benzyloxy)carbonyl]amino-3-[3-bromo-4-(1,1-dioxido-3-oxoisothiazolidin-5-yl)phenyl]- propanoylamino)-butoxy]-6-hydroxybenzoate (15.3 mg, 0.0209 mmol), zinc cyanide (7.36 mg, 0.0626 mmol), tetrakis-(triphenylphosphine)palladium(0) (4.83 mg, 4.18 µmol), and DMF (1 mL) were combined in a microwave vessel and processed at 175° C. for 4 minutes. The solution was filtered, washed with 1 mL of methanol and purified by preparative LCMS to afford a white solid (10.1 mg, 71%). $^1$H NMR (500 MHz, CD$_3$OD): δ 7.63 (m, 3H), 7.30 (m, 6H), 6.49 (dd, J=11.7, 8.3 Hz, 2H), 5.65 (m, 1H), 5.01 (d, J=2.9 Hz, 2H), 4.34 (m, 1H), 3.98 (t, J=5.9 Hz, 2H), 3.86 (s, 3H), 3.46 (m, 1H), 3.21 (m, 3H), 3.12 (m, 1H), 2.97 (m, 1H), 1.65 (m, 4H). LCMS found for C$_{33}$H$_{35}$N$_4$O$_{10}$S (M+H)$^+$: m/z=679.

Example 4.109

Methyl 2-[4-((2S)-2-[(benzyloxy)carbonyl]amino-3-[3-vinyl-4-(1,1-dioxido-3-oxoisothiazolidin-5-yl)-propanoylamino)-butoxy]-6-hydroxybenzoate

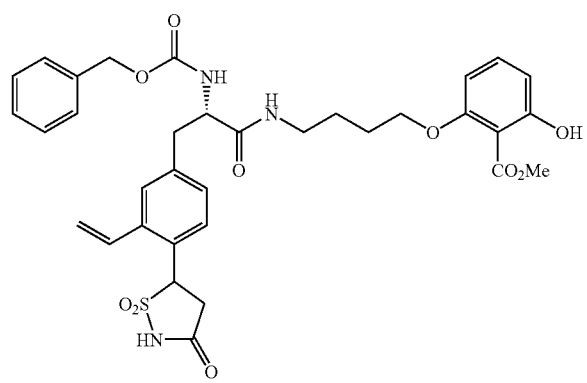

To a solution of methyl 2-[4-((2S)-2-[(benzyloxy)carbonyl]amino-3-[3-bromo-4-(1,1-dioxido-3-oxoisothiazolidin-5-yl)phenyl]propanoylamino)butoxy]-6-hydroxybenzoate (100.0 mg, 0.136 mmol) in N,N-dimethylformamide (0.5 mL) was added (2-ethenyl)tri-n-butyltin (120 mg, 0.377 mmol), tetrakis(triphenylphosphine)palladium(0) (16 mg, 0.014 mmol) and bis(triphenylphosphine)palladium(II) chloride (9.6 mg, 0.014 mmol). The resulting mixture was degassed with nitrogen and heated at 100° C. overnight. The reaction was diluted with a saturated KF solution. The resulting mixture was stirred overnight, filtered through celite and purified by preparative LCMS to afford a white solid (43.5 mg, 47%). $^1$H NMR (400 MHz, CD$_3$OD): δ 7.28 (m, 10H), 6.47 (m, 2H), 5.65 (dd, J=17.4, 1.2 Hz, 1H), 5.34 (dd, J=10.9, 1.2 Hz, 1H), 5.08 (dd, J=9.0, 6,6 Hz, 2H), 5.03 (s, 2H), 4.31 (m, 1H), 3.94 (t, J=5.2 Hz, 2H), 3.85 (s, 3H), 3.22 (m, 3H), 3.00 (m, 3H), 1.60 (m, 4H). LCMS found for C$_{34}$H$_{38}$N$_3$O$_{10}$S (M+H)$^+$: m/z=680.

Example 4.110

2-[4-((2S)-2-[(Benzyloxy)carbonyl]amino-3-[6-(1,1-dioxido-3-oxoisothiazolidin-5-yl)biphenyl-3-yl]propanoylamino)butoxy]-6-hydroxybenzoic acid

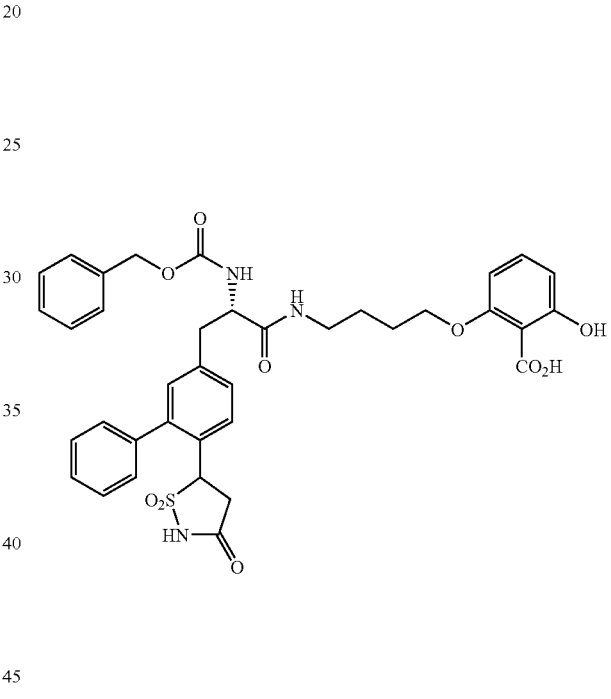

To a solution of methyl 2-[4-((2S)-2-[(benzyloxy)carbonyl]amino-3-[3-bromo-4-(1,1-dioxido-3-oxoisothiazolidin-5-yl)phenyl]propanoylamino)butoxy]-6-hydroxybenzoate (12.0 mg, 0.0164 mmol) in toluene (0.4 mL) and 1,4-dioxane (0.4 mL) was added phenylboronic acid (2.40 mg, 0.0196 mmol) and 2 M sodium carbonate in water (0.049 mL). The resulting mixture was degassed with nitrogen. Tetrakis(triphenylphosphine)palladium(0) (0.95 mg, 0.82 µmol) was then added to reaction mixture and heated at 100° C. overnight. The reaction mixture was filtered and purified by preparative LCMS to afford a white solid (3.9 mg, 33%). $^1$H NMR (400 MHz, CD$_3$OD): δ 7.59 (m, 1H), 7.36 (m, 13H), 6.57 (m, 2H), 5.04 (m, 3H), 4.36 (m, 1H), 4.11 (m, 2H), 3.22 (m, 5H), 2.96 (m, 1H), 1.78 (m, 2H), 1.59 (m, 2H). LCMS found for C$_{37}$H$_{378}$N$_3$O$_{10}$S (M+H)$^+$: m/z=716.

Example 4.111

Methyl 2-[4-((2S)-2-[(benzyloxy)carbonyl]amino-3-[6-(1,1-dioxido-3-oxoisothiazolidin-5-yl)biphenyl-3-yl]propanoylamino)butoxy]-6-hydroxybenzoate

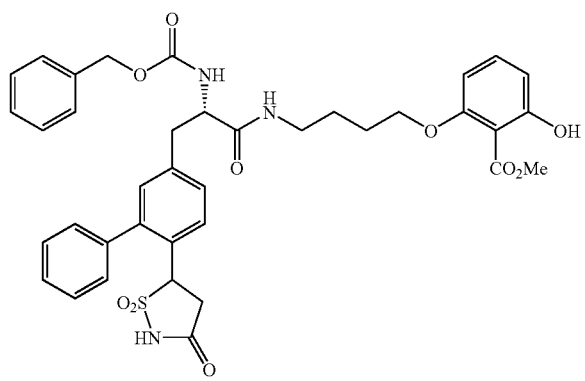

Step 1. Synthesis of (2S)-2-[(benzyloxy)carbonyl]amino-3-[6-(1,1-dioxido-3-oxoisothiazolidin-5-yl)biphenyl-3-yl]propanoic acid

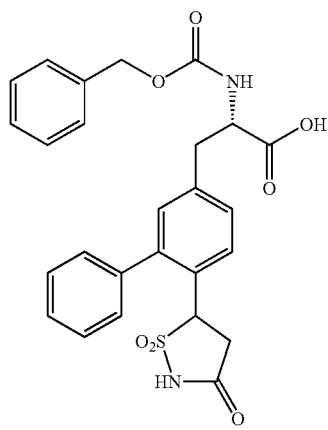

To a solution of methyl (2S)-2-[(benzyloxy)carbonyl]amino-3-[3-bromo-4-(1,1-dioxido-3-oxoisothiazolidin-5-yl)phenyl]propanoate (52.0 mg, 0.0990 mmol) in toluene (1.0 mL) and 1,4-dioxane (1.0 mL) was added phenylboronic acid (14.5 mg, 0.119 mmol), 2 M sodium carbonate in water (0.30 mL) and tetrakis(triphenylphosphine)palladium(0) (6 mg, 0.005 mmol) under an atmosphere of nitrogen. The resulting mixture was heated at 100° C. overnight. The reaction solution was filtered, and purified by preparative LCMS to afford product as a white solid (18 mg, 38%). $^1$H NMR (400 MHz, CD$_3$OD): δ 7.28 (m, 13H), 5.03 (m, 1H), 4.47 (m, 1H), 3.26 (m, 3H), 3.00 (m, 1H). LCMS found for C$_{26}$H$_{25}$N$_2$O$_7$S (M+H)$^+$: m/z=509.

Step 2. Synthesis of methyl 2-[4-((2S)-2-[(benzyloxy)carbonyl]amino-3-[6-(1,1-dioxido-3-oxoisothiazolidin-5-yl)biphenyl-3-yl]propanoylamino)butoxy]-6-hydroxybenzoate

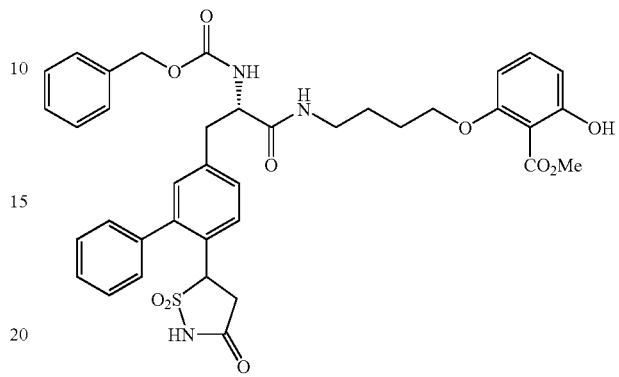

To a solution of (2S)-2-[(benzyloxy)carbonyl]amino-3-[6-(1,1-dioxido-3-oxoisothiazolidin-5-yl)biphenyl-3-yl]propanoic acid (18.0 mg, 0.0354 mmol) in N,N-dimethylformamide (1.00 mL) was added benzotriazol-1-yloxytris(dimethylamino)phosphonium hexafluorophosphate (16.4 mg, 0.0372 mmol) at 0° C. The reaction was stirred for 15 min and then methyl 2-(4-aminobutoxy)-6-hydroxybenzoate (9.32 mg, 0.0389 mmol) and N,N-diisopropylethylamine (18.5 μL, 0.106 mmol) was added. The resulting solution was stirred for 3 h and then diluted with acetonitrile and purified by preparative LCMS to afford a white solid (12.4 mg, 48%). $^1$H NMR (400 MHz, CD$_3$OD): δ 8.07 (m, 1H), 7.56 (m, 1H), 7.29 (m, 13H), 6.46 (m, 2H), 5.05 (m, 3H), 4.35 (m, 1H), 3.94 (m, 2H), 3.84 (s, 3H), 3.19 (m, 5H), 2.96 (m, 1H), 1.60 (m, 4H). LCMS found for C$_{38}$H$_{40}$N$_3$O$_{10}$S (M+H)$^+$: m/z=730.

Example 4.112

Methyl 2-[4-({(2S)-3-[3-bromo-4-(1,1-dioxido-3-oxoisothiazolidin-5-yl)phenyl]-2-[(morpholin-4-ylcarbonyl)amino]propanoyl}amino)butoxy]-6-hydroxybenzoate

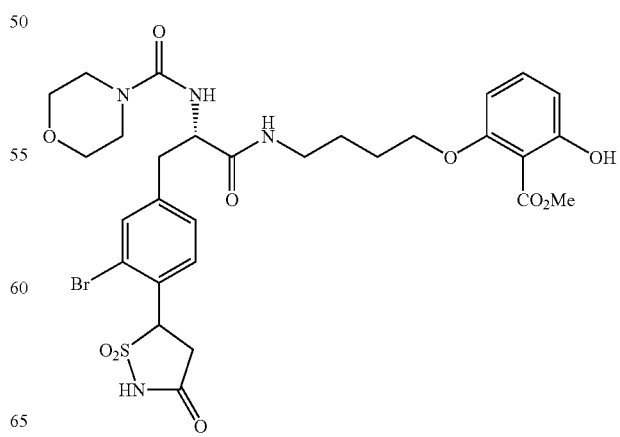

Step 1. Synthesis of methyl 2-[4-((2S)-2-amino-3-[3-bromo-4-(1,1-dioxido-3-oxoisothiazolidin-5-yl)phenyl]propanoylamino)butoxy]-6-hydroxybenzoate trifluoroacetate

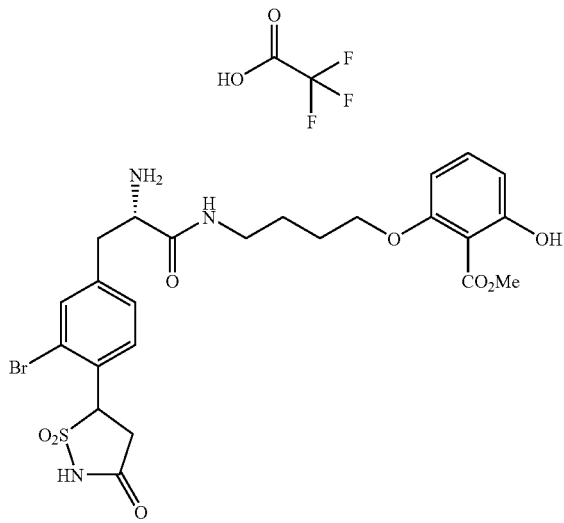

To a solution of methyl 2-[4-((2S)-2-[(benzyloxy)carbonyl]amino-3-[3-bromo-4-(1,1-dioxido-3-oxoisothiazolidin-5-yl)phenyl]propanoylamino)butoxy]-6-hydroxybenzoate (45 mg, 0.061 mmol) in acetonitrile (0.50 mL) was added iodotrimethylsilane (26 μL, 0.18 mmol) at room temperature. After stirring for 20 min, the reaction was quenched with 1 N HCl and diluted with acetonitrile. The mixture was purified by preparative LCMS to afford product as solid (36 mg, 82%). $^1$H NMR (400 MHz, CD$_3$OD): δ 7.64 (dd, J=11.3, 1.7 Hz, 1H), 7.53 (dd, J=11.9, 8.0 Hz, 1H), 7.37 (m, 1H), 7.23 (m, 1H), 6.47 (m, 2H), 5.65 (dd, J=15.6, 8.2 Hz, 1H), 3.98 (m, 3H), 3.87 (s, 3H), 3.46 (m, 1H), 3.32 (m, 1H), 3.09 (m, 3H), 1.64 (m, 4H). LCMS found for C$_{24}$H$_{29}$BrN$_3$O$_8$S (M+H)$^+$: m/z=598, 600.

Step 2. Synthesis of methyl 2-[4-({(2S)-3-bromo-4-(1,1-dioxido-3-oxoisothiazolidin-5-yl)phenyl]-2-[(morpholin-4-ylcarbonyl)amino]propanoyl}amino)butoxy]-6-hydroxybenzoate

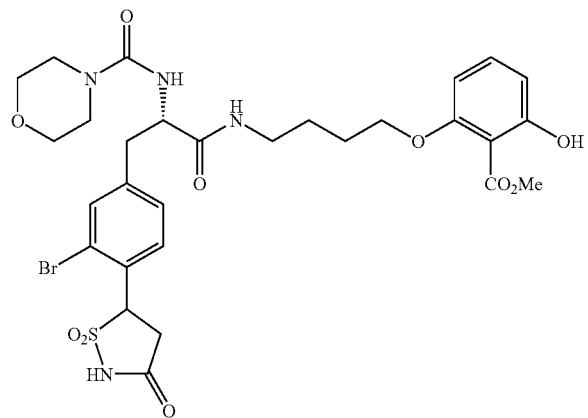

To a solution of methyl 2-[4-((2S)-2-amino-3-[3-bromo-4-(1,1-dioxido-3-oxoisothiazolidin-5-yl)phenyl]propanoylamino)butoxy]-6-hydroxybenzoate (30.0 mg, 0.0501 mmol) in methylene chloride (0.4 mL) and N,N-dimethylformamide (0.10 mL) was added N,N-diisopropylethylamine (26.4 μL, 0.152 mmol) and morpholine-4-carbonyl chloride (6.48 μL, 0.0556 mmol) at room temperature. The resulting solution was stirred for 2 h. The reaction was quenched with 1 N HCl solution and diluted with ethyl acetate. The aqueous layer was extracted with ethyl acetate twice. The combined organic solutions were dried over sodium sulfate, filtered, concentrated under reduced pressure. The residue was purified by preparative LCMS to afford a white solid (30 mg, 80%). $^1$H NMR (400 MHz, CD$_3$OD): δ 7.61 (dd, J=9.6, 1.8 Hz, 1H), 7.47 (dd, J=11.3, 8.0 Hz, 1H), 7.35 (m, 1H), 7.24 (t, J=8.3 Hz, 1H), 6.48 (m, 2H), 5.36 (m, 1H), 4.44 (dd, J=8.8, 6.6 Hz, 1H), 3.98 (t, J=5.8 Hz, 2H), 3.87 (s, 3H), 3.59 (m, 4H), 3.43 (dd, J=17.6, 8.4 Hz, 1H), 3.23 (m, 1H), 3.16 (m, 3H), 2.96 (m, 1H), 1.64 (m, 4H). LCMS found for C$_{29}$H$_{36}$BrN$_4$O$_{10}$S (M+H)$^+$: m/z=711, 713.

Example 4.113

Methyl 2-[4-({(2S)-3-[3-cyano-4-(1,1-dioxido-3-oxoisothiazolidin-5-yl)phenyl]-2-[(morpholin-4-ylcarbonyl)amino]propanoyl}amino)butoxy]-6-hydroxybenzoate

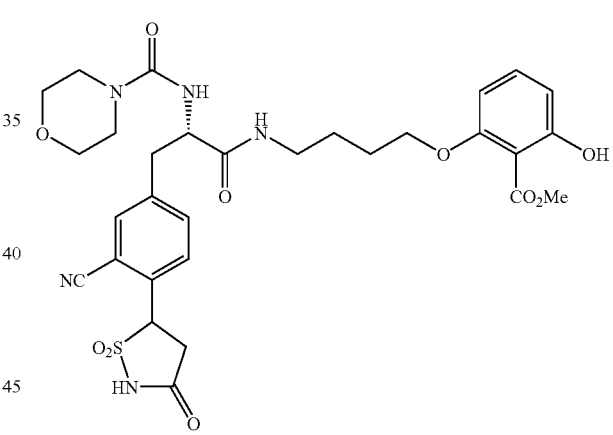

Methyl 2-[4-({(2S)-3-[3-bromo-4-(1,1-dioxoisothiazolidin-5-yl)phenyl]4-ylcarbonyl)amino]propanoyl}amino)butoxy]-6-hydroxybenzoate (8.7 mg, 0.0122 mmol), zinc cyanide (4.31 mg, 0.0367 mmol), tetrakis(triphenylphosphine)palladium(0) (2.8 mg, 0.00244 mmol) and DMF (0.3 mL) were combined in a microwave vessel and processed at 175° C. for 5 min. The reaction solution was filtered and purified by preparative LCMS to afford a white solid (4.0 mg, 50%). $^1$H NMR (400 MHz, CD$_3$OD): δ 7.73 (d, J=6.4 Hz, 1H), 7.65 (dd, J=9.0, 1.0 Hz, 2H), 7.24 (t, J=8.4 Hz, 1H), 6.48 (dd, J=12.7, 8.6 Hz, 2H), 5.46 (m, 1H), 4.47 (m, 1H), 3.99 (t, J=5.7 Hz, 2H), 3.87 (s, 3H), 3.59 (m, 4H), 3.43 (m, 2H), 3.19 (m, 2H), 2.99 (m, 1H), 1.85 (m, 4H). LCMS found for C$_{30}$H$_{36}$N$_5$O$_{10}$S (M+H)$^+$: m/z=658.

Example 4.114

N-2-[4-(1,1-dioxido-3-oxoisothiazolidin-5-yl)phenyl]ethyl-4-phenoxybenzenesulfonamide

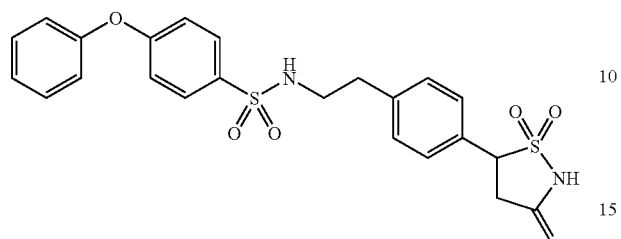

Step 1. Synthesis of [2-(4-Hydroxy-phenyl)-ethyl]-carbamic acid tert-butyl ester

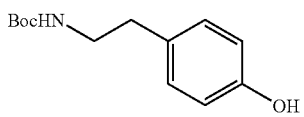

Into the reaction was dissolved 4-(2-amino-ethyl)-phenol; hydrochloride (11.6 g, 66.9 mmol) in water (30 mL) and tetrahydrofuran (30 mL). Sodium bicarbonate (12.5 g, 147 mmol) was added, followed by di-tert-butyldicarbonate (16.1 g, 73 mmol). The reaction was stirred overnight. Water (100 mL) was added and the mixture was extracted with ethyl acetate (100 mL) three times. The organic phases were combined and dried over MgSO$_4$, filtered and the solvent evaporated to give a clear glass (15.9 g, 100%). $^1$H NMR (400 MHz, CDCl$_3$): δ 7.03 (m, 2H), 6.77 (m, 2H), 4.55 (bs, 1H), 3.33 (m, 2H), 2.71 (t, J=7.0 Hz, 2H), 1.44 (s, 9H).

Step 2. Synthesis of trifluoro-methanesulfonic acid 4-(2-tert-butoxycarbonylamino-ethyl)-phenyl ester

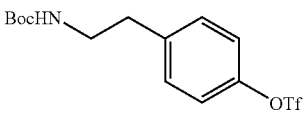

[2-(4-Hydroxy-phenyl)-ethyl]-carbamic acid tert-butyl ester (15.9 g, 66.7 mmol) was dissolved in methylene chloride (130 mL) and then pyridine (8.12 mL) was added. The reaction was cooled to 0° C. Trifluoromethanesulfonic anhydride (20.8 g, 73.6 mmol) was dissolved in methylene chloride (70 mL) and added to the reaction mixture via addition funnel over 30 minutes. The reaction was allowed to warm to room temperature overnight. Water (150 mL) was added and the mixture shaken then separated. The aqueous phase was extracted with methylene chloride (100 mL) twice. The organic phases were combined and dried over MgSO$_4$, filtered and evaporated. The mixture was chromatographed, eluting with 10–30% ethyl acetate in hexanes. Fractions containing the major component were combined, concentrated and place under high vacuum overnight to give a colorless oil (22.5 g, 91%), which gradually crystallized. $^1$H NMR (400 MHz, CDCl$_3$): δ 7.27 (m, 2H), 7.20 (m, 2H), 4.55 (bs, 1H), 3.37 (m, 2H), 2.83 (t, J=7.0 Hz, 2H), 1.43 (s, 9H); LCMS found for C$_{10}$H$_{11}$F$_3$NO$_5$S (M+H—tBu)$^+$: m/z=314.1.

Step 3. Synthesis of 1-(2-tert-Butoxycarbonylamino-ethyl)-4,4,5,5-tetramethyl-1,3,2-dioxaborolane

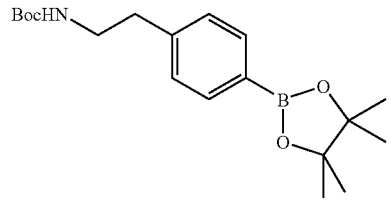

Trifluoro-methanesulfonic acid 4-(2-tert-butoxycarbonylamino-ethyl)-phenyl ester (22.5 g, 0.0609 mol), bis(tricyclohexylphosphine)palladium(II) chloride (1.35 g, 1.83 mmol), tricyclohexylphosphine (0.51 g, 1.83 mmol), potassium acetate (12.0 g, 122 mmol), and 4,4,5,5,4',4',5',5'-octamethyl-[2,2']bi[[1,3,2]dioxaborolanyl] (17.0 g, 67.0 mmol) were dissolved in dry N,N-dimethylformamide (370 mL). The reaction was heated in an oil bath at 100° C. overnight. The mixture was diluted with water (1 L) then was extracted with diethyl ether (250 mL) four times. The combined organic phases were combined and dried over MgSO$_4$. The solution was filtered and the solvent evaporated. The mixture was chromatographed, eluting with 10–50% ethyl acetate. Fractions containing the major component were combined and concentrated to give a lavender oil. The mixture was rechromatographed with 5–10% ethyl acetate. Fractions containing the major component were combined and concentrated to give a pale pink oil (12.5 g, 52%), which upon standing slowly solidified. $^1$H NMR (500 MHz, CDCl$_3$): δ 7.76 (m, 2H), 7.21 (m, 2H), 4.51 (bs, 1H), 3.38 (m, 2H), 2.81 (t, J=7.0 Hz, 2H), 1.43 (s, 9H), 1.34 (s, 12H); LCMS found for C$_{14}$H$_{22}$BNO$_2$ (M+H–Boc)$^+$: m/z=248.2.

Step 4. Synthesis of 2-[4-(2-tert-Butyl-1,1,3-trioxo-2,3-dihydro-1H-1λ6-isothiazol-5-yl)-phenyl]-ethyl-carbamic acid tert-butyl ester

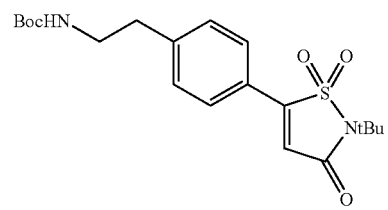

1-(2-tert-Butoxycarbonylamino-ethyl)-4,4,5,5-tetramethyl-1,3,2-dioxaborolane (0.328 g, 0.944 mmol), 2-tert-butyl-5-chloro-1,1-dioxo-1,2-dihydro-1λ6-isothiazol-3-one (0.253 g, 1.13 mmol), [1,1'-bis(diphenylphosphino)ferrocene]dichloropalladium(II), complex with dichloromethane (1:1) (0.095 g, 0.12 mmol), and potassium carbonate (0.652 g, 4.72 mmol) in 1,4-dioxane (6 mL) were added to a flask with a reflux condenser. The reaction atmosphere was evacuated and purged four times with dry nitrogen. The reaction was heated to 80° C. for 15 h. Additional catalyst, [1,1'-bis(diphenylphosphino)ferrocene]-dichloropalladium(II), complex with dichloromethane (1:1) (0.100 g, 0.122 mmol), was added and the reaction atmosphere was evacuated and purged four times with dry nitrogen. The reaction was heated overnight. The mixture was chromatographed, eluting with 10–20% ethyl acetate in hexanes. Fractions containing the major component were combined and concentrated to give a light brown oil (0.36 g, 92%). $^1$H NMR (500 MHz, CDCl$_3$): δ 7.76 (m, 2H), 7.21 (m, 2H), 4.51 (bs, 1H), 3.38 (m, 2H), 2.81 (y, J=6.8 Hz, 2H), 1.43 (bs, 9H), 1.34 (s, 9H).

Step 5 Synthesis of 5-[4-(2-aminoethyl)phenyl]-2-tert-butylisothiazol-3(2H)-one 1,1-dioxide trifluoroacetate

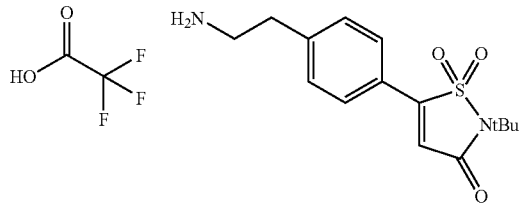

2-[4-(2-tert-Butyl-1,1,3-trioxo-2,3-dihydro-1H-1λ$^6$-isothiazol-5-yl)-phenyl]-ethyl-carbamic acid tert-butyl ester (200 mg, 0.490 mmol) was dissolved in methylene chloride (2 mL) and trifluoroacetic acid (2 mL) and the reaction was stirred for 2 h. The reaction was chromatographed on a 21 mm Luna C18 column using a 10–90% acetonitrile in water gradient with 0.05% trifluoroacetic acid at 12.5 mL per minute over a 15 minute period. The major fraction was lyophilized to give a white powder (207 mg, 100%). $^1$H NMR (500 MHz, CDCl$_3$): δ 7.90 (m, 2H), 7.52 (m, 2H), 3.25 (t, J=6.5 Hz, 2H), 3.06 (t, J=7.4 Hz, 2H), 1.73 (s, 9H); LCMS found for C$_{17}$H$_{22}$F$_3$N$_2$O$_5$S (M+H)$^+$: m/z=309.2.

Step 6. Synthesis of N-2-[4-(2-tert-butyl-1,1-dioxido-3-oxo-2,3-dihydroisothiazol-5-yl)phenyl]ethyl-4-phenoxybenzenesulfonamide

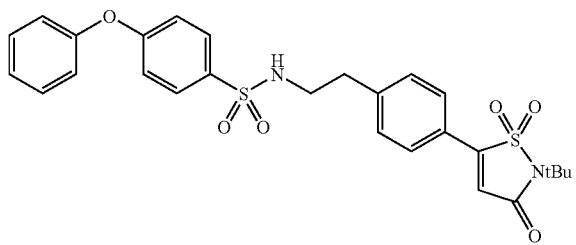

5-[4-(2-Aminoethyl)phenyl]-2-tert-butylisothiazol-3(2H)-one 1,1-dioxide trifluoroacetate (36.7 mg, 0.0869 mmol) and triethylamine (36.3 μL, 0.260 mmol) were dissolved in N,N-dimethylformamide (0.15 mL). 4-Phenoxybenzenesulfonyl chloride (29.2 mg, 0.109 mmol) was added and the reaction was allowed to stir at room temperature for 30 minutes. The reaction was chromatographed on a 21.2 mm Luna C18 column using a 10–90% acetonitrile in water gradient with 0.05% trifluoroacetic acid at 12.5 mL per minute over a 15 minute period. The major fraction was evaporated to a clear glass (18 mg, 38%). $^1$H NMR (500 MHz, CDCl$_3$): δ 7.75 (d, J=8.8 Hz, 2H), 7.69 (d, J=8.3 Hz, 2H), 7.41 (t, J=8.1 Hz, 2H), 7.27 (d, J=7.8 Hz, 3H), 7.23 (t, J=7.6 Hz, 1H), 7.07 (d, J=7.8 Hz, 2H), 7.02 (d, J=8.8 Hz, 2H), 3.25 (t, J=6.8 Hz, 2H), 2.87 (t, J=7.1 Hz, 2H), 1.73 (s, 9H); LCMS found for C$_{27}$H$_{32}$N$_3$O$_6$S$_2$ (M+NH$_4$)$^+$: m/z 558.2.

Step 7. Synthesis of N-2-[4-(2-tert-butyl-1,1-dioxido-3-oxoisothiazolidin-5-yl)phenyl]ethyl-4-phenoxybenzenesulfonamide

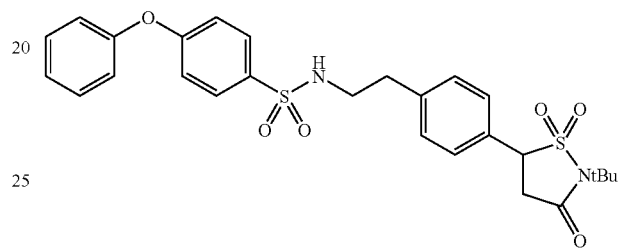

N-2-[4-(2-tert-Butyl-1,1-dioxido-3-oxo-2,3-dihydroisothiazol-5-yl)phenyl]ethyl-4-phenoxybenzenesulfonamide (26.0 mg, 0.0481 mmol) was dissolved in tetrahydrofuran (0.25 mL) and 2 M lithium tetrahydroborate in tetrahydrofuran (18 μL) was added to the reaction via syringe. After 10 minutes, 2 M lithium tetrahydroborate in tetrahydrofuran (18 μL) was added. After an additional 10 minutes, the reaction was added to 1 mL of saturated aqueous ammonium chloride and stirred vigorously. The reaction was chromatographed on a 21.2 mm Luna C 18 column using a 10–90% acetonitrile in water gradient with 0.05% trifluoroacetic acid at 12.5 mL per minute over a 15 minute period. The major fraction was evaporated to give a light orange solid (19 mg, 75%). $^1$H NMR (500 MHz, CDCl$_3$): δ 7.77 (d, J=8.8 Hz, 2H), 7.42 (t, J=8.3 Hz, 2H), 7.34 (d, J=8.3 Hz, 2H), 7.23 (t, J=7.8 Hz, 1H), 7.13 (d, J=7.8 Hz, 2H), 7.07 (d, J=7.9 Hz, 2H), 7.03 (d, J=8.8 Hz, 2H), 4.65 (m, 1H), 4.29 (m, 1H), 3.95 (m, 1H), 3.75 (m, 1H) 3.40 (m, 1H), 2.60 (m, 1H), 2.24 (m, 1H), 1.31 (s, 9H); LCMS found for C$_{27}$H$_{34}$N$_3$O$_6$S$_2$ (M+NH$_4$)$^+$: m/z 560.2.

Step 8. Synthesis of N-2-[4-(1,1-dioxido-3-oxoisothiazolidin-5-yl)phenyl]ethyl-4-phenoxybenzenesulfonamide

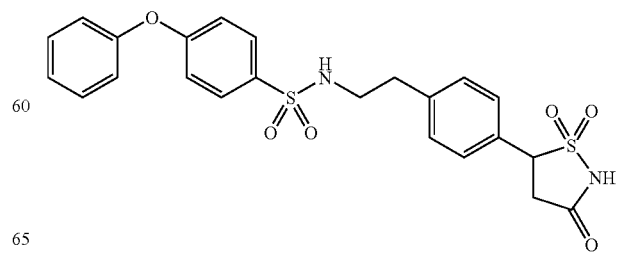

N-2-[4-(2-tert-butyl-1,1-dioxido-3-oxoisothiazolidin-5-yl)phenyl]ethyl-4-phenoxy-benzenesulfonamide (10.0 mg, 0.0184 mmol) was dissolved in trifluoroacetic acid (2 mL). The reaction was heated to 170° C. in the microwave and held at that temperature for 45 seconds. The reaction was chromatographed on a 21.2 mm Luna C18 column using a 20–80% acetonitrile in water gradient with 0.05% trifluoroacetic acid at 25 mL per minute over a 20 minute period. The major fraction was lyophilized to give a white powder (8 mg, 90%). $^1$H NMR (500 MHz, CD$_3$OD): δ 7.76 (d, J=9.2 Hz, 2H), 7.42 (t, J=7.8 Hz, 2H), 7.37 (d, J=7.8 Hz, 2H), 7.24 (d, J=7.8 Hz, 2H), 7.21 (m, 1H), 7.07 (d, J=7.8 Hz, 2H), 7.03 (d, J=8.8 Hz, 2H), 4.94 (m, 1H), 4.39 (m, 1H), 3.35 (m, 2H), 3.24 (m, 2H), 2.85 (m, 2H); LCMS found for C$_{23}$H$_{22}$N$_2$O$_6$S$_2$ (M+H)$^+$: m/z 487.1.

Example 4.115

5-(4-[(4-Phenoxybenzyl)oxy]methylphenyl)isothiazolidin-3-one 1,1-dioxide

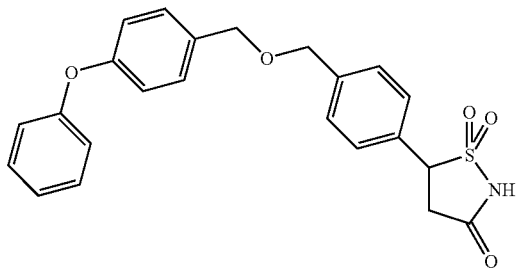

Step 1. Synthesis of 5-(4-[(4-phenoxybenzyl)oxy]methylphenyl)isothiazol-3(2H)-one 1,1-dioxide

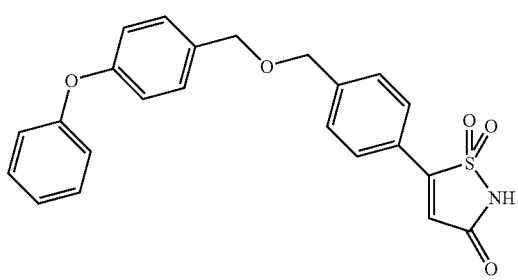

5-[4-(Hydroxymethyl)phenyl]isothiazol-3(2H)-one 1,1-dioxide (80 mg, 0.33 mmol) was suspended in 4 M hydrogen chloride in 1,4-dioxane (2.0 mL). 4-Phenoxybenzaldehyde (0.080 mL, 0.46 mmol) was added, followed 15 minutes later by triethylsilane (0.075 mL, 0.47 mmol). After stirring for 21 h, additional triethylsilane (0.050 mL, 0.31 mmol) was added, followed 3.5 h later by 4 M hydrogen chloride in 1,4-dioxane (1.0 mL, 4 mmol). The product was purified on a 50 mm Luna C18 column using a 20–100% acetonitrile in water gradient with 0.05% trifluoroacetic acid at 30 mL per minute over a 30 minute period. The product was lyophilized to give a white powder (7 mg, 5%). $^1$H NMR (400 MHz, CDCl$_3$): δ 7.80 (d, J=8.4 Hz, 2H), 7.54 (d, J=8.6 Hz, 2H), 7.34 (m, 4H), 7.11 (t, J=1.2 Hz, 1H), 7.01 (m, 4H), 6.71 (s, 1H), 4.63 (s, 2H), 4.56 (s, 2H); LCMS found for C$_{23}$H$_{19}$NNaO$_5$S (M+Na)$^+$: m/z=444.0.

Step 2. Synthesis of 5-(4-[(4-phenoxybenzyl)oxy]methylphenyl)isothiazolidin-3-one 1,1-dioxide

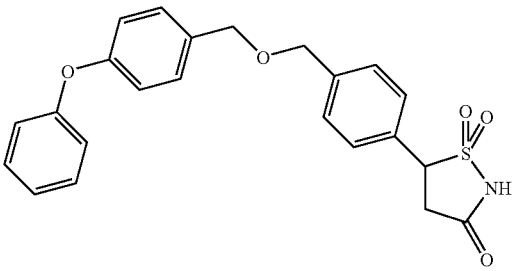

2 M Lithium borohydride in tetrahydrofuran (0.036 mL, 0.072 mmol) was added to 5-(4-[(4-phenoxybenzyl)oxy]methylphenyl)isothiazol-3(2H)-one 1,1-dioxide (40 mg, 0.009 mmol) in tetrahydrofuran (0.5 mL). After stirring for 25 minutes, the reaction was quenched with saturated aqueous ammonium chloride. The product was purified on a 50 mm Luna C18 column using a 20–100% acetonitrile in water gradient with 0.05% trifluoroacetic acid at 30 mL per minute over a 30 minute period. The major product was lyophilized to give a white powder (4 mg, 100%). $^1$H NMR (400 MHz, CDCl$_3$): δ 7.46 (m, 4H), 7.34 (m, 4H), 7.11 (t, J=7.4 Hz, 1H), 7.01 (m, 4H), 4.98 (t, J=8.4 Hz, 1H), 4.60 (s, 2H), 4.55 (s, 2H), 3.38 (dd, J=8.0 Hz, J'=1.3 Hz, 2H); LCMS found for C$_{23}$H$_{21}$NNaO$_5$S (M+Na)$^+$: m/z=446.1.

Example 4.116

Methyl 2-[4-([4-(1,1-dioxido-3-oxoisothiazolidin-5-yl)benzyl]oxymethyl)phenoxy]-6-methoxybenzoate

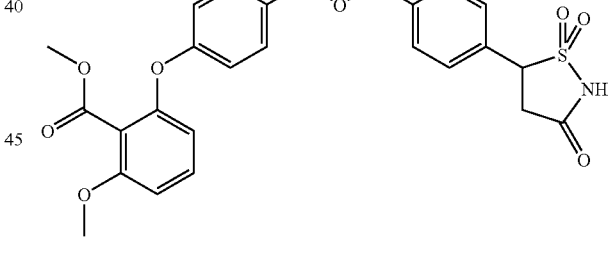

Step 1. Methyl 2-(4-formylphenoxy)-6-methoxybenzoate

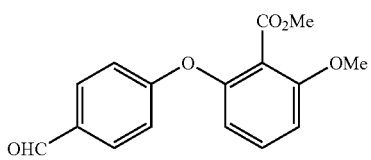

4-Fluorobenzaldehyde (1.00 g, 8.06 mmol) and methyl 2,6-dihydroxybenzoate (2.03 g, 12.1 mmol) were dissolved in N,N-dimethylformamide (50 mL) and potassium carbonate (1.11 g, 8.06 mmol) was added. The reaction was stirred at room temperature overnight. The reaction was diluted with water (25 mL) and the layers separated. The aqueous phase was extracted twice with ethyl acetate (25 mL) then twice with diethyl ether (50 mL). The organic phases were combined and dried over MgSO$_4$. The solution was filtered and the solvent evaporated then placed under high vacuum. The mixture was chromatographed, eluted with 25–50% ethyl acetate/hexanes. The desired fractions were combined and concentrated to give a light yellow oil. The product was redissolved in a minimum amount of dichloromethane, triturated with hexane and the solvent evaporated to give an oily yellow solid (0.21 g, 9%). $^1$H NMR (400 MHz, CDCl$_3$): δ 9.93 (s, 1H), 7.84 (m, 2H), 7.38 (t, J=8.4 Hz, 1H), 7.08 (m, 2H), 6.81 (d, J=8.3 Hz, 1H), 6.63 (d, J=8.2 Hz, 1H), 3.89 (s, 3H), 3.78 (s, 3H); LCMS found for C$_{16}$H$_{15}$O$_5$ (M+H)$^+$: m/z=287.0.

Step 2. Methyl 2-[4-([4-(1,1-dioxido-3-oxo-2,3-dihydroisothiazol-5-yl)benzyl]oxymethyl)phenoxy]-6-methoxybenzoate

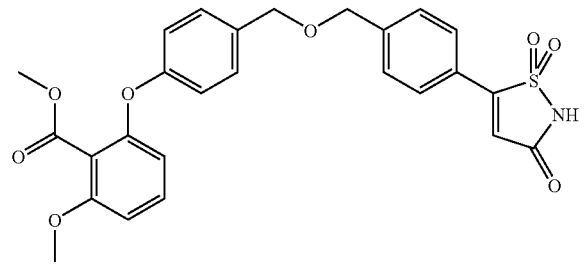

Methyl 2-(4-formylphenoxy)-6-methoxybenzoate (0.071 g, 0.24 mmol) and 5-[4-(hydroxymethyl)phenyl]isothiazol-3(2H)-one 1,1-dioxide (0.050 g, 0.21 mmol) were dissolved in 4 M hydrogen chloride in 1,4-dioxane (2.1 m). The reaction was stirred at ambient temperature for 1.25 h. Triethylsilane (0.13 mL, 0.84 mmol) was added and stirred for 18 h. The reaction was quenched with acetone and evaporated. The product was purified on a 50 mm Luna C18 column using a 20–100% acetonitrile in water gradient with 0.05% trifluoroacetic acid at 30 mL per minute over a 30 minute period. The product was lyophilized to give a white powder (6 mg, 6%). $^1$H NMR (400 MHz, CDCl$_3$): δ 7.79 (d, J=8.4 Hz, 2H), 7.53 (d, J=8.1 Hz, 2H), 7.32 (m, 2H), 6.71 (s, 1H), 6.69 (d, J=8.5 Hz, 1H), 6.49 (d, J=8.3 Hz, 1H), 4.62 (m, 2H), 4.55 (m, 2H), 3.87 (s, 3H), 3.85 (s, 3H); LCMS found for C$_{26}$H$_{23}$NNaO$_8$S (M+Na)$^+$: m/z=532.0.

Step 3. Synthesis of methyl 2-[4-([4-(1,1-dioxido-3-oxoisothiazolidin-5-yl)benzyl]oxymethyl)phenoxy]-6-methoxybenzoate

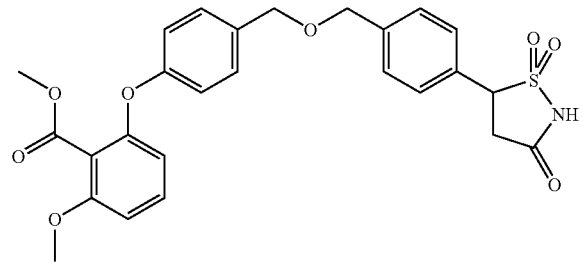

2 M Lithium borohydride in tetrahydrofuran (0.045 mL, 0.090 mmol) was added to methyl 2-[4-([4-(1,1-dioxido-3-oxo-2,3-dihydroisothiazol-5-yl)benzyl]oxymethyl)phenoxy]-6-methoxybenzoate (8 mg, 0.02 mmol) in tetrahydrofuran (1 mL). After stirring at ambient temperature for one hour, the reaction was quenched with saturated aqueous ammonium chloride. The product was purified on a 50 mm Luna C18 column using a 20–100% acetonitrile in water gradient with 0.05% trifluoroacetic acid at 30 mL per minute over a 30 minute period. The major product was lyophilized to give a white powder (7 mg, 87%). $^1$H NMR (400 MHz, CDCl$_3$): δ 7.47 (d, J=7.1 Hz, 2H), 7.42 (d, J=7.1 Hz, 2H), 7.31 (m, 4H), 6.68 (d, J=8.6 Hz, 1H), 6.48 (d, J=8.6 Hz, 1H), 4.98 (t, J=8.4 Hz, 1H), 4.56 (m, 4H), 3.87 (s, 3H), 3.85 (s, 3H), 3.37 (m, 2H); LCMS found for C$_{26}$H$_{25}$NNaO$_8$S (M+Na)$^+$: m/z=534.0.

Example 4.117

Methyl 2-[4-((2S)-2-[(2S)-2-(acetylamino)-3-phenylpropanoyl]amino-3-[4-(1,1-dioxido-3-oxoisothiazolidin-5-yl)phenyl]propylamino)butoxy]-6-hydroxybenzoate

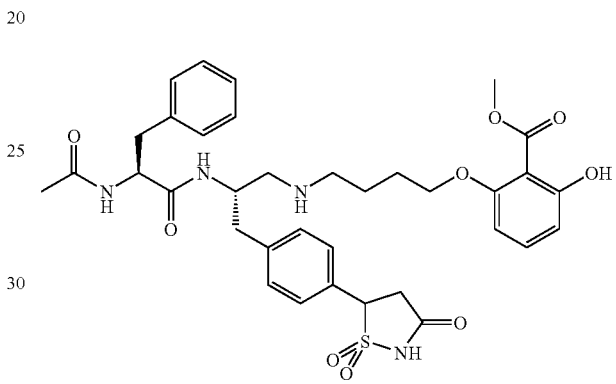

Step 1. (2S)-2-(acetylamino)-N-(1S)-1-[4-(2-tert-butyl-1,1-dioxido-3-oxoisothiazolidin-5-yl)benzyl]-2-hydroxyethyl-3-phenylpropanamide

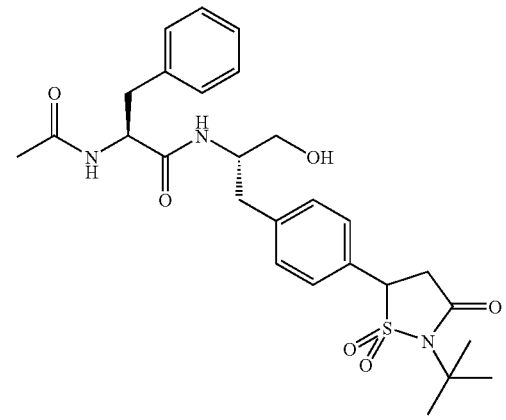

2 M Lithium borohydride in tetrahydrofuran (0.160 mL, 0.32 mmol) was added to methyl (2S)-2-[(2S)-2-(acetylamino)-3-phenylpropanoyl]amino-3-[4-(2-tert-butyl 1,1-dioxido-3-oxo-2,3-dihydroisothiazol-5-yl)phenyl]propanoate (0.188 g, 0.338 mmol) in tetrahydrofuran (1.5 mL). The reaction was stirred at ambient temperature for 21 h. Additional 2 M lithium borohydride in tetrahydrofuran (0.06 mL, 0.12 mmol) was added and stirred at ambient temperature for 22 h. The reaction was quenched with saturated aqueous ammonium chloride and extracted into ethyl acetate. The organic layer was extracted with brine solution. The combined aqueous layers were extracted with ethyl acetate. The combined organic layers were dried over sodium sulfate, filtered, and evaporated. The residue was purified on a 50 mm Luna C18 column using a 10–70% acetonitrile in water gradient with 0.05% trifluoroacetic acid at 30 mL per minute over a 30 minute period. The product was lyophilized to give a white solid (48 mg, 27%). $^1$H NMR (400 MHz, CDCl$_3$+ CD$_3$OD): δ7.27 (m, 7H), 7.19 (m, 2H), 6.84 (d, J=8.4 Hz, 1H), 4.77 (m, 1H), 4.50 (m, 1H), 4.05 (m, 1H), 3.37 (t, J=3.1 Hz, 2H), 3.19 (m, 2H), 3.02–2.83 (m, 3H), 2.74 (m, 1H), 1.93 (s, 3H), 1.66 (s, 9H); LCMS found for C$_{27}$H$_{36}$N$_3$O$_6$S (M+H)$^+$: m/z=530.2.

Step 2. Synthesis of methyl 2-[4-((2S)-2-[(2S)-2-(acetylamino)-3-phenylpropanoyl]amino-3-[4-(2-tert-butyl-1,1-dioxido-3-oxoisothiazolidin-5-yl)phenyl]propylamino)butoxy]-6-hydroxybenzoate trifluoroacetate

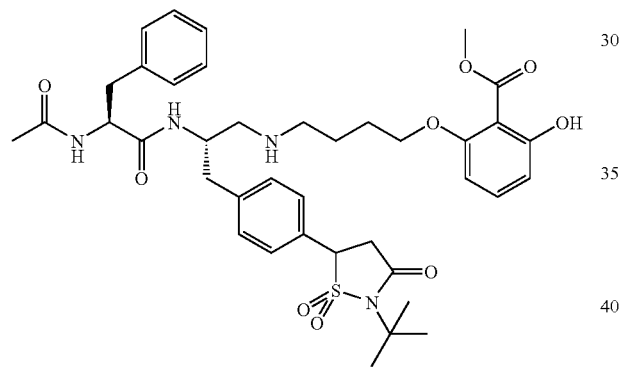

Dess-Martin periodinane (0.0415 g, 0.098 mmol) was added to (2S)-2-(acetylamino)-N-(1S)-1-[4-(2-tert-butyl 1,1-dioxido-3-oxoisothiazolidin-5-yl)benzyl]-2-hydroxyethyl-3-phenylpropanamide (48 mg, 0.091 mmol) in DMF (2 mL). The reaction was stirred at ambient temperature for 3.5 h, and additional Dess-Martin periodinane (5.2 mg, 0.012 mmol) and DMF (0.4 mL) were added. Methyl 2-(4-aminobutoxy)-6-hydroxybenzoate hydrochloride (40.4 mg, 0.146 mmol) was added, followed by sodium triacetoxyborohydride (95.7 mg, 0.452 mmol) and stirred at ambient temperature for 17.5 h, then quenched with water. The product was purified on a 50 mm Luna C18 column using a 10–70% acetonitrile in water gradient with 0.05% trifluoroacetic acid at 30 mL per minute over a 30 minute period. The product was lyophilized to give a white solid (0.036 g, 46%). $^1$H NMR (400 MHz, CD$_3$OD): δ 7.45–7.11 (m, 10H), 6.50 (m, 2H), 5.09 (m, 1H), 4.31 (m, 2H), 4.05 (bs, 2H), 3.86 (s, 3H), 3.35 (m, 1H), 3.28–2.74 (m, 11H), 1.87 (m, 7H), 1.61 (m, 9H); LCMS found for C$_{39}$H$_{51}$N$_4$O$_9$S (M+H)$^+$: m/z=751.3.

Step 3. Methyl 2-[4-((2S)-2-[(2S)-2-(acetylamino)-3-phenylpropanoyl]amino-3-[4-(1,1-dioxido-3-oxoisothiazolidin-5-yl)phenyl]propylamino)butoxy]-6-hydroxybenzoate trifluoroacetate

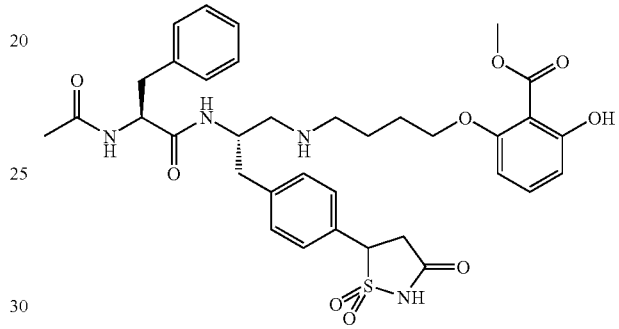

Methyl 2-[4-((2S)-2-[(2S)-2-(acetylamino)-3-phenylpropanoyl]amino-3-[4-(2-tert-butyl-1,1-dioxido-3-oxoisothiazolidin-5-yl)phenyl]propylamino)butoxy-]6-hydroxybenzoate trifluoroacetate (salt) was submitted in two batches to deprotection conditions in the a microwave. The first batch (5.1 mg, 0.0061 mmol) was combined with crushed 3 Å molecular sieves (7.9 mg) and trifluoroacetic acid (0.75 mL) and heated at 130° C. 3 times for one minute each time. The second batch (18 mg, 0.021 mmol) was combined with crushed 3 Å molecular sieves (29 mg) and trifluoroacetic acid (2.6 mL) and heated at 130° C. twice for one minute each time. The reactions were combined and filtered through a glass frit. The filtrate was purified on a 50 mm Luna C18 column using a 10–70% acetonitrile in water gradient with 0.05% trifluoroacetic acid at 30 mL per minute over a 30 minute period. The major product was lyophilized to obtain a white solid (12 mg), which was further purified on a 50 mm Luna C18 column using a 0–50% acetonitrile in water gradient with 0.05% trifluoroacetic acid at 30 mL per minute over a 30 minute period. The desired fractions were combined and lyophilized to give a white solid (6 mg, 24%). $^1$H NMR (400 MHz, CD$_3$OD): δ 7.50 (d, J=8.0 Hz, 2H), 7.30 (m, 6H), 7.17 (m, 2H), 6.55 (dd, J=7.3 Hz, J'=6.5 Hz, 2H), 5.17 (m, 1H), 4.36 (m, 2H), 4.09 (bs, 2H), 3.91 (s, 3H), 3.22–2.83 (m, 9H), 1.92 (m, 7H); LCMS found for C$_{35}$H$_{43}$N$_4$O$_9$S (M+H)$^+$: m/z=695.2.

Example 4.118

N-(1S)-1-(1H-benzimidazol-2-yl)-2-[4-(1,1-dioxido-3-oxoisothiazolidin-5-yl)phenyl]ethyl-3-(trifluoromethyl)benzenesulfonamide trifluoroacetate

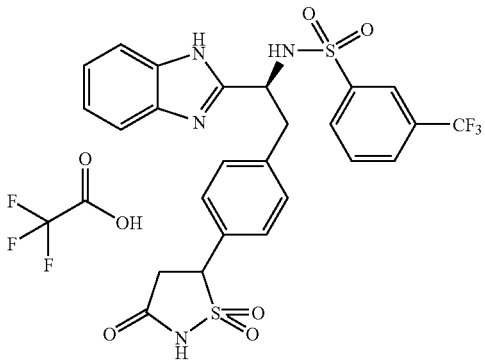

Step 1: Benzyl (2S)-2-[(tert-butoxycarbonyl)amino]-3-(4-hydroxyphenyl)propanoate

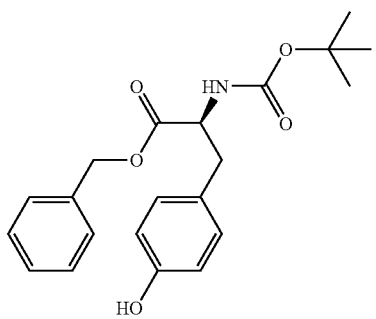

A solution of 2S-2-[(tert-butoxycarbonyl)amino]-3-(4-hydroxyphenyl)propanoic acid (38.0 g, 0.135 mol), 1,8-diazabicyclo[5.4.0]undec-7-ene (18 mL, 0.12 mol) and benzyl bromide (16.0 mL, 0.134 mol) in tetrahydrofuran (200 mL) was heated to reflux at 65° C. for 1.5 h. On cooling to rt, the DBU-HBr precipitate formed was filtered off, and the solvent evaporated. The residue was dissolved in ethyl acetate, washed with 1 N HCl, sodium bicarbonate and sodium chloride solution and dried over sodium sulfate and then filtered. The crude product was purified with 10–30% ethyl acetate/hexane as the eluant to give the products as a white solid (35.5 g, 70%). $^1$H NMR (400 MHz, CD$_3$OD): δ 7.38 (m, 5H), 6.95 (d, 2H), 6.65 (d, 2H), 5.15 (dd, 2H), d 4.3(t, 1H), 3.0 (dd, 1H), 2.85(dd, 1H), 1.4 (s, 9H). LCMS found for C$_{21}$H$_{26}$NO$_5$ (M+H)$^+$: m/z=372.

Step 2: Benzyl (2S)-2-[(tert-butoxycarbonyl)amino]-3-(4-[(trifluoromethyl)sulfonyl]-oxyphenyl)propanoate

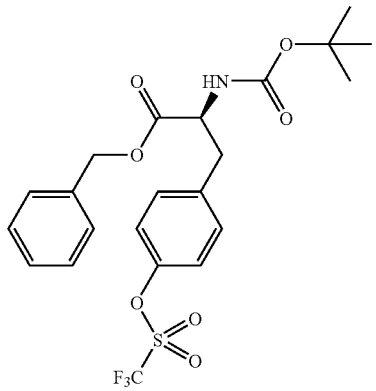

To a solution of benzyl (2S)-2-[(tert-butoxycarbonyl)amino]-3-(4-hydroxyphenyl)propanoate (30.7 g, 0.0826 mmol) in methylene chloride (100 mL), pyridine (10 mL) was added. The reaction was cooled to 0° C. and trifluoromethanesulfonic anhydride (16.7 mL, 0.0992 mol) was added slowly with a syringe over 20 minutes. The reaction was stirred for an additional 30 min in the ice-bath and then quenched with water. The organic layer was separated and washed with 1 M HCl and satd. brine, dried over anhyd. sodium sulfate, filtered and evaporated in vacuo to give the crude product which was purified on silicagel column using 10–50% ethyl acetate/hexanes as the eluant. Fractions containing the major component were combined, concentrated and to give a colorless oil which gradually crystallized to give the product (40.0 g, 96%). $^1$H NMR (400 MHz, CD$_3$OD): δ 7.4 (m, 9H), 5.2 (dd, 2H), 4.4 (d, 1H), 3.18 (dd, 1H), 2.9 (dd, 1H), 1.4 (s, 9H). LCMS found for C$_{22}$H$_{25}$F$_3$NO$_7$S (M+H)$^+$: m/z=504.

Step 3: Benzyl (2S)-2-[(tert-butoxycarbonyl)amino]-3-[4-(4,4,5,5-tetramethyl-1,3,2-dioxaborolan-2-yl)phenyl]propanoate

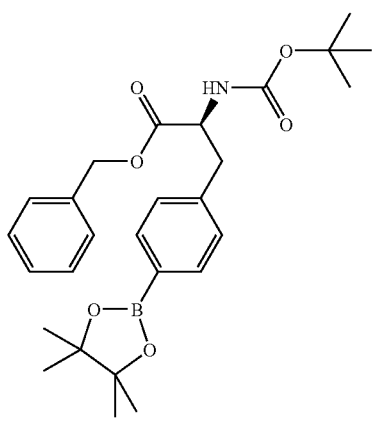

A solution of benzyl (2S)-2-[(tert-butoxycarbonyl)amino]-3-(4-[(trifluoromethyl)sulfonyl]oxyphenyl)propanoate (6.37 g, 0.0126 mol), bis(tricyclohexylphosphine)

palladium(II) chloride (0.3 g, 0.0004 mol), tricyclohexylphosphine (0.1 g, 0.0004 mol), potassium acetate (3.7 g, 0.038 mol), and 4,4,5,5,4',4',5',5'-octamethyl-[2,2']bi[[1,3,2]dioxaborolanyl] (3.5 g, 0.014 mol) (bis-pinocolato)diboron,) in dry DMF (50 mL) was heated in an oil bath at 130° C. for 2 h. The reaction appeared gray-green and was heated at 100° C. for an additional 2–3 h. The mixture was diluted with water (1 L) then was extracted with diethyl ether (250 mL) four times. The combined organic phases were combined, dried over MgSO$_4$, filtered and the solvents evaporated under reduced pressure. The crude mixture was loaded on a silica gel column using ethyl acetate/hexanes and eluted with 10% ethyl acetate in hexanes to 50% ethyl acetate. Fractions containing the major component were combined and concentrated to give a lavender oil, which upon standing solidified to give the product (5.95 g, 98%). LCMS found for $C_{27}H_{37}BNO_6$ (M+H)$^+$: m/z=482.

Step 4: Benzyl N-(tert-butoxycarbonyl)-4-(2-tert-butyl-1,1-dioxido-3-oxo-2,3-dihydroisothiazol-5-yl)-L-phenylalaninate

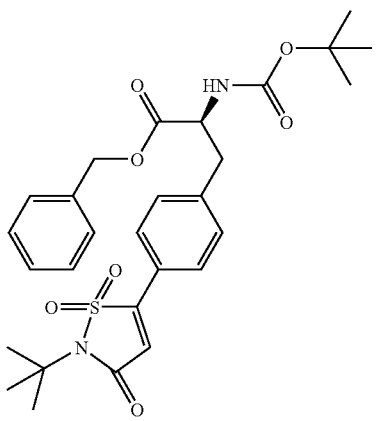

A solution of benzyl(2S)-2-[(tert-butoxycarbonyl)amino]-3-[4-(4,4,5,5-tetramethyl-1,3,2-dioxaborolan-2-yl)phenyl]propanoate (3.33 g, 6.92 mmol), 2-tert-Butyl-5-chloro-1,1-dioxo-1,2-dihydro-1$\lambda^6$-isothiazol-3-one (1.86 g, 8.31 mmol), [1,1'-bis(diphenylphosphino)ferrocene]dichloropalladium(II), complex with dichloromethane (1:1) (0.68 g, 0.83 mmol), and potassium carbonate (4.78 g, 0.0346 mol) in 1,4-dioxane (25 mL) were added to a flask with a reflux condenser. The reaction atmosphere was evacuated and purged four times with dry nitrogen. The reaction was heated at 80° C. overnight. The reaction mixture was diluted with water and extracted with ethyl acetate. ethyl acetate extracts were washed with saturated brine and dried over anhyd. sodium sulfate, filtered and concentrated to an oil. The crude was eluted with 10%–30% ethyl acetate in hexanes to give the product (1.4 g, 37%). LCMS found for $C_{28}H_{35}N_2O_7S$ (M+H)$^+$: m/z=543.

Step 5: (2S)-2-[(tert-butoxycarbonyl)amino]-3-[4-(2-tert-butyl-1,1-dioxido-3-oxoisothiazolidin-5-yl)phenyl]propanoic acid

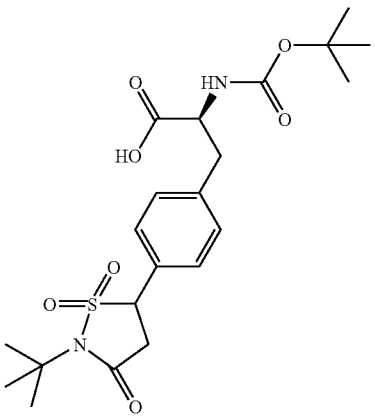

To a solution of benzyl N-(tert-butoxycarbonyl)-4-(2-tert-butyl-1,1-dioxido-3-oxo-2,3-dihydroisothiazol-5-yl)-L-phenylalaninate (1.3 g, 2.4 mmol) in ethanol (35 mL) in a parr shaker, palladium (0.700 g, 6.58 mmol) (Pd, 10% by weight on activated carbon) was added and hydrogenated overnight at 50 psi. The suspension was filtered through celite and concentrated to give the crude product. The crude was purified on preparative LCMS to give the product (0.71 g, 65%). LCMS found for $C_{21}H_{3}N_2O_7S$ (M+H)$^+$: m/z=455.

Step 6: tert-butyl (1S)-2-[(2-aminophenyl)amino]-1-[4-(2-tert-butyl-1,1-dioxido-3-oxoisothiazolidin-5-yl)benzyl]-2-oxoethylcarbamate

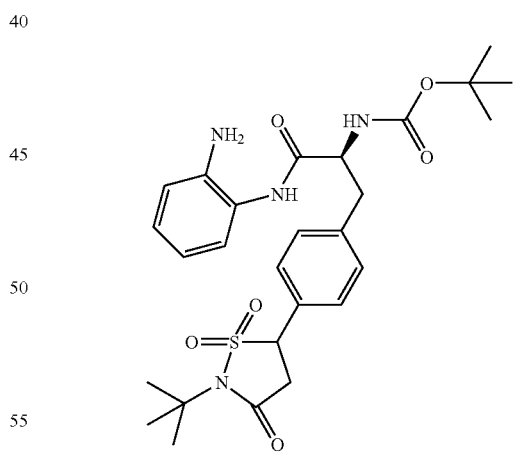

To a solution of N,N-dimethylformamide (5.0 mL) was added (2S)-2-[(tert-butoxycarbonyl)amino]-3-[4-(2-tert-butyl-1,1-dioxido-3-oxoisothiazolidin-5-yl)phenyl]propanoic acid (709.6 mg, 1.561 mmol), N,N,N',N'-tetramethyl-O-(7-azabenzotriazol-1-yl)uronium hexafluorophosphate (712 mg, 1.87 mmol), and N,N-diisopropylethylamine (1.3 mL, 7.80 mmol) and premixed for 5 minutes and then 1,2-benzenediamine (253 mg, 2.34 mmol) was added and stirred at room temperature overnight. Product was concentrated Step 7: 5-4-[(2S)-2-amino-2-(H-benzimidazol-2-yl)ethyl]phenyl-2-tert-butylisothiazolidin-3-one 1,1-dioxide bis(trifluoroacetate)

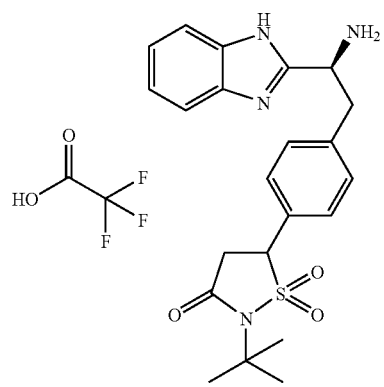

A solution of tert-butyl (1S)-2-[(2-aminophenyl)amino]-1-[4-(2-tert-butyl-1,1-dioxido-3-oxoisothiazolidin-5-yl)benzyl]-2-oxoethylcarbamate trifluoroacetate (690 mg, 1.04 mmol) in glacial acetic acid (10 mL) was heated in a microwave to 120° C. for 60 seconds. The solvents were stripped down and treated with trifluoroacetic acid (2 mL) and methylene chloride (2 mL) for 15 minutes and then concentrated. The crude residue was purified by preparative LCMS to give the product (578.5 mg, 84%). LCMS found for $C_{22}H_{27}N_4O_3S$ (M+H)$^+$: m/z=427.

Step 8: N-(1S)-1-(1H-benzimidazol-2-yl)-2-[4-(1,1-dioxido-3-oxoisothiazolidin-5-yl)phenyl]ethyl-3-(trifluoromethyl)benzenesulfonamide trifluoroacetate 5-4-[(2S)-2-Amino-2-(1H-benzimidazol-2-yl)ethyl]phenyl-2-tert-butylisothiazolidin-3one 1,1-dioxide bis(trifluoroacetate) (10.0 mg, 0.0153 mmol) was dissolved in methylene chloride (1 mL) and then N,N-diisopropylethylamine (8 μL, 0.04 mmol) was added followed by m-(trifluoromethyl)benzenesulfonyl chloride. After stirring overnight, the solvents were removed and 1 mL of TFA was added and the reaction heated in a microwave at 120° C. for 5 minutes. The crude was purified by preparative LCMS to give the product (6.2 mg, 58%). $^1$H NMR (400 MHz, CD$_3$OD): δ 8.0 (s, 1H), 7.8 (m, 2H), 7.7 (m, 2H), 7.6 (m, 3H), 7.25 (d, 2H), 7.12 (d, 2H), 5.16 (m, 2H), 3.3 (m, 4H). LCMS found for $C_{25}H_{22}F_3N_4O_5S_2$ (M+H)$^+$: m/z=579.

Example 4.119

N-{(1S)-1-(1H-Benzimidazol-2-yl)-2-[4-(1,1-dioxido-3-oxoisothiazolidin-5-yl)phenyl]ethyl}benzenesulfonamide trifluoroacetate

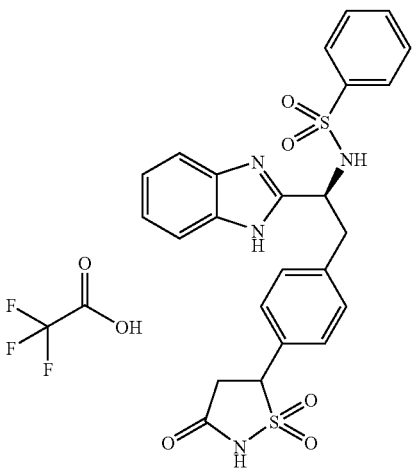

Title compound was prepared according to the procedure in Example 4.118 using the appropriate reagents and starting materials. $^1$H NMR (400 MHz, CD$_3$OD): δ 7.8–7.50 (m, 7H), 7.4 (m, 2H), 7.34 (m, 2H), 7.03 (m, 2H), 5.10 (m, 1H), 4.9 (m, 1H), 3.3 (m, 4H). LCMS found for $C_{24}H_{23}N_4O_5S_2$ (M+H)$^+$: m/z=511.

Example 4.120

N-{(1S)-1-(1H-Benzimidazol-2-yl)-2-[4-(1,1-dioxido-3-oxoisothiazolidin-5-yl)phenyl]ethyl}-4-cyanobenzenesulfonamide trifluoroacetate

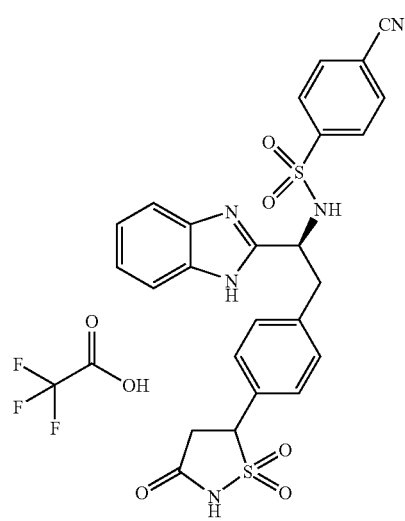

Title compound was prepared according to the procedure in Example 4.118 using the appropriate reagents and starting materials. $^1$H NMR (400 MHz, CD$_3$OD): δ 7.8 (m, 6H), 7.60 (m, 2H), 7.30 (m, 2H), 7.13 (m, 2H), 5.14 (m, 1H), 5.01 (m, 1H), 3.3 (m, 4H). LCMS found for $C_{25}H_{22}N_5O_5S_2$ (M+H)$^+$: m/z=536.

Example 4.121

N-{(1S)-1-(1H-Benzimidazol-2-yl)-2-[4-(1,1-di-oxido-3-oxoisothiazolidin-5-yl)phenyl]ethyl}-3-phenoxybenzenesulfonamide trifluroacetate

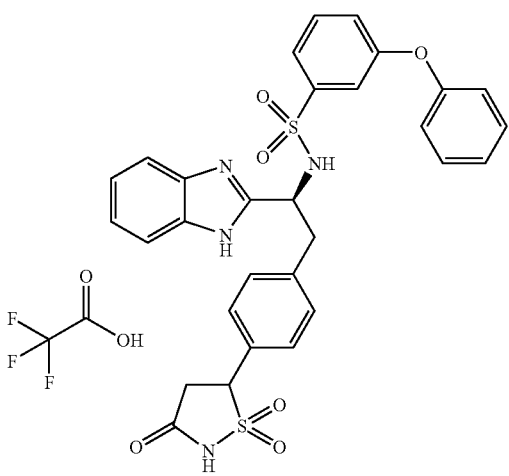

Title compound was prepared according to the procedure in Example 4.118 using the appropriate reagents and starting materials. $^1$H NMR (400 MHz, CD$_3$OD): δ 7.72 (m, 2H), 7.59 (m, 2H), 7.4–7.2 (m, 6H), 7.11 (m, 3H), 6.98 (d, 2H), 5.09 (m, 1H), 4.93 (m, 1H), 3.30 (m, 4H). LCMS found for C$_{30}$H$_{27}$N$_4$O$_6$S$_2$ (M+H)$^+$: m/z=603.

Example 4.122

N-{(1S)-1-(1H-Benzimidazol-2-yl)-2-[4-(1,1-di-oxido-3-oxoisothiazolidin-5-yl)phenyl]ethyl}-3-phenoxybenzenesulfonamide trifluoroacetate

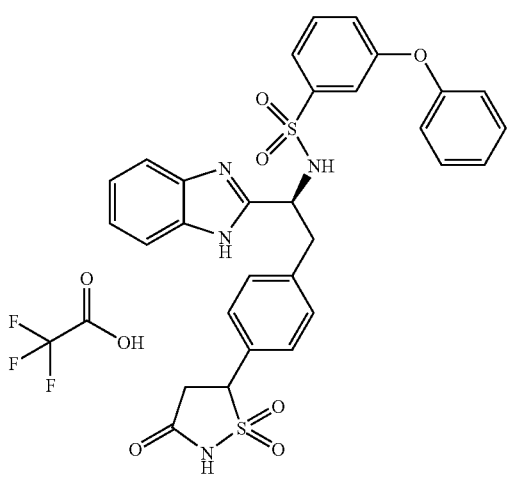

Title compound was prepared according to the procedure in Example 4.118 using the appropriate reagents and starting materials. $^1$H NMR (400 MHz, CD$_3$OD): δ 7.72 (m, 2H), 7.59 (m, 2H), 7.4–7.2 (m, 6H), 7.11 (m, 3H), 6.98 (d, 2H), 5.09 (m, 1H), 4.93 (m, 1H), 3.30 (m, 4H). LCMS found for C$_{30}$H$_{27}$N$_4$O$_6$S' (M+H)$^+$: m/z=603.

Example 4.123

N-{(1S)-1-(1H-Benzimidazol-2-yl)-2-[4-(1,1-di-oxido-3-oxoisothiazolidin-5-yl)phenyl]ethyl}-3-(trifluoromethyl)benzamide trifluoroacetate

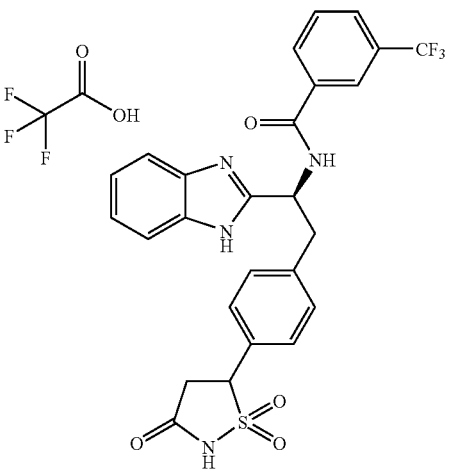

Title compound was prepared according to the procedure in Example 4.118 using the appropriate reagents and starting materials. $^1$H NMR (400 MHz, CD$_3$OD): δ 7.8 (m, 6H), 7.60 (m, 2H), 7.30 (m, 2H), 7.13 (m, 2H), 5.14 (m, 1H), 5.01 (m, 1H), 3.3 (m, 4H). LCMS found for C$_{26}$H$_{22}$F$_3$N$_4$O$_4$S (M+H)$^+$: m/z=543.

Example 4.124

N-{(1S)-1-(1H-benzimidazol-2-yl)-2-[4-(1,1-di-oxido-3-oxoisothiazolidin-5-yl)phenyl]ethyl}cyclopentanecarboxamide trifluoroacetate

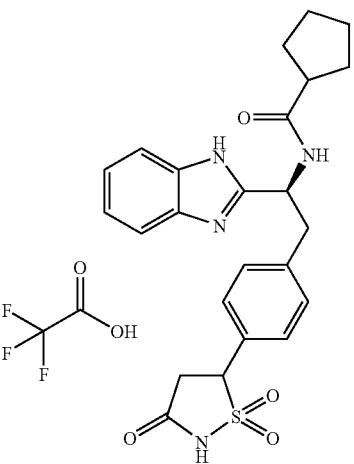

Title compound was prepared according to the procedure in Example 4.118 using the appropriate reagents and starting materials. LCMS found for C$_{24}$H$_{27}$N$_4$O$_4$S (M+H)$^+$: m/z=467.

Example 4.125

N-{(1S)-1-(1H-benzimidazol-2-yl)-2-[4-(1,1-di-oxido-3-oxoisothiazolidin-5-yl)phenyl]ethyl}-2-phenylacetamide trifluoroacetate

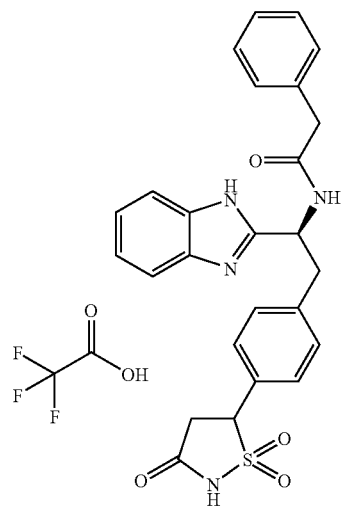

Title compound was prepared according to the procedure in Example 4.118 using the appropriate reagents and starting materials. LCMS found for $C_{26}H_{25}N_4O_4S$ (M+H)$^+$: m/z=489.

Example 4.126

N-{(1S)-1-(1H-benzimidazol-2-yl)-2-[4-(1,1-di-oxido-3-oxoisothiazolidin-5-yl)phenyl]ethyl}cyclopropanecarboxamide trifluroacetate

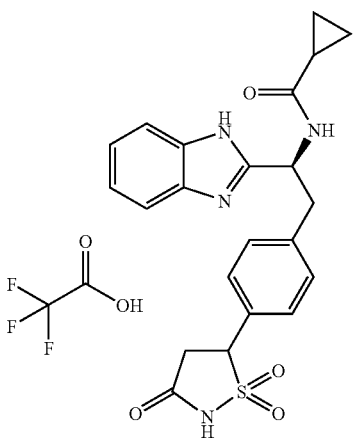

Title compound was prepared according to the procedure in Example 4.118 using the appropriate reagents and starting materials. LCMS found for $C_{22}H_{23}N_4O_4S$ (M+H)$^+$: m/z=439.

Example 4.127

N-{(1S)-1-(1H-benzimidazol-2-yl)-2-[4-(1,1-di-oxido-3-oxoisothiazolidin-5-yl)phenyl]ethyl}-2-methylpropanamide trifluoroacetate

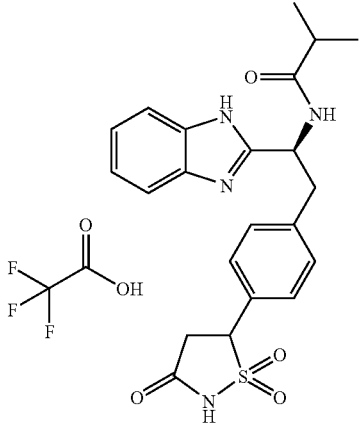

Title compound was prepared according to the procedure in Example 4.118 using the appropriate reagents and starting materials. $^1$H NMR (400 MHz, CD$_3$OD): δ 7.76 (m, 2H), 7.60 (m, 2H), 7.43 (m, 2H), 7.26 (m, 2H), 5.45 (m, 1H), 5.15 (m, 1H), 3.34 (m, 2H), 3.30 (m, 2H), 2.51 (m, 1H), 1.02 (d, 1.5H), 0.98 (d, 1.5H). LCMS found for $C_{22}H_{24}N_4O_4S$ (M+H)$^+$: m/z=441.

Example 4.128

N-{(1S)-1-(1H-benzimidazol-2-yl)-2-[4-(1,1-di-oxido-3-oxoisothiazolidin-5-yl)phenyl]ethyl}-2-methoxyacetamide trifluoroacetate

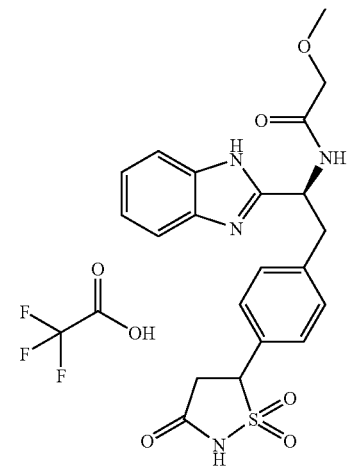

Title compound was prepared according to the procedure in Example 4.118 using the appropriate reagents and starting materials. LCMS found for $C_{21}H_{23}N_4O_5S$ (M+H)$^+$: m/z=443.

Example 4.129

N-{(1S)-1-(1H-benzimidazol-2-yl)-2-[4-(1,1-di-oxido-3-oxoisothiazolidin-5-yl)phenyl]ethyl}cyclobutanecarboxamide trifluoroacetate

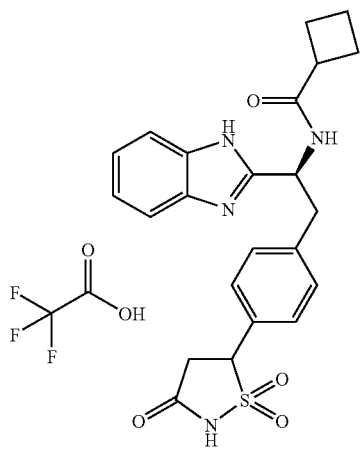

Title compound was prepared according to the procedure in Example 4.118 using the appropriate reagents and starting materials. LCMS found for $C_{23}H_{25}N_4O_4S$ (M+H)$^+$: m/z=453.

Example 4.130

N-{(1S)-1-(1H-benzimidazol-2-yl)-2-[4-(1,1-di-oxido-3-oxoisothiazolidin-5-yl)phenyl]ethyl}-3,3-dimethylbutanamide trifluoroacetate

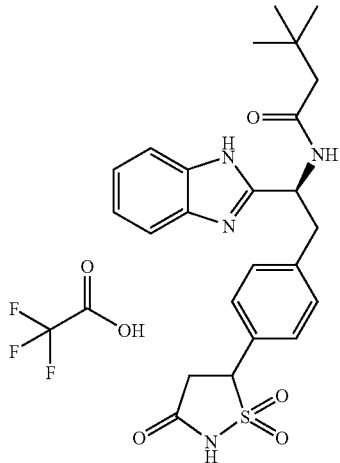

Title compound was prepared according to the procedure in Example 4.118 using the appropriate reagents and starting materials. LCMS found for $C_{24}H_{29}N_4O_4S$ (M+H)$^+$: m/z 469.

Example 4.131

N-{(1S)-1-(1H-benzimidazol-2-yl)-2-[4-(1,1-di-oxido-3-oxoisothiazolidin-5-yl)phenyl]ethyl}isonicotinamide bis(trifluoroacetate)

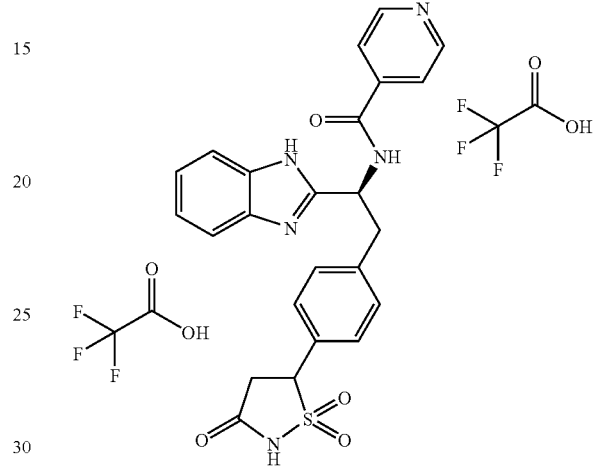

Title compound was prepared according to the procedure in Example 4.118 using the appropriate reagents and starting materials. LCMS found for $C_{24}H_{22}N_5O_4S$ (M+H)$^+$: m/z=476.

Example 4.132

N-{(1S)-1-(1H-benzimidazol-2-yl)-2-[4-(1,1-di-oxido-3-oxoisothiazolidin-5-yl)phenyl]ethyl}thiophene-2-carboxamide trifluoroacetate

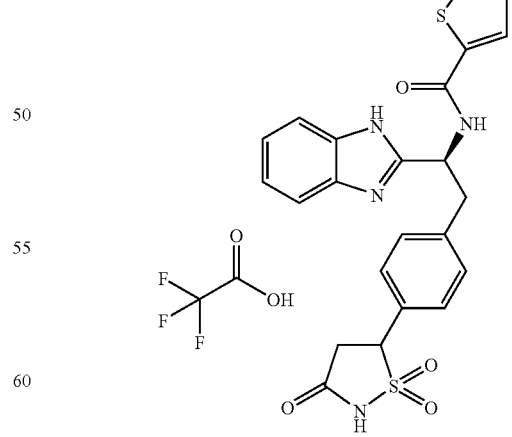

Title compound was prepared according to the procedure in Example 4.118 using the appropriate reagents and starting materials. LCMS found for $C_{23}H_{21}N_4O_4S_2$ (M+H)$^+$: m/z=481.

Example 4.133

N-{(1S)-1-(1H-benzimidazol-2-yl)-2-[4-(1,1-di-oxido-3-oxoisothiazolidin-5-yl)phenyl]ethyl}-3-methylbutanamide trifluoroacetate

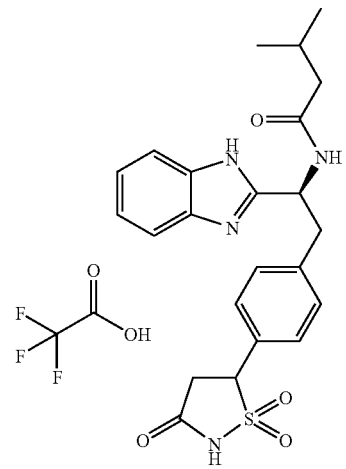

Title compound was prepared according to the procedure in Example 4.118 using the appropriate reagents and starting materials. LCMS found for $C_{23}H_{27}N_4O_4S$ (M+H)$^+$: m/z=455.

Example 4.134

N-{(1S)-1-(1H-benzimidazol-2-yl)-2-[4-(1,1-di-oxido-3-oxoisothiazolidin-5-yl)phenyl]ethyl}cyclohexanecarboxamide trifluoroacetate

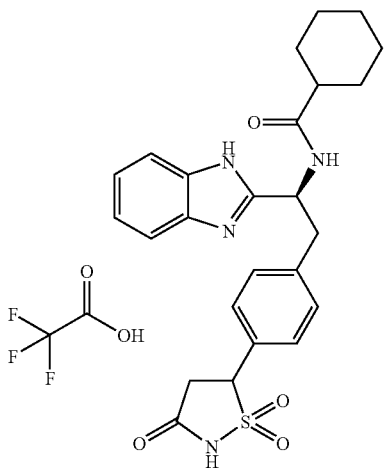

Title compound was prepared according to the procedure in Example 4.118 using the appropriate reagents and starting materials. LCMS found for $C_{21}H_{22}N_2O_6S$ (M+H)$^+$: m/z=429.

Example 4.135

N-{(1S)-1-(1H-benzimidazol-2-yl)-2-[4-(1,1-di-oxido-3-oxoisothiazolidin-5-yl)phenyl]ethyl}-3-phenylpropanamide trifluoroacetate

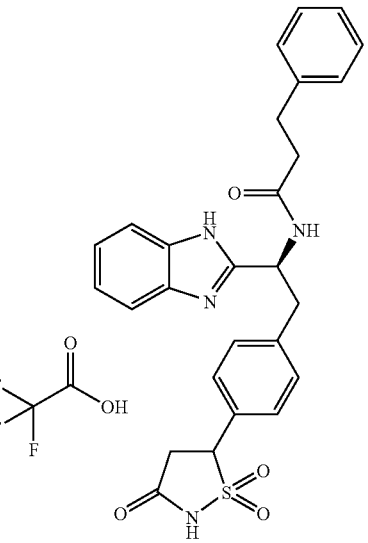

Title compound was prepared according to the procedure in Example 4.118 using the appropriate reagents and starting materials. LCMS found for $C_{25}H_{29}N_4O_4S$ (M+H)$^+$: m/z=481.

Example 4.136

N-{(1S)-1-(1H-benzimidazol-2-yl)-2-[4-(1,1-di-oxido-3-oxoisothiazolidin-5-yl)phenyl]ethyl}-4-phenoxybenzenesulfonamide trifluoroacetate

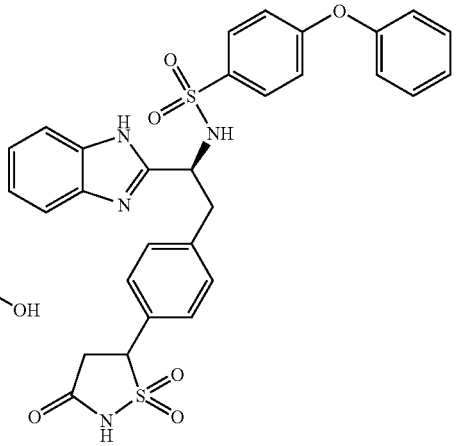

Title compound was prepared according to the procedure in Example 4.118 using the appropriate reagents and starting materials. $^1$H NMR (400 MHz, CD$_3$OD): δ 7.77 (m, 2H), 7.60 (m, 5H), 7.42 (m, 2H), 7.32 (m, 2H), 7.30 (m, 1H), 7.10

(m, 2H), 7.03 (m, 2H), 6.90 (m, 2H), 5.10 (m, 1H), 4.90 (m, 1H), 3.33 (m, 4H). LCMS found for $C_{30}H_{27}N_4O_6S_2$ (M+H)$^+$: m/z=603.

Example 4.137

N-{(1S)-1-(1H-benzimidazol-2-yl)-2-[4-(1,1-di-oxido-3-oxoisothiazolidin-5-yl)phenyl]ethyl}biphenyl-4-sulfonamide trifluoroacetate

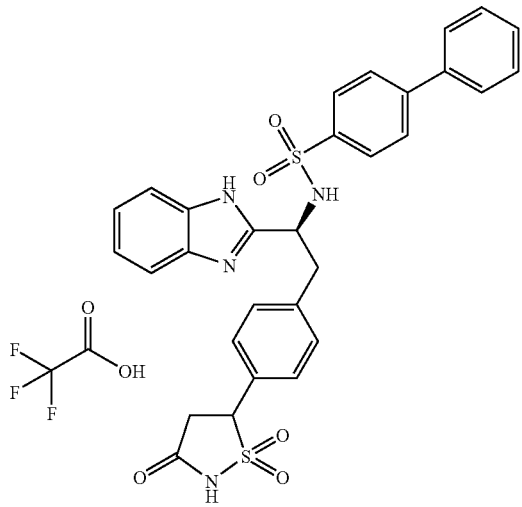

Title compound was prepared according to the procedure in Example 4.118 using the appropriate reagents and starting materials. LCMS found for $C_{30}H_{27}N_4O_5S_2$ (M+H)$^+$: m/z=587.

Example 4.138

N-{(1S)-1-(1H-benzimidazol-2-yl)-2-[4-(1,1-di-oxido-3-oxoisothiazolidin-5-yl)phenyl]ethyl}-4-chlorobenzenesulfonamide trifluoroacetate

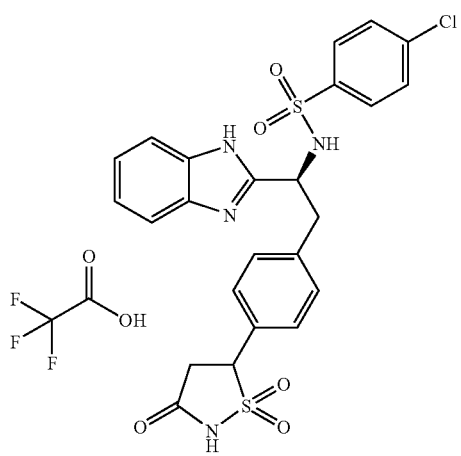

Title compound was prepared according to the procedure in Example 4.118 using the appropriate reagents and starting materials. $^1$H NMR (400 MHz, CD$_3$OD): δ 7.76 (m, 2H), 7.60 (m, 4H), 7.40 (m, 2H), 7.3)(m, 2H), 7.10 (m, 2H), 5.12 (m, 1H), 4.96 (m, 1H), 3.3 (m, 4H). LCMS found for $C_{24}H_{22}ClN_4O_5S_2$ (M+H)$^+$: m/z=545.

Example 4.139

N-{(1S)-1-(1H-benzimidazol-2-yl)-2-[4-(1,1-di-oxido-3-oxoisothiazolidin-5-yl)phenyl]ethyl}-3-chlorobenzenesulfonamide trifluoroacetate

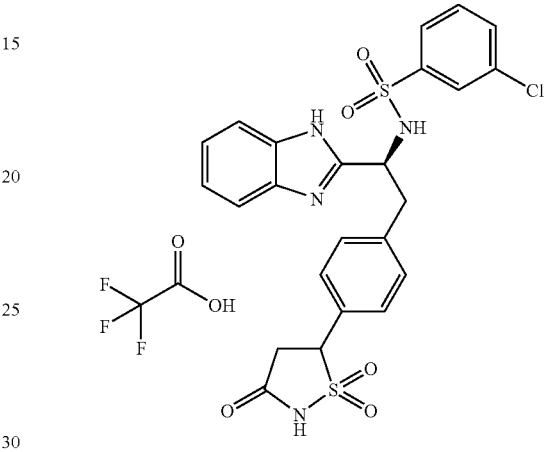

Title compound was prepared according to the procedure in Example 4.118 using the appropriate reagents and starting materials. LCMS found for $C_{24}H_{22}ClN_4O_5S_2$ (M+H)$^+$: m/z=545.

Example 4.140

N-{(1S)-1-(1H-benzimidazol-2-yl)-2-[4-(1,1-di-oxido-3-oxoisothiazolidin-5-yl)phenyl]ethyl}-2-chlorobenzenesulfonamide trifluoroacetate

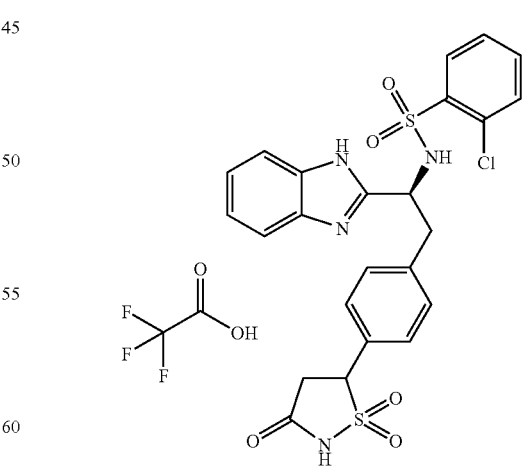

Title compound was prepared according to the procedure in Example 4.118 using the appropriate reagents and starting materials. LCMS found for $C_{24}H_{22}ClN_4O_5S_2$ (M+H)$^+$: m/z=545.

Example 4.141

N-{(1S)-1-(1H-benzimidazol-2-yl)-2-[4-(1,1-di-oxido-3-oxoisothiazolidin-5-yl)phenyl]ethyl}-2-methylbenzenesulfonamide trifluoroacetate

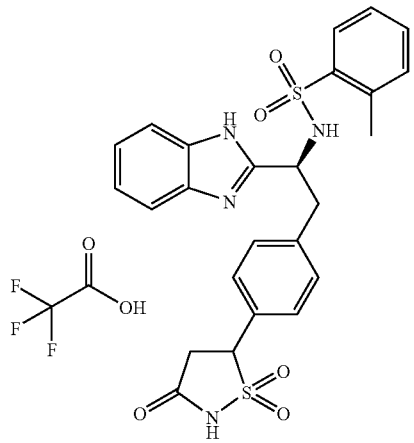

Title compound was prepared according to the procedure in Example 4.118 using the appropriate reagents and starting materials. LCMS found for $C_{25}H_{25}N_4O_5S_2$ $(M+H)^+$: m/z=525.

Example 4.142

N-{(1S)-1-(1H-benzimidazol-2-yl)-2-[4-(1,1-di-oxido-3-oxoisothiazolidin-5-yl)phenyl]ethyl}-3-methylbenzenesulfonamide trifluoroacetate

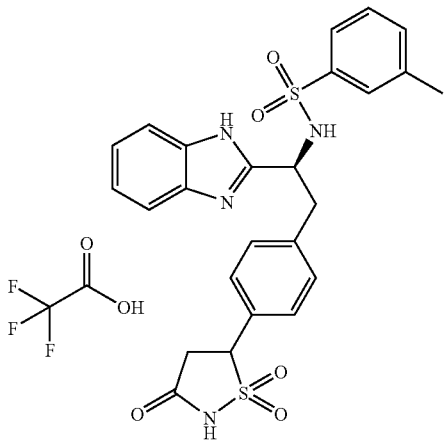

Title compound was prepared according to the procedure in Example 4.118 using the appropriate reagents and starting materials. $^1$H NMR (400 MHz, CD$_3$OD): δ 7.70 (m, 2H), 7.60 (m, 2H), 7.44 (m, 2H), 7.28 (m, 4H), 7.07 (d, 2H), 5.08 (m, 1H), 4.96 (m, 1H), 2.9 (m, 4H), 2.25 (s, 3H). LCMS found for $C_{25}H_{25}N_4O_5S_2$ $(M+H)^+$: m/z=525.

Example 4.143

N-{(1S)-1-(1H-benzimidazol-2-yl)-2-[4-(1,1-di-oxido-3-oxoisothiazolidin-5-yl)phenyl]ethyl}-4-methylbenzenesulfonamide trifluoroacetate

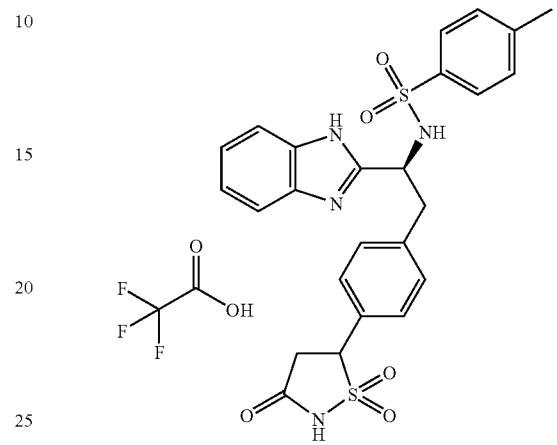

Title compound was prepared according to the procedure in Example 4.118 using the appropriate reagents and starting materials. LCMS found for $C_{25}H_{25}N_4O_5S_2$ $(M+H)^+$: m/z=525.

Example 4.144

N-{(1S)-1-(1H-benzimidazol-2-yl)-2-[4-(1,1-di-oxido-3-oxoisothiazolidin-5-yl)phenyl]ethyl}-3-methoxybenzenesulfonamide trifluoroacetate

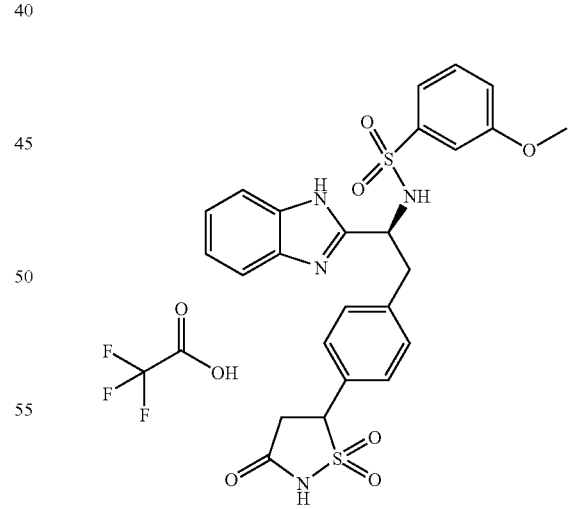

Title compound was prepared according to the procedure in Example 4.118 using the appropriate reagents and starting materials. $^1$H NMR (400 MHz, CD$_3$OD): δ 7.78 (m, 2H), 7.60 (m, 2H), 7.40–7.00 (m, 8H), 5.10 (m, 1H), 4.97 (m, 1H), 3.77 (s, 3H), 3.30 (m, 4H). LCMS found for $C_{25}H_{25}N_4O_6S'$ $(M+H)^+$: m/z=541.

Example 4.145

N-{(1S)-1-(1H-benzimidazol-2-yl)-2-[4-(1,1-di-oxido-3-oxoisothiazolidin-5-yl)phenyl]ethyl}-3,5-dimethylisoxazole-4-sulfonamide trifluoroacetate

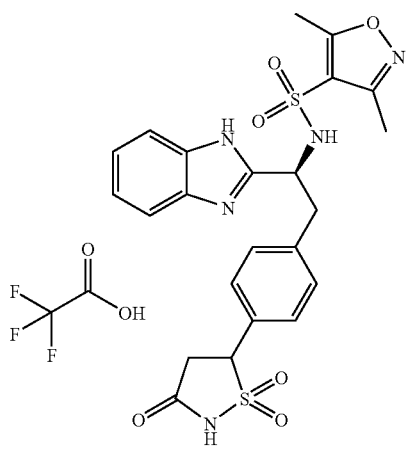

Title compound was prepared according to the procedure in Example 4.118 using the appropriate reagents and starting materials. LCMS found for $C_{23}H_{24}N_5O_6S_2$ $(M+H)^+$: m/z=530.

Example 4.146

N-{(1S)-1-(1H-benzimidazol-2-yl)-2-[4-(1,1-di-oxido-3-oxoisothiazolidin-5-yl)phenyl]ethyl}-1,3,5-trimethyl-1H-pyrazole-4-sulfonamide trifluoroacetate

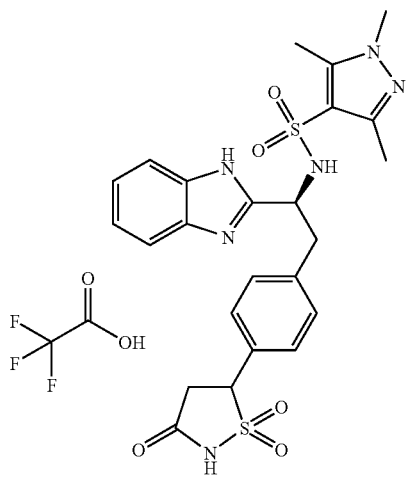

Title compound was prepared according to the procedure in Example 4.118 using the appropriate reagents and starting materials. LCMS found for $C_{24}H_{27}N_6O_5S_2$ $(M+H)^+$: m/z=543.

Example 4.147

N-{(1S)-1-(1H-benzimidazol-2-yl)-2-[4-(1,1-di-oxido-3-oxoisothiazolidin-5-yl)phenyl]ethyl}-5-chloro-1,3-dimethyl-1H-pyrazole-4-sulfonamide trifluoroacetate

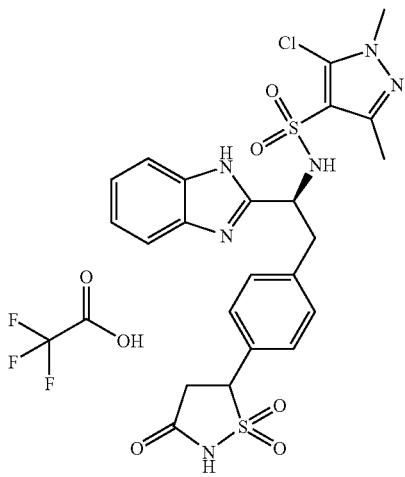

Title compound was prepared according to the procedure in Example 4.118 using the appropriate reagents and starting materials. LCMS found for $C_{23}H_{24}ClN_6O_5S_2$ $(M+H)^+$: m/z=563.

Example 4.148

N-{(1S)-1-(1H-benzimidazol-2-yl)-2-[4-(1,1-di-oxido-3-oxoisothiazolidin-5-yl)phenyl]ethyl}-2,4-dimethyl-1,3-thiazole-5-sulfonamide trifluoroacetate

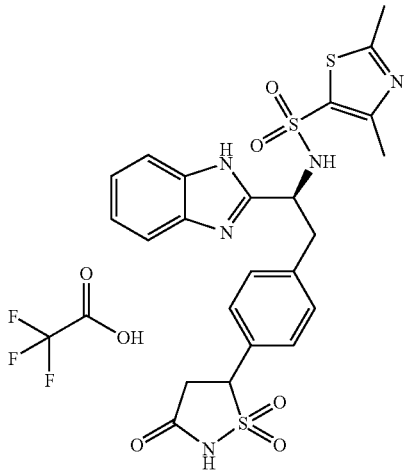

Title compound was prepared according to the procedure in Example 4.118 using the appropriate reagents and starting materials. LCMS found for $C_{23}H_{11}N_5O_5S_3$ $(M+H)^+$: m/z=546.

Example 4.149

N-{(1S)-1-(1H-benzimidazol-2-yl)-2-[4-(1,1-di-oxido-3-oxoisothiazolidin-5-yl)phenyl]ethyl}-2,6-difluorobenzenesulfonamide trifluoroacetate

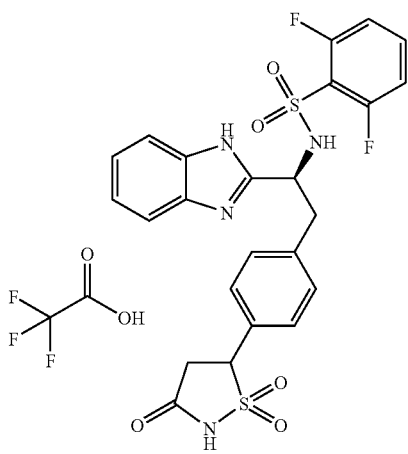

Title compound was prepared according to the procedure in Example 4.118 using the appropriate reagents and starting materials. $^1$H NMR (400 MHz, CD$_3$OD): δ 7.78 (m, 2H), 7.60 (m, 2H), 7.45 (m, 1H), 7.30 (m, 4H), 6.95 (m, 2H), 5.22 (m, 1H), 5.10 (m, 1H), 3.33 (m, 4H). LCMS found for C$_{24}$H$_{21}$F$_2$N$_4$O$_5$S$_2$ (M+H)$^+$: m/z=547.

Example 4.150

N-{(1S)-1-(1H-benzimidazol-2-yl)-2-[4-(1,1-di-oxido-3-oxoisothiazolidin-5-yl)phenyl]ethyl}naphthalene-1-sulfonamide trifluoroacetate

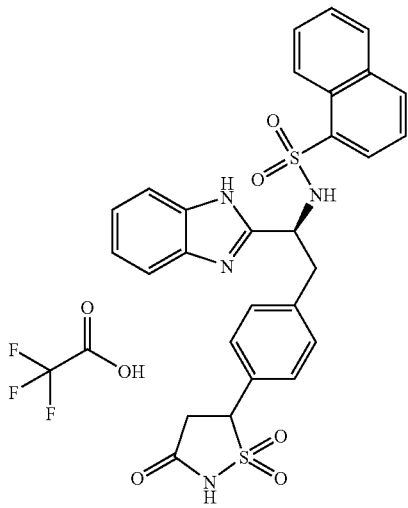

Title compound was prepared according to the procedure in Example 4.118 using the appropriate reagents and starting materials. $^1$H NMR (400 MHz, CD$_3$OD): δ 8.51 (d, 1H), 8.05 (m, 1H), 7.96 (m, 1H), 7.82 (m, 1H), 7.62–7.50 (m, 6H), 7.38 (m, 1H), 6.95 (m, 4H), 4.99 (m, 1H), 4.95 (m, 1H), 3.26 (m, 4H). LCMS found for C$_{28}$H$_{25}$N$_4$O$_5$S$_2$ (M+H)$^+$: m/z=561.

Example 4.151

N-{(1S)-1-(1H-benzimidazol-2-yl)-2-[4-(1,1-di-oxido-3-oxoisothiazolidin-5-yl)phenyl]ethyl}naphthalene-2-sulfonamide trifluoroacetate

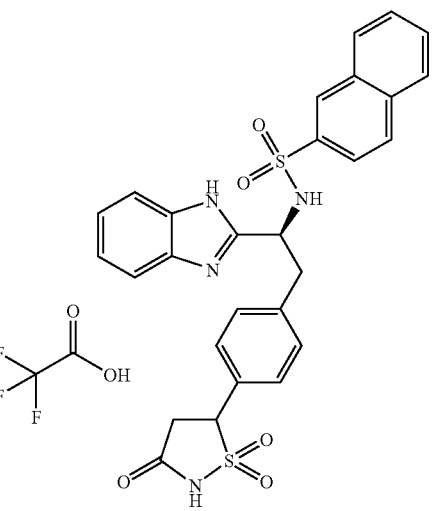

Title compound was prepared according to the procedure in Example 4.118 using the appropriate reagents and starting materials. LCMS found for C$_{28}$H$_{25}$N$_4$O$_5$S$_2$ (M+H)$^+$: m/z=561.

Example 4.152

N-{4-[({(1S)-1-(1H-benzimidazol-2-yl)-2-[4-(1,1-dioxido-3-oxoisothiazolidin-5-yl)phenyl]ethyl}amino)sulfonyl]phenyl}acetamide trifluoroacetate

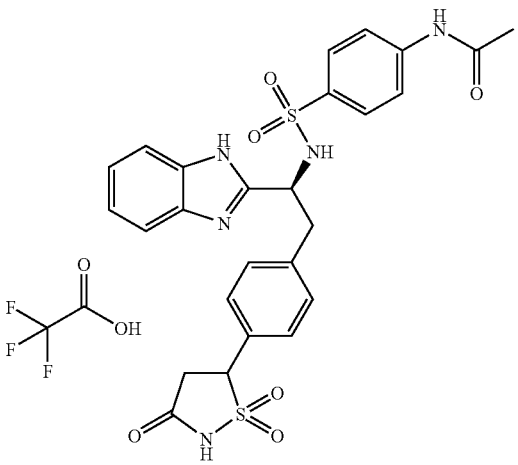

Title compound was prepared according to the procedure in Example 4.118 using the appropriate reagents and starting materials. LCMS found for $C_{26}H_{26}N_5O_6S_2$ (M+H)$^+$: m/z=568.

Example 4.153

N-{(1S)-1-(1H-benzimidazol-2-yl)-2-[4-(1,1-di-oxido-3-oxoisothiazolidin-5-yl)phenyl]ethyl}-1-sulfonamide trifluoroacetate

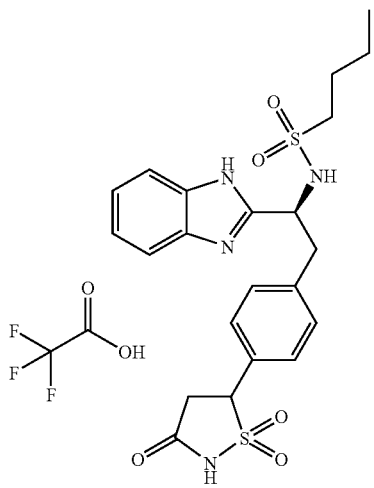

Title compound was prepared according to the procedure in Example 4.118 using the appropriate reagents and starting materials. LCMS found for $C_{22}H_{27}N_4O_5S_2$ (M+H)$^+$: m/z=491.

Example 4.154

N-{(1S)-1-(1H-benzimidazol-2-yl)-2-[4-(1,1-di-oxido-3-oxoisothiazolidin-5-yl)phenyl]ethyl}-1-phenylmethanesulfonamide trifluoroacetate

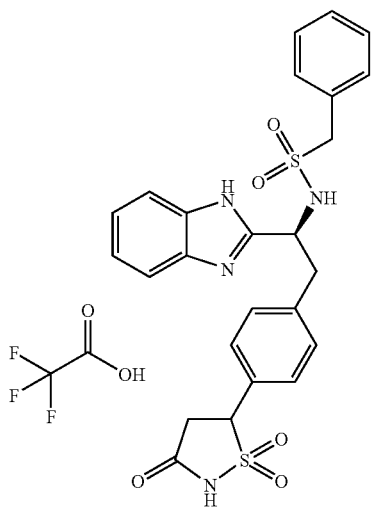

Title compound was prepared according to the procedure in Example 4.118 using the appropriate reagents and starting materials. $^1$H NMR (400 MHz, CD$_3$OD): δ 7.70 (m, 2H), 7.58 (m, 2H), 7.36 (m, 7H), 7.11 (m, 2H), 5.11 (m, 1H), 4.75 (m, 1H), 4.33 (m, 2H), 3.30 (m, 4H). LCMS found for $C_{25}H_{25}N_4O_5S_2$ (M+H)$^+$: m/z=525.

Example 4.155

N-{(1S)-1-(1H-benzimidazol-2-yl)-2-[4-(1,1-di-oxido-3-oxoisothiazolidin-5-yl)phenyl]ethyl}-2,2-diphenylethanesulfonamide trifluoroacetate

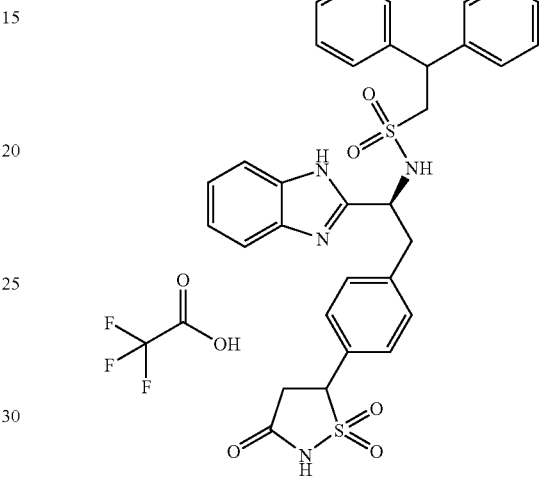

Title compound was prepared according to the procedure in Example 4.118 using the appropriate reagents and starting materials. $^1$H NMR (400 MHz, CD$_3$OD): δ 7.70 (m, 2H), 7.55 (m, 2H), 7.40–7.10 (m, 14H), 4.95 (m, 2H), 4.51 (m, 1H), 3.78 (m, 2H), 3.20 (m, 3H), 3.02 (m, 1H). LCMS found for $C_{32}H_{31}N_4O_5S_2$ (M+H)$^+$: m/z=615.

Example 4.156

N-{(1S)-1-(1H-benzimidazol-2-yl)-2-[4-(1,1-di-oxido-3-oxoisothiazolidin-5-yl)phenyl]ethyl}-2,6-dichlorobenzenesulfonamide trifluoroacetate

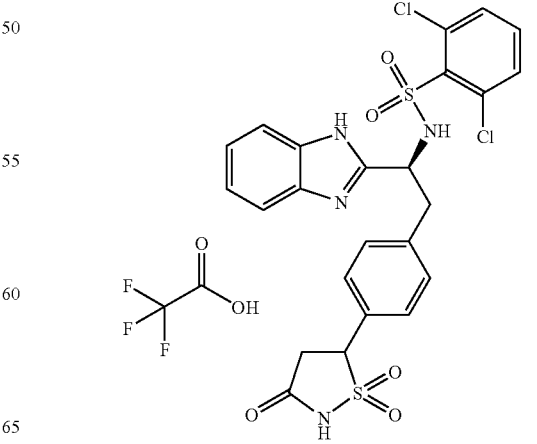

Title compound was prepared according to the procedure in Example 4.118 using the appropriate reagents and starting materials. LCMS found for $C_{24}H_{21}Cl_2N_4O_5S_2$ $(M+H)^+$: m/z=579.

Example 4.157

N-{(1S)-1-(1H-benzimidazol-2-yl)-2-[4-(1,1-dioxido-3-oxoisothiazolidin-5-yl)phenyl]ethyl}-2-methoxy-4-methylbenzenesulfonamide trifluoroacetate

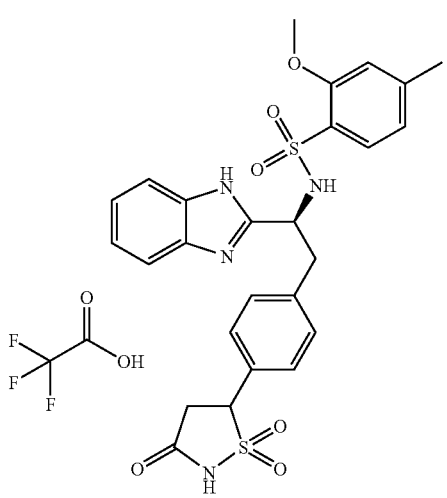

Title compound was prepared according to the procedure in Example 4.118 using the appropriate reagents and starting materials. LCMS found for $C_{26}H_{27}N_4O_6S_2$ $(M+H)^+$: m/z=555.

Example 4.158

N-{(S1)-1-(1H-benzimidazol-2-yl)-2-[4-(1,1-dioxido-3-oxoisothiazolidin-5-yl)phenyl]ethyl}thiophene-2-sulfonamide trifluoroacetate

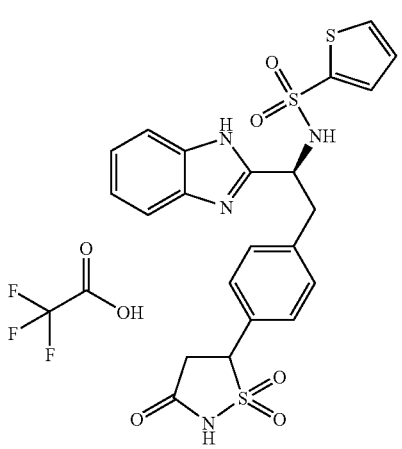

Title compound was prepared according to the procedure in Example 4.118 using the appropriate reagents and starting materials. LCMS found for $C_{22}H_{21}N_4O_5S_3(M+H)^+$: m/z=517.

Example 4.159

N-{(1S)-1-(1H-benzimidazol-2-yl)-2-[4-(1,1-dioxido-3-oxoisothiazolidin-5-yl)phenyl]ethyl}-3,5-bis(trifluoromethyl)benzenesulfonamide trifluoroacetate

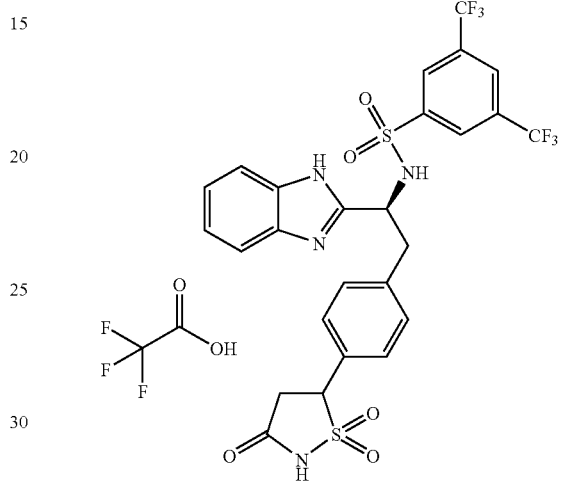

Title compound was prepared according to the procedure in Example 4.118 using the appropriate reagents and starting materials. LCMS found for $C_{26}H_{21}F_6N_4O_5S_2$ $(M+H)^+$: m/z=647.

Example 4.160

N-{(1S)-1-(1H-benzimidazol-2-yl)-2-[4-(1,1-dioxido-3-oxoisothiazolidin-5-yl)phenyl]ethyl}-2,5-dimethylbenzenesulfonamide trifluoroacetate

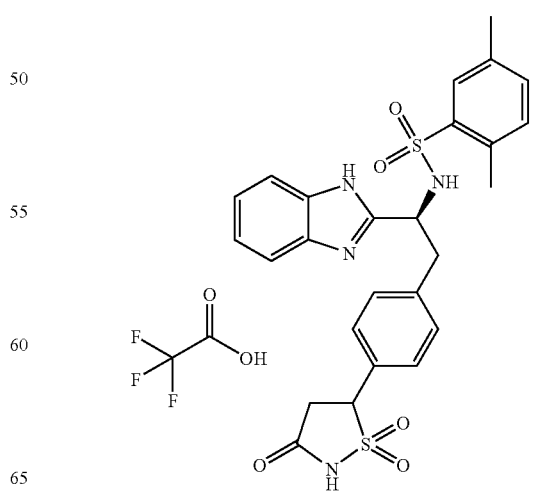

Title compound was prepared according to the procedure in Example 4.118 using the appropriate reagents and starting materials. LCMS found for $C_{26}H_{27}N_4O_5S_2$ (M+H)$^+$: m/z=539.

Example 4.161

N-{(1S)-1-(1H-benzimidazol-2-yl)-2-[4-(1,1-di-oxido-3-oxoisothiazolidin-5-yl)phenyl]ethyl}-4-chloro-3-(trifluoromethyl)benzenesulfonamide trifluoroacetate

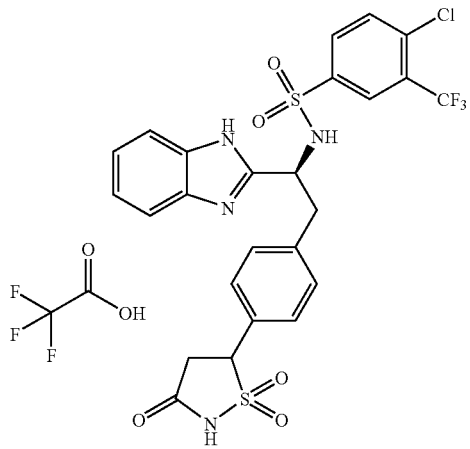

Title compound was prepared according to the procedure in Example 4.118 using the appropriate reagents and starting materials. LCMS found for $C_{25}H_{21}ClF_3N_4O_5S_2$ (M+H)$^+$: m/z=613.

Example 4.162

N-{(1S)-1-(1H-benzimidazol-2-yl)-2-[4-(1,1-di-oxido-3-oxoisothiazolidin-5-yl)phenyl]ethyl}-2,3-dihydro-1-benzofuran-5-sulfonamide trifluoroacetate

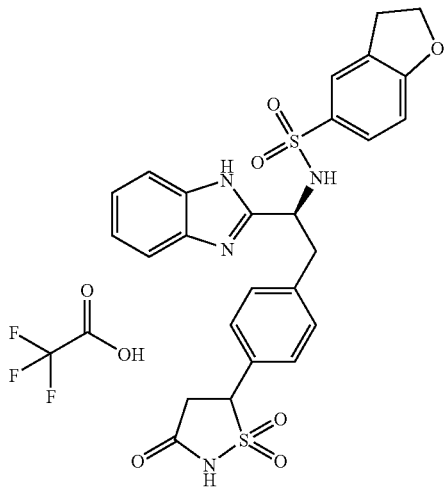

Title compound was prepared according to the procedure in Example 4.118 using the appropriate reagents and starting materials. LCMS found for $C_{26}H_{25}N_4O_6S_2$ (M+H)$^+$: m/z=553.

Example 4.163

N-{(1S)-1-(1H-benzimidazol-2-yl)-2-[4-(1,1-di-oxido-3-oxoisothiazolidin-5-yl)phenyl]ethyl}-2,3-dihydro-1,4-benzodioxine-6-sulfonamide trifluoroacetate

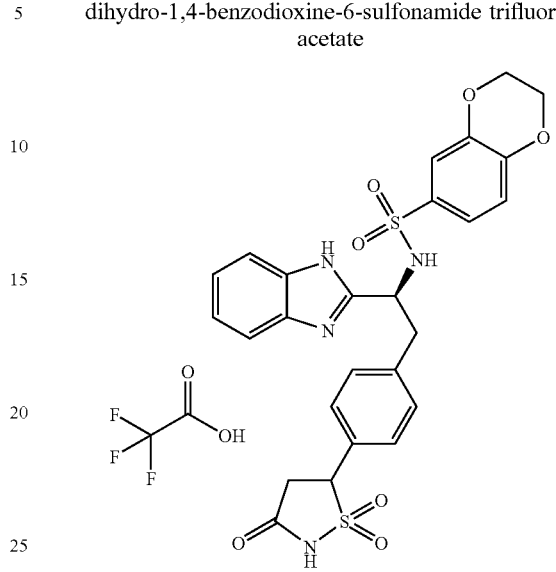

Title compound was prepared according to the procedure in Example 4.118 using the appropriate reagents and starting materials. LCMS found for $C_{26}H_{25}N_4O_7S_2$ (M+H)$^+$: m/z=569.

Example 4.164

N-{(1S)-1-(1H-benzimidazol-2-yl)-2-[4-(1,1-di-oxido-3-oxoisothiazolidin-5-yl)phenyl]ethyl}-4-methyl-3,4-dihydro-2H-1,4-benzoxazine-7-sulfonamide trifluoroacetate

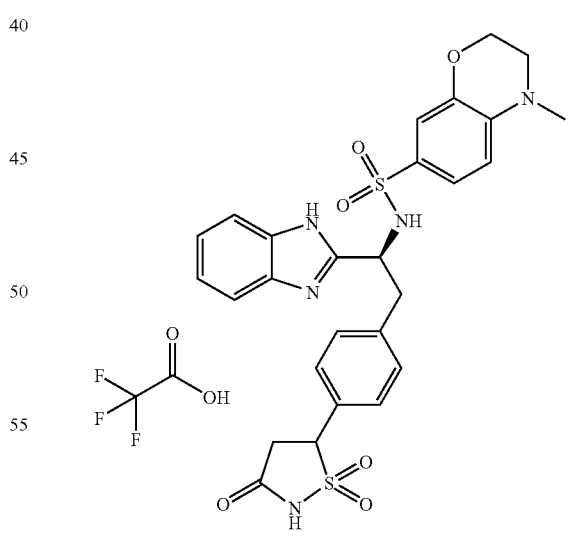

Title compound was prepared according to the procedure in Example 4.118 using the appropriate reagents and starting materials. $^1$H NMR (400 MHz, CD$_3$OD): δ 7.70 (m, 2H), 7.55 (m, 2H), 7.32 (m, 2H), 7.08 (m, 2H), 6.96 (m, 1H), 6.85 (m, 1H), 6.60 (m, 1H), 5.10 (m, 1H), 4.97 (m, 1H), 4.20 (m, 2H), 3.30 (m, 4H), 3.18 (m, 2H), 2.80 (m, 3H). LCMS found for $C_{27}H_{28}N_5O_6S_2$ (M+H)$^+$: m/z=582.

Example 4.165

N-{(1S)-1-(1H-benzimidazol-2-yl)-2-[4-(1,1-di-oxido-3-oxoisothiazolidin-5-yl)phenyl]ethyl}methanesulfonamide trifluoroacetate

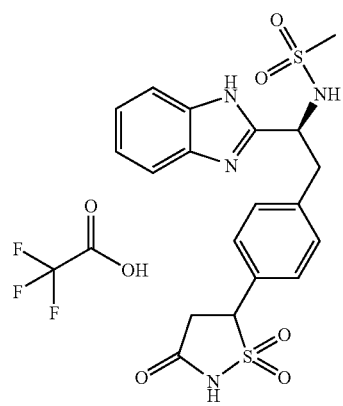

Title compound was prepared according to the procedure in Example 4.118 using the appropriate reagents and starting materials. LCMS found for $C_{19}H_{21}N_5O_5S_2$ (M+H)$^+$: m/z=449.

Example 4.166

N-{(1S)-1-(1H-benzimidazol-2-yl)-2-[4-(1,1-di-oxido-3-oxoisothiazolidin-5-yl)phenyl]ethyl}-4-methoxybenzenesulfonamide trifluoroacetate

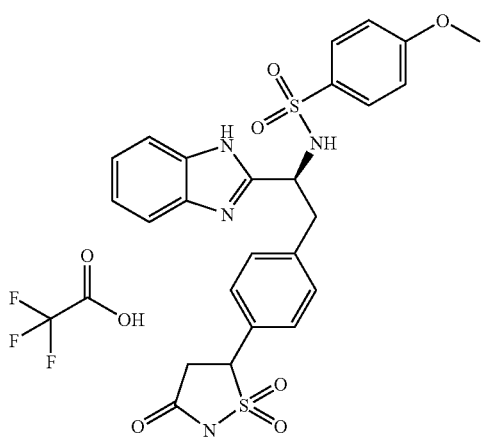

Title compound was prepared according to the procedure in Example 4.118 using the appropriate reagents and starting materials. LCMS found for $C_{25}H_{25}N_4O_6S_2$ (M+H)$^+$: m/z=541.

Example 4.167

(E)-N-{(1S)-1-(1H-benzimidazol-2-yl)-2-[4-(1,1-dioxido-3-oxoisothiazolidin-5-yl)phenyl]ethyl}-2-phenylethylenesulfonamide trifluoroacetate

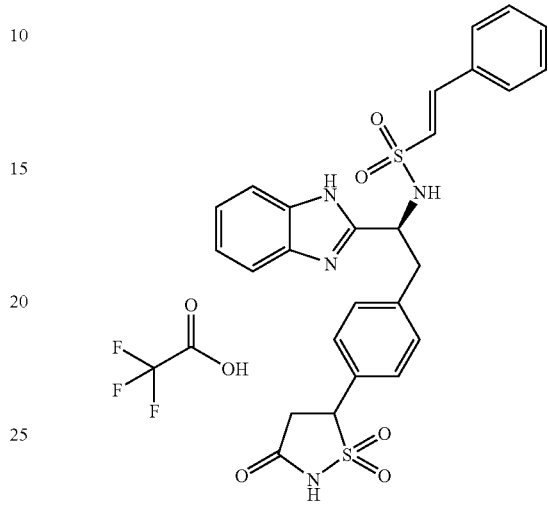

Title compound was prepared according to the procedure in Example 4.118 using the appropriate reagents and starting materials. $^1$H NMR (400 MHz, CD$_3$OD): δ 7.78 (m, 2H), 7.57 (m, 2H), 7.40 (m, 6H), 7.30 (m, 4H), 6.60 (dd, 1H), 5.10 (m, 1H), 5.00 (m, 1H), 3.40 (m, 2H), 3.20 (m, 1H). LCMS found for $C_{26}H_{25}N_4O_5S_2$ (M+H)$^+$: m/z=537.

Example 4.168

N-{(1S)-1-(1H-benzimidazol-2-yl)-2-[4-(1,1-di-oxido-3-oxoisothiazolidin-5-yl)phenyl]ethyl}-4-bromobenzenesulfonamide trifluoroacetate

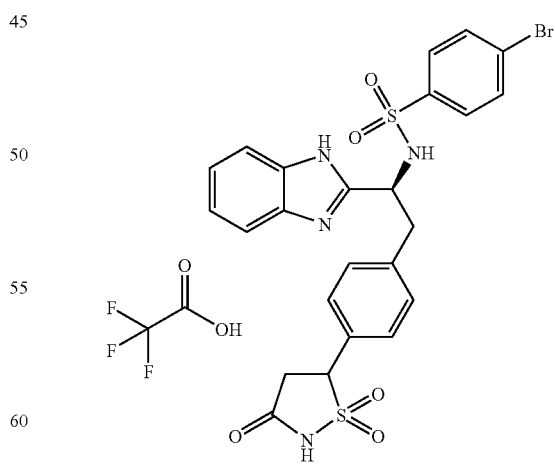

Title compound was prepared according to the procedure in Example 4.118 using the appropriate reagents and starting materials. LCMS found for $C_{24}H_{22}BrN_4O_5S_2$ (M+H)$^+$: m/z=589.

Example 4.169

N-{(1S)-1-(1H-benzimidazol-2-yl)-2-[4-(1,1-di-oxido-3-oxoisothiazolidin-5-yl)phenyl]ethyl}-4-fluorobenzenesulfonamide trifluoroacetate

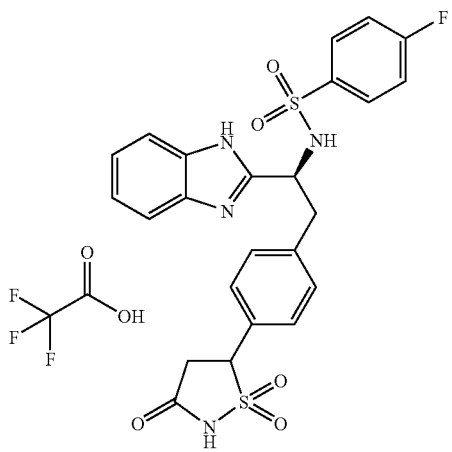

Title compound was prepared according to the procedure in Example 4.118 using the appropriate reagents and starting materials. LCMS found for $C_{24}H_{22}FN_4O_5S_2$ (M+H)$^+$: m/z=529.

Example 4.170

N-{(1S)-1-(1H-benzimidazol-2-yl)-2-[4-(1,1-di-oxido-3-oxoisothiazolidin-5-yl)phenyl]ethyl}-2-fluorobenzenesulfonamide trifluoroacetate

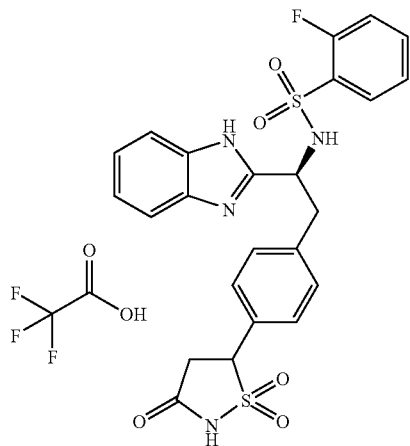

Title compound was prepared according to the procedure in Example 4.118 using the appropriate reagents and starting materials. LCMS found for $C_{24}H_{22}FN_4O_5S_2$ (M+H)$^+$: m/z=529.

Example 4.170

N-{(1S)-1-(1H-benzimidazol-2-yl)-2-[4-(1,1-di-oxido-3-oxoisothiazolidin-5-yl)phenyl]ethyl}-3-fluorobenzenesulfonamide trifluoroacetate

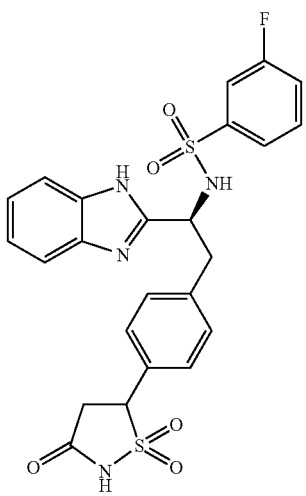

Title compound was prepared according to the procedure in Example 4.118 using the appropriate reagents and starting materials. LCMS found for $C_{24}H_{22}FN_4O_5S_2$ (M+H)$^+$: m/z=529.

Example 4.172

N-{(1S)-1-(1H-benzimidazol-2-yl)-2-[4-(1,1-di-oxido-3-oxoisothiazolidin-5-yl)phenyl]ethyl}-4-(trifluoromethoxy)benzenesulfonamide trifluoroacetate

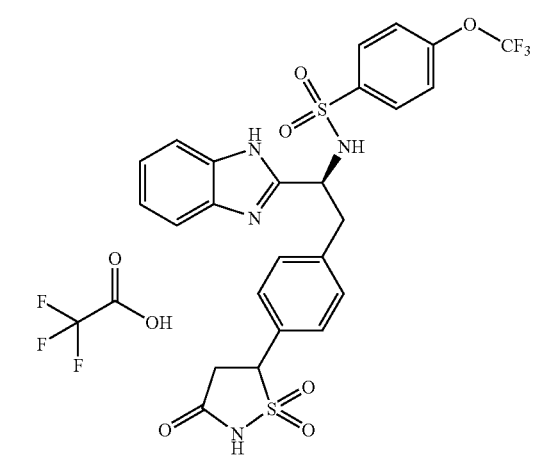

Title compound was prepared according to the procedure in Example 4.118 using the appropriate reagents and starting materials. LCMS found for $C_{25}H_{22}F_3N_4O_6S_2$ (M+H)$^+$: m/z=595.

Example 4.173

N-{(1S)-1-(1H-benzimidazol-2-yl)-2-[4-(1,1-di-oxido-3-oxoisothiazolidin-5-yl)phenyl]ethyl}-4-(trifluoromethyl)benzenesulfonamide trifluoroacetate

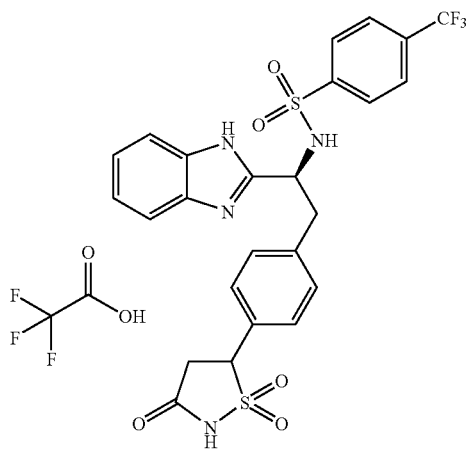

Title compound was prepared according to the procedure in Example 4.118 using the appropriate reagents and starting materials. LCMS found for $C_{25}H_{22}F_3N_4O_5S_2$ (M+H)$^+$: m/z=579.

Example 4.174

N-{(1S)-1-(1H-benzimidazol-2-yl)-2-[4-(1,1-di-oxido-3-oxoisothiazolidin-5-yl)phenyl]ethyl}-2-(trifluoromethyl)benzenesulfonamide trifluoroacetate

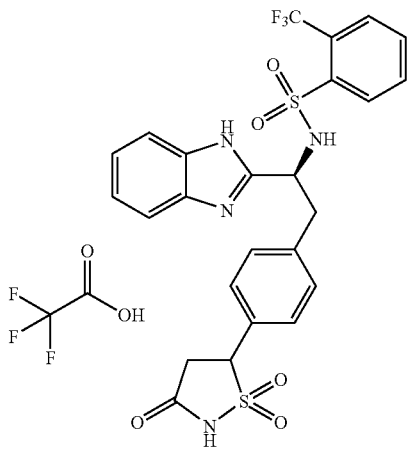

Title compound was prepared according to the procedure in Example 4.118 using the appropriate reagents and starting materials. LCMS found for $C_{25}H_{22}F_3N_4O_5S_2$ (M+H)$^+$: m/z=579.

Example 4.175

N-{(1S)-1-(1H-benzimidazol-2-yl)-2-[4-(1,1-di-oxido-3-oxoisothiazolidin-5-yl)phenyl]ethyl}-2-bromobenzenesulfonamide trifluoroacetate

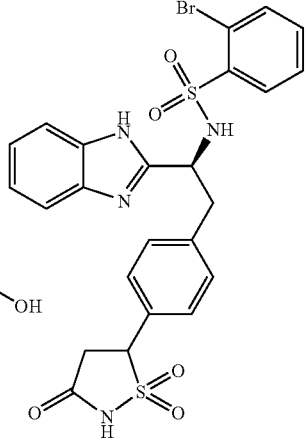

Title compound was prepared according to the procedure in Example 4.118 using the appropriate reagents and starting materials. LCMS found for $C_{24}H_{22}BrN_4O_5S_2$ (M+H)$^+$: m/z=589.

Example 4.176

N-{(1S)-1-(1H-benzimidazol-2-yl)-2-[4-(1,1-di-oxido-3-oxoisothiazolidin-5-yl)phenyl]ethyl}-3-bromobenzenesulfonamide trifluoroacetate

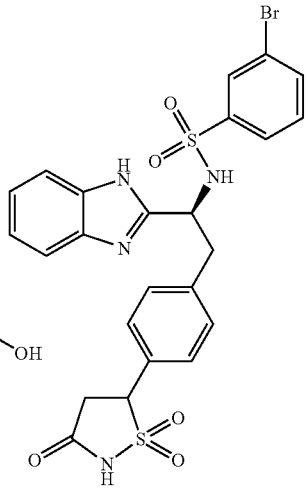

Title compound was prepared according to the procedure in Example 4.118 using the appropriate reagents and starting materials. LCMS found for $C_{24}H_{22}BrN_4O_5S_2$ (M+H)$^+$: m/z=589.

Example 4.177

N-{(1S)-1-(1H-benzimidazol-2-yl)-2-[4-(1,1-dioxido-3-oxoisothiazolidin-5-yl)phenyl]ethyl}-2-(trifluoromethoxy)benzenesulfonamide trifluoroacetate

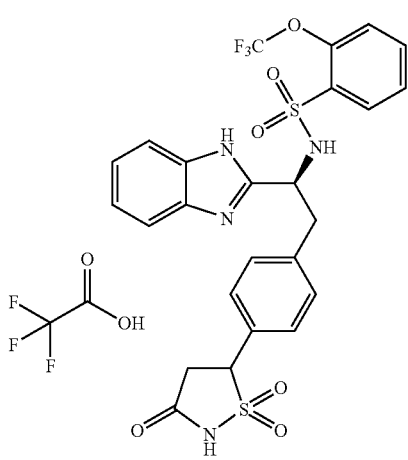

Title compound was prepared according to the procedure in Example 4.118 using the appropriate reagents and starting materials. LCMS found for $C_{25}H_{22}F_3N_4O_6S_2$ $(M+H)^+$: m/z=595.

Example 4.178

N-{(1S)-1-(1H-benzimidazol-2-yl)-2-[4-(1,1-dioxido-3-oxoisothiazolidin-5-yl)phenyl]ethyl}-2-cyanobenzenesulfonamide trifluoroacetate

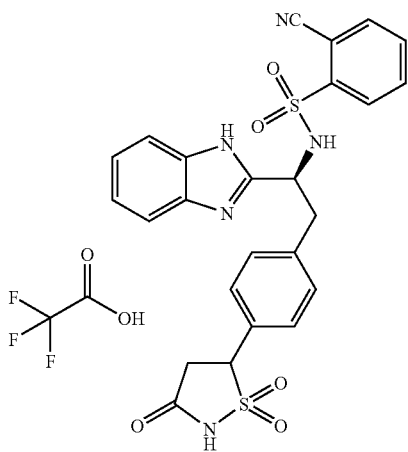

Title compound was prepared according to the procedure in Example 4.118 using the appropriate reagents and starting materials. LCMS found for $C_{25}H_{22}N_5O_5S_2$ $(M+H)^+$: m/z=536.

Example 4.179

(5S)-5-(4-{(2S)-2-(1H-Benzimidazol-2-yl)-2-[(5-fluoro-1,3-benzothiazol-2-yl)amino]ethyl}phenyl)isothiazolidin-3-one 1,1-dioxide trifluoroacetate and (5R)-5-(4-{(2S)-2-(1H-benzimidazol-2-yl)-2-[(5-fluoro-1,3-benzothiazol-2-yl)amino]ethyl}phenyl)isothiazolidin-3-one 1,1-dioxide trifluoroacetate

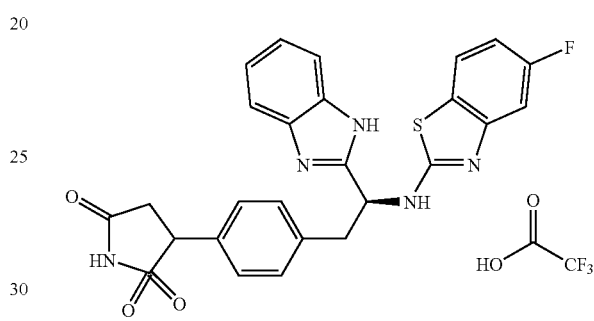

To a solution of 5-{4-[(2S)-2-amino-2-(1H-benzimidazol-2-yl)ethyl]phenyl}-2-tert-butylisothizolidin-3-one 1,1-dioxide bis(trifluoroacetate) (50.0 mg, 0.0764 mmol) in methylene chloride (1.9 mL) was added triethylamine (21 µL, 0.15 mmol) and the reaction was stirred for 15 minutes. 3-Fluorophenyl isothiocyanate (43.3 mg, 0.23 mmol) was added to the reaction mixture and stirred for 3 hour at rt. Benzyltrimethylammonium tribromide (0.045 g, 0.11 mmol) was then added and stirred at rt overnight. The solvents were evaporated and the crude reaction product purified by chiral HPLC to separate the diastereomers. A separation method using Chiral Technologies, Chiral Cel OD-H 20×250 mm column and 30% EtOH/70% hexanes mobile phase at 10 mL/min. over 30 minutes. Peak 1 eluted at 14.04 min and peak 2 eluted at 18.23 min. The two diastereomers were lyophilized to powders and then dissolved individually in trifluoroacetic acid (2.5 mL) and heated in a microwave at 130° C. for 1 minute to remove the t-butyl groups. The volatiles were evaporated in vacuo and the crude reaction purified by preparative LCMS to afford white powders; Isomer 1 (4.9 mg, 33%) was more biologically active in the enzyme assay, LCMS found for $C_{25}H_{20}FN_5O_3S_2$ $(M+H)^+$: m/z=522.1 and LCMS found for Isomer 2 (7.9 mg, 50%), $C_{25}H_{20}FN_5O_3S_2$ $(M+H)^+$: m/z=522.1.

Example 4.180

(5S)-5-(4-{(2S)-2-(1,3-Benzothiazol-2-ylamino)-2-[6-(trifluoromethyl)-1H-benzimidazol-2-yl]ethyl}phenyl)isothiazolidin-3-one 1,1-dioxide trifluoroacetate and (5R)-5-(4-{(2S)-2-(1,3-benzothiazol-2-ylamino)-2-[6-(trifluoromethyl)-1H-benzimidazol-2-yl]ethyl}phenyl)isothiazolidin-3-one 1,1-dioxide trifluoroacetate

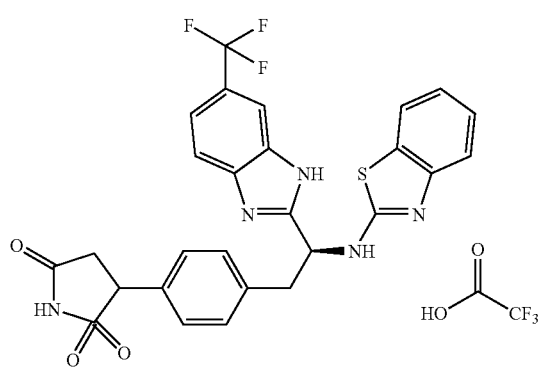

To a solution of 5-(4-{(2S)-2-amino-2-[6-(trifluoromethyl)-1H-benzimidazol-2-yl]ethyl}phenyl)-2-tert-butyl-isothiazolidin-3-one 1,1-dioxide bis(trifluoroacetate) (24.9 mg, 0.0344 mmol) (prepared using procedure 4.118, step 7, with appropriate starting materials) in methylene chloride (0.62 mL), was added triethylamine (9.6 µL, 0.069 mmol) and reaction was stirred for 15 minutes. Isothiocyanatobenzene (14.0 mg, 0.10 mmol) was added to the reaction mixture and stirred for 3 hour at rt. Benzyltrimethylammonium tribromide (15 mg, 0.038 mmol) was then added and stirred at rt overnight. The solvents were removed in vacuo and the crude reaction mixture purified by chiral HPLC to separate the diastereomers. A separation method using Chiral Technologies Chiral Cel OD-H 20×250 mm column with a 30% EtOH/70% hexanes mobile phase over 30 minutes was used. Peak 1 eluted at 19.60 min and peak 2 eluted at 21.90 min. The two diastereomers were lyophilized to powders and then dissolved individually in trifluoroacetic acid (2.5 mL) and heated in a microwave at 130° C. for 1 minute to remove the t-butyl groups. The volatiles were evaporated in vacuo and the crude reaction purified by preparative LCMS to afford white powders; Isomer 1 (3.6 mg, 38%) was more biologically active in the enzyme assay, LCMS found for $C_{26}H_{20}F_3N_5O_3S_2$ (M+H)$^+$: m/z=572.1 and Isomer 2 (3.5 mg, 38%) LCMS found for $C_{26}H_{20}F_3N_5O_3S_2$ (M+H)$^+$: m/z=572.1.

Example 4.181

N-[(1S)-2-[4-(1,1-dioxido-3-oxoisothiazolidin-5-yl)phenyl]-1-(5H-imidazo[4,5-f][2,1,3]benzoxadiazol-6-yl)ethyl]biphenyl-4-sulfonamide trifluoroacetate

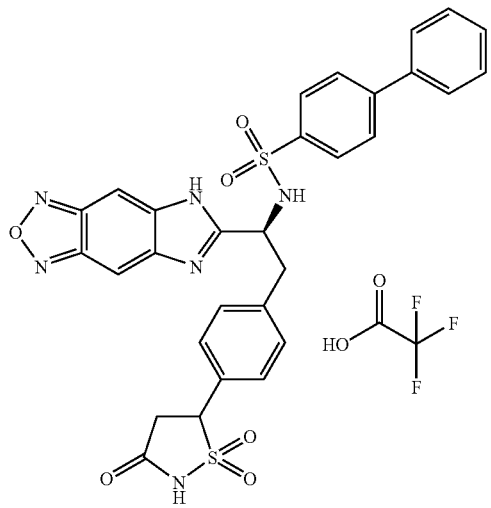

Title compound was prepared according to the procedure in Example 4.118 using the appropriate reagents and starting materials. LCMS found for $C_{30}H_{25}N_6O_6S_2$ (M+H)$^+$: m/z=629.

Example 4.182

N-[(1S)-2-[4-(1,1-dioxido-3-oxoisothiazolidin-5-yl)phenyl]-1-(3H-imidazo-[4,5-b]pyridin-2-yl)ethyl]biphenyl-4-sulfonamide trifluoroacetate

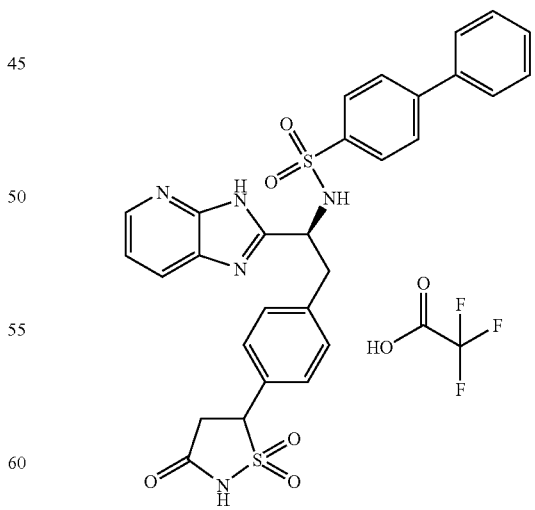

Title compound was prepared according to the procedure in Example 4.118 using the appropriate reagents and starting materials. LCMS found for $C_{29}H_{26}N_5O_5S_2$ (M+H)$^+$: m/z=588.

Example 4.183

N-((1S)-1-(1H-benzimidazol-2-yl)-2-{4-[(5S)-1,1-dioxido-3-oxoisothiazolidin-5-yl]phenyl}ethyl)biphenyl-4-sulfonamide trifluoroacetate and N-((1S)-1-(1H-benzimidazol-2-yl)-2-{4-[(5R)-1,1-dioxido-3-oxoisothiazolidin-5-yl]phenyl}ethyl)biphenyl-4-sulfonamide trifluoroacetate

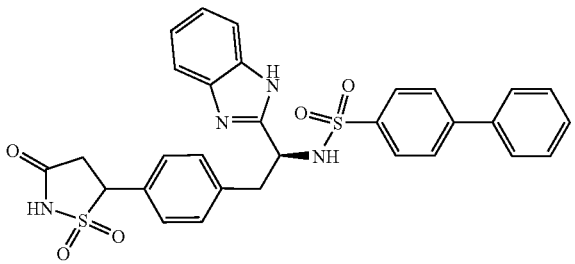

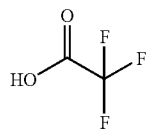

Step 1. (5S)-5-{4-[(2S)-2-amino-2-(1H-benzimidazol-2-yl)ethyl]phenyl}-2tert-butylisothiazolidin-3-one-1,1-dioxide bistrifluoroacetate and (5R)-5-{4-[(2S)-2-amino-2-(1H-benzimidazol-2-yl)ethyl]phenyl}-2-tert-butylisothiazolidin-3-one 1,1-dioxide bistrifluoroacetate

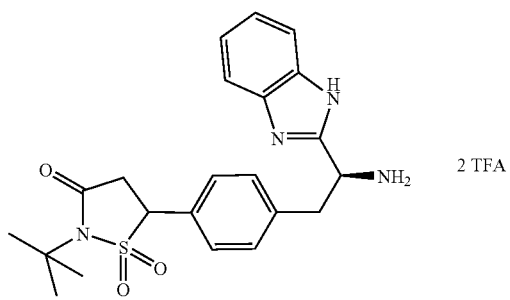

tert-Butyl {(1S)-2-[(2-aminophenyl)amino]-1-[4-(2-tert-butyl-1,1-dioxido-3-oxoisothiazolidin-5-yl)benzyl]-2-oxoethyl}carbamate (130 mg, 0.20 mmol). Purification by chiral HPLC to separate the diastereomers was done using a Chiral Technologies Chiral Cel OD-H 20×250 mm column with a 30% EtOH/70% hexanes mobile phase over 30 minutes. Isomer 2, second peak off HPLC column, was dissolved in acetic acid (3 mL) and heated to 40° C. for 2.5 h. The solvent was removed in vacuo and trifluoroacetic acid (2.5 mL) was added and the solution stirred for 1 hour at rt. Evaporation and purification on LCMS gave the isomerically pure amine as a bis-trifluoroacetate: Isomer 2 (50 mg, 39%) LCMS found for $C_{22}H_{27}N_4O_3S$ (M+H)$^+$: m/z=427.

Step 2. N-((1S)-1-(1H-benzimidazol-2-yl)-2-{4-[(5S)-1,1-dioxido-3-oxoisothiazolidin-5-yl]phenylethyl)biphenyl-4-sulfonamide bistrifluoroacetate or N-((1S)-1-(1H-benzimidazol-2-yl)-2-(4-[(5R)-1,1-dioxido-3-oxoisothiazolidin-5-yl]phenyl}ethyl)biphenyl-4-sulfonamide bistrifluoroacetate (5S)-5-{4-[(2S)-2-amino-2-(1H-benzimidazol-2-yl)ethyl]phenyl}-2-tert-butylisothiazolidin-3-one 1,1-dioxide bistrifluoroacetate or (5R)-5-{4-[(2S)-2-amino-2-(1H-benzimidazol-2-yl)ethyl]phenyl}-2-tert-butylisothiazolidin-3-one 1,1-dioxide bistrifluoroacetate (Isomer 2) (58.7 mg, 0.897 mmol) was stirred in methylene chloride (5.9 mL) with N,N'-diisopropylethylamine (47 µL, 0.27 mmol) and biphenyl-4-sulfonyl chloride (45.4 mg, 0.179 mmol) was added. The reaction mixture was stirred for 5 h at rt before evaporation and purification by LCMS to give the desired product (18 mg, 28%). This material was dissolved in trifluoroacetic acid (2.5 mL) and heated in a microwave at 130° C. for 1 minute. Evaporation and purification by preparative LCMS afforded the final product as a white powder (12.2 mg, 75%). LCMS found for $C_{30}H_{26}N_4O_5S_2$ (M+H)$^+$: m/z=587.

Example 4.184

N-{(1S)-2-{4-[(5S)-1,1-dioxido-3-oxoisothiazolidin-5-yl]phenyl}-1-[6-(trifluoromethyl)-1H-benzimidazol-2-yl]ethyl}biphenyl-4-sulfonamide and N-{(1S)-2-{4-[(5R)-1,1-dioxido-3-oxoisothiazolidin-5-yl]phenyl}-1-[6-(trifluoromethyl)-1H-benzimidazol-2-yl]ethyl}biphenyl-4-sulfonamide trifluoroacetate

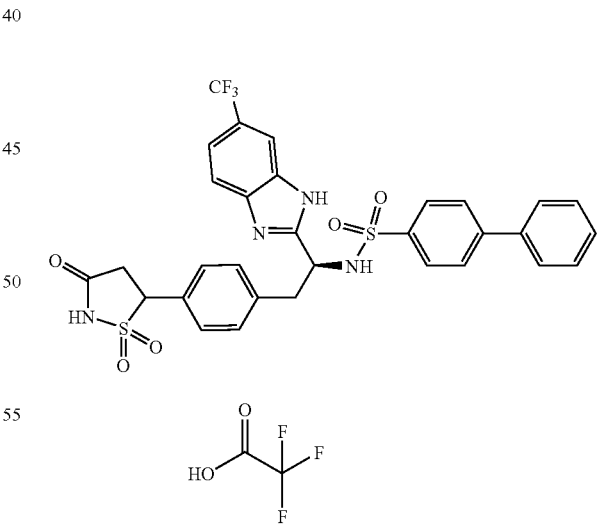

The final product was prepared according to the procedure of Example 4.183, using the appropriate starting material. LCMS found for $C_{31}H_{26}F_3N_4O_5S_2$ (M+H)$^+$: m/z=656.

Example 4.185

N-{(1S)-2-{4-[1,1-dioxido-3-oxoisothiazolidin-5-yl]phenyl}-[6-(trifluoromethyl)-1H-benzimidazol-2-yl]ethyl}-2,2,2-trifluoroacetamide trifluoroacetate

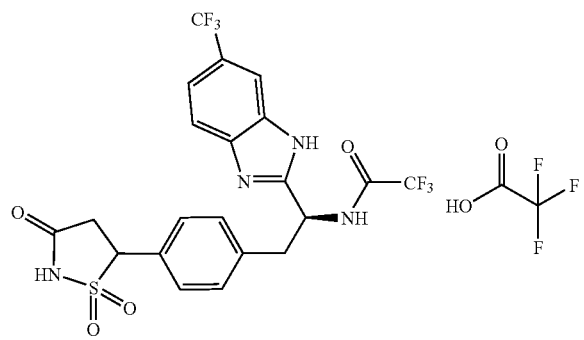

The final product was isolated from the synthesis of Example 4.183. LCMS found for $C_{21}H_{17}F_6N_4O_4S$ (M+H)$^+$: m/z=535.

Example 4.186

(5S)-5-{4-[(2S)-2-(1,3-benzothiazol-2-ylamino)-2-(6-chloro-1H-benzimidazol-2-yl)ethyl]phenyl}isothiazolidin-3-one 1,1-dioxide trifluoroacetate and (5R)-5-(4-{(2S)-2-(1,3-benzothiazol-2-ylamino)-2-[6-chloro-1H-benzimidazol-2-yl]ethyl}phenyl)isothiazolidin-3-one 1,1-dioxide trifluoroacetate

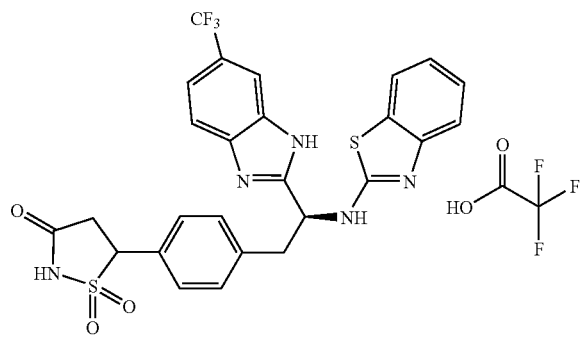

Step 1. N-[(1S)-2-[4-(2-tert-butyl-1,1-dioxido-3-oxoisothiazolidin-5-yl)phenyl]-1-(6-chloro-1H-benzimidazol-2-yl)ethyl]-N'-phenylthiourea trifluoroacetate

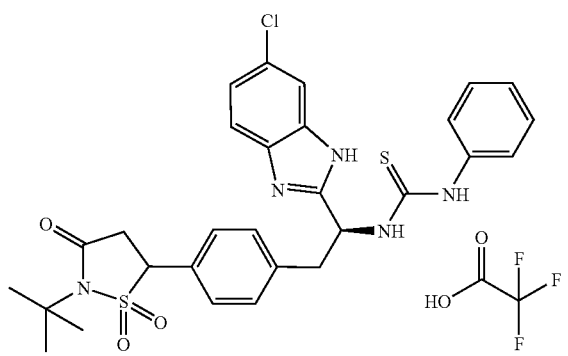

5-(4-{(2S)-2-amino-2-[6-chloro-1H-benzimidazol-2-yl]ethyl}phenyl)-2-tert-butylisothiazolidin-3-one 1,1-dioxide bis(trifluoroacetate) (130 mg, 0.19 mmol) in methylene chloride (6.5 mL), was added triethylamine (79 μL, 0.57 mmol) and the reaction was stirred for 15 minutes. Isothiocyanatobenzene (72 μL, 0.38 mmol) was added to the reaction mixture and stirred for 1 hour at rt. The solvent was removed and the residue purified by preparative LCMS to give the desired urea as a colorless film (100 mg, 89%). LCMS found for $C_{29}H_{31}ClN_5O_3S_2$ (M+H)$^+$: m/z=595.

Step 2. 5-{4-[(2S)-2-(1,3-benzothiazol-2-ylamino)-2-(6-chloro-1H-benzimidazol-2-yl)ethyl]phenyl}-2-tert-butylisothiazolidin-3-one 1,1-dioxide trifluoroacetate

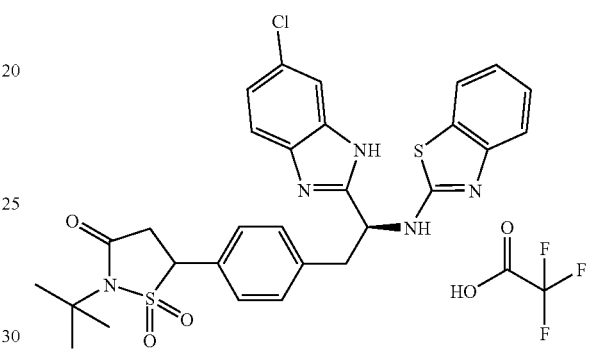

N-[(1S)-2-[4-(2-tert-butyl-1,1-dioxido-3-oxoisothiazolidin-5-yl)phenyl]-1-(6-chloro-1H-benzimidazol-2-yl)ethyl]-N'-phenylthiourea (100 mg, 0.17 mmol) was dissolved in acetic acid (3 mL) and benzyltrimethylammonium tribromide (81 mg, 0.21 mmol) was then added and stirred at rt for 45 minutes. The solvent was removed and the residue purified by preparative LCMS to give the desired product as a colorless film (64 mg, 57%). LCMS found for $C_{29}H_{29}ClN_5O_3S_2$ (M+H)$^+$: m/z=594.

Step 3. (5S)-5-{4-[(2S)-2-(1,3-benzothiazol-2-ylamino)-2-(6-chloro-1H-benzimidazol-2-yl)ethyl]-N'-phenyl}isothiazolidin-3-one 1,1-dioxide trifluoroacetate or (5R)-5-(4-{(2S)-2-(1,3-benzothiazol-2-ylamino)-2-[6-chloro-1H-benzimidazol-2-yl]ethyl}phenyl)isothiazolidin-3-one 1,1-dioxide trifluoroacetate 5-{4-[(2S)-2-(1,3-benzothiazol-2-ylamino)-2-(6-chloro-1H-benzimidazol-2-yl)ethyl]phenyl}-2-tert-butylisothiazolidin-3-one 1,1-dioxide (64 mg, 0.11 mmol) was purified by chiral HPLC to separate the diastereomers using Chiral Technologies, Chiral Cel OD-H column with a 15% EtOH/85% hexanes mobile phase over 30 minutes. Isomer 1, first peak off the column was dissolved in trifluoroacetic acid (2.5 mL) and heated in a microwave at 130° C. for 1 minute to remove the t-butyl group. Evaporation and purification by preparative LCMS afforded the desired product as a white powder Isomer 1 (19.3 mg, 33%). $^1$H NMR (400 MHz, CD$_3$OD): δ 7.68 (m, 3H), 7.50 (m, 1H), 7.28 (m, 2H), 7.25 (m, 3H), 7.20 (m, 1H), 7.08 (m, 1H), 5.60 (m, 1H), 5.20 (m, 1H), 3.60 (m, 2H), 3.25 (d, 2H); LCMS found for $C_{25}H_{21}ClN_5O_3S_2$ (M+H)$^+$: m/z=538

Example 4.187

N-(1S)-1-(1H-benzimidazol-2-yl)-2-[4-(1,1-dioxido-3-oxoisothiazolidin-5-yl)phenyl]ethyl-2-(trifluoromethyl)biphenyl-4-sulfonamide trifluoroacetate

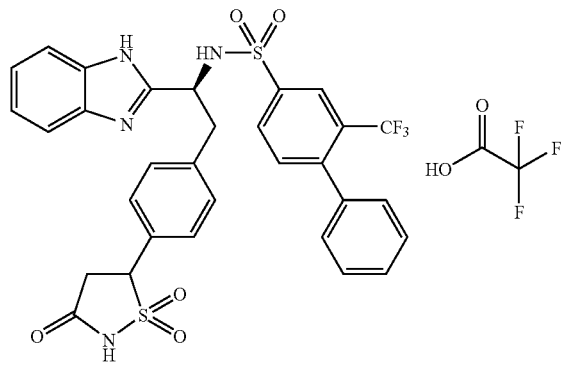

Step 1. N-{(1S)-1-(1H-benzimidazol-2-yl)-2-[4-(2-tert-butyl-1,1-dioxido-3-oxoisothiazolidin-5-yl)phenyl]ethyl}-4-bromo-3-(trifluoromethyl)benzenesulfonamide trifluoroacetate

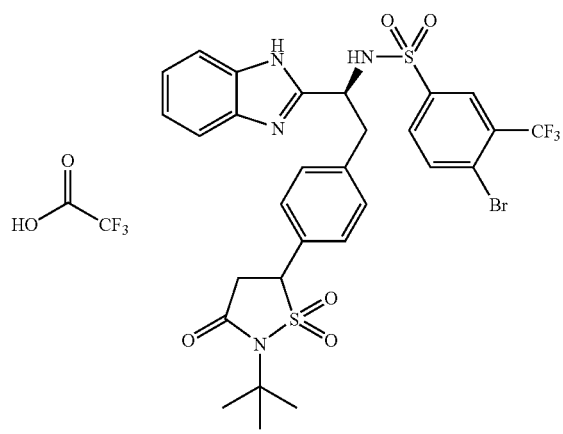

5-4-[(2S)-2-amino-2-(1H-benzimidazol-2-yl)ethyl]phenyl-2-tert-butylisothiazolidin-3-one 1,1-dioxide bis(trifluoroacetate) (100.0 mg, 0.15 mmol) was dissolved in methylene chloride (2.0 mL) and then N,N-diisopropylethylamine (80 μL, 0.46 mmol) was added followed by 4-bromo-3-(trifluoromethyl)benzenesulfonyl chloride (100 mg, 0.31 mmol). After stirring overnight, the solvents were removed and the residue was taken into acetonitrile and purified by preparative LCMS to give the desired product as white solid (86.6 mg, 68%). $^1$H NMR (400 MHz, CD3OD): δ 7.97 (s, 1H), 7.64 (m, 4H), 7.52 (m, 2H), 7.27 (m, 2H), 7.19 (m, 2H), 5.02 (m, 2H), 3.3 (m, 4H). LCMS found for $C_{29}H_{28}BrF_3N_4O_5S_2$ (M+H)$^+$: m/z=713, 715.

Step 2. N-(1S)-1-(1H-benzimidazol-2-yl)-2-[4-(1,1-dioxido-3-oxoisothiazolidin-5-yl)phenyl]ethyl}-2-(trifluoromethyl)biphenyl-4-sulfonamide trifluoroacetate

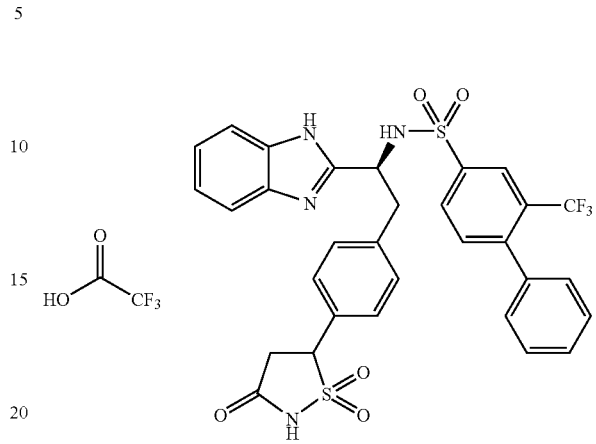

To a microwave tube was added N-{(1S)-1-(1H-benzimidazol-2-yl)-2-[4-(2-tert-butyl-1,1-dioxido-3-oxoisothiazolidin-5-yl)phenyl]ethyl}-4-bromo-3-(trifluoromethyl)benzenesulfonamide trifluoroacetate (86.6 mg, 0.105 mmol) and trifluoroacetic acid (1.0 mL). The resulting mixture was heated in a microwave at 120° C. for 4 min. TFA was removed under reduced pressure. The crude material was dissolved in a microwave tube. Potassium carbonate (10.9 mg, 7.90 μmol), water (0.10 mL), 1,4-dioxane (1.0 mL), bis(triphenylphosphine)palladium(II) chloride (1.58 mg, 2.26 μmol) and phenylboronic acid (2.75 mg, 2.26 [μmol) were added to microwave tube. The resulting mixture was degassed and heated at 150° C. for 4 min. The crude was diluted with acetonitrile and purified by preparative LCMS to desire product (4.5 mg, 61%). $^1$H NMR (400 MHz, CD$_3$OD): δ 8.0 (m, 1H), 7.8 (m, 1H), 7.6 (m, 2H), 7.5 (m, 2H), 7.4 (m, 3H), 7.3 (m, 3H), 7.2 (m, 4H), 5.05 (m, 2H), 3.3 (m, 4H). LCMS found for $C_{31}H_{25}F_3N_4O_5S_2$ (M+H)$^+$: m/z=655.

Example 4.188

N-{(1S)-1-(1H-benzimidazol-2-yl)-2-[4-(1,1-dioxido-3-oxoisothiazolidin-5-yl)phenyl]ethyl}-2'-chloro-2-(trifluoromethyl)biphenyl-4-sulfonamide trifluoroacetate

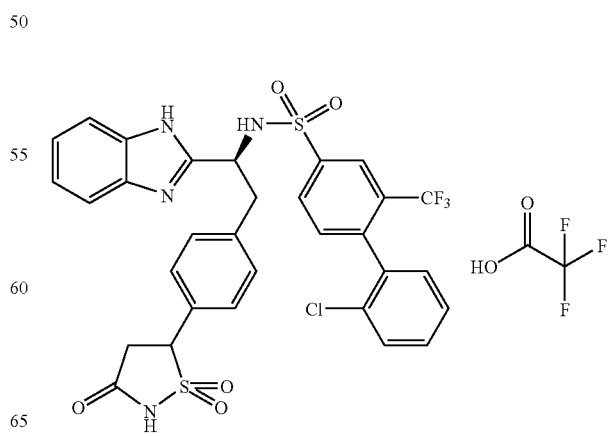

Title compound was prepared according to the procedure in Example 4.187 using the appropriate reagents and starting materials. $^1$H NMR (400 MHz, CD$_3$OD): δ 8.0 (m, 1H), 7.9 (m, 1H), 7.6 (m, 2H), 7.5–7.26 (m, 8H), 7.2 (m, 2H), 7.0 (m, 1H), 5.01 (m, 2H), 3.3 (m, 4H). LCMS found for C$_{31}$, H$_{24}$ClF$_3$N$_4$O$_5$S$_2$ (M+H)$^+$: m/z=689.

Example 4.189

N-{(1S)-1-(1H-benzimidazol-2-yl)-2-[4-(1,1-di-oxido-3-oxoisothiazolidin-5-yl)phenyl]ethyl}-4'-chloro-2-(trifluoromethyl)biphenyl-4-sulfonamide trifluoroacetate

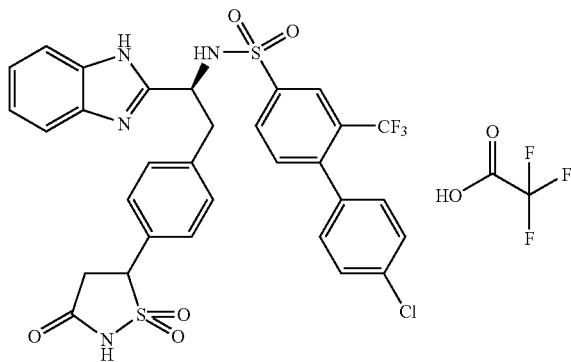

Title compound was prepared according to the procedure in Example 4.187 using the appropriate reagents and starting materials. $^1$H NMR (400 MHz, CD$_3$OD): δ 8.0 (m, 1H), 7.8 (m, 1H), 7.7–7.26 (m, 9H), 7.2 (m, 2H), 7.0 (m, 2H), 5.01 (m, 2H), 3.3 (m, 4H). LCMS found for C$_{31}$, H$_{24}$ClF$_3$N$_4$O$_5$S$_2$ (M+H)$^+$: m/z=689.

Example 4.190

N-{(1S)-1-(1H-benzimidazol-2-yl)-2-[4-(1,1-di-oxido-3-oxoisothiazolidin-5-yl)phenyl]ethyl}-3',4'-dichloro-2-(trifluoromethyl)biphenyl-4-sulfonamide trifluoroacetate

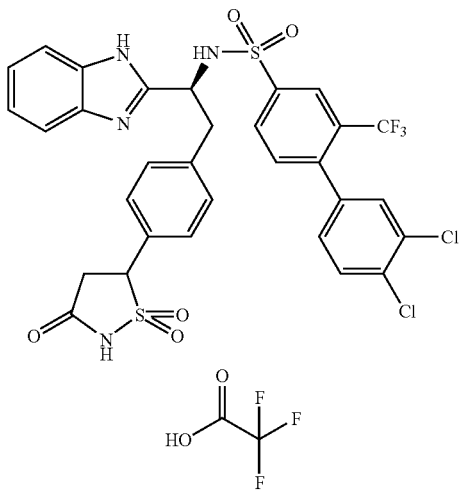

Title compound was prepared according to the procedure in Example 4.187 using the appropriate reagents and starting materials. $^1$H NMR (400 MHz, CD$_3$OD): δ 8.0 (m, 1H), 7.8 (m, 1H), 7.55 (d, 1H), 7.50 (m, 2H), 7.4 (m, 4H), 7.2 (m, 3H), 7.09 (m, 1H), 6.97 (m, 1H), 5.02 (m, 1H), 3.3 (m, 4H). LCMS found for C$_{31}$H$_{23}$Cl$_2$F$_3$N$_4$O$_5$S$_2$ (M+H)$^+$: m/z=723.

Example 4.191

N-{(1S)-1-(1H-benzimidazol-2-yl)-2-[4-(1,1-di-oxido-3-oxoisothiazolidin-5-yl)phenyl]ethyl}-4'-cyano-2-(trifluoromethyl)biphenyl-4-sulfonamide trifluoroacetate

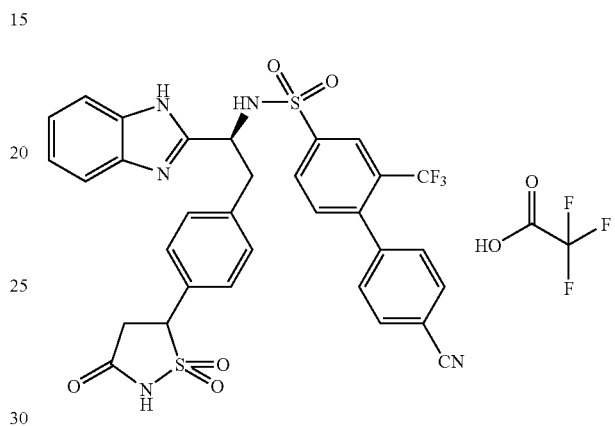

Title compound was prepared according to the procedure in Example 4.187 using the appropriate reagents and starting materials. $^1$H NMR (400 MHz, CD$_3$OD): δ 8.07 (m, 1H), 7.8 (m, 3H), 7.62 (m, 2H), 7.5 (m, 2H), 7.3 (m, 5H), 7.2 (m, 2H), 5.05 (t, 2H), 3.3 (m, 4H). LCMS found for C$_{32}$H$_{24}$F$_3$N$_5$O$_5$S$_2$ (M+H)$^+$: m/z=680.

Example 4.192

N-{(1S)-1-(1H-benzimidazol-2-yl)-2-[4-(1,1-di-oxido-3-oxoisothiazolidin-5-yl)phenyl]ethyl}-3'-cyano-2-(trifluoromethyl)biphenyl-4-sulfonamide trifluoroacetate

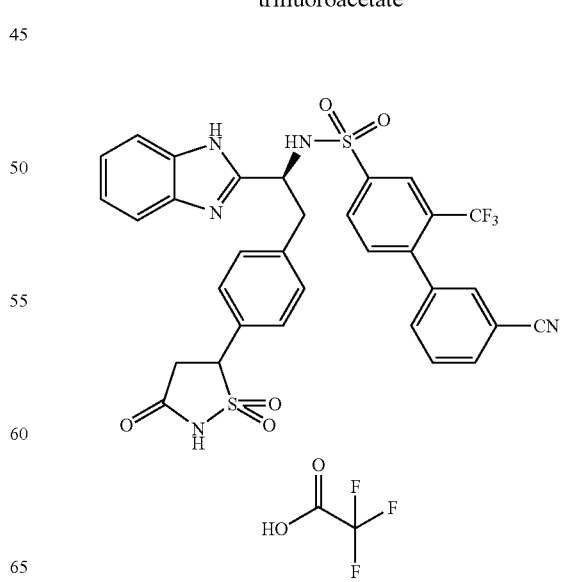

Title compound was prepared according to the procedure in Example 4.187 using the appropriate reagents and starting materials. ¹H NMR (400 MHz, CD₃OD): δ 8.08 (d, 1H), 7.9 (m, 2H), 7.65 (m, 3H), 7.56–7.34 (m, 7H), 7.2 (m, 2H), 5.08 (m, 2H), 3.3 (m, 4H). LCMS C₃₂H₂₄F₃N₅O₅S₂ (M+H)⁺: m/z=680.

Example 4.193

N-{(1S)-1-(1H-benzimidazol-2-yl)-2-[4-(1,1-di-oxido-3-oxoisothiazolidin-5-yl)phenyl]ethyl}-2',5'-dimethyl-2-(trifluoromethyl)biphenyl-4-sulfonamide trifluoroacetate

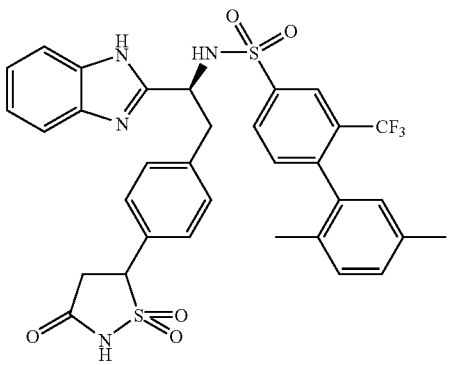

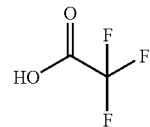

Title compound was prepared according to the procedure in Example 4.187 using the appropriate reagents and starting materials. ¹H NMR (400 MHz, CD₃OD): δ 8.0 (m, 1H), 7.9 (m, 1H), 7.5 (m, 2H), 7.4 (m, 4H), 7.2–7.08 (m, 5H), 6.5 (m, 1H), 4.8 (m, 2H), 3.3 3.3 (m, 4H), 2.31 (d, 3H), 1.76 (d, 3H). LCMS found for C₃₃H₂₉F₃N₅S₂ (M+H)₊: m/z=683.

Example 4.194

N-{(1S)-1-(1H-benzimidazol-2-yl)-2-[4-(1,1-di-oxido-3-oxoisothiazolidin-5-yl)phenyl]ethyl}-2',4',5'-trimethyl-2-(trifluoromethyl)biphenyl-4-sulfonamide trifluoroacetate

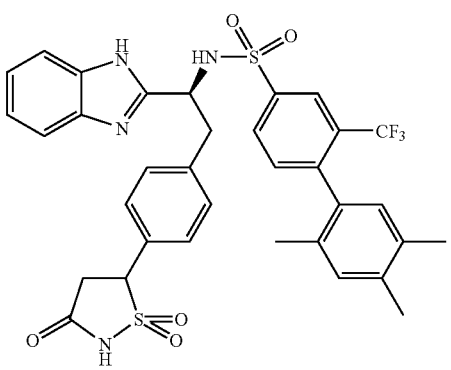

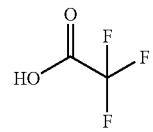

Title compound was prepared according to the procedure in Example 4.187 using the appropriate reagents and starting materials. ¹H NMR (400 MHz, CD₃OD): δ 8.1 (m, 1H), 7.9 (m, 1H), 7.65 (m, 2H), 7.56 (m, 2H), 7.36–7.15 (m, 5H), 7.02 (s, 1H), 6.5 (m, 1H), 507 (m, 2H), 3.3 (m, 4H), 2.67 (m, 6H), 1.81 (s, 3H). LCMS found for C₃₄H₃₁F₃N₄O₅S₂ (M+H)⁺: m/z=697.

Example 4.195

N-{(1S)-1-(1H-benzimidazol-2-yl)-2-[4-(1,1-di-oxido-3-oxoisothiazolidin-5-yl)phenyl]ethyl}-3',5'-dichloro-2-(trifluoromethyl)biphenyl-4-sulfonamide trifluoroacetate

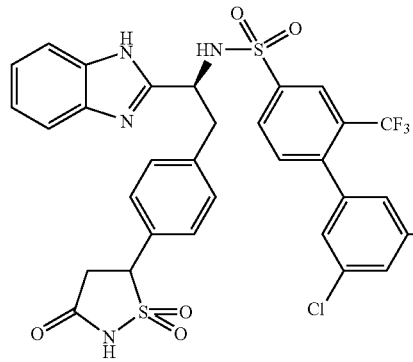

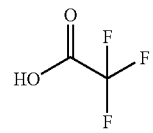

Title compound was prepared according to the procedure in Example 4.187 using the appropriate reagents and starting materials. ¹H NMR (400 MHz, CD₃OD): δ 8.02 (s, 1H), 7.84 (t, 1H), 7.55 (m, 3H), 7.44 (m, 2H), 7.34 (m, 2H), 7.2 (m, 3H), 6.99 (s, 2H), 5.05 (m, 2H), 3.3 (m, 4H). LCMS found for C₃₁H₂₃Cl₂F₃N₄O₅S₂ (M+H)⁺: m/z=723.

Example 4.196

N-{1-(1H-benzimidazol-2-yl)-2-[4-(1,1-dioxido-3-oxoisothiazolidin-5-yl)phenyl]ethyl}-3'-cyanobiphenyl-4-sulfonamide trifluoroacetate

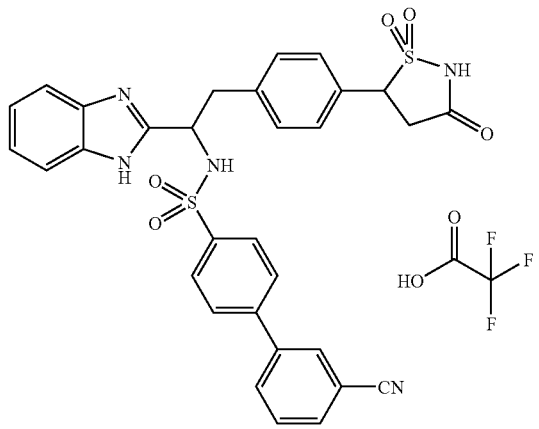

Title compound was prepared according to the procedure in Example 4.187 using the appropriate reagents and starting materials. $^1$H NMR (400 MHz, CD$_3$OD): δ 7.8–7.6 (m, 4H), 7.5 (m, 2H), 7.4–7.3 (m, 4H), 7.2–7.1 (m, 3H), 5.0–4.9 (m, 2H), 3.4–3.3 (m, 2H), 3.2–3.1 (m, 2H); MF=C$_{33}$H$_{26}$F$_3$N$_5$O$_7$S$_2$; LCMS found for C$_{31}$H$_{26}$N$_5$O$_5$S$_2$ (M+H)$^+$: m/z=612.

Example 4.197

N-{1-(1H-benzimidazol-2-yl)-2-[4-(1,1-dioxido-3-oxoisothiazolidin-5-yl)phenyl]ethyl}-4'-methoxybiphenyl-4-sulfonamide trifluoroacetate

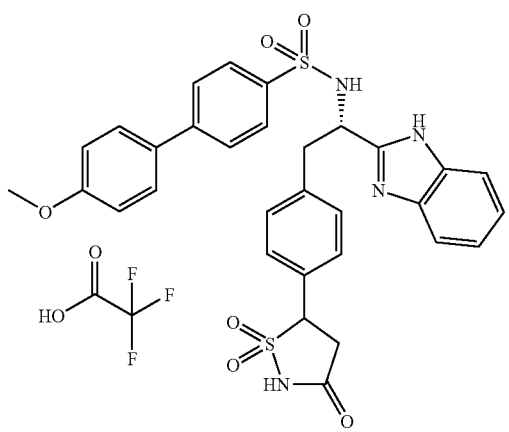

The title compound was prepared according to the procedures of Example 4.187 using appropriate starting materials. $^1$H NMR (400 MHz, CD$_3$OD): δ 7.7–7.6 (m, 4H), 7.6–7.5 (m, 2H), 7.2 (m, 2H), 7.1–7.0 (m, 4H), 5.0–4.9 (m, 2H), 3.9 (s, 3H), 3.4–3.3 (m, 2H), 3.1–3.0 (m, 2H); MF=C$_{33}$H$_{28}$F$_3$N$_4$O$_8$S$_2$; LCMS for C$_{31}$H$_{28}$N$_4$O$_6$S$_2$(M+H)$^+$: m/z=617.

Example 4.198

N-1-(1H-benzimidazol-2-yl)-2-[4-(1,1-dioxido-3-oxoisothiazolidin-5-yl)phenyl]ethyl-2',5'-dimethylbiphenyl-4-sulfonamide trifluoroacetate

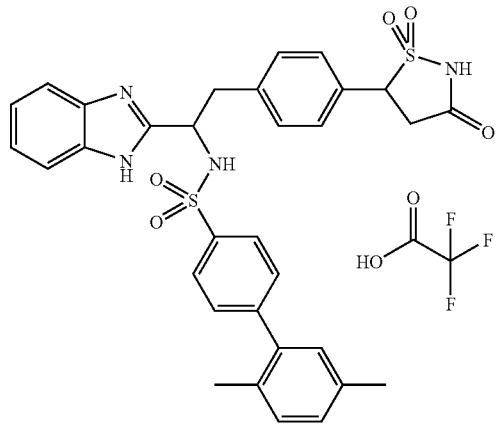

The title compound was prepared according to the procedures of Example 4.187 using appropriate starting materials. $^1$H NMR (400 MHz, CD$_3$OD): δ δ 7.8–7.6 (m, 4H), 7.5 (m, 2H), 7.4–7.3 (m, 4H), 7.2–7.1 (m, 3H), 6.7 (m, 1H), 5.0–4.9 (m, 2H), 3.4–3.3 (m, 2H), 3.2–3.0 (m, 2H), 2.4 (s, 3H), 2.1 (s, 3H); MF=C$_{34}$H$_{31}$F$_3$N$_4$O$_7$S$_2$; LCMS for C$_{32}$H$_{31}$N$_4$O$_5$S$_2$ (M+H)$^+$: m/z=615.

Example 4.199

N-1-(1H-benzimidazol-2-yl)-2-[4-(1,1-dioxido-3-oxoisothiazolidin-5-yl)phenyl]ethyl-4'-chlorobiphenyl-4-sulfonamide trifluoroacetate

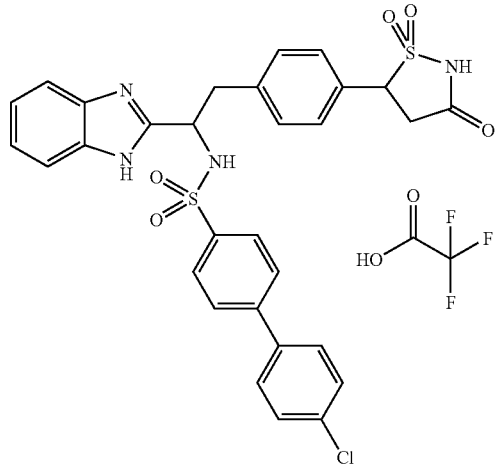

The title compound was prepared according to the procedures of Example 4.187 using appropriate starting materials. $^1$H NMR (400 MHz, CD$_3$OD): δ 7.4–7.2 (m, 12H), 7.3 (m, 2H), 7.1 (m, 2H), 5.0–4.9 (m, 2H), 3.4–3.3 (m, 2H), 3.1 (m, 2H); MF=C$_{32}$H$_{26}$ClF$_3$N$_4$O$_7$S$_2$; LCMS found for C$_{30}$H$_{26}$ClN$_4$O$_5$S$_2$ (M+H)$^+$: m/z=621.

Example 4.200

N-1-(1H-benzimidazol-2-yl)-2-[4-(1,1-dioxido-3-oxoisothiazolidin-5-yl)phenyl]ethyl-4'-(trifluoromethyl)biphenyl-4-sulfonamide trifluoroacetate

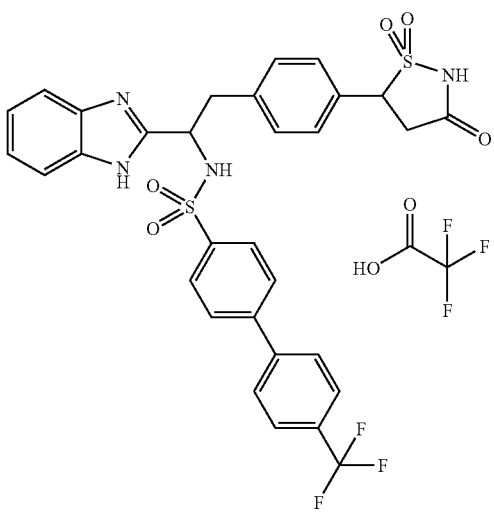

The title compound was prepared according to the procedures of Example 4.187 using appropriate starting materials. $^1$H NMR (400 MHz, CD$_3$OD): δ 7.8–7.7 (m, 6H), 7.6 (m, 4H), 7.5 (m, 2H), 7.3 (m, 2H), 7.1 (m, 2H), 4.9–5.0 (m, 2H), 3.3 (m, 2H), 3.1 (m, 2H); MF=C$_{33}$H$_{26}$F$_6$N$_4$O$_7$S$_2$; LCMS found for C$_{33}$H$_{27}$F$_6$N$_4$O$_7$S$_2$ (M+H)$^+$: m/z=655.

Example 4.201

N-1-(1H-benzimidazol-2-yl)-2-[4-(1,1-dioxido-3-oxoisothiazolidin-5-yl)phenyl]ethyl-4'-cyanobiphenyl-4-sulfonamide trifluoroacetate

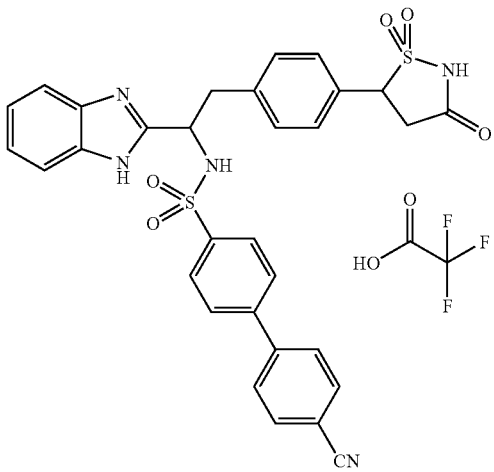

The title compound was prepared according to the procedures of Example 4.187 using appropriate starting materials. MF=C$_{33}$H$_{26}$F$_3$N$_5$O$_7$S$_2$; LCMS found for C$_{31}$H$_{26}$N$_5$O$_5$S$_2$ (M+H)$^+$: m/z=612.

Example 4.202

N-1-(1H-benzimidazol-2-yl)-2-[4-(1,1-dioxido-3-oxoisothiazolidin-5-yl)phenyl]ethyl-3-(trifluoromethoxy)biphenyl-4-sulfonamide trifluoroacetate

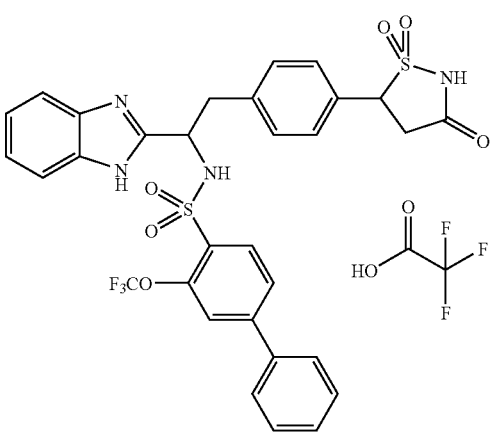

The title compound was prepared according to the procedures of Example 4.187 using appropriate starting materials. $^1$H NMR (400 MHz, CD$_3$OD): δ 7.8 (m, 2H), 7.6 (m, 2H), 7.5–7.1 (m, 12H), 5.1 (m, 2H), 3.3 (m, 2H), 3.1–3.0 (m, 2H); MF=C$_{33}$H$_{26}$F$_6$N$_4$O$_8$S$_2$; LCMS found for C$_{31}$H$_{26}$F$_3$N$_4$O$_6$S$_2$ (M+H)$^+$: m/z=671.

Example 4.203

N-1-(1H-benzimidazol-2-yl)-2-[4-(1,1-dioxido-3-oxoisothiazolidin-5-yl)phenyl]ethyl-3',5'-dichloro-3-(trifluoromethoxy)biphenyl-4-sulfonamide trifluoroacetate

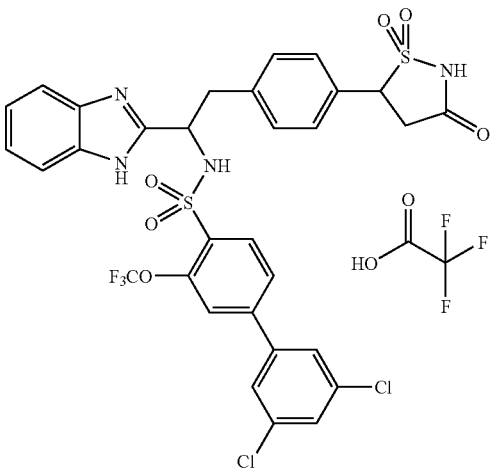

The title compound was prepared according to the procedures of Example 4.187 using appropriate starting. $^1$H NMR (400 MHz, CD$_3$OD): δ 7.8 (m, 2H), 7.6–7.2 (m, 12H), 5.1–5.0 (m, 2H), 3.4–3.3 (m, 2H), 3.1 (m, 2H); MF=C$_{33}$H$_{24}$Cl$_2$F$_6$N$_4$O$_8$S$_2$; LCMS found for C$_{31}$H$_{24}$Cl$_2$F$_6$N$_4$O$_{S2}$ (M+H)$^+$: m/z=739.

Example 4.204

N-(1S)-1-(1H-benzimidazol-2-yl)-2-[4-(1,1-dioxido-3-oxoisothiazolidin-5-yl)phenyl]ethyl-2-(trifluoromethyl)biphenyl-4-sulfonamide trifluoroacetate

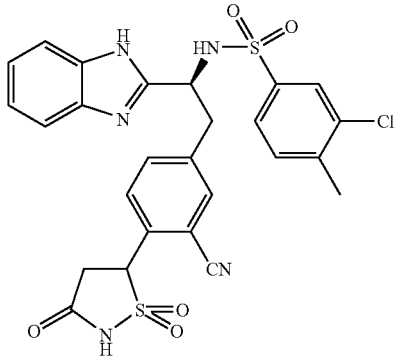

Step 1. tert-butyl [(1S)-2-[(2-aminophenyl)amino]-1-(3-bromo-4-iodobenzyl)-2-oxoethyl]carbamate

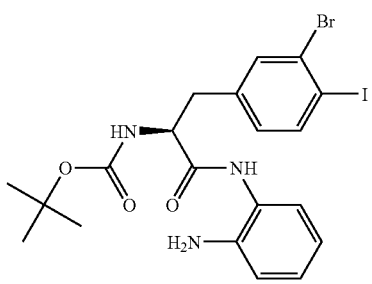

Benzyl (2S)-3-(3-bromo-4-iodophenyl)-2-[(tert-butoxycarbonyl)amino]propanoate (1.50 g, 2.68 mmol) was dissolved in acetonitrile (7.5 mL) and treated with 1.0 M of sodium hydroxide in water (5.4 mL). The solution was stirred at 25° C. for 30 min. The reaction was diluted with 1 N HCl solution and extracted with ethyl acetate three times, dried with sodium sulfate, filtered, and concentrated in vacuo. The crude was dissolved in DMF (4.0 mL) and treated with benzotriazol-1-yloxytris(dimethylamino)phosphonium hexafluorophosphate (1.03 g, 2.34 mmol) at 0° C. for 15 min. A solution of 1,2-benzenediamine (345 mg, 3.19 mmol) and N,N-diisopropylethylamine (1.85 mL, 10.6 mmol) in DMF (4.0 mL) was added to the reaction. The resulting mixture was warmed to room temperature for 2 h. The reaction was diluted with ethyl acetate and washed with saturated sodium bicarbonate solution (50 mL) and 1 N HCl solution (50 mL). The organic solutions were dried with sodium sulfate, filtered, and concentrated in vacuo. The crude residue was purified by preparative LCMS to yield the desired product (0.71 g, 60%). $^1$H NMR (400 MHz, CDCl$_3$): δ 7.85 (d, 1H), 7.62 (s, 1H), 7.25–6.98 (m, 5H), 4.40 (t, 1H), 3.11 (dd, 1H), 2.91 (dd, 1H), 1.41 (s, 9H); LCMS found for C$_{20}$H$_{24}$BrIN$_3$O$_3$ (M+H)$^+$: m/z=560, 562.

Step 2. tert-Butyl [(1S)-1-(1H-benzimidazol-2-yl)-2-(3-bromo-4-iodophenyl)ethyl]carbamate

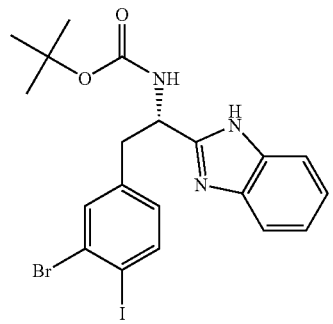

A solution of tert-butyl [(1S)-2-[(2-aminophenyl)amino]-1-(3-bromo-4-iodobenzyl)-2-oxoethyl]carbamate (640 mg, 1.14 mmol) in acetic acid (30.0 mL) was stirred at 40° C. for 2 h. The solution was concentrated in vacuo. The residue was diluted with ethyl acetate, washed with water, dried with sodium sulfate, filtered, and concentrated in vacuo to yield the desired product (610 mg, 98%). $^1$H NMR (400 MHz, CD$_3$OD): δ 7.80 (d, 1H), 7.6 (m, 3H), 7.3 (m, 2H), 6.94 (d, 1H), 5.13 (m, 1H), 3.39 (m, 1H), 3.09 (m, 1H), 1.37 (s, 9H); LCMS found for C$_{20}$H$_{22}$BrIN$_3$O$_2$ (M+H)$^+$: m/z=542, 544.

Step 3. tert-Butyl 2-(1S)-2-(3-bromo-4-iodophenyl)-1-[(tert-butoxycarbonyl)amino]ethyl-1H-benzimidazole-1-carboxylate

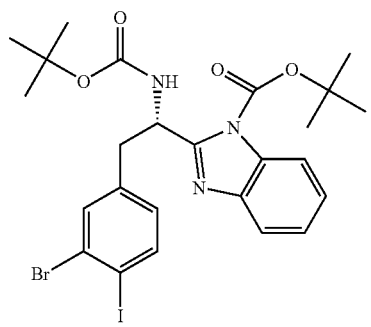

tert-Butyl [(1S)-1-(1H-benzimidazol-2-yl)-2-(3-bromo-4-iodophenyl)ethyl]carbamate (620 mg, 1.1 mmol) in tetrahydrofuran (15 mL) was treated with 1 M sodium hydroxide in water (7 mL) and then di-tert-butyldicarbonate (749 mg, 3.43 mmol) at room temperature. The solution stirred at 35° C. for 2 h. The solution was cooled to room temperature and diluted with ethyl acetate (100 mL). The solution was washed with aqueous hydrochloric acid (1.0 M, 100 mL), dried over sodium sulfate, and concentrated in vacuo. The crude residue was purified by flash column chromatography to afford product as a white foam/glass (630 mg, 86%). $^1$H NMR (400 MHz, CD$_3$OD): δ 7.9 (m, 1H), 7.68 (d, 2H), 7.3 (m, 3H), 6.75 (d, 1H), 5.97 (m, 1H), 5.67 (d, 1H), 3.30 (m, 1H), 2.90 (m, 1H), 1.72 (s, 9H), 1.39 (m, 9H); LCMS found for C$_{25}$H$_{30}$BrIN$_3$O$_4$ (M+H)$^+$: m/z=642, 644.

Step 4. tert-Butyl 2-(1S)-2-[3-bromo-4-(2-tert-butyl-1,1-dioxido-3-oxo-2,3-dihydroisothiazol-5-yl)phenyl]-1-[(tert-butoxycarbonyl)amino]ethyl-1H-benzimidazole-1-carboxylate

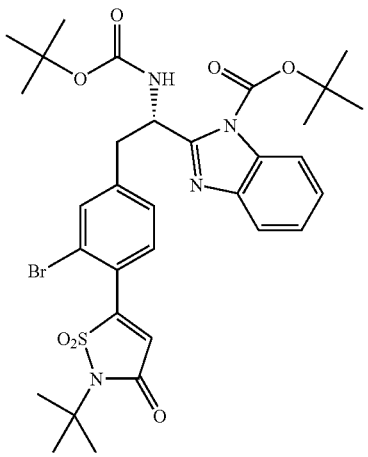

tert-butyl 2-(1S)-2-(3-bromo-4-iodophenyl)-1-[(tert-butoxycarbonyl)amino]ethyl-1H-benzimidazol-1-carboxylate (1.10 g, 1.71 mmol), 2-tert-butylisothiazol-3(2H)-one 1,1-dioxide (648 mg, 3.42 mmol), palladium acetate (190 mg, 0.86 mmol), tetra-N-butylammonium chloride (476 mg, 1.71 mmol), and triethylamine (1.43 mL, 10.3 mmol) were sequentially dissolved in N,N-dimethylformamide (50 mL) under nitrogen atmosphere. The solution was degassed and stirred with heating under nitrogen atmosphere at 70° C. for 2.5 h. The reaction was cooled to room temperature, diluted with ethyl acetate, washed with 1.0 N HCl solution and brine, dried with sodium sulfate, filtered, and concentrated in vacuo. The crude residue was purified by flash column chromatography to yield the desired product (0.41 g, 34%). $^1$H NMR (400 MHz, CDCl$_3$): δ 7.9 (m, 1H), 7.77–7.63 (m, 3H), 7.3 (m, 3H), 6.86 (s, 1H), 6.0 (m, 2H), 3.41 (m, 1H), 2.97 (m, 1H), 1.74 (s, 18H), 1.38 (s, 9H); LCMS found for $C_{32}H_{40}BrN_4O_7S$ (M+H)$^+$: m/z=703, 705.

Step 5. tert-Butyl 2-(1S)-2-[3-bromo-4-(2-tert-butyl-1,1-dioxido-3-oxoisothiazolidin-5-yl)phenyl]-1-[(tert-butoxycarbonyl)amino]ethyl-1H-benzimidazole-1-carboxylate

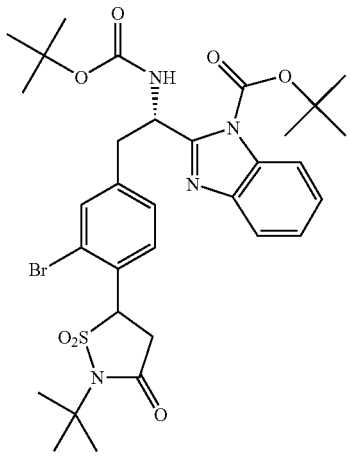

To a solution of tert-butyl 2-(1S)-2-[3-bromo-4-(2-tert-butyl-1,1-dioxido-3-oxo-2,3-dihydroisothiazol-5-yl)phenyl]-1-[(tert-butoxycarbonyl)amino]ethyl-1h-benzimidazole-1-carboxylate (700 mg, 995 μmol) in tetrahydrofuran (50.0 mL) was added 1.0 M of L-selectride in tetrahydrofuran (946 μL), at −78° C. for 10 min. The reaction was quenched by the addition of a small amount of glacial acetic acid (1.0 mL), dilute with EtOAc and wash with water (2×20 mL) and brine, dried with sodium sulfate, filtered, and concentrated in vacuo. The crude residue was purified by flash column chromatography to yield the desired product (0.55 g, 78%). $^1$H NMR (400 MHz, CDCl$_3$): δ 7.9 (m, 1H), 7.6 (m, 1H), 7.44–7.29 (m, 4H), 7.1 (m, 1H), 5.99 (m, 1H), 5.70 (d, 1H), 5.43 (t, 1H), 3.30 (m, 2H), 2.98 (m, 2H), 1.74 (s, 9H), 1.64 (s, 9H), 1.38 (s, 9H); MF=$C_{32}H_{41}BrN_4O_7S$; LCMS found for $C_{32}H_{42}BrN_4O_7S$ (M+H)$^+$: m/z=705, 707.

Step 6. 5-{4-[(2S)-2-Amino-2-(1H-benzimidazol-2-yl)ethyl]-2-bromophenyl}-2-tert-butylisothiazolidin-3-one 1,1-dioxide bistrifluoroacetate

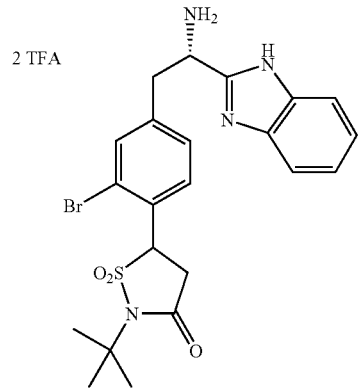

A solution of tert-butyl 2-(1S)-2-[3-bromo-4-(2-tert-butyl-1,1-dioxido-3-oxoisothiazolidin-5-yl)phenyl]-1-[(tert-butoxycarbonyl)amino]ethyl-1H-benzimidazole-1-carboxylate (50.0 mg, 70.8 μmol), methylene chloride (2.00 mL) and trifluoroacetic acid (500 μL) was stirred at 25° C. for 1 h. The reaction solution was concentrated in vacuo. The crude residue was purified by preparative LCMS to afford product (32.5 mg, 91%). $^1$H NMR (400 MHz, CD$_3$OD): δ 7.6 (m, 3H), 7.42–7.17 (m, 4H), 5.57 (m, 1H), 4.8 (m, 1H), 3.55–3.33 (m, 3H), 3.16 (m, 1H), 1.60 (s, 9H); MF=$C_{22}H_{25}BrN_4O_3S$; LCMS found for $C_{22}H_{26}BrN_4O_3S$ (M+H)$^+$: m/z=505, 507.

Step 7. N-{(1S)-1-(1H-Benzimidazol-2-yl)-2-[3-bromo-4-(1,1-dioxido-3-oxoisothiazolidin-5-yl)phenyl]ethyl}-3-chloro-4-methylbenzenesulfonamide trifluoroacetate

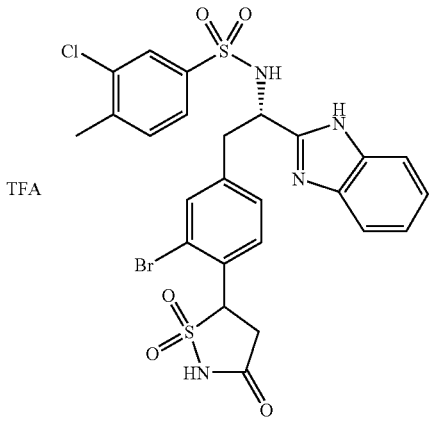

A solution of 5-4-[(2S)-2-amino-2-(1 h-benzimidazol-2-yl)ethyl]-2-bromophenyl-2-tert-butylisothiazolidin-3-one 1,1-dioxide bis(trifluoroacetate) (20.0 mg, 27.3 mmol), methylene chloride (2.0 mL), 3-chloro-4-methylbenzenesulfonyl chloride (12.3 mg, 54.5 μmol) and N,N-diisopropylethylamine (24 μL, 136 μmol) was stirred at 25° C. for 3 h. The reaction solution was concentrated in vacuo. The residue was dissolved in trifluoroacetic acid (2 mL) and heated in a microwave at 130° C. for 2 min. The TFA was removed in vacuo. The crude residue was purified by preparative LCMS to yield the desired product (10.5 mg, 51%). MF=$C_{25}H_{22}BrClN_4O_5S_2$; LCMS found for $C_{25}H_{23}BrClN_4O_5S_s$ (M+H)$^+$: m/z=637, 639.

Step 8. N-(1S)-1-(1H-benzimidazol-2-yl)-2-[3-cyano-4-(1,1-dioxido-3-oxoisothiazolidin-5-yl)phenyl/ethyl-3-chloro-4-methylbenzenesulfonamide trifluoroacetate

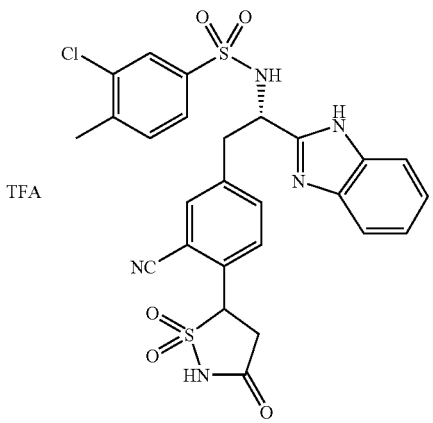

N-(1S)-1-(1H-benzimidazol-2-yl)-2-[3-bromo-4-(1,1-dioxido-3-oxoisothiazolidin-5-yl)phenyl]ethyl-3-chloro-4-methylbenzenesulfonamide (9.4 mg, 0.015 mmol), zinc cyanide (5.2 mg, 0.0442 mmol), tetrakis(triphenylphosphine) palladium (0) (3.4 mg, 2.9 μmol), and N,N-dimethylformamide (0.94 mL) were combined in a microwave vessel and heated at 175° C. for 4 min. The solution was filtered and washed with 1 mL of acetonitrile and purified with preparative LCMS to yield the desired product (4.0 mg, 46%). $^1$H NMR (400 MHz, CD$_3$OD): δ 7.7–7.6 (m, 2H), 7.5 (m, 6H), 7.3 (m, 2H), 5.29 (m, 1H), 5.01 (m, 1H), 3.5 (m, 2H), 3.3 (m, 2H), 2.33 (s, 3H); MF=$C_{26}H_{22}ClN_5O_5S_2$; LCMS found for $C_{26}H_{23}ClN_5O_5S_2$ (M+H)$^+$: m/z=584.

Example 4.205

N-{(1S)-1-(1H-benzimidazol-2-yl)-2-[3-cyano-4-(1,1-dioxido-3-oxoisothiazolidin-5-yl)phenyl]ethyl}-4-chloro-3-(trifluoromethyl)benzenesulfonamide trifluoroacetate

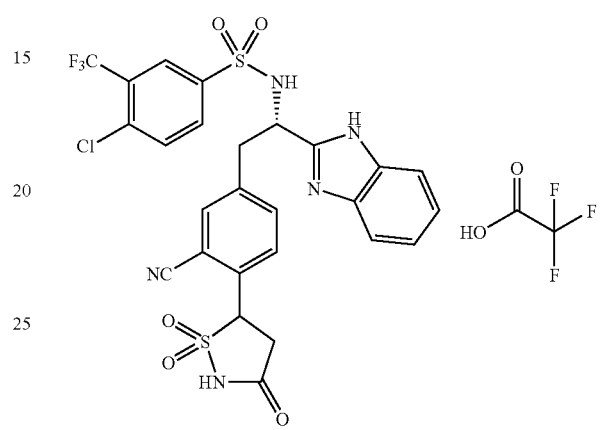

Title compound was prepared according to the procedure in Example 4.204 using the appropriate reagents and starting materials. $^1$H NMR (400 MHz, CD$_3$OD): δ 7.93 (m, 1H), 7.7–7.3 (m, 9H), 5.27 (t, 1H), 4.99 (m, 1H), 3.47 (m, 2H), 3.3 (m, 2H); MF=$C_{26}H_{19}ClF_3N_5O_5S_2$; LCMS found for $C_{26}H_{20}ClF_3N_5O_5S_2$ (M+H)$^+$: m/z=638.

Example 4.206

N-{(1S)-1-(1H-Benzimidazol-2-yl)-2-[3-cyano-4-(1,1-dioxido-3-oxoisothiazolidin-5-yl)phenyl]ethyl}-4-cyano-3-(trifluoromethyl)benzenesulfonamide trifluoroacetate

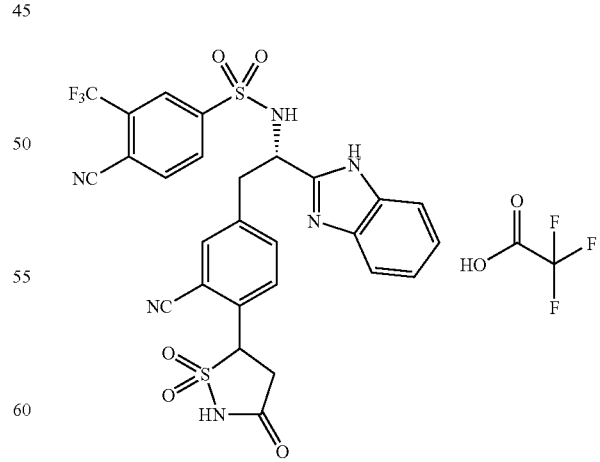

Title compound was prepared according to the procedure in Example 4.204 using the appropriate reagents and starting materials. $^1$H NMR (400 MHz, CD$_3$OD): δ 7.98 (d, 1H), 7.79 (m, 1H), 7.64 (m, 2H), 7.54 (m, 2H), 7.46 (m, 2H), 7.26

(m, 2H), 5.25 (t, 1H), 4.9 (m, 1H), 3.3 (m, 4H); MF=C$_{27}$H$_{19}$F$_3$N$_6$O$_5$S$_2$; LCMS found for C$_{27}$H$_{20}$F$_3$N$_6$O$_5$S$_2$ (M+H)$^+$: m/z=629.

Example 4.207

N-{(1S)-1-(1H-benzimidazol-2-yl)-2-[3-cyano-4-(1,1-dioxido-3-oxoisothiazolidin-5-)phenyl]ethyl}-3-fluorobenzenesulfonamide trifluoroacetate

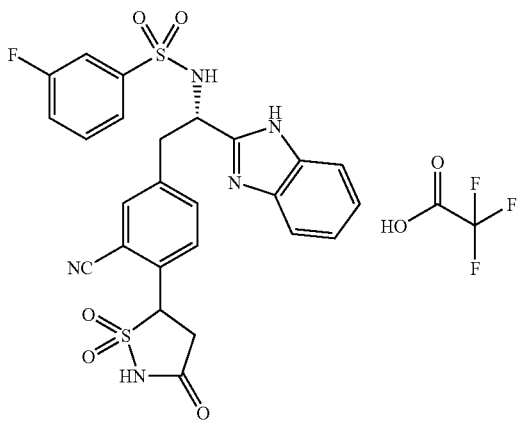

Title compound was prepared according to the procedure in Example 4.204 using the appropriate reagents and starting materials. $^1$H NMR (400 MHz, CD$_3$OD): δ 7.78 (m, 2H), 7.6–7.3 (m, 9H), 5.34 (m, 1H), 5.08 (m, 1H), 3.3 (m, 4H); MF=C$_{25}$H$_{20}$FN$_5$O$_5$S$_2$; LCMS found for C$_{25}$H$_{21}$FN$_5$O$_5$S$_2$ (M+H)$^+$: m/z=554.

Example 4.208

N-{(1S)-1-(1H-Benzimidazol-2-yl)-2-[3-bromo-4-(1,1-dioxido-3-oxoisothiazolidin-5-yl)phenyl]ethyl}-3-fluorobenzenesulfonamide trifluoroacetate

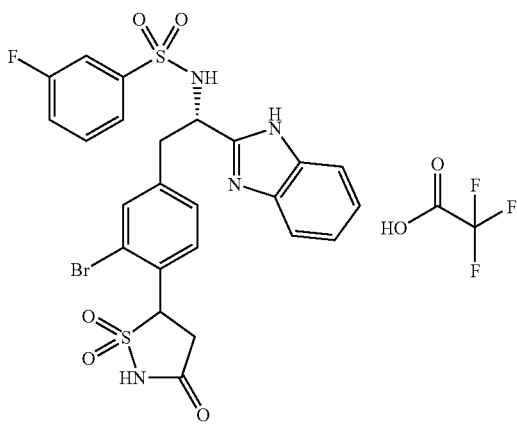

Title compound was prepared according to the procedure in Example 4.204 using the appropriate reagents and starting materials. $^1$H NMR (400 MHz, CD$_3$OD): δ 7.75 (m, 2H), 7.6 (m, 2H), 7.5–7.1 (m, 7H), 5.57 (t, 1H), 5.03 (m, 1H), 3.3 (m, 4H); MF=C$_{24}$H$_{20}$BrFN$_4$O$_5$S$_2$; LCMS found for C$_{24}$H$_{21}$BrFN$_4$O$_5$S$_2$ (M+H)$^+$: m/z=607, 609.

Example 4.209

5-{4-[(2S)-2-(1H-Benzimidazol-2-yl)-2-(1,3-benzothiazol-2-ylamino)ethyl]-2-ylamino)ethyl]-2-bromophenyl}isothiazolidin-3-one 1,1-dioxide trifluoroacetate

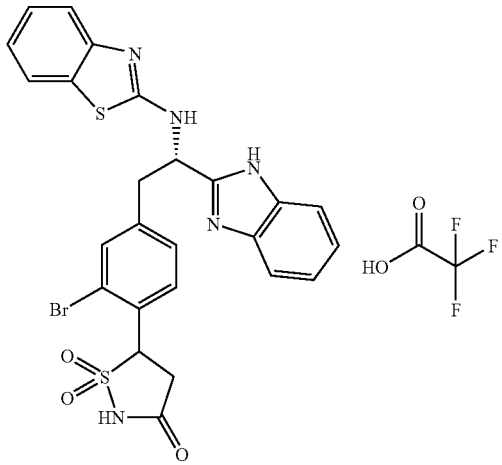

A solution of 5-{4-[(2S)-2-amino-2-(1H-benzimidazol-2-yl)ethyl]-2-bromophenyl}-2-tert-butylisothiazolidin-3-one 1,1-dioxide (69 mg, 136 μmol), triethylamine (57.0 μL, 409 μmol), methylene chloride (4.5 mL) was stirred at 25° C. for 15 min. Isothiocyanatobenzene (26.0 μL, 136 μmol) was added to the reaction mixture and stirred for 1 h at room temperature. Benzyltrimethylammonium tribromide (53.2 mg, 136 μmol) was added and stirred for 1 d. The solvents were removed and trifluoroacetic acid (1.5 mL) was added and heated in a microwave at 130° C. for 1 minute. The solvents were concentrated in vacuo. The crude residue was purified by preparative LCMS to yield the desired product (29 mg, 36%). $^1$H NMR (400 MHz, CD$_3$OD): δ 7.74–7.56 (m, 6H), 7.48–7.28 (m, 3H), 7.20 (t, 1H), 7.09 (t, 1H), 5.68 (t, 1H), 5.59 (m, 1H), 3.65 (m, 1H), 3.53 (m, 1H), 3.22 (m, 1H); MH=C$_{25}$H$_{20}$BrN$_5$O$_3$S$_2$; LCMS found for C$_{25}$H$_{21}$BrN$_5$O$_3$S$_2$ (M+H)$^+$: m/z=582, 584.

Example 4.210

5-[(2S)-2-(1H-Benzimidazol-2-yl)-2-(1,3-benzothiazol-2-ylamino)ethyl]-2-(1,1-dioxido-3-oxoisothiazolidin-5-yl)benzonitrile trifluoroacetate

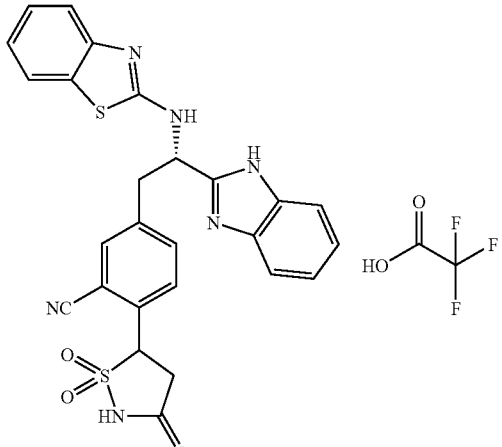

A solution of 5-{4-[(2S)-2-(1H-benzimidazol-2-yl)-2-(1,3-benzothiazol-2-ylamino)ethyl]-2-bromophenyl}isothiazolidin-3-one 1,1-dioxide (9.3 mg, 11.2 μmol), zinc cyanide (4.0 mg, 33.7 μmol), tetrakis(triphenylphosphine)palladium(0) (2.6 mg, 2.24 μmol) and N,N-dimethylformamide (1.0 mL) were combined in a microwave vessel and heated at 175° C. for 4 min. The solution was filtered and diluted with 1 mL of acetonitrile and purified with preparative LCMS to yield the desired product (2.8 mg, 47%). $^1$H NMR (400 MHz, CD$_3$OD): δ 7.82–7.72 (m, 3H), 7.6 (m, 5H), 7.29 (d, 1H), 7.21 (t, 1H), 7.09 (t, 1H), 5.73 (m, 1H), 5.32 (m, 1H), 3.76 (m, 1H), 3.66 (m, 1H), 3.4 (m, 2H); MF=C$_{26}$H$_{20}$N$_6$O$_3$S$_2$; LCMS found for C$_{26}$H$_{21}$N$_6$O$_3$S$_2$ (M+H)$^+$: m/z=529.

Example 4.211

5-(4-{(2S)-2-(1H-Benzimidazol-2-yl)-2-[(6-methoxy-1,3-benzothiazol-2-yl)amino]ethyl}-2-bromophenyl)isothiazolidin-3-one 1,1-dioxide trifluoroacetate

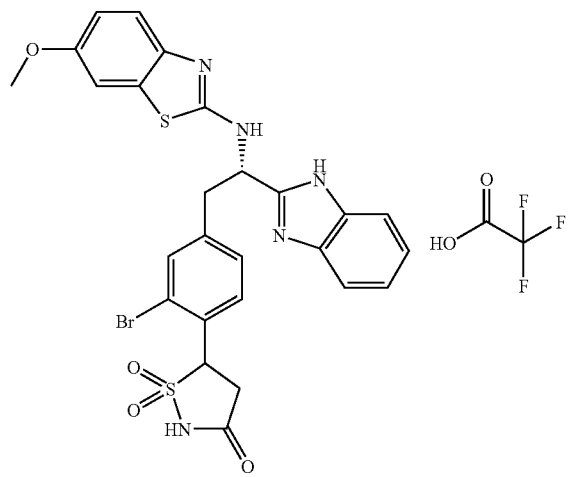

Title compound was prepared according to the procedure in Example 4.209 using the appropriate reagents and starting materials. $^1$H NMR (400 MHz, CD$_3$OD): δ 7.74–7.57 (m, 5H), 7.45 (m, 1H), 7.35–7.18 (m, 3H), 6.80 (m, 1H), 5.63 (m, 2H), 3.76 (s, 3H), 3.61 (m, 1H), 3.51 (m, 1H), 3.42 (m, 1H), 3.22 (m, 1H); MF=C$_{26}$H$_{22}$BrN$_5$O$_4$S$_2$; LCMS found for C$_{26}$H$_{23}$BrN$_5$O$_4$S$_2$ (M+H)$^+$: m/z=612, 614.

Example 4.212

Methyl 2-[4-((2S)-2-1 (benzyloxy)carbonyl]amino-3-[4-(1,1-dioxido-3-oxoisothiazolidin-5-yl)phenyl]propanoylamino)butoxy]-6-hydroxybenzoate

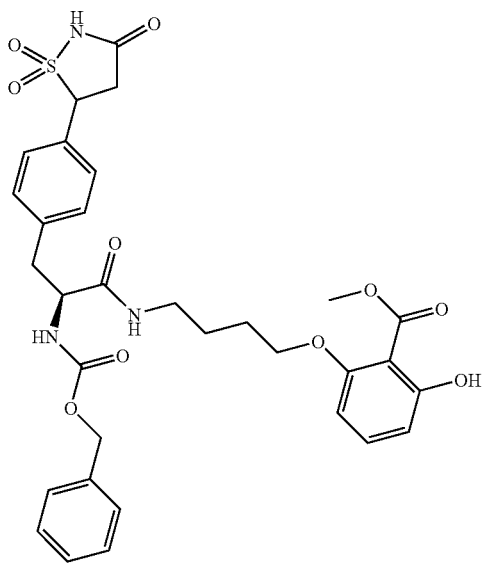

Step 1. (2S)-2-[(Benzyloxy)carbonyl]amino-3-[4-(1,1-dioxido-3-oxoisothiazolidin-5-yl)phenyl]propanoic acid

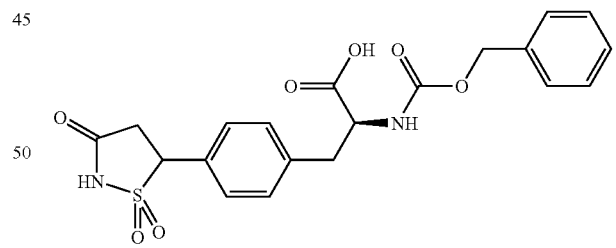

A solution of (2S)-2-amino-3-[4-(1,1-dioxido-3-oxoisothiazolidin-5-yl)phenyl]propanoic acid trifluoroacetate (45 mg, 109 μmol), sodium hydroxide (26.2 mg, 655 μmol), water (100 μL) and tetrahydrofuran (2 mL) was cooled to 0° C. and then benzyl chloroformate (18.7 μL, 131 μmol) was added. The reaction was warmed to 25° C. and stirred for 20 h. The solution was acidified with 1 N aq. HCl solution (1.00 mL) and the crude residue was purified by preparative LCMS to yield the desired product (13 mg, 28%). MF=C$_{20}$H$_{20}$N$_2$O$_7$S; LCMS found for C$_{20}$H$_{21}$N$_2$O$_7$S (M+H)$^+$: m/z=433.

Step 2. Methyl 2-[4-((2S)-2-[(benzyloxy)carbonyl]amino-3-[4-(1,1-dioxido-3-oxoisothiazolidin-5-yl)phenyl]propanoylamino)butoxy]-6-hydroxybenzoate

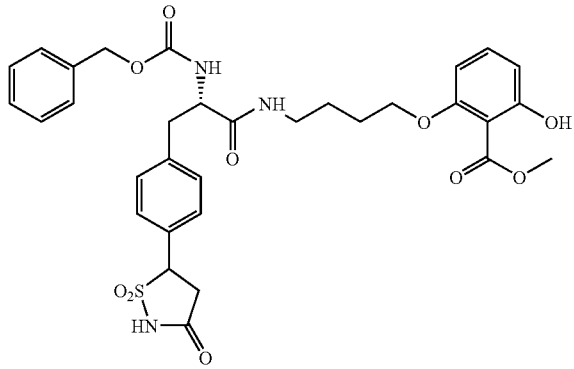

A solution of (2S)-2-[(benzyloxy)carbonyl]amino-3-[4-(1,1-dioxido-3-oxoisothiazolidin-5-yl)phenyl]propanoic acid (10 mg, 23.1 µmol), benzotriazol-1-yloxytris(dimethylamino)phosphonium hexafluorophosphate (10.7 mg, 24.3 µmol) and N,N-dimethylformamide (1 mL) was stirred at 0° C. After stirring for 15 min, methyl 2-(4-aminobutoxy)-6-hydroxybenzoate (6.09 mg, 25.4 µmol) and N,N-diisopropylethylamine (12.1 µL) were added to the reaction. The resulting mixture was stirred at 25° C. for 3 h. The reaction solution was diluted with acetonitrile and purified by preparative LCMS to yield the desired product (4.7 mg, 31%). MF=$C_{32}H_{35}N_3O_{10}S$; LCMS found for $C_{32}H_{36}N_3O_{10}S$ (M+H)$^+$: m/z=654.

Example 4.213

Methyl 2-[4-((2S)-2-[(benzyloxy)carbonyl]amino-3-[4-(1,1-dioxido-3-oxoisothiazolidin-5-yl)-3-methylphenyl]propanoylamino)butoxy]-6-hydroxybenzoate

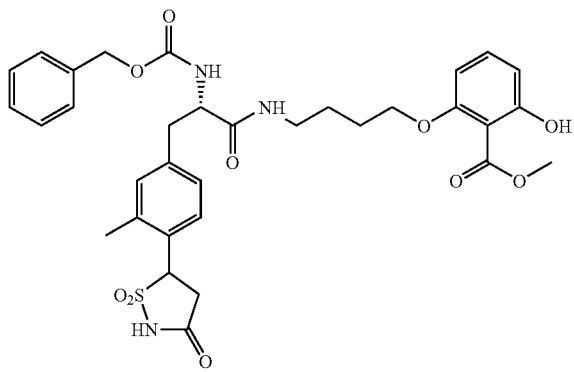

Step 1. (4-Bromo-3-methylphenyl)methanol

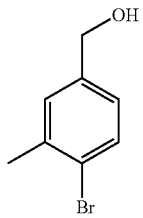

A solution of methyl 4-bromo-3-methylbenzoate (50.0 g, 218 mmol), lithium tetrahydroborate (5.70 g, 262 mmol) and tetrahydrofuran (500 mL) was stirred at 25° C. for 2 d. The reaction was cooled to 0° C., quenched with saturated NH$_4$Cl solution and diluted with ethyl acetate. The aqueous layers were extracted with ethyl acetate three times, dried with sodium sulfate, filtered, and concentrated in vacuo. The crude residue was purified by flash column chromatography to yield the desired product (36.0 g, 82%).

$^1$H NMR (400 MHz, CDCl$_3$): δ 7.49 (d, 1H), 7.21 (d, 1H), 7.02 (m, 1H), 4.59 (s, 2H), 2.39 (s, 3H); MF=$C_8H_9BrO$; LCMS found for $C_8H_{10}BrO$ (M+H–H$_2$O)$^+$: m/z=183, 185.

Step 2. 4-Bromo-3-methylbenzaldehyde

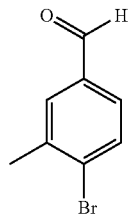

To a solution of dimethyl sulfoxide (21.2 mL, 0.298 mol) in DCM (150 mL) was added oxalyl chloride (5.0 mL, 0.060 mol) at –78° C. under an atmosphere of nitrogen. The resulting mixture was stirred for 20 min. A solution of (4-bromo-3-methylphenyl)methanol (6.0 g, 0.030 mol) in methylene chloride (50 mL) was cannulated into the reaction flask. After stirring for 1.0 h, triethylamine (21 mL, 0.15 mol) was added. The reaction mixture was stirred at –78° C. for 1 h, warmed to room temperature for 1 h. The reaction was quenched with 1 N HCl solution, the aqueous phase was separated and extracted with methylene chloride once. The combined organic solutions were washed with brine, dried over sodium sulfate, filtered, concentrated in vacuo. The crude residue was purified by flash column chromatography to yield the desired product (5.7 g, 96%). $^1$H NMR (400 MHz, CDCl$_3$): δ 9.96 (s, 1H), 7.73 (m, 1H), 7.71 (s, 1H), 7.55 (m, 1H), 2.49 (s, 3H).

Step 3. Methyl (2Z)-2-[(benzyloxy)carbonyl]amino-3-(4-bromo-3-methylphenyl)acrylate; methyl (2E)-2-[(benzyloxy)carbonyl]amino-3-(4-bromo-3-methylphenyl)acrylate

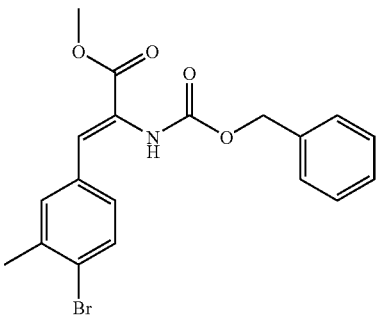

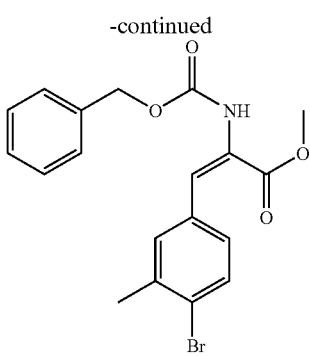

To a solution of N-(benzyloxycarbonyl)phosphonoglycine trimethyl ester (10.0 g, 30.2 mmol) in methylene chloride (200 mL) was added 1,8-diazabicyclo[5.4.0]undec-7-ene (4.96 mL, 33.2 mmol) at room temperature under an atmosphere of nitrogen. After stirring for 10 min, a solution of 4-bromo-3-methylbenzaldehyde (6.01 g, 30.2 mmol) in methylene chloride (50 mL) was cannulated into the reaction solution. The resulting solution was stirred at room temperature for 1.5 h. The reaction was diluted with ethyl acetate and quenched with 1.0 N HCl solution. The aqueous layer was extracted with ethyl acetate twice. The combined organic solutions were washed with brine, dried over sodium sulfate, filtered and concentrated in vacuo. The crude residue was purified by flash column chromatography to yield the desired product (10.4 g, 85.2%). $^1$H NMR (400 MHz, CDCl$_3$): δ 7.44 (d, 1H), 7.3 (m, 7H), 7.17 (d, 1H), 5.11 (s, 2H), 3.82 (s, 3H), 2.33 (s, 3H); MF=C$_{19}$H$_{18}$BrNO$_4$; LCMS found for C$_{19}$H$_{18}$BrNO$_4$Na (M+Na)$^+$: m/z=426, 428.

Step 4. Methyl (2S)-2-[(benzyloxy)carbonyl]amino-3-(4-bromo-3-methylphenyl)propanoate

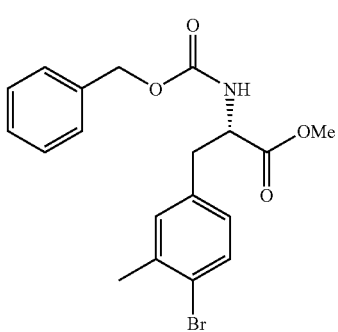

A solution of methyl-2-[(benzyloxy)carbonyl]amino-3-(4-bromo-3-methylphenyl)acrylate (10.4 g, 0.0257 mol) in ethanol (200 mL) was degassed with nitrogen. (R,R)-(−)-1,2-bis[(o-methoxyphenyl)(phenyl)phosphino]ethane(1,5-cyclooctadiene) rhodium (I) tetrafluroborate (194 mg, 257 μmol) was added to the reaction solution and nitrogen was bubble through. After five cycles of vacuum/H$_2$, the reaction was heated at a pressure of 50 psi of hydrogen at room temperature. After 24 h, the solvent was removed under reduced pressure. The crude residue was purified by flash column chromatography to yield the desired product (8.7 g, 83%). $^1$H NMR (400 MHz, CD$_3$OD): δ 7.40 (d, 1H), 7.3 (m, 5H), 7.13 (s, 1H), 6.91 (m, 1H), 5.00 (m, 2H), 4.42 (m, 1H), 3.70 (s, 3H), 3.09 (m, 1H), 2.84 (m, 1H), 2.32 (s, 3H); MF=C$_{19}$H$_{20}$BrNO$_4$; LCMS found for C$_{19}$H$_{20}$BrNO$_4$Na (M+Na)$^+$: m/z=428, 430.

Step 5. Methyl (2S)-2-[(benzyloxy)carbonyl]amino-3-[3-methyl-4-(4,4,5,5-tetramethyl-1,3,-dioxaborolan-2-yl)phenyl]propanoate

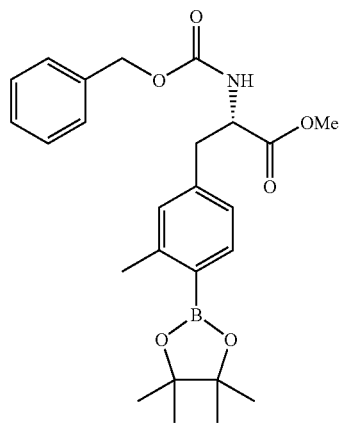

To a mixture of methyl (2S)-2-[(benzyloxy)carbonyl]amino-3-(4-bromo-3-methylphenyl)propanoate (1.23 g, 3.03 mmol), 1,4-dioxane (8 mL), triethylamine (1.69 mL, 12.1 mmol), palladium acetate (17 mg, 76 μmol), O-(dicyclohexylphosphino)biphenyl (106 mg, 0.303 mmol) was added 4,4,5,5-tetramethyl-1,3,2-dioxaborolane (1.10 mL, 7.57 mmol) dropwise. The greenish reaction mixture was stirred at 80° C. for 30 min. The reaction was quenched with saturated NH$_4$Cl solution. The aqueous solution was extracted with ethyl acetate twice. The organic solutions were washed with brine, dried with sodium sulfate, filtered, and concentrated in vacuo. The crude residue was purified by flash column chromatography to yield the desired product (1.25 g, 91%). $^1$H NMR (400 MHz, CDCl$_3$): δ 7.67 (d, 1H), 7.3 (m, 5H), 6.9 (m, 2H), 5.22 (d, 1H), 5.10 (m, 2H), 4.64 (m, 1H), 3.70 (s, 3H), 3.06 (m, 2H), 2.48 (s, 3H), 1.33 (s, 12H); MF=C$_{25}$H$_{32}$BNO$_6$; LCMS found for C$_{25}$H$_{33}$BNO$_6$ (M+H)$^+$: m/z=454.

Step 6. [4-((2S)-2-[(Benzyloxy)carbonyl]amino-3-methoxy-3-oxopropyl)-2-methylphenyl]boronic acid

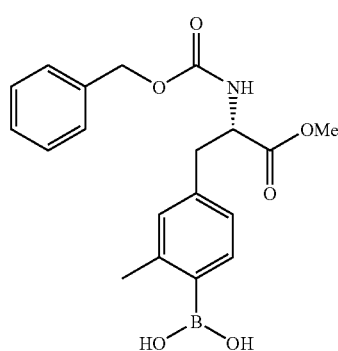

A solution of methyl (2S)-2-[(benzyloxy)carbonyl]amino-3-[3-methyl-4-(4,4,5,5-tetramethyl-1,3,2-dioxaborolan-2-yl)phenyl]propanoate (6.90 g, 15.2 mmol), sodium periodate (16.3 g, 76.1 mmol), tetrahydrofuran (156 mL), ammonium acetate (4.69 g, 60.9 mmol) and water (156 mL) was stirred at 25° C. for 24 h. The reaction was diluted with ethyl acetate and 1 N HCl solution. The aqueous solution was extracted with ethyl acetate once. The combined organic solutions were washed with brine, dried with sodium sulfate, filtered, and concentrated in vacuo. The crude residue was crystallized in ethyl acetate to yield the desired product (5.65 g, 80%). $^1$H NMR (400 MHz, CD$_3$OD): δ 7.3 (m, 5H), 7.16 (d, 1H), 7.0 (m, 2H), 5.02 (m, 2H), 4.42 (m, 1H), 3.68 (s, 3H), 3.10 (m, 1H), 2.88 (m, 1H), 2.28 (s, 3H); MF=C$_{19}$H$_{22}$BNO$_6$; LCMS found for C$_{19}$H$_{23}$BNO$_6$ (M+H)$^+$: m/z=372.

Step 7. Methyl (2S)-2-[(benzyloxy)carbonyl]amino-3-[4-(2-tert-butyl-1,1-dioxido-3-oxo-2,3-dihydroisothiazol-5-yl)-3-methylphenyl]propanoate

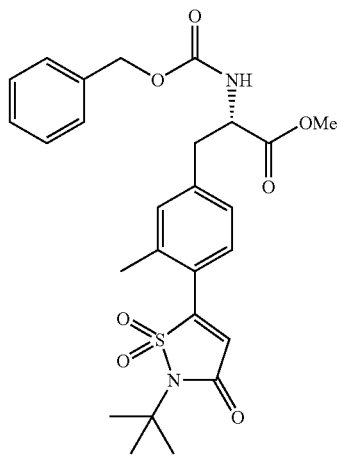

A solution of 2-tert-butyl-5-chloro-1,1-dioxo-1,2-dihydro-1□6-isothiazol-3-one (1.86 g, 8.30 mmol), [4-((2S)-2-[(benzyloxy)carbonyl]amino-3-methoxy-3-oxopropyl)-2-methylphenyl]boronic acid (2.80 g, 7.54 mmol), [1,1'-bis(diphenylphosphino)ferrocene]dichloropalladium(II), complex with dichloromethane (1:1) (924 mg, 1.13 mmol), potassium carbonate (5.21 g, 37.7 mmol) and 1,4-dioxane (38 mL) was degassed with nitrogen and stirred at 80° C. for 24 h. The reaction was diluted with water and extracted with ethyl acetate three times, dried with sodium sulfate, filtered, and concentrated in vacuo. The crude residue was purified by flash column chromatography to yield the desired product (2.4 g, 62%). $^1$H NMR (400 MHz, CDCl$_3$): δ 7.61 (d, 1H), 7.35 (m, 5H), 7.03 (m, 2H), 6.46 (s, 1H), 5.27 (d, 1H), 5.11 (m, 2H), 4.67 (m, 1H), 3.74 (s, 3H), 3.1 (m, 2H), 2.36 (s, 3H), 1.73 (s, 9H); MF=C$_{26}$H$_{30}$N$_2$O$_7$S; LCMS found for C$_{26}$H$_{31}$N$_2$O$_7$S (M+H)$^+$: m/z=515.

Step 8. Methyl (2S)-2-[(benzyloxy)carbonyl]amino-3-[4-(2-tert-butyl-1,1-dioxido-3-oxoisothiazolidin-5-yl)-3-methylphenyl]propanoate

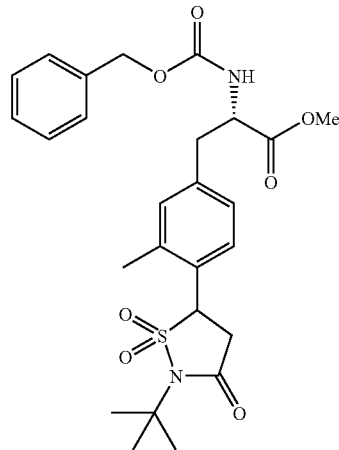

A solution of methyl (2S)-2-[(benzyloxy)carbonyl]amino-3)-[4-(2-tert-butyl-1,1-dioxido-3-oxo-2,3-dihydroisothiazol-5-yl)-3-methylphenyl]propanoate (570 mg, 1.111 mmol) in tetrahydrofuran (11 mL) was added 1 M L-selectride in tetrahydrofuran (2.1 mL) at −78° C. After stirring for 10 min, the reaction was quenched with acetic acid (1.0 mL) and diluted with water. The aqueous phase was separated and extracted with ethyl acetate three times. The combined organic solutions were dried with sodium sulfate, filtered, and concentrated in vacuo. The crude residue was purified by flash column chromatography to yield the desired product (501 mg, 88%). $^1$H NMR (400 MHz, CDCl$_3$): δ 7.3 (m, 5H), 7.2 (m, 2H), 7.0 (m, 2H), 5.21 (d, 1H), 5.10 (m, 2H), 4.65 (m, 1H), 3.72 (s, 3H), 3.23 (m, 1H), 3.1 (m, 3H), 2.43 (s, 3H), 1.65 (s, 9H); MF=C$_{26}$H$_{32}$N$_2$O$_7$S; LCMS found for C$_{26}$H$_{33}$N$_2$O$_7$S (M+H)$^+$: m/z=517.

Step 9. Methyl (2S)-2-amino-3-[4-(1,1-dioxido-3-oxoisothiazolidin-5-yl)-3-methylphenyl]propanoate trifluoroacetate

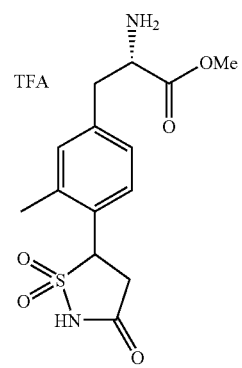

A solution of methyl (2S)-2-[(benzyloxy)carbonyl]amino-3-[4-(2-tert-butyl-1,1-dioxido-3-oxoisothiazolidin-5-yl)-3-methylphenyl]propanoate (450 mg, 0.871 mmol) in trifluoroacetic acid (3.00 mL) was heated in microwave reactor at 130° C. for 5 min. Solvent was removed in vacuo.

The residue was purified with preparative LCMS to give the desired product (210 mg, 74%). $^1$H NMR (400 MHz, CD$_3$OD): δ 7.45 (m, 1H), 7.2 (m, 2H), 5.47 (t, 1H), 4.34 (t, 1H), 3.81 (s, 3H), 3.3 (m, 2H), 3.25 (d, 1H), 3.13 (m, 1H), 2.49 (s, 3H); MF=C$_{14}$H$_{19}$N$_2$O$_5$S; LCMS found for C$_{14}$H$_{20}$N$_2$O$_5$S (M+H)$^+$: m/z=327.

Step 10. (2S)-2-[(Benzyloxy)carbonyl]amino-3-[4-(1,1-dioxido-3-oxoisothiazolidin-5-yl)-3-methylphenyl]propanoic acid

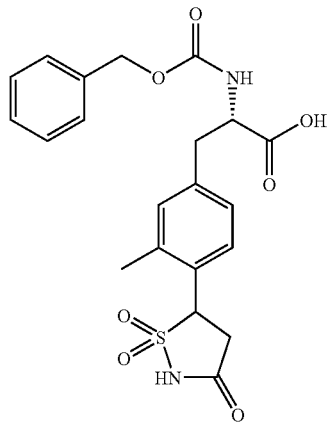

Methyl (2S)-2-amino-3-[4-(1,1-dioxido-3-oxoisothiazolidin-5-yl)-3-methylphenyl]propanoate trifluoroacetate (286 mg, 0.649 mmol) in methanol (7.0 mL) was treated with triethylamine (362 µL, 2.60 mmol) and cooled to 0° C. Benzyl chloroformate (116 µL, 0.812 mmol) was added and the solution stirred for 2 h. 2 M lithium hydroxide in water (0.81 mL) was added and the solution stirred for an additional 1 h. The reaction soluiton was acidified with 1 N HCl and extracted with ethyl acetate. The crude product was used in the next step without purification. MF=C$_{21}$H$_{22}$N$_2$O$_7$S; LCMS found for C$_{21}$H$_{23}$N$_2$O$_7$S (M+H)$^+$: m/z=447.

Step 11. Methyl 2-[4-((2S)-2-[(benzyloxy)carbonyl]amino-3-[4-(1,1-dioxido-3-oxoisothiazolidin-5-yl)-3-methylphenyl]propanoylamino)butoxy]-6-hydroxybenzoate

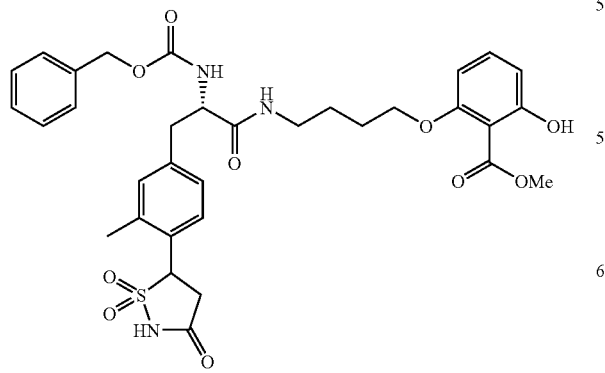

To a solution of (2S)-2-[(benzyloxy)carbonyl]amino-3-[4-(1,1-dioxido-3-oxoisothiazolidin-5-yl)-3-methylphenyl]propanoic acid (85 mg, 0.19 mmol) in N,N-dimethylformamide (2.0 mL) were added benzotriazol-1-yloxytris(dimethylamino)phosphonium hexafluorophosphate (88.4 mg, 0.200 mmol) at 0° C. under an atmosphere of nitrogen. After stirring for 15 min, methyl 2-(4-aminobutoxy)-6-hydroxybenzoate (54.7 mg, 0.228 mmol) and N,N-diisopropylethylamine (99.5 µL, 0.571 mmol) was added. The reaction mixture was warmed to room temperature for 1 h. The reaction was diluted with ethyl acetate and quenched with saturated sodium bicarbonate solution. The aqueous phase was extracted with EtOAc once. The combined organic solutions were washed with brine, dried over sodium sulfate, filtered and concentrated in vacuo. The crude residue was purified by preparative LCMS to yield the desired product (73 mg, 57%). $^1$H NMR (400 MHz, CD$_3$OD): δ 8.00 (m, 1H), 7.38–7.15 (m, 9H), 6.48 (m, 2H), 5.45 (m, 1H), 5.03 (m, 2H), 4.30 (m, 1H), 3.94 (m, 2H), 3.85 (s, 3H), 3.3 (m, 4H), 3.02 (m, 1H), 2.87 (m, 1H), 2.42 (s, 3H), 1.6 (m, 4H); MF=C$_{33}$H$_{37}$N$_3$O$_{10}$S; LCMS found for C$_{33}$H$_{38}$N$_3$O$_{10}$S (M+H)$^+$: m/z=668.

Example 4.214

N-{(1S)-1-(1H-benzimidazol-2-yl)-2-[4-(1,1-dioxido-3-oxoisothiazolidin-5-yl)-3-methylphenyl]ethyl}benzenesulfonamide trifluoroacetate

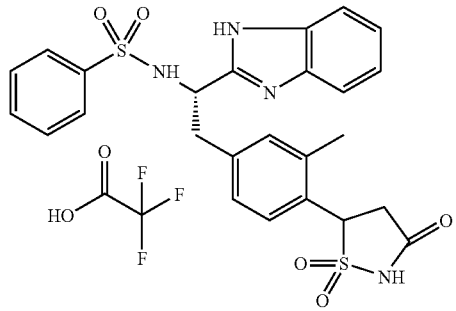

Step 1. benzyl (1S)-2-[(2-aminophenyl)amino-]-1-[4-(1,1-dioxido-3-oxoisothiazolidin-5-yl)-3-methylbenzyl]-2-oxoethylcarbamate

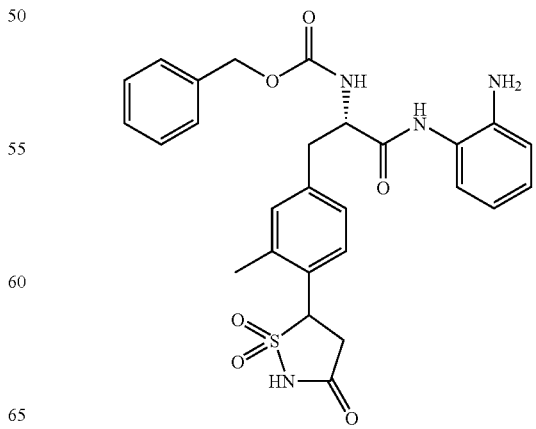

A solution of (2S)-2-[(benzyloxy)carbonyl]amino-3-[4-(1,1-dioxido-3-oxoisothiazolidin-5-yl)-3-methylphenyl]propanoic acid (200 mg, 0.448 mmol) in N,N-dimethylformamide (2.0 mL) was treated with benzotriazol-1-yloxytris(dimethylamino)phosphonium hexafluorophosphate (0.218 g, 0.493 mmol). After stirring for 10 minutes at 0° C., a solution of 1,2-benzenediamine (72.7 mg, 0.672 mmol) and N,N-diisopropylethylamine (0.39 mL, 2.24 mmol) in DMF (1.0 mL) was cannulated into the reaction flask. The solution was stirred at 25° C. for 2 h. The solution was diluted with ethyl acetate, washed with saturated aqueous sodium bicarbonate solution and 1.0 M hydrochloric acid solution. The organic phase was dried over sodium sulfate, filtered, and concentrated in vacuo. The crude residue was purified by preparative LCMS to yield the desired product (196 mg, 82%). $^1$H NMR (400 MHz, CD$_3$OD): δ 7.47 (d, 0.5H), 7.39–7.22 (m, 9H), 7.12 (d, 0.5H), 7.07 (s, 1H), 6.82 (d, 0.5H), 6.71 (d, 0.5H), 5.50 (t, 1H), 5.10 (s, 2H), 4.47 (m, 1H), 3.3 (m, 2H), 3.07 (m, 2H), 2.48 (s, 1.5H), 2.38 (s, 1.5H); MF=C$_{27}$H$_{28}$N$_4$O$_6$S; LCMS found for C$_{27}$H$_{29}$N$_4$O$_6$S (M+H)$^+$: m/z=537.

Step 2. Benzyl (1S)-1-(1H-benzimidazol-2-yl)-2-[4-(1,1-dioxido-3-oxoisothiazolidin-5-yl)-3-methylphenyl]ethylcarbamate acetate

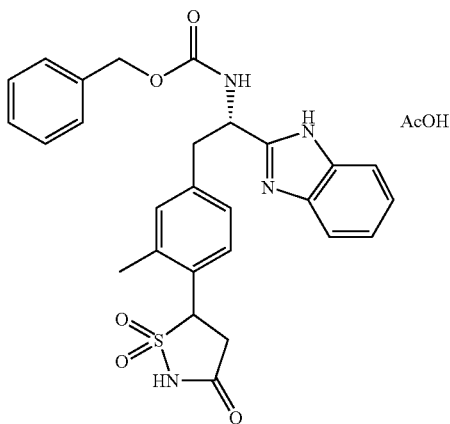

A solution of benzyl (1S)-2-[(2-aminophenyl)amino]-1-[4-(1,1-dioxido-3-oxoisothiazolidin-5-yl)-3-methylbenzyl]-2-oxoethylcarbamate trifluoroacetate (1.20 g, 1.84 mmol) and acetic acid (40.0 mL, 704 mmol) was stirred at 40° C. for 2 h. The solvent was removed in vacuo. The crude product was used in the next step without purification. MF=C$_{27}$H$_{26}$N$_4$O$_5$S; LCMS found for C$_{27}$H$_{27}$N$_4$O$_5$S (M+H)$^+$: m/z=519.

Step 3. Benzyl [(1S)-2-[4-(1,1-dioxido-3-oxo-2-[2-(trimethylsilyl)ethoxy]methylisothiazolidin-5-yl)-3-methylphenyl]-1-(1-[2-(trimethylsilyl)ethoxy]methyl-1H-benzimidazol-2-yl)ethyl]carbamate

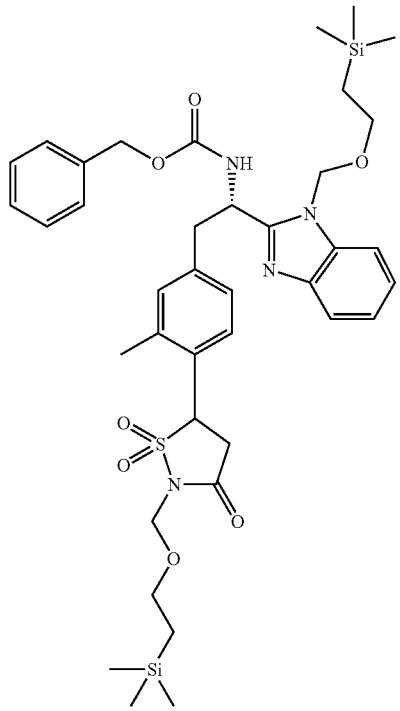

A solution of benzyl (1S)-1-(1H-benzimidazol-2-yl)-2-[4-(1,1-dioxido-3-oxoisothiazolidin-5-yl)-3-methylphenyl]ethylcarbamate acetate (956 mg, 1.65 mmol), [β-(trimethylsilyl)ethoxy]methyl chloride (731 μL, 4.13 mmol), N,N-diisopropylethylamine (1.73 mL, 9.91 mmol) and methylene chloride (30.0 mL) was stirred at 25° C. for 3 h. The reaction was diluted with 1 N HCl solution and extracted with ethyl acetate three times, dried with sodium sulfate, filtered, and concentrated in vacuo. The crude residue was purified by flash column chromatography to yield the desired product (0.82 g, 64%). $^1$H NMR (400 MHz, CD$_3$OD): δ 7.79 (m, 1H), 7.68 (m, 1H), 7.4 (m, 8H), 7.11 (s, 1H), 5.5 (m, 4H), 5.1 (m, 4H), 3.75 (m, 2H), 3.55 (m, 2H), 3.3 (m, 4H), 2.52 (s, 1.5H), 2.40 (s, 1.5H), 1.02 (m, 2H), 0.94 (m, 2H), 0.11 (s, 9H), 0.01 (s, 9H); MF=C$_{39}$H$_{54}$N$_3{_2}$O$_7$SSi$_2$; LCMS found for C$_{39}$H$_{55}$N$_4$O$_7$SSi$_2$ (M+H)$^+$: m/z=779.-

Step 4. 5-{4-[(2S)-2-Amino-2-(1-{[2-(trimethylsi-lyl)ethoxy]methyl}-1H-benzimidazol-2-yl)ethyl]-2-methylphenyl}-2-{[2-(trimethylsilyl)ethoxy]methyl}isothiazolidin-3-one 1,1-dioxide trifluoroacetate

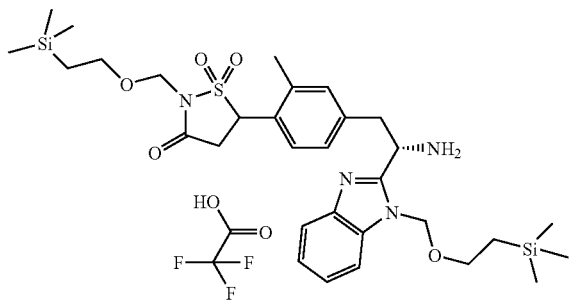

A solution of benzyl [(1S)-2-[4-(1,1-dioxido-3-oxo-2-[2-(trimethylsilyl)ethoxy]methylisothiazolidin-5-yl)-3-methylphenyl]-1-(1-[2-(trimethylsilyl)ethoxy]methyl-1H-benzimidazol-2-yl)ethyl]carbamate (50.0 mg, 64.2 μmol), methanol (3.50 mL) and 10% palladium on carbon (15 mg, 141 μmol) was degassed and placed under hydrogen balloon at 25° C. for 1.5 h. The reaction was diluted with methanol, filtered through celite, and concentrated in vacuo. The crude residue was purified by preparative LCMS to yield the desired product (41.4 mg, 83%). MF=$C_{33}H_{49}F_3N_4O_7SSi_2$; LCMS found for $C_{31}H_{49}N_4O_5SSi_2$ (M+H)$^+$: m/z=645.

Step 5. N-{(1S)-1-(1H-benzimidazol-2-yl)-2-[4-(1,1-dioxido-3-oxoisothiazolidin-5-yl)-3-methylphenyl]ethyl}benzenesulfonamide trifluoroacetate

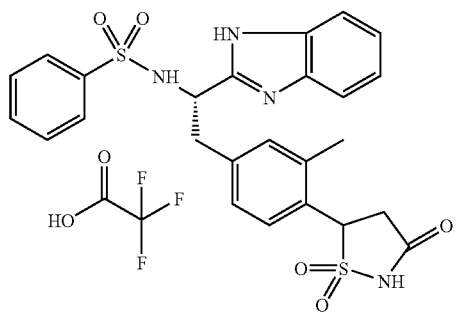

A solution of 5-4-[(2S)-2-amino-2-(1-[2-(trimethylsilyl)ethoxy]methyl-1H-benzimidazol-2-yl)ethyl]-2-methylphenyl-2-[2-(trimethylsilyl)ethoxy]methylisothiazolidin-3-one 1,1-dioxide (28.0 mg, 34.7 μmol), methylene chloride (1.7 mL), N,N-diisopropylethylamine (30.2 μL, 174 μmol), benzenesulfonyl chloride (8.86 μL, 69.5 μmol) was stirred at 25° C. for 5 h. The reaction was concentrated and treated with trifluoroacetic acid (1.3 mL). The reaction was heated at 130° C. for 2 min in the microwave. The reaction was concentrated and purified by preparative LCMS to yield the desired product (6.5 mg, 29%). $^1$H NMR (400 MHz, CD$_3$OD): δ 7.6 (m, 3H), 7.5 (m, 2H), 5.0–5.2 (m, 2H), 3.5–3.1 (m, 4H) 2.4 (dd, 3H); MF=$C_{27}H_{25}F_3N_4O_7S_2$; LCMS found for $C_{25}H_{25}N_4O_5S_2$ (M+H)$^+$: m/z=525.

Example 4.215

N-((1S)-1-(1H-benzimidazol-2-yl)-2-{4-[(5S)-1,1-dioxido-3-oxoisothiazolidin-5-yl]-3-methylphenyl}ethyl)benzenesulfonamide trifluoroacetate and N-((1S)-1-(1H-benzimidazol-2-yl)-2-{4-[(5R)-1,1-dioxido-3-oxoisothiazolidin-5-yl]-3-methylphenyl}ethyl)benzenesulfonamide trifluoroacetate

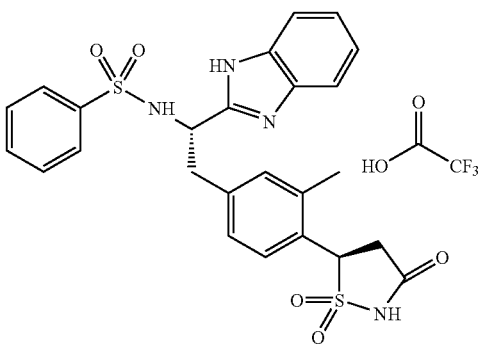

Step 1. Benzyl [(1S)-2-[4-((5R)-1,1-dioxido-3-oxo-2-{[2-(trimethylsilyl)ethoxy]methyl}isothiazolidin-5-yl)-3-methylphenyl]-1-(1-{[2-(trimethylsilyl)ethoxy]methyl}-1H-benzimidazol-2-yl)ethyl]carbamate benzyl [(1S)-2-[4-((5S)-1,1-dioxido-3-oxo-2-{[2-(trimethylsilyl)ethoxy]methyl}isothiazolidin-5-yl)-3-methylphenyl]-1-(1-{[2-(trimethylsilyl)ethoxy]methyl}-1H-benzimidazol-2-yl)ethyl]carbamate

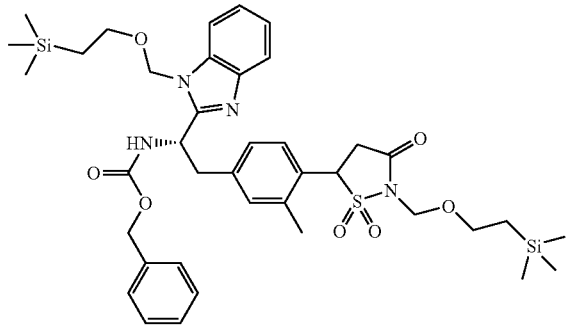

A solution of benzyl (1S)-1-(H-benzimidazol-2-yl)-2-[4-(1,1-dioxido-3-oxoisothiazolidin-5-yl)-3-methylphenyl]ethylcarbamate acetate (956 mg, 1.65 mmol) [beta-(trimethylsilyl)ethoxy]methyl chloride (731 μL, 4.13 mmol), N,N-diisopropylethylamine (1.73 mL, 9.91 mmol) and methylene chloride (30 mL) was stirred at 25° C. for 3 h. The reaction was diluted with 1 N HCl solution and extracted with ethyl acetate three times, dried with sodium sulfate, filtered, and concentrated in vacuo. The crude residue was purified by flash column chromatography to yield the desired product. The isomers were purified by chiral HPLC to separate the diastereomers. A separation method using Chiral Technologies Chiral Cel OD-H column and 30% EtOH/70% hexanes mobile phase at 10 mL/min. over 30 minutes was used. Peak 1 eluting at 9.24 min and peak two eluting at 18.74 min to afford Isomer 1 (390 mg, 30%), LCMS found for Isomer 1, $C_{39}H_{55}N_4O_7SSi_2$ (M+H)$^+$: m/z=779 and (360 mg, 28%) LCMS found for Isomer 2, $C_{39}H_{55}N_4O_7SSi_2$ (M+H)$^+$: m/z=779.

Step 2. N-((1S)-1-(1H-benzimidazol-2-yl)-2-{4-[(5R)-1,1-dioxido-3-oxoisothiazolidin-5-yl]-3-methylphenyl}ethyl)benzenesulfonamide trifluoroacetate and N-((1S)-1-(1H-benzimidazol-2-yl)-2-{4-[(5S)-1,1-dioxido-3-oxoisothiazolidin-5-yl]-3-methylphenyl}ethyl)benzenesulfonamide trifluoroacetate The title compounds were prepared according to the procedures of Example 4.21 using appropriate starting materials. LCMS for Isomer 1, which was more biologically active in the enzyme assay, $C_{25}H_{25}N_4O_5S_2$ (M+H)$^+$: m/z=525. LCMS for Isomer 2, $C_{25}H_{25}N_4O_5S_2$ (M+H)$^+$: m/z=525.

Example 4.216

5-4-[(2S)-2-(1H-Benzimidazol-2-yl)-2-(1,3-benzothiazol-2-ylamino)ethyl]-2-methylphenylisothiazolidin-3-one 1,1-dioxide trifluoroacetate

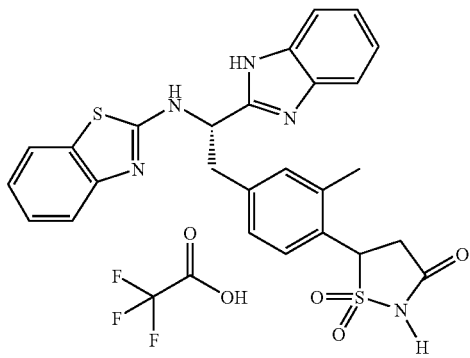

Step 1. N-[(1S)-2-[4-(1,1-dioxido-3-oxo-2-[2-(trimethylsilyl)ethoxy]methylisothiazolidin-5-yl)-3-methylphenyl]-1-(1-[2-(trimethylsilyl)ethoxy]methyl-1H-benzimidazol-2-yl)ethyl]-N'-phenylthiourea

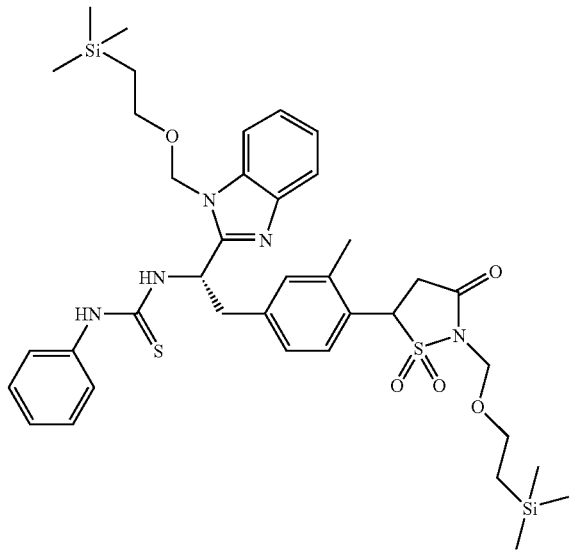

A solution of 5-4-[(2S)-2-amino-2-(1-[2-(trimethylsilyl)ethoxy]methyl-1H-benzimidazol-2-yl)ethyl]-2-methylphenyl-2-[2-(trimethylsilyl)ethoxy]methylisothiazolidin-3-one 1,1-dioxide (40.0 mg, 49.6 µmmol), methylene chloride (3 mL), triethylamine (41.5 µL, 298 µmol) was stirred at 25° C. After stirring for 5 min, the isothiocyanatobenzene (28.3 µL, 149 µmol) was added and the reaction stirred at 25° C. for additional 1.5 h. The reaction was diluted with 1.0 N hydrochloric acid and extracted with methylene chloride three times, dried with sodium sulfate, filtered, and concentrated in vacuo. The crude residue was purified by preparative LCMS to yield the desired product (28 mg, 72%). MF=$C_{38}H_{53}N_5O_5S_2Si_2$; LCMS found for $C_{38}H_{54}N_5O_5S_2Si_2$ (M+H)$^+$: m/z=780.

Step 2. 5-4-[(2S)-2-(1H-Benzimidazol-2-yl)-2-(1,3-benzothiazol-2-ylamino)ethyl]-2-methylphenylisothiazolidin-3-one 1,1-dioxide trifluoroacetate

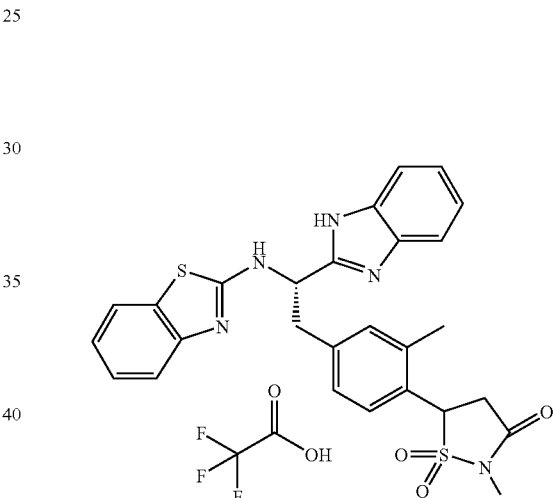

A solution of N-[(1S)-2-[4-(1,1-dioxido-3-oxo-2-[2-(trimethylsilyl)ethoxy]methylisothiazolidin-5-yl)-3-methylphenyl]-1-(1-[2-(trimethylsilyl)ethoxy]methyl-1H-benzimidazol-2-yl)ethyl]-n'-phenylthiourea (45 mg, 46.1 µmol), acetic acid (4.10 mL) and benzyltrimethylammonium tribromide (18.0 mg, 46.1 µmol) was stirred at 25° C. for 60 min. The reaction was concentrated and treated with trifluoroacetic acid (2 mL). The solution was heated at 130° C. for 2 min in the microwave. The reaction was concentrated in vacuo and purified by preparative LCMS to yield the desired product (13 mg, 45%). $^1$H NMR (400 MHz, CD$_3$OD): δ 7.7 (m, 2H), 7.6 (m, 3H), 7.4 (m, 1H), 7.3 (m, 1H), 7.2 (m, 2H), 7.1 (m, 2H), 5.7 (t, 1H), 5.4 (t, 1H), 3.6 (dd, 1H), 3.5 (dd, 1H), 3.3–3.2 (m, 2H), 2.4 (d, 3H); MF=$C_{28}H_{24}F_3N_5O_5S_2$; LCMS found for $C_{26}H_{24}N_5O_3S_2$ (M+H)$_+$: m/z=518.

Example 4.217

Benzyl {(1S)-1-(1H-benzimidazol-2-yl)-2-[4-(1,1-dioxido-3-oxoisothiazolidin-5-yl)-3-methylphenyl]ethyl}carbamate trifluoroacetate

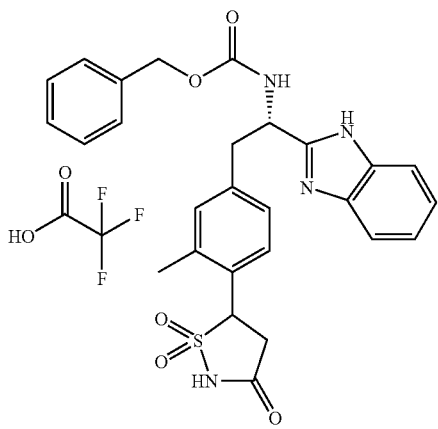

A solution of benzyl (1S)-2-[(2-aminophenyl)amino]-1-[4-(1,1-dioxido-3-oxoisothiazolidin-5-yl)-3-methylbenzyl]-2-oxoethylcarbamate (200 mg, 373 μmol) and acetic acid (20 mL) was stirred at 65° C. for 2 h. The reaction was diluted with water and extracted with ethyl acetate three times, dried with sodium sulfate, filtered, and concentrated in vacuo. The crude residue was purified by preparative LCMS to yield the desired product (173 mg, 72%). MF=$C_{29}H_{27}F_3N_4O_7S$; LCMS found for $C_{27}H_{27}N_4O_5S$ (M+H)$^+$: m/z=519.

Example 4.218

Ethyl {[({(1S)-1-(1H-benzimidazol-2-yl)-2-[4-(1,1-dioxido-3-oxoisothiazolidin-5-yl)phenyl]ethyl}amino)carbonyl]amino}acetate trifluoroacetate

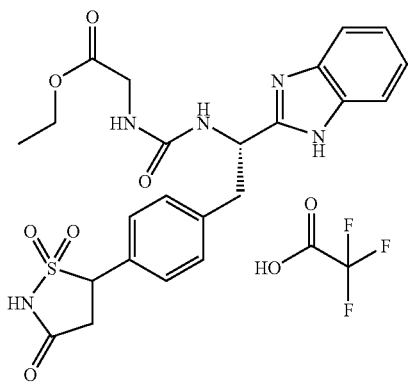

Step 1. Ethyl {[({(1S)-1-(1H-benzimidazol-2-yl)-2-[4-(2-tert-butyl-1,1-dioxido-3-oxoisothiazolidin-5-yl)phenyl]ethyl}amino)carbonyl]amino}acetate trifluoroacetate

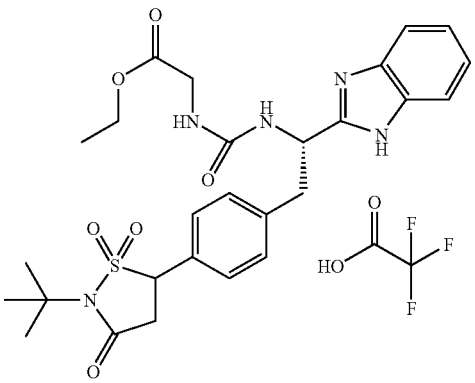

A solution of 5-4-[(2S)-2-amino-2-(1h-benzimidazol-2-yl)ethyl]phenyl-2-tert-butylisothiazolidin-3-one 1,1-dioxide (10 mg, 23.4 μmol), ethyl isocyanatoacetate (2.63 μL, 23.4 μmol), N,N-diisopropylethylamine (12.2 μL, 70.3 μmol), a few drops of N,N-dimethylformamide and methylene chloride (868 μL) was stirred at 25° C. for 20 h. The reaction was concentrated in vacuo and purified by preparative LCMS to yield the desired product (4.0 mg, 26%). MF=$C_{29}H_{34}F_3N_5O_8S$; LCMS found for $C_{27}H_{34}N_5O_6S$ (M−CF$_3$OH+H)$^+$: m/z=556.

Step 2. Ethyl {[({(1S)-1-(1H-benzimidazol-2-yl)-2-[4-(1,1-dioxido-3-oxoisothiazolidin-5-yl)phenyl]ethyl}amino)carbonyl]amino}acetate trifluoroacetate

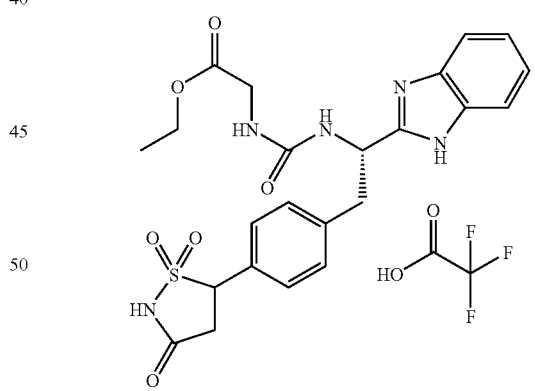

A solution of ethyl [((1S)-1-(1h-benzimidazol-2-yl)-2-[4-(2-tert-butyl-1,1-dioxido-3-oxoisothiazolidin-5-yl)phenyl]ethylamino)carbonyl]aminoacetate (4 mg, 7.20 μmol) and trifluoroacetic acid (1.50 mL) was heated at 120° C. for 5 min in the microwave. The reaction concentrated in vacuo and purified by preparative LCMS to yield the desired product (1.5 mg, 34%). $^1$H NMR (400 MHz, CD$_3$OD): δ 7.7 (m, 2H), 7.6 (m, 2H), 7.5 (m, 2H), 7.3 (m, 2H), 5.3 (m, 1H), 5.2 (m, 1H), 4.2 (m, 2H), 3.8 (m, 2H), 3.5–3.3 (m, 4H), 1.2 (t, 3H); MF=$C_{25}H_{26}F_3N_5O_8S$; LCMS found for $C_{23}H_{26}N_5O_6S$ (M+H)$^+$: m/z=500.

Example 4.219

N-[(1S)-2-[3-Bromo-4-(1,1-dioxido-3-oxoisothiazo-lidin-5-yl)phenyl]-1-(5-phenyl-1H-imidazol-2-yl)ethyl]benzenesulfonamide trifluoroacetate

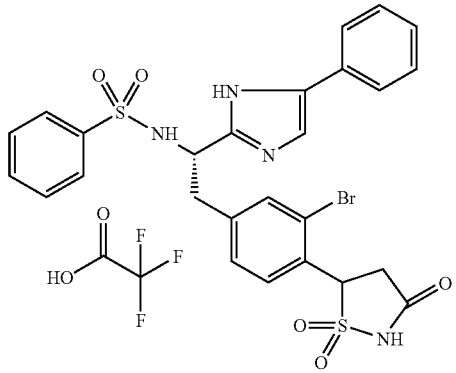

Step 1. tert-Butyl (1S)-1-(3-bromo-4-iodobenzyl)-2-oxo-2-[(2-oxo-2-phenylethyl)amino]ethylcarbamate

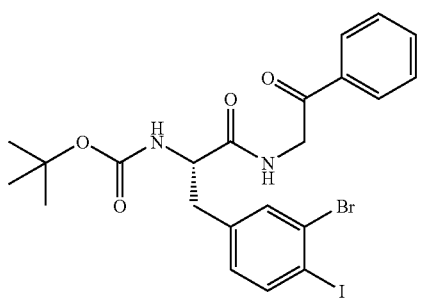

A solution of (2S)-3-(3-bromo-4-iodophenyl)-2-[(tert-butoxycarbonyl)amino]propanoic acid (4.10 g, 6.10 mmol), N,N-dimethylformamide (49 mL) and benzotriazol-1-yloxy-tris(dimethylamino)phosphonium hexafluorophosphate (4.24 g, 9.59 mmol) was stirred at 25° C. After stirring for 10 min, added 2-amino-1-phenylethanone hydrochloride (2.24 g, 13.1 mmol) and N,N-diisopropylethylamine (7.60 mL). The reaction was stirred at 25° C. for 2 h. The reaction was diluted with saturated sodium bicarbonate and extracted with ethyl acetate three times, dried with sodium sulfate, filtered, and concentrated in vacuo. The crude residue was purified by flash column chromatography to yield the desired product (1.2 g, 33%). MF=$C_{22}H_{24}BrIN_2O_4$; LCMS found for $C_{22}H_{25}BrIN_2O_4$ (M+H−Boc)$^+$: m/z=487.

Step 2. tert-Butyl [(1S)-2-(3-bromo-4-iodophenyl)-1-(5-phenyl-1H-imidazol-2-yl)ethyl]carbamate

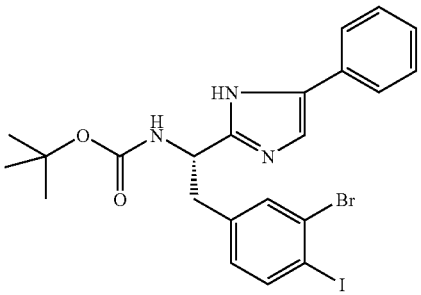

A solution of tert-butyl (1S)-1-(3-bromo-4-iodobenzyl)-2-oxo-2-[(2-oxo-2-phenylethyl)amino]ethylcarbamate (1.20 g, 1.63 mmol), ammonium acetate (6.30 g, 81.7 mmol) and N,N-dimethylformamide (15.1 mL) was microwave irradiated at 120° C. for 30 min. The reaction was diluted with water and extracted with ethyl acetate three times, dried with sodium sulfate, filtered, and concentrated in vacuo. The crude residue was purified by flash column chromatography to yield the desired product (440 mg, 38%).
MF=$C_{22}H_{23}BrIN_3O_2$; LCMS found for $C_{22}H_{24}BrIN_3O_2$ (M+H)$^+$: m/z=568.

Step 3. tert-Butyl [(1S)-2-(3-bromo-4-iodophenyl)-1-(5-phenyl-1-[2-(trimethylsilyl)ethoxy]methyl-1H-imidazol-2-yl)ethyl]carbamate

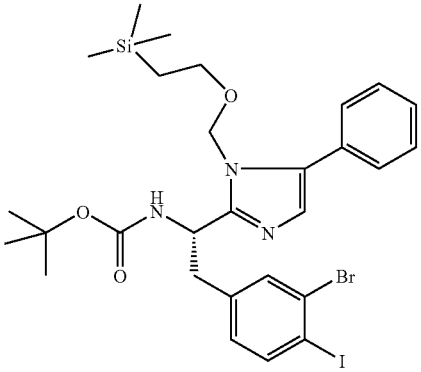

A solution of tert-butyl [(1S)-2-(3-bromo-4-iodophenyl)-1-(5-phenyl-1H-imidazol-2-yl)ethyl]carbamate (950 mg, 836 μmol), [β-(trimethylsilyl)ethoxy]methyl chloride (163 μL, 919 μmol), N,N-diisopropylethylamine (582 μL) and methylene chloride (8.91 mL) was stirred at 0° C. for 60 min and stirred at 25° C. for 2 h. The reaction was diluted with water and extracted with ethyl acetate three times, dried with sodium sulfate, filtered, and concentrated in vacuo. The crude residue was purified by flash column chromatography to yield the desired product (432 mg, 59%). MF=$C_{28}H_{37}BrIN_3O_3Si$; LCMS found for $C_{28}H_{38}BrIN_3O_3Si$ (M+H)$^+$: m/z=698.

Step 4. tert-Butyl [(1S)-2-[3-bromo-4-(2-tert-butyl-1,1-dioxido-3-oxo-2,3-dihydroisothiazol-5-yl)phenyl]-1-(5-phenyl-1-[2-(trimethylsilyl)ethoxy]methyl-1H-imidazol-2-yl)ethyl]carbamate

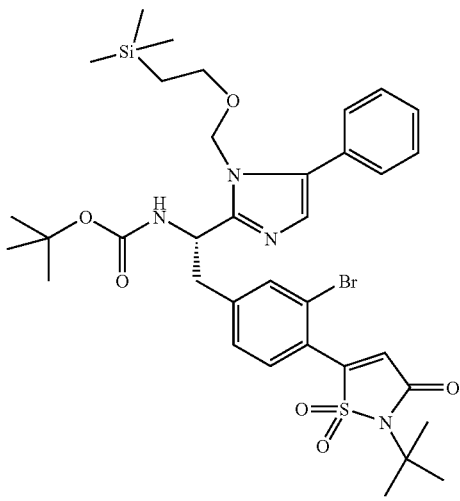

A solution of tert-butyl [(1S)-2-(3-bromo-4-iodophenyl)-1-(5-phenyl-1-[2-(trimethylsilyl)ethoxy]methyl-1H-imidazol-2-yl)ethyl]carbamate (130 mg, 112 µmol), 2-tert-butyl-isothiazol-3(2H)-one 1,1-dioxide (42.3 mg, 223 µmol), triethylamine (46.7 mL, 335 µmol), palladium acetate (25.1 mg, 112 µmol), N,N-dimethylformamide (3.0 mL) and tetra-N-butylammonium chloride (31.0 mg, 112 µmol) was degassed and stirred at 70° C. for 2 h. The reaction was diluted with water and extracted with ethyl acetate three times, dried with sodium sulfate, filtered, and concentrated in vacuo. The crude residue was purified by flash column chromatography to yield the desired product (20.0 mg, 24%). MF=$C_{35}H_{47}BrN_4O_6SSi$; LCMS found for $C_{35}H_{48}BrN_4O_6SSi$ (M+H)$^+$: m/z=759.

Step 5. tert-Butyl [(1S)-2-[3-bromo-4-(2-tert-butyl-1,1-dioxido-3-oxoisothiazolidin-5-yl)phenyl]-1-(5-phenyl-1-[2-(trimethylsilyl)ethoxy]methyl-1H-imidazol-2-yl)ethyl]carbamate

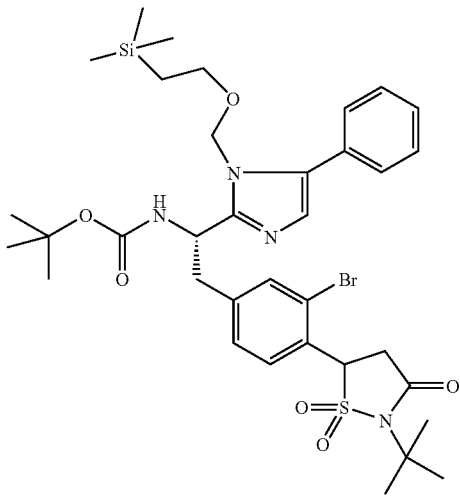

A solution of tert-butyl [(1S)-2-[3-bromo-4-(2-tert-butyl-1,1-dioxido-3-oxo-2,3-dihydroisothiazol-5-yl)phenyl]-1-(5-phenyl-1-[2-(trimethylsilyl)ethoxy]methyl-1H-imidazol-2-yl)ethyl]carbamate (70 mg, 92.1 µmol) and tetrahydrofuran (20 mL) was stirred at −78° C. After stirring for 5 min, 1.0 M L-selectride in tetrahydrofuran (92 µL) was added dropwise. The reaction was quenched with glacial acetic acid (0.7 mL). The reaction was diluted with water and extracted with ethyl acetate three times, dried with sodium sulfate, filtered, and concentrated in vacuo. The crude residue was purified by flash column chromatography to yield the desired product (65 mg, 83%). MF=$C_{35}H_{49}BrN_4O_6SSi$; LCMS found for $C_{35}H_{50}BrN_4O_6SSi$(M+H)$^+$: m/z=761.

Step 6. N-[(1S)-2-[3-bromo-4-(1,1-dioxido-3-oxoisothiazolidin-5-yl)phenyl]-1-(5phenyl-1H-imidazol-2-yl)ethyl]benzenesulfonamide trifluoroacetate

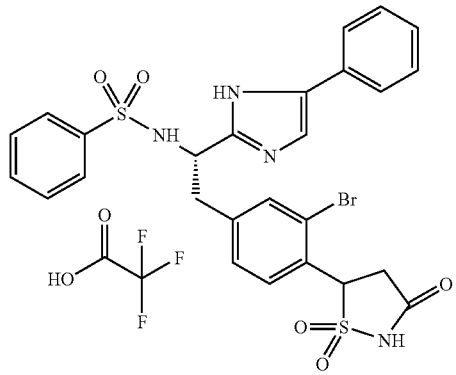

A solution of 5-4-[(2S)-2-amino-2-(5-phenyl-1-[2-(trimethylsilyl)ethoxy]methyl-1h-imidazol-2-yl)ethyl]-2-bromophenyl-2-tert-butylisothiazolidin-3-one 1,1-dioxide trifluoroacetate (30 mg, 38.7 µmol) in methylene chloride (2 mL) was added trifluoroacetic acid (2 mL). After stirring for 2 h, The solvent was removed in vacuo. The residue was dissolve in methylene chloride (2.0 mL), N,N-diisopropylethylamine (33.7 µL, 193 µmol) benzenesulfonyl chloride (9.87 µL, 77.3 µmol) and benzenesulfonyl chloride (9.87 µL, 77.3 µmol) were added and stirred at 25° C. for 3 h. The reaction was concentrated and treated with trifluoroacetic acid (2 mL, 26.0 mmol). The reaction was heated at 130° C. for 2 min in the microwave. The reaction was concentrated and purified by preparative LCMS to yield the desired product (5.0 mg, 20%). MF=$C_{28}H_{24}BrF_3N_4O_7S_2$; LCMS found for $C_{26}H_{24}BrN_4O_5S_2$(M+H)$^+$: m/z=615.

Example 4.220

N-[(1S)-2-[3-Bromo-4-(1,1-dioxido-3-oxoisothiazo-lidin-5-yl)phenyl]-1-(5-phenyl-1H-imidazol-2-yl)ethyl]-3-(trifluoromethyl)benzenesulfonamide trifluoroacetate

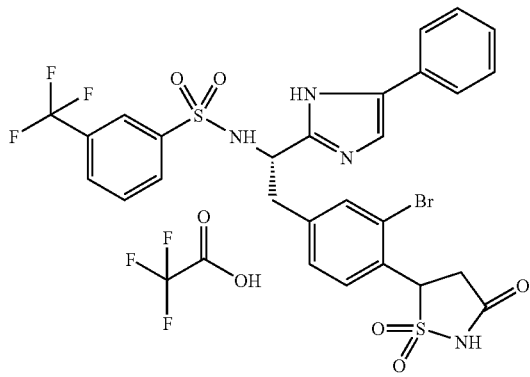

The title compound was prepared according to the procedures of Example 4.219 using appropriate starting. MF=$C_{29}H_{23}BrF_6N_4O_7S_2$; LCMS found for $C_{27}H_{23}BrF_3N_4O_5S_2(M+H)^+$: m/z=683.

Example 4.221

N-[(1S)-2-[3-Cyano-4-(1,1-dioxido-3-oxoisothiazo-lidin-5-yl)phenyl]-1-(5-phenyl-1H-imidazol-2-yl)ethyl]benzenesulfonamide trifluoroacetate

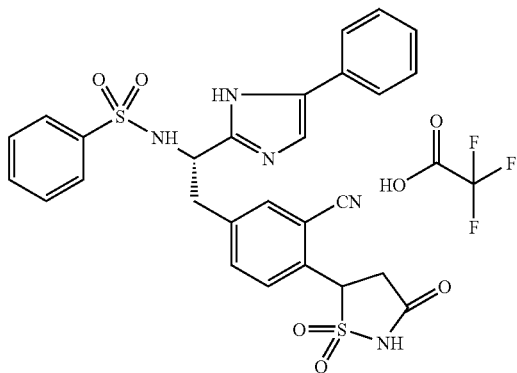

A solution of N-[(1S)-2-[3-bromo-4-(1,1-dioxido-3-oxoisothiazolidin-5-yl)phenyl]-1-(5-phenyl-1H-imidazol-2-yl)ethyl]benzenesulfonamide trifluoroacetate (3.5 mg, 4.8 µmol), zinc cyanide (1.7 mg, 14 µmol), tetrakis(triphenylphosphine)palladium(0) (1.11 mg, 960 nmol) and N,N-dimethylformamide (1.5 mL) was heated at 175° C. for 4 min in the microwave. The reaction filtered, concentrated in vacuo and purified by preparative LCMS to yield the desired product (2.0 mg, 60%). $^1$H NMR (400 MHz, $CD_3OD$): δ 7.8–7.3 (m, 13H), 5.3–5.0 (m, 2H), 3.5–3.4 (m, 2H), 3.3–3.2 (m, 2H); MF=$C_{29}H_{24}F_3N_5O_7S_2$; LCMS found for $C_{27}H_{24}N_5O_5S_2(M+H)^+$: m/z=562.

Example 4.222

N-[(1S)-2-[3-Cyano-4-(1,1-dioxido-3-oxoisothiazo-lidin-5-yl)phenyl]-1-(5-phenyl-1-imidazol-2-yl)ethyl]-3-(trifluoromethyl)benzenesulfonamide trifluoroacetate

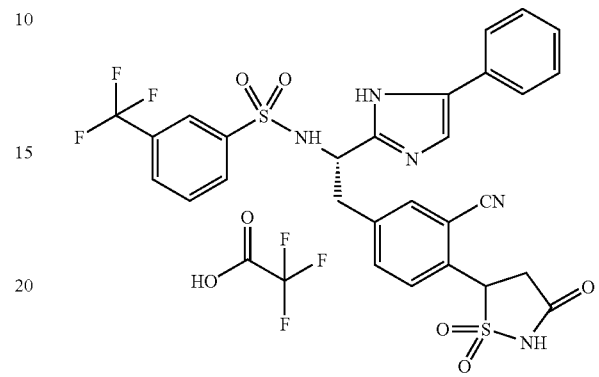

A solution of N-[(1S)-2-[3-bromo-4-(1,1-dioxido-3-oxoisothiazolidin-5-yl)phenyl]-1-(5-phenyl-1H-imidazol-2-yl)ethyl]-3-(trifluoromethyl)benzenesulfonamide (2.3 mg, 3.3 µmol, zinc cyanide (1.2 mg, 10 µmol), tetrakis(triphenylphosphine)palladium(0) (78 µg, 670 nmol) and N,N-dimethylformamide (1.4 mL) was heated at 175° C. for 4 min in the microwave. The reaction filtered, concentrated in vacuo and purified by preparative LCMS to yield the desired product (1.0 mg, 40%). MF=$C_{30}H_{23}F_6N_5O_7S_2$; LCMS found for $C_{28}H_{23}F_3N_5O_5S_2(M+H)^+$: m/z=630.

Example 4.223

5-(4-{(2S)-2-(1H-Benzimidazol-2-yl)-2-[(5-benzyl-1,3-thiazol-2-yl)amino]ethyl}phenyl)isothiazolidin-3-one 1,1-dioxide trifluoroacetate

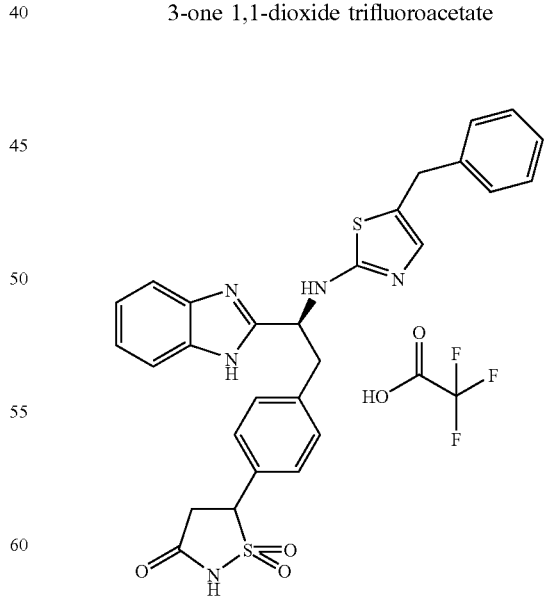

A solution of 5-4-[2-amino-2-(1H-benzimidazol-2-yl)ethyl]phenyl-2-tert-butylisothiazolidin-3-one 1,1-dioxide dihydrochloride (50 mg, 100 µmol), isothiocyanato(trimethyl)silane (14 µL, 100 µmol), tetrahydrofuran (2.5 mL), triethylamine (28 μL, 200 μmol) and methanol (8 mL) was stirred at 25° C. for 3 h. The reaction was concentrated in vacuo. The crude residue was treated with trifluoroacetic acid (1.8 mL) and heated at 130° C. for 2 min in the microwave. The reaction was concentrated and purified by preparative LCMS to yield the desired product (17.5 mg, 33%). $^1$H NMR (400 MHz, CD$_3$OD): δ 7.7–7.2 (m, 13H), 6.7 (s, 1H), 5.4 (m, 1H), 5.2 (m, 1H), 3.9 (s, 2H), 3.7 (m, 2H), 3.5 (m, 2H); MF=C$_{30}$H$_{26}$F$_3$N$_5$O$_5$S$_2$; LCMS found for C$_{28}$H$_{26}$N$_5$O$_3$S$_2$(M+H)$^+$: m/z=544.

Example 4.224

N-1-(1H-benzimidazol-2-yl)-2-[4-(1,1-dioxido-3-oxoisothiazolidin-5-yl)phenyl]ethyl-1-4-(4-fluorophenyl)-3,6-dihydropyridine-1(2H)-sulfonamide trifluoroacetate

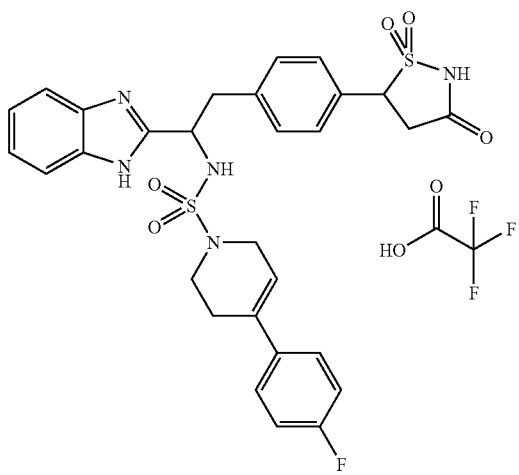

Step 1. 4-(4-Fluorophenyl)-1-[(2-methyl-1H-imidazol-1-yl)sulfonyl]-1,2,3,6-tetrahydropyridine

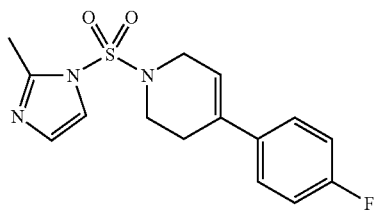

A solution of 4-(4-fluorophenyl)-1,2,3,6-tetrahydropyridine hydrochloride (150 mg, 700 μmol), 2,3-dimethyl-1-[(2-methyl-1H-imidazol-1-yl)sulfonyl]-1H-imidazol-3-ium trifluoromethanesulfonate (410 mg, 1.05 mmol), acetonitrile (5 mL) and triethylamine (98 μL, 700 μmol) was stirred at 25° C. for 24 h. The reaction was diluted with water and extracted with ethyl acetate three times, dried with sodium sulfate, filtered, and concentrated in vacuo. The crude residue was purified by preparative LCMS to yield the desired product (117 mg, 52%). MF=C$_{15}$H$_{16}$FN$_3$O$_2$S; LCMS found for C$_{15}$H$_{17}$FN$_3$O$_2$S(M+H)$^+$: m/z=322.

Step 2. 1-[4-(4-Fluorophenyl)-3,6-dihydropyridin-1(2H)-yl]sulfonyl-2,3-dimethyl-1H-imidazol-3-ium trifluoromethanesulfonate

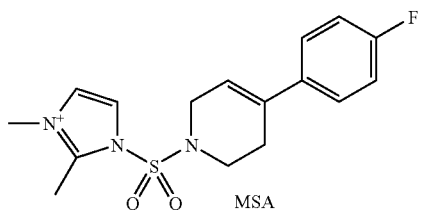

A solution of 4-(4-fluorophenyl)-1-[(2-methyl-1h-imidazol-1-yl)sulfonyl]-1,2,3,6-tetrahydropyridine (125 mg, 389 μmol), triethylamine (54 μL, 390 μmol) and methylene chloride (5.4 mL) was stirred at 0° C. and slowly added methyl trifluoromethanesulfonate (43 μL, 390 μmol). The reaction mixture was stirred at 0° C. for 1 h. The resulting precipitate was filtered to yield the desired product (80 mg, 42%). MF=C$_{17}$H$_{19}$F$_4$N$_3$O$_5$S$_2$; LCMS found for C$_{16}$H$_{20}$FN$_3$O$_2$S(M+H)$^+$: m/z=336.

Step 3. N-1-(1H-Benzimidazol-2-yl)-2-[4-(2-tert-butyl-1,1-dioxido-3-oxoisothiazolidin-5-yl)phenyl]ethyl-4-(4-fluorophenyl)-3,6-dihydropyridine-1(2H)-sulfonamide trifluoroacetate

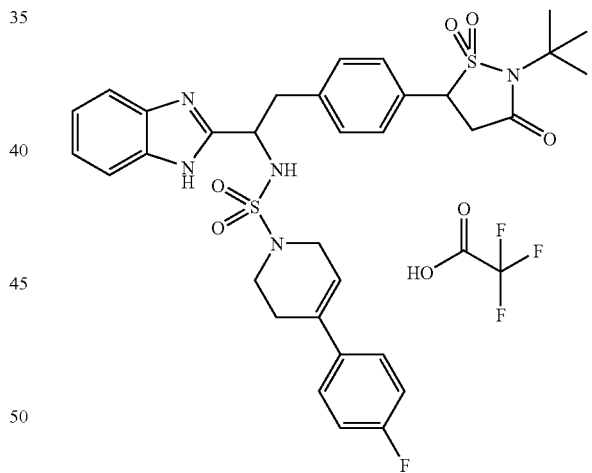

A solution of 5-4-[2-amino-2-(1H-benzimidazol-2-yl)ethyl]phenyl-2-tert-butylisothiazolidin-3-one 1,1-dioxide bis(trifluoroacetate) (61.4 mg, 93.8 μmol), 1-[4-(4-fluorophenyl)-3,6-dihydropyridin-1(2H)-yl]sulfonyl-2,3-dimethyl-1H-imidazol-3-ium trifluoromethanesulfonate (45.5 mg, 93.7 μmol), acetonitrile (5 mL) and triethylamine (92 μL, 660 μmol) was stirred at 35° C. for 18 h. The reaction was diluted with water and extracted with ethyl acetate three times, dried with sodium sulfate, filtered, and concentrated in vacuo. The crude residue was purified by preparative LCMS to yield the desired product (18 mg, 25%). MF=C$_{35}$H$_{37}$F$_4$N$_5$O$_7$S$_2$; LCMS found for C$_{33}$H$_{37}$F$_1$N$_5$O$_5$S$_2$ (M+H)$^+$: m/z=666.

387

Step 4. N-1-(1H-benzimidazol-2-yl)-2-[4-(1,1-di-oxido-3-oxoisothiazolidin-5-yl)phenyl]ethyl-4-(4-fluorophenyl)-3,6-dihydropyridine-1 (2H)-sulfonamide trifluoroacetate

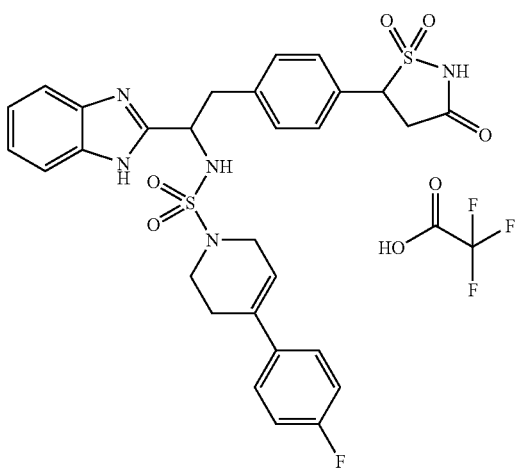

A solution of N-1-(1H-benzimidazol-2-yl)-2-[4-(2-tert-butyl-1,1-dioxido-3-oxoisothiazolidin-5-yl)phenyl]ethyl-4-(4-fluorophenyl)-3,6-dihydropyridine-1 (2H)-sulfonamide trifluoroacetate (23.4 mg, 30.0 μmol) and trifluoroacetic acid (2 mL) was heated at 120° C. for 5 min in the microwave. The reaction was concentrated in vacuo and purified by preparative LCMS to yield the desired product (14 mg, 64%). $^1$H NMR (400 MHz, CDCl$_3$): δ 7.7 (m 2H), 7.4 (m, 2H), 7.3–7.2 (m, 4H), 7.1 (m, 2H) 7.0–6.9 (t, 2H), 5.8 (m, 1H), 5.1 (m, 1H), 4.8 (m, 1H), 3.6 (m, 2H), 3.5–3.1 (m, 8H), 2.3 (s, 2H) ; MF=C$_{31}$H$_{29}$F$_4$N$_5$O$_7$S$_2$; LCMS found for C$_{29}$H$_{29}$F$_1$ $_{N5}$O$_5$S$_2$(M+H)$^+$: m/z=610.

Example 4.225 tert-Butyl (1S)-1-(1H-benzimidazol-2-yl)-2-[4-(1,1-dioxido-3-oxo-isothiazolidin-5-yl)-3-fluorophenyl]ethylcarbamate trifluoroacetate

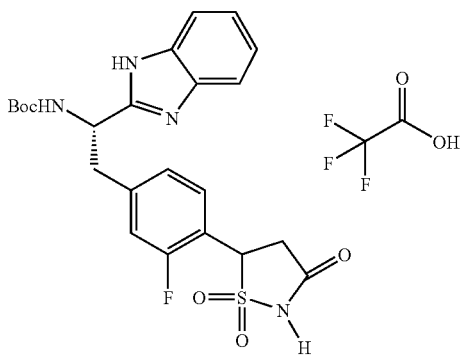

388

Step 1. 2-tert-Butyl-5-(2-fluoro-4-methylphenyl)isothiazol-3(2H)-one 1,1-dioxide

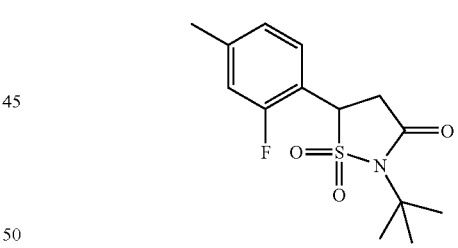

(2-Fluoro-4-methylphenyl)boronic acid (19.5 g, 0.127 mol), 2-tert-butyl-5-chloro-1,1-dioxo-1,2-dihydro-1λ$^6$-isothiazol-3-one (30.5 g, 0.136 mol) and [1,1'-bis(diphenylphosphino)ferrocene]dichloropalladium(II), complex with dichloromethane (1:1) (10.4 g, 12.7 mmol) were dissolved in toluene (500 mL) and treated with triethylamine (53.0 mL, 0.380 mol). The reaction was degassed and placed under an atmosphere of nitrogen. The reaction was then heated to 90° C. for 18 h. The reaction was diluted with ethyl acetate (500 mL) and washed with 1 N aqueous hydrochloric acid (500 mL). The ethyl acetate was dried over sodium sulfate, filtered and concentrated in vacuo. The crude material was filtered through celite and then silica gel. The crude material was then purified by silica gel chromatography (5–10% ethyl acetate:hexanes) to afford product as a white solid (24.5 g, 65%). $^1$H NMR (400 MHz, CDCl$_3$): δ 7.85 (t, J=7.8 Hz, 1H), 7.11–7.03 (m2H), 6.86 (d, J=1.8 Hz, 1H), 2.42 (s, 3H), 1.73 (s, 9H).

Step 2. 2-tert-Butyl-5-(2-fluoro-4-methylphenyl)isothiazolidin-3-one 1,1-dioxide 2-tert-Butyl-5-(2-fluoro-4-methylphenyl)isothiazol-3 (2H)-one 1,1-dioxide (4.5 g) in ethanol (120 mL) was treated with palladium (900 mg, 8.46 mmol) (10% palladium on carbon) and placed on a par hydrogenator under a 50 psi atmosphere of hydrogen for 24 h. The reaction was filtered though celite. After concentration, the crude material was purified by silica gel chromatography (3–10% ethyl acetate:hexanes) to afford product as a white solid (3.6 g, 79%). $^1$H NMR (400 MHz, CDCl$_3$): δ7.21–7.17 (m, 1H), 7.02–6.96 (m, 2H), 5.04 (dd, J=9.0, 7.0 Hz, 1H), 3.26 (dd, J=17.2, 9.0 Hz, 1H), 3.08 (dd, J=17.2, 7.0 Hz, 1H), 2.37 (s, 3H), 1.66 (s, 9H).-

Step 3. 2-tert-Butyl-5-[4-(dibromomethyl)-2-fluorophenyl]isothiazolidin-3-one 1,1-dioxide

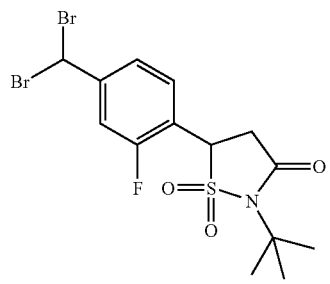

2-tert-Butyl-5-(2-fluoro-4-methylphenyl)isothiazolidin-3-one 1,1-dioxide (6.20 g, 20.7 mmol), N-bromosuccinimide (11.0 g, 62.1 mmol), and benzoyl peroxide (1.2 g, 5.2 mmol) in carbon tetrachloride (100 mL) were heated at reflux for 3.5 h. The solution was filtered to remove solid, washed with satd. aqueous sodium bicarbonate solution (200 mL), dried over sodium sulfate, and concentrated. Purification by silica gel chromatography (10–30% ethyl acetate:hexanes) afforded product as a white solid (5.8 g, 61%). $^1$H NMR (400 MHz, CDCl$_3$): δ 7.45–7.33 (m, 3H), 6.59 (s, 1H), 507 (dd, J=8.8, 7.2 Hz, 1H), 3.31 (dd, J=17.2, 8.8 Hz, 1H), 3.12 (dd, J=17.1, 7.2 Hz, 1H), 1.65 (s, 9H); LCMS found for $C_{14}H_{17}Br_2FNNaO_3S$ (M+Na)$^+$: m/z=480.

Step 4. 4-(2-tert-Butyl-1,1-dioxido-3-oxoisothiazolidin-5-yl)-3-fluorobenzaldehyde

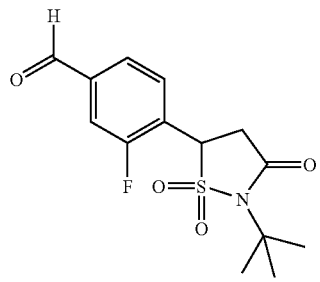

2-tert-Butyl-5-[4-(dibromomethyl)-2-fluorophenyl]isothiazolidin-3-one 1,1-dioxide (4.2 g, 9.2 mmol) and silver nitrate (3.12 g, 18.4 mmol) in ethanol (200 mL) and water (50 mL) were heated at reflux for 0.5 h. The solution was cooled to rt, filtered to remove precipitate, and concentrated to remove most of the ethanol. The residue was diluted with ethyl acetate (200 mL). The organic layer was washed with water (200 mL) and then dried over sodium sulfate. Concentration in vacuo followed by purification by silica gel chromatography (30% ethyl acetate:hexanes) afforded product as a white solid (2.4 g, 83%). $^1$H NMR (400 MHz, CDCl$_3$): δ 10.0 (d, J=2.0 Hz, 1H), 7.78–7.75 (m,1H), 7.70–7.65 (m, 1H), 7.56–7.52 (m, 1H), 5.13 (dd, J=8.9, 6.6 Hz, 1H), 3.35 (dd, J=17.2, 8.9 Hz, 1H), 3.15 (dd, J=17.2, 6.6 Hz, 1H), 1.66 (s, 9H). LCMS found for $C_{14}H_{17}FNNaO_4S$ (M+Na)$^+$: m/z=336.

Step 5. Methyl (2Z)-2-[(tert-butoxycarbonyl)amino]-3-[4-(2-tert-butyl-1,1-dioxido-3-oxoisothiazolidin-5-yl)-3-fluorophenyl]acrylate

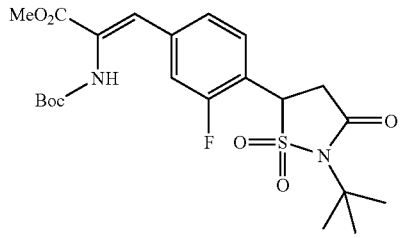

Methyl [(tert-butoxycarbonyl)amino](dimethoxyphosphoryl)acetate (3.53 g, 11.9 mmol) in methylene chloride (180 mL) was treated with 1,8-diazabicyclo[5.4.0]undec-7-ene (1.92 mL, 12.9 mmol). After five minutes 4-(2-tert-butyl-1,1-dioxido-3-oxoisothiazolidin-5-yl)-3-fluorobenzaldehyde (3.1 g, 9.9 mmol) was added and the solution stirred at rt for 1 h. The solution was diluted with methylene chloride (50 mL), washed with 1 N aqueous hydrochloric acid solution (250 mL), and the organic phase dried over sodium sulfate. Purification by silica gel chromatography (5–25% ethyl acetate:hexanes) afforded product as a white foam (3.7 g, 77%). $^1$H NMR (400 MHz, CDCl$_3$): δ 7.35–7.29 (m, 3H), 7.17 (s, 1H), 5.04 (dd, J=9.0, 7.1 Hz, 1H), 3.87 (s, 3H), 3.29 (dd, J=17.2, 9.0 Hz, 1H), 3.17 (dd, J=17.2, 7.0 Hz, 1H), 1.65 (s, 9H), 1.39 (s, 9H). LCMS found for $C_{22}H_{30}FN_2NaO_7S$ (M+Na)$^+$: m/z=507.

Step 6. Methyl (2S)-2-[(tert-butoxycarbonyl)amino]-3-[4-(2-tert-butyl-1,1-dioxido-3-oxoisothiazolidin-5-yl)-3-fluorophenyl]propanoate

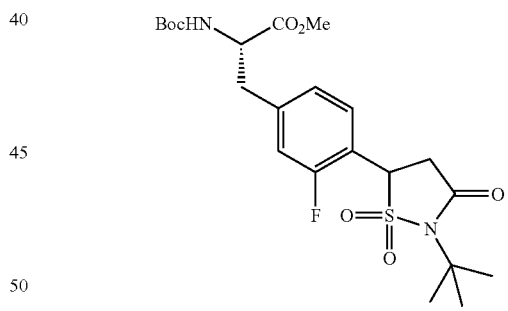

Methyl (2Z)-2-[(tert-butoxycarbonyl)amino]-3-[4-(2-tert-butyl-1,1-dioxido-3-oxoisothiazolidin-5-yl)-3-fluorophenyl]acrylate (1.24 g, 2.56 mmol) in ethanol (100 mL) was degassed and (R,R)-(−)-1,2-bis[(o-methoxyphenyl)(phenyl)phosphino]ethane(1,5-cyclooctadiene) rhodium (I) tetrafluroborate (58 mg, 0.077 mmol) was added under nitrogen. The solution was placed under a hydrogen atmosphere (50 psi) and shaken for 16 h. The solution was concentrated in vacuo and purified by silica gel chromatography (10–40% ethyl aceate:hexanes) to afford product as a white foam (1.14 g, 92%). $^1$H NMR (400 MHz, CDCl$_3$): δ 7.29–7.27 (m, 1H), 7.03–6.95 (m, 2H), 5.06–5.02 (m, 2H), 4.61–4.57 (brs, 1H), 3.73 (s, 3H), 3.31–3.27 (m, 1H), 3.15–3.06 (m, 3H), 1.66 (s, 9H), 1.42 (s, 9H). LCMS found for $C_{22}H_{32}FN_2NaO_7S$ (M+Na)$^+$: m/z=509.

391

Step 7. Methyl (2S)-2-amino-3-[4-(1,1-dioxido-3-oxoisothiazolidin-5-yl)-3-fluorophenyl]propanoate trifluoroacetate

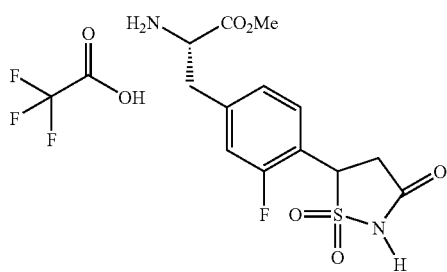

Methyl (2S)-2-[(tert-butoxycarbonyl)amino]-3-[4-(2-tert-butyl-1,1-dioxido-3-oxo-isothiazolidin-5-yl)-3-fluorophenyl]propanoate (1.10 g, 2.26 mmol) in trifluoroacetic acid (10.0 mL) was heated for 2 minutes at 130° C. in the microwave. The solution was concentrated in vacuo and purified by preparative LCMS to afford product as a white solid (614 mg, 61%). $^1$H NMR (400 MHz, CD$_3$OD): δ 7.53 (m, 1H), 7.18–7.14 (m, 2H), 5.33–5.30 (m, 1H), 4.39 (m, 1H), 3.82 (s, 3H), 3.43–3.12 (m, 4H). LCMS found for $C_{13}H_{16}FN_2O_5S$ (M+H)$^+$: m/z=331.

Step 8. (2S)-2-[(tert-Butoxycarbonyl)amino]-3-[4-(1,1-dioxido-3-oxoisothiazolidin-5-yl)-3-fluorophenyl]propanoic acid

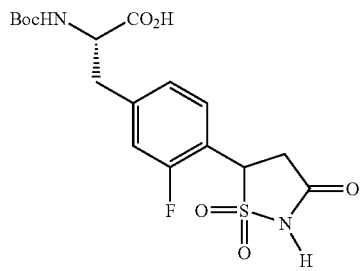

Methyl (2S)-2-amino-3-[4-(1,1-dioxido-3-oxoisothiazolidin-5-yl)-3-fluorophenyl]-propanoate trifluoroacetate (558 mg, 1.26 mmol) in methylene chloride (50 mL) was treated with di-tert-butyldicarbonate (548 mg, 2.51 mmol) and triethylamine (0.875 mL, 6.28 mmol). The solution stirred at rt for 2 h. The solution was concentrated in vacuo, diluted with methanol (8.0 mL), and then treated with 2 M lithium hydroxide in water (1.50 mL). After 2 h the solution was acidified using 1 N aqueous hydrochloric acid solution (2 mL), and the solution was directly purified by preparative LCMS to afford product as a white solid (507 mg, 97%). $^1$H NMR (400 MHz, CD$_3$OD): δ 7.47–7.42 (m, 1H), 7.18–7.11 (m, 2H), 5.39–5.35 (m, 1H), 4.39–4.35 (m, 1H), 3.35–3.28 (m, 2H), 3.25–3.20 (m, 1H), 2.97–2.91 (m, 1H), 1.35 (s, 9H). LCMS found for $C_{17}H_{22}FN_2NaO_7S$ (M+Na)$^+$: m/z=439.

392

Step 9. tert-Butyl (1S)-1-(1H-benzimidazol-2-yl)-2-[4-(1,1-dioxido-3-oxoisothiazolidin-3-yl)-3-fluorophenyl]ethylcarbamate trifluoroacetate (2S)-2-[(tert-Butoxycarbonyl)amino]-3-[4-(1,1-dioxido-3-oxoisothiazolidin-5-yl)-3-fluorophenyl]propanoic acid (402 mg, 0.965 mmol) in DMF (30.0 mL) was treated with benzotriazol-1-yloxytris(dimethylamino)phosphonium hexafluorophosphate (512 mg, 1.16 mmol). After 5 minutes at rt N,N-diisopropylethylamine (0.504 mL, 2.90 mmol) and 1,2-benzenediamine (156 mg, 1.45 mmol) were added and the solution stirred for 2 h. The solution was concentrated in vacuo and the residue dissolved in acetic acid (5 mL) and heated at 40° C. for 2 h. The acetic acid was removed in vacuo and the residue was purified by preparative LCMS to afford product as a white solid (373 mg, 64%). $^1$H NMR (400 MHz, CD$_3$OD): δ 7.75–7.71 (m, 2H), 7.59–7.56 (m, 2H), 7.47–7.43 (m, 1H), 7.15–7.09 (m, 2H), 5.43–5.39 (m, 2H), 3.44–3.21 (m, 4H), 1.42 (s, 9H). LCMS found for $C_{23}H_{26}FN_4O_5S$ (M+H)$^+$: m/z=489.

Example 4.226

N-(1S)-1-(1H-Benzimidazol-2-yl)-2-[4-(1,1-dioxido-3-oxoisothiazolidin-5-yl)-3fluorophenyl]ethyl-2,2-difluoropropanamide trifluoroacetate

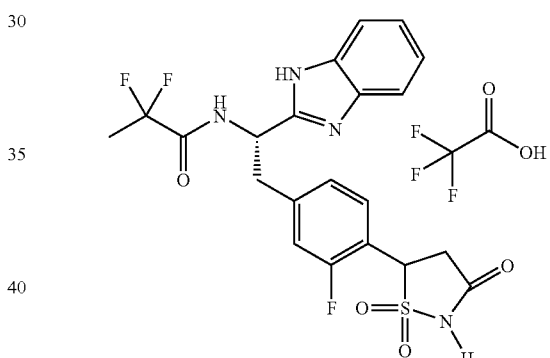

Step 1. 5-4-[(2S)-2-Amino-2-(1H-benzimidazol-2-yl)ethyl]-2-fluorophenylisothiazolidin-3-1,1-dioxide bis(trifluoroacetate)

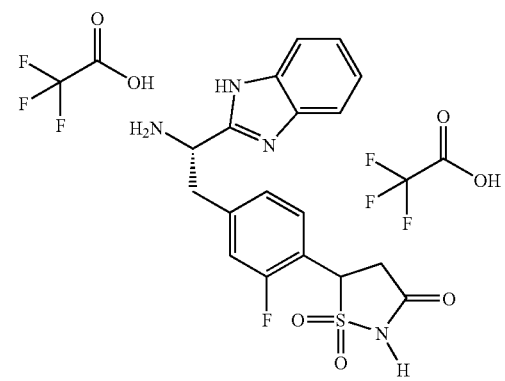

tert-Butyl (1S)-1-(1H-benzimidazol-2-yl)-2-[4-(1,1-dioxido-3-oxoisothiazolidin-5-yl)-3-fluorophenyl]ethylcarbamate trifluoroacetate (332 mg, 0.551 mmol) in methylene chloride (5.0 mL) was treated with trifluoroacetic acid (1.0 mL). The solution stirred at rt for 2 h. The solution was concentrated in vacuo to afford product as a slightly tan solid (337 mg, 99%). LCMS found for $C_{18}H_{18}FN_4O_5S$ (M+H)$^+$: m/z=389.

Step 2. N-(1S)-1-(1H-Benzimidazol-2-yl)-2-[4-(1,1-dioxido-3-oxoisothiazolidin-5-yl)-3-fluorophenyl]ethyl-2,2-difluoropropanamide trifluoroacetate 2,2-Difluoropropanoic acid (1.78 mg, 0.0162 mmol) in DMF (2.00 mL) was treated with benzotriazol-1-yloxytris(dimethylamino)phosphonium hexafluorophosphate (8.61 mg, 0.0195 mmol). After 5 minutes at rt the solution N,N-diisopropylethylamine (14.1 µL, 0.0811 mmol) and 5-4-[(2S)-2-amino-2-(1H-benzimidazol-2-yl)ethyl]-2-fluorophenylisothiazolidin-3-one 1,1-dioxide bis-(trifluoroacetate) (10.0 mg, 0.0162 mmol) were added and the solution was stirred at rt for 2 h. The reaction was purified by preparative LCMS to afford product as a white solid (7.1 mg, 74%). $^1$H NMR (400 MHz, CD$_3$OD: DMSO-d$_6$=5:1): δ 7.82–7.79 (m, 2H), 7.57–7.53 (m, 3H), 7.32–7.25 (m, 2H), 5.75 (m, 1H), 5.43 (m, 1H), 3.71–3.66 (m, 1H), 3.47–3.42 (m, 1H), 3.40–3.22 (m, 2H), 1.70 (t, J=19.5 Hz, 3H). LCMS found for $C_{21}H_{20}F_3N_4O_4S$ (M+H)$^+$: m/z=481.

Example 4.227

N-(1S)-1-(1H-Benzimidazol-2-yl)-2-[4-(1,1-dioxido-3-oxoisothiazolidin-5-yl)-3fluorophenyl]ethyl-3-fluorobenzenesulfonamide trifluoroacetate

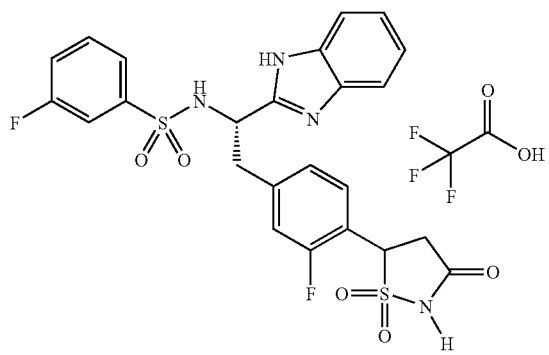

5-4-[(2S)-2-amino-2-(1H-benzimidazol-2-yl)ethyl]-2-fluorophenylisothiazolidin-3-one 1,1-dioxide bis(trifluoroacetate) (12 mg, 0.019 mmol) in methylene chloride (2.00 mL) was treated with triethylamine (16.3 µL, 0.117 mmol) and 3-fluorobenzenesulfonyl chloride (10.0 µL, 0.078 mmol). After 3 h at rt the solution was purified by preparative LCMS to afford product as a white solid (9.2 mg, 72%). $^1$H NMR (400 MHz, CD$_3$OD): δ 7.73–7.70 (m, 2H), 7.57–7.53 (m, 2H), 7.45–7.28 (m, 5H), 6.99–6.92 (m, 2H), 5.27–5.23 (m, 1H), 5.03–5.00 (m, 1H), 3.42–3.17 (m, 4H). LCMS found for $C_{24}H_{21}F_2N_4O_5S_2$ (M+H)$^+$: m/z=547.

Example 4.228

5-4-[(2S)-2-(1H-Benzimidazol-2-yl)-2-(1,3-benzothiazol-2-ylamino)ethyl]-2-fluorophenylisothiazolidin-3-one 1,1-dioxide bis(trifluoroacetate)

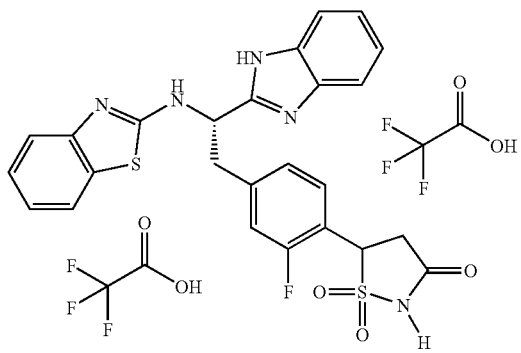

Step 1. N-(1S)-1-(1H-Benzimidazol-2-yl)-2-[4-(1,1-dioxido-3-oxoisothiazolidin-5-yl)-3-fluorophenyl]ethyl-N'-phenylthiourea trifluoroacetate

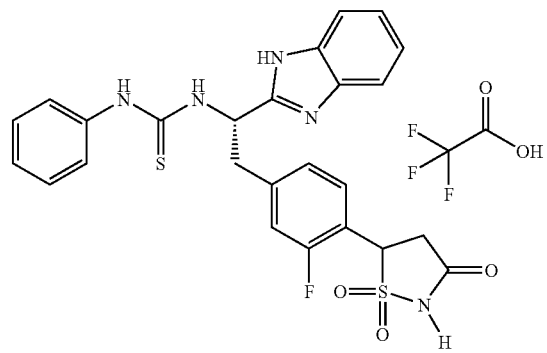

5-4-[(2S)-2-Amino-2-(1H-benzimidazol-2-yl)ethyl]-2-fluorophenylisothiazolidin-3-one 1,1-dioxide bis(trifluoroacetate) (15.0 mg, 0.0243 mmol) in methanol (2.0 mL) was treated with triethylamine (20.3 µL, 0.146 mmol) and isothiocyanatobenzene (13.9 µL, 0.0730 mmol). The solution was stirred 1 h at rt and then concentrated. Purification by preparative LCMS afforded product as a white solid (10.8 mg, 70%). $^1$H NMR (400 MHz, CD$_3$OD): δ 7.70–7.66 (m, 2H), 7.60–7.56 (m, 3H), 7.36–7.10 (m, 6H), 7.07–7.03 (m, 1H), 6.38–6.34 (m, 1H), 5.44–5.40 (m, 1H), 4.81–4.79 (m, 1H), 3.47–3.42 (m, 2H), 3.32–3.25 (m, 2H). LCMS found for $C_{25}H_{23}FN_5O_3S_2$ (M+H)$^+$: m/z=524.

Step 2. 5-4-[(2S)-2-(1H-Benzimidazol-2-yl)-2-(1,3-benzothiazol-2-ylamino)ethyl]-2-fluorophenylisothiazolidin-3-one 1,1-dioxide bis(trifluoroacetate)

N-(1S)-1-(1H-Benzimidazol-2-yl)-2-[4-(1,1-dioxido-3-oxoisothiazolidin-5-yl)-3-fluorophenyl]ethyl-N'-phenylthiourea trifluoroacetate (8.4 mg, 0.013 mmol) in acetic acid (2.0 mL) was treated with benzyltrimethylammonium tribromide (5.43 mg, 0.0139 mmol). The solution stirred at rt for 1.5 h. After concentration in vacuo the reaction mixture

Example 4.229

Methyl 2-[5-((2S)-2-[(tert-butoxycarbonyl)amino]-3-[4-(1,1-dioxido-3-oxoisothiazolidin-5-yl)-3-fluorophenyl]propanoylamino)pentyl]oxy-6-hydroxybenzoate

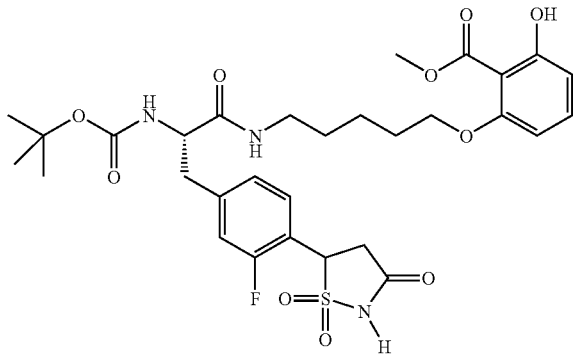

(2S)-2-[(tert-Butoxycarbonyl)amino]-3-[4-(1,1-dioxido-3-oxoisothiazolidin-5-yl)-3-fluorophenyl]propanoic acid (16.7 mg, 0.0400 mmol) in DMF (2.00 mL) was treated with benzotriazol-1-yloxytris(dimethylamino)phosphonium hexafluorophosphate (19.5 mg, 0.044 mmol). After five minutes N,N-diisopropylethylamine (20.9 µL, 0.120 mmol) and methyl 2-[(5-aminopentyl)oxy]-6-hydroxybenzoate hydrochloride (14.5 mg, 0.050 mmol) were added and the solution stirred at rt for 1 h. The product was directly purified by preparative LCMS to afford product as a white solid (17.8 mg, 68%). $^1$H NMR (400 MHz, CD$_3$OD): δ 7.45–7.42 (m, 1H), 7.24–7.21 (m, 1H), 7.16–7.10 (m, 2H), 6.50–6.45 (m, 2H), 5.37–5.34 (m, 1H), 4.27–4.24 (m, 1H), 3.97 (t, J=6.3 Hz, 2H), 3.87 (s, 3H), 3.42–3.05 (m, 7H), 2.99–2.94 (m, 1H), 1.79–1.75 (m, 2H), 1.47–1.40 (m, 4H), 1.36 (s, 9H). LCMS found for C$_{30}$H$_{39}$FN$_3$O$_{10}$S (M+H)$^+$: m/z=652.

Example 4.230

Methyl 2-[5-((2S)-2-[(2,2-difluoropropanoyl)amino]-3-[4-(1,1-dioxido-3-oxoisothiazolidin-5-yl)-3-fluorophenyl]propanoylamino)pentyl]oxy-6-hydroxybenzoate

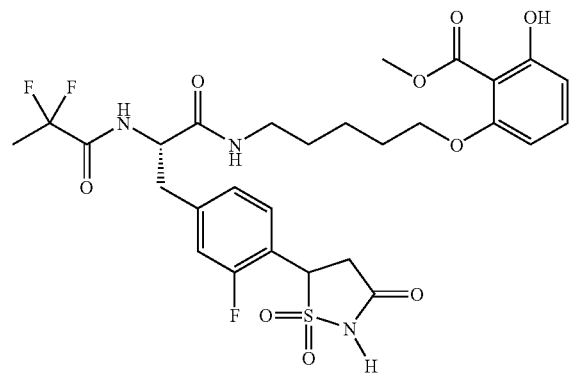

Step 1. Methyl 2-[5-((2S)-2-amino-3-[4-(1,1-dioxido-3-oxoisothiazolidin-5-yl)-3-fluorophenyl]propanoylamino)pentyl]oxy-6-hydroxybenzoate trifluoroacetate (salt)

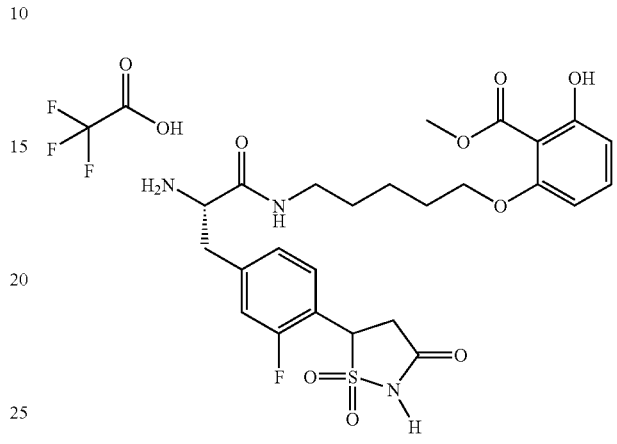

Methyl 2-[5-((2S)-2-[(tert-butoxycarbonyl)amino]-3-[4-(1,1-dioxido-3-oxoisothiazolidin-5-yl)-3-fluorophenyl]propanoylamino)pentyl]oxy-6-hydroxybenzoate (66.5 mg, 0.100 mmol) was dissolved in methylene chloride (5.0 mL) and treated with trifluoroacetic acid (1.0 mL). After 1 h of stirring at rt, the solution was concentrated in vacuo to afford a slightly tan oil (20.2 mg, 99%). The material was used in subsequent steps without purification. LCMS found for C$_{25}$H$_{31}$FN$_3$O$_8$S (M+H)$^+$: m/z=652.

Step 2. Methyl 2-[5-((2S)-2-[(2,2-difluoropropanoyl)amino]-3-[4-(1,1-dioxido-3-oxoisothiazolidin-5-yl)-3-fluorophenyl]propanoylamino)pentyl]oxy-6-hydroxybenzoate 2,2-Difluoropropanoic acid (2.31 mg, 0.0210 mmol) in DMF (1.00 mL) was treated with benzotriazol-1-yloxytris(dimethylamino)phosphonium hexafluorophosphate (9.97 mg, 0.0225 mmol). The solution was stirred at ambient temperature for 5 minutes. Methyl 2-[5-((2S)-2-amino-3-[4-(1,1-dioxido-3-oxoisothiazolidin-5-yl)-3-fluorophenyl]propanoylamino)pentyl]oxy-6-hydroxybenzoate trifluoroacetate (10.0 mg, 0.0150 mmol) in DMF (1.00 mL) was added followed by N,N-diisopropylethylamine (13.1 µL, 0.0751 mmol). The solution stirred at rt for 2 h. The product was directly purified by preparative LCMS to afford product as a white solid (7.1 mg, 73%). LCMS found for C$_{28}$H$_{33}$F$_3$N$_3$O$_9$S (M+H)$^+$: m/z=644.

--- was purified by preparative LCMS to afford product as a white solid (6.2 mg, 62%). $^1$H NMR (400 MHz, CD$_3$OD): δ 8.98 (brs, 1H), 7.71–7.67 (m, 3H), 7.55–7.17 (m, 7H), 7.05–7.02 (m, 1H), 5.64–5.62 (brs, 1H), 5.40–5.37 (m, 1H), 3.71–3.25 (m, 4H). LCMS found for C$_{25}$H$_{21}$FN$_5$O$_3$S$_2$ (M+H)$^+$: m/z=522.

Example 4.231

Methyl 2-[5-((2S)-2-[3-(2-chlorophenyl)propanoyl]amino-3-[4-(1,1-dioxido-3-oxoisothiazolidin-5-yl)-3-fluorophenyl]propanoylamino)pentyl]oxy-6-hydroxybenzoate

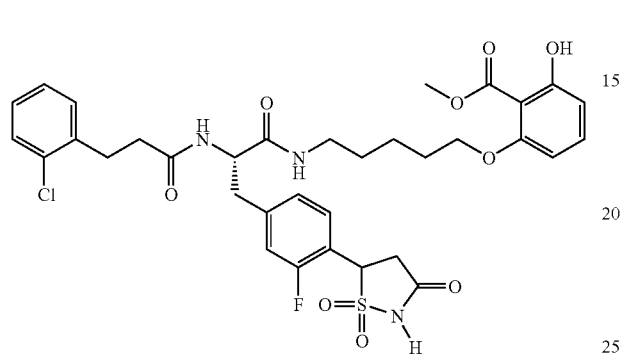

This compound was prepared according the procedure of Example 4.230 using the appropriate starting materials. LCMS found for $C_{34}H_{38}ClFN_3O_9S$ (M+H)$^+$: m/z=718.

Example 4.232

Methyl 2-[5-((2S)-3-[4-(1,1-dioxido-3-oxoisothiazolidin-5-yl)-3-fluorophenyl]-2-[(phenylsulfonyl)amino]propanoylamino)pentyl]oxy-6-hydroxybenzoate

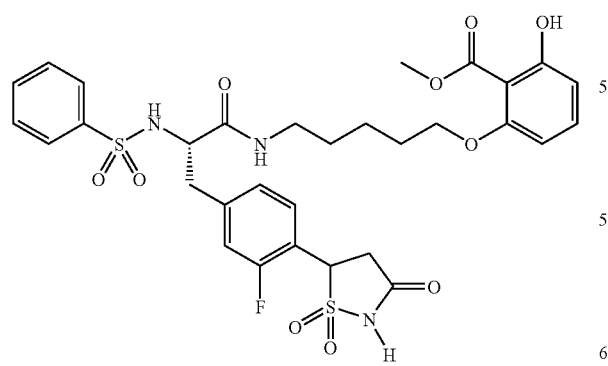

This compound was prepared according to the procedure of Example 4.227 using the appropriate starting materials. LCMS found for $C_{31}H_{35}FN_3O_{10}S_2$ (M+H)$^+$: m/z=692.

Example 4.233

3-Chloro-N-[(1S)-2-[3-chloro-4-(1,1-dioxido-3-oxoisothiazolidin-5-yl)phenyl]-1-(5-phenyl-1H-imidazol-2-yl)ethyl]-5-fluoro-2-methylbenzenesulfonamide trifluoroacetate

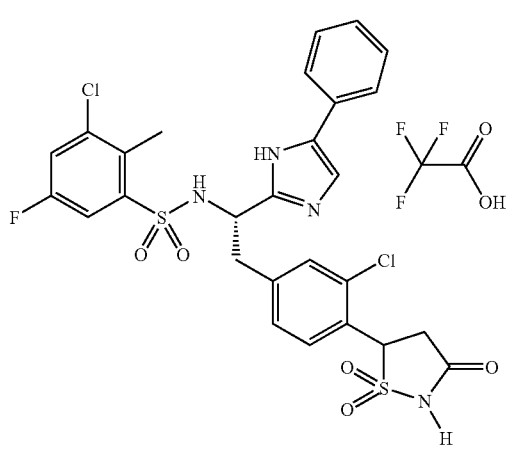

Step 1. tert-Butyl (1S)-1-(3-chloro-4-iodobenzyl)-2-oxo-2-[(2-oxo-2-phenylethyl)-amino]ethylcarbamate

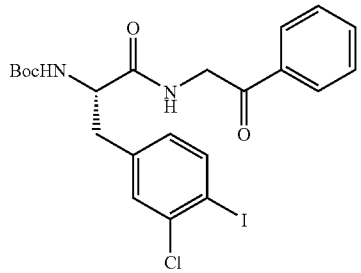

(2S)-2-[(tert-Butoxycarbonyl)amino]-3-(3-chloro-4-iodophenyl)propanoic acid (4.16 g, 9.77 mmol) in DMF (80 mL) was treated with benzotriazol-1-yloxytris(dimethylamino)phosphonium hexafluorophosphate (4.6 g, 10.0 mmol). After 10 minutes at rt the solution was treated with a solution of 2-amino-1-phenylethanone hydrochloride (2.52 g, 14.6 mmol) and N,N-diisopropylethylamine (8.5 mL, 49.0 mmol). The solution was stirred at rt for 2 h. The solution was diluted with ethyl acetate (250 mL) and washed with saturated aqueous sodium bicarbonate solution (200 mL). The organic phase was dried over sodium sulfate. Purification by silica gel chromatography (5–25% ethyl acetate:hexanes) afforded product as a white solid (3.1 g, 58%). LCMS found for $C_{22}H_{25}ClIN_2NaO_4$ (M+Na)$^+$: m/z=565.

Step 2. tert-Butyl [(1S)-2-(3-chloro-4-iodophenyl)-1-(5-phenyl-1H-imidazol-2-yl)ethyl]carbamate

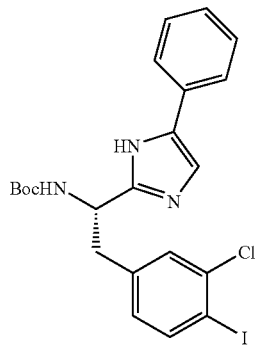

tert-Butyl (1S)-1-(3-chloro-4-iodobenzyl)-2-oxo-2-[(2-oxo-2-phenylethyl)-amino]ethylcarbamate (3.1 g, 5.7 mmol) and ammonium acetate (30.0 g, 0.389 mol) were dissolved in DMF (50 mL). The solution was separated into 6 batches, and each batch was heated in the microwave at 120° C. for 30 minutes. The solution was diluted with ethyl acetate (600 mL) and washed with water (600 mL). After the organic layer was dried over sodium sulfate, the solution was concentrated. Purification by silica gel chromatography (20–40% ethyl acetate:hexanes) afforded product as a white solid (2.0 g, 67%). $^1$H NMR (400 MHz, CD$_3$OD): δ 7.86–7.78 (m, 2H), 7.73–7.68 (m, 2H), 7.59–7.50 (m, 3H), 7.40–7.37 (m, 1H), 6.89–6.87 (m, 1H), 5.13–5.11 (m, 1H), 3.40–3.25 (m, 2H), 1.38 (s, 9H). LCMS found for C$_{22}$H$_{24}$ClIN$_3$O$_2$ (M+H)$^+$: m/z=524.

Step 3. tert-Butyl 2-[(1S)-1-[(tert-butoxycarbonyl)amino]-2-(3-chloro-4-iodophenyl)-ethyl]-5phenyl-1H-imidazole-1-carboxylate (1a)

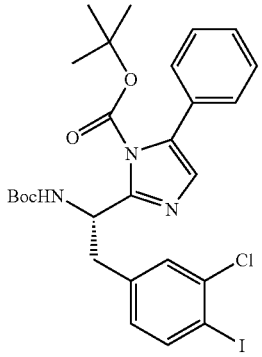

tert-Butyl [(1S)-2-(3-chloro-4-iodophenyl)-1-(5-phenyl-1H-imidazol-2-yl)ethyl]-carbamate (420 mg, 0.80 mmol) in tetrahydrofuran (100 mL) was treated with 1 N aqueous sodium hydroxide (20 mL). After five minutes di-tert-butyl-dicarbonate (1.05 g, 4.81 mmol) was added at rt. The solution stirred at 35° C. for 2 h. The solution was cooled to rt and then diluted with ethyl acetate (400 mL). The organic phase was separated and washed with aqueous hydrochloric acid (1.0 M, 200 mL), dried over sodium sulfate, and concentrated in vacuo. Purification by silica gel chromatography (5–10% ethyl acetate:hexanes). afforded product as a white foam (320 mg, 64%). LCMS found for C$_{27}$H$_{32}$ClIN$_3$O$_4$ (M+H)$^+$: m/z=624.

Step 4. tert-Butyl 2-(1S)-1-[(tert-butoxycarbonyl)amino]-2-[4-(2-tert-butyl-1,1-dioxido-3-oxo-2,3-dihydroisothiazol-5-yl)-3-chlorophenyl]ethyl-5-phenyl-1H-imidazole-1-carboxylate

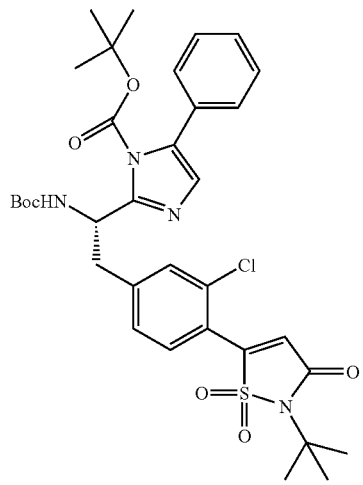

tert-Butyl 2-[(1S)-1-[(tert-butoxycarbonyl)amino]-2-(3-chloro-4-iodophenyl)-ethyl]-5-phenyl-1H-imidazole-1-carboxylate (200 mg, 0.321 mmol), dissolved in DMF (100 mL) was treated with 2-tert-butylisothiazol-3(2H)-one 1,1-dioxide (121 mg, 0.641 mmol), palladium acetate (110 mg, 0.48 mmol), and triethylamine (0.134 mL, 0.962 mmol). The solution was degassed and then stirred with heating at 70° C. under a nitrogen atmosphere for 2 h. The solution was diluted with water (100 mL) and ethyl acetate (100 mL). The organic phase was separated washed with water (100 mL) and 1 N aqueous hydrochloric acid. The organic phase was filtered through celite with ethyl acetate washing. The solution was dried over sodium sulfate, concentrated in vacuo. Purification by preparative LCMS afforded product as a white solid (62 mg, 28%). LCMS found for C$_{34}$H$_{42}$ClN$_4$O$_7$S (M+H)$^+$: m/z=685.

Step 5. tert-Butyl 2-(1S)-1-[(tert-butoxycarbonyl)amino]-2-[4-(2-tert-butyl-1,1-dioxido-3-oxoisothiazolidin-5-yl)-3-chlorophenyl]ethyl-5-phenyl-1H-imidazole-1-carboxylate

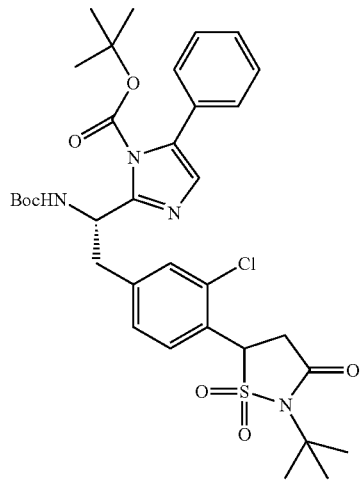

tert-Butyl 2-(1S)-1-[(tert-butoxycarbonyl)amino]-2-[4-(2-tert-butyl-1,1-dioxido-3-oxo-2,3-dihydroisothiazol-5-yl)-3-chlorophenyl]ethyl-5-phenyl-1H-imidazole-1-carboxylate (80.0 mg, 0.117 mmol) dissolved in tetrahydrofuran (30 mL) was cooled to −78° C. The solution was degassed and placed under a nitrogen atmosphere. 1 M L-Selectride in THF (0.12 mL) was added over 5 minutes. The solution was stirred for 0.5 h and then quenched with 0.5 mL of acetic acid. The solution was diluted with ethyl acetate (20 mL), washed with water (20 mL), and dried over sodium sulfate. Purification by preparative LCMS afforded product as a white solid (31.2 mg, 39%). LCMS found for $C_{29}H_{35}ClN_4O_5S$ (M+H-t-BuCO$_2$)$^+$: m/z=587.

Step 6. 5-4-[(2S)-2-Amino-2-(5-phenyl-1H-imidazol-2-yl)ethyl]-2-chlorophenyl-2-tert-butylisothiazolidin-3-one 1,1-dioxide bis(trifluoroacetate)

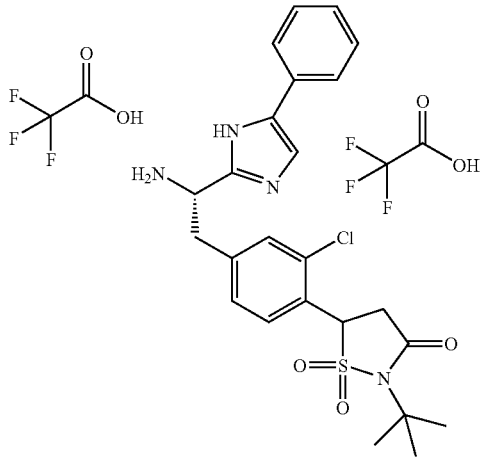

tert-Butyl 2-(1S)-1-[(tert-butoxycarbonyl)amino]-2-[4-(2-tert-butyl-1,1-dioxido-3-oxoisothiazolidin-5-yl)-3-chlorophenyl]ethyl-5-phenyl-1H-imidazole-1-carboxylate (29.9 mg, 0.0435 mmol) dissolved in methylene chloride (30 mL) was treated with trifluoroacetic acid (3 mL). After 2 h at rt, the solution was concentrated in vacuo to afford product as a colorless gel. The product was used without further purification in subsequent reactions. LCMS found for $C_{24}H_{28}ClN_4O_3S$ (M+H)$^+$: m/z=587.

Step 7. 3-Chloro-N-[(1S)-2-[3-chloro-4-(1,1-dioxido-3-oxoisothiazolidin-5-yl)phenyl]-1-(5-phenyl-1H-imidazol-2-yl)ethyl]-5-fluoro-2-methylbenzenesulfonamide trifluoroacetate 5-4-[(2S)-2-amino-2-(5-phenyl-1H-imidazol-2-yl)ethyl]-2-chlorophenyl-2-tert-butylisothiazolidin-3-one 1,1-dioxide bis(trifluoroacetate) (13.0 mg, 0.0182 mmol) in methylene chloride (1.25 mL) was treated with N,N-diisopropylethylamine (0.019 mL, 0.11 mmol) followed by 3-chloro-5-fluoro-2-methylbenzenesulfonyl chloride (10.0 mg, 0.0411 mmol). The solution was stirred at rt for 16 h. The solution was treated with 1 mL trifluoroacetic acid and then concentrated in vacuo. The residue was dissolved in 2.0 mL trifluoroacetic acid and heated in the microwave at 130° C. for two minutes. The solution was concentrated in vacuo and the residue purified by preparative LCMS to afford product as a white solid (6.1 mg, 45%). $^1$H NMR (400 MHz, CD$_3$OD): δ 7.75 (s, 1H), 7.62–7.21 (m, 10H), 5.58–5.53 (m, 1H), 5.00–4.96 (m, 1H), 3.55–3.40 (m, 2H), 3.35–3.23 (m, 2H), 2.25–2.21 (s, 3H). LCMS found for $C_{27}H_{24}Cl_2FN_4O_5S_2$ (M+H)$^+$: m/z=637.

Example 4.234

2,2,2-Trifluoro-N-{1-[5-(4-methoxy-phenyl)-1H-imidazol-2-yl]-2-[4-(1,1,3-trioxo-1λ$^6$-isothiazolidin-5-yl)-phenyl]-ethyl}-acetamide trifluoroacetate

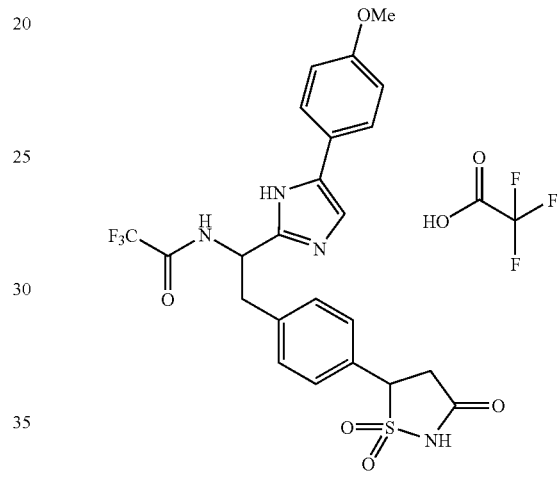

Step 1. (S)-2-Phenyl-1-carbamoyl-ethyl-carbamic acid tert-butyl ester

A solution of 9-B (24.8 g, 80.2 mmol) in 1,4-dioxane (388 mL) was treated with N,N-dimethylformamide (68 mL), pyridine (19.5 mL, 240 mmol), di-tert-butyldicarbonate (22.8 g, 104 mmol), and ammonium bicarbonate (12.7 g, 160 mmol). The reaction mixture was stirred at 25° C. for 60 h. The 1,4-dioxane was removed in vacuo and the reaction mixture was diluted with ethyl acetate (1.2 L) and washed with 0.1 N HCl (4×300 mL). The combined aqueous layers were re-extracted with ethyl acetate (2×200 mL). The combined organic extracts were washed with brine (2×150 mL), dried with Na$_2$SO$_4$, filtered, and concentrated to give the desired product (26 g, 99%) as an off-white solid. LCMS found for $C_{14}H_{21}BN_2O_5Na$ (M+Na)$^+$: m/z=331.

Step 2. {(S)-2-[4-(2-tert-Butyl-1,1,3-trioxo-2,3-dihydro-1H-1λ⁶-isothiazol-5-yl)-phenyl]1-carbamoyl-ethyl}-carbamic acid tert-butyl ester

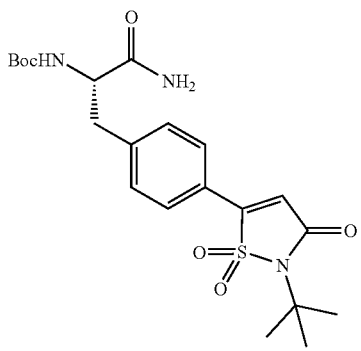

This compound was prepared according to the procedure of Example 1.1, Step 4, using (S)-2-phenyl-1-carbamoyl-ethyl-carbamic acid tert-butyl ester and 9-A as the starting materials. LCMS found for $C_{21}H_{29}N_3O_6SNa$ $(M+Na)^+$: m/z=474.

Step 3. {(S)-2-[4-(2-tert-Butyl-1,1,3-trioxo-1λ⁶-isothiazolidin-5-yl)-phenyl]-1-carbamoyl-ethyl}-carbamic acid tert-butyl ester

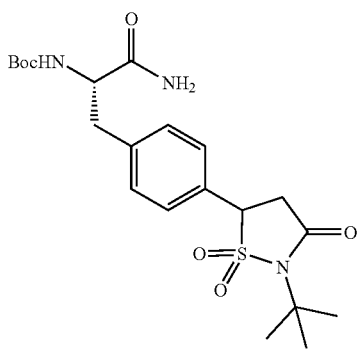

This compound was prepared according to the procedure of Example 4.115, Step 2, using {(S)-2-[4-(2-tert-butyl-1,1,3-trioxo-2,3-dihydro-1H-1λ⁶-isothiazol-5-yl)-phenyl]-1-carbamoyl-ethyl}-carbamic acid tert-butyl ester as the starting material. LCMS found for $C_{21}H_{31}N_3O_6SNa$ $(M+Na)^+$: m/z=476.

Step 4. (S)-2-Amino-3-[4-(2-tert-butyl-1,1,3-trioxo-1λ⁶-isothiazolidin-5-yl)-phenyl]-propionamide trifluoroacetate

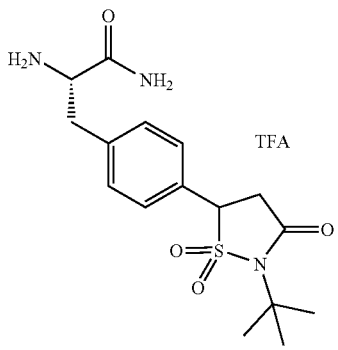

This compound was prepared according to the procedure of Example 1.9, Step 5, using {(S)-2-[4-(2-tert-butyl-1,1,3-trioxo-1λ⁶-isothiazolidin-5-yl)-phenyl]-1-carbamoyl-ethyl}-carbamic acid tert-butyl ester as the starting material. LCMS found for $C_{16}H_{24}N_3O_4S$ $(M+H)^+$: m/z=354.

Step 5. {(S)-2-[4-(2-tert-Butyl-1,1,3-trioxo-1λ⁶-isothiazolidin-5-yl)-phenyl]-1-carbamoyl-ethyl}-carbamic acid benzyl ester

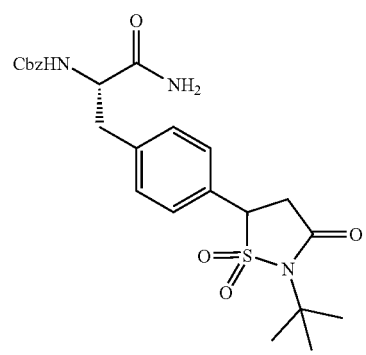

A solution of (S)-2-amino-3-[4-(2-tert-butyl-1,1,3-trioxo-1λ⁶-isothiazolidin-5-yl)-phenyl]-propionamide trifluoroacetate (600 mg, 1.5 mmol) and N,N-diisopropylethylamine (540 μL, 3.1 mmol) in tetrahydrofuran (7.6 mL) was cooled to 0° C. and treated with benzyl chloroformate (250 μL, 1.7 mmol). The reaction mixture was stirred for 2 h, diluted with water (20 mL), and extracted with ethyl acetate (60 mL). The organic layer was dried with $Na_2SO_4$, filtered, and concentrated to give a solid which was purified using flash column chromatography (10% methanol/dichloromethane) to yield the desired product (720 mg, 96%). LCMS found for $C_{24}H_{30}N_3O_6S$ $(M+H)^+$: m/z=488.

Step 6. {2-[4-(2-tert-Butyl-1,1,3-trioxo-1λ⁶-isothiazolidin-5-yl)-phenyl]-1-cyano-ethyl}-carbamic acid benzyl ester

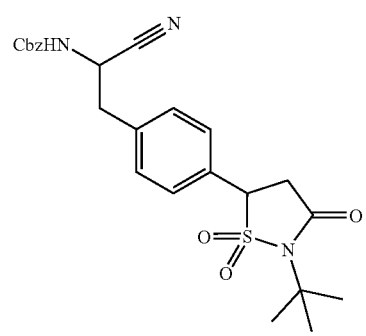

This compound was prepared according to the procedure of Example 1.37, Step 3, using {(S)-2-[4-(2-tert-butyl-1,1,3-trioxo-1λ⁶-isothiazolidin-5-yl)-phenyl]-1-carbamoyl-ethyl}-carbamic acid benzyl ester as the starting material and used in the next step without purification. LCMS found for $C_{24}H_{28}N_3O_5S$ $(M+H)^+$: m/z=470.

Step 7. 2-Benzyloxycarbonylamino-3-[4-(2-tert-butyl-1,1,3-trioxo-1λ⁶-isothiazolidin-5-yl)-phenyl]-propionimidic acid ethyl ester hydrochloride

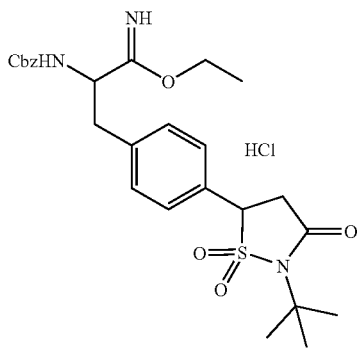

This compound was prepared according to the procedure of Example 1.37, Step 4, using {2-[4-(2-tert-butyl-1,1,3-trioxo-1λ⁶-isothiazolidin-5-yl)-phenyl]-1-cyano-ethyl}-carbamic acid benzyl ester as the starting material.

Step 8. {2-[4-(2-tert-Butyl-1,1,3-trioxo-1λ⁶-isothiazolidin-5-yl)-phenyl]-1-[5-(4-methoxy-phenyl)-1H-imadazol-2-yl]-ethyl}-carbamic acid benzyl ester trifluoroacetate

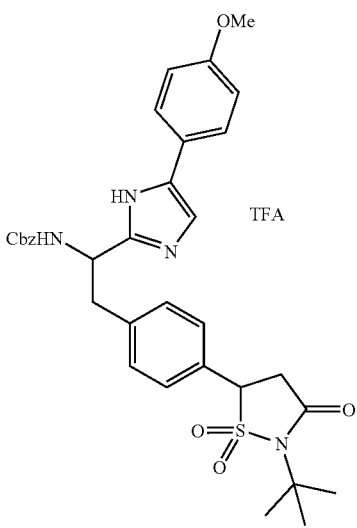

This compound was prepared according to the procedure of Example 4.22, Step 4, using 2-benzyloxycarbonylamino-3-[4-(2-tert-butyl-1,1,3-trioxo-1λ⁶-isothiazolidin-5-yl)-phenyl]-propionimidic acid ethyl ester hydrochloride and 2-amino-4'-methoxyacetophenone hydrochloride as the starting materials. LCMS found for $C_{33}H_{37}N_4O_6S$ (M+H)⁺: m/z=617.

Step 9. 5-(4-{2-Amino-2-[5-(4-methoxy-phenyl)-1H-imidazol-2-yl]-ethyl}-phenyl)-2-tert-butyl-1,1-dioxo-1λ⁶-isothiazolidin-3-one bistrifluoroacetate

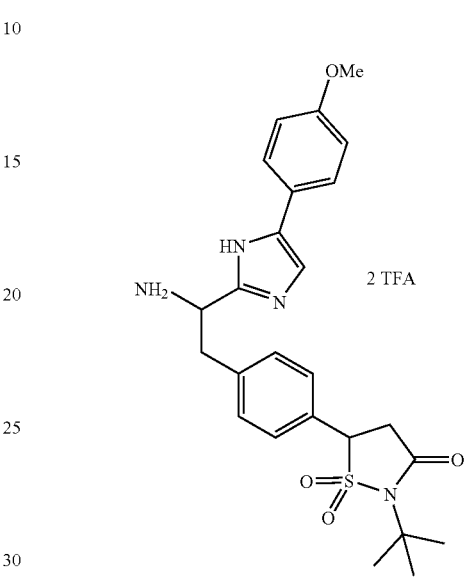

A solution of {2-[4-(2-tert-butyl-1,1,3-trioxo-1λ⁶-isothiazolidin-5-yl)-phenyl]-1-[5-(4-methoxy-phenyl)-1H-imidazol-2-yl]-ethyl}-carbamic acid benzyl ester trifluoroacetate (55 mg, 89 mmol) in acetonitrile (1.3 mL) was treated with iodotrimethylsilane (38 μL, 0.27 mmol) and stirred for 30 min. The reaction mixture was quenched with 1.0 M hydrogen chloride and concentrated to a residue which was purified by preparative LCMS to yield the desired product (25 mg, 58%). LCMS found for $C_{25}H_{31}N_4O_4S$ (M+H)⁺: m/z=483.

Step 10. 2,2,2-Trifluoro-N-{1-[5-(4-methoxy-phenyl)-1H-imidazol-2-yl]-2-[4-(1,1,3-trioxo-1λ⁶-isothiazolidin-5-yl)-phenyl]-ethyl}-acetamide trifluoroacetate A solution of 5-(4-{2-amino-2-[5-(4-methoxy-phenyl)-1H-imidazol-2-yl]-ethyl}-phenyl)-2-tert-butyl-1,1-dioxo-1λ⁶-isothiazolidin-3-one bistrifluoroacetate (25 mg, 52 mmol) in dichloromethane (2 mL) and N,N-dimethylformamide (1 mL) was treated with 1-hydroxy-7-azabenzotriazole (1.3 μL, 2.6 μmol, 2 M in N,N-dimethylformamide). N-(3-Dimethylaminopropyl)-N'-ethylcarbodiimide hydrochloride (20 mg, 0.1 mmol) was added and the reaction mixture was stirred at 25° C. for 16 h. The reaction mixture was concentrated and rediluted with trifluoroacetic acid (1.5 mL) and heated in a microwave at 130° C. for 1 min. The reaction mixture was concentrated and the crude residue was purified by preparative LCMS to yield the desired product (6.5 mg, 58%). LCMS found for $C_{23}H_{22}F_3N_4O_5S$ (M+H)⁺: m/z=523.

Example 4.235

2,2,2-Trifluoro-N-{1-[5-(4-hydroxy-phenyl)-1H-imidazol-2-yl]-2-[4-(1,1,3-trioxo-1$\lambda^6$-isothiazolidin-5-yl)-phenyl]-ethyl}-acetamide trifluoroacetate

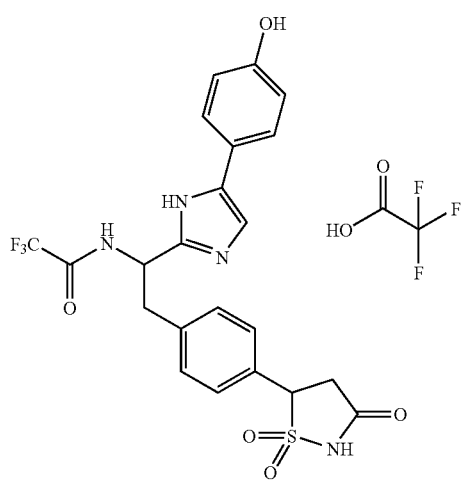

This compound was prepared according to the procedure of Example 4.234 using the appropriate reagents and starting materials. LCMS found for $C_{22}H_{20}F_3N_4O_5S$ (M+H)$^+$: m/z=509.

Example 4.236

2,2,2-Trifluoro-N-{1-[5-(2,5-dimethoxy-phenyl)-1H-imidazol-2-yl]-2-[4-(1,1,3-trioxo-1$\lambda^6$-isothiazolidin-5-yl)-phenyl]-ethyl}-acetamide trifluoroacetate

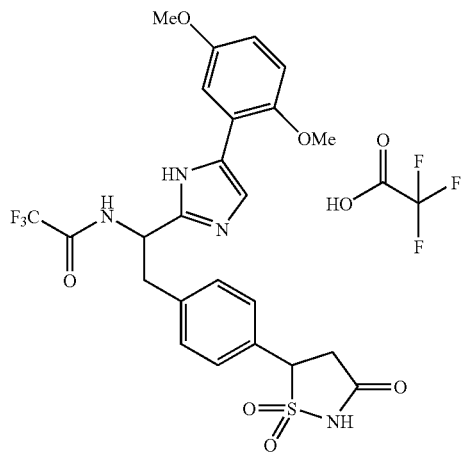

This compound was prepared according to the procedure of Example 4.234 using the appropriate reagents and starting materials. LCMS found for $C_{24}H_{24}F_3N_4O_6S$ (M+H)$^+$: m/z=553.

Example 4.237

2,2,2-Trifluoro-N-{1-[5-(3,4-dimethoxy-phenyl)-1H-imidazol-2-yl]-2-[4-(1,1,3-trioxo-1$\lambda^6$-isothiazolidin-5-yl)-phenyl]-ethyl}-acetamide trifluoroacetate

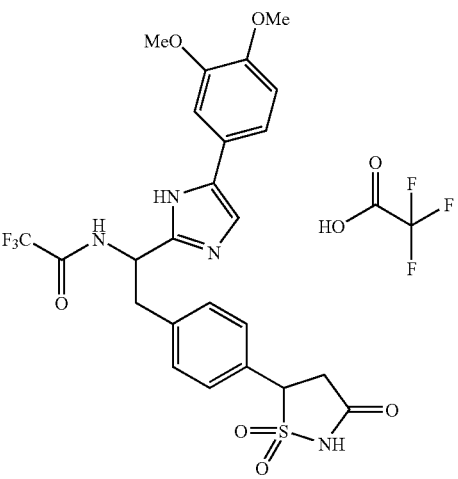

This compound was prepared according to the procedure of Example 4.234 using the appropriate reagents and starting materials. LCMS found for $C_{24}H_{24}F_3N_4O_6S$ (M+H)$^+$: m/z=553.

Example 4.238

2,2,2-Trifluoro-N-{1-[5-(3-methoxy-phenyl)-1H-imidazol-2-yl]-2-[4-(1,1,3-trioxo-1$\lambda^6$-isothiazolidin-5-yl)-phenyl]-ethyl}-acetamide trifluoroacetate

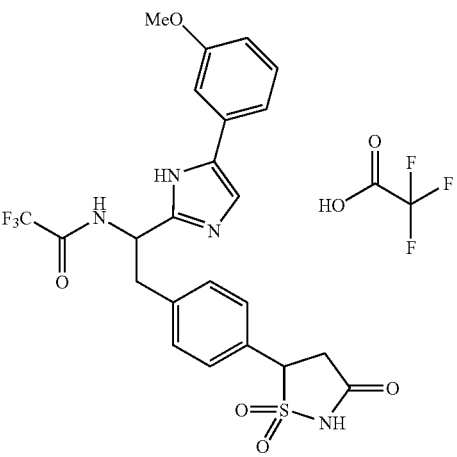

This compound was prepared according to the procedure of Example 4.234 using the appropriate reagents and starting materials. LCMS found for $C_{23}H_{22}F_3N_4O_5S$ (M+H)$^+$: m/z=523.

Example 4.239

N-{1-((4R,5R)-4,5-Diphenyl-4,5-dihydro-1H-imidazol-2-yl)-2-[4-(1,1,3-trioxo-1λ⁶-isothiazolidin-5-yl)phenyl]-ethyl}-3-trifluoromethyl-benzenesulfonamide trifluoroacetate

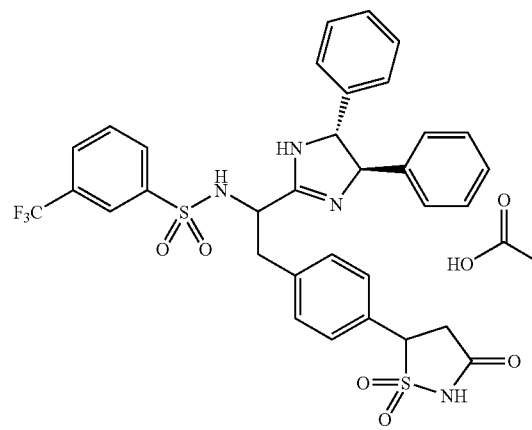

This compound was prepared according to the procedures of Example 1.37, Step 5, and of Example 4.22, Step 5, using the appropriate reagents and starting materials. LCMS found for $C_{33}H_{30}F_3N_4O_5S_2$ (M+H)⁺: m/z=683.

Example 4.240

N-{1-((4R,5S)-4,5-Diphenyl-4,5-dihydro-1H-imidazol-2-yl)-2-[4-(1,1,3-trioxo-1λ⁶-isothiazolidin-5-yl)-phenyl]-ethyl}-3-trifluoromethyl-benzenesulfonamide trifluoroacetate

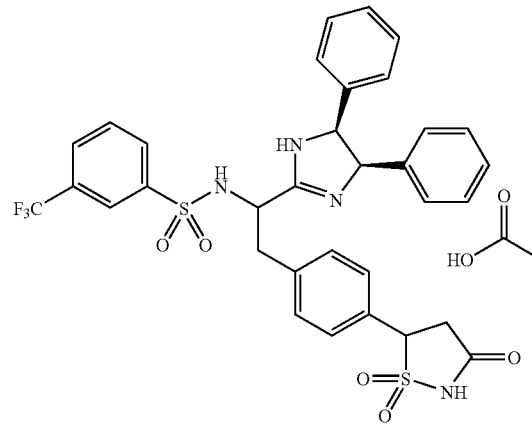

This compound was prepared according to the procedures of Example 1.37, Step 5, and of Example 4.22, Step 5, using the appropriate reagents and starting materials. LCMS found for $C_{33}H_{30}F_3N_4O_5S_2$ (M+H)⁺: m/z=683.

Example 4.241

N-{1-((4S,5S)-4,5-Diphenyl-4,5-dihydro-1H-imidazol-2-yl)-2-[4-(1,1,3-trioxo-1λ⁶-isothiazolidin-5-yl)-phenyl]-ethyl}-3-trifluoromethyl-benzenesulfonamide trifluoroacetate

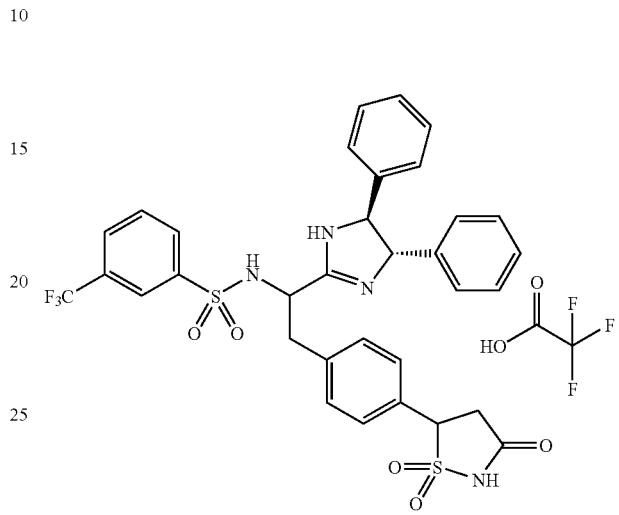

This compound was prepared according to the procedures of Example 1.37, Step 5, and of Example 4.22, Step 5, using the appropriate reagents and starting materials. LCMS found for $C_{33}H_{30}F_3N_4O_5S_2$ (M+H)⁺: m/z=683.

Example 4.242

N-{1-((S)-5-Methyl-4,5-dihydro-1H-imidazol-2-yl)-2-[4-(1,1,3-trioxo-1λ⁶-isothiazolidin-5-yl)-phenyl]-ethyl}-3-trifluoromethyl-benzenesulfonamide trifluoroacetate

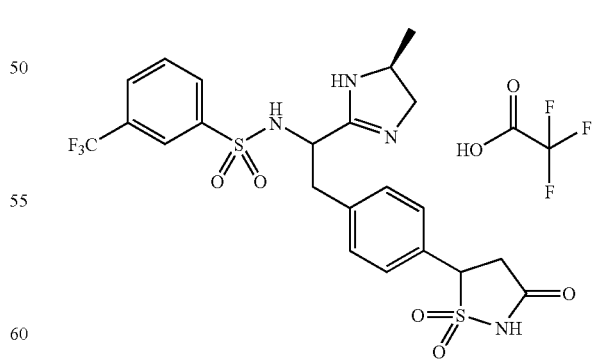

This compound was prepared according to the procedures of Example 1.37, Step 5, and of Example 4.22, Step 5, using the appropriate reagents and starting materials. LCMS found for $C_{22}H_{24}F_3N_4O_5S_2$ (M+H)⁺: m/z=545.

Example 4.243

N-{1-((R)-5-Methyl-4,5-dihydro-1H-imidazol-2-yl)-2-[4-(1,1,3-trioxo-1λ$^6$-isothiazolidin-5-yl)-phenyl]-ethyl}-3-trifluoromethyl-benzenesulfonamide trifluoroacetate

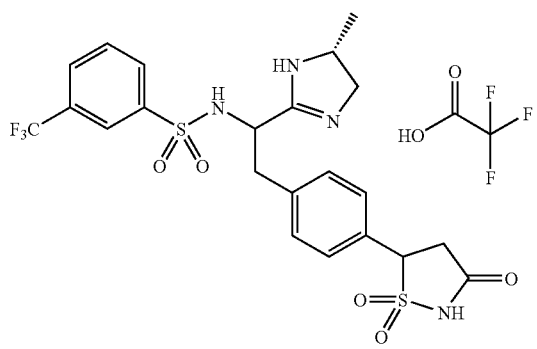

This compound was prepared according to the procedures of Example 1.37, Step 5, and of Example 4.22, Step 5, using the appropriate reagents and starting materials. LCMS found for $C_{22}H_{24}F_3N_4O_5S_2$ (M+H)$^+$: m/z=545.

Example 4.244

N-{(3aR,7aR)-1-3a,4,5,6,7,7a-Hexahydro-1H-benzoimidazol-2-yl-2-[4-(1,1,3-trioxo-1λ$^6$-isothiazolidin-5-yl)-phenyl]-ethyl}-3-trifluoromethyl-benzenesulfonamide trifluoroacetate

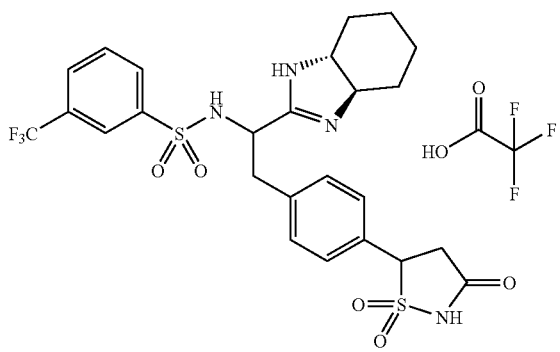

This compound was prepared according to the procedures of Example 1.37, Step 5, and of Example 4.22, Step 5, using the appropriate reagents and starting materials. LCMS found for $C_{25}H_{28}F_3N_4O_5S_2$ (M+H)$^+$: m/z=585.

Example 4.245

N-{(3aR,7aS)-1-3a,4,5,6,7,7a-Hexahydro-1H-benzoimidazol-2-yl-2-[4-(1,1,3-trioxo-1λ$^6$-isothiazolidin-5-yl)-phenyl]-ethyl}-3-trifluoromethyl-benzenesulfonamide trifluoroacetate

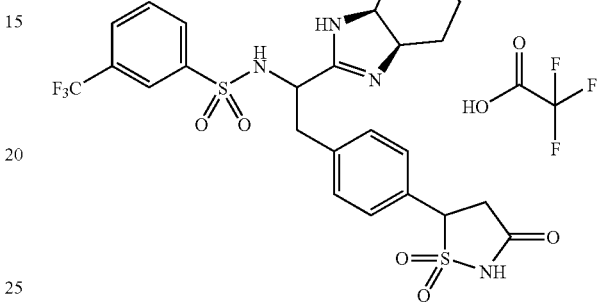

This compound was prepared according to the procedures of Example 1.37, Step 5, and of Example 4.22, Step 5, using the appropriate reagents and starting materials. LCMS found for $C_{25}H_{28}F_3N_4O_5S_2$ (M+H)$^+$: m/z=585.

Example 4.246

N-{1-(5,5-Dimethyl-4,5-dihydro-1H-imidazol-2-yl)-2-[4-(1,1,3-trioxo-1λ$^6$-isothiazolidin-5-yl)-phenyl]-ethyl}-3-trifluoromethyl-benzenesulfonamide trifluoroacetate

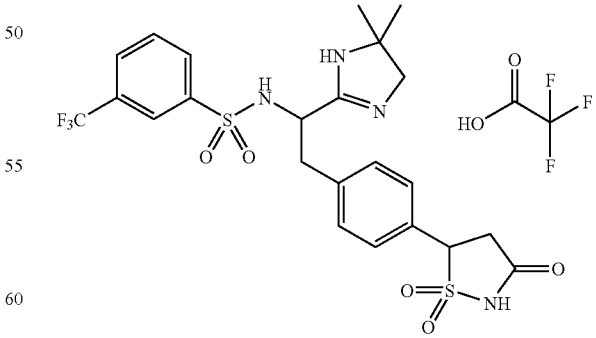

This compound was prepared according to the procedures of Example 1.37, Step 5, and of Example 4.22, Step 5, using the appropriate reagents and starting materials. LCMS found for $C_{23}H_{26}F_3N_4O_5S_2$ (M+H)$^+$: m/z=559.

Example 4.247

N-{1-((S)-5-Phenyl-4,5-dihydro-1H-imidazol-2-yl)-2-[4-(1,1,3-trioxo-1λ⁶-isothiazolidin-5-yl)-phenyl]-ethyl}-3-trifluoromethyl-benzenesulfonamide trifluoroacetate

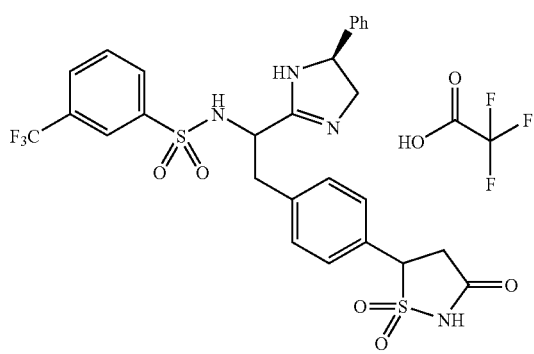

This compound was prepared according to the procedures of Example 1.37, Step 5, and of Example 4.22, Step 5, using the appropriate reagents and starting materials. LCMS found for $C_{27}H_{26}F_3N_4O_5S_2$ (M+H)⁺: m/z=607.

Example 4.248

N-{1-((R)-5-Phenyl-4,5-dihydro-1H-imidazol-2-yl)-2-[4-(1,1,3-trioxo-1λ⁶-isothiazolidin-5-yl)-phenyl]-ethyl}-3-trifluoromethyl-benzenesulfonamide trifluoroacetate

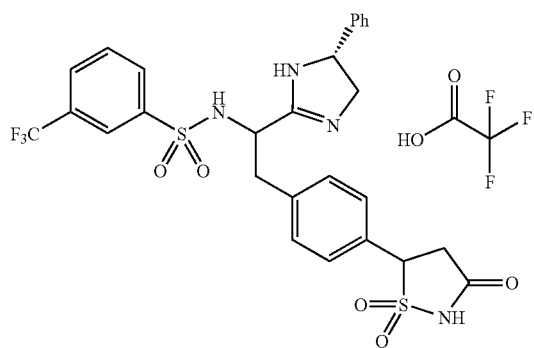

This compound was prepared according to the procedures of Example 1.37, Step 5, and of Example 4.22, Step 5, using the appropriate reagents and starting materials. LCMS found for $C_{27}H_{26}F_3N_4O_5S_2$ (M+H)⁺: m/z=607.

Example 4.249

3-Trifluoromethyl-N-{1-[(R)-5-(2-trifluoromethyl-benzyl)-4,5-dihydro-1H-imidazol-2-yl]-2-[4-(1,1,3-trioxo-1λ⁶-isothiazolidin-5-yl)-phenyl]-ethyl}-benzenesulfonamide trifluoroacetate

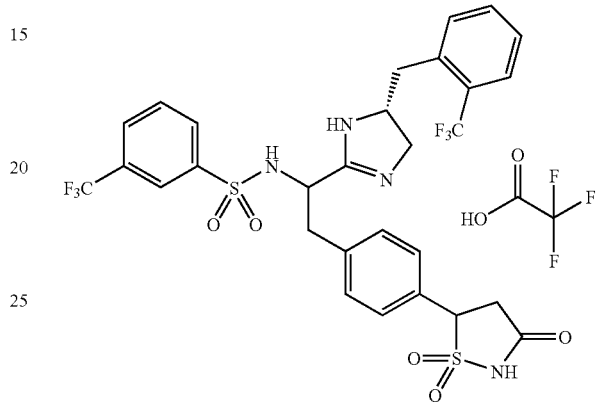

A solution of 4.359 (11 mg, 13 μmol) and 10% palladium on charcoal (10 mg) in methanol (3 mL) was hydrogenated at atmospheric pressure for 4 h. The reaction mixture was filtered and concentrated to yield the desired product (9 mg, 90%). LCMS found for $C_{29}H_{27}F_6N_4O_5S_2$ (M+H)⁺: m/z=689.

Example 4.250

3-Fluoro-N-{1-((R)-5-phenethyl-4,5-dihydro-1H-imidazol-2-yl)-2-[4-(1,1,3-trioxo-1λ⁶-isothiazolidin-5-yl)-phenyl]-ethyl}-benzenesulfonamide trifluoroacetate

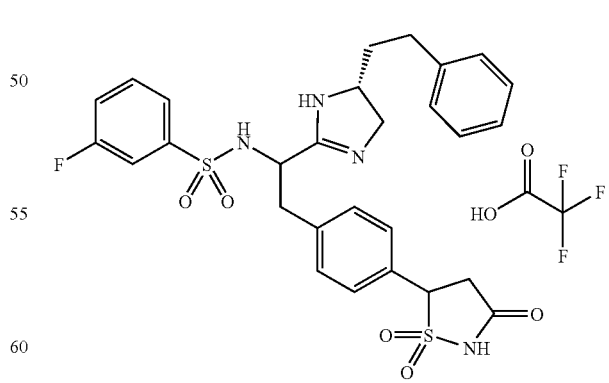

This compound was prepared according to the procedures of Example 1.37, Step 5, and of Example 4.22, Step 5, using the appropriate reagents and starting materials. LCMS found for $C_{28}H_{30}FN_4O_5S_2$ (M+H)⁺: m/z=585.

Example 4.251

2-Benzenesulfonylamino-3-[4-(1,1,3-trioxo-1λ$^6$-isothiazolidin-5-yl)-phenyl]-propionamide

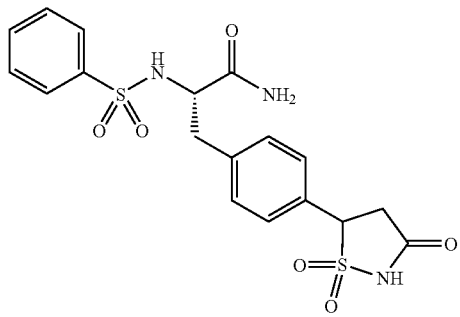

This compound was prepared according to the procedures of Example 1.37, Step 2, and of Example 4.22, Step 5, using the appropriate reagents and starting materials. LCMS found for $C_{18}H_{20}N_3O_6S_2$ (M+H)$^+$: m/z=438.

Example 4.252

N-{1-(5-Benzyl-1H-imidazol-2-yl)-2-[4-(1,1,3-trioxo-1λ$^6$-isothiazolidin-5-yl)-phenyl]-ethyl}-3-trifluoromethyl-benzenesulfonamide trifluoroacetate

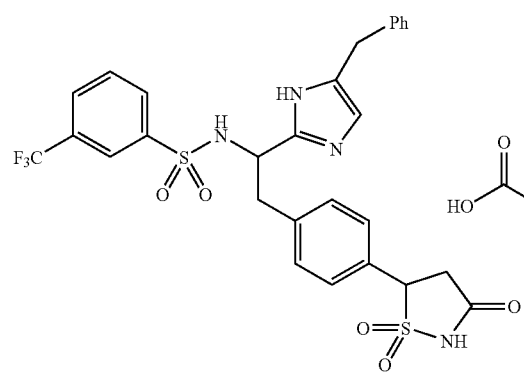

This compound was prepared according to the procedure of Example 4.22 using the appropriate reagents and starting materials. LCMS found for $C_{28}H_{26}F_3N_4O_5S_2$ (M+H)$^+$: m/z=619.

Example 4.253

4-Bromo-N-{1-(5-naphthalen-2-yl-1H-imidazol-2-yl)-2-[4-(1,1,3-trioxo-1λ$^6$-isothiazolidin-5-yl)-phenyl]-ethyl}-3-trifluoromethyl-benzenesulfonamide trifluoroacetate

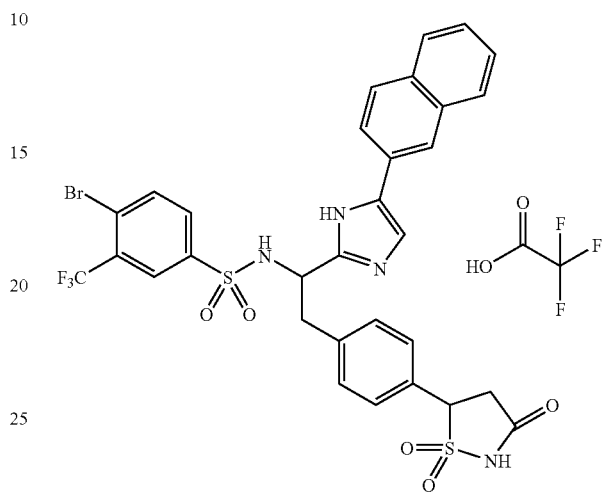

This compound was prepared according to the procedure of Example 4.22 using the appropriate reagents and starting materials. LCMS found for $C_{31}H_{25}BrF_3N_4O_5S_2$ (M+H)$^+$: m/z=733, 735.

Example 4.254

N-{1-(5-Naphthalen-2-yl-1H-imidazol-2-yl)-2-[4-(1,1,3-trioxo-1λ$^6$-isothiazolidin-5-yl)-phenyl]-ethyl}-3-trifluoromethyl-benzenesulfonamide trifluoroacetate

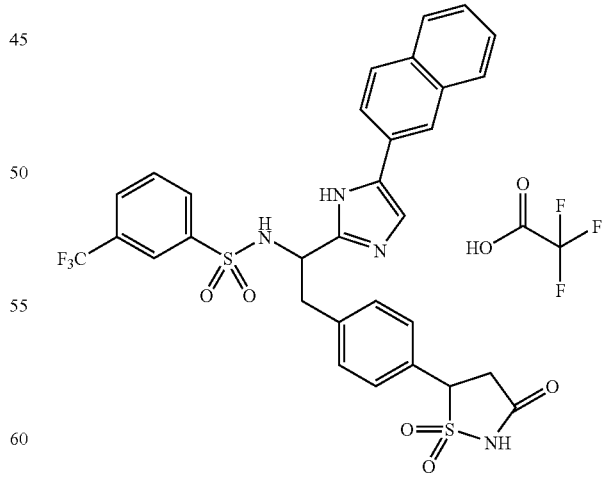

This compound was prepared according to the procedure of Example 4.249 using the appropriate reagents and starting materials. LCMS found for $C_{31}H_{26}F_3N_4O_5S_2$ (M+H)$^+$: m/z=655.

Example 4.255

3-Fluoro-N-{1-[5-(2-methoxy-benzyl)-1H-imidazol-2-yl]-2-[4-(1,1,3-trioxo-1$\lambda^6$-isothiazolidin-5-yl)-phenyl]-ethyl}-benzenesulfonamide trifluoroacetate

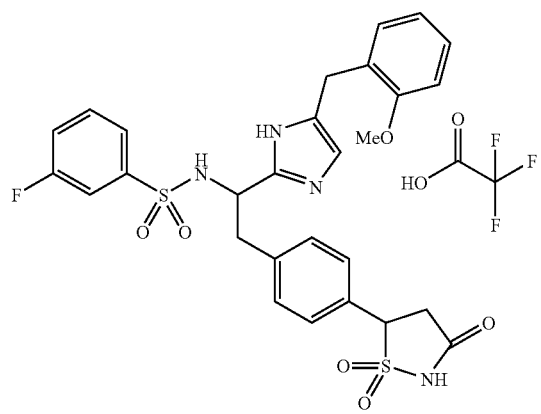

This compound was prepared according to the procedure of Example 4.22 using the appropriate reagents and starting materials. LCMS found for $C_{28}H_{28}FN_4O_6S_2$ (M+H)$^+$: m/z=599.

Example 4.256

3-Fluoro-N-{1-[5-(3-methoxy-benzyl)-1H-imidazol-2-yl]-2-[4-(1,1,3-trioxo-1$\lambda^6$-isothiazolidin-5-yl)-phenyl]-ethyl}-benzenesulfonamide trifluoroacetate

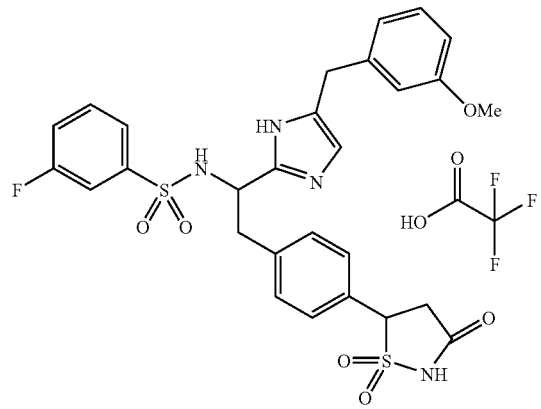

This compound was prepared according to the procedure of Example 4.22 using the appropriate reagents and starting materials. LCMS found for $C_{28}H_{28}FN_4O_6S_2$ (M+H)$^+$: m/z=599.

Example 4.257

3-Fluoro-N-{1-[5-(4-methoxy-benzyl)-1H-imidazol-2-yl]-2-[4-(1,1,3-trioxo-1$\lambda^6$-isothiazolidin-5-yl)-phenyl]-ethyl}-benzenesulfonamide trifluoroacetate

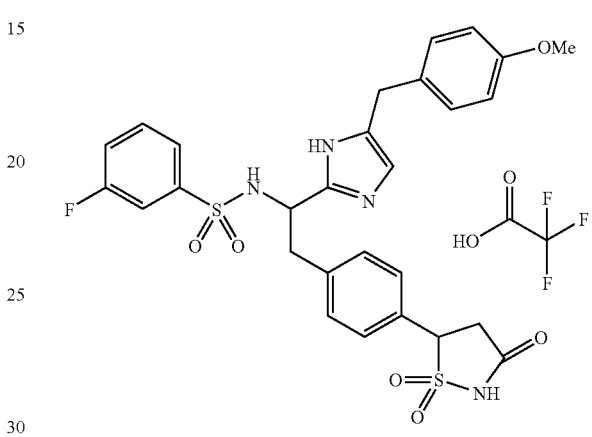

This compound was prepared according to the procedure of Example 4.22 using the appropriate reagents and starting materials. LCMS found for $C_{28}H_{28}F$ $N_4O_6S_2$ (M+H)$^+$: m/z=599.

Example 4.258

2-(5-{2-(Benzothiazol-2-ylamino)-3-[4-(1,1,3-trioxo-1$\lambda^6$-isothiazolidin-5-yl)-phenyl]-propionylamino}-pentyloxy)-6-hydroxy-benzoic acid methyl ester

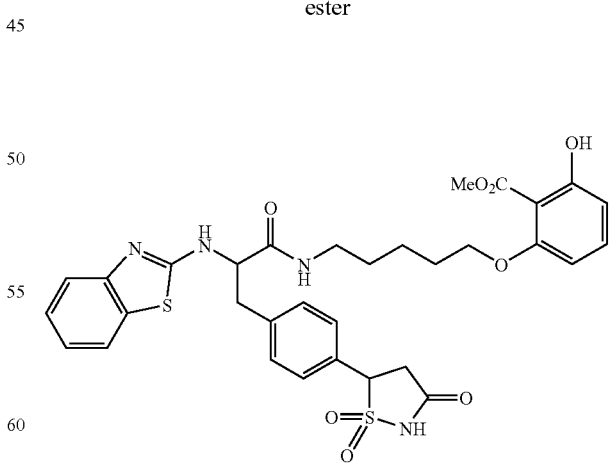

This compound was prepared according to the procedures of Example 4.35 and 4.186 using the appropriate reagents and starting materials. LCMS found for $C_{32}H_{35}N_4O_8S_2$ (M+H)$^+$: m/z=667.

Example 4.259

2-(5-{2-(Benzothiazol-2-ylamino)-3-[4-(1,1,3-tri-oxo-1λ$^6$-isothiazolidin-5-yl)-phenyl]-propionylamino}-pentyloxy)-6-hydroxy-benzoic acid

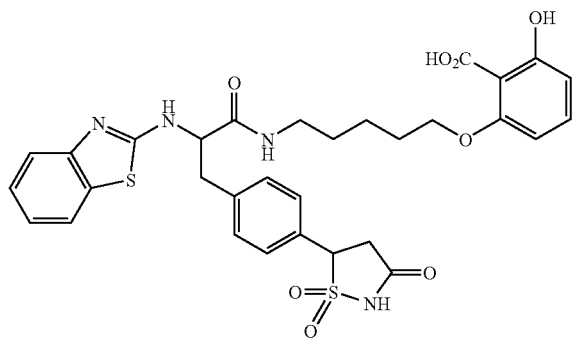

Isolated from the crude reaction mixture of Example 4.258. LCMS found for $C_{31}H_{33}N_4O_8S_2$ (M+H)$^+$: m/z=653.

Example 5.1

N-(1S)-1-(1H-Benzimidazol-2-yl)-2-[4-(1-oxido-3-oxoisothiazolidin-5-yl)phenyl]ethylbenzenesulfonamide trifluoroacetate

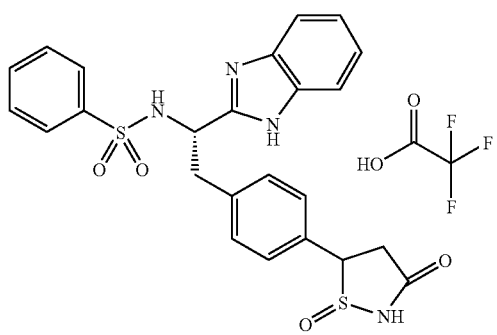

Step 1. (4-(2S)-3-[(2-Aminophenyl)amino]-2-[(tert-butoxycarbonyl)amino]-3-oxopropylphenyl)boronic acid trifluoroacetate

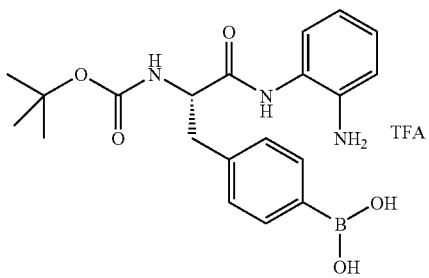

To N-(tert-butoxycarbonyl)-4-(dihydroxyboryl)-L-phenylalanine trifluoroacetate (112 mg, 0.362 mmol) dissolved in N,N-dimethylformamide (4.3 mL) was added N,N,N',N'-tetramethyl-O-(7-azabenzotriazol-1-yl)uronium hexafluorophosphate (138 mg, 0.362 mmol) and N,N-diisopropylethylamine (200 µL, 1 mmol). To this premixed solution was added 1,2-benzenediamine (47.0 mg, 0.435 mmol) and stirred overnight. The solution was diluted with methanol and purified by prep LCMS to yield the desired product (164 mg, 88%). MF=$C_{20}H_{26}BN_3O_5$; LCMS found for $C_{20}H_{27}BN_3O_5$ (M+H)$^+$: m/z=400.2; found m/z=400.1.

Step 2. 4-[(2S)-2-Amino-2-(1H-benzimidazol-2-yl)ethyl]phenylboronic acid bistrifluoroacetate

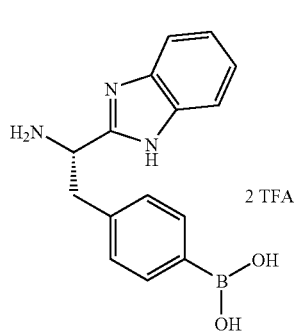

(4-(2S)-3-[(2-Aminophenyl)amino]-2-[(tert-butoxycarbonyl)amino]-3-oxopropylphenyl)boronic acid trifluoroacetate (164 mg, 0.320 mmol) was dissolved in acetic acid (4 mL) and heated at 50° C. for 4 h, then concentrated in vacuo. To the residue was added a mixture of trifluoroacetic acid (2 mL) and methylene chloride (2 mL) and the solution was stirred for 1 hour, then concentrated in vacuo to give the desired product (110 mg, 87%). MF=$C_{15}H_{16}BN_3O_2$; LCMS found for $C_{15}H_{17}BN_3O_2$ (M+H)$^+$: m/z=282.1; found m/z=282.1.

Step 3. (4-(2S)-2-(1H-Benzimidazol-2-yl)-2-[(phenylsulfonyl)amino]ethylphenyl)boronic acid

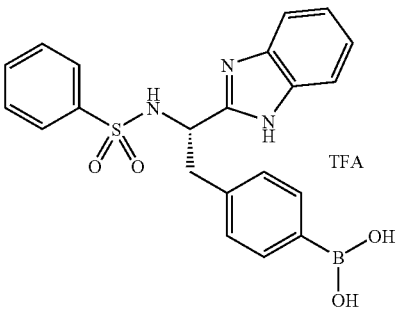

4-[(2S)-2-Amino-2-(1H-benzimidazol-2-yl)ethyl]phenylboronic acid trifluoroacetate (126.3 mg, 0.320 mmol) was dissolved in methylene chloride (10 mL). N',N'-Diisopropylethylamine (170 µL, 0.96 mmol) was added followed by benzenesulfonyl chloride (49 µL, 0.38 mmol) and stirred overnight. The solution was concentrated in vacuo, redissolved in MeOH, and purified by prep LCMS to give the desired product (95 mg, 70%). MF=$C_{21}H_{20}BN_3O_4S$; LCMS found for $C_{21}H_{21}BN_3O_4S$ (M+H)$^+$: m/z=422.1; found m/z=422.1.

Step 4. N-(1S)-1-(1H-Benzimidazol-2-yl)-2-[4-(2-tert-butyl-1-oxido-3-oxo-2,3-dihydroisothiazol-5-yl)phenyl]ethylbenzenesulfonamide trifluroacetate

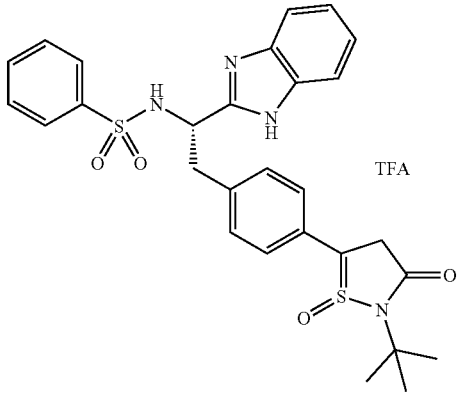

(4-(2S)-2-(1H-Benzimidazol-2-yl)-2-[(phenylsulfonyl)amino]ethylphenyl)boronic acid (40 mg, 0.09 mmol), 2-tert-butyl-5-chloroisothiazol-3(2H)-one 1-oxide trifluoroacetate (24 mg, 0.11 mmol), potassium carbonate (65.6 mg, 0.475 mmol), and [1,1'-bis(diphenylphosphino)ferrocene]dichloropalladium(II), complex with dichloromethane (1:1) (13.2 mg, 0.0161 mmol) were weighed into a 10 mL heavy-walled glass vial. To the vial was added 1,4-dioxane (4 mL). The vial was sealed and the solution was degassed by bubbling with nitrogen. The reaction was stirred at 80° C. for 18 h. The solution was filtered, then diluted with methanol and purified by prep LCMS to give the desired product (6.5 mg, 10%). MF=$C_{28}H_{28}N_4O_4S_2$; LCMS found for $C_{28}H_{29}N_4O_4S_2$(M+H)$^+$: m/z=549.2; found m/z=548.9.

Step 5. N-(1S)-1-(1H-Benzimidazol-2-yl)-2-[4-(2-tert-butyl-1-oxido-3-oxoisothiazolidin-5-yl)phenyl]ethylbenzenesulfonamide trifluoroacetate

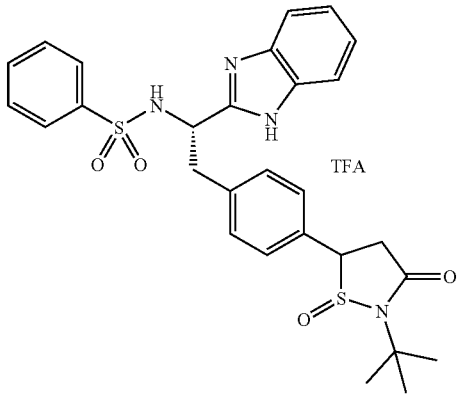

N-(1S)-1-(1H-Benzimidazol-2-yl)-2-[4-(2-tert-butyl-1-oxido-3-oxo-2,3-dihydroisothiazol-5-yl)phenyl]ethylbenzenesulfonamide trifluoroacetate (6.5 mg, 0.012 mmol) was dissolved in tetrahydrofuran (1.0 mL) and methanol (1.0 mL). The solution was cooled to 0° C. in an ice bath. To the solution was added sodium borohydride (0.45 mg, 0.012 mmol). The solution was stirred at 0° C. for 5 minutes, then quenched with acetic acid and concentrated in vacuo. The residue was used without further purification. MF=$C_{28}H_{30}N_4O_4S_2$; LCMS found for $C_{28}H_{31}N_4O_4S_2$(M+H)$^+$:m/z=551.2; found m/z=550.8.

Step 6. N-(1S)-1-(1H-benzimidazol-2-yl)-2-[4-(1-oxido-3-oxoisothiazolidin-5-yl)phenyl]ethylbenzenesulfonamide trifluoroacetate N-(1S)-1-(1H-Benzimidazol-2-yl)-2-[4-(2-tert-butyl-1-oxido-3-oxoisothiazolidin-5-yl)phenyl]ethylbenzenesulfonamide trifluoroacetate (6.5 mg, 0.012 mmol) was dissolved in methanesulfonic acid (1.0 mL) and stirred at 60° C. for 30 min. The solution was diluted with acetonitrile and purified by preparative LCMS to give the desired product (3.8 mg, 65%).
$^1$H NMR (400 MHz, CD$_3$OD): δ 7.65–7.68 (m, 4H), 7.48–7.55 (m, 3H), 7.36–7.40 (m, 2H), 7.24–7.27 (m, 2H), 7.04–7.06 (d, J=7.6 Hz, 2H), 4.84–4.92 (m, 1H), 4.66–4.71 (m, 1H), 3.22–3.33 (m, 3H), 2.87–2.93 (m, 1H); MF=$C_{24}H_{22}N_4O_4S_2$; LCMS found for $C_{24}H_{23}N_4O_4S_2$(M+H)$^+$: m/z=495.1; found m/z=495.1.

Example 6.1

N-(1S)-1-(1H-benzimidazol-2-yl)-2-[4-(1-oxido-3-oxo-2,3-dihydroisothiazol-5-yl)phenyl]ethylbenzenesulfonamide trifluoroacetate

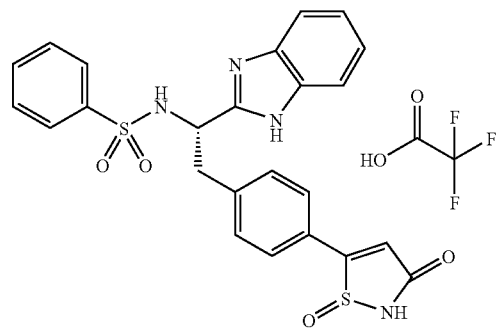

N-(1S)-1-(H-benzimidazol-2-yl)-2-[4-(2-tert-butyl-1-oxido-3-oxo-2,3-dihydroisothiazol-5-yl)phenyl]ethylbenzenesulfonamide trifluoroacetate (3.5 mg, 0.007 mmol) was dissolved in methanesulfonic acid (1.0 mL) and stirred at 60° C. for 30 min. The solution was diluted with acetonitrile and purified by preparative LCMS to give the desired product (2.8 mg, 80%). $^1$H NMR (400 MHz, CD$_3$OD): δ 7.70–7.72 (m, 2H), 7.54–7.61 (m, 6H), 7.43–7.49 (m, 1H), 7.31–7.35 (m, 2H), 7.20–7.22 (d, J=8.2 Hz, 2H), 6.96 (d, J=1.4 Hz, 1H), 4.95–5.01 (m, 1H), 3.24–3.39 (m, 2H); MF=$C_{24}H_{20}N_4O_4S_2$; LCMS found for $C_{24}H_{21}N_4O_4S_2$(M+H)$^+$: m/z=493.1; found m/z=493.0.

Additional example compounds of the invention, including their physical properties and preparation procedures, are provided in the Tables below.

TABLE 1

| Ex. No. | Name | $R^{ia}$ | $R^{ib}$ | $R^{ic}$ | $R^{id}$ | $R^{iib}$ | $R^{iic}$ | Proc. | MS $(M+H)^+$ |
|---|---|---|---|---|---|---|---|---|---|
| 4.260 | 4-Bromo-3-difluoromethyl-N-{1-[5-(2,3-dimethyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | Me | Me | H | H | $CF_3$ | Br | Ex. 4.22 | 711, 713 |
| 4.261 | 4-Bromo-3-difluoromethyl-N-{1-[5-(2,5-dimethyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | Me | H | H | Me | $CF_3$ | Br | Ex. 4.22 | 711, 713 |
| 4.262 | 4-Bromo-3-difluoromethyl-N-{1-[5-(2-methoxy-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide | OMe | H | H | H | $CF_3$ | Br | Ex. 4.22 | 713, 715 |
| 4.263 | 4-Bromo-3-difluoromethyl-N-{1-[5-(3,4-dimethyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Me | Me | H | $CF_3$ | Br | Ex. 4.22 | 711, 713 |
| 4.264 | 4-Bromo-3-difluoromethyl-N-{1-[5-(3,5-dimethyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Me | H | Me | $CF_3$ | Br | Ex. 4.22 | 711, 713 |
| 4.265 | 4-Bromo-3-difluoromethyl-N-{1-[5-(3-methoxy-phenyl)- | H | OMe | H | H | $CF_3$ | Br | Ex. 4.22 | 713, 715 |

TABLE 1-continued

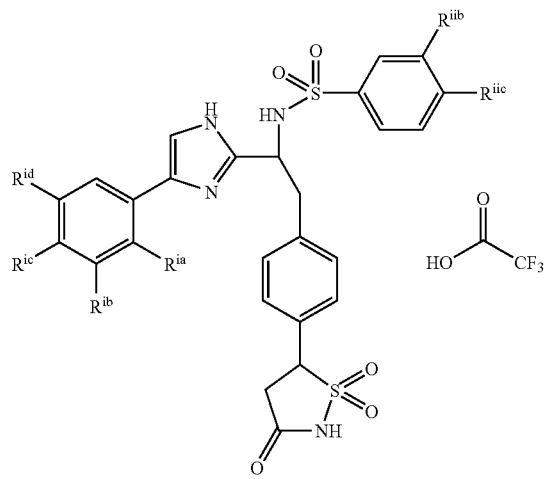

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| | 1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | | | | | | | | |
| 4.266 | 4-Bromo-3-difluoromethyl-N-{1-[5-(4-chloro-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | Cl | H | CF$_3$ | Br | Ex. 4.22 | 717, 719 |
| 4.267 | 4-Bromo-3-difluoromethyl-N-{1-[5-(4-fluoro-3-methyl-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide | H | Me | F | H | CF$_3$ | Br | Ex. 4.22 | 715, 717 |
| 4.268 | 4-Bromo-3-difluoromethyl-N-{1-[5-(3-methyl-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | Me | H | H | CF$_3$ | Br | Ex. 4.22 | 697, 699 |
| 4.269 | 4-Bromo-3-difluoromethyl-N-{1-[5-(2-methyl-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | Me | H | H | H | CF$_3$ | Br | Ex. 4.22 | 697, 699 |
| 4.270 | 4-Bromo-3-difluoromethyl-N-{1-(5-phenyl-1H-imidazol-2-yl)-2-[4-(1,1,3-trioxo-1λ$^6$-isothiazolidin-5-yl)-phenyl]-ethyl}-3- | H | H | H | H | CF$_3$ | Br | Ex. 4.22 | 683, 685 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M+H)^+$ |
|---|---|---|---|---|---|---|---|---|---|
| | trifluoromethyl-benzenesulfonamide trifluoroacetate | | | | | | | | |
| 4.271 | 4-Bromo-3-difluoromethyl-N-{1-[5-(3-fluoro-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | F | H | H | $CF_3$ | Br | Ex. 4.22 | 701, 703 |
| 4.272 | 4-Bromo-3-difluoromethyl-N-{1-[5-(4-phenoxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | OPh | H | $CF_3$ | Br | Ex. 4.22 | 775, 777 |
| 4.273 | 4-Bromo-N-{1-[5-(4-tert-butyl-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | t-Bu | H | $CF_3$ | Br | Ex. 4.22 | 739, 741 |
| 4.274 | 4-Bromo-N-{1-[5-(3,4-dimethoxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | OMe | OMe | H | $CF_3$ | Br | Ex. 4.22 | 743, 745 |
| 4.275 | 4-Bromo-N-{1-[5-(3,4-difluoro-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | F | F | H | $CF_3$ | Br | Ex. 4.22 | 719, 721 |
| 4.276 | 4-Bromo-N-{1-[5-(4-chloro-2-methyl- | Me | H | Cl | H | $CF_3$ | Br | Ex. 4.22 | 731, 733 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| | phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | | | | | | | | |
| 4.277 | 4-Bromo-N-{1-[5-(3-chloro-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Cl | H | H | $CF_3$ | Br | Ex. 4.22 | 717, 719 |
| 4.278 | 4-Bromo-N-{1-[5-(4-propyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | n-Pr | H | $CF_3$ | Br | Ex. 4.22 | 725, 727 |
| 4.279 | 4-Bromo-N-{1-[5-(3,5-difluoro-phenyl)-1H-imidazol-2-yl]-2-[4-(1,1,3-trioxo-1λ⁶-isothiazoltdin-5-yl)-phenyl]-ethyl}-3-trifluoromethyl-benzenesulfonamide trifluoroacetate | H | F | H | F | $CF_3$ | Br | Ex. 4.22 | 719, 721 |
| 4.280 | 4-Bromo-N-{1-[5-(4-fluoro-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | F | H | $CF_3$ | Br | Ex. 4.22 | 701, 703 |
| 4.281 | 4-Bromo-N-{1-[5-(4-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | Me | H | $CF_3$ | Br | Ex. 4.22 | 697, 699 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| 4.282 | 4-Bromo-N-{1-[5-(3-fluoro-2-methyl-phenyl)-1H-imidazol-2-yl]-2-[4-(1,3-trioxo-1$\lambda^6$-isothiazolidin-5-yl)-phenyl]-ethyl}-3-trifluoromethyl-benzenesulfonamide trifluoroacetate | Me | F | H | H | $CF_3$ | Br | Ex. 4.22 | 715, 717 |
| 4.283 | 4-Bromo-N-{1-[5-(4-ethyl-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | H | Et | H | $CF_3$ | Br | Ex. 4.22 | 711, 713 |
| 4.284 | 4-Bromo-N-{1-[5-(4-fluoro-2-methyl-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | Me | H | F | H | $CF_3$ | Br | Ex. 4.22 | 715, 717 |
| 4.285 | 4-Bromo-N-{1-[5-(5-fluoro-2-methyl-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | Me | H | H | F | $CF_3$ | Br | Ex. 4.22 | 715, 717 |
| 4.286 | 4-Bromo-N-{1-[5-(4-methoxy-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | H | OMe | H | $CF_3$ | Br | Ex. 4.22 | 713, 715 |
| 4.287 | N-{1-[5-(2,4-Dimethyl-phenyl)-1H-imidazol-2-yl]-2-[4-(1,1,3-trioxo-1$\lambda^6$-isothiazolidin-5-yl)-phenyl]-ethyl}-3-trifluoromethyl- | Me | H | Me | H | $CF_3$ | H | Ex. 4.249 | 633 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| 4.288 | N-{1-[5-(3,4-Dimethyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Me | Me | H | $CF_3$ | H | Ex. 4.249 | 633 |
| 4.289 | N-{1-[5-(3,5-Dimethyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Me | H | Me | $CF_3$ | H | Ex. 4.249 | 633 |
| 4.290 | N-{1-[5-(3-methoxy-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | OMe | H | H | $CF_3$ | H | Ex. 4.249 | 635 |
| 4.291 | N-{1-[5-(4-fluoro-3-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Me | F | H | $CF_3$ | H | Ex. 4.249 | 637 |
| 4.292 | N-{1-[5-(3-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Me | H | H | $CF_3$ | H | Ex. 4.249 | 619 |
| 4.293 | N-{1-[5-(4-ethyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | Me | H | $CF_3$ | H | Ex. 4.249 | 633 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| 4.294 | N-{1-[5-(2,3-dimethyl-phenyl)-1H-imidazol-2-yl]-2-[4-(1,1,3-trioxo-1$\lambda^6$-isothiazotidin-5-yl)-phenyl]-ethyl}-3-trifluoromethyl-benzenesulfonamide trifluoroacetate | Me | Me | H | H | $CF_3$ | H | Ex. 4.249 | 633 |
| 4.295 | N-{1-[5-(2,5-dimethyl-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | Me | H | H | Me | $CF_3$ | H | Ex. 4.249 | 633 |
| 4.296 | N-{1-[5-(2-methoxy-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | OMe | H | H | H | $CF_3$ | H | Ex. 4.249 | 635 |
| 4.297 | N-{1-[5-(4-chloro-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | H | Cl | H | $CF_3$ | H | Ex. 4.249 | 639, 641 |
| 4.298 | N-{1-[5-(2-methyl-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | Me | H | H | H | $CF_3$ | H | Ex. 4.249 | 619 |
| 4.299 | N-{1-[5-(3-fluoro-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | F | H | H | $CF_3$ | H | Ex. 4.249 | 623 |
| 4.300 | N-{1-{5-(4-phenoxy-phenyl)-1H-imidazol-2-yl]-2-[4-(1,1,3-trioxo-1$\lambda^6$-isothiazolidin-5-yl)- | H | H | OPh | H | $CF_3$ | H | Ex. 4.249 | 697 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS (M + H)+ |
|---|---|---|---|---|---|---|---|---|---|
| | phenyl]-ethyl}-3-trifluoromethyl-benzenesulfonamide trifluoroacetate | | | | | | | | |
| 4.301 | N-{1-[5-(4-tert-butyl-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | H | t-Bu | H | $CF_3$ | H | Ex. 4.249 | 661 |
| 4.302 | N-{1-[5-(3,4-dimethoxy-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | OMe | OMe | H | $CF_3$ | H | Ex. 4.249 | 665 |
| 4.303 | N-{1-[5-(3,4-difluoro-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | F | F | H | $CF_3$ | H | Ex. 4.249 | 641 |
| 4.304 | N-{1-{5-(3-chloro-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | Cl | H | H | $CF_3$ | H | Ex. 4.249 | 639, 641 |
| 4.305 | N-{1-[5-(3,5-difluoro-phenyl)-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | F | H | F | $CF_3$ | H | Ex. 4.249 | 641 |
| 4.306 | N-{1-[5-(4-propyl-phenyl)-1H-imidazol-2-yl]-2-[4-(1,1,3-trioxo-1$\lambda^6$-isothiazolidin-5-yl)-phenyl]-ethyl}-3-trifluoromethyl- | H | H | n-Pr | H | $CF_3$ | H | Ex. 4.249 | 647 |

| Ex. No. | Name | $R^{ia}$ | $R^{ib}$ | $R^{ic}$ | $R^{id}$ | $R^{iib}$ | $R^{iic}$ | Proc. | MS $(M+H)^+$ |
|---|---|---|---|---|---|---|---|---|---|
| | benzenesulfonamide trifluoroacetate | | | | | | | | |
| 4.307 | N-{1-[5-(4-fluoro-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | F | H | $CF_3$ | H | Ex. 4.249 | 623 |
| 4.308 | N-{1-[5-(4-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | Me | H | $CF_3$ | H | Ex. 4.249 | 619 |
| 4.309 | N-{1-[5-(3-fluoro-2-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | Me | F | H | H | $CF_3$ | H | Ex. 4.249 | 637 |
| 4.310 | N-{1-[5-(4-fluoro-2-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | Me | H | F | H | $CF_3$ | H | Ex. 4.249 | 637 |
| 4.311 | N-{1-[5-(5-fluoro-2-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | Me | H | H | F | $CF_3$ | H | Ex. 4.249 | 637 |
| 4.312 | N-{1-[5-(4-methoxy-phenyl)-1H-imidazol-2-yl]-2-[4-(1,1,3-trioxo-1λ⁶-isothiazolidin-5-yl)-phenyl]-ethyl}-3-trifluoromethyl- | H | H | OMe | H | $CF_3$ | H | Ex. 4.249 | 635 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| 4.313 | benzenesulfonamide trifluoroacetate 4-Bromo-N-{1-[5-(3-fluoro-4-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | F | Me | H | $CF_3$ | Br | Ex. 4.22 | 715, 717 |
| 4.314 | 4-Bromo-N-{1-[5-(3-chloro-4-fluoro-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Cl | F | H | $CF_3$ | Br | Ex. 4.22 | 735, 737 |
| 4.315 | 4-Bromo-N-{1-[5-(4-methoxy-2-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | Me | H | OMe | H | $CF_3$ | Br | Ex. 4.22 | 727, 729 |
| 4.316 | 4-Bromo-N-{1-[5-(5-fluoro-2-methoxy-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | OMe | H | H | F | $CF_3$ | Br | Ex. 4.22 | 731, 733 |
| 4.317 | 4-Bromo-N-{1-[5-(3-fluoro-4-methoxy-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | F | OMe | H | $CF_3$ | Br | Ex. 4.22 | 731, 733 |
| 4.318 | 4-Bromo-N-{1-[5-(3,4-dichloro-phenyl)-1H-imidazol-2-yl]-2-[4-(1,1,3-trioxo-1λ⁶-isothiazolidin-5-yl)- | H | Cl | Cl | H | $CF_3$ | Br | Ex. 4.22 | 751, 753 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| | phenyl]-ethyl}-3-trifluoromethyl-benzenesulfonamide trifluoroacetate | | | | | | | | |
| 4.319 | 4-Bromo-N-{1-[5-(3-methoxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | OMe | H | H | CF$_3$ | Br | Ex. 4.22 | 699, 701 |
| 4.320 | 4-Bromo-N-{1-[5-(3,5-dichloro-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | Cl | H | Cl | CF$_3$ | Br | Ex. 4.22 | 751, 753 |
| 4.321 | 4-Bromo-N-{1-[5-(2,4-dimethoxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | OMe | H | OMe | Cl | CF$_3$ | Br | Ex. 4.22 | 743, 745 |
| 4.322 | 4-Bromo-N-{1-[5-(4-methylsulfanyl-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | SMe | H | CF$_3$ | Br | Ex. 4.22 | 729, 731 |
| 4.323 | 4-Bromo-N-{1-[5-(2,5-dimethoxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | OMe | H | H | OMe | CF$_3$ | Br | Ex. 4.22 | 743, 745 |
| 4.324 | 4-Bromo-N-{1-[5-(4-dimethylamino-phenyl)-1H-imidazol-2-yl]-2-[4- | H | H | NMe$_2$ | H | CF$_3$ | Br | Ex. 4.22 | 726, 728 |

TABLE 1-continued

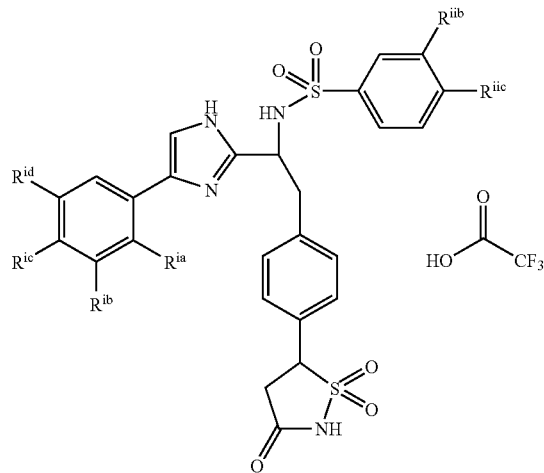

| Ex. No. | Name | $R^{ia}$ | $R^{ib}$ | $R^{ic}$ | $R^{id}$ | $R^{iib}$ | $R^{iic}$ | Proc. | MS (M + H)+ |
|---|---|---|---|---|---|---|---|---|---|
| | (1,1,3-trioxo-1λ⁶-isothiazolidin-5-yl)-phenyl]-ethyl}-3-trifluoromethyl-benzenesulfonamide trifluoroacetate | | | | | | | | |
| 4.325 | N-{1-[5-(3-Fluoro-4-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | F | Me | H | $CF_3$ | H | Ex. 4.249 | 637 |
| 4.326 | N-{1-[5-(3-Chloro-4-fluoro-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | Cl | F | H | $CF_3$ | H | Ex. 4.249 | 657, 659 |
| 4.327 | N-{1-[5-(4-Methoxy-2-methyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | Me | H | OMe | H | $CF_3$ | H | Ex. 4.249 | 649 |
| 4.328 | N-{1-[5-(5-Fluoro-2-methoxy-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | OMe | H | H | F | $CF_3$ | H | Ex. 4.249 | 653 |
| 4.329 | N-{1-[5-(3-Fluoro-4-methoxy-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | F | OMe | H | $CF_3$ | H | Ex. 4.249 | 653 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| 4.330 | N-{1-[5-(3,4-Dichloro-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | Cl | Cl | H | CF$_3$ | H | Ex. 4.249 | 673, 675 |
| 4.331 | N-{1-[5-(3-Hydroxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | OH | H | H | CF$_3$ | H | Ex. 4.249 | 653 |
| 4.332 | N-{1-[5-(2,4-Dimethoxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | OMe | H | OMe | H | CF$_3$ | H | Ex. 4.249 | 665 |
| 4.333 | N-{1-[5-(2,5-Dimethoxy-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | OMe | H | H | OMe | CF$_3$ | H | Ex. 4.249 | 665 |
| 4.334 | N-{1-[5-(4-Dimethylamino-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | NMe$_2$ | H | CF$_3$ | H | Ex. 4.249 | 648 |
| 4.335 | 3-Fluoro-N-{1-[5-(3-fluoro-4-methoxy-phenyl)-1H-imidazol-2-yl]-2-[4-(1,1,3-trioxo-1λ$^6$-isothiazolidin-5-yl)-phenyl]-ethyl}-benzenesulfonamide trifluoroacetate | H | F | OMe | H | F | H | Ex. 4.22 | 603 |

TABLE 1-continued

[Structure shown with substituents $R^{ia}$, $R^{ib}$, $R^{ic}$, $R^{id}$, $R^{iib}$, $R^{iic}$ on a compound containing imidazole, sulfonamide, and isothiazolidinone groups with trifluoroacetate counterion]

| Ex. No. | Name | $R^{ia}$ | $R^{ib}$ | $R^{ic}$ | $R^{id}$ | $R^{iib}$ | $R^{iic}$ | Proc. | MS (M + H)+ |
|---|---|---|---|---|---|---|---|---|---|
| 4.336 | 3-Fluoro-N-{1-[5-(4-hydroxy-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | H | OH | H | F | H | Ex. 4.22 | 571 |
| 4.337 | 3-Fluoro-N-{1-[5-(2,5-dimethoxy-phenyl)-1H-imidazol-2-yl]-2-[4-(1,1,3-trioxo-1λ⁶-isothiazolidin-5-yl)-phenyl]-ethyl}-benzenesulfonamide trifluoroacetate | OMe | H | H | OMe | F | H | Ex. 4.22 | 615 |
| 4.338 | 3-Fluoro-N-{1-[5-(3,4-dimethoxy-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | OMe | OMe | H | F | H | Ex. 4.22 | 615 |
| 4.339 | 3-Fluoro-N-{1-[5-(4-methoxy-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | H | OMe | H | F | H | Ex. 4.22 | 585 |
| 4.340 | 3-Fluoro-N-{1-[5-(3-methoxy-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | OMe | H | H | F | H | Ex. 4.22 | 585 |
| 4.341 | 3-Fluoro-N-{1-[5-(2,4-dimethoxy-phenyl)-1H-imidazol-2-yl]-2-[4-(1,1,3-trioxo-1λ⁶-isothiazolidin-5-yl)-phenyl]-ethyl}-benzenesulfonamide trifluoroacetate | OMe | H | OMe | H | F | H | Ex. 4.22 | 615 |
| 4.342 | 3-Fluoro-N-{1-[5-(2-methoxy-phenyl)-1H-imidazol-2-yl]-2-[4-(1,1,3-trioxo-1λ⁶- | OMe | H | H | H | F | H | Ex. 4.22 | 585 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS (M + H)+ |
|---|---|---|---|---|---|---|---|---|---|
| | isothiazolidin-5-yl)-phenyl]-ethyl}-benzenesulfonamide trifluoroacetate | | | | | | | | |
| 4.343 | 3-Fluoro-N-{1-[5-(2-methylsulfanyl-phenyl)-1H-imidazol-2-yl]-2-[4-(1,1,3-trioxo-1λ$^6$-isothiazolidin-5-yl)-phenyl]-ethyl}-benzenesulfonamide trifluoroacetate | SMe | H | H | H | F | H | Ex. 4.22 | 601 |
| 4.344 | 3-Fluoro-N-{1-[5-(3-trifluoromethoxy-phenyl)-1H-imidazol-2-yl]-2-[4-(1,1,3-trioxo-1λ$^6$-isothiazolidin-5-yl)-phenyl]-ethyl}-benzenesulfonamide trifluoroacetate | H | OCF$_3$ | H | H | F | H | Ex. 4.22 | 639 |
| 4.345 | 3-Fluoro-N-{1-[5-(4-trifluoromethoxy-phenyl)-1H-imidazol-2-yl]-2-[4-(1,1,3-trioxo-1λ$^6$-isothiazolidin-5-yl)-phenyl]-ethyl}-benzenesulfonamide trifluoroacetate | H | H | OCF$_3$ | H | F | H | Ex. 4.22 | 639 |
| 4.346 | 3-Fluoro-N-{1-[5-(3-methylsulfanyl-phenyl)-1H-imidazol-2-yl]-2-[4-(1,1,3-trioxo-1λ$^6$-isothiazolidin-5-yl)-phenyl]-ethyl}-benzenesulfonamide trifluoroacetate | H | SMe | H | H | F | H | Ex. 4.22 | 601 |
| 4.347 | 3-Fluoro-N-{1-[5-(4-methylsulfanyl-phenyl)-1H-imidazol-2-yl]-2-[4-(1,1,3-trioxo-1λ$^6$-isothiazolidin-5-yl)-phenyl]-ethyl}-benzenesulfonamide trifluoroacetate | H | H | SMe | H | F | H | Ex. 4.22 | 601 |
| 4.348 | N-{1-[5-(4-Methanesulfinyl-phenyl)-1H-imidazol-2-yl]-2-[4-(1,1,3-trioxo-1λ$^6$-isothiazolidin-5-yl)-phenyl]-ethyl}-3-trifluoromethyl-benzenesulfonamide | H | H | SOMe | H | CF$_3$ | H | Ex. 4.249 | 667 |

TABLE 1-continued

| Ex. No. | Name | $R^{ia}$ | $R^{ib}$ | $R^{ic}$ | $R^{id}$ | $R^{iib}$ | $R^{iic}$ | Proc. | MS $(M + H)^+$ |
|---|---|---|---|---|---|---|---|---|---|
| 4.349 | N-{1-[5-(4-Methanesulfonyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | SO₂Me | H | CF₃ | H | Ex. 4.249 | 683 |
| 4.350 | N-{1-[5-(4-methylsulfanyl-phenyl)-1H-imidazol-2-yl]-2-[4-(1,1,3-trioxo-1λ⁶-isothiazolidin-5-yl)-phenyl]-ethyl}-3-trifluoromethyl-benzenesulfonamide trifluoroacetate | H | H | SMe | H | CF₃ | H | Ex. 4.249 | 651 |
| 4.351 | 3-Fluoro-N-{1-[5-(3-methanesulfinyl-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | SOMe | H | H | F | H | Ex. 4.22 | 617 |
| 4.352 | 3-Fluoro-N-{1-[5-(3-methanesulfonyl-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | SO₂Me | H | H | F | H | Ex. 4.22 | 633 |
| 4.353 | 3-Fluoro-N-{1-[5-(4-methanesulfinyl-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | H | SOMe | H | F | H | Ex. 4.22 | 617 |
| 4.354 | 3-Fluoro-N-{1-[5-(4-methanesulfonyl-phenyl)-1H-imidazol-2-yl]-2-[4-(1,1,3-trioxo-1λ⁶-isothiazolidin-5-yl)-phenyl]-ethyl}-benzenesulfonamide trifluoroacetate | H | H | SO₂Me | H | F | H | Ex. 4.22 | 633 |

TABLE 2

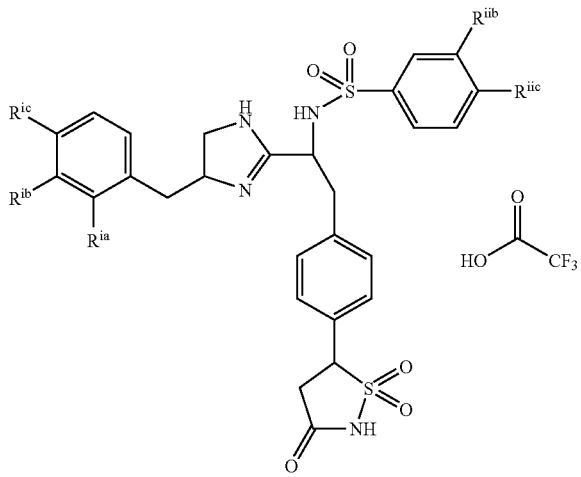
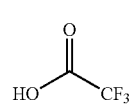

| Ex. No. | Name | $R^{ia}$ | $R^{ib}$ | $R^{ic}$ | $R^{iib}$ | $R^{iic}$ | Ex. Proc. | MS $(M + H)^+$ |
|---|---|---|---|---|---|---|---|---|
| 4.355 | N-{1-((S)-5-Benzyl-4,5-dihydro-1H-imidazol-2-yl)-2-[4-(1,1,3-trioxo-1$\lambda^6$-isothiazolidin-5-yl)-phenyl]-ethyl}-3-trifluoromethyl-benzenesulfonamide trifluoroacetate | H | H | H | $CF_3$ | H | 1.37, Step 5 4.22, Step 5 | 621 |
| 4.356 | N-{1-((R)-5-Benzyl-4,5-dihydro-1H-imidazol-2-yl)-2-[4-(1,1,3-trioxo-1$\lambda^6$-isothiazolidin-5-yl)-phenyl]-ethyl}-3-trifluoromethyl-benzenesulfonamide trifluoroacetate | H | H | H | $CF_3$ | H | 1.37, Step 5 4.22, Step 5 | 621 |
| 4.357 | 4-Bromo-3-trifluoromethyl-N-{1-[(R)-5-(3-trifluoromethyl-benzyl)-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | H | $CF_3$ | H | $CF_3$ | Br | 1.37, Step 5 4.22, Step 5 | 767, 769 |
| 4.358 | 4-Bromo-3-trifluoromethyl-N-{1-[(R)-5-(4-trifluoromethyl-benzyl)-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | H | H | $CF_3$ | $CF_3$ | Br | 1.37, Step 5 4.22, Step 5 | 767, 769 |
| 4.359 | 4-Bromo-3-trifluoromethyl-N-{1-[(R)-5-(2-trifluoromethyl-benzyl)-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | $CF_3$ | H | H | $CF_3$ | Br | 1.37, Step 5 4.22, Step 5 | 767, 769 |
| 4.360 | 4-Bromo-N-{1-[(R)-5-(2-methyl-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | Me | H | H | $CF_3$ | Br | 1.37, Step 5 4.22, Step 5 | 713, 715 |
| 4.361 | 4-Bromo-N-{1-[(R)-5-(3-methyl-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl- | H | Me | H | $CF_3$ | Br | 1.37, Step 5 4.22, Step 5 | 713, 715 |

TABLE 2-continued

| Ex. No. | Name | $R^{ia}$ | $R^{ib}$ | $R^{ic}$ | $R^{iib}$ | $R^{iic}$ | Ex. Proc. | MS (M + H)+ |
|---|---|---|---|---|---|---|---|---|
| 4.362 | benzenesulfonamide trifluoroacetate 4-Bromo-N-{1-[(R)-5-(2-fluoro-benzyl)-4,5-dihydro-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | F | H | H | CF$_3$ | Br | 1.37, Step 5 4.22, Step 5 | 717, 719 |
| 4.363 | 4-Bromo-N-{1-[(R)-5-(4-fluoro-benzyl)-4,5-dihydro-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | F | CF$_3$ | Br | 1.37, Step 5 4.22, Step 5 | 717, 719 |
| 11 4.364 | 4-Bromo-N-{1-[(R)-5-(4-chloro-benzyl)-4,5-dihydro-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | Cl | CF$_3$ | Br | 1.37, Step 5 4.22, Step 5 | 733, 735 |
| 4.365 | 3-Trifluoromethyl-N-{1-[(R)-5-(2-methyl-benzyl)-4,5-dihydro-1H-imidazol-2-yl]-2-[4-(1,1,3-trioxo-1λ$^6$-isothiazolidin-5-yl)-phenyl]-ethyl}-benzenesulfonamide trifluoroacetate | Me | H | H | CF$_3$ | H | Ex. 4.249 | 635 |
| 4.366 | 3-Trifluoromethyl-N-{1-[(R)-5-(3-methyl-benzyl)-4,5-dihydro-1H-imidazol-2-yl]-2-[4-(1,1,3-trioxo-1λ$^6$-isothiazolidin-5-yl)-phenyl]-ethyl}-benzenesulfonamide trifluoroacetate | H | Me | H | CF$_3$ | H | Ex. 4.249 | 635 |
| 4.367 | 3-Trifluoromethyl-N-{1-[(R)-5-(3-trifluoromethyl-benzyl)-4,5-dihydro-1H-imidazol-2-yl]-2-[4-(1,1,3-trioxo-1λ$^6$-isothiazolidin-5-yl)-phenyl]-ethyl}-benzenesulfonamide trifluoroacetate | H | CF$_3$ | H | CF$_3$ | H | Ex. 4.249 | 689 |
| 4.368 | 3-Trifluoromethyl-N-{1-[(R)-5-(2-fluoro-benzyl)-4,5-dihydro-1H-imidazol-2-yl]-2-[4-(1,1,3-trioxo-1λ$^6$-isothiazolidin-5-yl)-phenyl]-ethyl}- | F | H | H | CF$_3$ | H | Ex. 4.249 | 639 |

TABLE 2-continued

| Ex. No. | Name | $R^{ia}$ | $R^{ib}$ | $R^{ic}$ | $R^{iib}$ | $R^{iic}$ | Ex. Proc. | MS $(M + H)^+$ |
|---|---|---|---|---|---|---|---|---|
| 4.369 | 3-Trifluoromethyl-N-{1-[(R)-5-(4-fluoro-benzyl)-4,5-dihydro-1H-imidazol-2-yl]-2-[4-(1,1,3-trioxo-1λ$^6$-isothiazolidin-5-yl)-phenyl]-ethyl}-benzenesulfonamide trifluoroacetate | H | H | F | CF$_3$ | H | Ex. 4.249 | 639 |
| 4.370 | 3-Trifluoromethyl-N-{1-[(R)-5-(4-trifluoromethyl-benzyl)-4,5-dihydro-1H-imidazol-2-yl]-2-[4-(1,1,3-trioxo-1λ$^6$-isothiazolidin-5-yl)-phenyl]-ethyl}-benzenesulfonamide trifluoroacetate | H | H | CF$_3$ | CF$_3$ | H | Ex. 4.249 | 689 |
| 4.371 | N-{1-((R)-5-Benzyl-4,5-dihydro-1H-imidazol-2-yl]-2-[4-(1,1,3-trioxo-1λ$^6$-isothiazolidin-5-yl)-phenyl]-ethyl}-4-bromo-3-trifluoromethyl-benzenesulfonamide trifluoroacetate | H | H | H | CF$_3$ | Br | 1.37, Step 5 4.22, Step 5 | 699, 701 |
| 4.372 | 4-Bromo-N-{1-[(R)-5-(3-chloro-benzyl)-4,5-dihydro-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | Cl | H | CF$_3$ | Br | 1.37, Step 5 4.22, Step 5 | 733, 735 |
| 4.373 | 4-Bromo-N-{1-[(R)-5-(2-chloro-benzyl)-4,5-dihydro-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | Cl | H | H | CF$_3$ | Br | 1.37, Step 5 4.22, Step 5 | 733, 735 |
| 4.374 | 4-Bromo-N-{1-[(R)-5-(4-methyl-benzyl)-4,5-dihydro-1H-imidazol-2-yl]-2-[4-(1,1,3-trioxo-1λ$^6$-isothiazolidin-5-yl)-phenyl]-ethyl}-3-trifluoromethyl-benzenesulfonamide trifluoroacetate | H | H | CH$_3$ | CF$_3$ | Br | 1.37, Step 5 4.22, Step 5 | 713, 715 |
| 4.375 | 4-Bromo-N-{1-[(R)-5-(3-fluoro-benzyl)-4,5-dihydro-1H-imidazol-2-yl]-2-[4-(1,1,3-trioxo-1λ$^6$-isothiazolidin-5-yl)-phenyl]-ethyl}-3- | H | F | H | CF$_3$ | Br | 1.37, Step 5 4.22, Step 5 | 717, 719 |

TABLE 2-continued

| Ex. No. | Name | $R^{ia}$ | $R^{ib}$ | $R^{ic}$ | $R^{iib}$ | $R^{iic}$ | Ex. Proc. | MS $(M + H)^+$ |
|---|---|---|---|---|---|---|---|---|
| 4.376 | N-{1-[(R)-5-(3-Fluoro-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | F | H | $CF_3$ | H | Ex. 4.249 | 639 |
| 4.377 | N-{1-[(R)-5-(3-Chloro-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | Cl | H | $CF_3$ | H | Ex. 4.249 | 655, 657 |
| 4.378 | N-{1-[(R)-5-(2-Chloro-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | Cl | H | H | $CF_3$ | H | Ex. 4.249 | 655, 657 |
| 4.379 | N-{1-[(R)-5-(4-Chloro-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | H | Cl | $CF_3$ | H | Ex. 4.249 | 622, 657 |
| 4.380 | N-{1-[(R)-5-(4-Methoxy-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | H | OMe | $CF_3$ | H | Ex. 4.249 | 651 |
| 4.381 | N-{1-[(R)-5-(4-Methyl-benzyl)-4,5-dihydro-1H-imidazol-2-yl]-2-[4-(1,1,3-trioxo-1$\lambda^6$-isothiazolidin-5-yl)-phenyl]-ethyl}-3-trifluoromethyl-benzenesulfonamide trifluoroacetate | H | H | Me | $CF_3$ | H | Ex. 4.249 | 635 |
| 4.382 | N-{1-((R)-5-Benzyl-4,5-dihydro-1H-imidazol-2-yl)-2-[4-(1,1,3-trioxo-1$\lambda^6$-isothiazolidin-5-yl)-phenyl]-ethyl}-3-fluoro-benzenesulfonamide trifluoroacetate | H | H | H | F | H | 1.37, Step 5 4.22, Step 5 | 571 |

TABLE 2-continued

| Ex. No. | Name | $R^{ia}$ | $R^{ib}$ | $R^{ic}$ | $R^{iib}$ | $R^{iic}$ | Ex. Proc. | MS $(M + H)^+$ |
|---|---|---|---|---|---|---|---|---|
| 4.383 | 3-Fluoro-N-{1-[(R)-5-(2-fluoro-benzyl)-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | F | H | H | F | H | 1.37, Step 5 4.22, Step 5 | 589 |
| 4.384 | 3-Fluoro-N-{1-[(R)-5-(2-chloro-benzyl)-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | Cl | H | H | F | H | 1.37, Step 5 4.22, Step 5 | 605, 607 |
| 4.385 | 3-Fluoro-N-{1-[(R)-5-(3-chloro-benzyl)-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | H | Cl | H | F | H | 1.37, Step 5 4.22, Step 5 | 605, 607 |
| 4.386 | 3-Fluoro-N-{1-[(R)-5-(3-methoxy-benzyl)-4,5-dihydro-1H-imidazol-2-yl]-2-{4-(1,1,3-trioxo-1$\lambda^6$-isothiazolidin-5-yl)-phenyl]-ethyl}-benzenesulfonamide trifluoroacetate | H | OMe | H | F | H | 1.37, Step 5 4.22, Step 5 | 601 |
| 4.387 | 3-Fluoro-N-{1-[(R)-5-(4-hydroxy-benzyl)-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | H | H | OH | F | H | Isolated during the synthesis of 4.388 | 587 |
| 4.388 | N-{1-[(R)-5-(4-Benzyloxy-benzyl)-4,5-dihydro-1H-imidazol-2-yl]-2-[4-(1,1,3-trioxo-1$\lambda^6$-isothiazolidin-5-yl)-phenyl]-ethyl}-3-fluoro-benzenesulfonamide trifluoroacetate | H | H | OBn | F | H | 1.37, Step 5 4.22, Step 5 | 677 |
| 4.389 | 3-Fluoro-N-{1-[(R)-5-(2-methoxy-benzyl-4,5-dihydro-1H-imidazol-2-yl]-2-[4-(1,1,3-trioxo-1$\lambda^6$-isothiazolidin-5-yl)-phenyl]-ethyl}-benzenesulfonamide trifluoroacetate | OMe | H | H | F | H | 1.37, Step 5 4.22, Step 5 | 601 |
| 4.390 | N-{1-[(R)-5-(3,4-Dimethoxy-benzyl)-4,5-dihydro-1H-imidazol-2-yl]-2-(4-(1,1,3- | H | OMe | OMe | F | H | 1.37, Step 5 | 631 |

TABLE 2-continued trioxo-1λ⁶-isothiazolidin-5-yl)-
phenyl]-ethyl}-3-fluoro-
benzenesulfonamide
trifluoroacetate

TABLE 3

| Ex. No. | Name | $X^A$ | $y^A$ | $R^i$ | Ex. Proc. | MS $(M + H)^+$ |
|---|---|---|---|---|---|---|
| 4.391 | N-{(1S)-1-(5-chloro-1H-benzimidazol-2-yl)-2-[4-(1,1-dioxido-3-oxoisothiazolidin-5-yl)phenyl]ethyl}-4-phenylbutanamide trifluoroacetate | Cl | —(CH₂)₃— | Ph | Ex. 4.118 | 552 |
| 4.392 | N-{(1S)-1-(1H-benzimidazol-2-yl)-2-[4-(1,1-dioxido-3-oxoisothiazolidin-5-yl)phenyl]ethyl}-3-(3-bromophenyl)propanamide trifluoroacetate | H | —(CH₂)₂— | 3-Br-Ph | Ex. 4.118 | 581 |
| 4.393 | N-{(1S)-1-(1H-benzimidazol-2-yl)-2-[4-(1,1-dioxido-3-oxoisothiazolidin-5- | H | —(CH₂)₂— | 4-Br-Ph | Ex. 4.118 | 581 |

TABLE 3-continued

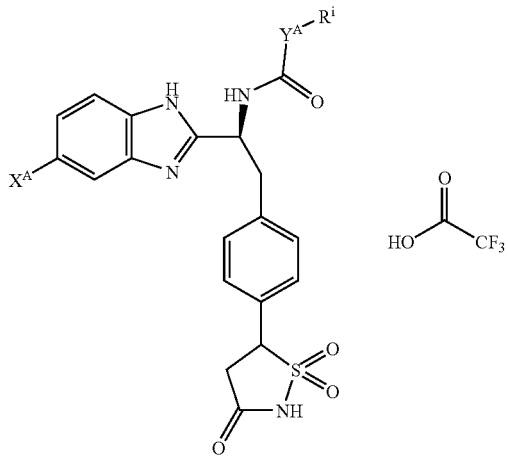

| Ex. No. | Name | $X^A$ | $y^A$ | $R^i$ | Ex. Proc. | MS $(M + H)^+$ |
|---|---|---|---|---|---|---|
| | yl)phenyl]ethyl}-3-(4-bromophenyl)propanamide trifluoroacetate | | | | | |
| 4.394 | N-{(1S)-1-(1H-benzimidazol-2-yl)-2-[4-(1,1-dioxido-3-oxoisothiazolidin-5-yl)phenyl]ethyl}-3-(4-chlorophenyl)propanamide trifluoroacetate | H | —(CH$_2$)$_2$— | 4-Cl-Ph | Ex. 4.118 | 537 |
| 4.395 | N-{(1S)-1-(1H-benzimidazol-2-yl)-2-[4-(1,1-dioxido-3-oxoisothiazolidin-5-yl)phenyl]ethyl}-3-(3-chlorophenyl)propanamide trifluoroacetate | H | —(CH$_2$)$_2$— | 3-Cl-Ph | Ex. 4.118 | 537 |
| 4.396 | N-{(1S)-1-(1H-benzimidazol-2-yl)-2-[4-(1,1-dioxido-3-oxoisothiazolidin-5-yl)phenyl]ethyl}-3-(2-fluorophenyl)propanamide trifluoroacetate | H | —(CH$_2$)$_2$— | 2-F-Ph | Ex. 4.118 | 521 |
| 4.397 | N-{(1S)-1-(1H-benzimidazol-2-yl)-2-[4-(1,1-dioxido-3-oxoisothiazolidin-5-yl)phenyl]ethyl}-3-(3-fluorophenyl)propanamide trifluoroacetate | H | —(CH$_2$)$_2$— | 3-F-Ph | Ex. 4.118 | 521 |
| 4.398 | N-{(1S)-1-(1H-benzimidazol-2-yl)-2-[4-(1,1-dioxido-3-oxoisothiazolidin-5-yl)phenyl]ethyl}-3-(2-chlorophenyl)propanamide trifluoroacetate | H | —(CH$_2$)$_2$— | 2-Cl-Ph | Ex. 4.118 | 537 |
| 4.399 | N-{(1S)-1-(1H-benzimidazol-2-yl)-2-[4-(1,1-dioxido-3-oxoisothiazolidin-5-yl)phenyl]ethyl}-3-(3-methylphenyl)propanamide trifluoroacetate | H | —(CH$_2$)$_2$— | 3-Me-Ph | Ex. 4.118 | 517 |
| 4.400 | N-{(1S)-1-(1H-benzimidazol-2-yl)-2-[4-(1,1-dioxido-3-oxoisothiazolidin-5-yl)phenyl]ethyl}-3-(3-trifluoromethylphenyl)propanamide trifluoroacetate | H | —(CH$_2$)$_2$— | 3-CF$_3$-Ph | Ex. 4.118 | 571 |

TABLE 3-continued

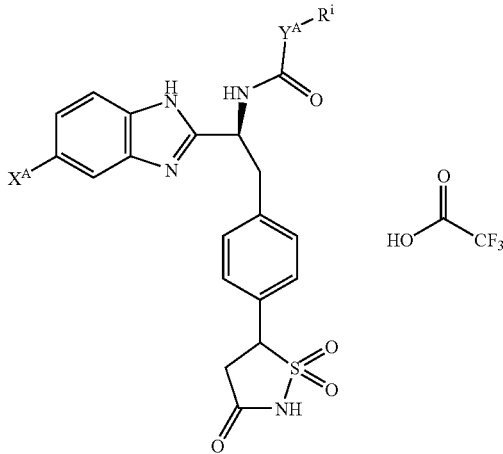

| Ex. No. | Name | X^A | Y^A | R^i | Ex. Proc. | MS (M + H)+ |
|---|---|---|---|---|---|---|
| 4.401 | N-{(1S)-1-(1H-benzimidazol-2-yl)-2-[4-(1,1-dioxido-3-oxoisothiazolidin-5-yl)phenyl]ethyl}-3-(4-fluorophenyl)propanamide trifluoroacetate | H | —(CH$_2$)$_2$— | 4-F-Ph | Ex. 4.118 | 521 |
| 4.402 | N-{(1S)-1-(1H-benzimidazol-2-yl)-2-[4-(1,1-dioxido-3-oxoisothiazolidin-5-yl)phenyl]ethyl}-3-(2-methoxyphenyl)propanamide trifluoroacetate | H | —(CH$_2$)$_2$— | 2-OMe-Ph | Ex. 4.118 | 533 |
| 4.403 | N-{(1S)-1-(1H-benzimidazol-2-yl)-2-[4-(1,1-dioxido-3-oxoisothiazolidin-5-yl)phenyl]ethyl}-3-(3-methoxyphenyl)propanamide trifluoroacetate | H | -(CH$_2$)$_2$— | 3-OMe-Ph | Ex. 4.118 | 533 |
| 4.404 | N-{(1S)-1-(1H-benzimidazol-2-yl)-2-[4-(1,1-dioxido-3-oxoisothiazolidin-5-yl)phenyl]ethyl}-3-(4-methoxyphenyl)propanamide trifluoroacetate | H | —(CH$_2$)$_2$— | 4-OMe-Ph | Ex. 4.118 | 533 |
| 4.405 | N-{(1S)-1-(1H-benzimidazol-2-yl)-2-[4-(1,1-dioxido-3-oxoisothiazolidin-5-yl)phenyl]ethyl}-3-(4-methylphenyl)propanamide trifluoroacetate | H | —(CH$_2$)$_2$— | 4-Me-Ph | Ex. 4.118 | 517 |
| 4.406 | N-{(1S)-1-(1H-benzimidazol-2-yl)-2-[4-(1,1-dioxido-3-oxoisothiazolidin-5-yl)phenyl]ethyl}-3-(4-trifluoromethylphenyl)propanamide trifluoroacetate | H | —(CH$_2$)$_2$— | 4-CF$_3$-Ph | Ex. 4.118 | 571 |
| 4.407 | N-{(1S)-1-(1H-benzimidazol-2-yl)-2-[4-(1,1-dioxido-3-oxoisothiazolidin-5-yl)phenyl]ethyl}-3-[2,5-bis(trifluoromethyl)phenyl]propanamide trifluoroacetate | H | —(CH$_2$)$_2$— | 2,5-diCF$_3$-Ph | Ex. 4.118 | 639 |
| 4.408 | N-{(1S)-1-(1H-benzimidazol-2-yl)-2-[4-(1,1-dioxido-3-oxoisothiazolidin-5- | H | —(CH$_2$)$_2$— | 3,5-diCF$_3$-Ph | Ex. 4.118 | 639 |

TABLE 3-continued

| Ex. No. | Name | X^A | y^A | R^i | Ex. Proc. | MS (M + H)+ |
|---|---|---|---|---|---|---|
| | yl)phenyl]ethyl}-3-[3,5-bis(trifluoromethyl)phenyl]propanamide trifluoroacetate | | | | | |
| 4.409 | (2S)-N-{(1S)-1-(1H-benzimidazol-2-yl)-2-[4-(1,1-dioxido-3-oxoisothiazolidin-5-yl)phenyl]ethyl}-2-hydroxy-3-phenylpropanamide trifluoroacetate | H | absent | (OH)(Ph) substituent | Ex. 4.118 | 519 |
| 4.410 | N-{(1S)-1-(1H-benzimidazol-2-yl)-2-[4-(1,1-dioxido-3-oxoisothiazolidin-5-yl)phenyl]ethyl}-2-methyl-3-phenylpropanamide trifluoroacetate | H | absent | (Me)(CH2Ph) substituent | Ex. 4.118 | 517 |
| 4.411 | N-{(1S)-1-(1H-benzimidazol-2-yl)-2-[4-(1,1-dioxido-3-oxoisothiazolidin-5-yl)phenyl]ethyl}-2-benzyl-3,3-dimethylbutanamide trifluoroacetate | H | absent | (t-Bu)(CH2Ph) substituent | Ex. 4.118 | 559 |
| 4.412 | N-{(1S)-1-(1H-benzimidazol-2-yl)-2-[4-(1,1-dioxido-3-oxoisothiazolidin-5-yl)phenyl]ethyl}-3-(2-methylphenyl)propanamide trifluoroacetate | H | —(CH$_2$)$_2$— | 2-Me-Ph | Ex. 4.118 | 517 |
| 4.413 | N-{(1S)-1-(1H-benzimidazol-2-yl)-2-[4-(1,1-dioxido-3-oxoisothiazolidin-5-yl)phenyl]ethyl}-2-phenoxyacetamide trifluoroacetate | H | absent | —CH$_2$—O-Ph | Ex. 4.118 | 505 |
| 4.414 | N-{(1S)-1-(1H-benzimidazol-2-yl)-2-[4-(1,1-dioxido-3-oxoisothiazolidin-5-yl)phenyl]ethyl}-2-(phenylthio)acetamide trifluoroacetate | H | absent | —CH$_2$—S-Ph | Ex. 4.118 | 521 |
| 4.415 | N-{(1S)-1-(1H-benzimidazol-2-yl)-2-[4-(1,1-dioxido-3-oxoisothiazolidin-5- | H | —(CH$_2$)$_2$— | 3-Pyridyl | Ex. 4.118 | 504 |

TABLE 3-continued

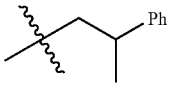

| Ex. No. | Name | $X^A$ | $Y^A$ | $R^i$ | Ex. Proc. | MS $(M + H)^+$ |
|---|---|---|---|---|---|---|
| | yl)phenyl]ethyl}-3-pyridin-3-ylpropanamide trifluoroacetate | | | | | |
| 4.416 | N-{(1S)-1-(1H-benzimidazol-2-yl)-2-[4-(1,1-dioxido-3-oxoisothiazolidin-5-yl)phenyl]ethyl}-4-phenylbutanamide trifluoroacetate | H | —(CH$_2$)$_3$— | Ph | Ex. 4.118 | 517 |
| 4.417 | N-{(1S)-1-(1H-benzimidazol-2-yl)-2-[4-(1,1-dioxido-3-oxoisothiazolidin-5-yl)phenyl]ethyl}-4-(4-methoxyphenyl)butanamide trifluoroacetate | H | —(CH$_2$)$_3$— | 4-OMe-Ph | Ex. 4.118 | 547 |
| 4.418 | N-{(1S)-1-(1H-benzimidazol-2-yl)-2-[4-(1,1-dioxido-3-oxoisothiazolidin-5-yl)phenyl]ethyl}-3-phenylbutanamide trifluoroacetate | H | absent | 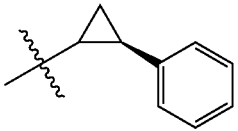 | Ex. 4.118 | 517 |
| 4.419 | (2R)-N-{(1S)-1-(1H-benzimidazol-2-yl)-2-[4-(1,1-dioxido-3-oxoisothiazolidin-5-yl)phenyl]ethyl}-2-phenylcyclopropanecarboxamide trifluoroacetate | H | absent | | Ex. 4.118 | 515 |

TABLE 3-continued

| Ex. No. | Name | X^A | y^A | R^i | Ex. Proc. | MS (M + H)^+ |
|---|---|---|---|---|---|---|
| 4.420 | N-{(1S)-1-(1H-benzimidazol-2-yl)-2-[4-(1,1-dioxido-3-oxoisothiazolidin-5-yl)phenyl]ethyl}-1,2,3,4-tetrahydronaphthalene-2-carboxamide trifluoroacetate | H | absent | 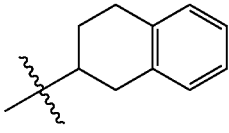 | Ex. 4.118 | 529 |
| 4.421 | N-{(1S)-1-(1H-benzimidazol-2-yl)-2-[4-(1,1-dioxido-3-oxoisothiazolidin-5-yl)phenyl]ethyl}bicyclo[4.2.0]octa-1,3,5-triene-7-carboxamide trifluoroacetate | H | absent | 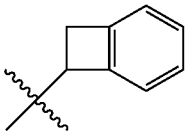 | Ex. 4.118 | 501 |
| 4.422 | N-{(1S)-1-(1H-benzimidazol-2-yl)-2-[4-(1,1-dioxido-3-oxoisothiazolidin-5-yl)phenyl]ethyl}-2-(1-methyl-1H-indol-3-yl)acetamide trifluoroacetate | H | absent | 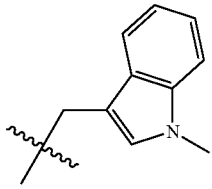 | Ex. 4.118 | 542 |
| 4.423 | N-{(1S)-1-(1H-benzimidazol-2-yl)-2-[4-(1,1-dioxido-3-oxoisothiazolidin-5-yl)phenyl]ethyl}-2-(6-methoxy-3-oxo-2,3-dihydro-1H-inden-1-yl)acetamide triflouroacetate | H | absent | 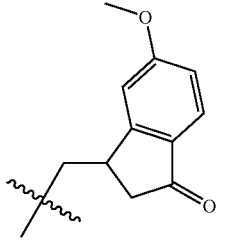 | Ex. 4.118 | 573 |

TABLE 4

| Ex. No. | Name | R$^I$ | R$^{ib}$ | R$^{ic}$ | R$^{iia}$ | R$^{iib}$ | R$^{iic}$ | R$^{iid}$ | Ex. Proc. | MS (M + H)$^+$ |
|---|---|---|---|---|---|---|---|---|---|---|
| 4.424 | 5-(4-{(2S)-2-(1,3-benzothiazol-2-ylamino)-2-[6-(trifluoromethyl)-1H-benzimidazol-2-yl]ethyl}phenyl) isothiazolidin-3-one 1,1-dioxide trifluoroacetate | H | CF$_3$ | H | H | H | H | H | Ex. 4.118 | 572 |
| 4.425 | 5-(4-{(2S)-2-(1,3-benzothiazol-2-ylamino)-2-[6-cyano-1H-benzimidazol-2-yl]ethyl}phenyl) isothiazolidin-3-one 1,1-dioxide trifluoroacetate | H | CN | H | H | H | H | H | Ex. 4.118 | 529 |
| 4.426 | 5-4-[(2S)-2-(1H-benzimidazol-2-yl)-2-(1,3-benzothiazol-2-ylamino)ethyl]-2-chlorophenylisothiazolidin-3-one 1,1-dioxide trifluoroacetate | Cl | H | H | H | H | H | H | Ex. 4.228 | 538 |
| 4.428 | 5-(4-{(2S)-2-(1H-benzimidazol-2-yl)-2-[(5-fluoro-1,3-benzothiazol-2-yl)amino]ethyl}phenyl) isothiazolidin-3-one 1,1-dioxide trifluoroacetate | H | H | H | H | F | H | H | Ex. 4.118 | 522 |
| 4.429 | 5-(4-{(2S)-2-(1H-benzimidazol-2-yl)-2-[(5-bromo-1,3-benzothiazol-2-yl)amino]ethyl}phenyl) isothiazolidin-3-one 1,1-dioxide trifluoroacetate | H | H | H | H | Br | H | H | Ex. 4.118 | 582 |
| 4.430 | 5-(4-{(2S)-2-(1H-benzimidazol-2-yl)-2-[(5-chloro-1,3-benzothiazol-2-yl)amino]ethyl}phenyl) isothiazolidin-3-one 1,1-dioxide trifluoroacetate | H | H | H | H | Cl | H | H | Ex. 4.118 | 538 |
| 4.431 | 5-[4-((2S)-2-(1H-benzimidazol-2-yl)-2-{[5-(trifluoromethyl)-1,3-benzothiazol-2-yl]amino}ethyl)phenyl] isothiazolidin-3-one 1,1-dioxide trifluoroacetate | H | H | H | H | CF$_3$ | H | H | Ex. 4.118 | 572 |
| 4.432 | 2-({(1S)-1-(1H-benzimidazol-2-yl)-2-[4-(1,1-dioxido-3-oxoisothiazolidin-5-yl)phenyl]ethyl}amino)- | H | H | H | H | CN | H | H | Ex. 4.118 | 529 |

TABLE 4-continued

| Ex. No. | Name | $R^1$ | $R^{ib}$ | $R^{ic}$ | $R^{iia}$ | $R^{iib}$ | $R^{iic}$ | $R^{iid}$ | Ex. Proc. | MS $(M + H)^+$ |
|---|---|---|---|---|---|---|---|---|---|---|
| | 1,3-benzothiazole-5-carbonitrile trifluoroacetate | | | | | | | | | |
| 4.433 | 5-{4-[(2S)-2-[(5-acetyl-1,3-benzothiazol-2-yl)amino]-2-(1H-benzimidazol-2-yl)ethyl]phenyl}isothiazolidin-3-one 1,1-dioxide trifluoroacetate | H | H | H | H | COMe | H | H | Ex. 4.118 | 546 |
| 4.434 | 5-(4-{(2S)-2-(1H-benzimidazol-2-yl)-2-[(6-chloro-4-fluoro-1,3-benzothiazol-2-yl)amino]ethyl}phenyl)isothiazolidin-3-one 1,1-dioxide trifluoroacetate | H | H | H | F | H | Cl | H | Ex. 4.118 | 556 |
| 4.435 | 5-(4-{(2S)-2-(1H-benzimidazol-2-yl)-2-[(4,6-difluoro-1,3-benzothiazol-2-yl)amino]ethyl}phenyl)isothiazolidin-3-one 1,1-dioxide trifluoroacetate | H | H | H | F | H | F | H | Ex. 4.118 | 540 |
| 4.436 | 5-(4-{(2S)-2-(1H-benzimidazol-2-yl)-2-[(4,7-difluoro-1,3-benzothiazol-2-yl)amino]ethyl}phenyl)isothiazolidin-3-one 1,1-dioxide trifluoroacetate | H | H | H | F | H | H | F | Ex. 4.118 | 540 |
| 4.437 | 5-(4-{(2S)-2-(1H-benzimidazol-2-yl)-2-[(5,7-dimethyl-1,3-benzothiazol-2-yl)amino]ethyl}phenyl)isothiazolidin-3-one 1,1-dioxide trifluoroacetate | H | H | H | H | Me | H | Me | Ex. 4.118 | 532 |
| 4.438 | 5-(4-{(2S)-2-(1H-benzimidazol-2-yl)-2-{(6-fluoro-4-methyl-1,3-benzothiazol-2-yl)amino]ethyl}phenyl)isothiazolidin-3-one 1,1-dioxide trifluoroacetate | H | H | H | Me | H | F | H | Ex. 4.118 | 536 |
| 4.439 | 5-(4-{(2S)-2-(1H-benzimidazol-2-yl)-2-[(5,6-difluoro-1,3-benzothiazol-2-yl)amino]ethyl}phenyl)isothiazolidin-3-one 1,1-dioxide trifluoroacetate | H | H | H | H | F | F | H | Ex. 4.118 | 540 |
| 4.440 | 5-(4-{(2S)-2-(1H-benzimidazol-2-yl)-2-[(7-chloro-4-fluoro-1,3-benzothiazol-2- | H | H | H | F | H | H | Cl | Ex. 4.118 | 556 |

TABLE 4-continued

| Ex. No. | Name | R¹ | R^ib | R^ic | R^iia | R^iib | R^iic | R^iid | Ex. Proc. | MS (M + H)⁺ |
|---|---|---|---|---|---|---|---|---|---|---|
| | yl)amino]ethyl}phenyl) isothiazolidin-3-one 1,1-dioxide trifluoroacetate | | | | | | | | | |
| 4.441 | 5-(4-{(2S)-2-(1H-benzimidazol-2-yl)-2-[(5,7-difluoro-1,3-benzothiazol-2-yl)amino]ethyl}phenyl) isothiazolidin-3-one 1,1-dioxide trifluoroacetate | H | H | H | H | F | H | F | Ex. 4.118 | 540 |
| 4.442 | 5-(4-{(2S)-2-(1H-benzimidazol-2-yl)-2-[(4,5,6-trifluoro-1,3-benzothiazol-2-yl)amino]ethyl}phenyl) isothiazolidin-3-one 1,1-dioxide trifluoroacetate | H | H | H | F | F | F | H | Ex. 4.118 | 558 |
| 4.443 | 5-(4-{(2S)-2-(1H-benzimidazol-2-yl)-2-[(6-bromo-4-fluoro-1,3-benzothiazol-2-yl)amino]ethyl}phenyl) isothiazolidin-3-one 1,1-dioxide trifluoroacetate | H | H | H | F | H | Br | H | Ex. 4.118 | 558 |
| 4.444 | 5-(4-{(2S)-2-(1H-benzimidazol-2-yl)-2-[(6-bromo-4-fluoro-1,3-benzothiazol-2-yl)amino]ethyl}phenyl) isothiazolidin-3-one 1,1-dioxide trifluoroacetate | H | H | H | F | H | Br | H | Ex. 4.118 | 600 |
| 4.445 | 5-(4-{(2S)-2-(6-chloro-1H-benzimidazol-2-yl)-2-[(5-fluoro-1,3-benzothiazol-2-yl)amino]ethyl}phenyl) isothiazolidin-3-one 1,1-dioxide trifluoroacetate | H | Cl | H | H | F | H | H | Ex. 4.118 | 556 |
| 4.446 | 5-(4-{(2S)-2-(6-chloro-1H-benzimidazol-2-yl)-2-[(6-fluoro-1,3-benzothiazol-2-yl)amino]ethyl}phenyl) isothiazolidin-3-one 1,1-dioxide trifluoroacetate | H | Cl | H | H | H | F | H | Ex. 4.118 | 556 |
| 4.447 | 5-(4-{(2S)-2-(6-chloro-1H-benzimidazol-2-yl)-2-[(6-chloro-1,3-benzothiazol-2-yl)amino]ethyl}phenyl) isothiazolidin-3-one 1,1-dioxide trifluoroacetate | H | Cl | H | H | H | Cl | H | Ex. 4.118 | 572 |
| 4.448 | 5-{4-[(2S)-2-(1H-benzimidazol-2-yl)-2-(1,3- | H | H | H | H | H | H | H | Ex. 4.118 | 504 |

TABLE 4-continued

| Ex. No. | Name | R¹ | R^ib | R^ic | R^iia | R^iib | R^iic | R^iid | Ex. Proc. | MS (M + H)⁺ |
|---|---|---|---|---|---|---|---|---|---|---|
| | benzothiazol-2-ylamino)ethyl]phenyl} isothiazolidin-3-one 1,1-dioxide trifluoroacetate | | | | | | | | | |
| 4.449 | 5-{4-[(2S)-2-(1,3-benzothiazol-2-ylamino)-2-(5-chloro-1H-benzimidazo 1-2-yl)ethyl]phenyl}isothiazolidin-3-one 1,1-dioxide trifluoroacetate | H | H | Cl | H | H | H | H | Ex. 4.118 | 539 |
| 4.450 | 5-(4-{(2S)-2-(1H-benzimidazol-2-yl)-2-[(4-bromo-1,3-benzothiazol-2-yl)amino]ethyl}phenyl) isothiazolidin-3-one 1,1-dioxide trifluoroacetate | H | H | H | Br | H | H | H | Ex. 4.118 | 582 |
| 4.451 | 5-(4-{(2S)-2-(1H-benzimidazol-2-yl)-2-[(4-fluoro-1,3-benzothiazol-2-yl)amino]ethyl}phenyl) isothiazolidin-3-one 1,1-dioxide trifluoroacetate | H | H | H | F | H | H | H | Ex. 4.118 | 522 |
| 4.452 | 5-(4-{(2S)-2-(1H-benzimidazol-2-yl)-2-[(4-chloro-1,3-benzothiazol-2-yl)amino]ethyl}phenyl) isothiazolidin-3-one 1,1-dioxide trifluoroacetate | H | H | H | Cl | H | H | H | Ex. 4.118 | 539 |
| 4.453 | 5-(4-{(2S)-2-(1H-benzimidazol-2-yl)-2-[(4-methoxy-1,3-benzothiazol-2-yl)amino]ethyl}phenyl) isothiazolidin-3-one 1,1-dioxide trifluoroacetate | H | H | H | OMe | H | H | H | Ex. 4.118 | 534 |
| 4.454 | 5-[4-((2S)-2-(1H-benzimidazol-2-yl)-2-{[4-(trifluoromethyl)-1,3-benzothiazol-2-yl]amino}ethyl)phenyl] isothiazolidin-3-one 1,1-dioxide trifluoroacetate | H | H | H | CF₃ | H | H | H | Ex. 4.118 | 572 |
| 4.455 | 5-(4-{(2S)-2-(1H-benzimidazol-2-yl)-2-[(6-bromo-1,3-benzothiazol-2-yl)amino]ethyl}phenyl) isothiazolidin-3-one 1,1-dioxide trifluoroacetate | H | H | H | H | H | Br | H | Ex. 4.118 | 583 |
| 4.456 | 5-(4-{(2S)-2-(1H-benzimidazol-2-yl)-2-[(6- | H | H | H | H | H | F | H | Ex. 4.118 | 522 |

TABLE 4-continued

| Ex. No. | Name | R¹ | $R^{ib}$ | $R^{ic}$ | $R^{iia}$ | $R^{iib}$ | $R^{iic}$ | $R^{iid}$ | Ex. Proc. | MS $(M + H)^+$ |
|---|---|---|---|---|---|---|---|---|---|---|
| | fluoro-1,3-benzothiazol-2-yl)amino]ethyl}phenyl)isothiazolidin-3-one 1,1-dioxide trifluoroacetate | | | | | | | | | |
| 4.457 | 5-(4-{(2S)-2-(1H-benzimidazol-2-yl)-2-[(6-chloro-1,3-benzothiazol-2-yl)amino]ethyl}phenyl)isothiazolidin-3-one 1,1-dioxide trifluoroacetate | H | H | H | H | H | Cl | H | Ex. 4.118 | 539 |
| 4.458 | 5-(4-{(2S)-2-(1H-benzimidazol-2-yl)-2-[(6-methyl-1,3-benzothiazol-2-yl)amino]ethyl}phenyl)isothiazolidin-3-one 1,1-dioxide trifluoroacetate | H | H | H | H | H | Me | H | Ex. 4.118 | 518 |
| 4.459 | 5-(4-{(2S)-2-(1H-benzimidazol-2-yl)-2-[(6-methoxy-1,3-benzothiazol-2-yl)amino]ethyl}phenyl)isothiazolidin-3-one 1,1-dioxide trifluoroacetate | H | H | H | H | H | OMe | H | Ex. 4.118 | 534 |
| 4.460 | 5-[4-((2S)-2-(1H-benzimidazol-2-yl)-2-{[6-(trifluoromethyl)-1,3-benzothiazol-2-yl]amino}ethyl]phenyl]isothiazolidin-3-one 1,1-dioxide trifluoroacetate | H | H | H | H | H | CF₃ | H | Ex. 4.118 | 572 |
| 4.461 | 2-({(1S)-1-(1H-benzimidazol-2-yl)-2-[4-(1,1-dioxido-3-oxoisothiazolidin-5-yl)phenyl]ethyl}amino)-1,3-benzothiazole-6-carbonitrile trifluoroacetate | H | H | H | H | H | CN | H | Ex. 4.118 | 529 |
| 4.462 | 5-(4-{(2S)-2-(1H-benzimidazol-2-yl)-2-[(5-bromo-1,3-benzothiazol-2-yl)amino]ethyl}phenyl)isothiazolidin-3-one 1,1-dioxide trifluoroacetate | H | H | H | H | Br | H | H | Ex. 4.118 | 583 |
| 4.463 | 5-(4-{(2S)-2-[(6-methoxy-1,3-benzothiazol-9-yl)amino]-2-[5-(trifluoromethyl)-1H-benzimidazol-2-yl]ethyl}phenyl)isothiazolidin-3-one 1,1-dioxide trifluoroacetate | H | H | CF₃ | H | H | OMe | H | Ex. 4.118 | 602 |

TABLE 4-continued

| Ex. No. | Name | R¹ | $R^{ib}$ | $R^{ic}$ | $R^{iia}$ | $R^{iib}$ | $R^{iic}$ | $R^{iid}$ | Ex. Proc. | MS (M + H)⁺ |
|---|---|---|---|---|---|---|---|---|---|---|
| 4.464 | 5-{4-[(2S)-2-(1H-benzimidazol-2-yl)-2-(1,3-benzothiazol-2-ylamino)ethyl]phenyl} isothiazolidin-3-one 1,1-dioxide trifluoroacetate (Isomer 1) | H | H | H | H | H | H | H | Ex. 4.118 | 504 |
| 4.465 | 5-{4-[(2S)-2-(1H-benzimidazol-2-yl)-2-(1,3-benzothiazol-2-ylamino)ethyl]phenyl} isothiazolidin-3-one 1,1-dioxide trifluoroacetate (Isomer 2) | H | H | H | H | H | H | H | Ex. 4.118 | 504 |

TABLE 5

| Ex. No. | Name | R¹ | $Y^A$ | $R^{ii}$ | Ex. Proc. | MS (M + H)⁺ |
|---|---|---|---|---|---|---|
| 4.466 | N-(1S)-1-(1H-benzimidazol-2-yl)-2-[4-(1,1-dioxido-3-oxoisothiazolidin-5-yl)-3-fluorophenyl]ethyl-3-(2-chlorophenyl)propanamide trifluoroacetate | F | (CH₂)₂ | 2-Cl-Ph | Ex. 4.226 | 555 |
| 4.467 | N-(1S)-1-(1H-benzimidazol-2-yl)-2-[4-(1,1-dioxido-3- | H | CF₂ | Me | Ex. 4.226 | 562 |

TABLE 5-continued

| Ex. No. | Name | R¹ | $Y^A$ | $R^{ii}$ | Ex. Proc. | MS (M + H)⁺ |
|---|---|---|---|---|---|---|
| | oxoisothiazolidin-5-yl)phenyl]ethyl-2,2-difluoropropanamide trifluoroacetate | | | | | |
| 4.468 | N-(1S)-1-(1H-benzimidazol-2-yl)-2-[4-(1,1-dioxido-3-oxoisothiazolidin-5-yl)phenyl]ethyl-2,2-difluoro-2-phenylacetamide trifluoroacetate | H | $CF_2$ | Ph | Ex. 4.226 | 524 |
| 4.469 | (2Z)-N-(1S)-1-(1H-benzimidazol-2-yl)-2-[4-(1,1-dioxido-3-oxoisothiazolidin-5-yl)phenyl]ethyl-2-fluoro-3-phenylacrylamide trifluoroacetate | H | CF | CHPh | Ex. 4.226 | 518 |

TABLE 6

| Ex. No. | Name | $R^{iia}$ | $R^{iib}$ | $R^{iid}$ | Ex. Proc. | MS (M + H)⁺ |
|---|---|---|---|---|---|---|
| 4.470 | N-[(1S)-2-[3-chloro-4-(1,1-dioxido-3-oxoisothiazolidin-5-yl)phenyl]-1-(5-phenyl-1H-imidazol-2-yl)ethyl]-3-(trifluoromethyl)benzenesulfonamide trifluoroacetate | H | $CF_3$ | H | Ex. 4.233 | 639 |
| 4.471 | N-[(1S)-2-[3-chloro-4-(1,1-dioxido-3-oxoisothiazolidin-5-yl)phenyl]-1-(5-phenyl-1H-imidazol-2-yl)ethyl]-2- | $OCF_3$ | H | H | Ex. 4.233 | 655 |

TABLE 6-continued

[Structure shown]

| Ex. No. | Name | $R^{iia}$ | $R^{iib}$ | $R^{iid}$ | Ex. Proc. | MS $(M + H)^+$ |
|---|---|---|---|---|---|---|
| | (trifluoromethoxy) benzenesulfonamide trifluoroacetate | | | | | |
| 4.472 | 3-bromo-N-[(1S)-2-[3-chloro-4-(1,1-dioxido-3-oxoisothiazolidin-5-yl)phenyl]-1-(5-phenyl-1H-imidazol-2-yl)ethyl]benzenesulfonamide trifluoroacetate | H | Br | H | Ex. 651 4.233 | |

TABLE 7

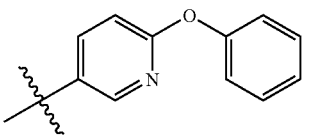

| Ex. No. | Name | $R^{ia}$ | $R^{iia}$ | Ex. Proc. | MS $(M + H)^+$ |
|---|---|---|---|---|---|
| 4.473 | N-{(1S)-1-(1H-benzimidazol-2-yl)-2-[4-(1,1-dioxido-3-oxoisothiazolidin-5-yl)phenyl]ethyl}-5-methyl-2-(trifluoromethyl)furan-3-sulfonamide trifluoroacetate | H | [structure] | Ex. 4.118 | 583 |
| 4.474 | N-{(1S)-1-(1H-benzimidazol-2-yl)-2-[4-(1,1-dioxido-3-oxoisothiazolidin-5-yl)phenyl]ethyl}-6-phenoxypyridine-3-sulfonamide trifluoroacetate | H | [structure] | Ex. 4.118 | 604 |

TABLE 7-continued

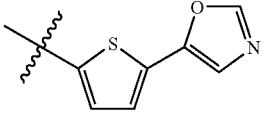

| Ex. No. | Name | $R^{ia}$ | $R^{iia}$ | Ex. Proc. | MS (M + H)$^+$ |
|---|---|---|---|---|---|
| 4.475 | N-{(1S)-1-(1H-benzimidazol-2-yl)-2-[4-(1,1-dioxido-3-oxoisothiazolidin-5-yl)phenyl]ethyl}-5-(1,3-oxazol-5-yl)thiophene-2-sulfonamide trifluoroacetate | H | 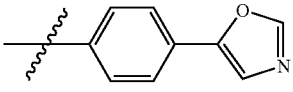 | Ex. 4.118 | 584 |
| 4.476 | N-{(1S)-1-(1H-benzimidazol-2-yl)-2-[4-(1,1-dioxido-3-oxoisothiazolidin-5-yl)phenyl]ethyl}-4-(1,3-oxazol-5-yl)benzenesulfonamide trifluoroacetate | H | 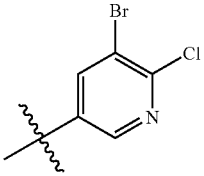 | Ex. 4.118 | 578 |
| 4.477 | N-{(1S)-1-(1H-benzimidazol-2-yl)-2-[4-(1,1-dioxido-3-oxoisothiazolidin-5-yl)phenyl]ethyl}-5-bromo-6-chloropyridine-3-sulfonamide trifluoroacetate | H | 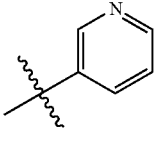 | Ex. 4.118 | 625 |
| 4.478 | N-{(1S)-1-(1H-benzimidazol-2-yl)-2-[4-(1,1-dioxido-3-oxoisothiazolidin-5-yl)phenyl]ethyl}pyridine-3-sulfonamide trifluoroacetate | H | 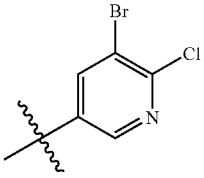 | Ex. 4.118 | 512 |
| 4.479 | 5-bromo-6-chloro-N-{(1S)-1-(5-chloro-1H-benzimidazol-2-yl)-2-[4-(1,1-dioxido-3-oxoisothiazolidin-5-yl)phenyl]ethyl}pyridine-3-sulfonamide trifluoroacetate | Cl | 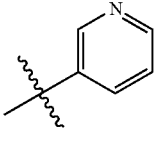 | Ex. 4.118 | 660 |

TABLE 8

| Ex. No. | Name | R$^{ic}$ | R$^{iib}$ | R$^{iic}$ | Ex. Proc. | MS (M + H)$^+$ |
|---|---|---|---|---|---|---|
| 4.480 | N-{(1S)-1-(1H-benzimidazol-2-yl)-2-[4-(1,1-dioxido-3-oxoisothiazolidin-5-yl)phenyl]ethyl}-4-(3,5-dichlorophenoxy)benzenesulfonamide trifluoroacetate | H | H | —O-(3,5-diCl-Ph) | Ex. 4.118 | 672 |
| 4.481 | N-{(1S)-1-(1H-benzimidazol-2-yl)-2-[4-(1,1-dioxido-3-oxoisothiazolidin-5-yl)phenyl]ethyl}-4-(3,4-dichlorophenoxy)benzenesulfonamide trifluoroacetate | H | H | —O-(3,4-diCl-Ph) | Ex. 4.118 | 672 |
| 4.482 | N-{(1S)-1-(1H-benzimidazol-2-yl)-2-[4-(1,1-dioxido-3-oxoisothiazolidin-5-yl)phenyl]ethyl}-4-(4-methylphenoxy)benzenesulfonamide trifluoroacetate trifluoroacetate | H | H | —O-(4-Me-Ph) | Ex. 4.118 | 617 |
| 4.483 | N-{(1S)-1-(1H-benzimidazol-2-yl)-2-[4-(1,1-dioxido-3-oxoisothiazolidin-5-yl)phenyl]ethyl}-4-[4-(trifluoromethyl)phenoxy]benzenesulfonamide trifluoroacetate | H | H | —O-(4-CF$_3$-Ph) | Ex. 4.118 | 671 |
| 4.484 | N-{(1S)-1-(1H-benzimidazol-2-yl)-2-[4-(1,1-dioxido-3-oxoisothiazolidin-5-yl)phenyl]ethyl}-3-(2-chlorophenoxy)benzenesulfonamide trifluoroacetate | H | —O-(2-Cl-Ph) | H | Ex. 4.118 | 638 |
| 4.485 | N-{(1S)-1-(1H-benzimidazol-2-yl)-2-[4-(1,1-dioxido-3-oxoisothiazolidin-5-yl)phenyl]ethyl}-3-(2-methylphenoxy)benzenesulfonamide trifluoroacetate | H | —O-(2-Me-Ph) | H | Ex. 4.118 | 617 |
| 4.486 | N-{(1S)-1-(1H-benzimidazol-2-yl)-2-[4-(1,1-dioxido-3-oxoisothiazolidin-5-yl)phenyl]ethyl}-4-[2-(trifluoromethyl)phenoxy]benzenesulfonamide trifluoroacetate | H | H | —O-(2-CF$_3$-Ph) | Ex. 4.118 | 671 |
| 4.487 | N-{(1S)-1-(1H-benzimidazol-2-yl)-2-[4-(1,1-dioxido-3-oxoisothiazolidin-5-yl)phenyl]ethyl}-4-(pyridin-4-yloxy)benzenesulfonamide trifluoroacetate | H | H | —O-(4-pyridyl) | Ex. 4.118 | 604 |

TABLE 8-continued

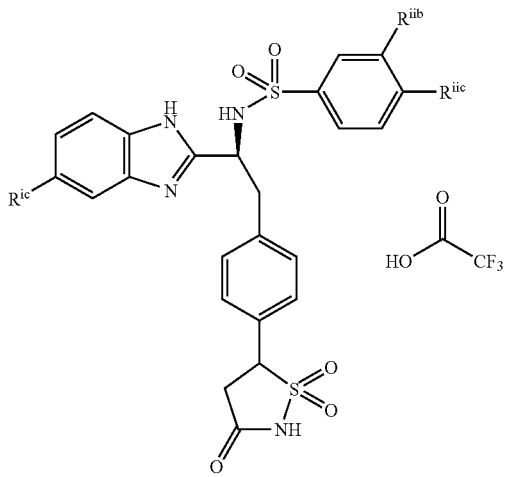

| Ex. No. | Name | $R^{ic}$ | $R^{iib}$ | $R^{iic}$ | Ex. Proc. | MS $(M + H)^+$ |
|---|---|---|---|---|---|---|
| 4.488 | N-{(1S)-1-(1H-benzimidazol-2-yl)-2-[4-(1,1-dioxido-3-oxoisothiazolidin-5-yl)phenyl]ethyl}-4-(2-chlorophenoxy)benzenesulfonamide trifluoroacetate | H | H | —O-(2-Cl-Ph) | Ex. 4.118 | 638 |
| 4.489 | N-{(1S)-1-(1H-benzimidazol-2-yl)-2-[4-(1,1-dioxido-3-oxoisothiazolidin-5-yl)phenyl]ethyl}-4-(2-methylphenoxy)benzenesulfonamide trifluoroacetate | H | H | —O-(2-Me-Ph) | Ex. 4.118 | 617 |
| 4.490 | N-{(1S)-1-(1H-benzimidazol-2-yl)-2-[4-(1,1-dioxido-3-oxoisothiazolidin-5-yl)phenyl]ethyl}-4-(pyridin-2-yloxy)benzenesulfonamide trifluoroacetate | H | H | —O-(2-pyridyl) | Ex. 4.118 | 604 |
| 4.491 | N-{(1S)-1-(1H-benzimidazol-2-yl)-2-[4-(1,1-dioxido-3-oxoisothiazolidin-5-yl)phenyl]ethyl}-4-(pyridin-3-yloxy)benzenesulfonamide trifluoroacetate | H | H | —O-(3-pyridyl) | Ex. 4.118 | 604 |
| 4.492 | N-{(1S)-1-(1H-benzimidazol-2-yl)-2-[4-(1,1-dioxido-3-oxoisothiazolidin-5-yl)phenyl]ethyl}-3-(4-chlorophenoxy)benzenesulfonamide trifluoroacetate | H | —O-(4-Cl-Ph) | H | Ex. 4.118 | 638 |
| 4.493 | N-{(1S)-1-(1H-benzimidazol-2-yl)-2-[4-(1,1-dioxido-3-oxoisothiazolidin-5-yl)phenyl]ethyl}-3-(3,5-dichlorophenoxy)benzenesulfonamide trifluoroacetate | H | —O-(3,5-diCl-Ph) | H | Ex. 4.118 | 672 |
| 4.494 | N-{(1S)-1-(1H-benzimidazol-2-yl)-2-[4-(1,1-dioxido-3-oxoisothiazolidin-5-yl)phenyl]ethyl}-3-(3,4-dichlorophenoxy)benzenesulfonamide trifluoroacetate | H | —O-(3,4-diCl-Ph) | H | Ex. 4.118 | 672 |
| 4.495 | N-{(1S)-1-(1H-benzimidazol-2-yl)-2-[4-(1,1-dioxido-3-oxoisothiazolidin-5-yl)phenyl]ethyl}-3-(4-fluorophenoxy)benzenesulfonamide trifluoroacetate | H | —O-(4-F-Ph) | H | Ex. 4.118 | 621 |
| 4.496 | N-{(1S)-1-(1H-benzimidazol-2-yl)-2-[4-(1,1-dioxido-3-oxoisothiazolidin-5- | H | —O-(4-Me-Ph) | H | Ex. 4.118 | 617 |

TABLE 8-continued

| Ex. No. | Name | $R^{ic}$ | $R^{iib}$ | $R^{iic}$ | Ex. Proc. | MS $(M + H)^+$ |
|---|---|---|---|---|---|---|
| | yl)phenyl]ethyl}-3-(4-methylphenoxy)benzenesulfonamide trifluoroacetate | | | | | |
| 4.497 | N-{(1S)-1-(1H-benzimidazol-2-yl)-2-[4-(1,1-dioxido-3-oxoisothiazolidin-5-yl)phenyl]ethyl}-3-[4-(trifluoromethyl)phenoxy]benzenesulfonamide trifluoroacetate | H | —O-(4-CF$_3$-Ph) | H | Ex. 4.118 | 671 |
| 4.498 | N-{(1S)-1-(1H-benzimidazol-2-yl)-2-[4-(1,1-dioxido-3-oxoisothiazolidin-5-yl)phenyl]ethyl}-3-[2-(trifluoromethyl)phenoxy]benzenesulfonamide trifluoroacetate | H | —O-(2-CF$_3$-Ph) | H | Ex. 4.118 | 671 |
| 4.499 | N-{(1S)-1-(5-chloro-1H-benzimidazol-2-yl)-2-[4-(1,1-dioxido-3-oxoisothiazolidin-5-yl)phenyl]ethyl}-3-(3,4-dichlorophenoxy)benzenesulfonamide trifluoroacetate | Cl | —O-(3,4-diCl-Ph) | H | Ex. 4.118 | 707 |
| 4.500 | N-{(1S)-1-(5-chloro-1H-benzimidazol-2-yl)-2-[4-(1,1-dioxido-3-oxoisothiazolidin-5-yl)phenyl]ethyl}-3-[4-(trifluoromethyl)phenoxy]benzenesulfonamide trifluoroacetate | Cl | —O-(4-CF$_3$-Ph) | H | Ex. 4.118 | 706 |
| 4.501 | N-{(1S)-1-(5-chloro-1H-benzimidazol-2-yl)-2-[4-(1,1-dioxido-3-oxoisothiazolidin-5-yl)phenyl]ethyl}-3-(4-chlorophenoxy)benzenesulfonamide trifluoroacetate | Cl | —O-(4-Cl-Ph) | H | Ex. 4.118 | 672 |

TABLE 9

| Ex. No. | Name | $R^{ia}$ | $R^{iia}$ | $R^{iib}$ | $R^{iic}$ | $R^{iid}$ | Ex. Proc. | MS $(M + H)^+$ |
|---|---|---|---|---|---|---|---|---|
| 3.12 | N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}benzenesulfonamide trifluoroacetate | Cl | H | H | H | H | Ex. 3.3 | 580 |
| 3.13 | N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}-2-cyanobenzenesulfonamide trifluoroacetate | Cl | CN | H | H | H | Ex. 3.3 | 605 |
| 3.14 | N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}-4-cyanobenzenesulfonamide trifluoroacetate | Cl | H | H | CN | H | Ex. 3.3 | 605 |
| 3.15 | N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}-3-phenoxybenzenesulfonamide | Cl | H | OPh | H | H | Ex. 3.3 | 672 |
| 3.16 | N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}-3,4-dimethoxybenzenesulfonamide trifluoroacetate | Cl | H | OMe | OMe | H | Ex. 3.3 | 640 |
| 3.17 | N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}-3,5-dimethylbenzenesulfonamide trifluoroacetate | Cl | H | Me | H | Me | Ex. 3.3 | 608 |
| 3.18 | N-{(1S)-1-(1H-benzimidazol-2-yl)-2-[3-chloro-4-(1,1-dioxido-4-oxo-1,2,5-thiadiazolidin-2-yl)phenyl]ethyl}-benzenesulfonamide trifluoroacetate | H | H | H | H | H | Ex. 3.3 | 546 |
| 3.19 | N-{(1S)-1-(1H-benzimidazol-2-yl)-2-[3-chloro-4-(1,1-dioxido-4-oxo-1,2,5-thiadiazolidin-2-yl)phenyl]ethyl}-2- | H | CN | H | H | H | Ex. 3.3 | 571 |

TABLE 9-continued

| Ex. No. | Name | $R^{ia}$ | $R^{iia}$ | $R^{iib}$ | $R^{iic}$ | $R^{iid}$ | Ex. Proc. | MS (M + H)$^+$ |
|---|---|---|---|---|---|---|---|---|
| | cyanobenzenesulfonamide trifluoroacetate | | | | | | | |
| 3.20 | N-{(1S)-1-(1H-benzimidazol-2-yl)-2-[3-chloro-4-(1,1-dioxido-4-oxo-1,2,5-thiadiazolidin-2-yl)phenyl]ethyl}-4-cyanobenzenesulfonamide trifluoroacetate | H | H | H | CN | H | Ex. 3.3 | 571 |
| 3.21 | N-{(1S)-1-(1H-benzimidazol-2-yl)-2-[3-chloro-4-(1,1-dioxido-4-oxo-1,2,5-thiadiazolidin-2-yl)phenyl]ethyl}-3-phenoxybenzenesulfonamide trifluoroacetate | H | H | OPh | H | H | Ex. 3.3 | 638 |
| 3.22 | N-{(1S)-1-(1H-benzimidazol-2-yl)-2-[3-chloro-4-(1,1-dioxido-4-oxo-1,2,5-thiadiazolidin-2-yl)phenyl]ethyl}-3,4-dimethoxybenzenesulfonamide trifluoroacetate | H | H | OMe | OMe | H | Ex. 3.3 | 606 |
| 3.23 | N-{(1S)-1-(1H-benzimidazol-2-yl)-2-[3-chloro-4-(1,1-dioxido-4-oxo-1,2,5-thiadiazolidin-2-yl)phenyl]ethyl}-3,5-dimethylbenzenesulfonamide trifluoroacetate | H | H | Me | H | Me | Ex. 3.3 | 574 |
| 3.24 | 3-chloro-N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}benzenesulfonamide trifluoroacetate | Cl | H | Cl | H | H | Ex. 3.3 | 614 |
| 3.25 | N-{(1S)-1-(5-chloro-1H-benzimidazol-2-yl)-2-[3-chloro-4-(1,1-dioxido-4-oxo-1,2,5-thiadiazolidin-2-yl)phenyl]ethyl}-3-fluorobenzenesulfonamide trifluoroacetate | Cl | H | F | H | H | Ex. 3.3 | 598 |
| 3.26 | N-{(1S)-1-(1H-benzimidazol-2-yl)-2-[3-chloro-4-(1,1-dioxido-4-oxo-1,2,5-thiadiazolidin-2-yl)phenyl]ethyl}-3-chlorobenzenesulfonamide trifluoroacetate | H | H | Cl | H | H | Ex. 3.3 | 580 |
| 3.27 | N-{(1S)-1-(1H-benzimidazol-2-yl)-2-[3-chloro-4-(1,1- | H | H | F | H | H | Ex. 3.3 | 564 |

TABLE 9-continued

[Structure diagram showing a benzimidazole-containing compound with sulfonamide, chlorophenyl, thiadiazolidinone groups, and trifluoroacetate]

| Ex. No. | Name | R$^{ia}$ | R$^{iia}$ | R$^{iib}$ | R$^{iic}$ | R$^{iid}$ | Ex. Proc. | MS (M + H)$^+$ |
|---|---|---|---|---|---|---|---|---|
| | dioxido-4-oxo-1,2,5-thiadiazolidin-2-yl)phenyl]ethyl}-3-fluorobenzenesulfonamide trifluoroacetate | | | | | | | |

TABLE 10

[Structure diagram showing a benzimidazole compound with trifluoroacetamide, phenyl, oxoisothiazolidine dioxide groups, and trifluoroacetate]

| Ex. No. | Name | R$^{ib}$ | R$^{ic}$ | Ex. Proc. | MS (M + H)$^+$ |
|---|---|---|---|---|---|
| 4.502 | N-{(1S)-1-(6-cyano-1H-benzimidazol-2-yl)-2-[4-(1,1-dioxido-3-oxoisothiazolidin-5-yl)phenyl]ethyl}-2,2,2-trifluoroacetamide trifluoroacetate | CN | H | Ex. 4.185 | 492 |
| 4.503 | N-{(1S)-1-(6-chloro-1H-benzimidazol-2-yl)-2-[4-(1,1-dioxido-3-oxoisothiazolidin-5-yl)phenyl]ethyl}-2,2,2-trifluoroacetamide trifluoroacetate | Cl | H | Ex. 4.185 | 501 |
| 4.504 | methyl 2-{(1S)-2-[4-(1,1-dioxido-3-oxoisothiazolidin-5-yl)phenyl]-1-[(trifluoroacetyl)amino]ethyl}-1H-benzimidazole-6-carboxylate trifluoroacetate | CO$_2$Me | H | Ex. 4.185 | 525 |
| 4.505 | N-{(1S)-1-(6-(trifluoromethyl)-1H-benzimidazol-2-yl)-2-[4-(1,1-dioxido-3-oxoisothiazolidin-5-yl)phenyl]ethyl}-2,2,2-trifluoroacetamide trifluoroacetate | CF$_3$ | H | Ex. 4.185 | 535 |

TABLE 10-continued

| Ex. No. | Name | R$^{ib}$ | R$^{ic}$ | Ex. Proc. | MS (M + H)$^+$ |
|---|---|---|---|---|---|
| 4.506 | N-{(1S)-1-(6-methoxy-1H-benzimidazol-2-yl)-2-[4-(1,1-dioxido-3-oxoisothiazolidin-5-yl)phenyl]ethyl}-2,2,2-trifluoroacetamide trifluoroacetate | OMe | H | Ex. 4.185 | 497 |
| 4.507 | N-{(1S)-1-(5,6-dichloro-1H-benzimidazol-2-yl)-2-[4-(1,1-dioxido-3-oxoisothiazolidin-5-yl)phenyl]ethyl}-2,2,2-trifluoroacetamide trifluoroacetate | Cl | Cl | Ex. 4.185 | 535 |

TABLE 11

| Ex. No. | Name | R$^{ib}$ | R$^{ic}$ | R$^{id}$ | Ex. Proc. | MS (M + H)$^+$ |
|---|---|---|---|---|---|---|
| 4.508 | N-[(1S)-2-[4-(1,1-dioxido-3-oxoisothiazolidin-5-yl)phenyl]-1-(3H-imidazo[4,5-c]pyridin-2-yl)ethyl]biphenyl-4-sulfonamide trifluoroacetate | H | Ph | H | Ex. 4.118 | 588 |
| 4.509 | N-[(1S)-2-[4-(1,1-dioxido-3-oxoisothiazolidin-5-yl)phenyl]-1-(3H-imidazo[4,5-c]pyridin-2-yl)ethyl]-3-phenoxybenzenesulfonamide trifluoroacetate | OPh | H | H | Ex. 4.118 | 604 |
| 4.510 | 4-chloro-N-[(1S)-2-[4-(1,1-dioxido-3-oxoisothiazolidin-5-yl)phenyl]-1-(3H-imidazo[4,5- | CF$_3$ | Cl | H | Ex. 4.118 | 614 |

TABLE 11-continued

| Ex. No. | Name | $R^{ib}$ | $R^{ic}$ | $R^{id}$ | Ex. Proc. | MS (M + H)+ |
|---|---|---|---|---|---|---|
| | c]pyridin-2-yl)ethyl]-3-(trifluoromethyl)benzenesulfonamide trifluoroacetate | | | | | |
| 4.511 | 3-chloro-N-[(1S)-2-[4-(1,1-dioxido-3-oxoisothiazolidin-5-yl)phenyl]-1-(3H-imidazo[4,5-c]pyridin-2-yl)ethyl]-4-methylbenzenesulfonamide trifluoroacetate | Cl | Me | H | Ex. 4.118 | 560 |
| 4.512 | N-[(1S)-2-[4-(1,1-dioxido-3-oxoisothiazolidin-5-yl)phenyl]-1-(3H-imidazo[4,5-c]pyridin-2-yl)ethyl]-3,5-bis(trifluoromethyl)benzenesulfonamide trifluoroacetate | $CF_3$ | H | $CF_3$ | Ex. 4.118 | 648 |

TABLE 12

| Ex. No. | Name | $R^1$ | $R^{ia}$ | $R^{ib}$ | $R^{ic}$ | $R^{iia}$ | $R^{iib}$ | $R^{iic}$ | $R^{iid}$ | $R^{iie}$ | Ex. Proc. | MS (M + H)+ |
|---|---|---|---|---|---|---|---|---|---|---|---|---|
| 4.513 | N-{(1S)-1-(1H-benzimidazol-2-yl)-2-[4-(1,1-dioxido-3-oxoisothiazolidin-5-yl)-3-methylphenyl]ethyl}-3- | Me | H | H | H | H | Cl | H | H | H | Ex. 4.215 | 559 |

TABLE 12-continued

[Structure diagram showing a benzimidazole compound with sulfonamide group and isothiazolidinone moiety, with trifluoroacetate counterion]

| Ex. No. | Name | R¹ | $R^{ia}$ | $R^{ib}$ | $R^{ic}$ | $R^{iia}$ | $R^{iib}$ | $R^{iic}$ | $R^{iid}$ | $R^{iie}$ | Ex. Proc. | MS (M + H)⁺ |
|---|---|---|---|---|---|---|---|---|---|---|---|---|
| | chlorobenzenesulfonamide trifluoroacetate | | | | | | | | | | | |
| 4.514 | N-{(1S)-1-(1H-benzimidazol-2-yl)-2-[4-(1,1-dioxido-3-oxoisothiazolidin-5-yl)-3-methylphenyl]ethyl}-3-fluorobenzenesulfonamide trifluoroacetate | Me | H | H | H | H | F | H | H | H | Ex. 4.215 | 543 |
| 4.516 | N-{(1S)-1-(1H-benzimidazol-2-yl)-2-[4-(1,1-dioxido-3-oxoisothiazolidin-5-yl)-3-methylphenyl]ethyl}-2-cyanobenzenesulfonamide trifluoroacetate | Me | H | H | H | CN | H | H | H | H | Ex. 4.215 | 550 |
| 4.517 | N-{(1S)-1-(1H-benzimidazol-2-yl)-2-[4-(1,1-dioxido-3-oxoisothiazolidin-5-yl)-3-methylphenyl]ethyl}-4-methylbenzenesulfonamide trifluoroacetate | Me | H | H | H | H | H | Me | H | H | Ex. 4.215 | 539 |
| 4.518 | N-{(1S)-1-(1H-benzimidazol-2-yl)-2-[4-(1,1-dioxido-3-oxoisothiazolidin-5-yl)-3-methylphenyl]ethyl}-4-(trifluoromethyl)benzenesulfonamide trifluoroacetate | Me | H | H | H | H | H | CF₃ | H | H | Ex. 4.215 | 593 |
| 4.519 | N-{(1S)-1-(1H-benzimidazol-2-yl)-2-[4-(1,1-dioxido-3-oxoisothiazolidin-5-yl)-3-methylphenyl]ethyl}-3-methoxybenzenesulfonamide trifluoroacetate | Me | H | H | H | H | OMe | H | H | H | Ex. 4.215 | 555 |
| 4.520 | N-{(1S)-1-(1H-benzimidazol-2-yl)-2-[4-(1,1-dioxido-3-oxoisothiazolidin-5-yl)-3-methylphenyl]ethyl}-3-bromobenzenesulfonamide trifluoroacetate | Me | H | H | H | H | Br | H | H | H | Ex. 4.215 | 603,605 |
| 4.521 | N-{(1S)-1-(1H-benzimidazol-2-yl)-2-[4-(1,1-dioxido-3-oxoisothiazolidin-5-yl)-3-methylphenyl]ethyl}-3-chloro-5-fluoro-2- | Me | H | H | H | Me | Cl | H | F | H | Ex. 4.215 | 591 |

TABLE 12-continued

[Structure diagram showing benzimidazole-sulfonamide compound with substituents R¹, Rⁱᵃ, Rⁱᵇ, Rⁱᶜ, Rⁱⁱᵃ, Rⁱⁱᵇ, Rⁱⁱᶜ, Rⁱⁱᵈ, Rⁱⁱᵉ and trifluoroacetate counterion]

| Ex. No. | Name | $R^1$ | $R^{ia}$ | $R^{ib}$ | $R^{ic}$ | $R^{iia}$ | $R^{iib}$ | $R^{iic}$ | $R^{iid}$ | $R^{iie}$ | Ex. Proc. | MS (M + H)⁺ |
|---|---|---|---|---|---|---|---|---|---|---|---|---|
| 4.522 | N-{(1S)-1-(1H-benzimidazol-2-yl)-2-[4-(1,1-dioxido-3-oxoisothiazolidin-5-yl)-3-methylphenyl]ethyl}-3-chloro-4-methylbenzenesulfonamide trifluoroacetate | Me | H | H | H | H | Cl | Me | H | H | Ex. 4.215 | 573 |
| 4.523 | N-{(1S)-1-(1H-benzimidazol-2-yl)-2-[4-(1,1-dioxido-3-oxoisothiazolidin-5-yl)-3-methylphenyl]ethyl}-4-bromo-3-(trifluoromethyl)benzenesulfonamide trifluoroacetate | Me | H | H | H | H | CF₃ | Br | H | H | Ex. 4.215 | 671 |
| 4.524 | N-[4-(Aminosulfonyl)benzyl]-4-[(1,1-dioxido-3-oxoisothiazolidin-5-yl)-methyl]-benzamide trifluoroacetate | H | H | H | H | H | Cl | H | H | Cl | Ex. 4.118 | 580 |
| 4.525 | N-{(1S)-1-(1H-benzimidazol-2-yl)-2-[4-(1,1-dioxido-3-oxoisothiazolidin-5-yl)phenyl]ethyl}-3-fluoro-4-methylbenzenesulfonamide trifluoroacetate | H | H | H | H | H | H | Me | F | H | Ex. 4.118 | 543 |
| 4.526 | N-{(1S)-1-(1H-benzimidazol-2-yl)-2-[4-(1,1-dioxido-3-oxoisothiazolidin-5-yl)phenyl]ethyl}-3,4-dichlorobenzenesulfonamide trifluoroacetate | H | H | H | H | H | H | Cl | Cl | H | Ex. 4.118 | 580 |
| 4.527 | N-{(1S)-1-(1H-benzimidazol-2-yl)-2-[4-(1,1-dioxido-3-oxoisothiazolidin-5-yl)phenyl]ethyl}-4-fluoro-2-methylbenzenesulfonamide trifluoroacetate | H | H | H | H | Me | H | F | H | H | Ex. 4.118 | 543 |
| 4.528 | N-{(1S)-1-(1H-benzimidazol-2-yl)-2-[4-(1,1-dioxido-3-oxoisothiazolidin-5-yl)phenyl]ethyl}-2,5- | H | H | H | H | OMe | H | H | OMe | H | Ex. 4.118 | 571 |

TABLE 12-continued

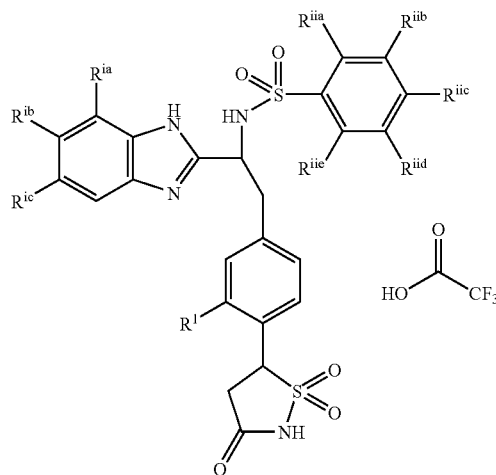

| Ex. No. | Name | R¹ | Rⁱᵃ | Rⁱᵇ | Rⁱᶜ | Rⁱⁱᵃ | Rⁱⁱᵇ | Rⁱⁱᶜ | Rⁱⁱᵈ | Rⁱⁱᵉ | Ex. Proc. | MS (M + H)⁺ |
|---|---|---|---|---|---|---|---|---|---|---|---|---|
| | dimethoxybenzenesulfonamide trifluoroacetate | | | | | | | | | | | |
| 4.529 | N-{(1S)-1-(1H-benzimidazol-2-yl)-2-[4-(1,1-dioxido-3-oxoisothiazol din-5-yl)phenyl]ethyl}-3-chloro-2-fluorobenzenesulfonamide trifluoroacetate | H | H | H | H | F | Cl | H | H | H | Ex. 4.118 | 564 |
| 4.530 | N-{(1S)-1-(1H-benzimidazol-2-yl)-2-[4-(1,1-dioxido-3-oxoisothiazolidin-5-yl)phenyl]ethyl}-3-chloro-4-fluorobenzenesulfonamide trifluoroacetate | H | H | H | H | H | Cl | F | H | H | Ex. 4.118 | 564 |
| 4.531 | N-{(1S)-1-(1H-benzimidazol-2-yl)-2-[4-(1,1-dioxido-3-oxoisothiazolidin-5-yl)phenyl]ethyl}-2,4-difluorobenzenesulfonamide trifluoroacetate | H | H | H | H | F | H | F | H | H | Ex. 4.118 | 547 |
| 4.532 | N-{(1S)-1-(1H-benzimidazol-2-yl)-2-[4-(1,1-dioxido-3-oxoisothiazolidin-5-yl)phenyl]ethyl}-3,4-dimethoxybenzenesulfonamide trifluoroacetate | H | H | H | H | H | OMe | OMe | H | H | Ex. 4.118 | 571 |
| 4.533 | N-{(1S)-1-(1H-benzimidazol-2-yl)-2-[4-(1,1-dioxido-3-oxoisothiazolidin-5-yl)phenyl]ethyl}-2,3-dichlorobenzenesulfonamide trifluoroacetate | H | H | H | H | Cl | Cl | H | H | H | Ex. 4.118 | 580 |
| 4.534 | N-{(1S)-1-(1H-benzimidazol-2-yl)-2-[4-(1,1-dioxido-3-oxoisothiazolidin-5-yl)phenyl]ethyl}-3-chloro-2-methylbenzenesulfonamide trifluoroacetate | H | H | H | H | Me | Cl | H | H | H | Ex. 4.118 | 560 |
| 4.535 | N-{(1S)-1-(1H-benzimidazol-2-yl)-2-[4-(1,1-dioxido-3-oxoisothiazolidin-5-yl)phenyl]ethyl}-2,4- | H | H | H | H | Cl | H | Cl | H | H | Ex. 4.118 | 580 |

TABLE 12-continued

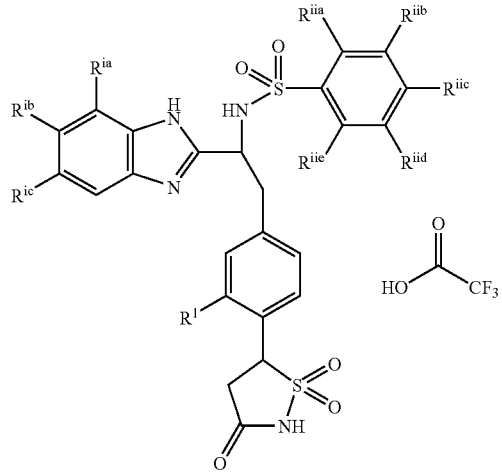

| Ex. No. | Name | $R^1$ | $R^{ia}$ | $R^{ib}$ | $R^{ic}$ | $R^{iia}$ | $R^{iib}$ | $R^{iic}$ | $R^{iid}$ | $R^{iie}$ | Ex. Proc. | MS $(M + H)^+$ |
|---|---|---|---|---|---|---|---|---|---|---|---|---|
| | dichlorobenzenesulfonamide trifluoroacetate | | | | | | | | | | | |
| 4.536 | N-{(1S)-1-(1H-benzimidazol-2-yl)-2-[4-(1,1-dioxido-3-oxoisothiazolidin-5-yl)phenyl]ethyl}-2-bromo-5-(trifluoromethyl)benzenesulfonamide trifluoroacetate | H | H | H | H | Br | H | H | $CF_3$ | H | Ex. 4.118 | 658 |
| 4.537 | N-{(1S)-1-(1H-benzimidazol-2-yl)-2-[4-(1,1-dioxido-3-oxoisothiazolidin-5-yl)phenyl]ethyl}-2-chloro-5-(trifluoromethyl)benzenesulfonamide trifluoroacetate | H | H | H | H | Cl | H | H | $CF_3$ | H | Ex. 4.118 | 614 |
| 4.538 | N-{(1S)-1-(1H-benzimidazol-2-yl)-2-[4-(1,1-dioxido-3-oxoisothiazolidin-5-yl)phenyl]ethyl}-2-chloro-4-(trifluoromethyl)benzenesulfonamide trifluoroacetate | H | H | H | H | Cl | H | $CF_3$ | H | H | Ex. 4.118 | 614 |
| 4.539 | N-{(1S)-1-(1H-benzimidazol-2-yl)-2-[4-(1,1-dioxido-3-oxoisothiazolidin-5-yl)phenyl]ethyl}-3,5-dimethylbenzenesulfonamide trifluoroacetate | H | H | H | H | H | Me | H | Me | H | Ex. 4.118 | 539 |
| 4.540 | N-{(1S)-1-(1H-benzimidazol-2-yl)-2-[4-(1,1-dioxido-3-oxoisothiazolidin-5-yl)phenyl]ethyl}-2-fluoro-5-(trifluoromethyl)benzenesulfonamide trifluoroacetate | H | H | H | H | F | H | H | $CF_3$ | H | Ex. 4.118 | 597 |
| 4.541 | N-{(1S)-1-(1H-benzimidazol-2-yl)-2-[4-(1,1-dioxido-3-oxoisothiazolidin-5-yl)phenyl]ethyl}-4-fluoro-2-(trifluoromethyl)benzenesulfonamide trifluoroacetate | H | H | H | H | $CF_3$ | H | F | H | H | Ex. 4.118 | 597 |
| 4.542 | N-{(1S)-1-(1H-benzimidazol-2-yl)-2-[4- | H | H | H | H | OPh | H | H | H | H | | 603 |

TABLE 12-continued

| Ex. No. | Name | R¹ | $R^{ia}$ | $R^{ib}$ | $R^{ic}$ | $R^{iia}$ | $R^{iib}$ | $R^{iic}$ | $R^{iid}$ | $R^{iie}$ | Ex. Proc. | MS (M + H)⁺ |
|---|---|---|---|---|---|---|---|---|---|---|---|---|
| | (1,1-dioxido-3-oxoisothiazolidin-5-yl)phenyl]ethyl}-2-phenoxybenzenesulfonamide trifluoroacetate | | | | | | | | | | | |
| 4.543 | N-{(1S)-1-(1H-benzimidazol-2-yl)-2-[4-(1,1-dioxido-3-oxoisothiazolidin-5-yl)phenyl]ethyl}-3-(difluoromethoxy)benzenesulfonamide trifluoroacetate | H | H | H | H | H | OCHF₂ | H | H | H | Ex. 4.118 | 577 |
| 4.544 | N-{(1S)-1-(1H-benzimidazol-2-yl)-2-[4-(1,1-dioxido-3-oxoisothiazolidin-5-yl)phenyl]ethyl}-3-chloro-5-fluoro-2-methylbenzenesulfonamide trifluoroacetate | H | H | H | H | Me | Cl | H | F | H | Ex. 4.118 | 578 |
| 4.545 | N-{(1S)-1-(1H-benzimidazol-2-yl)-2-[4-(1,1-dioxido-3-oxoisothiazolidin-5-yl)phenyl]ethyl}-4-(1,1-dimethylpropyl)benzenesulfonamide trifluoroacetate | H | H | H | H | H | H | C(Me)₂CH₂CH₃ | H | H | Ex. 4.118 | 581 |
| 4.546 | N-{(1S)-1-(1H-benzimidazol-2-yl)-2-[4-(1,1-dioxido-3-oxoisothiazolidin-5-yl)phenyl]ethyl}-4-chloro-2,5-dimethylbenzenesulfonamide trifluoroacetate | H | H | H | H | Me | H | Cl | Me | H | Ex. 4.118 | 574 |
| 4.547 | N-{(1S)-1-(1H-benzimidazol-2-yl)-2-[4-(1,1-dioxido-3-oxoisothiazolidin-5-yl)phenyl]ethyl}-3-chloro-5-fluoro-2-methylbenzenesulfonamide | H | H | H | H | Me | Cl | H | F | H | Ex. 4.118 | 612 |
| 4.548 | N-{(1S)-1-(1H-benzimidazol-2-yl)-2-[4-(1,1-dioxido-3-oxoisothiazolidin-5-yl)phenyl]ethyl}-4-bromo-3-(trifluoromethyl) | H | H | H | H | H | CF₃ | Br | H | H | Ex. 4.118 | 692 |

TABLE 12-continued

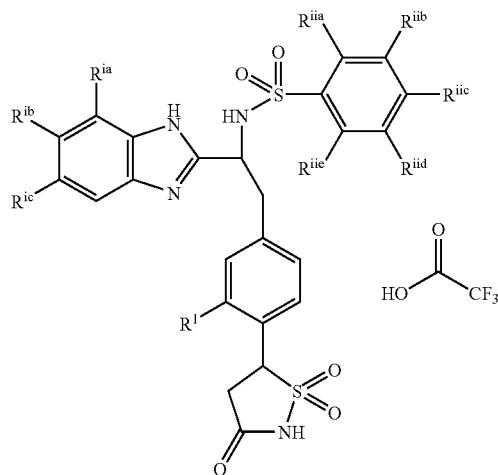

| Ex. No. | Name | R¹ | $R^{ia}$ | $R^{ib}$ | $R^{ic}$ | $R^{iia}$ | $R^{iib}$ | $R^{iic}$ | $R^{iid}$ | $R^{iie}$ | Ex. Proc. | MS $(M+H)^+$ |
|---|---|---|---|---|---|---|---|---|---|---|---|---|
| | benzenesulfonamide trifluoroacetate | | | | | | | | | | | |
| 4.549 | N-{(1S)-1-(1H-benzimidazol-2-yl)-2-[4-(1,1-dioxido-3-oxoisothiazolidin-5-yl)phenyl]ethyl}-4-bromo-2-(trifluoromethoxy)benzenesulfonamide trifluoroacetate | H | H | H | H | $OCF_3$ | H | Br | H | H | Ex. 4.118 | 708 |
| 4.550 | N-(1S)-1-(1H-benzimidazol-2-yl)-2-[3-chloro-4-(1,1-dioxido-3-oxoisothiazolidin-5-yl)phenyl]ethylbiphenyl-4-sulfonamide trifluoroacetate | Cl | H | H | H | H | H | Ph | H | H | Ex. 4.227 | 621 |
| 4.551 | N-(1S)-1-(1H-benzimidazol-2-yl)-2-[4-(1,1-dioxido-3-oxoisothiazolidin-5-yl)-3-fluorophenyl]ethylbenzenesulfonamide trifluoroacetate | F | H | H | H | H | H | H | H | H | Ex. 4.227 | 529 |
| 4.552 | N-(1S)-1-(1H-benzimidazol-2-yl)-2-[4-(1,1-dioxido-3-oxoisothiazolidin-5-yl)-3-fluorophenyl]ethyl-3-fluorobenzenesulfonamide trifluoroacetate | F | H | H | H | H | F | H | H | H | Ex. 4.227 | 547 |
| 4.553 | N-(1S)-1-(1H-benzimidazol-2-yl)-2-[3-chloro-4-(1,1-dioxido-3-oxoisothiazolidin-5-yl)phenyl]ethyl-4-phenoxybenzenesulfonamide trifluoroacetate | Cl | H | H | H | H | H | OPh | H | H | Ex. 4.227 | 637 |
| 4.554 | N-(1S)-1-(1H-benzimidazol-2-yl)-2-[3-chloro-4-(1,1-dioxido-3-oxoisothiazolidin-5-yl)phenyl]ethyl-3-chloro-4-methylbenzenesulfonamide trifluoroacetate | Cl | H | H | H | H | Cl | Me | H | H | Ex. 4.227 | 595 |
| 4.555 | N-(1S)-1-(1H-benzimidazol-2-yl)-2-[3-chloro-4-(1,1-dioxido-3-oxoisothiazolidin-5-yl)phenyl]ethyl-4-bromo- | Cl | H | H | H | H | $CF_3$ | Br | H | H | Ex. 4.227 | 693 |

TABLE 12-continued

[Structure diagram showing a benzimidazole with R^ia, R^ib, R^ic substituents, connected through a chiral carbon bearing an NHSO2-aryl group (with R^iia, R^iib, R^iic, R^iid, R^iie substituents), and a CH2-phenyl group (with R^1 substituent) bearing a 1,1-dioxido-3-oxoisothiazolidin-5-yl group; with trifluoroacetate counterion]

| Ex. No. | Name | R¹ | R^ia | R^ib | R^ic | R^iia | R^iib | R^iic | R^iid | R^iie | Ex. Proc. | MS (M + H)⁺ |
|---|---|---|---|---|---|---|---|---|---|---|---|---|
| | 3-(trifluoromethyl)benzenesulfonamide trifluoroacetate | | | | | | | | | | | |
| 4.556 | N-(1S)-1-(1H-benzimidazol-2-yl)-2-[3-chloro-4-(1,1-dioxido-3-oxoisothiazolidin-5-yl)phenyl]ethyl-2-(trifluoromethoxy)benzenesulfonamide trifluoroacetate | Cl | H | H | H | OCF₃ | H | H | H | H | Ex. 4.227 | 629 |
| 4.557 | N-(1S)-1-(1H-benzimidazol-2-yl)-2-[3-chloro-4-(1,1-dioxido-3-oxoisothiazolidin-5-yl)phenyl]ethyl-3-bromobenzenesulfonamide trifluoroacetate | Cl | H | H | H | H | Br | H | H | H | Ex. 4.227 | 625 |
| 4.558 | N-(1S)-1-(1H-benzimidazol-2-yl)-2-[3-chloro-4-(1,1-dioxido-3-oxoisothiazolidin-5-yl)phenyl]ethyl-3-chloro-5-fluoro-2-methylbenzenesulfonamide trifluoroacetate | Cl | H | H | H | Me | Cl | H | F | H | Ex. 4.227 | 611 |
| 4.559 | N-[(1S)-2-[4-(1,1-dioxido-3-oxoisothiazolidin-5-yl)phenyl]-1-(7-methyl-1H-benzimidazol-2-yl)ethyl]biphenyl-4-sulfonamide trifluoroacetate | H | Me | H | H | H | H | Ph | H | H | Ex. 4.118 | 601 |
| 4.560 | N-{(1S)-2-[4-(1,1-dioxido-3-oxoisothiazolidin-5-yl)phenyl]-1-(7-hydroxy-1H-benzimidazol-2-yl)ethyl]biphenyl-4-sulfonamide trifluoroacetate | H | OH | H | H | H | H | Ph | H | H | Ex. 4.118 | 603 |
| 4.561 | N-[(1S)-2-[4-(1,1-dioxido-3-oxoisothiazolidin-5-yl)phenyl]-1-(6-methyl-1H-benzimidazol-2-yl)ethyl]biphenyl-4-sulfonamide trifluoroacetate | H | H | Me | H | H | H | Ph | H | H | Ex. 4.118 | 601 |
| 4.562 | N-[(1S)-2-[4-(1,1-dioxido-3-oxoisothiazolidin-5-yl)phenyl]-1-(6-fluoro-1H-benzimidazol-2-yl)ethyl]biphenyl-4- | H | H | F | H | H | H | Ph | H | H | Ex. 4.118 | 605 |

TABLE 12-continued

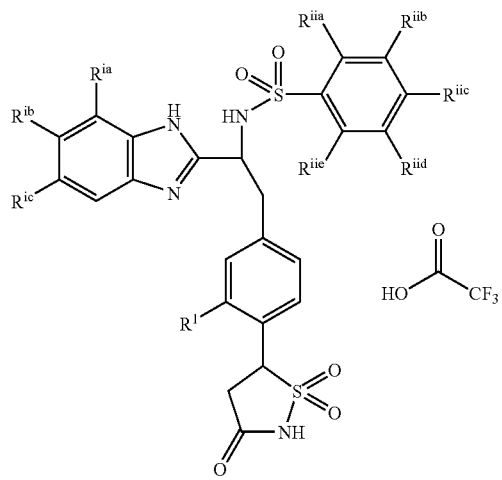

| Ex. No. | Name | R¹ | Rⁱᵃ | Rⁱᵇ | Rⁱᶜ | Rⁱⁱᵃ | Rⁱⁱᵇ | Rⁱⁱᶜ | Rⁱⁱᵈ | Rⁱⁱᵉ | Ex. Proc. | MS (M + H)⁺ |
|---|---|---|---|---|---|---|---|---|---|---|---|---|
| 4.563 | N-{(1S)-1-(6-cyano-1H-benzimidazol-2-yl)-2-[4-(1,1-dioxido-3-oxoisothiazolidin-5-yl)phenyl]ethyl}biphenyl-4-sulfonamide trifluoroacetate | H | H | CN | H | H | H | Ph | H | H | Ex. 4.118 | 612 |
| 4.564 | N-{(1S)-1-(6-chloro-1H-benzimidazol-2-yl)-2-[4-(1,1-dioxido-3-oxoisothiazolidin-5-yl)phenyl]ethyl}biphenyl-4-sulfonamide trifluoroacetate | H | H | Cl | H | H | H | Ph | H | H | Ex. 4.118 | 621 |
| 4.565 | methyl 2-{(1S)-1-[(biphenyl-4-ylsulfonyl)amino]-2-[4-(1,1-dioxido-3-oxoisothiazolidin-5-yl)phenyl]ethyl}-1H-benzimidazole-6-carboxylate trifluoroacetate | H | H | CO₂Me | H | H | H | Ph | H | H | Ex. 4.118 | 645 |
| 4.566 | N-{(1S)-2-[4-(1,1-dioxido-3-oxosothiazolidin-5-yl)phenyl]-1-[6-(trifluoromethyl)-1H-benzimidazol-2-yl]ethyl}biphenyl-4-sulfonamide trifluoroacetate | H | H | CF₃ | H | H | H | Ph | H | H | Ex. 4.118 | 655 |
| 4.567 | N-[(1S)-2-[4-(1,1-dioxido-3-oxoisothiazolidin-5-yl)phenyl]-1-(6-methoxy-1H-benzimidazol-2-yl)ethyl]biphenyl-4-sulfonamide trifluoroacetate | H | H | OMe | H | H | H | Ph | H | H | Ex. 4.118 | 617 |
| 4.568 | N-[(1S)-2-[4-(1,1-dioxido-3-oxoisothiazolidin-5-yl)phenyl]-1-(7-methyl-1H-benzimidazol-2-yl)ethyl]-3-phenoxybenzenesulfonamide trifluoroacetate | H | Me | H | H | H | OPh | H | H | H | Ex. 4.118 | 617 |
| 4.569 | N-[(1S)-2-[4-(1,1-dioxido-3-oxoisothiazolidin-5-yl)phenyl]-1-(6-methyl-1H-benzimidazol-2- | H | H | Me | H | H | OPh | H | H | H | Ex. 4.118 | 617 |

TABLE 12-continued

| Ex. No. | Name | R¹ | Rⁱᵃ | Rⁱᵇ | Rⁱᶜ | Rⁱⁱᵃ | Rⁱⁱᵇ | Rⁱⁱᶜ | Rⁱⁱᵈ | Rⁱⁱᵉ | Ex. Proc. | MS (M + H)⁺ |
|---|---|---|---|---|---|---|---|---|---|---|---|---|
| 4.570 | N-[(1S)-2-[4-(1,1-dioxido-3-oxoisothiazolidin-5-yl)phenyl]-1-(6-fluoro-1H-benzimidazol-2-yl)ethyl]-3-phenoxybenzenesulfonamide trifluoroacetate | H | H | F | H | H | OPh | H | H | H | Ex. 4.118 | 621 |
| 4.571 | N-[(1S)-2-[4-(1,1-dioxido-3-oxoisothiazolidin-5-yl)phenyl]-1-(6-cyano-1H-benzimidazol-2-yl)ethyl]-3-phenoxybenzenesulfonamide trifluoroacetate | H | H | CN | H | H | OPh | H | H | H | Ex. 4.118 | 628 |
| 4.572 | N-[(1S)-2-[4-(1,1-dioxido-3-oxoisothiazolidin-5-yl)phenyl]-1-(6-chloro-1H-benzimidazol-2-yl)ethyl]-3-phenoxybenzenesulfonamide trifluoroacetate | H | H | Cl | H | H | OPh | H | H | H | Ex. 4.118 | 637 |
| 4.573 | methyl 2-((1S)-2-[4-(1,1-dioxido-3-oxoisothiazolidin-5-yl)phenyl]-1-{[(3-phenoxyphenyl)sulfonyl]amino}ethyl)-1H-benzimidazole-6-carboxylate trifluoroacetate | H | H | CO₂Me | H | H | OPh | H | H | H | Ex. 4.118 | 661 |
| 4.574 | N-{(1S)-2-[4-(1,1-dioxido-3-oxoisothiazolidin-5-yl)phenyl]-1-[6-(trifluoromethyl)-1H-benzimidazol-2-yl]ethyl}-3-phenoxybenzenesulfonamide trifluoroacetate | H | H | CF₃ | H | H | OPh | H | H | H | Ex. 4.118 | 671 |
| 4.575 | N-[(1S)-2-[4-(1,1-dioxido-3-oxoisothiazolidin-5-yl)phenyl]-1-(6-methoxy-1H-benzimidazol-2-yl)ethyl]-3-phenoxybenzenesulfonamide trifluoroacetate | H | H | OMe | H | H | OPh | H | H | H | Ex. 4.118 | 633 |
| 4.576 | N-{(1S)-2-[4-(1,1-dioxido-3-oxoisothiazolidin-5- | H | Me | H | H | H | CF₃ | H | CF₃ | H | Ex. 4.118 | 661 |

TABLE 12-continued

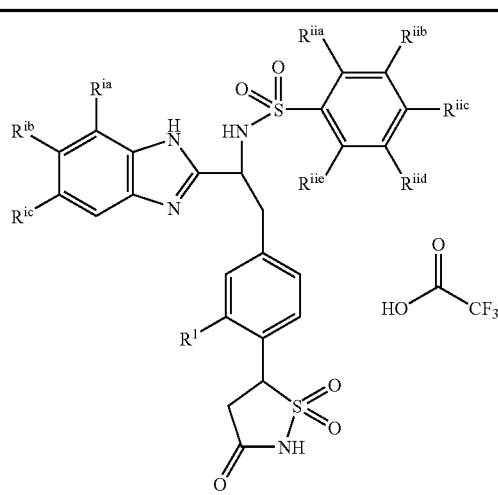

| Ex. No. | Name | R[1] | R[ia] | R[ib] | R[ic] | R[iia] | R[iib] | R[iic] | R[iid] | R[iie] | Ex. Proc. | MS (M + H)+ |
|---|---|---|---|---|---|---|---|---|---|---|---|---|
| | yl)phenyl]-1-[7-methyl-1H-benzimidazol-2-yl]ethyl}-3,5-bis(trifluoromethyl) benzenesulfonamide trifluoroacetate | | | | | | | | | | | |
| 4.577 | N-{(1S)-2-[4-(1,1-dioxido-3-oxoisothiazolidin-5-yl)phenyl]-1-[6-methyl-1H-benzimidazol-2-yl]ethyl}-3,5-bis(trifluoromethyl) benzenesulfonamide trifluoroacetate | H | H | Me | H | H | CF$_3$ | H | CF$_3$ | H | Ex. 4.118 | 661 |
| 4.578 | N-{(1S)-2-[4-(1,1-dioxido-3-oxoisothiazolidin-5-yl)phenyl]-1-[6-fluoro-1H-benzimidazol-2-yl]ethyl}-3,5-bis(trifluoromethyl) benzenesulfonamide trifluoroacetate | H | H | F | H | H | CF$_3$ | H | CF$_3$ | H | Ex. 4.118 | 665 |
| 4.579 | N-{(1S)-2-[4-(1,1-dioxido-3-oxoisothiazolidin-5-yl)phenyl]-1-[6-cyano-1H-benzimidazol-2-yl]ethyl}-3,5-bis(trifluoromethyl) benzenesulfonamide trifluoroacetate | H | H | CN | H | H | CF$_3$ | H | CF$_3$ | H | Ex. 4.118 | 672 |
| 4.580 | N-{(1S)-2-[4-(1,1-dioxido-3-oxoisothiazolidin-5-yl)phenyl]-1-[6-chloro-1H-benzimidazol-2-yl]ethyl}-3,5-bis(trifluoromethyl) benzenesulfonamide trifluoroacetate | H | H | Cl | H | H | CF$_3$ | H | CF$_3$ | H | Ex. 4.118 | 681 |
| 4.581 | methyl 2-{(1S)-1-({[3,5-bis(trifluoromethyl)phenyl]sulfonyl}amino)-2-[4-(1,1-dioxido-3-oxoisothiazolidin-5-yl)phenyl]ethyl}-1H-benzimidazole-6-carboxylate trifluoroacetate | H | H | CO$_2$Me | H | H | CF$_3$ | H | CF$_3$ | H | Ex. 4.118 | 705 |

TABLE 12-continued

[Structure: benzimidazole with substituents R$^{ia}$, R$^{ib}$, R$^{ic}$ connected via CH(NHSO$_2$-aryl)CH$_2$ to a phenyl group bearing R$^1$ and a 1,1-dioxido-3-oxoisothiazolidin-5-yl group; aryl sulfonamide bears R$^{iia}$, R$^{iib}$, R$^{iic}$, R$^{iid}$, R$^{iie}$; with CF$_3$COOH]

| Ex. No. | Name | R$^1$ | R$^{ia}$ | R$^{ib}$ | R$^{ic}$ | R$^{iia}$ | R$^{iib}$ | R$^{iic}$ | R$^{iid}$ | R$^{iie}$ | Ex. Proc. | MS (M + H)$^+$ |
|---|---|---|---|---|---|---|---|---|---|---|---|---|
| 4.582 | N-{(1S)-2-[4-(1,1-dioxido-3-oxoisothiazolidin-5-yl)phenyl]-1-[6-(trifluoromethyl)-1H-benzimidazol-2-yl]ethyl}-3,5-bis(trifluoromethyl)benzenesulfonamide trifluoroacetate | H | H | CF$_3$ | H | H | CF$_3$ | H | CF$_3$ | H | Ex. 4.118 | 715 |
| 4.583 | N-{(1S)-2-[4-(1,1-dioxido-3-oxoisothiazolidin-5-yl)phenyl]-1-[6-methoxy-1H-benzimidazol-2-yl]ethyl}-3,5-bis(trifluoromethyl)benzenesulfonamide trifluoroacetate | H | H | OMe | H | H | CF$_3$ | H | CF$_3$ | H | Ex. 4.118 | 677 |
| 4.584 | 4-chloro-N-[(1S)-2-[4-(1,1-dioxido-3-oxoisothiazolidin-5-yl)phenyl]-1-(7-methyl-1H-benzimidazol-2-yl)ethyl]-3-(trifluoromethyl)benzenesulfonamide trifluoroacetate | H | Me | H | H | H | CF$_3$ | Cl | H | H | Ex. 4.118 | 627 |
| 4.585 | 4-chloro-N-[(1S)-2-[4-(1,1-dioxido-3-oxoisothiazolidin-5-yl)phenyl]-1-(6-fluoro-1H-benzimidazol-2-yl)ethyl]-3-(trifluoromethyl)benzenesulfonamide trifluoroacetate | H | H | F | H | H | CF$_3$ | Cl | H | H | Ex. 4.118 | 631 |
| 4.586 | 4-chloro-N-[(1S)-2-[4-(1,1-dioxido-3-oxoisothiazolidin-5-yl)phenyl]-1-(6-cyano-1H-benzimidazol-2-yl)ethyl]-3-(trifluoromethyl)benzenesulfonamide trifluoroacetate | H | H | CN | H | H | CF$_3$ | Cl | H | H | Ex. 4.118 | 638 |
| 4.587 | 4-chloro-N-[(1S)-2-[4-(1,1-dioxido-3-oxoisothiazolidin-5-yl)phenyl]-1-(6-chloro-1H-benzimidazol-2-yl)ethyl]-3-(trifluoromethyl) | H | H | Cl | H | H | CF$_3$ | Cl | H | H | Ex. 4.118 | 647 |

TABLE 12-continued

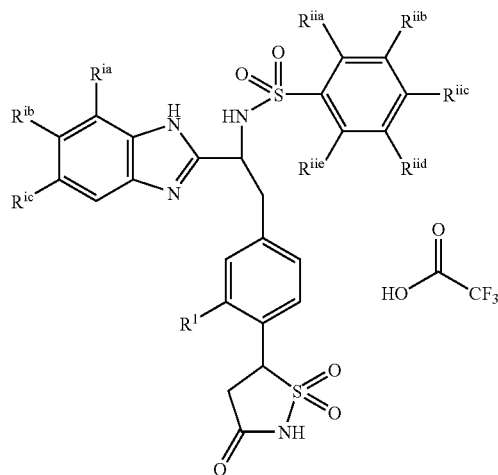

| Ex. No. | Name | R¹ | R^ia | R^ib | R^ic | R^iia | R^iib | R^iic | R^iid | R^iie | Ex. Proc. | MS (M + H)⁺ |
|---|---|---|---|---|---|---|---|---|---|---|---|---|
| | benzenesulfonamide trifluoroacetate | | | | | | | | | | | |
| 4.588 | methyl 2-{(1S)-1-({[4-chloro-3-(trifluoromethyl)phenyl]sulfonyl}amino)-2-[4-(1,1-dioxido-3-oxoisothiazolidin-5-yl)phenyl]ethyl}-1H-benzimidazole-6-carboxylate trifluoroacetate | H | H | CO₂Me | H | H | CF₃ | Cl | H | H | Ex. 4.118 | 671 |
| 4.589 | 4-chloro-N-[(1S)-2-[4-(1,1-dioxido-3-oxoisothiazolidin-5-yl)phenyl]-1-(6-(trifluoromethyl)-1H-benzimidazol-2-yl)ethyl]-3-(trifluoromethyl)benzenesulfonamide trifluoroacetate | H | H | CF₃ | H | H | CF₃ | Cl | H | H | Ex. | 681 |
| 4.590 | 3-chloro-N--[(1S)-2-[4-(1,1-dioxido-3-oxoisothiazolidin-5-yl)phenyl]-1-(7-methyl-1H-benzimidazol-2-yl)ethyl]-4-methylbenzenesulfonamide trifluoroacetate | H | Me | H | H | H | Cl | Me | H | H | Ex. 4.118 | 573 |
| 4.591 | 3-chloro-N-[(1S)-2-[4-(1,1-dioxido-3-oxoisothoiazolidin-5-yl)phenyl]-1-(6-methyl-1H-benzimidazol-2-yl)ethyl]-4-methylbenzenesulfonamide trifluoroacetate | H | H | Me | H | H | Cl | Me | H | H | Ex. 4.118 | 573 |
| 4.592 | 3-chloro-N-[(1S)-2-[4-(1,1-dioxido-3-oxoisothiazolidin-5-yl)phenyl]-1-(6-fluoro-1H-benzimidazol-2-yl)ethyl]-4-methylbenzenesulfonamide trifluoroacetate | H | H | F | H | H | Cl | Me | H | H | Ex. 4.118 | 577 |
| 4.593 | 3-chloro-N-[(1S)-2-[4-(1,1-dioxido-3-oxoisothiazolidin-5-yl)phenyl]-1-(6-cyano-1H-benzimidazol-2-yl)ethyl]-4- | H | H | CN | H | H | Cl | Me | H | H | Ex. 4.118 | 584 |

TABLE 12-continued

| Ex. No. | Name | R¹ | R^ia | R^ib | R^ic | R^iia | R^iib | R^iic | R^iid | R^iie | Ex. Proc. | MS (M + H)⁺ |
|---|---|---|---|---|---|---|---|---|---|---|---|---|
| | methylbenzenesulfonamide trifluoroacetate | | | | | | | | | | | |
| 4.594 | 3-chloro-N-[(1S)-2-[4-(1,1-dioxido-3-oxoisothiazolidin-5-yl)phenyl]-1-(6-chloro-1H-benzimidazol-2-yl)ethyl]-4-methylbenzenesulfonamide trifluoroacetate | H | H | Cl | H | H | Cl | Me | H | H | Ex. 4.118 | 593 |
| 4.595 | methyl 2-{(1S)-1-{[(3-chloro-4-methylphenyl)sulfonyl]amino}-2-[4-(1,1-dioxido-3-oxoisothiazolidin-5-yl)phenyl]ethyl}-1H-benzimidazole-6-carboxylate trifluoroacetate | H | H | CO₂Me | H | H | Cl | Me | H | H | Ex. 4.118 | 617 |
| 4.596 | 3-chloro-N-[(1S)-2-[4-(1,1-dioxido-3-oxoisothiazolidin-5-yl)phenyl]-1-(6-(trifluoromethyl)-1H-benzimidazol-2-yl)ethyl]-4-methylbenzenesulfonamide trifluoroacetate | H | H | CF₃ | H | H | Cl | Me | H | H | Ex. 4.118 | 627 |
| 4.597 | 4-chloro-N-[(1S)-2-[4-(1,1-dioxido-3-oxoisothiazolidin-5-yl)phenyl]-1-(6-methyl-1H-benzimidazol-2-yl)ethyl]-3-(trifluoromethyl)benzenesulfonamide trifluoroacetate | H | H | Me | H | H | CF₃ | Cl | H | H | Ex. 4.118 | 627 |
| 4.598 | N-{(1S)-1-(5-bromo-6,7-dimethyl-1H-benzimidazol-2-yl)-2-[4-(1,1-dioxido-3-oxoisothiazolidin-5-yl)phenyl]ethyl}biphenyl-4-sulfonamide trifluoroacetate | H | Me | Me | Br | H | Ph | H | H | H | Ex. 4.118 | 694 |
| 4.599 | N-{(1S)-1-(5,6-dichloro-1H-benzimidazol-2-yl)-2-[4-(1,1-dioxido-3-oxoisothiazolidin-5-yl)phenyl]ethyl}biphenyl-4-sulfonamide trifluoroacetate | H | H | Cl | Cl | H | Ph | H | H | H | Ex. 4.118 | 655 |

TABLE 12-continued

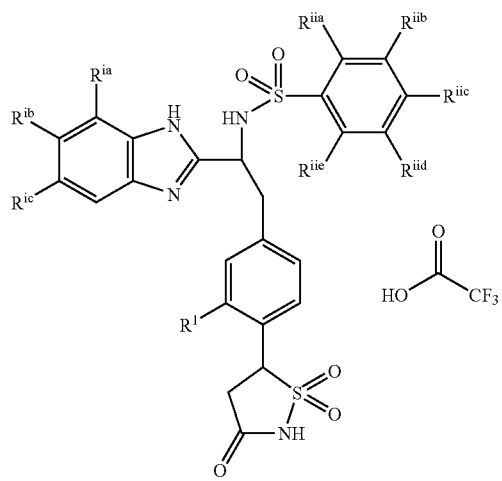

| Ex. No. | Name | $R^1$ | $R^{ia}$ | $R^{ib}$ | $R^{ic}$ | $R^{iia}$ | $R^{iib}$ | $R^{iic}$ | $R^{iid}$ | $R^{iie}$ | Ex. Proc. | MS (M + H)+ |
|---|---|---|---|---|---|---|---|---|---|---|---|---|
| 4.600 | N-{(1S)-1-(6-tert-butyl-1H-benzimidazol-2-yl)-2-[4-(1,1-dioxido-3-oxoisothiazolidin-5-yl)phenyl]ethyl}biphenyl-4-sulfonamide trifluoroacetate | H | H | t-Bu | H | H | Ph | H | H | H | Ex. 4.118 | 643 |
| 4.601 | N-{(1S)-1-[6-fluoro-5-chloro-1H-benzimidazol-2-yl]-2-[4-(1,1-dioxido-3-oxoisothiazolidin-5-yl)phenyl]ethyl}biphenyl-4-sulfonamide trifluoroacetate | H | H | F | Cl | H | Ph | H | H | H | Ex. 4.118 | 639 |
| 4.602 | N-{(1S)-1-[6-chloro-5-methyl-1H-benzimidazol-2-yl]-2-[4-(1,1-dioxido-3-oxoisothiazolidin-5-yl)phenyl]ethyl}biphenyl-4-sulfonamide trifluoroacetate | H | H | Me | Cl | H | Ph | H | H | H | Ex. 4.118 | 635 |
| 4.603 | N-{(1S)-1-[7-chloro-5-(trifluoromethyl)-1H-benzimidazol-2-yl]-2-[4-(1,1-dioxido-3-oxoisothiazolidin-5-yl)phenyl]ethyl}biphenyl-4-sulfonamide trifluoroacetate | H | Cl | H | $CF_3$ | H | Ph | H | H | H | Ex. 4.118 | 689 |
| 4.604 | N-{(1S)-1-(6-bromo-1H-benzimidazol-2-yl)-2-[4-(1,1-dioxido-3-oxoisothiazolidin-5-yl)phenyl]ethyl}biphenyl-4-sulfonamide trifluoroacetate | H | H | Br | H | H | Ph | H | H | H | Ex. 4.118 | 666 |
| 4.605 | N-[(1S)-2-[4-(1,1-dioxido-3-oxoisothiazolidin-5-yl)phenyl]-1-(7-phenyl-1H-benzimidazol-2-yl)ethyl]benzenesulfonamide trifluoroacetate | H | Ph | H | H | H | H | H | H | H | Ex. 4.118 | 587 |

Example A hPTP1B In Vitro Activity Assay

The assay described below is useful for determining inhibitory activity of compounds of the invention. Compounds having $IC_{50}$ values less than about 100 µM according to this assay are considered active.

The catalytic domain (residues 1–298) of human PTP1B with an N-terminal his tag was expressed in *E. coli* and purified to homogeneity. Compounds were serially diluted in DMSO and spotted into the assay plate. Both the enzyme and substrate were diluted into the assay buffer containing 25 mM tris-bis-propone (pH 7.0 @ rt) and 0.1 mg/ml of BSA. 40 of µL enzyme solution was added to the assay plate containing compounds and was incubated for 30 minutes. 40 µL of substrate solution was then added to the assay plate to initiate the reaction. The initial reaction rates of the dephosphorylation of p-nitrophenylphosphate to p-nitrophenol are measured by monitoring absorbance at 410 nM on a SpectraMax for 15–30 min.

Example B

Insulin Receptor (IR) Phosphorylation Cellular Assay

Human HEK293 cells engineered to overexpress human IR and PTP1b were grown to approximately 50% confluence in complete medium. The medium was changed to serum-free medium, and cells were serum deprived for 18 hours. Cells were exposed to PTP1b inhibitors (diluted from DMSO stock solutions) overnight in serum free medium. Basal phosphorylation of IR was determined by sandwich ELISA. Cells were lysed in buffer containing 25 mM Hepes (pH 7.2), 150 mM NaCl, 1 mM EDTA, 5% glycerol, 1% Triton x-100, 0.5% deoxycholic acid, 2 mM $Na_3VO_4$, 10 mM NaF, and a cocktail of protease inhibitors (Roche) on ice for 30 min. The lysates were clarified by centrifugation at 14,000 rpm for 10 min at 4° C. The amount of phosphorylated IR was determined using a sandwich ELISA kit (Biosource International) that detects phospho-tyrosines 1162 and 1163 of the IR. Values were normalized to total protein content in the lysates as determined by the Bicinchoninic Acid Assay (Pierce) using Bovine serum albumin standards. In some experiments potentiation of a submaximal level of insulin (1–10 nM recombinant human insulin, Sigma) was performed by adding to the wells for 5 to 30 min.

Example C

Glucose Transport Cellular Assays

The following assays are adapted from Sweeney et al., *J. Biol. Chem.*, 1999, 274, 10071.

Myotubule Model

L6 rat myoblasts were cultured in MEMalpha with 10% FBS. To induce differentiation of the myotubules, cells were subcultured into differentiation medium (MEMalpha with 2% FBS). Medium was replaced every other day until greater than 70% of the cells showed fusion into characteristic myotubules. Cells were starved overnight in DMEM with 5 mM glucose and 1% BSA. Cells were exposed to PTP1b inhibitors (diluted from DMSO stock solutions) for 3 hours in serum free DMEM containing 5 mM glucose. The medium was aspirated and replaced with Krebs-Ringer Buffer with or without 100 nM insulin and incubated for 15 min. This buffer was aspirated and fresh KRB containing 1 µCi of [3H]-2-deoxyglucose (2-DOG) and 25 mM unlabeled 2-DOG was added to the cells to initiate the glucose uptake assay. After 30 min incubation, the KRB was removed and the cells washed three times with cold PBS containing 20 µM cytochalasin B, lysed with 0.1 N NaOH, neutralized with 1 N HCl and an aliquot transferred into vials for liquid scintillation counting. Non-specific glucose transport was determined by preincubation of cells with 20 µM cytochalasin B in KRB during the stimulation period with insulin and subtracting the amount of [3H] 2-DOG transported under this condition from the corresponding value in the absence of cytochalasin B pretreatment.

Example D

SH2 Domain in vitro Binding Assay

A binding assay to measure the relative affinity of SH2 inhibitor compounds for SH2 domains is adapted from published procedures ("Dual specificity of Src homology 2 domains for phosphotyrosine peptide ligands", *Biochemistry*, 1997, 36, 5712). Briefly, a biotinylated peptide, is added to the wells of streptavidin-coated microtiter plates at 10 ng/ml in 50 mM Tris-HCl, pH 7.5. After 16 hours, unbound peptide is removed by washing the wells three times with Tris-buffered saline (TBS). The plate is then incubated with blocking solution (3% bovine serum albumin, 1 mM $Na_3VO_4$ in TBS) for 8 hours. Gst fusion proteins containing the SH2 domain of interest are constructed and purified using standard procedures, such as described in *Current Protocols in Molecular Biology* (John Wiley & Sons). For instance, the Gst-Src-SH2 fusion protein contains amino acids 144–251 of the Src protein while the Gst-Grb2-SH2 protein contains the entire Grb2 polypeptide. A mixture of the relevant Gst fusion protein, such as 120 ng/ml of the Gst-Src-SH2 protein, plus various concentrations of a potential SH2 inhibitor compound in blocking solution is added to wells containing the bound biotinylated phosphopeptide. After one hour, the wells are washed three times with TBS and then incubated with an anti-GST-horseradish peroxidase conjugate. After one hour, wells are washed three times with TBS and the amount of horseradish peroxidase activity is measured using tetramethylbenzidine, a compound that generates a horseradish peroxidase product that can be detected at 655 nM. Using the amount of Gst-SH2 protein bound to the biotinylated peptide at various concentrations of the known SH2 binding peptide or the potential SH2 binding protein, one can construct curves to determine the $IC_{50}$ values for inhibition of binding of the Gst-SH2 fusion protein to the biotinylated phosphopeptide. Such values can be used to identify compounds that bind SH2 domains and determine their relative affinity. Compounds are defined as active for SH2 binding if they have $IC_{50}$ values less than about 10 micromolar.

Example E

In vivo Assays for Diabetes and Obesity

The compounds described herein can be evaluated for efficacy against non-insulin dependent diabetes mellitus (NIDDM) using one of several experimental models having high serum glucose and insulin insensitivity that approximate the human disease. These include the leptin-deficient ob/ob mouse, and the leptin receptor deficient db/db mouse, the diet induced obesity (DIO) C57BL mouse, and the Zucker diabetic fatty (ZDF) rat. Blood glucose levels, insulin tolerance tests (ITT) and glucose tolerance tests (GTT) can be used to evaluate efficacy in any of the models described above.

Treatments consisting of the described compounds are expected to reduce blood glucose levels in these animals when administered orally, parenterally or by absorption through mucous membranes. After an acclimation period, diabetic rodents and glucose-normal controls are weighed and blood glucose levels determined by analysis of samples drawn by retro-orbital or tail vein bleed using standard clinical chemistry methods. Animals are randomized into treatment groups (typically 10/group) based upon blood glucose, and treatment with the described compounds are administered for a period of one to several weeks. Blood glucose levels, insulin levels, food consumption and body weights will be assessed during the treatment period and at the end of the study. For the ITT and GTT, study animals after the treatment period are fasted, tested for baseline glucose levels, and then challenged with injection of insulin, glucose, or vehicle control. Subsequent to this injection, blood glucose is assessed over a period of up to three hours.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Various modifications of the invention, in addition to those described herein, will be apparent to those skilled in the art from the foregoing description. Such modifications are also intended to fall within the scope of the appended claims. Each reference, including patents, patent applications, and publications, cited in the present application is incorporated herein by reference in its entirety.

What is claimed is:
1. A compound of Formula Va:

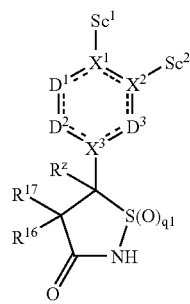

Va or pharmaceutically acceptable salt or prodrug thereof, wherein:
a dashed line indicates an optional bond;
$Sc^1$ is a first molecular scaffold or is absent;
$Sc^2$ is a second molecular scaffold or is absent, wherein at least one of $Sc^1$ and $Sc^2$ is present;
$X^1$ is C or N when $Sc^1$ is present;
$X^1$ is $CR^1$, N, $NR^2$, CO, CS, SO, or $SO_2$ when $Sc^1$ is absent;
$X^2$ is C or N when $Sc^2$ is present;
$X^2$ is $CR^1$, N, $NR^2$, CO, CS, SO, or $SO_2$ when $Sc^2$ is absent;
$X^3$ is C or N;
each $D^1$, $D^2$, and $D^3$ is, independently, $CR^1$, N, $NR^2$, CO, CS, SO, or $SO_2$, wherein the ring formed by $X^1$, $X^2$, $X^3$, $D^1$, $D^2$, and $D^3$ is an aromatic ring;
$R^Z$ is H, halo, $C_1$–$C_4$ alkyl, $C_3$–$C_6$ cycloalkyl, haloalkyl, $OR^{28}$, $SR^{28}$, $NO_2$, CN, $SOR^{29}$, $SO_2R^{29}$, $COR^{30}$, $COOR^{31}$, $NR^{32}R^{33}$, a 5- or 6-membered heterocarbocyclyl group, or tetrazolyl;
each $R^1$ is, independently, H, halo, $C_1$–$C_4$ alkyl, $C_2$–$C_4$ alkenyl, $C_2$–$C_4$ alkynyl, $C_3$–$C_6$ cycloalkyl, $C_1$–$C_4$ haloalkyl, $OR^5$, $SR^5$, $NO_2$, CN, $SOR^6$, $SO_2R^6$, $COR^7$, $COOR^8$, $NR^9R^{10}$, aryl, a 5- or 6-membered heterocarbocyclyl group, or tetrazolyl;
each $R^2$ is, independently, H, $C_1$–$C_4$ alkyl, $C_1$–$C_4$ haloalkyl, $C_3$–$C_6$ cycloalkyl, $SOR^6$, $SO_2R^6$, $COR^7$, or $COOR^8$;
or i) $R^1$ and a second $R^1$, ii) $R^2$ and second $R^2$, or iii) $R^1$ and $R^2$, together with the atoms to which they are attached, form a fused 5- or 6-membered carbocycyl or heterocarbocyclyl group, provided said i) $R^1$ and second $R^1$, ii) $R^2$ and second $R^2$, or iii) $R^1$ and $R^2$ are attached to adjacent atoms;
each $R^5$ is, independently, H, $C_1$–$C_4$ alkyl, $C_2$–$C_4$ alkenyl, $C_2$–$C_4$ alkynyl, $C_3$–$C_6$ cycloalkyl, or $C_1$–$C_4$ haloalkyl;
each $R^6$ is, independently, H, $C_1$–$C_4$ alkyl, $C_3$–$C_6$ cycloalkyl, $C_1$–$C_4$ haloalkyl, $N(R^{6a})_2$, or 5- or 6-membered heterocycloalkyl;
each $R^{6a}$ is, independently, H, $C_1$–$C_4$ alkyl, $C_3$–$C_6$ cycloalkyl, $C_4$–$C_{10}$ cycloalkylalkyl, aryl, or aralkyl;
each $R^7$ is, independently, H, $C_3$–$C_6$ cycloalkyl, $C_1$–$C_4$ alkyl, $N(R^{7a})_2$, or 5- or 6-member heterocycloalkyl;
each $R^{7a}$ is, independently, H, $C_1$–$C_4$ alkyl, $C_3$–$C_6$ cycloalkyl, $C_4$–$C_{10}$ cycloalkylalkyl, aryl, or aralkyl;
each $R^8$ is, independently, H, $C_1$–$C_4$ alkyl, $C_3$–$C_6$ cycloalkyl, or $C_1$–$C_4$ haloalkyl;
each $R^9$ and $R^{10}$ is, independently, H, $C_1$–$C_4$ alkyl, $C_3$–$C_6$ cycloalkyl, $C_1$–$C_4$ haloalky, $SO_2R^{11}$, $COR^{12}$, $COOR^{13}$, or $R^9$ and $R^{10}$ together with the N atom to which they are attached form a 5- or 6-membered heterocycloalkyl group;
$R^{11}$ is H, $C_1$–$C_4$ alkyl, $C_3$–$C_6$ cycloalkyl, $C_1$–$C_4$ haloalkyl, $N(C_1$–$C_4$ alkyl$)_2$, $NH(C_1$–$C_4$ alkyl), $NH_2$, or 5- or 6-membered heterocycloalkyl;
$R^{12}$ is H, $C_3$–$C_6$ cycloalkyl, $C_1$–$C_4$ alkyl, $N(C_1$–$C_4$ alkyl$)_2$, $NH(C_1$–$C_4$ alkyl), $NH_2$, or 5- or 6-membered heterocycloalkyl;
$R^{13}$ is H, $C_1$–$C_4$ alkyl, $C_3$–$C_6$ cycloalkyl, or $C_1$–$C_4$ haloalkyl;
$R^{15}$ is H, halo, $C_1$–$C_4$ alkyl, $C_3$–$C_6$ cycloalkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SO(C_3$–$C_6$ cycloalkyl), $SONH_2$, $SO_3H$ $SO_2(C_1$–$C_4$ alkyl), $SO_2(C_1$–$C_4$ haloalkyl), $SO_2(C_3$–$C_6$ cycloalkyl), $SO_2NH_2$, CHO, COOH, $CO(C_1$–$C_4$alkyl), $CO(C_3$–$C_6$ cycloalkyl), $CO(C_1$–$C_4$ haloalkyl), CO-(heterocarbocyclyl), $COO(C_1$–$C_4$ alkyl), $COO(C_3$–$C_6$ cycloalkyl), $COO(C_1$–$C_4$ haloalkyl), $CONH_2$, $CONH(C_1$–$C_4$ alkyl), $CON(C_1$–$C_4$ alkyl$)_2$, $CONH(C_3$–$C_6$ cycloalkyl), $CON(C_3$–$C_6$ cycloalkyl$)_2$, $NH_2$, $NH(C_1$–$C_4$ alkyl), $N(C_1$–$C_4$ alkyl$)_2$, $NH(C_3$–$C_6$ cycloalkyl), or $N(C_3$–$C_6$ cycloalkyl$)_2$;
$R^{16}$ and $R^{17}$ is, independently, H, halo, $C_1$–$C_4$ alkyl, $C_3$–$C_6$ cycloalkyl, haloalkyl, OH, $C_1$–$C_4$ alkoxy, $C_1$–$C_4$ haloalkoxy, SH, $C_1$–$C_4$ thioalkoxy, CN, $NO_2$, $SO(C_1$–$C_4$ alkyl), $SO(C_1$–$C_4$ haloalkyl), $SO(C_3$–$C_6$ cycloalkyl), $SONH_2$, $SO_3H$, $SO_2(C_1$–$C_4$ alkyl), $SO_2(C_1$–$C_4$ haloalkyl), $SO_2(C_3$–$C_6$ cycloalkyl), $SO_2NH_2$, CHO, COOH, CO($C_1$–$C_4$ alkyl), CO($C_3$–$C_6$ cycloalkyl), CO($C_1$–$C_4$ haloalkyl), CO-(heterocarbocyclyl), COO($C_1$–$C_4$ alkyl), COO($C_3$–$C_6$ cycloalkyl), COO($C_1$–$C_4$ haloalkyl), $CONH_2$, CONH($C_1$–$C_4$ alkyl), CON($C_1$–$C_4$ alkyl)$_2$, CONH($C_3$–$C_6$ cycloalkyl), CON($C_3$–$C_6$ cycloalkyl)$_2$, $NH_2$, NH($C_1$–$C_4$ alkyl), N($C_1$–$C_4$ alkyl)$_2$, NH($C_3$–$C_6$ cycloalkyl), or N($C_3$–$C_6$ cycloalkyl)$_2$;

or $R^{16}$ and $R^{17}$ together with the carbon atom to which they are attached form a $C_3$–$C_6$ cycloalkyl group or a 3–7 membered heterocycloalkyl group;

each $R^{28}$ is, independently, H, $C_1$–$C_4$ alkyl, $C_2$–$C_4$ alkenyl, $C_2$–$C_4$ alkynyl, $C_3$–$C_6$ cycloalkyl, or haloalkyl;

each $R^{29}$ is, independently, H, $C_1$–$C_4$ alkyl, $C_3$–$C_6$ cycloalkyl, haloalkyl, N($C_1$–$C_4$ alkyl)$_2$, NH($C_1$–$C_4$ alkyl), or $NH_2$;

each $R^{30}$ is, independently, H, $C_3$–$C_6$ cycloalkyl, $C_1$–$C_4$ alkyl, N($C_1$–$C_4$ alkyl)$_2$, NH($C_1$–$C_4$ alkyl), $NH_2$, or 5- or 6-membered heterocarbocyclyl;

each $R^{31}$ is, independently, H, $C_1$–$C_4$ alkyl, $C_3$–$C_6$ cycloalkyl, or haloalkyl;

each $R^{32}$ and $R^{33}$ is, independently, H, $C_1$–$C_4$ alkyl, $C_3$–$C_6$ cycloalkyl, haloalkyl, $SO_3H$, $SO_2$($C_1$–$C_4$ alkyl), $SO_2$($C_1$–$C_4$ haloalkyl), $SO_2$($C_3$–$C_6$ cycloalkyl), CHO, COOH, CO($C_1$–$C_4$ alkyl), CO($C_3$–$C_6$ cycloalkyl), CO($C_1$–$C_4$ haloalkyl), CO-(heterocarbocyclyl), COO($C_1$–$C_4$ alkyl), COO($C_3$–$C_6$ cycloalkyl), COO($C_1$–$C_4$ haloalkyl), or $R^{32}$ and $R^{33}$ together with the N atom to which they are attached form a 5- or 6-membered heterocycloalkyl group;

$R^{a1}$ and $R^{a2}$ are each, independently, H, halo, $C_1$–$C_4$ alkyl, $C_2$–$C_4$ alkenyl, $C_2$–$C_4$ alkynyl or $C_1$–$C_4$ haloalkyl;

$R^{a3}$ is H, $C_1$–$C_4$ alkyl, $C_1$–$C_4$ haloalkyl, aryl, or $C_3$–$C_7$ cycloalkyl;

$R^{a4}$ is H, $C_1$–$C_6$ alkyl, $C_1$–$C_6$ haloalkyl, aryl or $C_3$–$C_7$ cycloalkyl;

$R^{a5}$ and $R^{a6}$ are each, independently, H, $C_1$–$C_6$ alkyl, $C_1$–$C_6$ haloalkyl or $C_3$–$C_7$ cycloalkyl, or $R^{a5}$ and $R^{a6}$ together with the N atom to which they are attached form a 5- or 6-membered heterocycloalkyl ring;

$R^{a7}$ is H, $C_1$–$C_6$ alkyl, aryl, heteroaryl, $C_3$–$C_7$ cycloalkyl or heterocycloalkyl;

p2 is 0, 1, or 2;

p3 is 0, 1, or 2; and q1 is 1 or 2, wherein said firs molecular scaffold and said second molecular scaffold each have the Formula S:

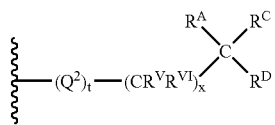

S $R^A$ has the Formula:

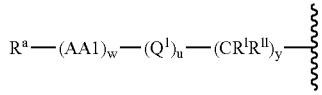

$R^C$ has the Formula:

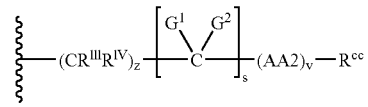

$R^D$ is H, halo, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, $COR^e$, $OCOR^e$, $COOR^f$, $SOR^g$, $SO_2R^g$, $OR^h$, $SR^h$, or $NR^iR^j$, wherein $R^D$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

or $R^A$ and $R^D$ together form the divalent moiety —$NR^y$—CO—$(CR^{z1}R^{z2})_{xx}$—;

or $R^C$ and $R^D$ together with the carbon atom to which they are attached form a cycloalkyl or heterocycloalkyl group optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

$Q^1$ is O, S, CO, COO, $CONR^b$, $NR^bCONR^b$, $NR^bSO_2NR^b$, SO, $SO_2$, $SONR^b$, $SO_2NR^b$, or $NR^b$;

$Q^2$ is O, S, CO, COO, $CONR^d$, $NR^dCONR^d$, $NR^bSO_2NR^b$, SO, $SO_2$, $SONR^d$, $SO_2NR^d$, or $NR^d$;

$R^a$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heteroeycloalkylalkyl, biaryl, biheteroaryl, arylheteroaryl, heteroarylaryl, $COR^k$, $OCOR^k$, $CONR^{k1}R^{k2}$, $COOR^L$, $C(S)R^k$, $OC(S)R^k$, $C(S)NR^{k1}R^{k2}$, $SOR^k$, or $SO_2R^k$, wherein $R^a$ is optionally substituted by one or more halo, $C_1$–$C_6$ alkyl, $C_1$–$C_6$ haloalkyl, $C_2$–$C_6$ alkenyl, $C_2$–$C_6$m alkynyl, $C_3$–$C_7$ cycloalkyl, aryl, heterocycloalkyl, heteroaryl, hydroxy, alkoxy, haloalkoxy, aryloxy, cycloalkyloxy, mercapto, thioalkoxy, thioaryloxy, cyano, nitro, $NR^rR^s$, carboxy, carboxy alkyl ester, carboxy aryl ester, —$(CH_2)_k$—$R^q$, —$(CF_2)_k$—$R^q$, $SOR^m$, or $SO_2R^m$;

or $R^a$ is —$(CR^{VII}R^{VII})_p$—$Cy^1$—$(L^1)_q$—$Cy^2$;

$R^b$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, $COR^k$, $OCOR^k$, $CONR^{k1}R^{k2}$, $COOR^L$, $C(S)R^k$, $OC(S)R^k$, $C(S)NR^{k1}R^{k2}$, $SOR^k$, or $SO_2R^k$, wherein $R^b$ is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cyctoalkyl, aryl, heterocycloalkyl, heteroaryl, hydroxy, alkoxy, haloalkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

or $R^a$ and $R^b$ together with the N atom to which they are attached form a 5- or 6-membered heterocycloalkyl ring when w is 0, wherein said 5- or 6-membered heterocycloalkyl ring is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$cycloalkyl, aryl, heterocycloalkyl, heteroaryl, aralkyl, hydroxy, alkoxy, aryloxy, cycloalkyloxy, mercapto, thioalkoxy, thioaryloxy, cyano, nitro, amino, alkylamino, dialkylamino, carboxy, carboxy alkyl ester, or carboxy aryl ester;

$R^{cc}$ is H, $C_1$–$C_{10}$ alkyl, $C_1$–$C_{10}$ baloalkyl, $C_3$–$C_7$ cycloalkyl, $C_2$–$C_{10}$ alkenyl, $C_2$–$C_{10}$ alkynyl, aryl, heteroaryl, heterocycloalkyl, aralkyl, heteroarylalkyl, cycloalkylalkyl, heterocycloalkylalkyl, biaryl, biheteroaryl, arylheteroaryl, heteroarylaryl, -aryl-heterocycloalkyl, -heteroaryl-heterocycloalkyl, $OR^n$, $SR^n$, or $NR^OR_P$, wherein $R^{cc}$ is oplionaliy substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, aralkyl, hydroxy, alkoxy, aryloxy, cycloalkyloxy, mercapto, thioalkoxy, thioaryloxy, cyano, nitro, amino, alkylamino, dialkylamino, or carboxy;

or $R^{cc}$ is a moiety of Formula:

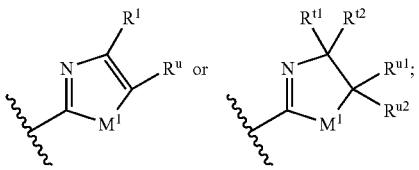

$R^d$ is H, $C_1$–$C_{10}$ alkyl, $C_1$–$C_{10}$ haloalkyl, $C_3$–$C_7$ cycloalkyl, $C_2$–$C_{10}$ alkenyl, $C_2$–$C_{10}$ alkynyl, aryl, heteroaryl, heterocycloalicyl, aralkyl, heteroarylalkyl, cycloalkylalkyl, heterocycloalkylalkyl, wherein Rd is optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, hydroxy, alkoxy, aryloxy, aralkyloxy, cycloalkyloxy, mercapto, thioalkoxy, thioaryloxy, cyano, nitro, amino, alkylamino, dialkylamino, carboxy, carboxy alkyl ester, or carboxy aryl ester;

each $R^e$ and $R^k$ is, independently, H, $C_1$–$C_6$ alkyl, $C_1$–$C_6$ haloalkyl, $C_3$–$C_{14}$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein $R^e$ and $R^k$ is optionally substituted by one or more halo, C–$C_4$ alkyl, $C_1$–$C_4$ haloalkyl, cyano, nitro, COOH, carboxy alkyl ester, carboxy aryl ester, OH, SH, alkoxy, thioakoxy, haloalkoxy, amino, alkylamino, dialkylamino, $Cy^3$, —$OCy^3$, —$SCy^3$ or heterocycloalkyl;

$R^{k1}$ and $R^{k2}$ are each, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino, wherein $R^{k1}$ and $R^{k2}$ are optionally substituted by one or more halo, $C_1$–$C_4$ alkyl, $C_1$–$C_4$haloalkyl, $C_3$–$C_6$ cycloalkyl, cyano, nitro, COOH, carboxy alkyl ester, carboxy aryl ester, OH, SH, alkoxy, thioalkoxy, aryloxy, thioaryloxy, aryl, heteroaryl, heterocycloalkyl, amino, alkylamino, dialkylamino, or heterocycloalkyl;

or $R^{k1}$ and $R^{k2}$ together with the N atom to which they are attached form a 5- or 6-membered heterocarbocyclyl group;

each $R^f$ and $R^L$ is, independently, H, $C_1$–$C_6$ alkyl, $C_1$–$C_6$ haloalkyl, $C_3$–$C_7$ cycloalkyl, $C^2$–$C_6$ alkenyl, $C_2$–$C_6$ alkynyl, aryl, heteroaryl, heterocycloalkyl, aralkyl, heteroarylalkyl, cycloalkylalkyl, or heterocycloalkylalkyl;

each $R^g$ and $R^m$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, amino, alkylamino, or dialkylamino;

each $R^h$ and $R^n$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, or heterocycloalkylalkyl, wherein said $R^h$ or $R^n$ is optionally substituted by one or more halo, hydroxy, carboxy, carboxy alkyl ester, carboxy aryl ester, amino, alkylamino, dialkylamino, or heterocycloalkyl;

each $R^i$ and $R^j$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, CO-alkyl, CO-aryl, CO-cycloalkyl, CO-heterocycloalkyl, CO-aryl, CO-heteroaryl, CO-amino, CO-alkylamino, CO-dialkylamino, COO-alkyl, COO-aryl, COO-cycloalkyl, COO-heterocycloalkyl, COO-aryl, or COO-heteroaryl, or $R^i$ and $R^j$ together with the N atom to which they are attached form a heterocycloalkyl group;

each $R^o$ and $R^p$ is, independently, H, $C_1$–$C_6$ alkyl, $C_1$–$C_6$ haloalkyl, $C_3$–$C_7$ cycloalkyl, $C_2$–$C_6$ alkenyl, $C_2$–$C_6$ alkynyl, aryl, heteroaryl, heterocycloalkyl, aralkyl, heteroarylalkyl, cycloalkylalkyl, heterocycloalkylalkyl, CO-alkyl, CO-aryl, CO-cycloalkyl, CO-heterocycloalkyl, CO-aryl, CO-heteroaryl, CO-amino, CO-alkylamino, CO-dialkylamino, COO-alkyl, COO-aryl, COO-cycloalkyl, COO-heterocycloalkyl, COO-aryl, COO-heteroaryl, or —$(CH_2)_n$—$(J^l)_m$—$K^l$, or $R^o$ and $R^p$ together with the N atom to which they are attached form a heterocycloalkyl group;

$Cy^1$, $Cy^2$, $Cy^3$ and $Cy^4$ are each, independently, carbocyclyl, heterocarbocyclyl, carbocyclylalkyl or heterocarbocyclylalkyl, each optionally substituted by one or more halo, $C_1$–$C_6$ alkyl, $C_1$–$C_6$ haloalkyl, $C_2$–$C_6$ alkenyl, $C_2$–$C_6$ alkynyl, $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $SOR^{b6}$, $SO_2R^{b6}$, $NR^{b4}COR^{b6}$, $NR^{b4}SO_2R^{b6}$, $COOR^{b3}$ $COR^{b6}$;

$R^q$ is OH, alkoxy, carboxy, alkoxycarbonyl, aryloxycarbonyl, carbocyclyl, heterocarbocyclyl, amino, alkylamino, dialkylamino, or $PO(OR^{Ph})_2$, wherein $R^{Ph}$ is H or $C_1$–$C_4$ alkyl;

$R^r$ and $R^s$ are each, independently, H, $C_1$–$C_4$ alkyl, carbocyclyl, alkylcarbonyl, arylcarbonyl or aralkyl carbonyl, or $R^r$ and $R^s$ together with the N atom to which they are attached form a 5- or 6-membered heterocycloalkyl group;

$L^1$ is O, S, $NR^{b1}$, SO, $SO_2$, $NR^{b1}CO$, $N(R^{b1})CON(R^{b1})$, $N(R^{b1})SO$, $N(R^b)SO_2$, CO or COO:

$J^1$ is O, S, $NR^{b2}$, SO, $SO_2$, $NR^{b2}CO$, $N(R^{b2})CON(R^{b2})$, $N(R^{b2})SO$, $N(R^{b2})SO_2$, CO or COO;

$K^1$ is $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylakyl, wherein said $K^1$ is optionally substituted by one or more halo, $C_1$–$C_4$ alkyl, $C_1$–$C_4$ haloalkyl, CN, $NO_2$, OH, $C_1$–$C_4$ alkoxy, $C_1$–$C_4$ haloalkoxy, COOH, COO($C_1$–$C_4$ alkyl), $NH_2$, NH($C_1$–$C_4$ alkyl), or N($C_1$–$C_4$ alkyl)$_2$, CONH$_2$, CONH($C_1$–$C_4$ alkyl), or CON($C_1$–$C_{alkyl)2}$;

$M^1$ is NR$^{v1}$, O, S, or CR$^{v2}$R$^{v3}$;

$R^{b1}$ and $R^{b2}$ are each, independently, H, $C_1$–$C_6$ alkyl, $C_1$–$C_6$ haloalkyl or $C_3$–$C_7$ cycloalkyl:

$R^{b3}$ is H, $C_1$–$C_6$ alkyl, $C_1$–$C_6$ haloalkyl, aryl or $C_3$–$C_7$ cycloalkyl;

$R^{b4}$ and $R^{b5}$ are each, independently, H, $C_1$–$C_6$ alkyl, $C_1$–$C_6$ haloalkyl or $C_3$–$C_7$ cycloalkyl, or $R^{b4}$ and $R^{b5}$ together with the N atom to which they are attached form a 5- or 6-membered heterocycloalkyl ring;

$R^{b6}$ is H, $C_1$–$C_6$ alkyl, aryl, heteroaryl, $C_3$–$C_7$ cycloalkyl or heterocycloalkyl;

each $R^I$, $R^{II}$, $R^{III}$, $R^{IV}$, $R^V$, $R^{VI}$, $R^{VII}$, and $R^{VIII}$ is, independently, H, $C_1$–$C_6$ alkyl, $C_1$–$C_6$ haloalkyl, aryl or $C_3$–$C_7$ cycloalkyl;

$R^t$ and $R^u$ are each, independently, H, $C_1$–$C_{10}$ alkyl, $C_2$–$C_{10}$ alkenyl, $C_2$–$C_{10}$ alkynyl, carbocyclyl, heterocarbocyclyl, carbocyclylalkyl, heterocarbocyclylalkyl, carbocyclalkenyl, or heterocarbocyclylalkenyl, each optionally substituted by one or more halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COOH, COO($C_1$–$C_4$ alkyl), COH, CO($C_1$–$C_4$ alkyl), NH$_2$, NH($C_1$–$C_4$ alkyl), N($C_1$–$C_4$alkyl)$_2$, NHCONH$_2$, CONH$_2$, CONH($C_1$–$C_4$ alkyl), CON($C_1$–$C_4$ alkyl)$_2$, —L$^3$—W$^4$ or —L$^3$—Cy$^4$;

or $R^t$ and $R^u$ together with the carbon atoms to which they are attached form a 4–14 membered carbocyclyl group or a 4–14 membered heterocarbocyclyl group, each optionally substituted by 1, 2, 3 or 4 substituents selected from halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COOH COO($C_1$–$C_4$ alkyl), COH, CO($C_1$–$C_4$ alkyl), NH$_2$, NH($C_1$–$C_4$ alkyl), N($C_1$–$C_4$ alkyl)$_2$, NHCONH$_2$, CONH$_2$, CONH($C_1$–$C_4$ alkyl), CON($C_1$–$C_4$ alkyl)$_2$, —L$^3$—W$^4$ or L$^3$—Cy$^4$;

or $R^t$ and $R^u$ together with the carbon atoms to which they are attached form the divalent group —P$^1$=P$^2$—P$^3$=P$^4$—;

$R^{t1}$, $R^{t2}$, $R^{u1}$, and $R^{u2}$ are each, independently, H, $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylalkyl, each optionally substituted by one or more halo, $C_1$–$C_4$ alkyl, $C_1$–$C_4$ haloalkyl, CN, NO$_2$, OH, $C_1$–$C_4$ alkoxy $C_1$–$C_4$ haloalkoxy, COOH COO($C_1$–$C_4$ alkyl), COH, CO($C_1$–$C_4$ alkyl), NH$_2$, NH($C_1$–$C_4$ alkyl), N($C_1$–$C_4$ alkyl)$_2$, NHCONH$_2$, CONH$_2$, CONH($C_1$–$C_4$ alkyl), CON($C_1$–$C_4$ alkyl)$_2$, —L$^3$—W$^4$ or —L$^3$—Cy$^4$;

or $R^{t1}$ and $R^{u1}$ together with the carbon atoms to which they are attached form a 4–14 membered carboalkyl group or a 4–14 membered heterocarbocyclyl group, each optionally substituted by 1, 2, 3 or 4 substituents selected from halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COOH, COO($C_1$–$C_4$ alkyl), COH, CO($C_1$–$C_4$ alkyl), NH$_2$, NH($C_1$–$C_4$ alkyl), N($C_1$–$C_4$ alkyl)$_2$, NHCONH$_2$, CONH$_2$, CONH($C_1$–$C_4$ alkyl), CON($C_1$–$C_4$ alkyl)$_2$, —L$^3$—W$^4$ or —L$^3$—Cy$^4$;

or $R^{t1}$ and $R^{t2}$ together with the carbon atoms to which they are attached form a 4–14 membered carboalkyl group or a 4–14 membered heterocarbocyclyl group, each optionally substituted by 1, 2, 3 or 4 substituents selected from halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COOH, COO($C_1$–$C_4$ alkyl), COH, CO($C_1$–$C_4$ alkyl), NH$_2$, NH($C_1$–$C_4$ alkyl), N($C_1$–$C_4$ alkyl)$_2$, NHCONH$_2$, CONH$_2$, CONH($C_1$–$C_4$ alkyl), CON($C_1$–$C_4$ alkyl)$_2$, —L$^3$—W$^4$ or —L$^3$—Cy$^4$;

or $R^{u1}$ and $R^{u2}$ together with the carbon atoms to which they are attached form a 4–14 membered carboalkyl group or a 4–14 membered heterocarbocyclyl group, each optionally substituted by 1, 2, 3 or 4 substituents selected from halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COOH, COO($C_1$–$C_4$ alkyl), COH, CO($C_1$–$C_4$ alkyl), NH$_2$, NH($C_1$–$C_4$ alkyl), N($C_1$–$C_4$ alkyl)$_2$, NHCONH$_2$, CONH$_2$, CONH($C_1$–$C_4$ alkyl), CON($C_1$–$C_4$ alkyl)$_2$, —L$^3$—W$^4$ or —L$^3$—Cy$^4$;

$L^3$ is (CR$^{a8}$R$^{a9}$)$_{p4}$, (CR$^{a8}$R$^{a9}$)$_{p4}$O(CR$^{a8}$R$^{a9}$)$_{p5}$, (CR$^{a8}$R$^{a9}$)$_{p4}$S(CR$^{a8}$R$^{a9}$)$_{p5}$, (CR$^{a8}$R$^{a9}$)$_{p4}$NR$^{a10}$(CR$^{a8}$R$^{a9}$)$_{p5}$, (CR$^{a8}$R$^{a9}$)$_{p4}$CONR$^{a10}$(CR$^{a8}$R$^{a9}$)$_{p5}$, (CR$^{a8}$R$^{a9}$)$_{p4}$SONR$^{a10}$(CR$^{a8}$R$^{a9}$)$_{p5}$, (CR$^{a8}$R$^{a9}$)$_{p4}$SO$_2$NR$^{a10}$(CR$^{a8}$R$^{a9}$)$_{p5}$, (CR$^{a8}$R$^{a9}$)$_{p4}$CO(CR$^{a8}$R$^{a9}$)$_{p5}$, (CR$^{a8}$R$^{a9}$)$_{p4}$COO(CR$^{a8}$R$^{a9}$)$_{p5}$, (CR$^{a8}$R$^{a9}$)$_{p4}$NR$^{a10}$CONR$^{a10}$(CR$^{a8}$R$^{a9}$)$_{p5}$, (CR$^{a8}$R$^{a9}$)$_{p4}$NR$^{a10}$C(=NR$^{a10}$)NR$^{a10}$(CR$^{a8}$R$^{a9}$)$_{p5}$ or (CR$^{a8}$R$^{a9}$)$_{p4}$OCO(CR$^{a8}$R$^{a9}$)$_{p5}$;

$R^{a8}$ and $R^{a9}$ are each, independently, H, halo, $C_1$–$C_4$ alkyl, $C_2$–$C_4$ alkenyl, $C_2$–$C_4$ alkynyl or $C_1$–$C_4$ haloalkyl;

$R^{a10}$ is H, $C_1$–$C_4$ alkyl, $C_1$–$C_4$ haloalkyl, aryl, or $C_3$–$C_7$ cycloalkyl;

W$^4$ is $C_1$–$C_8$ alkyl, $C_2$–$C_8$ alkenyl, $C_2$–$C_8$ alkynyl carbocyclyl or heterocarbocyclyl, each optionally substituted by 1, 2 or 3 halo, $C_1$–$C_6$ haloalkyl, $C_3$–$C_7$ cycloalkyl, aryl, heterocycloalkyl, heteroaryl, CN, SOR$^{b6}$, SO$_2$R$^{b6}$, ORb3, SR$^{b3}$, NR$^{b4}$R$^{b5}$, SONR$^{b4}$R$^{b5}$, SO$_2$NR$^{b4}$R$^{b5}$, CONR$^{b4}$R$^{b5}$, COOR$^{b3}$ or COR$^{b6}$;

$P^1$, $P^2$, $P^3$, and $P^4$ are each, independently, N or CR$^{v4}$;

$R^{v1}$ is H or $C_1$–$C_4$ alkyl;

$R^{v2}$ and $R^{v3}$ are each, independently, H, $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylalkyl, each optionally substituted by one or more halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COOH, COO($C_1$–$C_4$ alkyl), NH$_2$, NH($C_1$–$C_4$ alkyl), or N($C_1$–$C_4$ alkyl)$_2$;

$R^{v4}$ is H, halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COOH, COO($C_1$–$C_4$ alkyl), NH$_2$, NH($C_1$–$C_4$ alkyl), or N($C_1$–$C_4$ alkyl)$_2$;

or two $R^{v4}$, each on adjacent carbon atoms, together with the carbon atoms to which they are attached form a fused 3–14 membered carbocyclyl group or fused 3–14 membered heterocarbocyclyl group, each optionally substituted by 1, 2, or3 halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, COON, COO($C_1$–$C_4$ alkyl), NH$_2$, NH($C_1$–$C_4$ alkyl), or N($C_1$–$C_4$ alkyl)$_2$;

$R^y$ is H or $C_1$–$C_4$ alkyl;

$R^{z1}$ and $R^{z2}$ are each, independently, H, $C_1$–$C_{10}$ alkyl, $C_2$–$C_{10}$ alkenyl, $C_2$–$C_{10}$ alkynyl, carbocyclyl, heterocarbocyclyl, carbocyclylalkyl, or heterocarbocyclylalkyl, each optionally substituted by one or more halo, $C_1$–$C_4$ alkyl, $C_1$–$C_4$ haloalkyl, CN, NO$_2$, OH, $C_1$–$C_4$ alkoxy, $C_1$–$C_4$ haloalkoxy, alkyl), NH$_2$, NH($C_1$–$C_4$ alkyl), or N($C_1$–$C_4$ alkyl)$_2$;

$G^1$ is H, $C_1$–$C_6$ alkyl, $C_1$–$C_6$ haloalkyl, or $C_3$–$C_7$ cycloalkyl;

$G^2$ is H, $C_1$–$C_6$ alkyl, $C_1$–$C_6$ haloalkyl, or $C_3$–$C_7$ cycloalkyl;

or $G^1$ and $G^2$ together form O or S;

each AA1 and AA2 is, independently, an amino acid residue;

a dashed line indicates an optional bond;
k is 1, 2, 3, 4, 5 or 6;
n is 1 to 12;
m is 0 or 1;
each s, t, and u is, independently, 0 or 1;
p is 0, 1, 2, 3, 4, 5 or 6;
p4 and p5 are each, independently, 0,1,2,3,4 or 5;
q is 0 or 1;
each v and w is, independently, 0, 1, 2, 3, 4, or 5;
x is 0, 1, 2, 3, or 4;
xx is 1, 2 or 3;
y is 0, 1, 2, 3, 4, or 5; and
z is 0, 1, 2, 3, 4, or 5.

2. The compound of claim 1 wherein $Sc^1$ is present and $Sc^2$ is absent.

3. The compound of claim 1 wherein $Sc^2$ is present and $Sc^1$ is absent.

4. The compound of claim 1 wherein both $Sc^1$ and $Sc^2$ is present.

5. The compound of claim 1 wherein the ring formed by $X^1$, $X^2$, $X^3$, $D^1$, $D^2$, and $D^3$ is substituted or unsubstituted phenyl.

6. The compound of claim 1 wherein the ring formed by $X^1$, $X^2$, $X^3$, $D^1$, $D^2$, and $D^3$ is substituted or unsubstituted pyridinyl, pyrimidinyl, triazinyl, or pyridonyl.

7. The compound of claim 1 wherein at least one of $D^2$ or $D^3$ is $CR^1$ wherein $R^1$ is other than H.

8. The compound of claim 1 wherein at least one of $D^2$ or $D^3$ is $CR^1$ wherein $R^1$ is halo, $C_1$–$C_4$ alkyl, $C_2$–$C_4$ alkenyl, $C_2$–$C_4$ alkynyl, $C_1$–$C_4$ haloalkyl, CN, $OR^5$, $SR^5$, $COOR^8$, aryl, heteroaryl or tetrazolyl.

9. The compound of claim 1 wherein at least one of $D^2$ or $D^3$ is C—F, C—Cl, C—Br, C—Me, C—Et, C—CH=$CH_2$, C—C≡CH, C—Ph, C—OMe or C—CN.

10. The compound of claim 1 wherein $R^{15}$ is H, halo, $C_1$–$C_4$ alkyl, haloalkyl, OH, $C_1$–$C_4$ alkoxy, $C_1$–$C_4$ haloalkoxy, SH, $C_1$–$C_4$ thioalkoxy, CN, $NO_2$, SO($C_1$–$C_4$ alkyl), SO($C_1$–$C_4$ haloalkyl), $SONH_2$, $SO_3H$, $SO_2$($C_1$–$C_4$ alkyl), $SO_2$($C_1$–$C_4$ haloalkyl), $SO_2NH_2$, CHO, COOH, CO($C_1$–$C_4$ alkyl), CO($C_1$–$C_4$ haloalkyl), COO($C_1$–$C_4$ alkyl), COO($C_1$–$C_4$ haloalkyl), $CONH_2$, CONH($C_1$–$C_4$ alkyl), CON($C_1$–$C_4$ alkyl)$_2$, $NH_2$, NH($C_1$–$C_4$ alkyl), or N($C_1$–$C_4$ alkyl)$_2$.

11. The compound of claim 1 wherein $R^{15}$ is H, halo, $C_1$–$C_4$ alkyl, haloalkyl, OH, $C_1$–$C_4$ alkoxy, $C_1$–$C_4$ haloalkoxy, CN, $NO_2$, $NH_2$, NH($C_1$–$C_4$ alkyl), or N($C_1$–$C_4$ alkyl)$_2$.

12. The compound of claim 1 wherein $R^{15}$ is H, halo, $C_1$–$C_4$ alkyl, haloalkyl, OH, $C_1$–$C_4$ alkoxy, $C_1$–$C_4$ haloalkoxy.

13. The compound of claim 1 wherein each $R^{16}$ and $R^{17}$ is, independently, H, halo, $C_1$–$C_4$ alkyl, haloalkyl, OH, $C_1$–$C_4$ alkoxy, $C_1$–$C_4$ haloalkoxy, SH, $C_1$–$C_4$ thioalkoxy, CN, $NO_2$, SO($C_1$–$C_4$ alkyl), SO($C_1$–$C_4$ haloalkyl), $SONH_2$, $SO_3H$, $SO_2$($C_1$–$C_4$ alkyl), $SO_2$($C_1$–$C_4$ haloalkyl), $SO_2NH_2$, CHO, COOH, CO($C_1$–$C_4$ alkyl), CO($C_1$–$C_4$ haloalkyl), COO($C_1$–$C_4$ alkyl), COO($C_1$–$C_4$ haloalkyl), $CONH_2$, CONH($C_1$–$C_4$ alkyl), CON($C_1$–$C_4$ alkyl)$_2$, $NH_2$, NH($C_1$–$C_4$ alkyl), or N($C_1$–$C_4$ alkyl)$_2$.

14. The compound of claim 1 wherein each $R^{16}$ and $R^{17}$ is, independently, H, halo, $C_1$–$C_4$ alkyl, haloalkyl, OH, $C_1$–$C_4$ alkoxy, $C_1$–$C_4$ haloalkoxy, CN, $NO_2$, $NH_2$, NH($C_1$–$C_4$ alkyl), or N($C_1$–$C_4$ alkyl)$_2$.

15. The compound of claim 1 wherein $R^{16}$ and $R^{17}$ together with the carbon atom to which they are attached form a $C_3$–$C_6$ cycloalkyl group.

16. The compound of claim 1 wherein $R^z$ is H.

17. The compound of claim 1 wherein q1 is 2.

18. The compound of claim 1 wherein q1 is 1.

19. The compound of claim 1 wherein at least one of said first and second molecular scaffolds has the Formula S1:

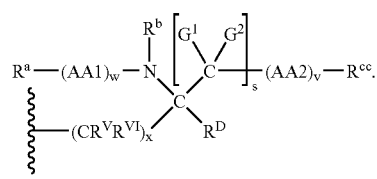

20. The compound of claim 1 wherein at least one of said first and second molecular scaffolds has the Formula S2:

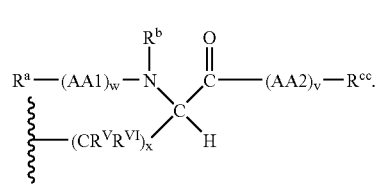

21. The compound of claim 1 wherein at least one of said first and second molecular scaffolds has the Formula S3:

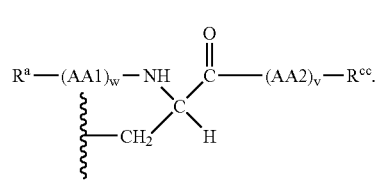

22. The compound of claim 1 wherein at least one of said first and second molecular scaffolds has the Formula S4:

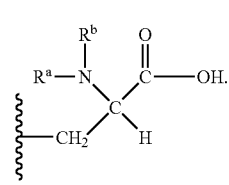

23. The compound of claim 1 wherein at least one of said first and second molecular scaffolds has the Formula S5:

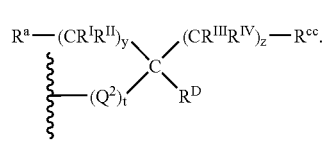

24. The compound of claim 1 wherein at least one of said first and second molecular scaffolds has the Formula S6a or S6b:

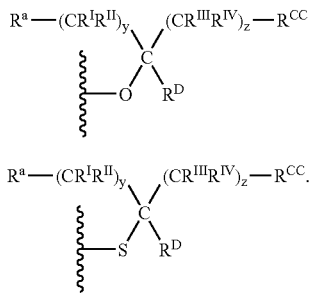

S6a

S6b

25. The compound of claim 1 wherein at least one of said first and second molecular scaffolds has the Formula S7:

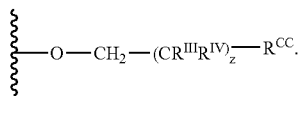

S7

26. The compound of claim 1 wherein at least one of said first and second molecular scaffolds has the Formula S8:

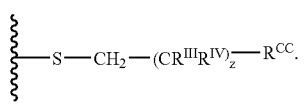

S8

27. The compound of claim 1 wherein at least one of said first and second molecular scaffolds has the Formula S9:

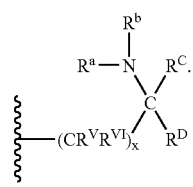

S9

28. The compound of claim 27 wherein $R^b$ is substituted or unsubstituted heteroaryl.

29. The compound of claim 27 wherein $R^b$ is substituted or unsubstituted benzothiazoloyl.

30. The compound of claim 1 wherein at least one of said first and second molecular scaffolds has the Formula S10a or S10b:

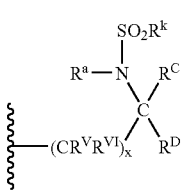

S10a

-continued

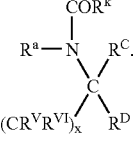

S10b

31. The compound of claim 1 wherein at least one of said first and second molecular scaffolds has the Formula S11a or S11b:

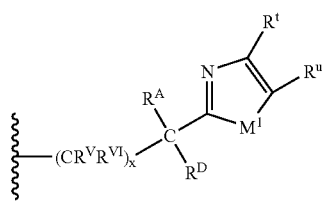

S11a

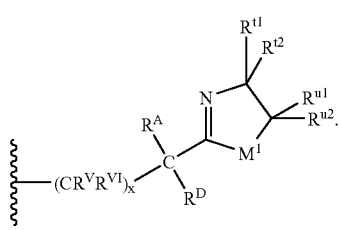

S11b

32. The compound of claim 1 wherein at least one of said first and second molecular scaffolds has the Formula S12a or S12b:

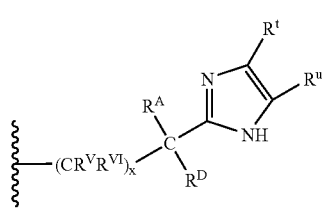

S12a

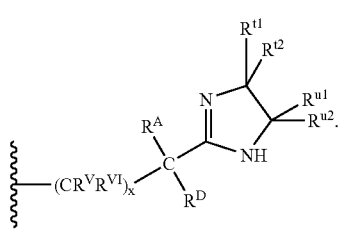

S12b

33. The compound of claim 1 wherein at least one of said first and second molecular scaffolds has the Formula S13:

S13

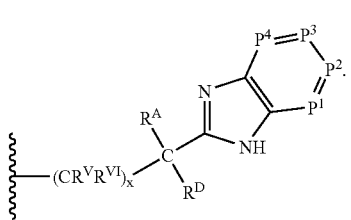

S15c

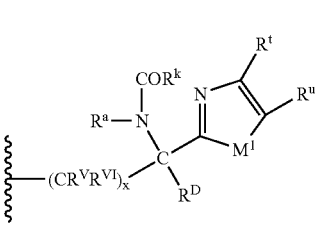

S15d

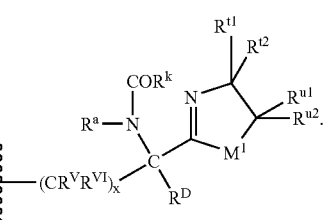

34. The compound of claim 1 wherein at least one of said first and second molecular scaffolds has the Formula S14a or S14b:

S14a

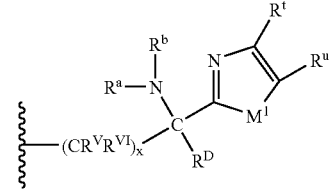

38. The compound of claim 1 wherein at least one of said first and second molecular scaffolds has the Formula S16a, S16b, S16c or S16d:

S16a

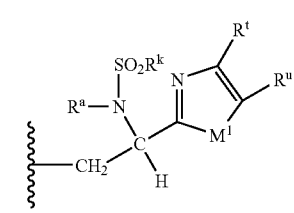

S14b

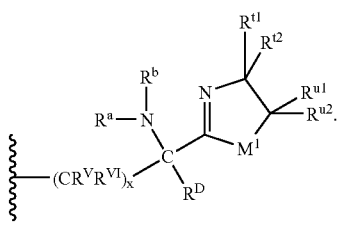

35. The compound of claim 34 wherein $R^b$ is substituted or unsubstituted heteroaryl.

36. The compound of claim 34 wherein $R^b$ is substituted or unsubstituted benzothiazolyl.

37. The compound of claim 1 wherein at least one of said first and second molecular scaffolds has the Formula S15a, S15b, S15c or S15d:

S16b

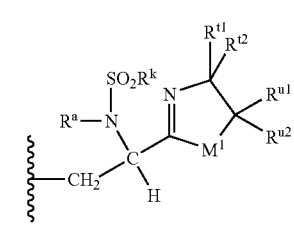

S16c

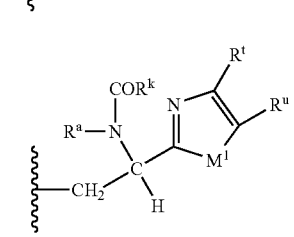

S15a

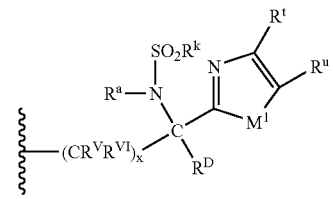

S16d

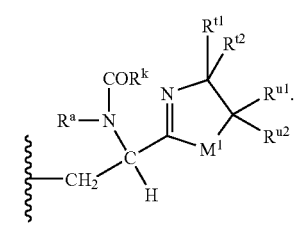

S15b

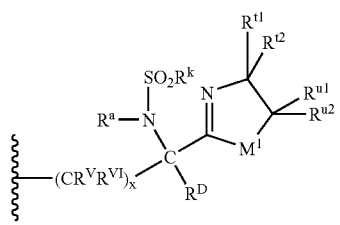

39. The compound of claim 1 wherein at least one of said first and second molecular scaffolds has the Formula S17:

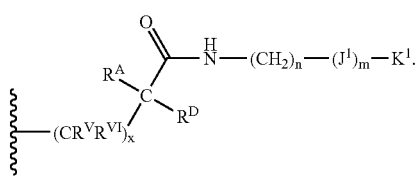

40. The compound of claim 1 wherein at least one of said first and second molecular scaffolds has the Formula S18:

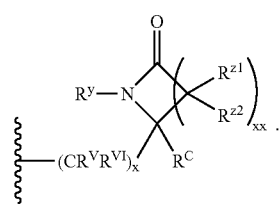

41. The compound of claim 1 wherein at least one of said first and second molecular scaffolds has the Formula S19:

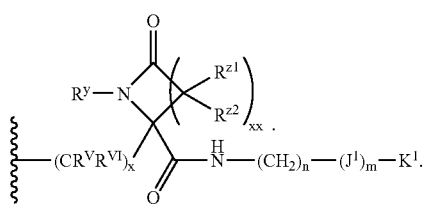

42. The compound of claim 1 wherein at least one of said first and second molecular scaffolds has the Formula S20:

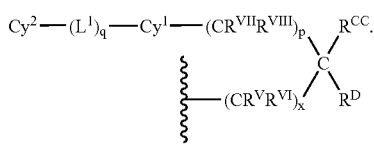

43. The compound of claim 1 wherein at least one of said first and second molecular scaffolds has the Formula S21:

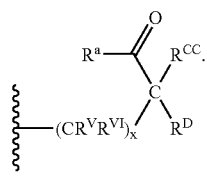

44. The compound of claim 1 wherein at least one of said first and second molecular scaffolds has the Formula S22:

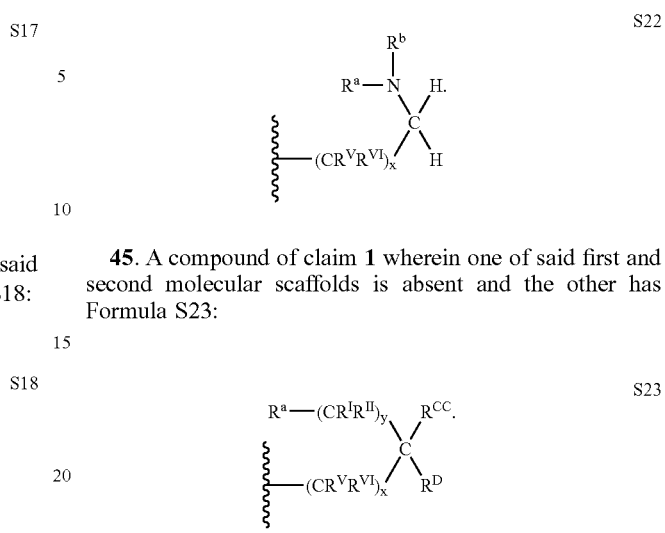

45. A compound of claim 1 wherein one of said first and second molecular scaffolds is absent and the other has Formula S23:

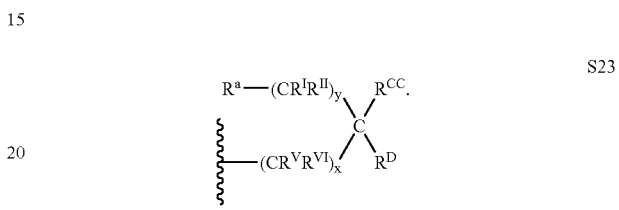

46. The compound of claim 45 wherein $R^{cc}$ is optionally substituted aryl or biaryl, $R^a$ is optionally substituted aryl, heteroaryl, cycloancyl, or heterocycloalkyl, and y is 1 or 2.

47. The compound of claim 46 wherein $R^D$ is H.

48. A compound of claim 1 wherein one of said first and second molecular scaffolds is absent and the other has the Formula $-(CR^VR^{VI})_x-CH_2-Q^1R^a$.

49. A compound of claim 1 wherein one of said first and second molecular scaffolds is absent and the other has the Formula $-(CR^VR^{VI})_x-CH_2-Q^1-(CR^{VII}R^{VIII})_p-Cy^1-(L^1)_qCy^2$.

50. A compound of claim 1 wherein one of said first and second molecular scaffolds is absent and the other has the Formula $-(CR^VR^{VI})_x-CH_2-O-(CR^{VII}R^{VIII})_p-Cy^1-(L^1)_qCy^2$.

51. A compound of claim 1 wherein one of said first and second molecular scaffolds is absent and the other has the Formula $-(CR^VR^{VI})_x-CH_2-S-(CR^{VII}R^{VIII})_p-Cy^1-(L^1)_qCy^2$.

52. A compound of claim 1 wherein one of said first and second molecular scaffolds is absent and the other has the Formula $-CH_2-Q^1-CH_2-Cy^1-(L^1)_qCy^2$.

53. A compound of claim 1 wherein one of said first and second molecular scaffolds is absent and the other has the Formula $-CH_2-Q^1-(CH_2)_p-Cy^1-Cy^2$.

54. A compound of claim 1 wherein one of said first and second molecular scaffolds is absent and the other has the Formula $-CH_2-Q^1-CH_2-Cy^1-Cy^2$.

55. A compound of claim 1 wherein $Cy^1$ is aryl or heteroaryl each optionally substituted by one or more halo, $C_1-C_6$ alkyl, $C_1-C_6$ haloalkyl, $C_2-C_6$ alkenyl, $C_2-C_6$ alkynyl $C_3-C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

56. A compound of claim 1 wherein $Cy^1$ is phenyl optionally substituted by one or more halo, $C_1-C_6$ alkyl, $C_1-C_6$ haloalkyl, $C_2-C_6$ alkenyl, $C_2-C_6$ alkynyl $C_3-C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

57. A compound of claim 1 wherein $Cy^2$ is aryl or heteroaryl each optionally substituted by one or more halo, $C_1-C_6$ alkyl, $C_1-C_6$ haloalkyl, $C_2-C_6$ alkenyl, $C_2-C_6$ alkynyl, $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

58. A compound of claim 1 wherein $Cy^2$ is phenyl optionally substituted by one or more halo, $C_1$–$C_6$ alkyl, $C_1$–$C_6$ haloalkyl, $C_2$–$C_6$ alkenyl, $C_2$–$C_6$ alkynyl $C_3$–$C_7$ cycloalkyl, aryl, heterocycloalkyl, heteroaryl, cyano, nitro, $OR^{b3}$, $SR^{b3}$, $NR^{b4}R^{b5}$, $SONR^{b4}R^{b5}$, $SO_2NR^{b4}R^{b5}$, $CONR^{b4}R^{b5}$, $COOR^{b3}$ or $COR^{b6}$.

59. A compound of claim 1 wherein one of said first and second molecular scaffolds is absent and the other is a 3- to 7- membered carbocyclk or 3- to 7-membered heterocarbocyclic group optionally substituted by one or more halo, $C_1$–$C_{10}$ alkyl, $C_2$–$C_{10}$ alkenyl, $C_2$–$C_{10}$alkenyl, $C_1$–$C_{10}$ haloalkyl, cyano, nitro, carbocyclyl, heterocarbocyclyl, carbocyclylalkyl, heterocarbocyclylalkyl, hydroxy, alkoxy, haloalkoxy, aryloxy, amino, alkylamino, dialkylamino, carboxy, carboxy alkylester, or carboxy aryl ester.

60. A compound of claim 1 selected from

N-{1-(4,5-Dihydro-1H-imidazol-2-yl)-2-[4-(1,1,3-trioxo-1λ6-isothiazolidin-5-yl)-phenyl[-ethyl}-3-trifluoromethyl-benzenesulfonamide;

N-{1-(1H-Imidazol-2-yl)-2-[4-(1,1,3-trioxo-1λ6-isothiazolidin-5-yl)-phenyl]-ethyl}-benzenesulfonamide;

N-{1-(5-Phenyl-1H-imidazol-2-yl)-2-[4-(1,1,3-trioxo-1λ6-isothiazolidin-5-yl)-phenyl]-eghyl}-3-trifluoromethl-benzenesulfonamide trifluoroacetate;

(2S)-2-(acetylamino)-N-{(1R)-1-(1H-benzimidazol-2-yl)-2-[4-(1.1-dioxido-3-oxoisothiazolidin-5-yl)phenyl]ethyl}-3-phenyloporpanamide;

(2S)-2-(Acetylamino)-N-{(1s)-1-(1H-benzimidazol-2-yl)-2-[4-(1,1-dioxido-3-oxisothiazolidin-5-yl)phenyl]ethyl{-3-phenylpropanamide;

N-(1S)-1-(1H-benzimidazol-2-yl)-2-[4-(1,1-dioxido-3-oxoisothiazolidin-5-yl)phenyl[ethylacetamide;

N-(1S)-1-(1H-Benzimidazol-2-yl)-2-[4-(1,1-dioxido-3-oxoisothiazolidin-5-yl)phenyl]ethyl-2-benzyl-5-oxopyrrolidine-2-carboxamide;

N-[(1S)-2-[4-(1,1-dioxido-3-oxoisothiazolidin-5-yl)phenyl]-1-(6-methoxy-1H-benzimidazol-2-yl)ethyl]morpholine-4-carboxamide;

N-{(1S)-1-(6-chloro-1H-benzimidazol-2-yl)-2-[4-(1,1-dioxido-3-oxoisothiazolidin-5-yl)phenyl]ethyl}morpholine-4-carboxamide;

N-[(1S)-2-[4-(1,1-dioxido-3-oxoisothiazolidin-5-yl)phenyl]-1-(7-methyl-1H-benzimidazol-2-yl)ethyl]morpholine-4-carboxamide;

Methyl (2R)-2-[({2-[4-(1,1-dioxido-3-oxoisothiazolidin-5-yl)phenyl]-1-(3H-imidazo[4,5-c]pyridin-2-yl)ethyl]amino}carbonyl)amino]-3-phenylpropanoate;

Methyl 2-{1-[({[(1R)-1-benzyl-2-methoxy-2-oxoethyl]amino}carbonyl)amino]-2-[4-(1,1-dioxido-3-oxoisothiazolidin-5-yl)phenyl]ethyl}-1H-benzimidazole-6-carboxylate;

Methyl (2S)-2-[((1S)-1-(1H-benzimidazol-2-yl)-2-[4-(1,1-dioxido-3-oxoisothiazolidin-5-yl)phenyl]ethylamino)carbonyl]amino-3-phenylpropanoate;

Benzyl (1S)-1-(1H-benzimidazol-2-yl)-2-[3-bromo-4-(1,1-dioxido-3-oxoisothiazolidin-5-yl)phenyl]ethylcarbamate;

Benzyl (1S)-1-(1H-benzimidazol-2-yl-2-[3-cyano-4-(1,1-dioxido-3-oxoisothiazolidin-5-yl)phenyl]ethylcarbamate;

Methyl 2-[5-(3-[3-bromo-4-(1,1-dioxido-3-oxoisothiazolidin-5-yl)phenyl]-2-[(phenylsulfonyl)-amino]propanoylamino)pentyl]oxy-6-hydroxybenzoate;

3-[3-bromo-4-(1,1-dioxido-3-oxoisothiazolidin-5-yl)phenyl]-N-(4-phenylbutyl)-2-[(phenylsulfonyl)-amino]propanamide;

3-[3-Bromo-4-(1,1-dioxido-3-oxoisothiazolidin-5-yl)phenyl]-N-(4-phenoxybutyl)2-[(phenylsulfonyl)-amino]propanamide Methyl 2-[4-(3-[3-bromo-4-(1,1-dioxido-3-oxoisothiazolidin-5-yl)phenyl]-2-[(phenylsulfonyl) -amino]porpanoylamino)butoxy]benzoate;

3-[3-Bromo-4-(1,1-dioxido-3-oxoisothiazolidin-5-yl)phenyl]-N-[4-(3-hydroxyphenoxy)butyl]-2-[(phenylsulfonyl)-amino]propanamide;

N-1-(1H-benzimidazol-2-yl)-2-[3-bromo-4-(1,1-dioxido-3-oxoisothiazolidin-5-yl)phenyl]ethylbenzenesulfonamide;

N-1-(1H-Benzimidazol-2-yl)-2-[3-cyano-4-(1,1-dioxido-3-oxoisothiazolidin-5-yl)phenyl]ethylbenzenesulfonamide;

3-[3-Cyano-4-(1,1-dioxido-3-oxoisothiazolidin-5-yl)phenyl]-N-(4-phenylbutyl)-2-[(phenylsulfonyl)-amino]propanamide;

Benzyl (1S)-1-(1H-benzimidazol-2-yl)-2-[3-chloro-4-(1,1-dioxido-3-oxoisothiazolidin-5-yl)phenyl]ethylcarbamate;

3-[3-Chloro-4-(1,1-dioxido-3-oxoisothiazolidin-5-yl)phenyl]-N-(4-phenylbutyl)-2-[(phenylsulfonyl)-amino]propanamide;

3-[3-Chloro-4-(1,1-dioxido-3-oxoisothiazolidin-5-yl)phenyl]-N-(4-phenoxybutyl)-2-[(phenylsulfonyl)-amino]propanamide;

Methyl 2-[4-(3-[3-chloro-4-(1,1-dioxido-3-oxoisothiazolidin-5-yl)pheny]-2-[(phenylsulfonyl)-amino]propanoylamino)butoxy]benzoate;

N-(1S)-1-(1H-benzimidazol-2-yl)-2-[4-(1,1-dioxido-3-oxoisothiazolidin-5-yl)phenyl]ethyl-3-(trifluoromethyl)benzenesulfonamide;

N-{(1S)-1-(1H-Benzimidazol-2-yl)-2-[4-(1,1-dioxido-3-oxoisothiazolidin-5-yl)phenyl]ethyl}benzenesulfonamide;

N-{(1S)-1-(1H-Benzimidazol-2-yl)-2-[4-(1,1-dioxido-3-oxoisothiazolidin-5-yl)phenyl]ethyl}-4-cyanobenzenesulfonamide;

N-{(1S)-1-(1H-Benzimidazol-2-yl)-2-[4-(1,1-dioxido-3-oxoisothiazolidin-5-yl)phenyl]ethyl}-3-phenoxybenzenesulfonamide;

N-{(1S)-1-(1H-Benzimidazol-2-yl)-2-[4-(1,1-dioxido-3-oxoisothiazolidin-5-yl)phenyl]ethyl}-3-phenoxybenzenesulfonamide;

N-{(1S)-1-(1H-Benzimidazol-2-yl)-2-[4-(1,1-dioxido-3-oxoisothiazolidin-5-yl)phenyl]ethyl}-3-(trifluoromethyl)benzamide;

N-{(1S)-1-(1H-benzimidazol-2-yl)-2-[4-(1,1-dioxido-3-oxoisothiazolidin-5-yl)phenyl]ethyl}cyclopentanecarboxamide;

N-{(1S)-1-(1H-benzimidazol-2-yl)-2-[4-(1,1-dioxido-3-oxoisothiazolidin-5-yl)phenyl]ethyl}-2-phenylacetamide;

N-{(1S)-1-(1H-benzimidazol-2-yl)-2-[4-(1,1-dioxido-3-oxoisothiazolidin-5-yl)phenyl]ethyl}cyclopropanecarboxamide;

N-{(1S)-1-(1H-benzimidazol-2-yl)-2-[4-(1,1-dioxido-3-oxoisothiazolidin-5-yl)phenyl]ethyl}-4-phenoxybenzenesulfonamide;

N-{(1S)-1-(1H-benzimidazol-2-yl)-2-[4-(1,1-dioxido-3-oxoisothiazolidin-5-yl)phenyl]ethyl}biphenyl-4-sulfonamide;

N-{(1S)-1-(1H-benzimidazol-2-yl)-2-[4-(1,1-dioxido-3-oxoisothiazolidin-5-yl)phenyl]ethyl}-4-chlorobenzenesulfonamide;
N-{(1S)-1-(1H-benzimidazol-2-yl)-2-[4-(1,1-dioxido-3-oxoisothiazolidin-5-yl)phenyl]ethyl}-3-chlorobenzenesulfonamide;
N-{(1S)-1-(1H-benzimidazol-2-yl)-2-[4-(1,1-dioxido-3-oxoisothiazolidin-5-yl)phenyl]ethyl}-2-chlorobenzenesulfonamide;
N-{(1S)-1-(1H-benzimidazol-2-yl)-2-[4-(1,1-dioxido-3-oxoisothiazolidin-5-yl)phenyl]ethyl}-2-methylbenzenesulfonamide;
N-{(1S)-1-(1H-benzimidazol-2-yl)-2-[4-(1,1-dioxido-3-oxoisothiazolidin-5-yl)phenyl]ethyl}-3-methylbenzenesulfonamide;
N-{(1S)-1-(1H-benzimidazol-2-yl)-2-[4-(1,1-dioxido-3-oxoisothiazolidin-5-yl)phenyl]ethyl}-4-methylbenzenesulfonamide;
N-{(1S)-1-(1H-benzimidazol-2-yl)-2-[4-(1,1-dioxido-3-oxoisothiazolidin-5-yl)phenyl]ethyl}-3-methyoxybenzenesulfonamide;
N-{(1S)-1-(1H-benzimidazol-2-yl)-2-[4-(1,1-dioxido-3-oxoisothiazolidin-5-yl)phenyl]ethyl}-3,5-dimethyl-isoxazole-4-sulfonamide;
N-{(1S)-1-(1H-benzimidazol-2-yl)-2-[4-(1,1-dioxido-3-oxoisothiazolidin-5-yl)phenyl]ethyl}-1,3,5trimethyl-1H-pyrazole-4-sulfonamide;
N-{(1S)-1-(1H-benzimidazol-2-yl)-2-[4-(1,1-dioxido-3-oxoisothiazolidin-5-yl)phenyl]ethyl}-5-chloro-1,3-dimethyl-1H-pyrazole-4-sulfonamide;
N-{(1S)-1-(1H-benzimidazol-2-yl)-2-[4-(1,1-dioxido-3-oxoisothiazolidin-5-yl)phenyl]ethyl}-5-chloro-1,3-dimethyl-1H-pyrazole-4-sulfonamide;
N-{(1S)-1-(1H-benzimidazol-2-yl)-2-[4-(1,1-dioxido-3-oxoisothiazolidin-5-yl)phenyl]ethyl-2-(trifluoromethyl)biphenyl-4-sulfonamide;
N-{(1S)-1-(1H-benzimidazol-2-yl)-2-[3-cyano-4-(1,1-dioxido-3-oxoisothiazolidin-5-yl)phenyl]ethyl}-4-chloro-3-(trifluoromethyl)benzenesulfonamide;
N-{(1S)-1-(1H-Benzimidazol-2-yl)-2-[3-cyano-4-(1,1-dioxido-3-oxoisothiazolidin-5-yl)phenyl]ethyl}-4-cyano-3-(trifluoromethyl)benzenesulfonamide;
N-{(1S)-1-(1H-benzimidazol-2-yl)-2-[3-cyano-4-(1,1-dioxido-3-oxoisothiazolidin-5-yl)phenyl]ethyl}-3-fluorobenzenesulfonamide;
N-{(1S)-1-(1H-Benzimidazol-2-yl)-2-[3-bromo-4-(1,1-dioxido-3-oxoisothiazolidin-5-yl)phenyl]ethyl}-3-fluorobenzenesulfonamide;
5-{4-[(2S)-2-(1H-Benzimidazol-2-yl)-2-(1,3-benzothiazol-2-ylamino)ethyl]-2-bromophenyl}isothiazolidin-3-one1,1-dioxide;
5-[(2S)-2-(1H-Benzimidazol-2-yl)-2-(1,3-benzothiazol-2-ylamino)ethyl]-2-(1,1-dioxide-3-oxoisothiazolidin-5-yl)benzonitrile;
5-(4-{(2S)-2-(1H-Benzimidazol-2-yl)-2[-(6-methoxy-1,3-benzothiazol-2-yl)amino]ethyl}-2-bromophenyl)isothiazolidin-3-one1,1-dioxide;
N-{(1S)-1-(1H-benzimidazol-2-yl)-2-[4-(1,1-dioxido-3-oxoisothiazolidin-5-yl)-3-methylphenyl]ethyl}benzenesulfonamide;
N-((1S)-1-(1H-benzimidazol-2-yl)-2-{4-[(5S)-1,1-dioxido-3-oxoisothiazolidin-5-yl]-3-methylphenyl}ethyl)benzenesulfonamide;
N-((1S)-1-(1H-benzimidazol-2-yl)-2-{4-[(5R)-1,1-dioxido-3-oxoisothiazolidin-5-yl]-3-methylphenyl}ethyl)benzenesulfonamide;
5-4-[(2S)-2-(1H-Benzimidazol-2-yl)-2-(1,3-benzothiazol-2-ylamino)ethyl]-2-methylphenylisothiazolidin-3-one1,1-dioxide;
Benzyl {(1S)-1-(1H-benzimidazol-2-yl)-2-[4-(1.1-dioxido-3-oxoisothiazolidin-5-yl)-3-methylpenyl]ethyl}carbamate;
N-[(1S)-2-[3-Bromo-4-(1,1-dioxido-3-oxoisothiazolidin-5-yl)phenyl]-1-(5-phenyl-1H-imidazol -2-yl)ethyl]benzenesulfonamide;
N-[(1S)-2-[3-Bromo-4-(1,1-dioxido-3-oxoisothiazolidin-5-yl)phenyl]-1-(5-phenyl-1H-imidazol -2-yl)ethyl]-3-(trifluoromethyl)benzenesulfonamide;
N-[(1S)-2-[3-Cyano-4-(1,1-dioxido-3-oxoisothiazolidin-5-yl)phenyl]-1-(5-phenyl-1H-imidazol-2-yl)ethyl]benzenesulfonamide;
N-[(1S)-2-[3-Cyano-4-(1,1-dioxido-3-oxoisothiazolidin-5-yl)phenyl]-1-(5-phenyl-1H-imidazol-2-yl)ethyl]-3-(trifluoromethyl)benzenesulfonamide;
5-(4-{(2S)-2(1H-Benzimidazol-2-yl)-2-[(5-benzyl-1,3-thiazol-2-yl)amino]ethyl}phenyl)isothiazolidin-3-one1.1-dioxide;
tert-Butyl (1S)-1-(1H-benzimidazol-2-yl)-2-[4-(1,1-dioxido-3-oxo-isothiazolidin-5-yl)-3-fluorophenyl]ethyl-carbamate;
N-(1S)-1-(1H-Benzimidazol-2-yl)-2-[4-(1,1-dioxido-3-oxoisothiazolidin-5-yl)-3-fluorophenyl]ethyl-2,2-difluoropropanamide;
N-(1S)-1-(1H-Benzimidazol-2-yl)-2-[4-(1,1-dioxido-3-oxoisothiazolidin-5-yl)-3-fluorophenyl]ethyl-3-fluorobenzenesulfonamide;
5-4-(2S)-2-(1H-Benzimidazol-2-yl)-2-(1,3-benzothiazol-2-ylamino)ethyl]-2-fluorophenylisothiazolidin-3-one1,1-dioxide;
3-Chloro-N-[(1S)-2-[3-chloro-4-(1,1-dioxido-3-oxoisothiazolidin-5-yl)phenyl]-1-(5-phenyl-1H-imidazol-2-yl)ethyl]-5-fluoro-2-methylbenzenesulfonamide;
N-{(1S)-1-(1H-benzimidazol-2yl)-2-[4-(1,1-dioxido-3-oxoisothiazolidin-5-yl)-3-methylphenyl]ethyl}-3-chlorobenzenesulfonamide;
N-{(1S)-1-(1H-benzimidazol-2yl)-2-[4-(1,1-dioxido-3-oxoisothiazolidin-5-yl)-3-methylphenyl]ethyl}-3-fluorobenzenesulfonamide;
N-{(1S)-1-(1H-benzimidazol-2yl)-2-[4-(1,1-dioxido-3-oxoisothiazolidin-5-yl)-3-methylphenyl]ethyl}-2-cyanobenzenesulfonamide;
N-{(1S)-1-(1H-benzimidazol-2yl)-2-[4-(1,1-dioxido-3-oxoisothiazolidin-5-yl)-3-methylphenyl]ethyl}-4-methylbenzenesulfonamide;
N-{(1S)-1-(1H-benzimidazol-2yl)-2-[4-(1,1-dioxido-3-oxoisothiazolidin-5-yl)-3-methylphenyl]ethyl}-4-(trifluoromethyl)benzenesulfonamide;
N-{(1S)-1-(1H-benzimidazol-2yl)-2-[4-(1,1-dioxido-3-oxoisothiazolidin-5-yl)-3-methylphenyl]ethyl}-3-methoxybenzenesulfonamide;
N-{(1S)-1-(1H-benzimidazol-2yl)-2-[4-(1,1-dioxido-3-oxoisothiazolidin-5-yl)-3-methylphenyl]ethyl}-3-bromobenzenesulfonamide;
N-{(1S)-1-(1H-benzimidazol-2yl)-2-[4-(1,1-dioxido-3-oxoisothiazolidin-5-yl)-3-methylphenyl]ethyl}-3-chloro-5-fluoro-2-methylbenzenesulfonamide;
N-{(1S)-1-(1H-benzimidazol-2yl)-2-[4-(1,1-dioxido-3-oxoisothiazolidin-5-yl)-3-methylphenyl]ethyl}-3-chloro-4-methylbenzenesulfonamide;
N-{(1S)-1-(1H-benzimidazol-2-yl)-2-[4-(1,1-dioxido-3-oxoisothiazolidin-5-yl)-3-methylphenyl]ethyl}-4-bromo-3-(trifluoromethyl)benzenesulfonamide;

N-[4-(Aminosulfonyl)benzyl]-4-[(1.1-dioxido-3-oxoisothiazolidin-5-yl)-methyl]-benzamide;
N-{(1S)-1-(1H-benzimidazol-2-yl)-2-[4-(1,1-dioxido-3-oxoisothiazolidin-5-yl)phenyl]ethyl}-3-fluoro-4-methylbenzenesulfonamide;
N-{(1S)-1-(1H-benzimidazol-2-yl)-2-[4-(1,1-dioxido-3-oxoisothiazolidin-5-yl)phenyl]ethyl}-3,4-dichlorobenzenesulfonamide;
N-{(1S)-1-(1H-benzimidazol-2-yl)-2-[4-(1,1-dioxido-3-oxoisothiazolidin-5-yl)phenyl]ethyl}-4-fluoro-2-methylbenzenesulfonamide;
N-{(1S)-1-(1H-benzimidazol-2-yl)-2-[4-(1,1-dioxido-3-oxoisothiazolidin-5-yl)phenyl]ethyl}-2,5-dimethoxybenzenesulfonamide;
N-{(1S)-1-(1H-benzimidazol-2-yl)-2-[4-(1,1-dioxido-3-oxoisothiazolidin-5-yl)phenyl]ethyl}-3-chloro-2-fluorobenzenesulfonamide;
N-{(1S)-1-(1H-benzimidazol-2-yl)-2-[4-(1,1-dioxido-3-oxoisothiazolidin-5-yl)phenyl]ethyl}-3-chloro-4-fluorobenzenesulfonamide;
N-{(1S)-1-(1H-benzimidazol-2-yl)-2-[4-(1,1-dioxido-3-oxoisothiazolidin-5-yl)phenyl]ethyl}-2,4-difluorobenzenesulfonamide;
N-{(1S)-1-(1H-benzimidazol-2-yl)-2-[4-(1,1-dioxido-3-oxoisothiazolidin-5-yl)phenyl]ethyl}-3,4-dimethoxybenzenesulfonamide;
N-{(1S)-1-(1H-benzimidazol-2-yl)-2-[4-(1,1-dioxido-3-oxoisothiazolidin-5-yl)phenyl]ethyl}-2,3-dichlorobenzenesulfonamide;
N-{(1S)-1-(1H-benzimidazol-2-yl)-2-[4-(1,1-dioxido-3-oxoisothiazolidin-5-yl)phenyl]ethyl}-3-chloro-2-methylbenzenesulfonamide;
N-{(1S)-1-(1H-benzimidazol-2-yl)-2-[4-(1,1-dioxido-3-oxoisothiazolidin-5-yl)phenyl]ethyl}-2,4-dichlorobenzenesulfonamide;
N-{(1S)-1-(1H-benzimidazol-2-yl)-2-[4-(1,1-dioxido-3-oxoisothiazolidin-5-yl)phenyl]ethyl}-2-bromo-5-(trifluoromethyl)benzenesulfonamide;
N-{(1S)-1-(1H-benzimidazol-2-yl)-2-[4-(1,1-dioxido-3-oxoisothiazolidin-5-yl)phenyl]ethyl}-2-chloro-5-(trifluoromethyl)benzenesulfonamide;
N-{(1S)-1-(1H-benzimidazol-2-yl)-2-[4-(1,1-dioxido-3-oxoisothiazolidin-5-yl)phenyl]ethyl}-2-chloro-4-(trifluoromethyl)benzenesulfonamide;
N-{(1S)-1-(1H-benzimidazol-2-yl)-2-[4-(1,1-dioxido-3-oxoisothiazolidin-5-yl)phenyl]ethyl}-3,5-dimethylbenzenesulfonamide;
N-{(1S)-1-(1H-benzimidazol-2-yl)-2-[4-(1,1-dioxido-3-oxoisothiazolidin-5-yl)phenyl]ethyl}-2-fluoro-5-(trifluoromethyl)benzenesulfonamide;
N-{(1S)-1-(1H-benzimidazol-2-yl)-2-[4-(1,1-dioxido-3-oxoisothiazolidin-5-yl)phenyl]ethyl}-4-fluoro-2-(trifluoromethyl)benzenesulfonamide;
N-{(1S)-1-(1H-benzimidazol-2-yl)-2-[4-(1,1-dioxido-3-oxoisothiazolidin-5-yl)phenyl]ethyl}-2-phenoxybenzenesulfonamide;
N-{(1S)-1-(1H-benzimidazol-2-yl)-2-[4-(1,1-dioxido-3-oxoisothiazolidin-5-yl)phenyl]ethyl}-3-(difluoromethoxy)benzenesulfonamide;
N-{(1S)-1-(1H-benzimidazol-2-yl)-2-[4-(1,1-dioxido-3-oxoisothiazolidin-5-yl)phenyl]ethyl}-3-chloro-5-fluoro-2-methylbenzenesulfonamide;
N-{(1S)-1-(1H-benzimidazol-2-yl)-2-[4-(1,1-dioxido-3-oxoisothiazolidin-5-yl)phenyl]ethyl}-4-(1,1-dimethylpropyl)benzenesulfonamide;
N-{(1S)-1-(1H-benzimidazol-2-yl)-2-[4-(1,1-dioxido-3-oxoisothiazolidin-5-yl)phenyl]ethyl}-4-chloro-2,5-dimethylbenzenesulfonamide;
N-{(1S)-1-(1H-benzimidazol-2-yl)-2-[4-(1,1-dioxido-3-oxoisothiazolidin-5-yl)phenyl]ethyl}-3-chloro-5-fluoro-2-methylbenzenesulfonamide;
N-{(1S)-1-(1H-benzimidazol-2-yl)-2-[4-(1,1-dioxido-3-oxoisothiazolidin-5-yl)phenyl]ethyl}-4-bromo-3-(trifluoromethyl)benzenesulfonamide;
N-{(1S)-1-(1H-benzimidazol-2-yl)-2-[4-(1,1-dioxido-3-oxoisothiazolidin-5-yl)phenyl]ethyl}-4-bromo-2-(trifluoromethoxy)benzenesulfonamide;
N-{(1S)-1-(1H-benzimidazol-2-yl)-2-[3-chloro-4-(1,1-dioxido-3-oxoisothiazolidin-5-yl)phenyl]ethylbiphenyl-4-sulfonamide;
N-{(1S)-1-(1H-benzimidazol-2-yl)-2-[4-(1,1-dioxido-3-oxoisothiazolidin-5-yl)-3-fluorophenyl]ethylbenzenesulfonamide;
N-{(1S)-1-(1H-benzimidazol-2-yl)-2-[4-(1,1-dioxido-3-oxoisothiazolidin-5-yl)-3-fluorophenyl]ethyl-3-fluorobenzenesulfonamide;
N-{(1S)-1-(1H-benzimidazol-2-yl)-2-[3-chloro-4-(1,1-dioxido-3-oxoisothiazolidin-5-yl)phenyl]ethyl-4-phenoxybenzenesulfonamide;
N-{(1S)-1-(1H-benzimidazol-2-yl)-2-[3-chloro-4-(1,1-dioxido-3-oxoisothiazolidin-5-yl)phenyl]ethyl-3-chloro-4-methylbenzenesulfonamide;
N-{(1S)-1-(1H-benzimidazol-2-yl)-2-[3-chloro-4-(1,1-dioxido-3-oxoisothiazolidin-5-yl)phenyl]ethyl-4-bromo-3-(trifluoromethyl)benzenesulfonamide;
N-{(1S)-1-(1H-benzimidazol-2-yl)-2-[3-chloro-4-(1,1-dioxido-3-oxoisothiazolidin-5-yl)phenyl]ethyl-2-(trifluoromethoxy)benzenesulfonamide;
N-{(1S)-1-(1H-benzimidazol-2-yl)-2-[3-chloro-4-(1,1-dioxido-3-oxoisothiazolidin-5-yl)phenyl]ethyl-3-bromobenzenesulfonamide;
N-{(1S)-1-(1H-benzimidazol-2-yl)-2-[3-chloro-4-(1,1-dioxido-3-oxoisothiazolidin-5-yl)phenyl]ethyl-3-chloro-5-fluoro-2-methylbenzenesulfonamide;
N-[(1S)-2-[4-(1,1-dioxido-3-oxoisothiazolidin-5-yl)phenyl]-1-(7-methyl-1H-benzimidazol-2-yl)ethyl]bipenyl-4-sulfonamide;
N-[(1S)-2-[4-(1,1-dioxido-3-oxoisothiazolidin-5-yl)phenyl]-1-(7-hydroxy-1H-benzimidazol-2-yl)ethyl]bipenyl-4-sulfonamide;
N-[(1S)-2-[4-(1,1-dioxido-3-oxoisothiazolidin-5-yl)phenyl]-1-(6-methyl-1H-benzimidazol-2-yl)ethyl]bipenyl-4-sulfonamide;
N-[(1S)-2-[4-(1,1-dioxido-3-oxoisothiazolidin-5-yl)phenyl]-1-(6-fluoro-1H-benzimidazol-2-yl)ethyl]bipenyl-4-sulfonamide;
N-{(1S)-1-(6-cyano-1H-benzimidazol-2-yl)-2-[4-(1,1-dioxido-3-oxoisothiazolidin-5-yl)pheny]ethyl}biphenyl-4-sulfonamide;
N-{(1S)-1-(6-chloro-1H-benzimidazol-2-yl)-2-[4-(1,1-dioxido-3-oxoisothiazolidin-5-yl)pheny]ethyl}biphenyl-4-sulfonamide;
methyl 2-{(1S)-1-[(biphenyl-4-ylsulfonyl)amino]-2-[4-(1,1-dioxido-3-oxoisothiazolidin-5-yl)phenyl]ethyl}-1H-benzimidazole-6-carboxylate;
N-{(1S)-2-[4-(1,1-dioxido-3-oxoisothiazolidin-5-yl)phenyl]-1-[6-(trifluoromethyl-1H-benzimidazol-2-yl]ethyl}biphenyl-4-sulfonamide;
N-[(1S)-2-[4-(1,1-dioxido-3-oxoisothiazolidin-5-yl)phenyl]-1-(6-methoxy-1H-benzimidazol-2-yl(ethyl]biphenyl-4sulfonamide;

N-[(1S)-2-[4-(1,1-dioxido-3-oxoisothiazolidin-5-yl)phenyl]-1-(7-methyl-1H-benzimidazol-2-yl(ethyl]-3-phenoxybenzenesulfonamide;

N-[(1S)-2-[4-(1,1-dioxido-3-oxoisothiazolidin-5-yl)phenyl]-1-(6-methyl-1H-benzimidazol-2-yl(ethyl]-3-phenoxybenzenesulfonamide;

N-[(1S)-2-[4-(1,1-dioxido-3-oxoisothiazolidin-5-yl)phenyl]-1-(6-fluoro-1H-benzimidazol-2-yl(ethyl]-3-phenoxybenzenesulfonamide;

N-[(1S)-2-[4-(1,1-dioxido-3-oxoisothiazolidin-5-yl)phenyl]-1-(6-cyano-1H-benzimidazol-2-yl(ethyl]-3-phenoxybenzenesulfonamide;

N-[(1S)-2-[4-(1,1-dioxido-3-oxoisothiazolidin-5-yl)phenyl]-1-(6-chloro-1H-benzimidazol-2-yl(ethyl]-3-phenoxybenzenesulfonamide;

methyl 2-(1S)-2-[4-(1,1-dioxido-3-oxoisothiazolidin-5-yl)phenyl]-1-1{[(3-phenoxyphenyl)sulfonyl]amino}ethyl)-1H-benzimidazole-6-carboxylate;

N-{(1S)-2-[4-(1,1-dioxido-3-oxoisothiazolidin-5-yl)phenyl]-1-[6-(trifluoromethyl)-1H-benzimidazol-2-yl]ethyl}-3phenoxybenzenesulfonamide;

N-[(1S)-2-[4-(1,1-dioxido-3-oxoisothiazolidin-5-yl)phenyl]-1-(6-methoxy-1H-benzimidazol-2-yl)ethyl]-3-phenoxybenzenesulfonamide;

N-[(1S)-2-[4-(1,1-dioxido-3-oxoisothiazolidin-5-yl)phenyl]-1-[7-methyl-1H-benzimidazol-2-yl)ethyl]-3,5-bis(trifluoromethyl)benzenesulfonamide;

N-[(1S)-2-[4-(1,1-dioxido-3-oxoisothiazolidin-5-yl)phenyl]-1-[6-methyl-1H-benzimidazol-2-yl)ethyl]-3,5-bis(trifluoromethyl)benzenesulfonamide;

N-[(1S)-2-[4-(1,1-dioxido-3-oxoisothiazolidin-5-yl)phenyl-]1-[6-fluoro-1H-benzimidazol-2-yl)ethyl]-3,5-bis(trifluoromethyl)benzenesulfonamide;

N-[(1S)-2-[4-(1,1-dioxido-3-oxoisothiazolidin-5-yl)phenyl]-1-[6-cyano-1H-benzimidazol-2-yl)ethyl]-3,5-bis(trifluoromethyl)benzenesulfonamide;

N-[(1S)-2-[4-(1,1-dioxido-3-oxoisothiazolidin-5-yl)phenyl]-1-[6-chloro-1H-benzimidazol-2-yl)ethyl]-3,5-bis(trifluoromethyl)benzenesulfonamide;

methyl 2-{(1S)-1-({[3,5-bis(trifluoromethyl)phenyl]sulfonyl}amino)-2-[4-(1,1-dioxido-3-oxoisothiazolidin-5-yl)phenyl]ethyl}-1H-benzimidazole-6-carboxylate;

N-{(1S)-2-[4-(1,1-dioxido-3-oxoisothiazolidin-5-yl)phenyl]-1-[6-(trifluoromethyl)-1H-benzimidazol-2-yl]ethyl}-3,5bis(trifluoromethyl)benzenesulfonamide;

N-{(1S)-2-[4-(1,1-dioxido-3-oxoisothiazolidin-5-yl)phenyl[-1-[6-methoxy-1H-benzimidazol-2-yl)ethyl]-3,5-bis(trifluoromethyl)benzenesulfonamide;

4-chloro-N-[(1S)-2-[4-(1,1-dioxido-3-oxoisothiazolidin-5-yl)phenyl]-1-(7-methyl-1H-benzimidazol-2-yl)ethyl]-3-(trifluoromethyl)benzenesulfonamide;

4-chloro-N-[(1S)-2-[4-(1,1-dioxido-3-oxoisothiazolidin-5-yl)phenyl]-1-(6-fluoro-1H-benzimidazol-2-yl)ethyl]-3-(trifluoromethyl)benzenesulfonamide;

4-chloro-N-[(1S)-2-[4-(1,1-dioxido-3-oxoisothiazolidin-5-yl)phenyl]-1-(6-cyano-1H-benzimidazol-2-yl)ethyl]-3-(trifluoromethyl)benzenesulfonamide;

4-chloro-N-[(1S)-2-[4-(1,1-dioxido-3-oxoisothiazolidin-5-yl)phenyl]-1-(6-cyano-1H-benzimidazol-2-yl)ethyl]-3-(trifluoromethyl)benzenesulfonamide;

methyl 2-{(1S)-1-({[4-chloro-3-(trifluoromethyl)phenyl]sulfonyl}amino)-2-[4-(1,1-dioxido-3-oxoisothiazolidin-5-yl)phenyl]ethyl}-1H-benzimidazole-6-carboxylate;

4-chloro-N-[(1S)-2-[4-(1,1-dioxido-3-oxoisothiazolidin-5-yl)phenyl]-1-(6-(trifluoromethyl)-1H -benzimidazol-2yl)ethyl]-3-(trifluoromethyl)benzenesulfonamide;

3-chloro-N-[(1S)-2-[4-(1,1-dioxido-3-oxoisothiazolidin-5-yl)phenyl]-1-(7-methyl-1H-benzimidazol-2-yl)ethyl]-3-methylbezenesulfonamide;

3-chloro-N-[(1S)-2-[4-(1,1-dioxido-3-oxoisothiazolidin-5-yl)phenyl]-1-(6-methyl-1H-benzimidazol-2-yl)ethyl]-3-methylbezenesulfonamide;

3-chloro-N-[(1S)-2-[4-(1,1-dioxido-3-oxoisothiazolidin-5-yl)phenyl]-1-(6-fluoro-1H-benzimidazol-2-yl)ethyl]-3-methylbezenesulfonamide;

3-chloro-N-[(1S)-2-[4-(1,1-dioxido-3-oxoisothiazolidin-5-yl)phenyl]-1-(6-cyano-1H-benzimidazol-2-yl)ethyl]-3-methylbezenesulfonamide;

3-chloro-N-[(1S)-2-[4-(1,1-dioxido-3-oxoisothiazolidin-5-yl)phenyl]-1-(6-chloro-1H-benzimidazol-2-yl)ethyl]-3-methylbezenesulfonamide;

methyl 2-{(1S)-1-{[(3-chloro-4-methylphenyl)sulfonyl]amino}-2-[4-(1,1-dioxido-3-oxoisothiazolidin-5-yl)phenyl]ethyl}-1H-benzimidazole-6-carboxylate;

3-chloro-N-[(1S)-2-[4-(1,1-dioxido-3-oxoisothiazolidin-5-yl)phenyl]-1-(6-(trifluoromethyl)-1H -benzimidazol-2yl)ethyl]-4-methylbenzenesulfonamide;

4-chloro-N-[(1S)-2-[4-(1,1-dioxido-3-oxoisothiazolidin-5-yl)phenyl]-1-(6-methyl-1H-benzimidazol-2-yl)ethyl]-3-(trifluoromethyl)benzenesulfonamide; benzimidazol-2-yl)ethy-4h3-(trifluoromethyl) benzenesulfonamide N-{(1S)-1-(5-bromo-6,7-dimethyl-1H-benzimidazol-2-yl)-2-[4-(1,1-dioxido-3-oxoisothiazolidin -5-yl)phenyl]ethyl}biphenyl-4-sulfonamide;

N-{(1S)-1-(5,6-dichloro-1H-benzimidazol-2yl)-2-[4-(1,1-dioxido-3-oxoisothiazolidin-5-yl)phenyl]ethyl}biphenyl-4-sulfonamide;

N-{(1S)-1-(6-tert-butyl-1H-benzimidazol-2yl)-2-[4-(1,1-dioxido-3-oxoisothiazolidin-5-yl)phenyl]ethyl}biphenyl-4-sulfonamide;

N-{(1S)-1-[6-fluoro-5-chloro-1H-benzimidazol-2yl]-2-[4-(1,1-dioxido-3-oxoisothiazolidin-5-yl)phenyl]ethyl}biphenyl-4-sulfonamide;

N-{(1S)-1-[6-chloro-5-methyl-1H-benzimidazol-2yl]-2-[4-(1,1-dioxido-3-oxoisothiazolidin-5-yl)phenyl]ethyl}biphenyl-4-sulfonamide;

N-{(1S)-1-[7-chloro-5-trifluoromethyl-1H-benzimidazol-2yl]-2-[4-(1,1-dioxido-3-oxoisothiazolidin-5-yl)phenyl]ethyl}biphenyl-4-sulfonamide;

N-{(1S)-1-(6-bromo-1H-benzimidazol-2yl)-2-[4-(1,1-dioxido-3-oxoisothiazolidin-5-yl)phenyl]ethyl}biphenyl-4-sulfonamide; and N-[(1S)-2-[4-(1,1-dioxido-3-oxoisothiazolidin-5-yl]phenyl]-1-(7-phenyl-1H-benzimidazol-2-yl)ethyl]benzenesulfonamide;

or a phannaceutically acceptable salt thereof.

61. A composition comprising a compound according to claim 1 and a pharmaceutically acceptable carrier.

\* \* \* \* \*